US009309285B2

(12) United States Patent
Roberts et al.

(10) Patent No.: US 9,309,285 B2
(45) Date of Patent: Apr. 12, 2016

(54) MACROCYCLIC BROAD SPECTRUM ANTIBIOTICS

(71) Applicant: RQx Pharmaceuticals, Inc., La Jolla, CA (US)

(72) Inventors: Tucker Curran Roberts, San Diego, CA (US); Peter Andrew Smith, La Jolla, CA (US); Robert I. Higuchi, Solana Beach, CA (US); David Campbell, San Diego, CA (US); Prasuna Paraselli, San Diego, CA (US)

(73) Assignee: RQX PHARMACEUTICALS, INC., La Jolla, CA (US)

( * ) Notice: Subject to any disclaimer, the term of this patent is extended or adjusted under 35 U.S.C. 154(b) by 0 days.

(21) Appl. No.: 14/086,908

(22) Filed: Nov. 21, 2013

(65) Prior Publication Data

US 2014/0142029 A1     May 22, 2014

Related U.S. Application Data

(60) Provisional application No. 61/729,249, filed on Nov. 21, 2012, provisional application No. 61/729,253, filed on Nov. 21, 2012.

(51) Int. Cl.

| | |
|---|---|
| *A61K 38/07* | (2006.01) |
| *C07K 5/10* | (2006.01) |
| *C07K 7/06* | (2006.01) |
| *C07K 5/02* | (2006.01) |
| *C07K 5/083* | (2006.01) |
| *C07K 5/087* | (2006.01) |
| *C07K 5/11* | (2006.01) |
| *A61K 38/55* | (2006.01) |

(52) U.S. Cl.
CPC . *C07K 7/06* (2013.01); *A61K 38/07* (2013.01); *A61K 38/55* (2013.01); *C07K 5/0202* (2013.01); *C07K 5/081* (2013.01); *C07K 5/0812* (2013.01); *C07K 5/1019* (2013.01)

(58) Field of Classification Search
None
See application file for complete search history.

(56) References Cited

U.S. PATENT DOCUMENTS

| | | | |
|---|---|---|---|
| 5,204,328 | A | 4/1993 | Nutt et al. |
| 6,025,350 | A | 2/2000 | Masamune et al. |
| 2005/0153876 | A1 | 7/2005 | Cameron et al. |
| 2007/0099885 | A1 | 5/2007 | Endermann et al. |
| 2008/0275018 | A1 | 11/2008 | Endermann et al. |
| 2008/0300231 | A1 | 12/2008 | Endermann et al. |
| 2013/0130985 | A1 | 5/2013 | Alewood et al. |
| 2014/0249073 | A1 | 9/2014 | Roberts et al. |

FOREIGN PATENT DOCUMENTS

| | | |
|---|---|---|
| WO | WO-01/14346 | 3/2001 |
| WO | WO-2011/112441 | 9/2011 |
| WO | WO 2011112441 A1 * | 9/2011 |
| WO | WO-2012/036907 | 3/2012 |
| WO | WO-2012/166665 | 12/2012 |
| WO | WO-2013/138187 | 9/2013 |

OTHER PUBLICATIONS

Butler et al. Natural Products—The Future Scaffold for Novel Antibotics. Biochemical Pharmacology, 2006; 71:919-929.
Dufour, J.; Neuville, L.; Zhu, J. P. Synlett 2008, 2355-2359.
Liu et al., Efforts toward broadening the spectrum of arylomycin antibiotic activity, Bioorganic & Medicinal Chemistry Letters, 2013, 23:5654-5659.
Liu et al., Synthesis and Characterization of the Arylomycin Lipoglycopeptide Antibiotics and the Crystallographic Analysis of Their Complex with Signal Peptidase, J. Am. Chem. Soc. 2011, 133:17869-17877.
PCT/US2012/39727 International Preliminary Report on Patentability mailed Dec. 12, 2013.
PCT/US2012/39727 International Search Report and Written Opinion mailed Jan. 3, 2013.
PCT/US2013/071093 International Search Report and Written Opinion mailed Apr. 1, 2014.
Roberts et al., Initial efforts toward the optimization of arylomycins for antibiotic activity, J Med Chem. 2011, 54(14),:4954-4963.
Roberts et al., Synthesis and Biological Characterization of Arylomycin B Antibiotics, J. Nat. Prod. 2011, 74:956-961.
Roberts, et al. (2007), J. Am. Chem. Soc. 129:15830-15838.
Smith et al., Broad Spectrum Antibiotic Activity of the Arylomycin Natural Products Is Masked by Natural Target Mutations, Chemisty & Biology, Nov. 24, 2010, 17:1223-1231.
Therien et al., Broadening the Spectrum of β-Lactam Antibiotics through Inhibition of Signal Peptidase Type 1, Antimicrobial Agents and Chemotherapy, 2012, 56:4662-4670.
PCT/US2013/071093 International Preliminary Report on Patentability dated Jun. 4, 2015.
U.S. Appl. No. 14/123,024 Office Action dated May 1, 2015.
U.S. Appl. No. 14/123,024 Office Action dated Oct. 15, 2015.

* cited by examiner

*Primary Examiner* — Jeffrey E Russel
(74) *Attorney, Agent, or Firm* — Wilson Sonsini Goodrich & Rosati

(57) ABSTRACT

Provided herein are antibacterial compounds, wherein the compounds in some embodiments have broad spectrum bioactivity. In various embodiments, the compounds act by inhibition of bacterial type 1 signal peptidase (SpsB), an essential protein in bacteria. Pharmaceutical compositions and methods for treatment using the compounds described herein are also provided.

16 Claims, No Drawings

```
                        SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal decanoyl
<220> FEATURE:
<221> NAME/KEY: VARIANT
<222> LOCATION: (6)..(6)
<223> OTHER INFORMATION: Fluorescence acceptor 3-nitrotyrosine
<220> FEATURE:
<221> NAME/KEY: MISC_FEATURE
<222> LOCATION: (7)..(8)
<223> OTHER INFORMATION: Cleavage site between residues 7 and 8
<220> FEATURE:
<221> NAME/KEY: VARIANT
<222> LOCATION: (10)..(10)
<223> OTHER INFORMATION: Residue is Lysine with substituent
      2-aminobenzamide fluorescence donor

<400> SEQUENCE: 1

Leu Ser Ser Pro Ala Xaa Ala Ala Asp Lys Pro Asp
1               5                   10

<210> SEQ ID NO 2
<211> LENGTH: 13
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal decanoyl
<220> FEATURE:
<221> NAME/KEY: VARIANT
<222> LOCATION: (6)..(6)
<223> OTHER INFORMATION: Fluorescence acceptor 3-nitrotyrosine
<220> FEATURE:
<221> NAME/KEY: MISC_FEATURE
<222> LOCATION: (7)..(8)
<223> OTHER INFORMATION: Cleavage site between residues 7 and 8
<220> FEATURE:
<221> NAME/KEY: VARIANT
<222> LOCATION: (11)..(11)
<223> OTHER INFORMATION: Residue is Lysine with substituent
      2-aminobenzamide fluorescence donor

<400> SEQUENCE: 2

Leu Thr Pro Thr Ala Xaa Ala Ala Ser Lys Lys Asp Asp
1               5                   10
```

MACROCYCLIC BROAD SPECTRUM ANTIBIOTICS

CROSS-REFERENCE

This application claims the benefit of priority from U.S. Provisional Application No. 61/729,249, filed Nov. 21, 2012; and U.S. Provisional Application No. 61/729,253, filed Nov. 21, 2012; both of which are incorporated by reference in their entirety.

SEQUENCE LISITING

The instant application contains a Sequence Listing which has been submitted in ASCII Format via EFS-Web and is hereby incorporated by reference in its entirety. Said ASCII copy, Created on Jul. 28, 2015, is named 0681-708-201SEQ2.txt and is 1,667 bytes in size.

BACKGROUND OF THE INVENTION

Antibiotic resistance is a serious and growing phenomenon in contemporary medicine and has emerged as a major public health concern of the 21st century. Therefore, novel classes of broad-spectrum antibiotics, especially those that target novel mechanisms of action, are needed to treat multidrug-resistant pathogens.

SUMMARY OF THE INVENTION

Described herein are novel macrocyclic compounds for the treatment of microbial infections, such as for the treatment of bacterial infections. In various embodiments, the present disclosure provides lipopeptide macrocyclic compounds for the treatment of bacterial infections. In various embodiments, the present disclosure provides classes and subclasses of chemical compounds structurally related to arylomycin for the treatment of bacterial infections. In various embodiments, the macrocyclic compounds act by inhibition of bacterial type 1 signal peptidase (SpsB), an essential protein in bacteria.

In one aspect described herein are compounds of Formula (I):

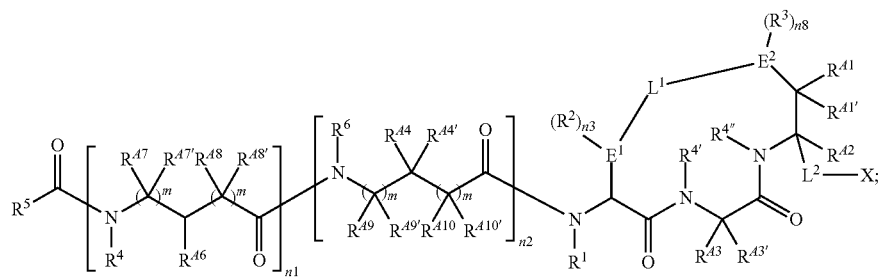

Formula (I)

wherein:
$E^1$ is $(C_1-C_6)$alkyl, $(C_2-C_7)$alkenyl, $(C_2-C_7)$alkynyl, $(C_3-C_7)$ cycloalkyl, heterocyclyl, heteroaryl, or aryl;
$E^2$ is $(C_2-C_7)$alkenyl, $(C_2-C_7)$alkynyl, $(C_3-C_7)$cycloalkyl, heterocyclyl, heteroaryl, or aryl;
$L^1$ is a bond, —O—, —S—, —NR⁴—, —C(O)—, —CH₂O—, —OCH₂—, —CH₂S—, —SCH₂—, —CH₂NR⁴—, —NR⁴CH₂—, —NR⁴C(O)—, —C(O)NR⁴—, —NR⁴S(O)₂—, —S(O)₂NR⁴—, —NR⁴C(O)NR⁴—, —NR⁴C(O)O—, —OC(O)NR⁴—, or $(C_1-C_4)$ alkylene optionally substituted with OH, CN, NO₂, halogen, $(C_1-C_6)$alkyl;
$L^2$ is a bond, or optionally substituted $(C_1-C_6)$alkylene;

X is a group of formula

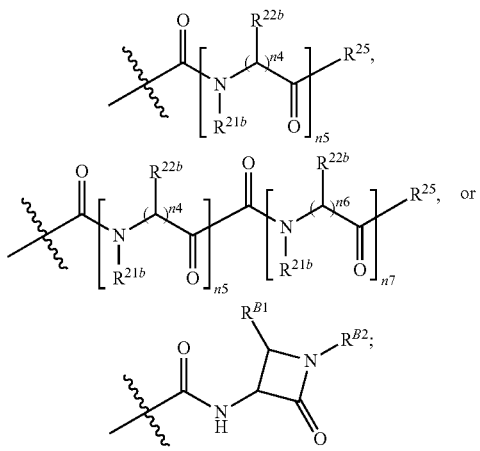

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

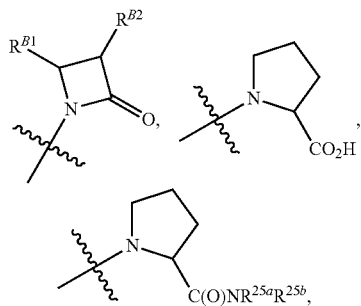

or $NR^{25a}R^{25b}$ where $R^{25}$ and $R^{25b}$ are each independently H, $SO_2(C_1-C_6)$alkyl, or optionally substituted alkyl; $R^{B1}$ and $R^{B2}$ are each independently H, $(C_1-C_6)$alkyl, $(C_3-C_6)$cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$alkyl, and a wavy line indicates a point of attachment of X to a carbon of formula (I) bearing X; or
X is $CO_2H$, $CH_2CO_2H$, $C(=O)NHCH_2C(O)H$, $CH_2C(=O)H$, $C(=O)N(H)CH(R^7)B(OR^{B3})(OR^{B4})$, or

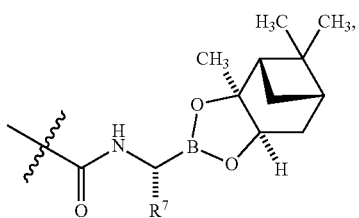

wherein $R^7$ is H, methyl, ethyl, or —$CH_2OH$; or $R^7$ and $R^{B3}$ together with the boron atom form a 5- or 6-membered boron containing ring; $R^{B3}$ and $R^{B4}$ are each independently H, ($C_1$-$C_6$)alkyl, —$CH_2CO_2H$, —$CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

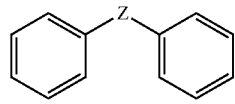

wherein Z is a bond, O, S, NH, $CH_2$ or C≡C;

$R^2$ and $R^3$ are each independently nitro, halo, cyano, hydroxy, glycosyloxy, amino, ($C_1$-$C_4$)alkoxy, ($C_1$-$C_4$)acyloxy, ($C_1$-$C_4$)alkyl, or a group cleavable under physiological conditions to provide a compound of formula (I) wherein $R^2$ or $R^3$ respectively is hydroxy, wherein any carbon atom is optionally substituted with J;

n1 and n2 are independently 0 or 1;

n3 and n8 are independently 0, 1, or 2;

each m is independently 0 or 1;

$R^1$ is hydrogen or ($C_1$-$C_6$)alkyl optionally substituted with 1 to 3 J; or $R^1$ together with $E^1$ form a ring;

$R^4$, $R^{4'}$, and $R^{4''}$ are each independently at each occurrence hydrogen, or ($C_1$-$C_6$)alkyl optionally substituted with 1 to 3 J;

$R^6$ is hydrogen, or ($C_1$-$C_6$)alkyl optionally substituted with 1 to 3 J; or $R^6$ together with $R^{A4}$ form a ring;

$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

$R^{A6}$ is amino, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, ($C_1$-$C_6$)-alkyl, ($C_2$-$C_7$)-alkenyl, ($C_2$-$C_7$)-alkynyl, ($C_3$-$C_{10}$)-cycloalkyl, ($C_3$-$C_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1$-$C_4)alkyl)_2$—, —$NH(C_1$-$C_4)alkyl$, $C_1$-$C_6$alkyl, $C_3$-$C_8$cycloalkyl, or $C_1$-$C_6$heteroalkyl; or a pharmaceutically acceptable salt, solvate, or prodrug thereof.

In another embodiment described herein are compounds of Formula (I) having the structure of Formula (Ia):

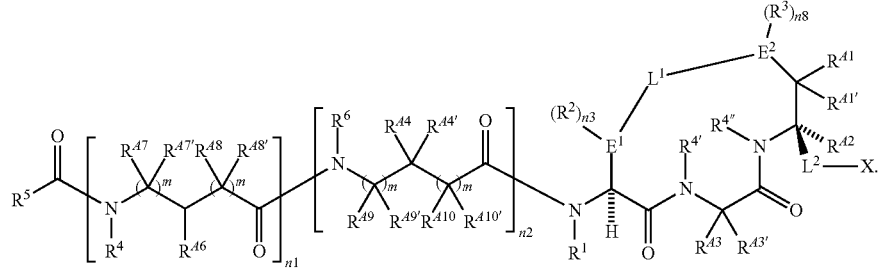

Formula (Ia)

In another embodiment described herein are compounds of Formula (I) having the structure of Formula (Ib):

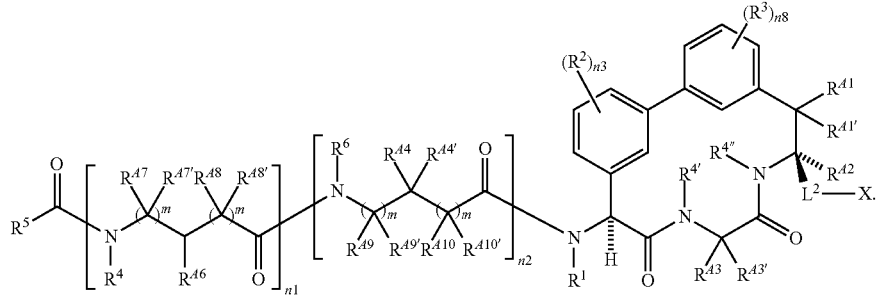

Formula (Ib)

In another embodiment described herein are compounds of Formula (I) having the structure of Formula (Ic):

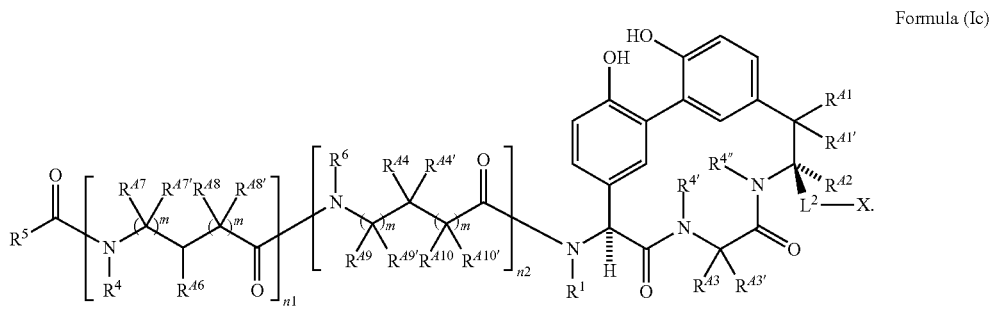

Formula (Ic)

In some embodiments is a compound of Formula (I), (Ia), (Ib), or (Ic) wherein $R^{A1}$, $R^{A1'}$, $R^{4'}$, and $R^{4''}$ are H. In further embodiments is a compound of Formula (I), (Ia), (Ib), or (Ic) wherein $L^2$ is a bond. In further embodiments is a compound of Formula (I), (Ia), (Ib), or (Ic) wherein $R^1$ is $CH_3$. In further embodiments is a compound of Formula (I), (Ia), (Ib), or (Ic) wherein n1 is 1 and n2 is 1. In further embodiments is a compound of Formula (I), (Ia), (Ib), or (Ic) wherein $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are each independently hydrogen, or $(C_1\text{-}C_6)$alkyl optionally substituted with 1 to 3 J. In further embodiments is a compound of Formula (I), (Ia), (Ib), or (Ic) wherein $R^{A6}$ is amino, or $(C_1\text{-}C_6)$alkyl optionally substituted with 1 to 3 J. In further embodiments is a compound of Formula (I), (Ia), (Ib), or (Ic) wherein each m is 0. In another embodiment is a compound of Formula (I), (Ia), (Ib), or (Ic) wherein n1 is 0 and n2 is 1. In further embodiments is a compound of Formula (I), (Ia), (Ib), or (Ic) wherein $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are each independently hydrogen, or $(C_1\text{-}C_6)$alkyl optionally substituted with 1 to 3 J. In a further embodiment is a compound of Formula (I), (Ia), (Ib), or (Ic) wherein $R^4$ is hydrogen. In another embodiment is a compound of Formula (I), (Ia), (Ib), or (Ic) wherein n1 is 0 and n2 is 0.

In another embodiment of the aforementioned embodiments is a compound of Formula (I), (Ia), (Ib), or (Ic) wherein X is $CO_2H$. In another embodiment of the aforementioned embodiments is a compound of Formula (I), (Ia), (Ib), or (Ic) wherein X is $C(=O)NHCH_2B(OH)_2$. In another embodiment of the aforementioned embodiments is a compound of Formula (I), (Ia), (Ib), or (Ic) wherein X is $C(=O)NHCH(CH_3)B(OH)_2$. In another embodiment of the aforementioned embodiments is a compound of Formula (I), (Ia), (Ib), or (Ic) wherein X is

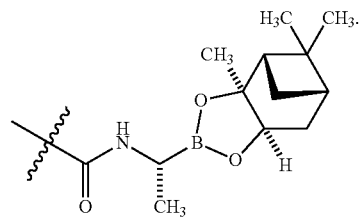 [SMILES: *C(=O)N[C@@H](C)B1O[C@@H]2C[C@@H]3C[C@@H](C3(C)C)[C@]2(C)O1]

In another aspect described herein are compounds of Formula (II):

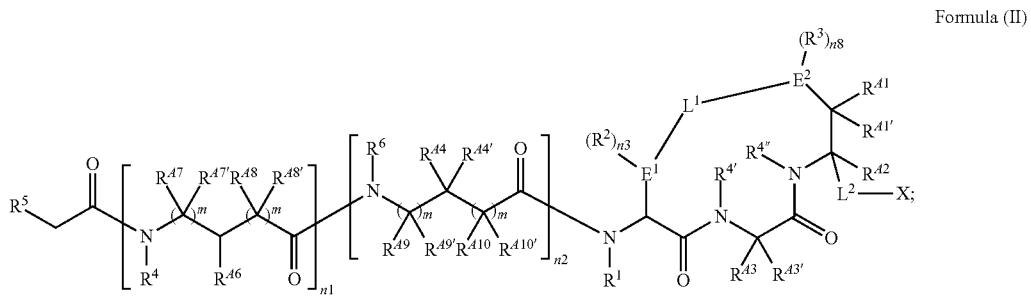

Formula (II)

wherein:
$E^1$ is $(C_1\text{-}C_6)$alkyl, $(C_2\text{-}C_7)$alkenyl, $(C_2\text{-}C_7)$alkynyl, $(C_3\text{-}C_7)$cycloalkyl, heterocyclyl, heteroaryl, or aryl;
$E^2$ is $(C_2\text{-}C_7)$alkenyl, $(C_2\text{-}C_7)$alkynyl, $(C_3\text{-}C_7)$cycloalkyl, heterocyclyl, heteroaryl, or aryl;
$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or $(C_1\text{-}C_4)$alkylene optionally substituted with OH, CN, $NO_2$, halogen, $(C_1\text{-}C_6)$alkyl;
$L^2$ is a bond, or optionally substituted $(C_1\text{-}C_6)$alkylene;
X is a group of formula

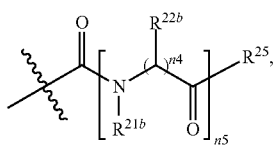

-continued

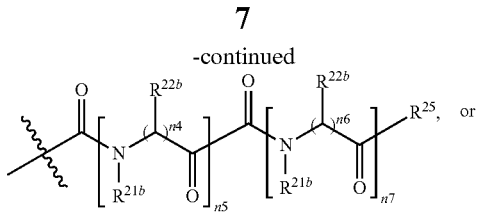

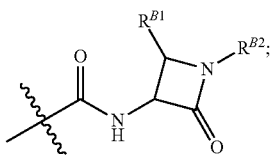

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

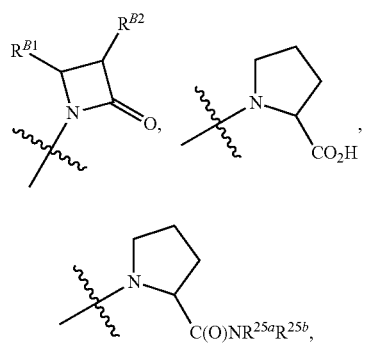

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$alkyl, $(C_3-C_6)$cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$alkyl, and a wavy line indicates a point of attachment of X to a carbon of formula (II) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

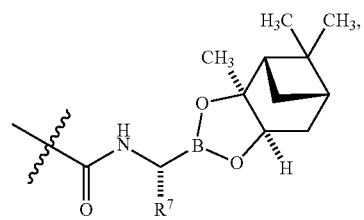

wherein $R^7$ is H, methyl, ethyl, or $-CH_2OH$; or $R^7$ and $R^{B3}$ together with the boron atom form a 5- or 6-membered boron containing ring; $R^{B3}$ and $R^{B4}$ are each independently H, $(C_1-$ $C_6)$alkyl, $-CH_2CO_2H$, $-CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, optionally comprising within the chain or at a chain terminus optionally substituted aryl, optionally substituted heteroaryl, or optionally substituted

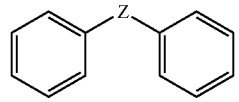

wherein Z is a bond, O, S, NH, $CH_2$ or $C\equiv C$;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (II) wherein $R^2$ or $R^3$ respectively is hydroxy, wherein any carbon atom is optionally substituted with J;

n1 and n2 are independently 0 or 1;

n3 and n8 are independently 0, 1, or 2;

each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{44}$ form a ring;

$R^{A1}$, $R^{A1'}$, $R^{A2}$, $R^{A3}$, $R^{A3'}$, $R^{A4}$, $R^{A4'}$, $R^{A6}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH-C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, $-CN$, $-NO_2$, $-OH$, $-CF_3$, $-OCF_3$, $-OCH_3$, $-NH_2$, $-N((C_1-C_4)$alkyl$)_2-$, $-NH(C_1-C_4)$alkyl, $C_1-C_6$alkyl, $C_3-C_8$cycloalkyl, or $C_1-C_6$heteroalkyl; or a pharmaceutically acceptable salt, solvate, or prodrug thereof.

In another embodiment described herein are compounds of Formula (II) having the structure of Formula (IIa):

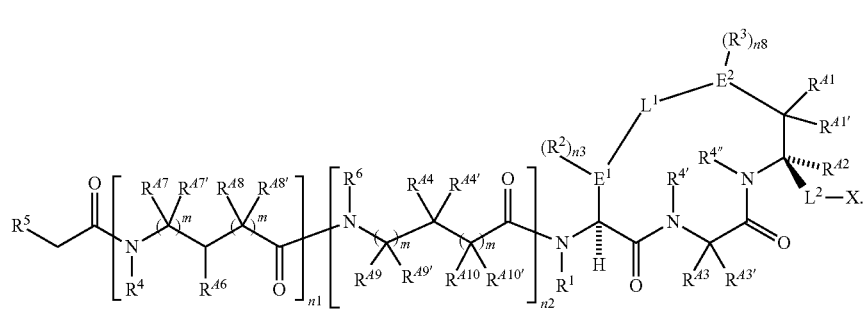

Formula (IIa)

In another embodiment described herein are compounds of Formula (II) having the structure of Formula (IIb):

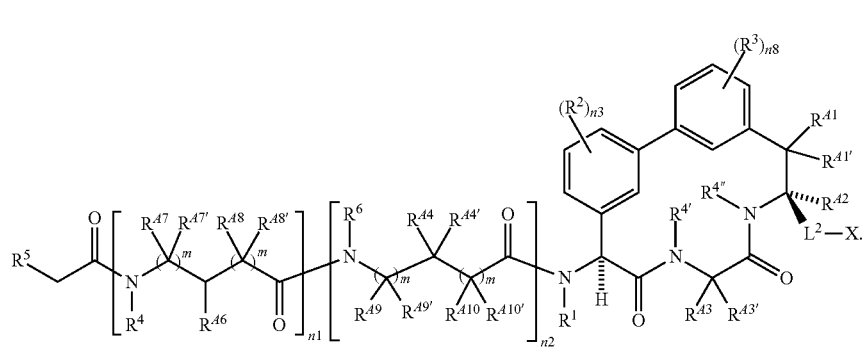

Formula (IIb)

In another embodiment described herein are compounds of Formula (II) having the structure of Formula (IIc):

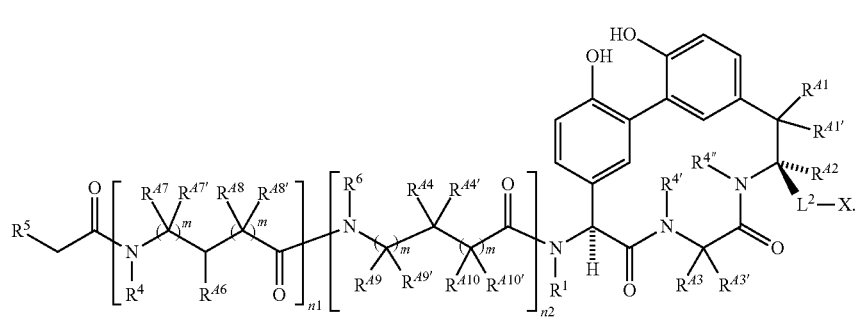

Formula (IIc)

In some embodiments is a compound of Formula (II), (IIa), (IIb), or (IIc) wherein $R^{A1}$, $R^{A1'}$, $R^{4'}$, and $R^{4''}$ are H. In further embodiments is a compound of Formula (II), (IIa), (IIb), or (IIc) wherein $L^2$ is a bond. In further embodiments is a compound of Formula (II), (IIa), (IIb), or (IIc) wherein $R^1$ is $CH_3$. In further embodiments is a compound of Formula (II), (IIa), (IIb), or (IIc) wherein n1 is 1 and n2 is 1. In further embodiments is a compound of Formula (II), (IIa), (IIb), or (IIc) wherein $R^{A2}$, $R^{A3}$, $R^{A3'}$, $R^{A4}$, $R^{A4'}$, $R^{A6}$, $R^{A7}$, $R^{A7'}$, $R^{A8}$, $R^{A8'}$, $R^{A9}$, $R^{A9'}$, $R^{A10}$ and $R^{A10'}$ are each independently hydrogen, or $(C_1-C_6)$alkyl optionally substituted with 1 to 3 J. In further embodiments is a compound of Formula (II), (IIa), (IIb), or (IIc) wherein $R^{A6}$ is hydrogen. In further embodiments is a compound of Formula (II), (IIa), (IIb), or (IIc) wherein each m is 0. In another embodiment is a compound of Formula (II), (IIa), (IIb), or (IIc) wherein n1 is 0 and n2 is 1. In further embodiments is a compound of Formula (II), (IIa), (IIb), or (IIc) wherein $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are each independently hydrogen, or $(C_1-C_6)$alkyl optionally substituted with 1 to 3 J. In a further embodiment is a compound of Formula (II), (IIa), (IIb), or (IIc) wherein $R^4$ is hydrogen. In another embodiment is a compound of Formula (II), (IIa), (IIb), or (IIc) wherein n1 is 0 and n2 is 0.

In another embodiment of the aforementioned embodiments is a compound of Formula (II), (IIa), (IIb), or (IIc) wherein X is $CO_2H$. In another embodiment of the aforementioned embodiments is a compound of Formula (II), (IIa), (IIb), or (IIc) wherein X is $C(=O)NHCH_2B(OH)_2$. In another embodiment of the aforementioned embodiments is a compound of Formula (II), (IIa), (IIb), or (IIc) wherein X is $C(=O)NHCH(CH_3)B(OH)_2$. In another embodiment of the aforementioned embodiments is a compound of Formula (II), (IIa), (IIb), or (IIc) wherein X is

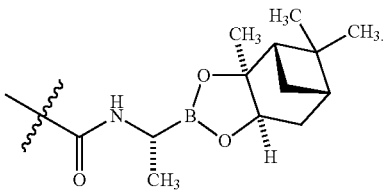 [SMILES: *C(=O)N[C@@H](C)B1O[C@@H]2C[C@@H]3C[C@@H](C3(C)C)[C@]2(C)O1]

In another aspect described herein are compounds of Formula (III):

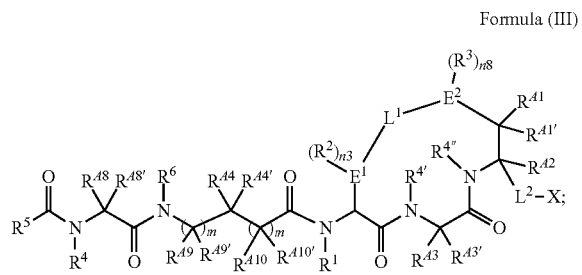
Formula (III)

wherein:
$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;
$E^2$ is $(C_2-C_7)$alkenyl, $(C_2-C_7)$alkynyl, $(C_3-C_7)$cycloalkyl, heterocyclyl, heteroaryl, or aryl;
$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$—CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1-C_4)$alkylene optionally substituted with OH, CN, NO$_2$, halogen, $(C_1-C_6)$alkyl;
$L^2$ is a bond, or optionally substituted $(C_1-C_6)$alkylene;
X is a group of formula

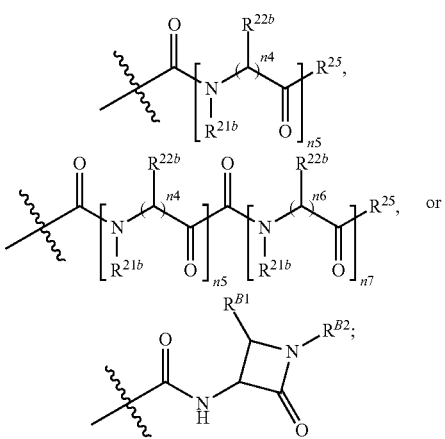

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, OR$^C$,

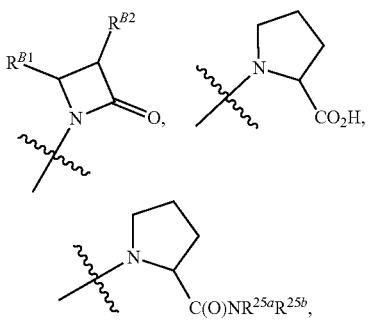

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$)alkyl, (C$_3$-C$_6$)cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$)alkyl, and a wavy line indicates a point of attachment of X to a carbon of formula (III) bearing X; or
X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

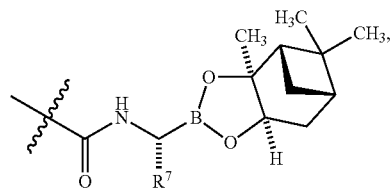

wherein R$^7$ is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, —CH$_2$CH$_2$CO$_2$H; or R$^{B3}$ and R$^{B4}$ together with the boron atom form an optionally substituted 5- or 6-membered boron containing ring;
R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

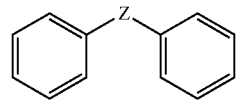

wherein Z is a bond, O, S, NH, CH$_2$ or C≡C;
R$^2$ and R$^3$ are each independently nitro, halo, cyano, hydroxy, glycosyloxy, amino, (C$_1$-C$_4$)alkoxy, (C$_1$-C$_4$)acyloxy, (C$_1$-C$_4$)alkyl, or a group cleavable under physiological conditions to provide a compound of formula (III) wherein R$^2$ or R$^3$ respectively is hydroxy, wherein any carbon atom is optionally substituted with J;
n3 and n8 are independently 0, 1, or 2;
each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{44}$ form a ring;

$R^{41}$, $R^{41'}$, $R^{42}$, $R^{43}$, $R^{43'}$, $R^{44}$, $R^{44'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heterocyclyl, 5- to 7-membered heteroaryl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$—, —$NH(C_1-C_4)$alkyl, $C_1-C_6$alkyl, $C_3-C_8$cycloalkyl, or $C_1-C_6$heteroalkyl; or a pharmaceutically acceptable salt, solvate, or prodrug thereof.

In another embodiment described herein are compounds of Formula (III) having the structure of Formula (IIIa):

Formula (IIIa)

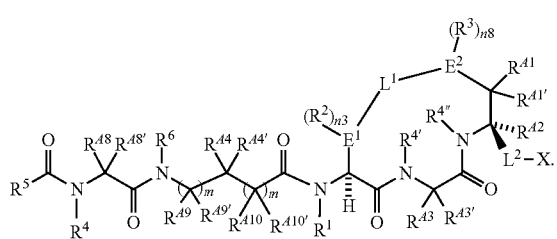

In another embodiment described herein are compounds of Formula (III) having the structure of Formula (IIIb):

Formula (IIIb)

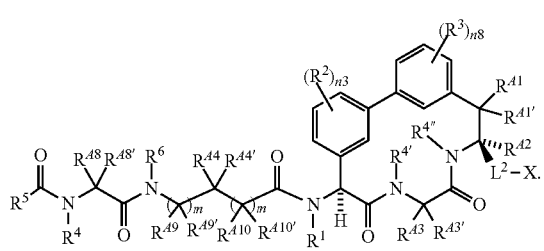

In another embodiment described herein are compounds of Formula (III) having the structure of Formula (IIIc):

Formula (IIIc)

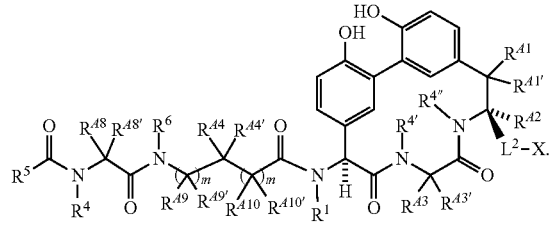

In some embodiments is a compound of Formula (III), (IIIa), (IIIb), or (IIIc) wherein $R^{41}$, $R^{41'}$, $R^{4'}$, and $R^{4''}$ are H. In further embodiments is a compound of Formula (III), (IIIa), (IIIb), or (IIIc) wherein $L^2$ is a bond. In further embodiments is a compound of Formula (III), (IIIa), (IIIb), or (IIIc) wherein $R^1$ is $CH_3$. In further embodiments is a compound of Formula (III), (IIIa), (IIIb), or (IIIc) wherein $R^{42}$, $R^{43}$, $R^{43'}$, $R^{44}$, $R^{44'}$, $R^{48}$, $R^{48'}$, $R^{49}$, $R^{49'}$, $R^{410}$, and $R^{410'}$ are each independently hydrogen, or $(C_1-C_6)$alkyl optionally substituted with 1 to 3 J. In further embodiments is a compound of Formula (III), (IIIa), (IIIb), or (IIIc) wherein $R^{48}$ and $R^{48'}$ are hydrogen. In further embodiments is a compound of Formula (III), (IIIa), (IIIb), or (IIIc) wherein each m is 0. In further embodiments is a compound of Formula (III), (IIIa), (IIIb), or (IIIc) wherein $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are each independently hydrogen, or $(C_1-C_6)$ alkyl optionally substituted with 1 to 3 J. In a further embodiment is a compound of Formula (III), (IIIa), (IIIb), or (IIIc) wherein $R^4$ is hydrogen.

In another embodiment of the aforementioned embodiments is a compound of Formula (III), (IIIa), (IIIb), or (IIIc) wherein X is $CO_2H$. In another embodiment of the aforementioned embodiments is a compound of Formula (III), (IIIa), (IIIb), or (IIIc) wherein X is $C(=O)NHCH_2B(OH)_2$. In another embodiment of the aforementioned embodiments is a compound of Formula (III), (IIIa), (IIIb), or (IIIc) wherein X is $C(=O)NHCH(CH_3)B(OH)_2$. In another embodiment of the aforementioned embodiments is a compound of Formula (III), (IIIa), (IIIb), or (IIIc) wherein X is

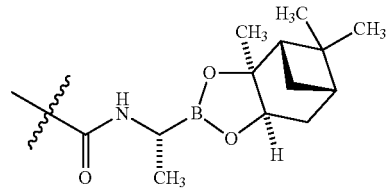

In another aspect is a hydrate or metabolite of a compound of Formula (I), (Ia), (Ib), (Ic), (Id), (Ie), (II), (IIa), (IIb), (IIc), (III), (IIIa), (IIIb), or (IIIc).

In another aspect is a hydrate or metabolite of a compound of Formula (I), (Ia), (Ib), (Ic), (Id), (Ie), (II), (IIa), (IIb), (IIc), (III), (IIIa), (IIIb), (IIIc), (IV), (IVa), or (IVb).

In another aspect is a pharmaceutical composition comprising a compound of Formula (I), (Ia), (Ib), (Ic), (Id), (Ie), (II), (IIa), (IIb), (IIc), (III), (IIIa), (IIIb), or (IIIc) and a pharmaceutically acceptable excipient thereof.

In another aspect is a pharmaceutical composition comprising a compound of Formula (I), (Ia), (Ib), (Ic), (Id), (Ie), (II), (IIa), (IIb), (IIc), (III), (IIIa), (IIIb), (IIIc), (IV), (IVa), or (IVb) and a pharmaceutically acceptable excipient thereof.

In another aspect is the use of a compound of Formula (I), (Ia), (Ib), (Ic), (Id), (Ie), (II), (IIa), (IIb), (IIc), (III), (IIIa), (IIIb), or (IIIc) or a pharmaceutically acceptable salt, pharmaceutically acceptable solvate, or pharmaceutically acceptable prodrug thereof, for the preparation of a medicament for the treatment of a bacterial infection in a patient.

another aspect is the use of a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, pharmaceutically acceptable solvate, or pharmaceutically acceptable prodrug thereof, for the preparation of a medicament for the treatment of a bacterial infection in a patient.

In one aspect is a method for treating a bacterial infection in a mammal comprising administering to the mammal a compound of Formula (I), (Ia), (Ib), (Ic), (Id), (Ie), (II), (IIa), (IIb), (IIc), (III), (IIIa), (IIIb), or (IIIc) or a pharmaceutically acceptable salt or prodrug thereof at a frequency and for a duration sufficient to provide a beneficial effect to the mammal. In another embodiment is a method for treating a bacterial infection in a mammal comprising administering to the mammal a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt or prodrug thereof at a frequency and for a duration sufficient to provide a beneficial effect to the mammal. In another embodiment, the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In another embodiment the bacterial infection is an infection involving a Gram-negative bacteria. In another embodiment, administering comprises a topical administration.

In a further embodiment are methods of treating a mammal in need of such treatment comprising administering to the mammal a second therapeutic agent. In another embodiment, the second therapeutic agent is not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid. In another embodiment, the second therapeutic agent is a β-lactam antibiotic. In another embodiment, the β-lactam antibiotic is selected from penicillins, monobactams, cephalosporins, and carbapenems. A further embodiment comprises administering a β-lactamase inhibitor.

In another aspect described herein are compounds of Formula (IV):

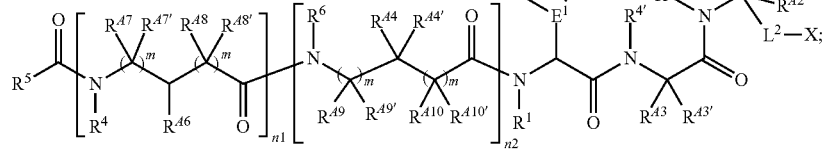

Formula (IV)

wherein:

$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$E^2$ is independently $(C_1-C_6)$alkyl, $(C_2-C_7)$alkenyl, $(C_2-C_7)$alkynyl, $(C_3-C_7)$cycloalkyl, heterocyclyl, or heteroaryl;

$E^3$ is a bond or —O—;

$L^1$ is a bond, —O—, —S—, —NR$^4$—, —C(O)—, —CH$_2$O—, —OCH$_2$—, —OCH$_2$CH$_2$O—, —OCH$_2$CH$_2$CH$_2$O—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, or $(C_1-C_4)$alkylene optionally substituted with OH, CN, NO$_2$, halogen, $(C_1-C_6)$alkyl;

$L^2$ is a bond, or optionally substituted $(C_1-C_6)$alkylene;

X is a group of formula

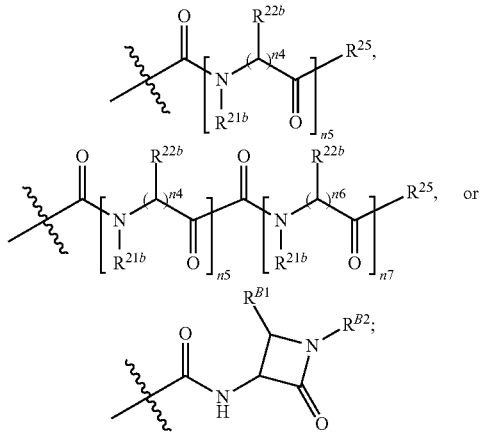

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

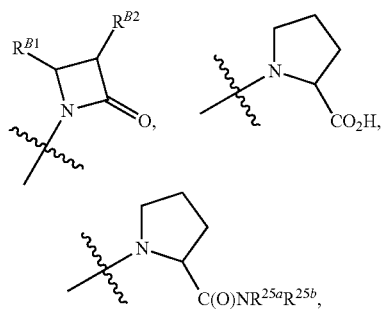

or $NR^{25a}R^{25b}$ where $R^{25}$ and $R^{25b}$ are each independently H, $SO_2(C_1-C_6)$alkyl, or optionally substituted alkyl; $R^{B1}$ and $R^{B2}$ are each independently H, $(C_1-C_6)$alkyl, $(C_3-C_6)$cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$alkyl, and a wavy line indicates a point of attachment of X to a carbon of formula (IV) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

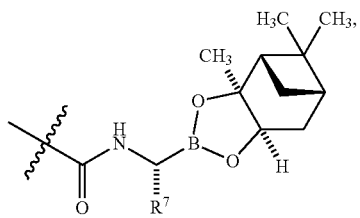

wherein $R^7$ is H, methyl, ethyl, or —$CH_2OH$; or $R^7$ and $R^{B3}$ together with the boron atom form a 5- or 6-membered boron containing ring; $R^{B3}$ and $R^{B4}$ are each independently H, $(C_1-C_6)$alkyl, —$CH_2CO_2H$, or —$CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

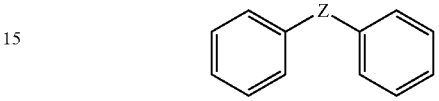

wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (IV) wherein $R^2$ or $R^3$ respectively is hydroxy, wherein any carbon atom is optionally substituted with J;

n1 and n2 are independently 0 or 1;

n3 and n8 are independently 0, 1, or 2; each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{44}$ form a ring;

$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{46}$ is amino, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)$alkyl$)_2$—, —$NH(C_1-C_4)$alkyl, $C_1-C_6$alkyl, $C_3-C_8$cycloalkyl, or $C_1-C_6$heteroalkyl; or a pharmaceutically acceptable salt, solvate, or prodrug thereof.

In another embodiment described herein are compounds of Formula (IVa):

Formula (IVa)

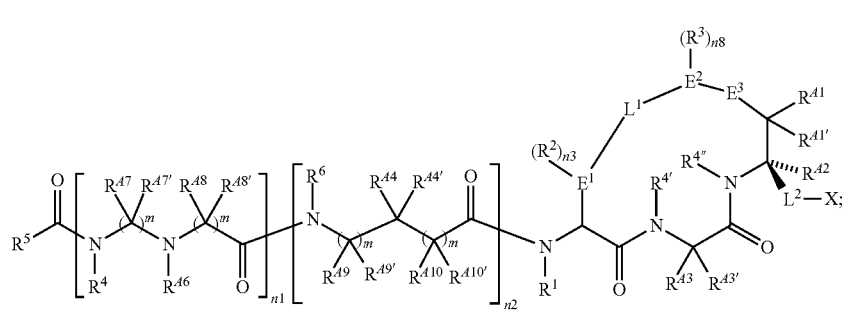

wherein:
E¹ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;
E² is independently $(C_1-C_6)$alkyl, $(C_2-C_7)$alkenyl, $(C_2-C_7)$alkynyl, $(C_3-C_7)$cycloalkyl, heterocyclyl, or heteroaryl;
E³ is a bond or —O—;
L¹ is a bond, —O—, —S—, —NR⁴—, —C(O)—, —CH₂O—, —OCH₂—, —OCH₂CH₂CH₂O—, —OCH₂CH₂CH₂CH₂O—, —CH₂S—, —SCH₂—, —CH₂NR⁴—, —NR⁴—CH₂—, —NR⁴C(O)—, —C(O)NR⁴—, —NR⁴S(O)₂—, —S(O)₂NR⁴—, —NR⁴C(O)NR⁴—, or $(C_1-C_4)$alkylene optionally substituted with OH, CN, NO₂, halogen, $(C_1-C_6)$alkyl;
L² is a bond, or optionally substituted $(C_1-C_6)$alkylene;
X is a group of formula

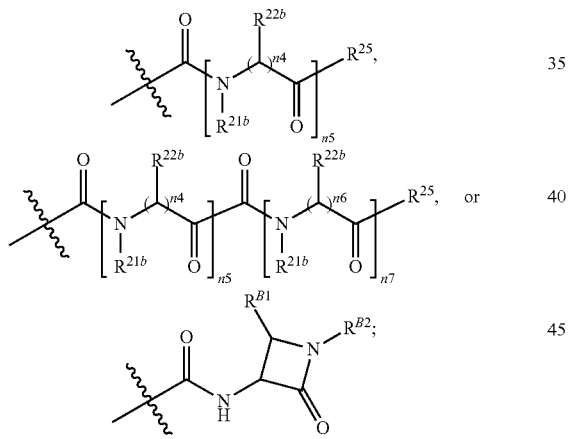

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$aryl, wherein any alkyl, cycloalkyl, heterocyclyl, aryl or heteroaryl is optionally substituted with 1 to 3 J; $R^{25}$ is H, OH, OR$^C$,

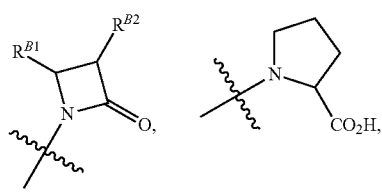

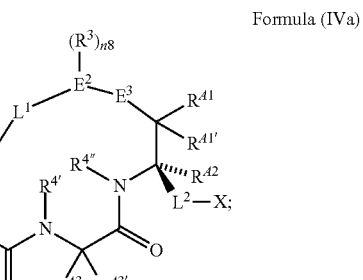

or NR$^{25a}$R$^{25b}$ where R$^{25a}$ and R$^{25b}$ are each independently H, SO₂(C₁-C₆)alkyl, or optionally substituted alkyl; $R^{B1}$ and $R^{B2}$ are each independently H, $(C_1-C_6)$alkyl, $(C_3-C_6)$cycloalkyl, OR$^C$, C(=O)N(R$^C$)₂, OC(=O)N(R$^C$)₂, C(=O)OR$^C$, OC(=O)OR$^C$, nitro, trifluoromethyl, trifluoromethoxy, $(C_1-C_6)$alkoxy, $(C_1-C_6)$thioalkoxy, N(R$^C$)₂, 5-7 membered heterocyclyl or 5-7 membered heteroaryl, or $(C_6-C_{10})$aryl; R$^C$ is independently at each occurrence H or $(C_1-C_6)$alkyl, and a wavy line indicates a point of attachment of X to a carbon of formula (IVa) bearing X; or
X is CO₂H, CH₂CO₂H, C(=O)NHCH₂C(=O)H, CH₂C(=O)H, C(=O)N(H)CH(R⁷)B(OR$^{B3}$)(OR$^{B4}$), or

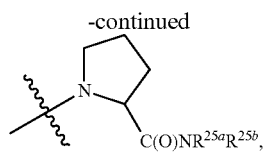

wherein R⁷ is H, methyl, ethyl, or —CH₂OH; or R⁷ and R$^{B3}$ together with the boron atom form a 5- or 6-membered boron containing ring; R$^{B3}$ and R$^{B4}$ are each independently H, $(C_1-C_6)$alkyl, —CH₂CO₂H, or —CH₂CH₂CO₂H; or R$^{B3}$ and R$^{B4}$ together with the boron atom form an optionally substituted 5- or 6-membered boron containing ring;
R⁵ is aryl, heteroaryl, or a linear or branched alkyl chain of about 1-22 carbon atoms, wherein R⁵ is bonded to the carbonyl carbon to which it is attached directly or by an O or NR⁴, to provide an amide, carbamate, or urea linkage, respectively; optionally comprising within the chain or at a chain terminus optionally substituted aryl, optionally substituted heteroaryl, or optionally substituted

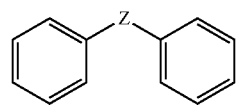

wherein Z is a bond, O, S, NH, CH₂ or C≡C;

R² and R³ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (IVa) wherein R² or R³ respectively is hydroxy, wherein any carbon atom is optionally substituted with J;

n1 and n2 are independently 0 or 1;

n3 and n8 are independently 0, 1, or 2;

each m is independently 0 or 1;

R¹ is hydrogen or $(C_1-C_6)$alkyl optionally substituted with 1 to 3 J; or R¹ together with E¹ form a ring;

R⁴, R⁴', and R⁴" are each independently at each occurrence hydrogen, or $(C_1-C_6)$alkyl optionally substituted with 1 to 3 J;

R⁶ is hydrogen, or $(C_1-C_6)$alkyl optionally substituted with 1 to 3 J; or R⁶ together with R⁴⁴ form a ring;

R⁴¹, R⁴¹', R⁴², R⁴³, R⁴³', R⁴⁴, R⁴⁴', R⁴⁷, R⁴⁷', R⁴⁸, R⁴⁸', R⁴⁹, R⁴⁹', R⁴¹⁰, and R⁴¹⁰' are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

R⁴⁶ is amino, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, CF₃, OCF₃, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH$—$C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO₂, —OH, —CF₃, —OCF₃, —OCH₃, —NH₂, —N(($C_1-C_4$)alkyl)₂—, —NH($C_1-C_4$)alkyl, $C_1-C_6$alkyl, $C_3-C_8$cycloalkyl, or $C_1-C_6$heteroalkyl; or a pharmaceutically acceptable salt, solvate, or prodrug thereof.

In some embodiments is a compound of Formula IV or Formula IVa wherein R⁴¹, R⁴¹', R⁴', and R⁴" are H. In further embodiments is a compound of Formula IV or Formula IVa wherein L² is a bond. In further embodiments is a compound of Formula IV or Formula IVa wherein R¹ is H. In further embodiments is a compound of Formula IV or Formula IVa wherein R⁴², R⁴³, R⁴³', R⁴⁴, R⁴⁴', R⁴⁷, R⁴⁷', R⁴⁸, R⁴⁸', R⁴⁹, R⁴⁹', R⁴¹⁰, and R⁴¹⁰' are each independently hydrogen, or $(C_1-C_6)$alkyl optionally substituted with 1 to 3 J. In further embodiments is a compound of Formula IV or Formula IVa wherein n1 is 1 and n2 is 0. In further embodiments is a compound of Formula IV or Formula IVa wherein R⁴⁶ is $(C_1-C_6)$alkyl optionally substituted with 1 to 3 J. In further embodiments is a compound of Formula IV or Formula IVa wherein E¹ is $(C_1-C_6)$alkyl. In further embodiments is a compound of Formula IV or Formula IVa wherein E² is $(C_1-C_6)$ alkyl. In further embodiments is a compound of Formula IV or Formula IVa wherein L¹ is —O—. In another embodiment is a compound of Formula IV or Formula IVa wherein L¹ is —OCH₂CH₂CH₂CH₂O—. In another embodiment is a compound of Formula IV or Formula IVa wherein L¹ is —C(O) NH—. In another embodiment is a compound of Formula IV or Formula IVa wherein E¹ is aryl. In a further embodiment is a compound of Formula IV or Formula IVa wherein E¹ is phenyl. In yet a further embodiment is a compound of Formula IV or Formula IVa wherein E² is $(C_1-C_6)$alkyl. In further embodiments is a compound of Formula IV or Formula IVa wherein L¹ is —O—. In another embodiment is a compound of Formula IV or Formula IVa wherein L¹ is —OCH₂CH₂CH₂CH₂O—. In another embodiment is a compound of Formula IV or Formula IVa wherein L¹ is —C(O)NH—.

In another embodiment of the aforementioned embodiments is a compound of Formula IV or Formula IVa wherein E³ is a bond. In another embodiment of the aforementioned embodiments is a compound of Formula IV or Formula IVa wherein E³ is —O—. In another embodiment of the aforementioned embodiments is a compound of Formula IV or Formula IVa wherein each m is 0. In another embodiment of the aforementioned embodiments is a compound of Formula IV or Formula IVa wherein n3 is 0 and n8 is 0. In another embodiment of the aforementioned embodiments is a compound of Formula IV or Formula IVa wherein n3 is 1 and n8 is 0. In another embodiment of the aforementioned embodiments is a compound of Formula IV or Formula IVa wherein X is CO₂H. In another embodiment of the aforementioned embodiments is a compound of Formula IV or Formula IVa wherein X is C(=O)NHCH₂B(OH)₂. In another embodiment of the aforementioned embodiments is a compound of Formula IV or Formula IVa wherein X is C(=O)NHCH(CH₃)B(OH)₂. In another embodiment of the aforementioned embodiments is a compound of Formula IV or Formula IVa wherein X is

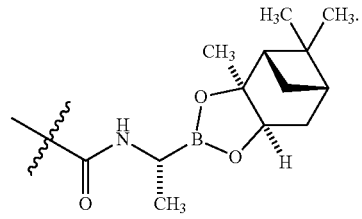 [SMILES: *C(=O)N[C@@H](C)B1O[C@@H]2C[C@@H]3C[C@@H](C3(C)C)[C@]2(C)O1]

In another aspect is a hydrate or metabolite of a compound of Formula (IV) or (IVa).

In another aspect is a pharmaceutical composition comprising a compound of Formula (IV) or (IVa) and a pharmaceutically acceptable excipient thereof.

In another aspect is the use of a compound of Formula (IV) or (IVa) or a pharmaceutically acceptable salt, pharmaceutically acceptable solvate, or pharmaceutically acceptable prodrug thereof, for the preparation of a medicament for the treatment of a bacterial infection in a patient.

In one aspect is a method for treating a bacterial infection in a mammal comprising administering to the mammal a compound of Formula (IV) or (IVa) or a pharmaceutically acceptable salt or prodrug thereof at a frequency and for a duration sufficient to provide a beneficial effect to the mammal. In another embodiment, the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mira-*

*bilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In another embodiment the bacterial infection is an infection involving a Gram-negative bacteria. In another embodiment, administering comprises a topical administration.

In a further embodiment are methods of treating a mammal in need of such treatment comprising administering to the mammal a second therapeutic agent. In another embodiment, the second therapeutic agent is not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid. In another embodiment, the second therapeutic agent is a β-lactam antibiotic. In another embodiment, the β-lactam antibiotic is selected from penicillins, monobactams, cephalosporins, and carbapenems. A further embodiment comprises administering a β-lactamase inhibitor.

Incorporation by Reference

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

The expression "effective amount", when used to describe therapy to an individual suffering from a disorder, refers to the amount of a compound described herein that is effective to inhibit or otherwise act on SPase in the individual's tissues wherein SPase involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds described herein are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^3H$ can be prepared using neutrons generated in a nuclear reactor. Following nuclear transformation, $^{14}C$ and $^3H$ are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or nonadjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR$_{12}$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups. A description herein that a group is alkyl chain "optionally comprising within the chain or at a chain terminus" a moiety, the term signifies that the moiety can be disposed between two subunits of the alkyl chain, or can be disposed at an unsubstituted end of the chain, or can be disposed between the chain and a point of attachment of the chain, for example to a carbonyl, NR, or O group. For example, an alkylbenzoyl group is an alkyl chain with a phenyl group disposed between the alkyl and a carbonyl, fitting the above description; an N-alkylphenylcarboxamido is an alkyl chain with a phenyl group displosed between the alkyl and the aminocarbonyl group, filling within the above description.

The term "alkylene" means a linear saturated divalent hydrocarbon radical of one to six carbon atoms or a branched saturated divalent hydrocarbon radical of one to six carbon atoms unless otherwise stated, such as methylene, ethylene, propylene, 1-methylpropylene, 2-methylpropylene, butylene, pentylene, and the like.

The term "carbonyl" means C=O.

The terms "carboxy" and "hydroxycarbonyl" mean COOH.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, —$CH_2CH_2$—S(O)—$CH_3$, and —$CH_2CH_2$—O—$CH_2CH_2$—O—$CH_3$. Up to two heteroatoms may be consecutive, such as, for example, —$CH_2$—NH—$OCH_3$, or —$CH_2$—$CH_2$—S—S—$CH_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, —$CH_2$—CH=CH—$CH_2$—SH, and —CHCH—O—$CH_2CH_2$—O—$CH_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl.

Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b] furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "thioalkoxy" refers to an alkyl group previously defined attached to the parent molecular moiety through a sulfur atom.

The term "glycosyloxyoxy" refers to a glycoside attached to the parent molecular moiety through an oxygen atom.

The term "alkoxycarbonyl" represents as ester group; i.e. an alkoxy group, attached to the parent molecular moiety through a carbonyl group such as methoxycarbonyl, ethoxycarbonyl, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$-$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2$NH wherein each R is independently selected, such as dialkylamines, diarylamines, aralkylamines, heterocyclylamines and the like; and $R_3$N wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)$NR_2$, and —NRC(O)R groups, respectively. Amide groups therefore include but are not limited to primary carboxamide groups (—C(O)$NH_2$) and formamide groups (—NHC(O)H). A "carboxamido" or "aminocarbonyl" group is a group of the formula C(O)$NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —OC(O)$NR_2$ groups, respectively.

The term "sulfonamide" (or "sulfonamido") includes S- and N-sulfonamide groups, i.e., —$SO_2NR_2$ and —$NRSO_2$R groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)$NR_2$. Typically, an amidino group is —C(NH)$NH_2$.

The term "guanidine" or "guanidino" includes groups of the formula —NRC(NR)NR$_2$. Typically, a guanidino group is —NHC(NH)NH$_2$.

The term "ring derived from a sugar" refers to a compound that forms a ring by removing the hydrogen atoms from two hydroxyl groups of any sugar.

The term "boronate ester" refers to an ester of a boronic acid, for example—B(OR$^{B3}$)(OR$^{B4}$) wherein at least one of R$^{B3}$ and R$^{B4}$ are not hydrogen.

The term "boronic acid" refers to a chemical compound containing a —B(OH)$_2$. In some embodiments, boronic acid compounds can form oligomeric anhydrides by dehydration of the boronic acid moiety.

The term "boronic acid anhydride" refers to a chemical compound formed by combination of two or more molecules of a boronic acid compound, with loss of one or more water molecules. When mixed with water, the boronic acid anhydride compound is hydrated to release the free boronic acid compound. In various embodiments, the boronic acid anhydride can comprise two, three, four, or more boronic acid units, and can have a cyclic or linear configuration. Non-limiting examples of oligomeric boronic acid anhydrides of peptide boronic acids compound of Formula YY are illustrated below:

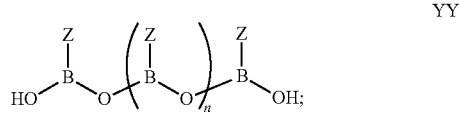

YY wherein n is an integer from 0 to about 10, preferably 0, 1, 2, 3, or 4, and Z is a macrocyclic compound of Formula (I), (Ia), (Ib), (Ic), (Id), (Ie), (II), (IIa), (IIb), (IIc), (III), (IIIa), (IIIb), (IIIc), (IV), (IVa), or (IVb).

In some embodiments, the boronic acid anhydride compound comprises a cyclic trimer ("boroxine") of formula XX,

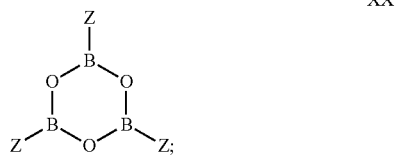

XX wherein Z is a macrocyclic compound of Formula (I), (Ia), (Ib), (Ic), (Id), (Ie), (II), (IIa), (IIb), (IIc), (III), (IIIa), (IIIb), (IIIc), (IV), (IVa), or (IVb).

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds described herein may take the form of salts. The term "salts" embraces addition salts of free acids or free bases which are compounds described herein. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the present disclosure.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the present disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I), (Ia), (Ib), (Ic), (Id), (Ie), (II), (IIa), (IIb), (IIc), (III), (IIIa), (IIIb), (IIIc), (IV), (IVa), or (IVb) compounds, for example in their purification by recrystallization. All of these salts may be prepared by conventional means from the corresponding compound according to Formula (I), (Ia), (Ib), (Ic), (Id), (Ie), (II), (IIa), (IIb), (IIc), (III), (IIIa), (IIIb), (IIIc), (IV), (IVa), or (IVb) by reacting, for example, the appropriate acid or base with the compound according to Formula (I), (Ia), (Ib), (Ic), (Id), (Ie), (II), (IIa), (IIb), (IIc), (III), (IIIa), (IIIb), (IIIc), (IV), (IVa), or (IVb). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Further examples examples of prodrugs include boronate esters which can be hydrolyzed under physiological conditions to afford the corresponding boronic acid. Conventional procedures for the selection and preparation of suitable prodrug derivatives are described, for example, in "Design of Prodrugs", ed. H. Bundgaard, Elsevier, 1985.

In addition, where features or aspects of the present disclosure are described in terms of Markush groups, those skilled in the art will recognize that the presently described compounds is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the present disclosure are described in terms of Markush groups, those skilled in the art will recognize that the present disclosure is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present disclosure further embraces isolated compounds according to formula (I), (Ia), (Ib), (Ic), (Id), (Ie), (II), (IIa), (IIb), (IIc), (III), (IIIa), (IIIb), (IIIc), (IV), (IVa), or (IVb). The expression "isolated compound" refers to a preparation of a compound of formula (I), (Ia), (Ib), (Ic), (Id), (Ie), (II), (IIa), (IIb), (IIc), (III), (IIIa), (IIIb), (IIIc), (IV), (IVa), or (IVb), or a mixture of compounds according to formula (I), (Ia), (Ib), (Ic), (Id), (Ie), (II), (IIa), (IIb), (IIc), (III), (IIIa), (IIIb), (IIIc), (IV), (IVa), or (IVb), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically.

Preferably an "isolated compound" refers to a preparation of a compound of formula (I), (Ia), (Ib), (Ic), (Id), (Ie), (II), (IIa), (IIb), (IIc), (III), (IIIa), (IIIb), (IIIc), (IV), (IVa), or (IVb) or a mixture of compounds according to formula (I), (Ia), (Ib), (Ic), (Id), (Ie), (II), (IIa), (IIb), (IIc), (III), (IIIa), (IIIb), (IIIc), (IV), (IVa), or (IVb), which contains the named compound or mixture of compounds according to formula (I), (Ia), (Ib), (Ic), (Id), (Ie), (II), (IIa), (IIb), (IIc), (III), (IIIa), (IIIb), (IIIc), (IV), (IVa), or (IVb) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds described herein and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds Described Herein

Tautomerism

Within the present disclosure it is to be understood that a compound of formula (I), (Ia), (Ib), (Ic), (Id), (Ie), (II), (IIa), (IIb), (IIc), (III), (IIIa), (IIIb), (IIIc), (IV), (IVa), or (IVb) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the present disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

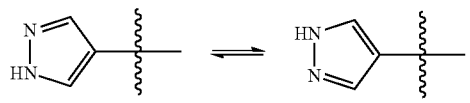 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

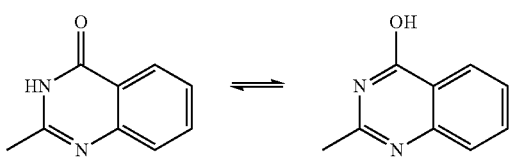

is an example of tautomerism. Accordingly, a structure depicted herein as one tautomer is intended to also include the other tautomer.

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

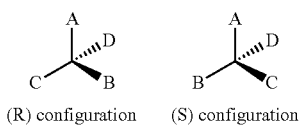

The present disclosure is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present disclosure therefore includes any possible stable rotamers of formula (I) which are biologically active in the treatment of cancer or other proliferative disease states.

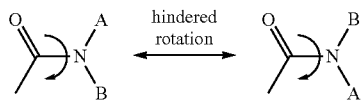

Regioisomerism

In some embodiments, the compounds described herein have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

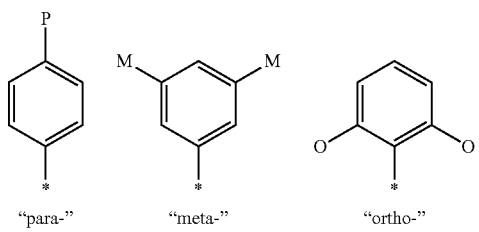

In various embodiments, the compound or set of compounds, such as are among the inventive compounds or are used in the inventive methods, can be any one of any of the combinations and/or sub-combinations of the above-listed embodiments.

Compounds

In one aspect described herein are compounds of Formula (I):

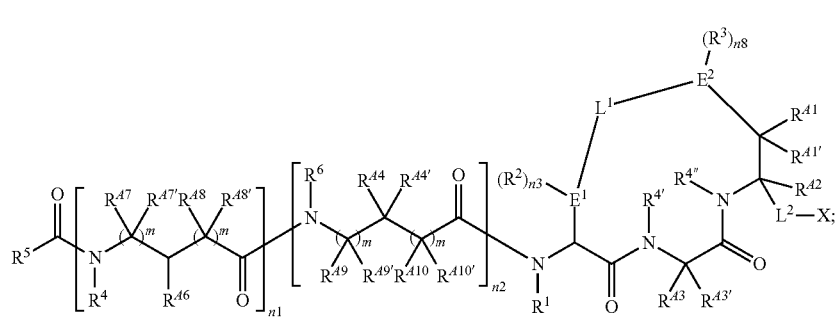

Formula (I)

wherein:

E$^1$ is (C$_1$-C$_6$)alkyl, (C$_2$-C$_7$)alkenyl, (C$_2$-C$_7$)alkynyl, (C$_3$-C$_7$) cycloalkyl, heterocyclyl, heteroaryl, or aryl;

E$^2$ is (C$_2$-C$_7$)alkenyl, (C$_2$-C$_7$)alkynyl, (C$_3$-C$_7$)cycloalkyl, heterocyclyl, heteroaryl, or aryl;

L$^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$—CH$_2$—, —NR$^4$C(O)—, —C(O) NR$^4$—, —NR$^4$S(O)$_2$—, —S(O)$_2$NR$^4$—, —NR$^4$C(O) NR$^4$—, —NR$^4$C(O)O—, —OC(O)NR$^4$—, or (C$_1$-C$_4$) alkylene optionally substituted with OH, CN, NO$_2$, halogen, (C$_1$-C$_6$)alkyl;

L$^2$ is a bond, or optionally substituted (C$_1$-C$_6$)alkylene;

X is a group of formula

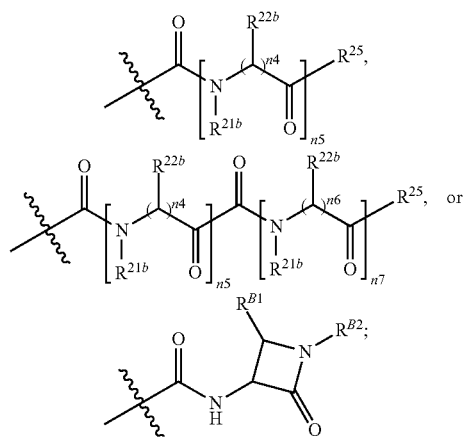

wherein n4, n5, and n6 are each independently 1, 2 or 3; n7 is 0, 1 or 2; R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; R$^{25}$ is H, OH, OR$^C$,

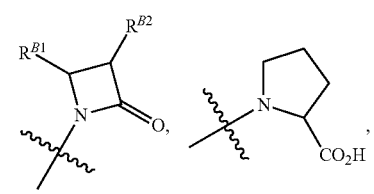

or NR$^{25a}$R$^{25b}$ where R$^{25}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$)alkyl, (C$_3$-C$_6$)cycloalkyl, OR$^C$, C(=O)N(R$^C$)$_2$, OC(=O)N(R$^C$)$_2$, C(=O) OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$)alkyl, and a wavy line indicates a point of attachment of X to a carbon of formula (I) bearing X; or X is CO$_2$H, CH$_2$CO$_2$H, C(=O)NHCH$_2$C(=O)H, CH$_2$C (=O)H, C(=O)N(H)CH(R$^7$)B(OR$^{B3}$)(OR$^{B4}$), or

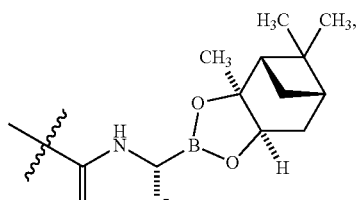

wherein R$^7$ is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, —CH$_2$CH$_2$CO$_2$H; or R$^{B3}$ and R$^{B4}$ together with the boron atom form an optionally substituted 5- or 6-membered boron containing ring;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

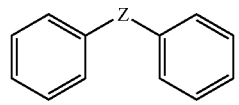

wherein Z is a bond, O, S, NH, $CH_2$ or C≡C; $R^2$ and $R^3$ are each independently nitro, halo, cyano, hydroxy, glycosyloxy, amino, ($C_1$-$C_4$)alkoxy, ($C_1$-$C_4$)acyloxy, ($C_1$-$C_4$)alkyl, or a group cleavable under physiological conditions to provide a compound of formula (I) wherein $R^2$ or $R^3$ respectively is hydroxy, wherein any carbon atom is optionally substituted with J;

n1 and n2 are independently 0 or 1;

n3 and n8 are independently 0, 1, or 2;

each m is independently 0 or 1;

$R^1$ is hydrogen or ($C_1$-$C_6$)alkyl optionally substituted with 1 to 3 J; or $R^1$ together with $E^1$ form a ring;

$R^4$, $R^{4'}$, and $R^{4''}$ are each independently at each occurrence hydrogen, or ($C_1$-$C_6$)alkyl optionally substituted with 1 to 3 J;

$R^6$ is hydrogen, or ($C_1$-$C_6$)alkyl optionally substituted with 1 to 3 J; or $R^6$ together with $R^{44}$ form a ring;

$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

$R^{46}$ is amino, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}—C(=NH)N(R')_2$, wherein p is 4;

each R' is independently at each occurrence hydrogen, ($C_1$-$C_6$)-alkyl, ($C_2$-$C_7$)-alkenyl, ($C_2$-$C_7$)-alkynyl, ($C_3$-$C_{10}$)-cycloalkyl, ($C_3$-$C_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —N(($C_1$-$C_4$)alkyl)$_2$—, —NH($C_1$-$C_4$)alkyl, $C_1$-$C_6$alkyl, $C_3$-$C_8$cycloalkyl, or $C_1$-$C_6$heteroalkyl; or a pharmaceutically acceptable salt, solvate, or prodrug thereof.

In one embodiment is a compound of Formula (I) wherein $E^1$ and $E^2$ are each independently aryl or heteroaryl. In another embodiment is a compound of Formula (I) wherein $E^1$ and $E^2$ are each independently aryl. In another embodiment is a compound of Formula (I) wherein $E^1$ and $E^2$ are each phenyl. In another embodiment is a compound of Formula (I) wherein $E^1$ is aryl and $E^2$ is heteroaryl. In another embodiment is a compound of Formula (I) wherein $E^1$ and $E^2$ are each heteroaryl.

In another embodiment is a compound of Formula (I) wherein $L^1$ is a bond, —O—, —$OCH_2$—, or —$CH_2O$—. In some embodiments is a compound of Formula (I) wherein $L^1$ is a bond. In some embodiments is a compound of Formula (I) wherein $L^1$ is —O—. In some embodiments is a compound of Formula (I) wherein $L^1$ is —$OCH_2$—. In some embodiments is a compound of Formula (I) wherein $L^1$ is —$CH_2O$—.

In another embodiment is a compound of Formula (I) wherein $E^1$ and $E^2$ are each phenyl and $L^1$ is a bond. In another embodiment is a compound of Formula (I) wherein $E^1$ and $E^2$ are each phenyl and $L^1$ is —O—. In another embodiment is a compound of Formula (I) wherein $E^1$ and $E^2$ are each phenyl and $L^1$ is —$OCH_2$—. In another embodiment is a compound of Formula (I) wherein $E^1$ and $E^2$ are each phenyl and $L^1$ is —$CH_2O$—.

In another embodiment is a compound of Formula (I) wherein $L^2$ is a bond. In another embodiment is a compound of Formula (I) wherein $L^2$ is optionally substituted ($C_1$-$C_6$) alkylene. In a further embodiment, $L^2$ is methylene, ethylene, n-propylene, iso-propylene, n-butylene, iso-butylene, or tert-butylene.

In one embodiment is a compound of Formula (I) wherein X is $CO_2H$, $CH_2CO_2H$, C(=O)NHCH$_2$C(=O)H, $CH_2$C(=O)H, C(=O)N(H)CH($R^7$)B(OR$^{B3}$)(OR$^B$), or

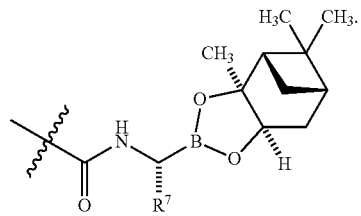

In some embodiments is a compound of Formula (I) wherein X is $CO_2H$. In some embodiments is a compound of Formula (I) wherein X is $CH_2CO_2H$. In some embodiments is a compound of Formula (I) wherein X is $CH_2$C(=O)NHCH$_2$C(=O)H. In some embodiments is a compound of Formula (I) wherein X is $CH_2$C(=O)H.

In some embodiments is a compound of Formula (I) wherein X is C(=O)N(H)CH($R^7$)B(OR$^{B3}$)(OR$^{B4}$). In further embodiments is a compound of Formula (I) wherein X is C(=O)N(H)CH$_2$B(OH)$_2$. In further embodiments is a compound of Formula (I) wherein X is C(=O)N(H)CH(CH$_3$)B(OH)$_2$. In further embodiments is a compound of Formula (I) wherein X is C(=O)N(H)CH(CH$_2$CH$_3$)B(OH)$_2$. In further embodiments is a compound of Formula (I) wherein X is C(=O)N(H))CH(CH$_2$OH)B(OH)$_2$. In further embodiments is a compound of Formula (I) wherein X is C(=O)N(H)CH$_2$B(OCH$_3$)$_2$. In further embodiments is a compound of Formula (I) wherein X is C(=O)N(H)CH(CH$_3$)B(OCH$_3$)$_2$. In further embodiments is a compound of Formula (I) wherein X is C(=O)N(H)CH(CH$_2$CH$_3$)B(OCH$_3$)$_2$. In further embodiments is a compound of Formula (I) wherein X is C(=O)N(H)CH(CH$_2$OH)B(OCH$_3$)$_2$.

In some embodiments is a compound of Formula (I) wherein X is C(=O)N(H)CH($R^7$)B(OR$^{B3}$)(OR$^{B4}$) and $R^{B3}$ and $R^7$ together with the boron atom form an optionally substituted 5- or 6-membered boron containing ring. In some embodiments is a compound of Formula (I) wherein X is

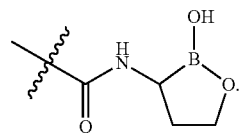 [SMILES: *C(=O)NC1CCOB1O]

In some embodiments is a compound of Formula (I) wherein X is

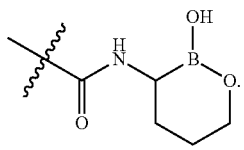 [SMILES: *C(=O)NC1CCCOB1O]

In some embodiments is a compound of Formula (I) wherein X is $C(=O)N(H)CH(R^7)B(OR^{B3})(OR^{B4})$ and $R^{B3}$ and $R^{B4}$ together with the boron atom form an optionally substituted 5- or 6-membered boron containing ring. In some embodiments is a compound of Formula (I) wherein X is

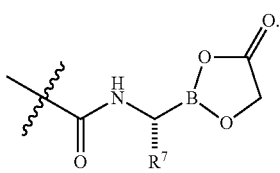

In some embodiments is a compound of Formula (I) wherein X is

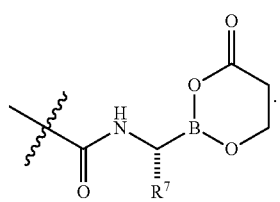

In some embodiments is a compound of Formula (I) wherein X is $C(=O)N(H)CH(R^7)B(OR^{B3})(OR^{B4})$ and $R^{B3}$ and $R^{B4}$ together with the boron atom form an optionally substituted 5- or 6-membered boron containing ring derived from a sugar. In some embodiments is a compound of Formula (I) wherein X is

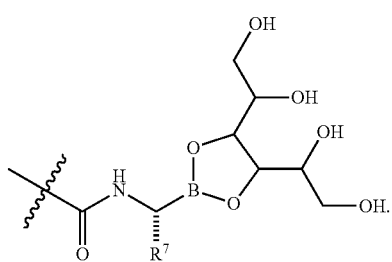

In some embodiments is a compound of Formula (I) wherein X is

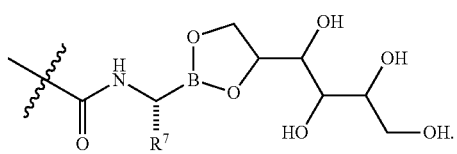

In some embodiments is a compound of Formula (I) wherein X is

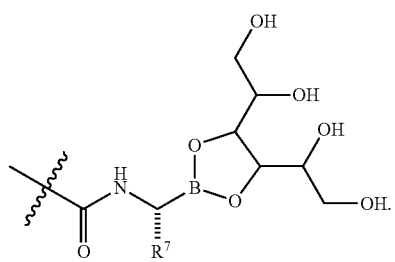

In some embodiments is a compound of Formula (I) wherein X is

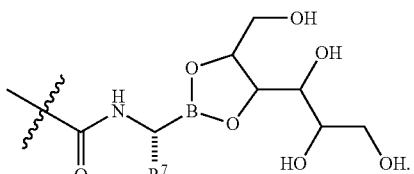

In some embodiments is a compound of Formula (I) wherein X is

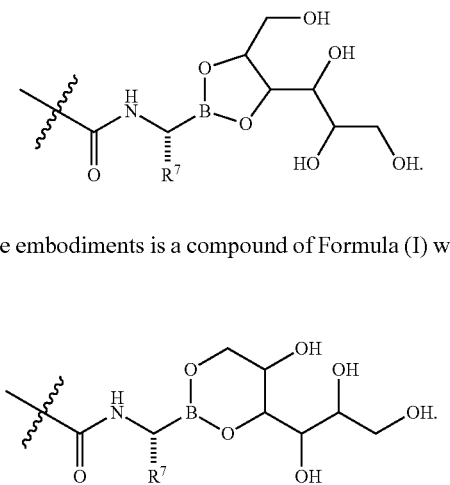

In some embodiments is a compound of Formula (I) wherein X is

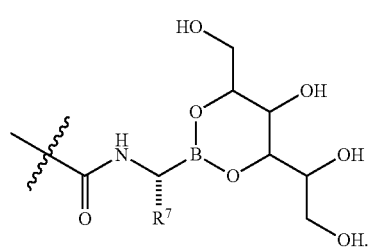

In some embodiments is a compound of Formula (I) wherein X is

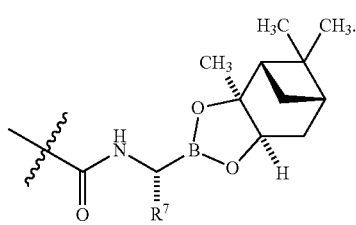

In further embodiments is a compound of Formula (I) wherein X is

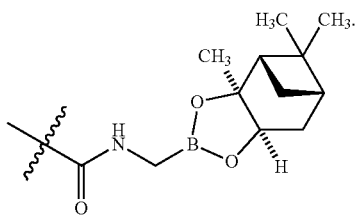 [SMILES: *C(=O)NCB1O[C@@H]2C[C@@H]3C[C@@H](C3(C)C)[C@]2(C)O1]

In further embodiments is a compound of Formula (I) wherein X is

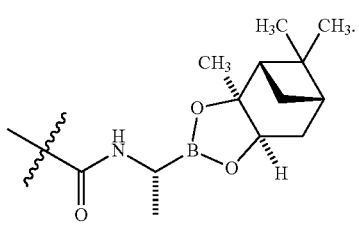 [SMILES: *C(=O)N[C@@H](C)B1O[C@@H]2C[C@@H]3C[C@@H](C3(C)C)[C@]2(C)O1]

In further embodiments is a compound of Formula (I) wherein X is

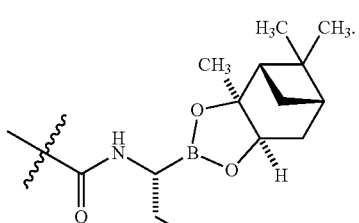

In further embodiments is a compound of Formula (I) wherein X is

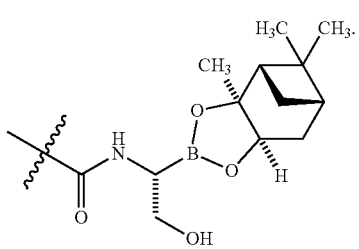 [SMILES: *C(=O)N[C@@H](CO)B1O[C@@H]2C[C@@H]3C[C@@H](C3(C)C)[C@]2(C)O1]

In some embodiments is a compound of Formula (I) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

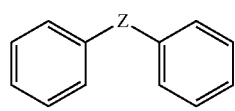

wherein Z is a bond, O, S, NH, $CH_2$ or C≡C. In some embodiments is a compound of Formula (I) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

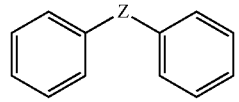

wherein Z is a bond, O, S, NH, $CH_2$ or C≡C. In some embodiments is a compound of Formula (I) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

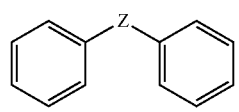

wherein Z is a bond. In some embodiments is a compound of Formula (I) wherein $R^5$ is a linear alkyl chain of about 4-22 carbon atoms, wherein $R^5$ is bonded to the carbonyl carbon to which it is attached directly to provide an amide linkage, comprising at a chain terminus

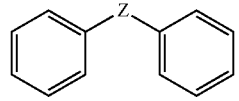

wherein Z is a bond. In some embodiments is a compound of Formula (I) wherein $R^5$ is a linear alkyl chain of about 4-22 carbon atoms, wherein $R^5$ is bonded to the carbonyl carbon to which it is attached directly to provide an amide linkage, comprising within the chain

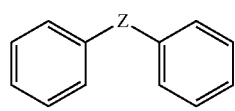

wherein Z is a bond. In some embodiments is a compound of Formula (I) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (I) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (I) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (I) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (I) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (I) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (I) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (I) wherein n1 is 0 and n2 is 1. In another embodiment is a compound of Formula (I) wherein n1 is 0, n2 is 1, and $R^{44}$ is H. In another embodiment is a compound of Formula (I) wherein n1 is 0, n2 is 1, and $R^{44}$ is $(C_1-C_6)$alkyl optionally substituted with 1 to 3 J. In another embodiment is a compound of Formula (I) wherein n1 is 0, n2 is 1, and $R^{44}$ is $CH_3$. In another embodiment is a compound of Formula (I) wherein n1 is 0, n2 is 1, and $R^{44}$ is $CH_2CH_3$. In another embodiment is a compound of Formula (I) wherein n1 is 0, n2 is 1, and $R^{44}$ is $CH_2CH(CH_3)_2$. In another embodiment is a compound of Formula (I) wherein n1 is 0, n2 is 1, and $R^{44}$ is $CH_2OH$. In another embodiment is a compound of Formula (I) wherein n1 is 0, n2 is 1, and $R^{44}$ is $CH(OH)CH_3$. In another embodiment is a compound of Formula (I) wherein n1 is 0, n2 is 1, and $R^{44}$ is $CH_2C(O)NH_2$. In another embodiment is a compound of Formula (I) wherein n1 is 0, n2 is 1, and $R^{44}$ is $CH_2CH_2CH_2CH_2NH_2$.

In another embodiment is a compound of Formula (I) wherein n1 is 1 and n2 is 1. In another embodiment is a compound of Formula (I) wherein n1 is 1, n2 is 1, $R^{46}$ is $CH_3$, and $R^{44}$ is $(C_1-C_6)$alkyl optionally substituted with 1 to 3 J. In another embodiment is a compound of Formula (I) wherein n1 is 1, n2 is 1, $R^{46}$ is $CH_3$, and $R^{44}$ is $CH_3$. In another embodiment is a compound of Formula (I) wherein n1 is 1, n2 is 1, $R^{46}$ is $CH_3$, and $R^{44}$ is $CH_2CH_3$. In another embodiment is a compound of Formula (I) wherein n1 is 1, n2 is 1, $R^{46}$ is $CH_3$, and $R^{44}$ is $CH_2CH(CH_3)_2$. In another embodiment is a compound of Formula (I) wherein n1 is 1, n2 is 1, $R^{46}$ is $CH_3$, and $R^{44}$ is $CH_2OH$. In another embodiment is a compound of Formula (I) wherein n1 is 1, n2 is 1, $R^{46}$ is $CH_3$, and $R^{44}$ is $CH(OH)CH_3$. In another embodiment is a compound of Formula (I) wherein n1 is 1, n2 is 1, $R^{46}$ is $CH_3$, and $R^{44}$ is $CH_2C(O)NH_2$. In another embodiment is a compound of Formula (I) wherein n1 is 1, n2 is 1, $R^{46}$ is $CH_3$, and $R^{44}$ is $CH_2CH_2CH_2CH_2NH_2$.

In another embodiment of the aforementioned embodiments is a compound of Formula (I) wherein $R^{47}$, $R^{47'}$, $R^{48}$, $R^{48'}$, $R^{49}$, $R^{49'}$, $R^{44'}$, $R^{410}$, and $R^{410'}$ are each independently H. In another embodiment of the aforementioned embodiments is a compound of Formula (I) wherein each m is 0. In another embodiment of the aforementioned embodiments is a compound of Formula (I) wherein $R^{41}$, $R^{41'}$, $R^2$, $R^{4'}$, and $R^{4''}$ are each independently H. In another embodiment of the aforementioned embodiments is a compound of Formula (I) wherein n3 is 1 and n8 is 1.

In another embodiment is a compound of Formula (I) having the structure of Formula (Ia):

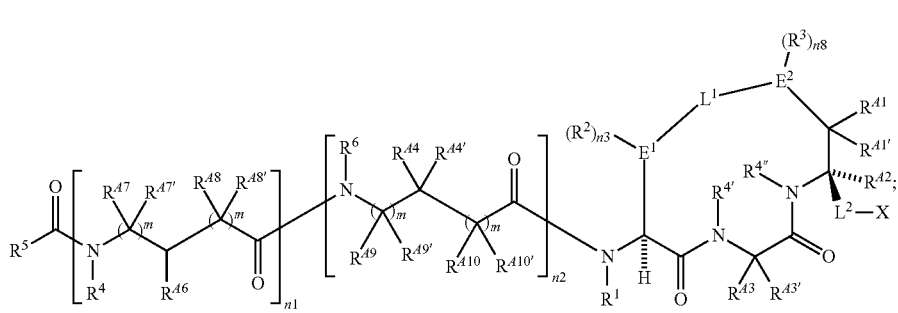

Formula (Ia)

wherein:

$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$E^2$ is $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4$—$CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;

$L^2$ is a bond, or optionally substituted $(C_1-C_6)$alkylene;

X is a group of formula

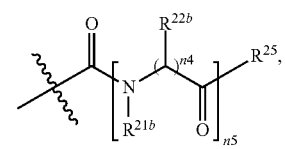

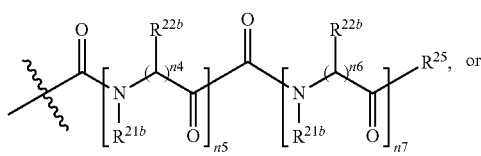

or

-continued

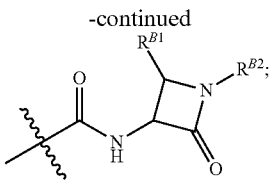

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

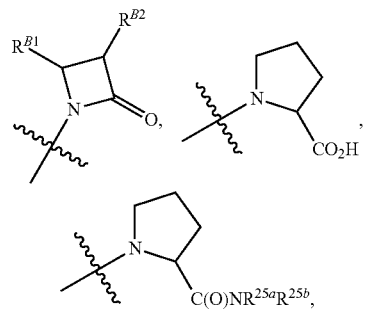

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$alkyl, $(C_3-C_6)$cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$alkyl, and a wavy line indicates a point of attachment of X to a carbon of formula (Ia) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

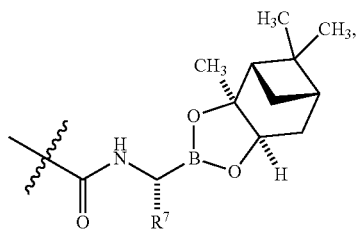

wherein $R^7$ is H, methyl, ethyl, or —$CH_2OH$; or $R^7$ and $R^{B3}$ together with the boron atom form a 5- or 6-membered boron containing ring; $R^{B3}$ and $R^{B4}$ are each independently H, $(C_1-C_6)$alkyl, —$CH_2CO_2H$, —$CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

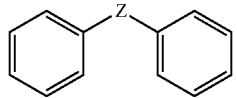

wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (Ia) wherein $R^2$ or $R^3$ respectively is hydroxy, wherein any carbon atom is optionally substituted with J;

n1 and n2 are independently 0 or 1;

n3 and n8 are independently 0, 1, or 2;

each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{44}$ form a ring;

$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{46}$ is amino, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)$alkyl$)_2$—, —$NH(C_1-C_4)$alkyl, $C_1-C_6$alkyl, $C_3-C_8$cycloalkyl, or $C_1-C_6$heteroalkyl; or a pharmaceutically acceptable salt, solvate or prodrug thereof.

In one embodiment is a compound of Formula (Ia) wherein $E^1$ and $E^2$ are each independently aryl or heteroaryl. In another embodiment is a compound of Formula (Ia) wherein $E^1$ and $E^2$ are each independently aryl. In another embodiment is a compound of Formula (Ia) wherein $E^1$ and $E^2$ are each phenyl. In another embodiment is a compound of Formula (Ia) wherein $E^1$ is aryl and $E^2$ is heteroaryl. In another embodiment is a compound of Formula (Ia) wherein $E^1$ and $E^2$ are each heteroaryl.

In another embodiment is a compound of Formula (Ia) wherein $L^1$ is a bond, —O—, —$OCH_2$—, or —$CH_2O$—. In some embodiments is a compound of Formula (Ia) wherein $L^1$ is a bond. In some embodiments is a compound of Formula (Ia) wherein $L^1$ is —O—. In some embodiments is a compound of Formula (Ia) wherein $L^1$ is —OCH$_2$—. In some embodiments is a compound of Formula (Ia) wherein $L^1$ is —CH$_2$O—.

In another embodiment is a compound of Formula (Ia) wherein $E^1$ and $E^2$ are each phenyl and $L^1$ is a bond. In another embodiment is a compound of Formula (Ia) wherein $E^1$ and $E^2$ are each phenyl and $L^1$ is —O—. In another embodiment is a compound of Formula (Ia) wherein $E^1$ and $E^2$ are each phenyl and $L^1$ is —OCH$_2$—. In another embodiment is a compound of Formula (Ia) wherein $E^1$ and $E^2$ are each phenyl and $L^1$ is —CH$_2$O—.

In another embodiment is a compound of Formula (Ia) wherein $L^2$ is a bond. In another embodiment is a compound of Formula (Ia) wherein $L^2$ is optionally substituted (C$_1$-C$_6$) alkylene. In a further embodiment, $L^2$ is methylene, ethylene, n-propylene, iso-propylene, n-butylene, iso-butylene, or tert-butylene.

In one embodiment is a compound of Formula (Ia) wherein X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

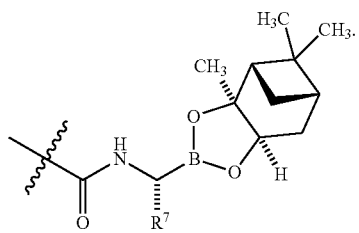

In some embodiments is a compound of Formula (Ia) wherein X is CO$_2$H. In some embodiments is a compound of Formula (Ia) wherein X is CH$_2$CO$_2$H. In some embodiments is a compound of Formula (Ia) wherein X is C(=O)NHCH$_2$C(=O)H. In some embodiments is a compound of Formula (Ia) wherein X is CH$_2$C(=O)H.

In some embodiments is a compound of Formula (Ia) wherein X is C(=O)N(H)CH(R$^7$)B(OR$^{B3}$)(OR$^{B4}$). In further embodiments is a compound of Formula (Ia) wherein X is C(=O)N(H)CH$_2$B(OH)$_2$. In further embodiments is a compound of Formula (Ia) wherein X is C(=O)N(H)CH(CH$_3$)B(OH)$_2$. In further embodiments is a compound of Formula (Ia) wherein X is C(O)N(H)CH(CH$_2$CH$_3$)B(OH)$_2$. In further embodiments is a compound of Formula (Ia) wherein X is C(=O)N(H)CH(CH$_2$OH)B(OH)$_2$. In further embodiments is a compound of Formula (Ia) wherein X is C(=O)N(H)CH$_2$B(OCH$_3$)$_2$. In further embodiments is a compound of Formula (Ia) wherein X is C(=O)N(H)CH(CH$_3$)B(OCH$_3$)$_2$. In further embodiments is a compound of Formula (Ia) wherein X is C(=O)N(H)CH(CH$_2$CH$_3$)B(OCH$_3$)$_2$. In further embodiments is a compound of Formula (Ia) wherein X is C(=O)N(H)CH(CH$_2$OH)B(OCH$_3$)$_2$.

In some embodiments is a compound of Formula (Ia) wherein X is C(=O)N(H)CH(R$^7$)B(OR$^{B3}$)(OR$^{B4}$) and R$^{B3}$ and R$^7$ together with the boron atom form an optionally substituted 5- or 6-membered boron containing ring. In some embodiments is a compound of Formula (Ia) wherein X is

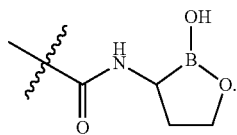 [SMILES: *C(=O)NC1CCOB1O]

In some embodiments is a compound of Formula (Ia) wherein X is

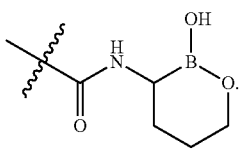 [SMILES: *C(=O)NC1CCCOB1O]

In some embodiments is a compound of Formula (Ia) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring. In some embodiments is a compound of Formula (Ia) wherein X is

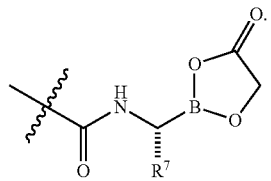

In some embodiments is a compound of Formula (Ia) wherein X is

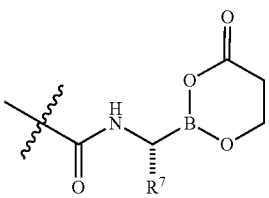

In some embodiments is a compound of Formula (Ia) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring derived from a sugar. In some embodiments is a compound of Formula (Ia) wherein X is

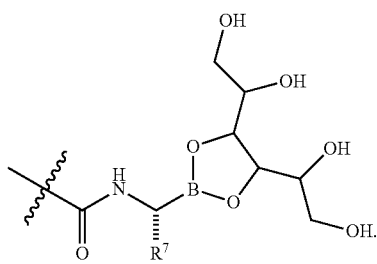

In some embodiments is a compound of Formula (Ia) wherein X is

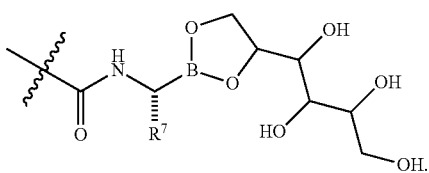

In some embodiments is a compound of Formula (Ia) wherein X is

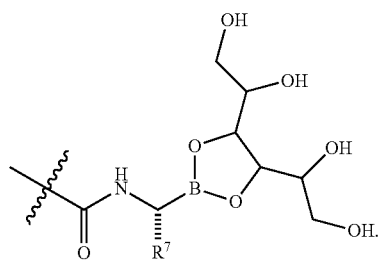

In some embodiments is a compound of Formula (Ia) wherein X is

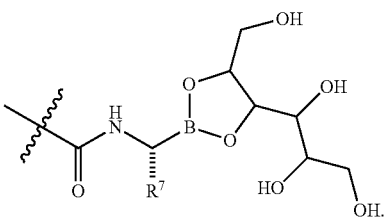

In some embodiments is a compound of Formula (Ia) wherein X is

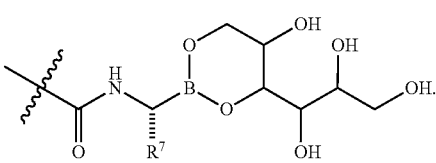

In some embodiments is a compound of Formula (Ia) wherein X is

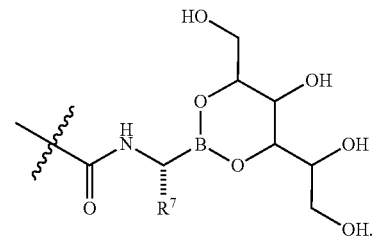

In some embodiments is a compound of Formula (Ia) wherein X is

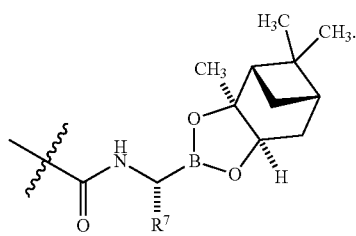

In further embodiments is a compound of Formula (Ia) wherein X is

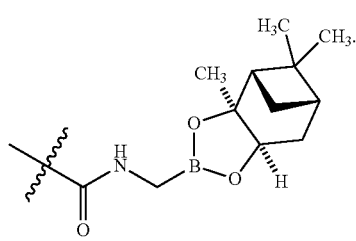

In further embodiments is a compound of Formula (Ia) wherein X is

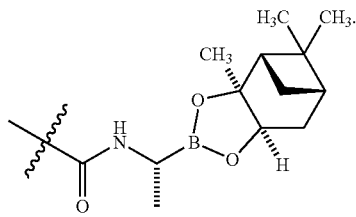 [SMILES: *C(=O)N[C@@H](C)B1O[C@@H]2C[C@@H]3C[C@@H](C3(C)C)[C@]2(C)O1]

In further embodiments is a compound of Formula (Ia) wherein X is

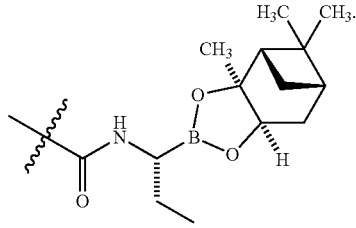 [SMILES: *C(=O)N[C@@H](CC)B1O[C@@H]2C[C@@H]3C[C@@H](C3(C)C)[C@]2(C)O1]

In further embodiments is a compound of Formula (Ia) wherein X is

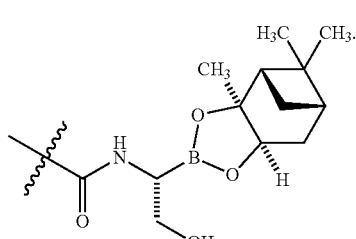

In some embodiments is a compound of Formula (Ia) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

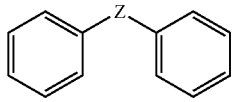

wherein Z is a bond, O, S, NH, $CH_2$ or C≡C. In some embodiments is a compound of Formula (Ia) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

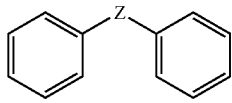

wherein Z is a bond, O, S, NH, $CH_2$ or C≡C. In some embodiments is a compound of Formula (Ia) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

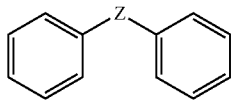

wherein Z is a bond. In some embodiments is a compound of Formula (Ia) wherein $R^5$ is a linear alkyl chain of about 4-22 carbon atoms, wherein $R^5$ is bonded to the carbonyl carbon to which it is attached directly to provide an amide linkage, comprising at a chain terminus

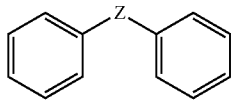

wherein Z is a bond. In some embodiments is a compound of Formula (Ia) wherein $R^5$ is a linear alkyl chain of about 4-22 carbon atoms, wherein $R^5$ is bonded to the carbonyl carbon to which it is attached directly to provide an amide linkage, comprising within the chain

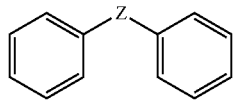

wherein Z is a bond. In some embodiments is a compound of Formula (Ia) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (Ia) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (Ia) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (Ia) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (Ia) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (Ia) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (Ia) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (Ia) wherein n1 is 0 and n2 is 1. In another embodiment is a compound of Formula (Ia) wherein n1 is 0, n2 is 1, and $R^{44}$ is H. In another embodiment is a compound of Formula (Ia) wherein n1 is 0, n2 is 1, and $R^{44}$ is $(C_1-C_6)$alkyl optionally substituted with 1 to 3 J. In another embodiment is a compound of Formula (Ia) wherein n1 is 0, n2 is 1, and $R^{44}$ is $CH_3$. In another embodiment is a compound of Formula (Ia) wherein n1 is 0, n2 is 1, and $R^{44}$ is $CH_2CH_3$. In another embodiment is a compound of Formula (Ia) wherein n1 is 0, n2 is 1, and $R^{44}$ is $CH_2CH(CH_3)_2$. In another embodiment is a compound of Formula (Ia) wherein n1 is 0, n2 is 1, and $R^{44}$ is $CH_2OH$. In another embodiment is a compound of Formula (Ia) wherein n1 is 0, n2 is 1, and $R^{44}$ is $CH(OH)CH_3$. In another embodiment is a compound of Formula (Ia) wherein n1 is 0, n2 is 1, and $R^{44}$ is $CH_2C(O)NH_2$. In another embodiment is a compound of Formula (Ia) wherein n1 is 0, n2 is 1, and $R^{44}$ is $CH_2CH_2CH_2CH_2NH_2$.

In another embodiment is a compound of Formula (Ia) wherein n1 is 1 and n2 is 1. In another embodiment is a compound of Formula (Ia) wherein n1 is 1, n2 is 1, $R^{46}$ is $CH_3$, and $R^{44}$ is $(C_1-C_6)$alkyl optionally substituted with 1 to 3 J. In another embodiment is a compound of Formula (Ia) wherein n1 is 1, n2 is 1, $R^{46}$ is $CH_3$, and $R^{44}$ is $CH_3$. In another embodiment is a compound of Formula (Ia) wherein n1 is 1, n2 is 1, $R^{46}$ is $CH_3$, and $R^{44}$ is $CH_2CH_3$. In another embodiment is a compound of Formula (Ia) wherein n1 is 1, n2 is 1, $R^{A6}$ is $CH_3$, and $R^{A4}$ is $CH_2CH(CH_3)_2$. In another embodiment is a compound of Formula (Ia) wherein n1 is 1, n2 is 1, $R^{A6}$ is $CH_3$, and $R^{A4}$ is $CH_2OH$. In another embodiment is a compound of Formula (Ia) wherein n1 is 1, n2 is 1, $R^{A6}$ is $CH_3$, and $R^{A4}$ is $CH(OH)CH_3$. In another embodiment is a compound of Formula (Ia) wherein n1 is 1, n2 is 1, $R^{A6}$ is $CH_3$, and $R^{A4}$ is $CH_2C(O)NH_2$. In another embodiment is a compound of Formula (Ia) wherein n1 is 1, n2 is 1, $R^{A6}$ is $CH_3$, and $R^{A4}$ is $CH_2CH_2CH_2CH_2NH_2$.

In another embodiment of the aforementioned embodiments is a compound of Formula (Ia) wherein $R^{A7}$, $R^{A7'}$, $R^{A8}$, $R^{A8'}$, $R^{A9}$, $R^{A9'}$, $R^{A4'}$, $R^{A10}$, and $R^{A10'}$ are each independently H. In another embodiment of the aforementioned embodiments is a compound of Formula (Ia) wherein each m is 0. In another embodiment of the aforementioned embodiments is a compound of Formula (Ia) wherein $R^{A1}$, $R^{A1'}$, $R^{A2}$, $R^{4'}$, and $R^{4''}$ are each independently H. In another embodiment of the aforementioned embodiments is a compound of Formula (Ia) wherein n3 is 1 and n8 is 1.

In another embodiment is a compound of Formula (I) having the structure of Formula (Ib):

embodiments is a compound of Formula (Ib) wherein X is $C(=O)N(H)CH_2B(OH)_2$. In further embodiments is a compound of Formula (Ib) wherein X is $C(=O)N(H)CH(CH_3)B(OH)_2$. In further embodiments is a compound of Formula (Ib) wherein X is $C(=O)N(H)CH(CH_2CH_3)B(OH)_2$. In further embodiments is a compound of Formula (Ib) wherein X is $C(=O)N(H)CH(CH_2OH)B(OH)_2$. In further embodiments is a compound of Formula (Ib) wherein X is $C(=O)N(H)CH_2B(OCH_3)_2$. In further embodiments is a compound of Formula (Ib) wherein X is $C(=O)N(H)CH(CH_3)B(OCH_3)_2$. In further embodiments is a compound of Formula (Ib) wherein X is $C(=O)N(H)CH(CH_2CH_3)B(OCH_3)_2$. In further embodiments is a compound of Formula (Ib) wherein X is $C(=O)N(H)CH(CH_2OH)B(OCH_3)_2$.

In some embodiments is a compound of Formula (Ib) wherein X is $C(=O)N(H)CH(R^7)B(OR^{B3})(OR^{B4})$ and $R^{B3}$ and $R^7$ together with the boron atom form an optionally substituted 5- or 6-membered boron containing ring. In some embodiments is a compound of Formula (Ib) wherein X is

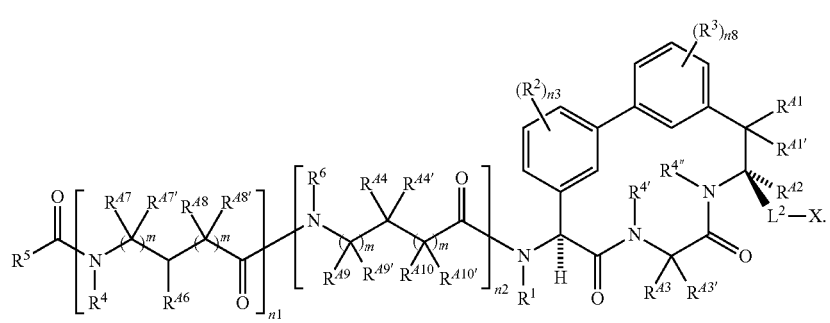

Formula (Ib)

In another embodiment is a compound of Formula (Ib) wherein $L^2$ is a bond. In another embodiment is a compound of Formula (Ib) wherein $L^2$ is optionally substituted $(C_1-C_6)$ alkylene. In a further embodiment, $L^2$ is methylene, ethylene, n-propylene, iso-propylene, n-butylene, iso-butylene, or tert-butylene.

In one embodiment is a compound of Formula (Ib) wherein X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

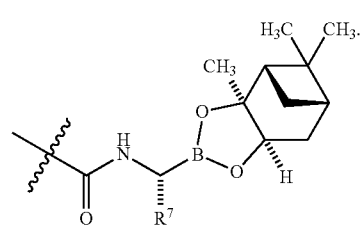

In some embodiments is a compound of Formula (Ib) wherein X is $CO_2H$. In some embodiments is a compound of Formula (Ib) wherein X is $CH_2CO_2H$. In some embodiments is a compound of Formula (Ib) wherein X is $C(=O)NHCH_2C(=O)H$. In some embodiments is a compound of Formula (Ib) wherein X is $CH_2C(=O)H$.

In some embodiments is a compound of Formula (Ib) wherein X is $C(=O)N(H)CH(R^7)B(OR^{B3})(OR^{B4})$. In further

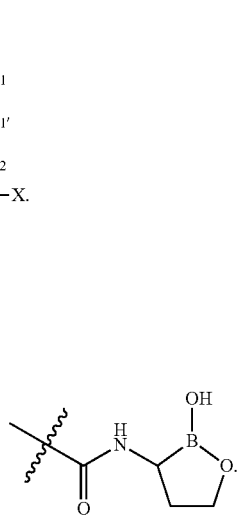

In some embodiments is a compound of Formula (Ib) wherein X is

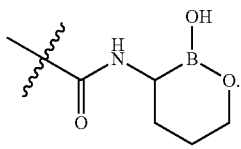 [SMILES: *C(=O)NC1CCCOB1O]

In some embodiments is a compound of Formula (Ib) wherein X is $C(=O)N(H)CH(R^7)B(OR^{B3})(OR^{B4})$ and $R^{B3}$ and $R^{B4}$ together with the boron atom form an optionally substituted 5- or 6-membered boron containing ring. In some embodiments is a compound of Formula (Ib) wherein X is

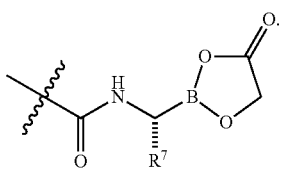

In some embodiments is a compound of Formula (Ib) wherein X is

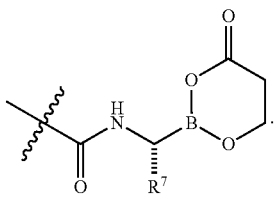

In some embodiments is a compound of Formula (Ib) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring derived from a sugar. In some embodiments is a compound of Formula (Ib) wherein X is

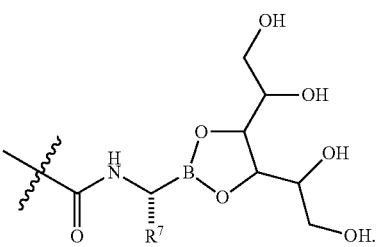

In some embodiments is a compound of Formula (Ib) wherein X

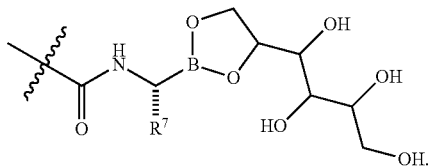

In some embodiments is a compound of Formula (Ib) wherein X is

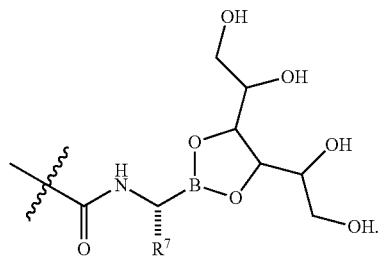

In some embodiments is a compound of Formula (Ib) wherein X is

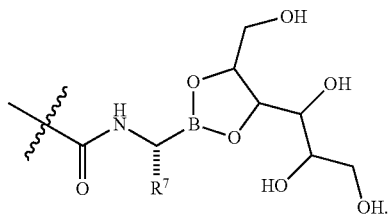

In some embodiments is a compound of Formula (Ib) wherein X is

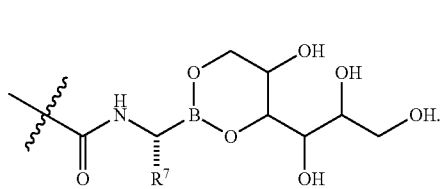

In some embodiments is a compound of Formula (Ib) wherein X is

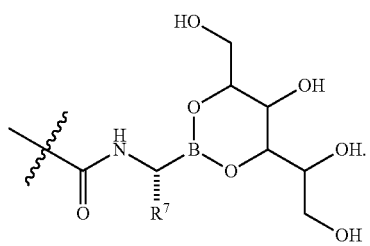

In some embodiments is a compound of Formula (Ib) wherein X is

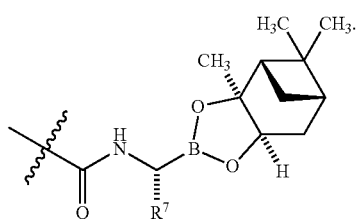

In further embodiments is a compound of Formula (Ib) wherein X is

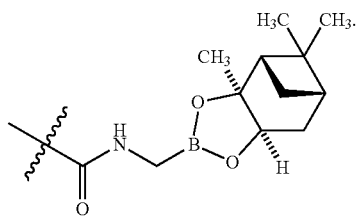 [SMILES: *C(=O)NCB1O[C@@H]2C[C@@H]3C[C@@H](C3(C)C)[C@]2(C)O1]

In further embodiments is a compound of Formula (Ib) wherein X is

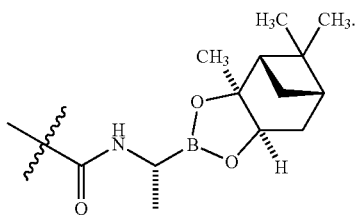

In further embodiments is a compound of Formula (Ib) wherein X is

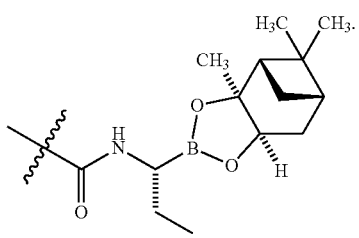 [SMILES: *C(=O)N[C@@H](CC)B1O[C@@H]2C[C@@H]3C[C@@H](C3(C)C)[C@]2(C)O1]

In further embodiments is a compound of Formula (Ib) wherein X is

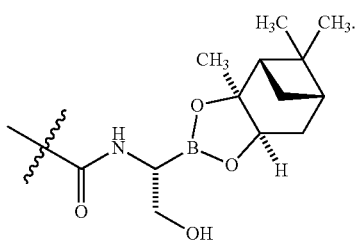 [SMILES: *C(=O)N[C@@H](CO)B1O[C@@H]2C[C@@H]3C[C@@H](C3(C)C)[C@]2(C)O1]

In some embodiments is a compound of Formula (Ib) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

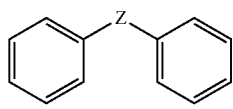

wherein Z is a bond, O, S, NH, $CH_2$ or C≡C. In some embodiments is a compound of Formula (Ib) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

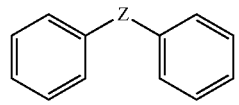

wherein Z is a bond, O, S, NH, $CH_2$ or C≡C. In some embodiments is a compound of Formula (Ib) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

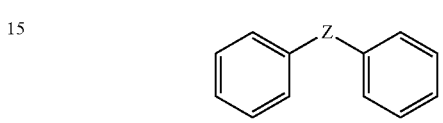

wherein Z is a bond. In some embodiments is a compound of Formula (Ib) wherein $R^5$ is a linear alkyl chain of about 4-22 carbon atoms, wherein $R^5$ is bonded to the carbonyl carbon to which it is attached directly to provide an amide linkage, comprising at a chain terminus

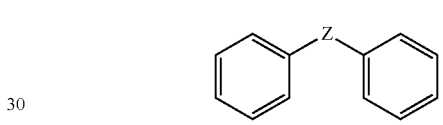

wherein Z is a bond. In some embodiments is a compound of Formula (Ib) wherein $R^5$ is a linear alkyl chain of about 4-22 carbon atoms, wherein $R^5$ is bonded to the carbonyl carbon to which it is attached directly to provide an amide linkage, comprising within the chain

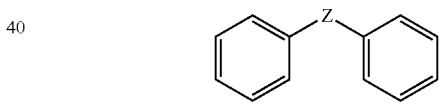

wherein Z is a bond. In some embodiments is a compound of Formula (Ib) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (Ib) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (Ib) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (Ib) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (Ib) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (Ib) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (Ib) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (Ib) wherein n1 is 0 and n2 is 1. In another embodiment is a compound of Formula (Ib) wherein n1 is 0, n2 is 1, and $R^{A4}$ is H. In another embodiment is a compound of Formula (Ib) wherein n1 is 0, n2 is 1, and $R^{A4}$ is $(C_1-C_6)$alkyl optionally substituted with 1 to 3 J. In another embodiment is a compound of Formula (Ib) wherein n1 is 0, n2 is 1, and $R^{A4}$ is $CH_3$. In another embodiment is a compound of Formula (Ib) wherein n1 is 0, n2 is 1, and $R^{A4}$ is $CH_2CH_3$. In another embodiment is a compound of Formula (Ib) wherein n1 is 0, n2 is 1, and $R^{A4}$ is $CH_2CH(CH_3)_2$. In another embodiment is a compound of Formula (Ib) wherein n1 is 0, n2 is 1, and $R^{A4}$ is $CH_2OH$. In another embodiment is a compound of Formula (Ib) wherein n1 is 0, n2 is 1, and $R^{A4}$ is $CH(OH)CH_3$. In another embodiment is a compound of Formula (Ib) wherein n1 is 0, n2 is 1, and $R^{A4}$ is $CH_2C(O)NH_2$. In another embodiment is a compound of Formula (Ib) wherein n1 is 0, n2 is 1, and $R^{A4}$ is $CH_2CH_2CH_2CH_2NH_2$.

In another embodiment is a compound of Formula (Ib) wherein n1 is 1 and n2 is 1. In another embodiment is a compound of Formula (Ib) wherein n1 is 1, n2 is 1, $R^{A6}$ is $CH_3$, and $R^{A4}$ is $(C_1-C_6)$alkyl optionally substituted with 1 to 3 J. In another embodiment is a compound of Formula (Ib) wherein n1 is 1, n2 is 1, $R^{A6}$ is $CH_3$, and $R^{A4}$ is $CH_3$. In another embodiment is a compound of Formula (Ib) wherein n1 is 1, n2 is 1, $R^{A6}$ is $CH_3$, and $R^{A4}$ is $CH_2CH_3$. In another embodiment is a compound of Formula (Ib) wherein n1 is 1, n2 is 1, $R^{A6}$ is $CH_3$, and $R^{A4}$ is $CH_2CH(CH_3)_2$. In another embodiment is a compound of Formula (Ib) wherein n1 is 1, n2 is 1, $R^{A6}$ is $CH_3$, and $R^{A4}$ is $CH_2OH$. In another embodiment is a compound of Formula (Ib) wherein n1 is 1, n2 is 1, $R^{A6}$ is $CH_3$, and $R^{A4}$ is $CH(OH)CH_3$. In another embodiment is a compound of Formula (Ib) wherein n1 is 1, n2 is 1, $R^{A6}$ is $CH_3$, and $R^{A4}$ is $CH_2C(O)NH_2$. In another embodiment is a compound of Formula (Ib) wherein n1 is 1, n2 is 1, $R^{A6}$ is $CH_3$, and $R^{A4}$ is $CH_2CH_2CH_2CH_2NH_2$.

In another embodiment of the aforementioned embodiments is a compound of Formula (Ib) wherein $R^{A7}$, $R^{A7'}$, $R^{A8}$, $R^{A8'}$, $R^{A9}$, $R^{A9'}$, $R^{A4'}$, $R^{A10}$, and $R^{A10'}$ are each independently H. In another embodiment of the aforementioned embodiments is a compound of Formula (Ib) wherein each m is 0. In another embodiment of the aforementioned embodiments is a compound of Formula (Ib) wherein $R^{A1}$, $R^{A1'}$, $R^{A2}$, $R^{4'}$, and $R^{4'}$ are each independently H. In another embodiment of the aforementioned embodiments is a compound of Formula (Ib) wherein n3 is 1 and n8 is 1.

In another embodiment is a compound of Formula (I) having the structure of Formula (Ic):

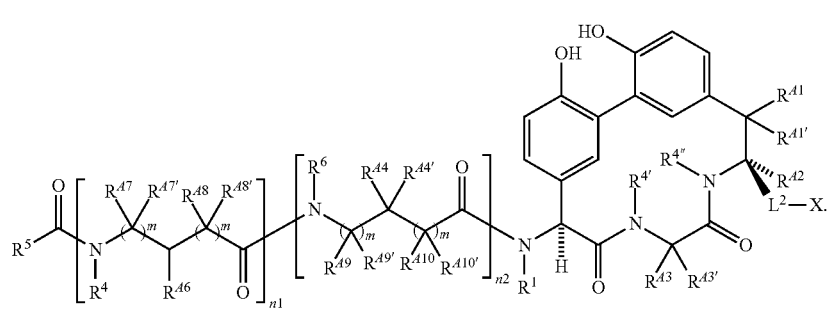

Formula (Ic)

In another embodiment is a compound of Formula (Ic) wherein $L^2$ is a bond. In another embodiment is a compound of Formula (Ic) wherein $L^2$ is optionally substituted $(C_1-C_6)$ alkylene. In a further embodiment, $L^2$ is methylene, ethylene, n-propylene, iso-propylene, n-butylene, iso-butylene, or tert-butylene.

In one embodiment is a compound of Formula (Ic) wherein X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

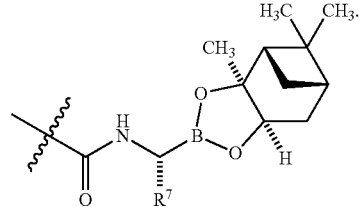

In some embodiments is a compound of Formula (Ic) wherein X is $CO_2H$. In some embodiments is a compound of Formula (Ic) wherein X is $CH_2CO_2H$. In some embodiments is a compound of Formula (Ic) wherein X is $C(=O)NHCH_2C(=O)H$. In some embodiments is a compound of Formula (Ic) wherein X is $CH_2C(=O)H$.

In some embodiments is a compound of Formula (Ic) wherein X is $C(=O)N(H)CH(R^7)B(OR^{B3})(OR^{B4})$. In further embodiments is a compound of Formula (Ic) wherein X is $C(=O)N(H)CH_2B(OH)_2$. In further embodiments is a compound of Formula (Ic) wherein X is $C(=O)N(H)CH(CH_3)B(OH)_2$. In further embodiments is a compound of Formula (Ic) wherein X is $C(O)N(H)CH(CH_2CH_3)B(OH)_2$. In further embodiments is a compound of Formula (Ic) wherein X is $C(=O)N(H)CH(CH_2OH)B(OH)_2$. In further embodiments is a compound of Formula (Ic) wherein X is $C(O)N(H)CH_2B(OCH_3)_2$. In further embodiments is a compound of Formula (Ic) wherein X is $C(O)N(H)CH(CH_3)B(OCH_3)_2$. In further embodiments is a compound of Formula (Ic) wherein X is $C(=O)N(H)CH(CH_2CH_3)B(OCH_3)_2$. In further embodiments is a compound of Formula (Ic) wherein X is $C(=O)N(H)CH(CH_2OH)B(OCH_3)_2$.

In some embodiments is a compound of Formula (Ic) wherein X is C(=O)N(H)CH(R⁷)B(OR^{B3})(OR^{B4}) and R^{B3} and R⁷ together with the boron atom form an optionally substituted 5- or 6-membered boron containing ring. In some embodiments is a compound of Formula (Ic) wherein X is

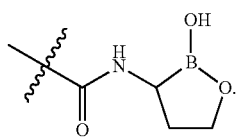 [SMILES: *C(=O)NC1CCOB1O]

In some embodiments is a compound of Formula (Ic) wherein X is

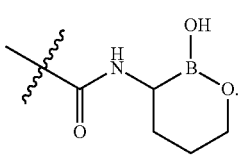 [SMILES: *C(=O)NC1CCCOB1O]

In some embodiments is a compound of Formula (Ic) wherein X is C(=O)N(H)CH(R⁷)B(OR^{B3})(OR^{B4}) and R^{B3} and R^{B4} together with the boron atom form an optionally substituted 5- or 6-membered boron containing ring. In some embodiments is a compound of Formula (Ic) wherein X is

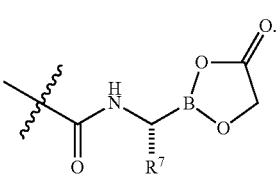

In some embodiments is a compound of Formula (Ic) wherein X is

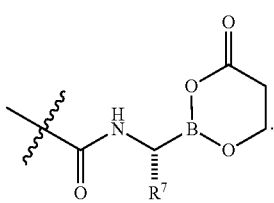

In some embodiments is a compound of Formula (Ic) wherein X is C(=O)N(H)CH(R⁷)B(OR^{B3})(OR^{B4}) and R^{B3} and R^{B4} together with the boron atom form an optionally substituted 5- or 6-membered boron containing ring derived from a sugar. In some embodiments is a compound of Formula (Ic) wherein X is

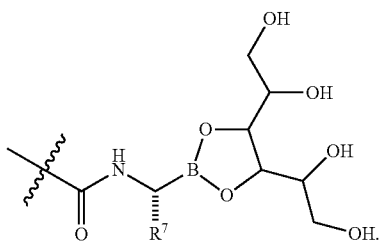

In some embodiments is a compound of Formula (Ic) wherein X is

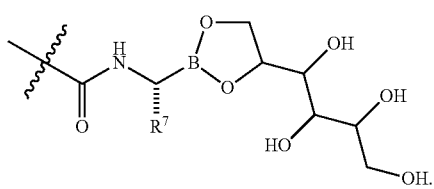

In some embodiments is a compound of Formula (Ic) wherein X is

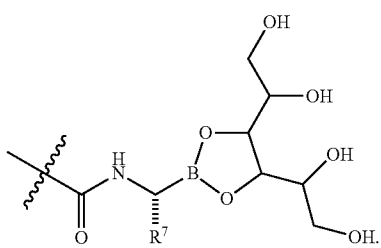

In some embodiments is a compound of Formula (Ic) wherein X is

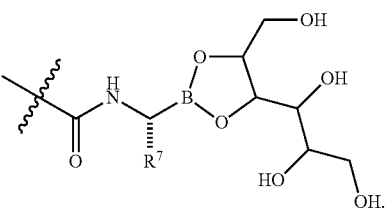

In some embodiments is a compound of Formula (Ic) wherein X is

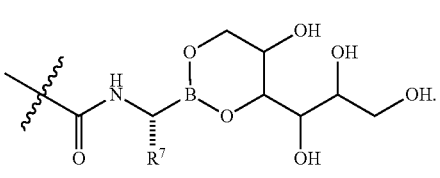

In some embodiments is a compound of Formula (Ic) wherein X is

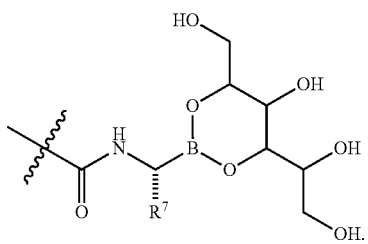

In some embodiments is a compound of Formula (Ic) wherein X is

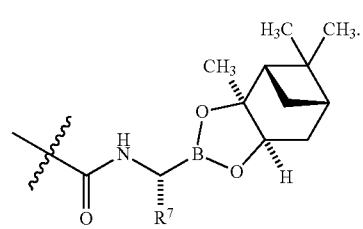

In further embodiments is a compound of Formula (Ic) wherein X

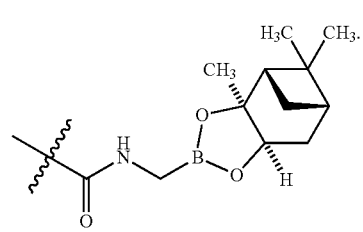 [SMILES: *C(=O)NCB1O[C@@H]2C[C@@H]3C[C@@H](C3(C)C)[C@]2(C)O1]

In further embodiments is a compound of Formula (Ic) wherein X is

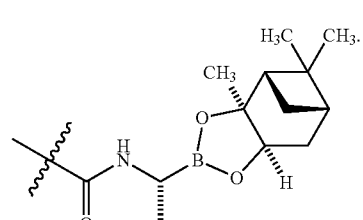

In further embodiments is a compound of Formula (Ic) wherein X is

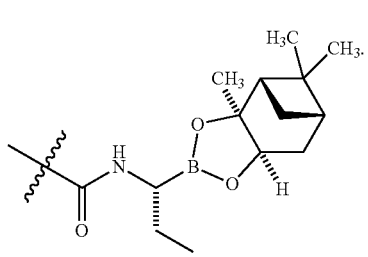 [SMILES: *C(=O)N[C@@H](CC)B1O[C@@H]2C[C@@H]3C[C@@H](C3(C)C)[C@]2(C)O1]

In further embodiments is a compound of Formula (Ic) wherein X is OH

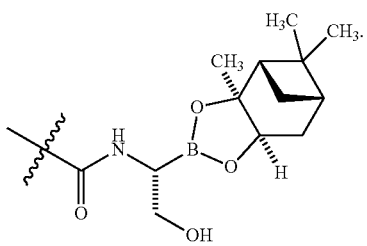 [SMILES: *C(=O)N[C@@H](CO)B1O[C@@H]2C[C@@H]3C[C@@H](C3(C)C)[C@]2(C)O1]

In some embodiments is a compound of Formula (Ic) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

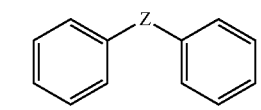

wherein Z is a bond, O, S, NH, $CH_2$ or C≡C. In some embodiments is a compound of Formula (Ic) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

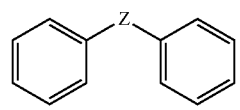

wherein Z is a bond, O, S, NH, $CH_2$ or C≡C. In some embodiments is a compound of Formula (Ic) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

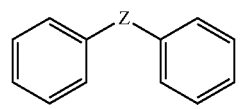

wherein Z is a bond. In some embodiments is a compound of Formula (Ic) wherein $R^5$ is a linear alkyl chain of about 4-22 carbon atoms, wherein $R^5$ is bonded to the carbonyl carbon to which it is attached directly to provide an amide linkage, comprising at a chain terminus

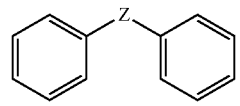

wherein Z is a bond. In some embodiments is a compound of Formula (Ic) wherein $R^5$ is a linear alkyl chain of about 4-22 carbon atoms, wherein $R^5$ is bonded to the carbonyl carbon to which it is attached directly to provide an amide linkage, comprising within the chain

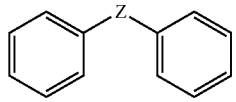

wherein Z is a bond. In some embodiments is a compound of Formula (Ic) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (Ic) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (Ic) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (Ic) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (Ic) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (Ic) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (Ic) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (Ic) wherein n1 is 0 and n2 is 1. In another embodiment is a compound of Formula (Ic) wherein n1 is 0, n2 is 1, and $R^{A4}$ is H. In another embodiment is a compound of Formula (Ic) wherein n1 is 0, n2 is 1, and $R^{A4}$ is $(C_1-C_6)$alkyl optionally substituted with 1 to 3 J. In another embodiment is a compound of Formula (Ic) wherein n1 is 0, n2 is 1, and $R^{A4}$ is $CH_3$. In another embodiment is a compound of Formula (Ic) wherein n1 is 0, n2 is 1, and $R^{A4}$ is $CH_2CH_3$. In another embodiment is a compound of Formula (Ic) wherein n1 is 0, n2 is 1, and $R^{A4}$ is $CH_2CH(CH_3)_2$. In another embodiment is a compound of Formula (Ic) wherein n1 is 0, n2 is 1, and $R^{A4}$ is $CH_2OH$. In another embodiment is a compound of Formula (Ic) wherein n1 is 0, n2 is 1, and $R^{A4}$ is $CH(OH)CH_3$. In another embodiment is a compound of Formula (Ic) wherein n1 is 0, n2 is 1, and $R^{A4}$ is $CH_2C(O)NH_2$. In another embodiment is a compound of Formula (Ic) wherein n1 is 0, n2 is 1, and $R^{A4}$ is $CH_2CH_2CH_2CH_2NH_2$.

In another embodiment is a compound of Formula (Ic) wherein n1 is 1 and n2 is 1. In another embodiment is a compound of Formula (Ic) wherein n1 is 1, n2 is 1, $R^{A6}$ is $CH_3$, and $R^{A4}$ is $(C_1-C_6)$alkyl optionally substituted with 1 to 3 J. In another embodiment is a compound of Formula (Ic) wherein n1 is 1, n2 is 1, $R^{A6}$ is $CH_3$, and $R^{A4}$ is $CH_3$. In another embodiment is a compound of Formula (Ic) wherein n1 is 1, n2 is 1, $R^{A6}$ is $CH_3$, and $R^{A4}$ is $CH_2CH_3$. In another embodiment is a compound of Formula (Ic) wherein n1 is 1, n2 is 1, $R^{A6}$ is $CH_3$, and $R^{A4}$ is $CH_2CH(CH_3)_2$. In another embodiment is a compound of Formula (Ic) wherein n1 is 1, n2 is 1, $R^{A6}$ is $CH_3$, and $R^{A4}$ is $CH_2OH$. In another embodiment is a compound of Formula (Ic) wherein n1 is 1, n2 is 1, $R^{A6}$ is $CH_3$, and $R^{A4}$ is $CH(OH)CH_3$. In another embodiment is a compound of Formula (Ic) wherein n1 is 1, n2 is 1, $R^{A6}$ is $CH_3$, and $R^{A4}$ is $CH_2C(O)NH_2$. In another embodiment is a compound of Formula (Ic) wherein n1 is 1, n2 is 1, $R^{A6}$ is $CH_3$, and $R^{A4}$ is $CH_2CH_2CH_2CH_2NH_2$.

In another embodiment of the aforementioned embodiments is a compound of Formula (Ic) wherein $R^{A7}$, $R^{A7'}$, $R^{A8}$, $R^{A8'}$, $R^{A9}$, $R^{A9'}$, $R^{A4'}$, $R^{A10}$, and $R^{A10'}$ are each independently H. In another embodiment of the aforementioned embodiments is a compound of Formula (Ic) wherein each m is 0. In another embodiment of the aforementioned embodiments is a compound of Formula (Ic) wherein $R^{A1}$, $R^{A1'}$, $R^{A2}$, $R^{4'}$, and $R^{4''}$ are each independently H.

In another embodiment is a compound of Formula (I) having the structure of Formula (Id):

Formula (Id)

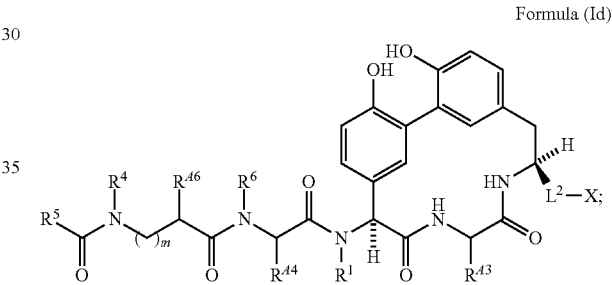

wherein:
$L^2$ is a bond, or optionally substituted $(C_1-C_6)$alkylene;
X is a group of formula

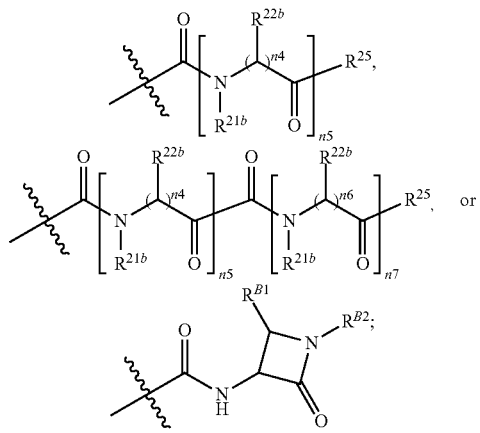

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J; $R^{25}$ is H, OH, $OR^C$,

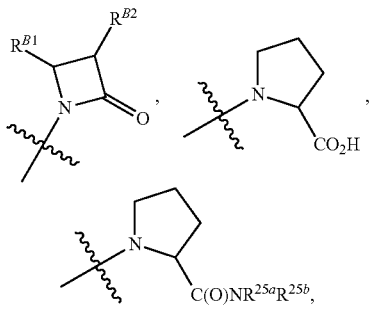

or $NR^{25a}R^{25b}$ where $R^{25a}$ and $R^{25b}$ are each independently H, $SO_2(C_1$-$C_6)$alkyl, or optionally substituted alkyl; $R^{B1}$ and $R^{B2}$ are each independently H, ($C_1$-$C_6$)alkyl, ($C_3$-$C_6$)cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, ($C_1$-$C_6$)alkoxy, ($C_1$-$C_6$)thioalkoxy, $N(R^C)_2$, 5-7 membered heterocyclyl or 5-7 membered heteroaryl, or ($C_6$-$C_{10}$) aryl; $R^C$ is independently at each occurrence H or ($C_1$-$C_6$)alkyl, and a wavy line indicates a point of attachment of X to a carbon of formula (Id) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

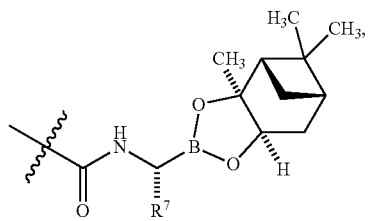

wherein $R^7$ is H, methyl, ethyl, or —$CH_2OH$; or $R^7$ and $R^{B3}$ together with the boron atom form a 5- or 6-membered boron containing ring; $R^{B3}$ and $R^{B4}$ are each independently H, ($C_1$-$C_6$)alkyl, —$CH_2CO_2H$, —$CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

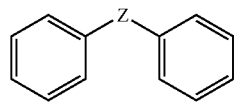

wherein Z is a bond, O, S, NH, $CH_2$ or C=C;
m is independently 0 or 1;
$R^1$ is hydrogen or ($C_1$-$C_6$)alkyl optionally substituted with 1 to 3 J;

$R^4$ is hydrogen, or ($C_1$-$C_6$)alkyl optionally substituted with 1 to 3 J;
$R^6$ is hydrogen, or ($C_1$-$C_6$)alkyl optionally substituted with 1 to 3 J; or $R^6$ together with $R^{44}$ form a ring;
$R^{43}$ is hydrogen, or ($C_1$-$C_6$)alkyl optionally substituted with 1 to 3 J;
$R^{44}$ is ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;
$R^{46}$ is amino, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;
J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;
each R' is independently at each occurrence hydrogen, ($C_1$-$C_6$)-alkyl, ($C_2$-$C_7$)-alkenyl, ($C_2$-$C_7$)-alkynyl, ($C_3$-$C_{10}$)-cycloalkyl, ($C_3$-$C_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1$-$C_4)$alkyl$)_2$—, —NH($C_1$-$C_4$)alkyl, $C_1$-$C_6$alkyl, $C_3$-$C_8$cycloalkyl, or $C_1$-$C_6$heteroalkyl; or a pharmaceutically acceptable salt, solvate or prodrug thereof.

In another embodiment is a compound of Formula (Id) wherein $L^2$ is a bond. In another embodiment is a compound of Formula (Id) wherein $L^2$ is optionally substituted ($C_1$-$C_6$) alkylene. In a further embodiment, $L^2$ is methylene, ethylene, n-propylene, iso-propylene, n-butylene, iso-butylene, or tert-butylene.

In one embodiment is a compound of Formula (Id) wherein X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

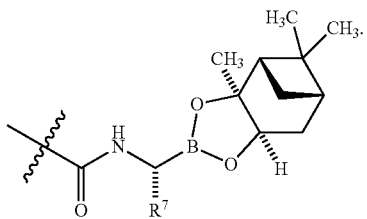

In some embodiments is a compound of Formula (Id) wherein X is $CO_2H$. In some embodiments is a compound of Formula (Id) wherein X is $CH_2CO_2H$. In some embodiments is a compound of Formula (Id) wherein X is $C(=O)NHCH_2C(=O)H$. In some embodiments is a compound of Formula (Id) wherein X is $CH_2C(=O)H$.

In some embodiments is a compound of Formula (Id) wherein X is $C(=O)N(H)CH(R^7)B(OR^{B3})(OR^{B4})$. In further embodiments is a compound of Formula (Id) wherein X is $C(=O)N(H)CH_2B(OH)_2$. In further embodiments is a compound of Formula (Id) wherein X is $C(=O)N(H)CH(CH_3)B(OH)_2$. In further embodiments is a compound of Formula (Id) wherein X is $C(=O)N(H)CH(CH_2CH_3)B(OH)_2$. In further embodiments is a compound of Formula (Id) wherein X is $C(=O)N(H)CH(CH_2OH)B(OH)_2$. In further embodiments is a compound of Formula (Id) wherein X is C(=O)N(H)CH₂B(OCH₃)₂. In further embodiments is a compound of Formula (Id) wherein X is C(=O)N(H)CH(CH₃)B(OCH₃)₂. In further embodiments is a compound of Formula (Id) wherein X is C(=O)N(H)CH(CH₂CH₃)B(OCH₃)₂. In further embodiments is a compound of Formula (Id) wherein X is C(=O)N(H)CH(CH₂OH)B(OCH₃)₂.

In some embodiments is a compound of Formula (Id) wherein X is C(=O)N(H)CH(R⁷)B(OR^{B3})(OR^{B4}) and R^{B3} and R⁷ together with the boron atom form an optionally substituted 5- or 6-membered boron containing ring. In some embodiments is a compound of Formula (Id) wherein X is

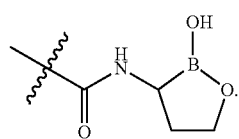 [SMILES: *C(=O)NC1CCOB1O]

In some embodiments is a compound of Formula (Id) wherein X is

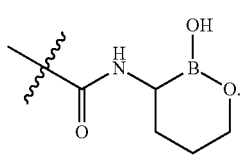 [SMILES: *C(=O)NC1CCCOB1O]

In some embodiments is a compound of Formula (Id) wherein X is C(=O)N(H)CH(R⁷)B(OR^{B3})(OR^{B4}) and R^{B3} and R^{B4} together with the boron atom form an optionally substituted 5- or 6-membered boron containing ring. In some embodiments is a compound of Formula (Id) wherein X is

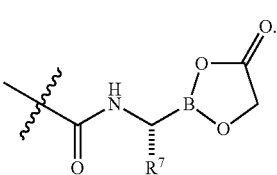

In some embodiments is a compound of Formula (Id) wherein X is

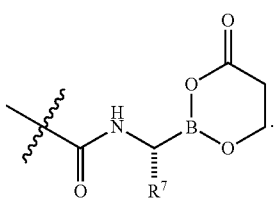

In some embodiments is a compound of Formula (Id) wherein X is C(=O)N(H)CH(R⁷)B(OR^{B3})(OR^{B4}) and R^{B3} and R^{B4} together with the boron atom form an optionally substituted 5- or 6-membered boron containing ring derived from a sugar. In some embodiments is a compound of Formula (Id) wherein X is

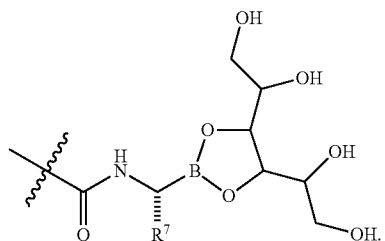

In some embodiments is a compound of Formula (Id) wherein X is

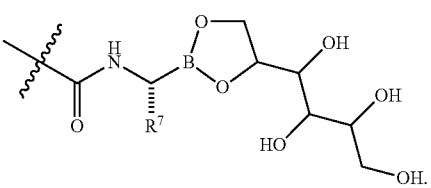

In some embodiments is a compound of Formula (Id) wherein is

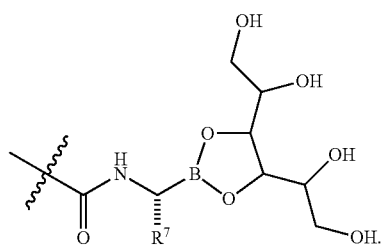

In some embodiments is a compound of Formula (Id) wherein X is

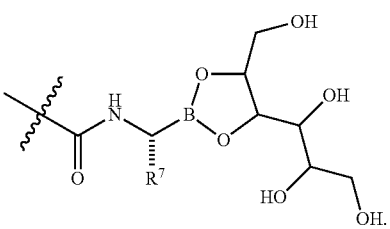

In some embodiments is a compound of Formula (Id) wherein X is

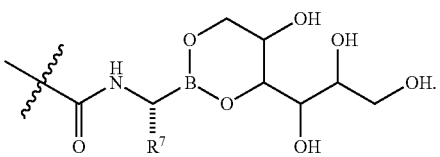

In some embodiments is a compound of Formula (Id) wherein X is

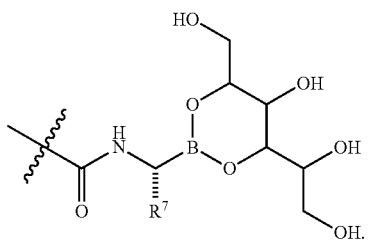

In some embodiments is a compound of Formula (Id) wherein X is

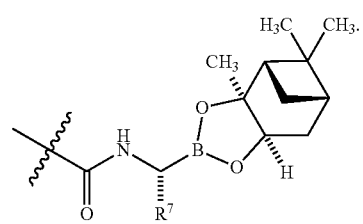

In further embodiments is a compound of Formula (Id) wherein X is

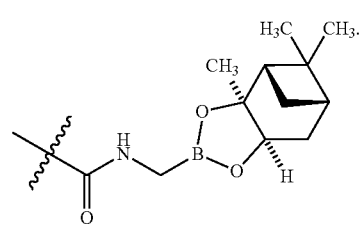 [SMILES: *C(=O)NCB1O[C@@H]2C[C@@H]3C[C@@H](C3(C)C)[C@]2(C)O1]

In further embodiments is a compound of Formula (Id) wherein X is

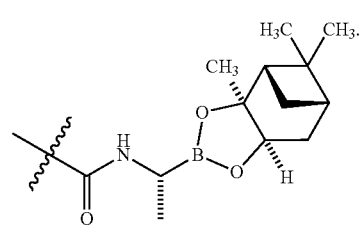 [SMILES: *C(=O)N[C@@H](C)B1O[C@@H]2C[C@@H]3C[C@@H](C3(C)C)[C@]2(C)O1]

In further embodiments is a compound of Formula (Id) wherein X is

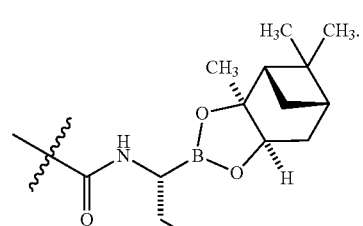

In further embodiments is a compound of Formula (Id) wherein X is

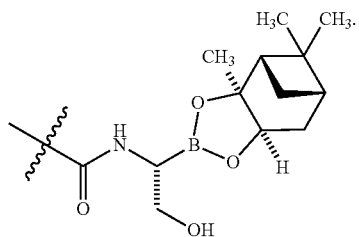 [SMILES: *C(=O)N[C@@H](CO)B1O[C@@H]2C[C@@H]3C[C@@H](C3(C)C)[C@]2(C)O1]

In some embodiments is a compound of Formula (Id) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

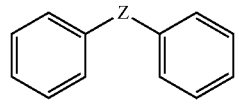

wherein Z is a bond, O, S, NH, $CH_2$ or C≡C. In some embodiments is a compound of Formula (Id) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

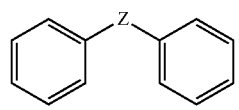

wherein Z is a bond, O, S, NH, $CH_2$ or C≡C. In some embodiments is a compound of Formula (Id) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

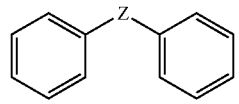

wherein Z is a bond. In some embodiments is a compound of Formula (Id) wherein $R^5$ is a linear alkyl chain of about 4-22 carbon atoms, wherein $R^5$ is bonded to the carbonyl carbon to which it is attached directly to provide an amide linkage, comprising at a chain terminus

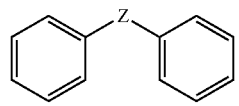

wherein Z is a bond. In some embodiments is a compound of Formula (Id) wherein $R^5$ is a linear alkyl chain of about 4-22 carbon atoms, wherein $R^5$ is bonded to the carbonyl carbon to which it is attached directly to provide an amide linkage, comprising within the chain

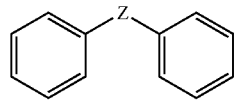

wherein Z is a bond. In some embodiments is a compound of Formula (Id) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (Id) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (Id) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (Id) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (Id) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (Id) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (Id) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (Id) wherein $R^{44}$ is $(C_1-C_6)$alkyl optionally substituted with 1 to 3 J. In another embodiment is a compound of Formula (Id) wherein $R^{44}$ is $CH_3$. In another embodiment is a compound of Formula (Id) wherein $R^{44}$ is $CH_2CH_3$. In another embodiment is a compound of Formula (Id) wherein $R^{44}$ is $CH_2CH(CH_3)_2$. In another embodiment is a compound of Formula (Id) wherein $R^{44}$ is $CH_2OH$. In another embodiment is a compound of Formula (Id) wherein $R^{44}$ is $CH(OH)CH_3$. In another embodiment is a compound of Formula (Id) wherein $R^{44}$ is $CH_2C(O)NH_2$. In another embodiment is a compound of Formula (Id) wherein $R^{44}$ is $CH_2H_2CH_2CH_2NH_2$.

In another embodiment is a compound of Formula (Id) wherein $R^{46}$ is $CH_3$, and $R^{44}$ is $(C_1-C_6)$alkyl optionally substituted with 1 to 3 J. In another embodiment is a compound of Formula (Id) $R^{46}$ is $CH_3$, and $R^{44}$ is $CH_3$. In another embodiment is a compound of Formula (Id) wherein $R^{46}$ is $CH_3$, and $R^{44}$ is $CH_2CH_3$. In another embodiment is a compound of Formula (Id) wherein $R^{46}$ is $CH_3$, and $R^{44}$ is $CH_2CH(CH_3)_2$. In another embodiment is a compound of Formula (Id) wherein $R^{46}$ is $CH_3$, and $R^{44}$ is $CH_2OH$. In another embodiment is a compound of Formula (Id) wherein $R^{46}$ is $CH_3$, and $R^{44}$ is $CH(OH)CH_3$. In another embodiment is a compound of Formula (Id) wherein $R^{46}$ is $CH_3$, and $R^{44}$ is $CH_2C(O)NH_2$. In another embodiment is a compound of Formula (Id) wherein $R^{46}$ is $CH_3$, and $R^{44}$ is $CH_2CH_2CH_2CH_2NH_2$.

In another embodiment of the aforementioned embodiments is a compound of Formula (Id) wherein $R^{43}$ is $CH_3$. In another embodiment of the aforementioned embodiments is a compound of Formula (Id) wherein $R^1$ is $CH_3$. In another embodiment of the aforementioned embodiments is a compound of Formula (Id) wherein $R^4$ is H. In another embodiment of the aforementioned embodiments is a compound of Formula (Id) wherein $R^6$ is H. In another embodiment of the aforementioned embodiments is a compound of Formula (Id) wherein m is 1. In another embodiment of the aforementioned embodiments is a compound of Formula (Id) wherein m is 0.

In another embodiment is a compound of Formula (I) having the structure of Formula (Ie):

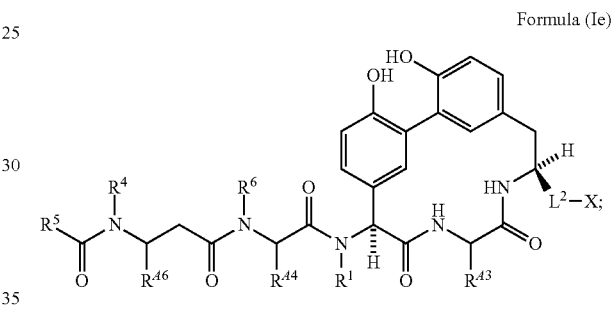

Formula (Ie)

wherein:

$L^2$ is a bond, or optionally substituted $(C_1-C_6)$alkylene;

X is a group of formula

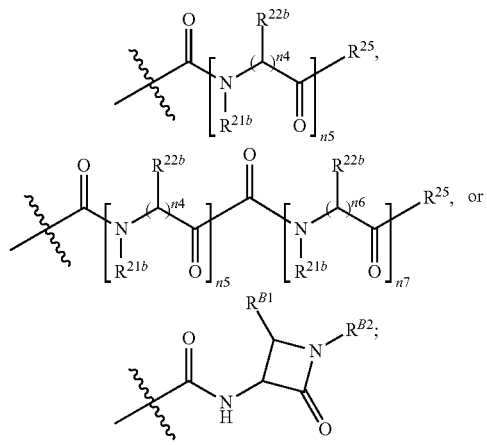

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

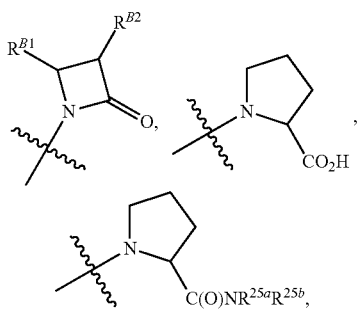

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$)alkyl, (C$_3$-C$_6$)cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$_C$ is independently at each occurrence H or (C$_1$-C$_6$)alkyl, and a wavy line indicates a point of attachment of X to a carbon of formula (Ie) bearing X; or X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

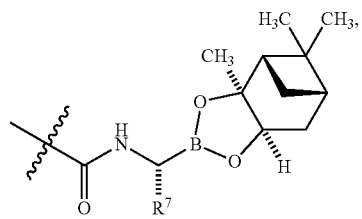

wherein R$^7$ is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, —CH$_2$CH$_2$CO$_2$H; or R$^{B3}$ and R$^{B4}$ together with the boron atom form an optionally substituted 5- or 6-membered boron containing ring;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

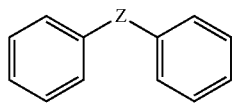

wherein Z is a bond, O, S, NH, CH$_2$ or C≡C;

R$^1$ is hydrogen or (C$_1$-C$_6$)alkyl optionally substituted with 1 to 3 J;

R$^4$ is hydrogen, or (C$_1$-C$_6$)alkyl optionally substituted with 1 to 3 J;

R$^6$ is hydrogen, or (C$_1$-C$_6$)alkyl optionally substituted with 1 to 3 J; or R$^6$ together with R$^{A4}$ form a ring;

R$^{A3}$ is hydrogen, or (C$_1$-C$_6$)alkyl optionally substituted with 1 to 3 J;

R$^{A4}$ is (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

R$^{A6}$ is amino, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

J is halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;

each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$—, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate or prodrug thereof.

In another embodiment is a compound of Formula (Ie) wherein L$^2$ is a bond. In another embodiment is a compound of Formula (Ie) wherein L$^2$ is optionally substituted (C$_1$-C$_6$) alkylene. In a further embodiment, L$^2$ is methylene, ethylene, n-propylene, iso-propylene, n-butylene, iso-butylene, or tert-butylene.

In one embodiment is a compound of Formula (Ie) wherein X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

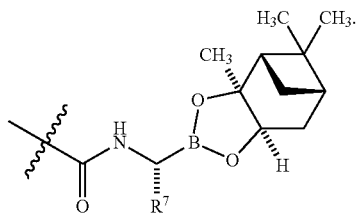

In some embodiments is a compound of Formula (Ie) wherein X is CO$_2$H. In some embodiments is a compound of Formula (Ie) wherein X is CH$_2$CO$_2$H. In some embodiments is a compound of Formula (Ie) wherein X is C(=O)NHCH$_2$C(=O)H. In some embodiments is a compound of Formula (Ie) wherein X is CH$_2$C(=O)H.

In some embodiments is a compound of Formula (Ie) wherein X is C(=O)N(H)CH(R$^7$)B(OR$^{B3}$)(OR$^{B4}$). In further embodiments is a compound of Formula (Ie) wherein X is C(=O)N(H)CH$_2$B(OH)$_2$. In further embodiments is a compound of Formula (Ie) wherein X is C(=O)N(H)CH(CH$_3$)B(OH)$_2$. In further embodiments is a compound of Formula (Ie) wherein X is C(=O)N(H)CH(CH$_2$CH$_3$)B(OH)$_2$. In further embodiments is a compound of Formula (Ie) wherein X is C(=O)N(H)CH(CH$_2$OH)B(OH)$_2$. In further embodiments is a compound of Formula (Ie) wherein X is C(=O)N(H)CH$_2$B(OCH$_3$)$_2$. In further embodiments is a compound of Formula (Ie) wherein X is C(=O)N(H)CH(CH$_3$)B(OCH$_3$)$_2$. In further embodiments is a compound of Formula (Ie) wherein X is C(=O)N(H)CH(CH$_2$CH$_3$)B(OCH$_3$)$_2$. In further embodiments is a compound of Formula (Ie) wherein X is C(=O)N(H)CH(CH₂OH)B(OCH₃)₂.

In some embodiments is a compound of Formula (Ie) wherein X is C(=O)N(H)CH(R⁷)B(OR^{B3})(OR^{B4}) and R^{B3} and R⁷ together with the boron atom form an optionally substituted 5- or 6-membered boron containing ring. In some embodiments is a compound of Formula (Ie) wherein X is

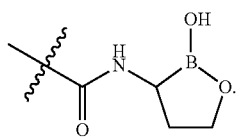 [SMILES: *C(=O)NC1CCOB1O]

In some embodiments is a compound of Formula (Ie) wherein X is

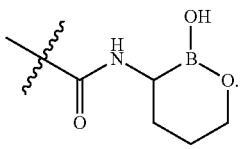 [SMILES: *C(=O)NC1CCCOB1O]

In some embodiments is a compound of Formula (Ie) wherein X is C(=O)N(H)CH(R⁷)B(OR^{B3})(OR^{B4}) and R^{B3} and R^{B4} together with the boron atom form an optionally substituted 5- or 6-membered boron containing ring. In some embodiments is a compound of Formula (Ie) wherein X is

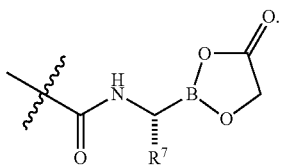

In some embodiments is a compound of Formula (Ie) wherein X is

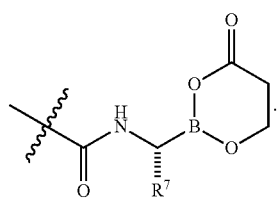

In some embodiments is a compound of Formula (Ie) wherein X is C(=O)N(H)CH(R⁷)B(OR^{B3})(OR^{B4}) and R^{B3} and R^{B4} together with the boron atom form an optionally substituted 5- or 6-membered boron containing ring derived from a sugar. In some embodiments is a compound of Formula (Ie) wherein X is

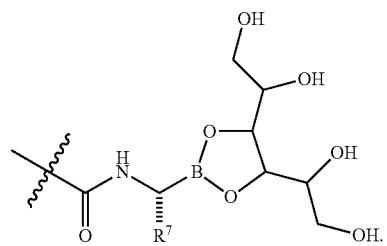

In some embodiments is a compound of Formula (Ie) wherein X is

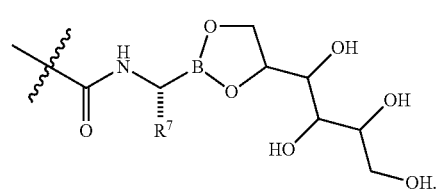

In some embodiments is a compound of Formula (Ie) wherein X is

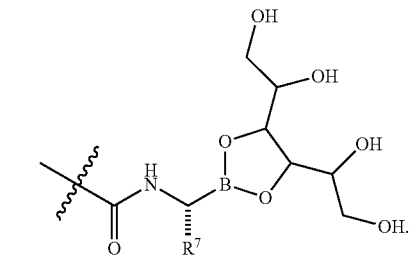

In some embodiments is a compound of Formula (Ie) wherein X is

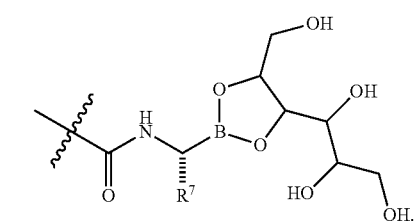

In some embodiments is a compound of Formula (Ie) wherein X is

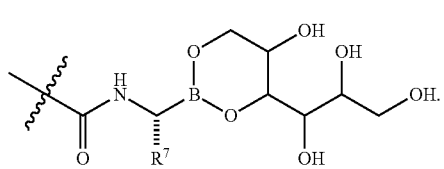

In some embodiments is a compound of Formula (Ie) wherein X is

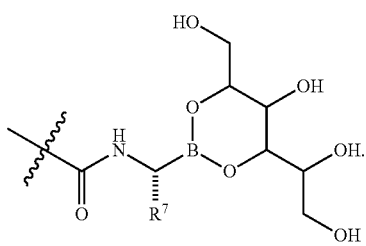

In some embodiments is a compound of Formula (Ie) wherein X is

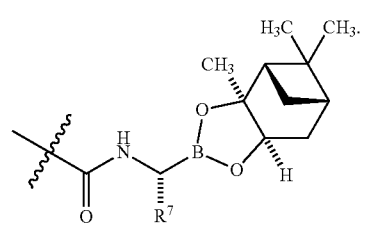

In further embodiments is a compound of Formula (Ie) wherein X is

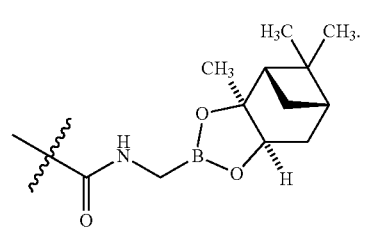

In further embodiments is a compound of Formula (Ie) wherein X is

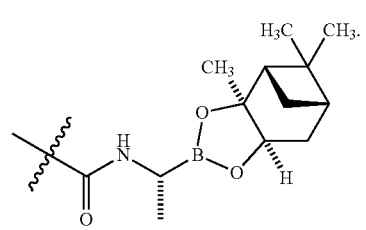

In further embodiments is a compound of Formula (Ie) wherein X is

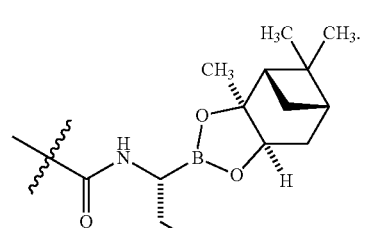

In further embodiments is a compound of Formula (Ie) wherein X is

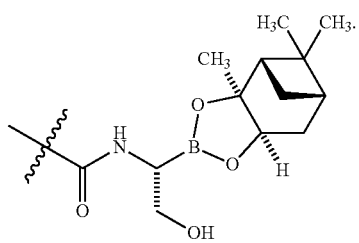 [SMILES: *C(=O)N[C@@H](CO)B1O[C@@H]2C[C@@H]3C[C@@H](C3(C)C)[C@]2(C)O1]

In some embodiments is a compound of Formula (Ie) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

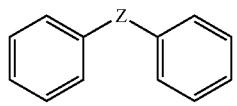

wherein Z is a bond, O, S, NH, $CH_2$ or C≡C. In some embodiments is a compound of Formula (Ie) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

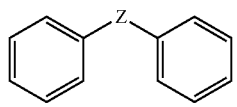

wherein Z is a bond, O, S, NH, $CH_2$ or C≡C. In some embodiments is a compound of Formula (Ie) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

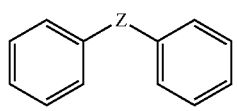

wherein Z is a bond. In some embodiments is a compound of Formula (Ie) wherein $R^5$ is a linear alkyl chain of about 4-22 carbon atoms, wherein $R^5$ is bonded to the carbonyl carbon to which it is attached directly to provide an amide linkage, comprising at a chain terminus

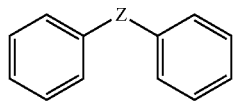

wherein Z is a bond. In some embodiments is a compound of Formula (Ie) wherein $R^5$ is a linear alkyl chain of about 4-22 carbon atoms, wherein $R^5$ is bonded to the carbonyl carbon to which it is attached directly to provide an amide linkage, comprising within the chain

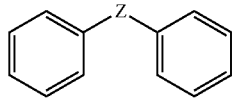

wherein Z is a bond. In some embodiments is a compound of Formula (Ie) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (Ie) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (Ie) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (Ie) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (Ie) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (Ie) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (Ie) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (Ie) wherein $R^{44}$ is $(C_1-C_6)$alkyl optionally substituted with 1 to 3 J. In another embodiment is a compound of Formula (Ie) wherein $R^{44}$ is $CH_3$. In another embodiment is a compound of Formula (Ie) wherein $R^{44}$ is $CH_2CH_3$. In another embodiment is a compound of Formula (Ie) wherein $R^{44}$ is $CH_2CH(CH_3)_2$.

In another embodiment is a compound of Formula (Ie) wherein $R^{44}$ is $CH_2OH$. In another embodiment is a compound of Formula (Ie) wherein $R^{44}$ is $CH(OH)CH_3$. In another embodiment is a compound of Formula (Ie) wherein $R^{44}$ is $CH_2C(O)NH_2$. In another embodiment is a compound of Formula (Ie) wherein $R^{44}$ is $CH_H2(H_2CH_2H2$.

In another embodiment is a compound of Formula (Ie) wherein $R^{46}$ is $CH_3$, and $R^{44}$ is $(C_1-C_6)$alkyl optionally substituted with 1 to 3 J. In another embodiment is a compound of Formula (Ie) $R^{46}$ is $CH_3$, and $R^{44}$ is $CH_3$. In another embodiment is a compound of Formula (Ie) wherein $R^{46}$ is $CH_3$, and $R^{44}$ is $CH_2CH_3$. In another embodiment is a compound of Formula (Ie) wherein $R^{46}$ is $CH_3$, and $R^{44}$ is $CH_2CH(CH_3)_2$. In another embodiment is a compound of Formula (Ie) wherein $R^{46}$ is $CH_3$, and $R^{44}$ is $CH_2OH$. In another embodiment is a compound of Formula (Ie) wherein $R^{46}$ is $CH_3$, and $R^{44}$ is $CH(OH)CH_3$. In another embodiment is a compound of Formula (Ie) wherein $R^{46}$ is $CH_3$, and $R^{44}$ is $CH_2C(O)NH_2$. In another embodiment is a compound of Formula (Ie) wherein $R^{46}$ is $CH_3$, and $R^{44}$ is $CH_2CH_2CH_2CH_2NH_2$.

In another embodiment of the aforementioned embodiments is a compound of Formula (Ie) wherein $R^{43}$ is $CH_3$. In another embodiment of the aforementioned embodiments is a compound of Formula (Ie) wherein $R^1$ is $CH_3$. In another embodiment of the aforementioned embodiments is a compound of Formula (Ie) wherein $R^4$ is H. In another embodiment of the aforementioned embodiments is a compound of Formula (Ie) wherein $R^6$ is H.

In another embodiment described herein are compounds of Formula (II):

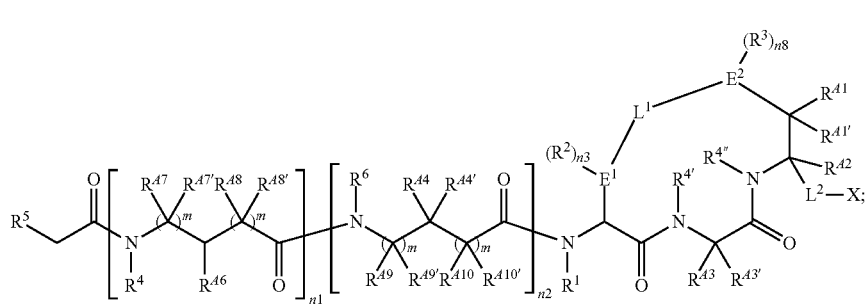

Formula (II)

wherein:

$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$E^2$ is $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;

$L^2$ is a bond, or optionally substituted $(C_1-C_6)$alkylene;

X is a group of formula

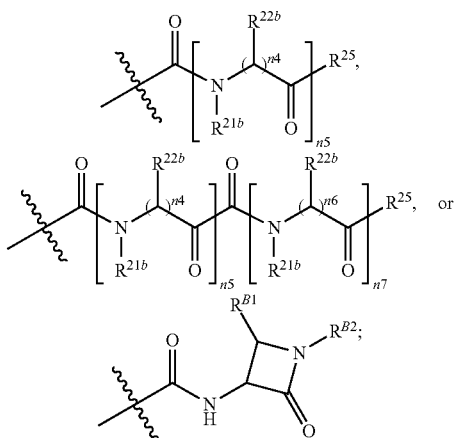

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

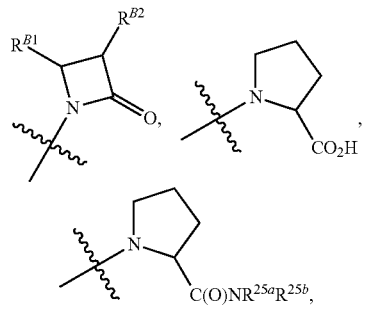

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$alkyl, $(C_3-C_6)$cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$alkyl, and a wavy line indicates a point of attachment of X to a carbon of formula (II) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

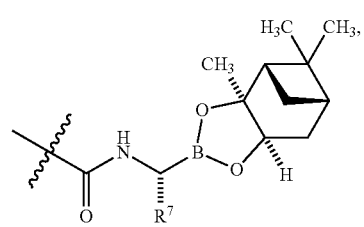

wherein $R^7$ H, methyl, ethyl, or $-CH_2OH$; or $R^7$ and $R^{B3}$ together with the boron atom form a 5- or 6-membered boron containing ring; $R^{B3}$ and $R^{B4}$ are each independently H, $(C_1-C_6)$alkyl, $-CH_2CO_2H$, $-CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, optionally comprising within the chain or at a chain terminus optionally substituted aryl, optionally substituted heteroaryl, or optionally substituted

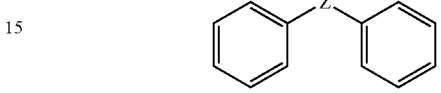

wherein Z is a bond, O, S, NH, $CH_2$ or $C\equiv C$;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (II) wherein $R^2$ or $R^3$ respectively is hydroxy, wherein any carbon atom is optionally substituted with J;

n1 and n2 are independently 0 or 1;

n3 and n8 are independently 0, 1, or 2;

each m is independently 0 or 1;

$R^1$ is hydrogen or $(C_1-C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1-C_6)$alkyl optionally substituted with 1 to 3 J;

$R^6$ is hydrogen, or $(C_1-C_6)$alkyl optionally substituted with 1 to 3 J; or $R^6$ together with $R^{A4}$ form a ring;

$R^{A1}$, $R^{A1'}$, $R^{A2}$, $R^{A3}$, $R^{A3'}$, $R^4$, $R^{A4'}$, $R^{A6}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH-C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, $-CN$, $-NO_2$, $-OH$, $-CF_3$, $-OCF_3$, $-OCH_3$, $-NH_2$, $-N((C_1-C_4)$alkyl$)_2$$-$, $-NH(C_1-C_4)$alkyl, $C_1-C_6$alkyl, $C_3-C_8$cycloalkyl, or $C_1-C_6$heteroalkyl; or a pharmaceutically acceptable salt, solvate, or prodrug thereof.

In another embodiment described herein are compounds of Formula (II) having the structure of Formula (IIa):

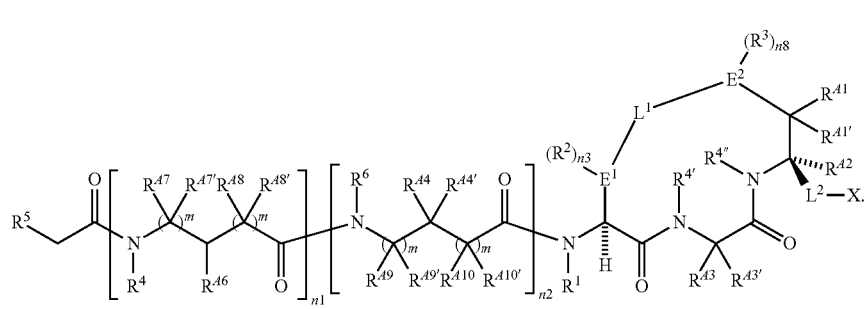

Formula (IIa)

In another embodiment described herein are compounds of Formula (II) having the structure of Formula (IIb):

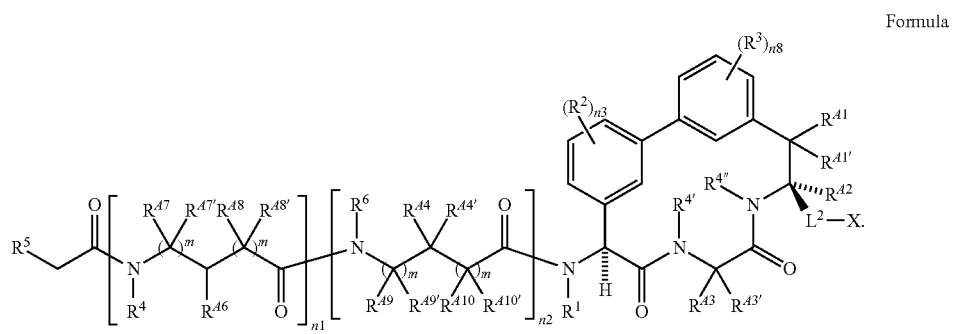

Formula (IIb)

In another embodiment described herein are compounds of Formula (II) having the structure of Formula (IIc):

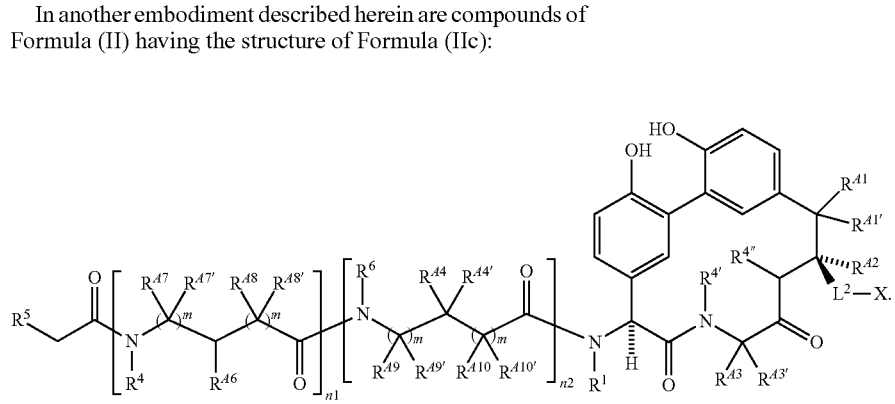

Formula (IIc)

In another embodiment is a compound of Formula (II), (IIa), (IIb), or (IIc) wherein $L^2$ is a bond. In another embodiment is a compound of Formula (II), (IIa), (IIb), or (IIc) wherein $L^2$ is optionally substituted $(C_1-C_6)$alkylene. In a further embodiment, $L^2$ is methylene, ethylene, n-propylene, iso-propylene, n-butylene, iso-butylene, or tert-butylene.

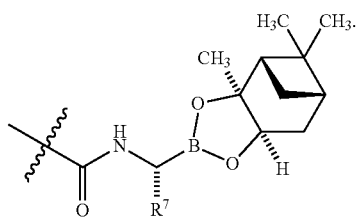

In one embodiment is a compound of Formula (II), (IIa), (IIb), or (IIc) wherein X is $CO_2H$, $CH_2CO_2H$, $C(=O)NHCH_2C(=O)H$, $CH_2C(=O)H$, $C(=O)N(H)CH(R)B(OR^{B3})(OR^{B4})$, or In some embodiments is a compound of Formula (II), (IIa), (IIb), or (IIc) wherein X is $CO_2H$. In some embodiments is a compound of Formula (II), (IIa), (IIb), or (IIc) wherein X is $CH_2CO_2H$. In some embodiments is a compound of Formula (II), (IIa), (IIb), or (IIc) wherein X is $C(=O)NHCH_2C(=O)$ H. In some embodiments is a compound of Formula (II), (IIa), (IIb), or (IIc) wherein X is CH$_2$C(=O)H.

In some embodiments is a compound of Formula (II), (IIa), (IIb), or (IIc) wherein X is C(=O)N(H)CH(R$^7$)B(OR$^{B3}$)(OR$^{B4}$). In further embodiments is a compound of Formula (II), (IIa), (IIb), or (IIc) wherein X is C(=O)N(H)CH$_2$B(OH)$_2$. In further embodiments is a compound of Formula (II), (IIa), (IIb), or (IIc) wherein X is C(=O)N(H)CH(CH$_3$)B(OH)$_2$. In further embodiments is a compound of Formula (II), (IIa), (IIb), or (IIc) wherein X is C(=O)N(H)CH(CH$_2$CH$_3$)B(OH)$_2$. In further embodiments is a compound of Formula (II), (IIa), (IIb), or (IIc) wherein X is C(=O)N(H)CH(CH$_2$OH)B(OH)$_2$. In further embodiments is a compound of Formula (II), (IIa), (IIb), or (IIc) wherein X is C(=O)N(H)CH$_2$B(OCH$_3$)$_2$. In further embodiments is a compound of Formula (II), (IIa), (IIb), or (IIc) wherein X is C(=O)N(H)CH(CH$_3$)B(OCH$_3$)$_2$. In further embodiments is a compound of Formula (II), (IIa), (IIb), or (IIc) wherein X is C(=O)N(H)CH(CH$_2$CH$_3$)B(OCH$_3$)$_2$. In further embodiments is a compound of Formula (II), (IIa), (IIb), or (IIc) wherein X is C(=O)N(H)CH(CH$_2$OH)B(OCH$_3$)$_2$.

In some embodiments is a compound of Formula (II), (IIa), (IIb), or (IIc) wherein X is C(=O)N(H)CH(R$^7$)B(OR$^{B3}$)(OR$^{B4}$) and R$^{B3}$ and R$^7$ together with the boron atom form an optionally substituted 5- or 6-membered boron containing ring. In some embodiments is a compound of Formula (II), (IIa), (IIb), or (IIc) wherein X is

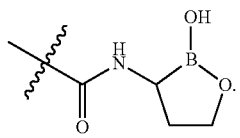 [SMILES: *C(=O)NC1CCOB1O]

In some embodiments is a compound of Formula (II), (IIa), (IIb), or (IIc) wherein X is

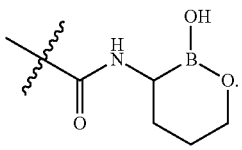 [SMILES: *C(=O)NC1CCCOB1O]

In some embodiments is a compound of Formula (II), (IIa), (IIb), or (IIc) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring. In some embodiments is a compound of Formula (II), (IIa), (IIb), or (IIc) wherein X is

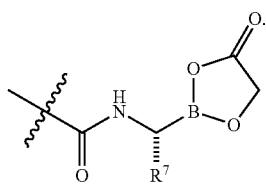

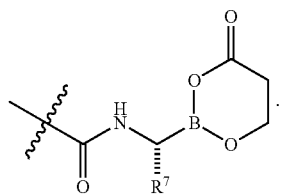

In some embodiments is a compound of Formula (II), (IIa), (IIb), or (IIc) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring derived from a sugar. In some embodiments is a compound of Formula (II), (IIa), (IIb), or (IIc) wherein X is

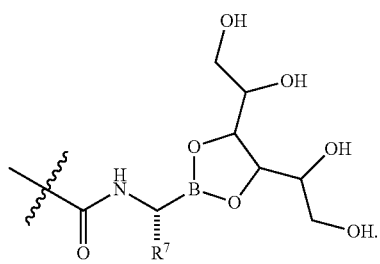

In some embodiments is a compound of Formula (II), (IIa), (IIb), or (IIc) wherein X is

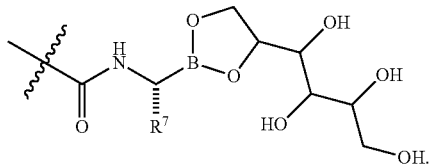

In some embodiments is a compound of Formula (II), (IIa), (IIb), or (IIc) wherein X is

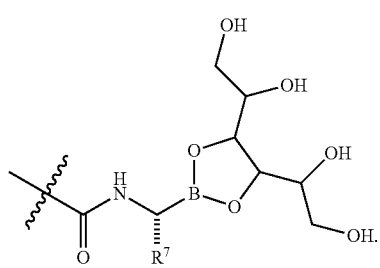

In some embodiments is a compound of Formula (II), (IIa), (IIb), or (IIc) wherein X is

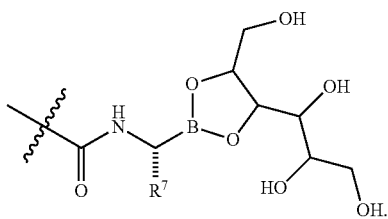

In some embodiments is a compound of Formula (II), (IIa), (IIb), or (IIc) wherein X is

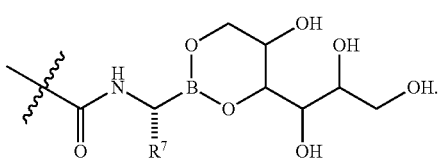

In some embodiments is a compound of Formula (II), (IIa), (IIb), or (IIc) wherein X is

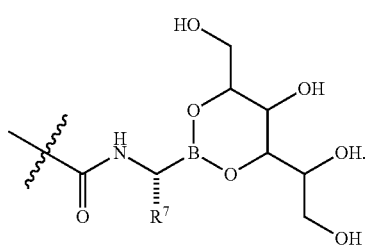

In some embodiments is a compound of Formula (II), (IIa), (IIb), or (IIc) wherein X is

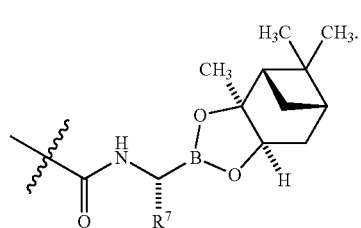

In further embodiments is a compound of Formula (II), (IIa), (IIb), or (IIc) wherein X is

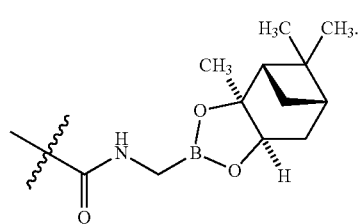

In further embodiments is a compound of Formula (II), (IIa), (IIb), or (IIc) wherein X is

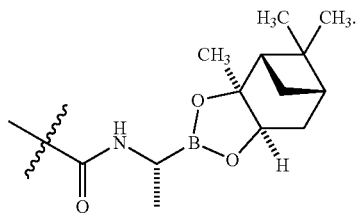 [SMILES: *C(=O)N[C@@H](C)B1O[C@@H]2C[C@@H]3C[C@@H](C3(C)C)[C@]2(C)O1]

In further embodiments is a compound of Formula (II), (IIa), (IIb), or (IIc) wherein X is

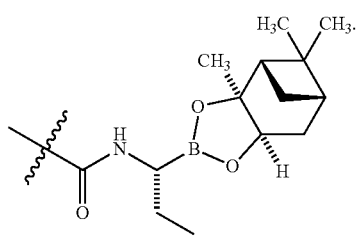 [SMILES: *C(=O)N[C@@H](CC)B1O[C@@H]2C[C@@H]3C[C@@H](C3(C)C)[C@]2(C)O1]

In further embodiments is a compound of Formula (II), (IIa), (IIb), or (IIc) wherein X is

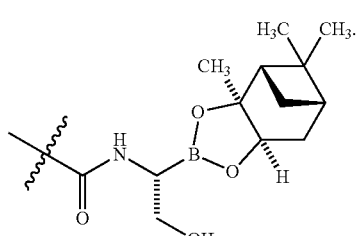

In some embodiments is a compound of Formula (II), (IIa), (IIb), or (IIc) wherein $R^5$ is a linear alkyl chain of about 1-22 carbon atoms comprising within the chain or at a chain terminus

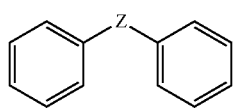

wherein Z is a bond. In some embodiments is a compound of Formula (II), (IIa), (IIb), or (IIc) wherein $R^5$ is a linear alkyl chain of about 4-22 carbon atoms comprising at a chain terminus

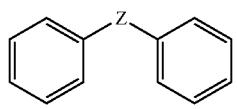

wherein Z is a bond. In some embodiments is a compound of Formula (II), (IIa), (IIb), or (IIc) wherein $R^5$ is a linear alkyl chain of about 4-22 carbon atoms comprising within the chain

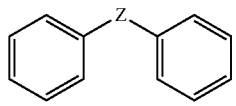

wherein Z is a bond. In some embodiments is a compound of Formula (II), (IIa), (IIb), or (IIc) wherein $R^5$ is a linear or branched alkyl chain of about 1-22 carbon atoms, optionally comprising within the chain or at a chain terminus optionally substituted aryl. In some embodiments is a compound of Formula (II), (IIa), (IIb), or (IIc) wherein $R^5$ is a linear or branched alkyl chain of about 2-22 carbon atoms comprising within the chain or at a chain terminus optionally substituted aryl. In some embodiments is a compound of Formula (II), (IIa), (IIb), or (IIc) wherein $R^5$ is a linear or branched alkyl chain of about 2-22 carbon atoms comprising at a chain terminus optionally substituted aryl. In some embodiments is a compound of Formula (II), (IIa), (IIb), or (IIc) wherein $R^5$ is a linear or branched alkyl chain of about 2-22 carbon atoms comprising within the chain optionally substituted aryl. In some embodiments is a compound of Formula (II), (IIa), (IIb), or (IIc) wherein $R^5$ is a linear or branched alkyl chain of about 1-22 carbon atoms. In some embodiments is a compound of Formula (II), (IIa), (IIb), or (IIc) wherein $R^5$ is a linear or branched alkyl chain of about 4-18 carbon atoms. In some embodiments is a compound of Formula (II), (IIa), (IIb), or (IIc) wherein $R^5$ is a linear or branched alkyl chain of about 6-16 carbon atoms.

In another embodiment is a compound of Formula (II), (IIa), (IIb), or (IIc) wherein n1 is 0 and n2 is 1. In another embodiment is a compound of Formula (II), (IIa), (IIb), or (IIc) wherein n1 is 0, n2 is 1, and $R^{44}$ is H. In another embodiment is a compound of Formula (II), (IIa), (IIb), or (IIc) wherein n1 is 0, n2 is 1, and $R^{44}$ is ($C_1$-$C_6$)alkyl optionally substituted with 1 to 3 J. In another embodiment is a compound of Formula (II), (IIa), (IIb), or (IIc) wherein n1 is 0, n2 is 1, and $R^{44}$ is $CH_3$. In another embodiment is a compound of Formula (II), (IIa), (IIb), or (IIc) wherein n1 is 0, n2 is 1, and $R^{44}$ is $CH_2CH_3$. In another embodiment is a compound of Formula (II), (IIa), (IIb), or (IIc) wherein n1 is 0, n2 is 1, and $R^{44}$ is $CH_2CH(CH_3)_2$. In another embodiment is a compound of Formula (II), (IIa), (IIb), or (IIc) wherein n1 is 0, n2 is 1, and $R^{44}$ is $CH_2OH$. In another embodiment is a compound of Formula (II), (IIa), (IIb), or (IIc) wherein n1 is 0, n2 is 1, and $R^{44}$ is $CH(OH)CH_3$. In another embodiment is a compound of Formula (II), (IIa), (IIb), or (IIc) wherein n1 is 0, n2 is 1, and $R^{44}$ is $CH_2C(O)NH_2$. In another embodiment is a compound of Formula (II), (IIa), (IIb), or (IIc) wherein n1 is 0, n2 is 1, and $R^{44}$ is $CH_2CH_2CH_2CH_2NH_2$.

In another embodiment is a compound of Formula (II), (IIa), (IIb), or (IIc) wherein n1 is 1 and n2 is 1. In another embodiment is a compound of Formula (II), (IIa), (IIb), or (IIc) wherein n1 is 1, n2 is 1, $R^{46}$ is H, and $R^{44}$ is H. In another embodiment is a compound of Formula (II), (IIa), (IIb), or (IIc) wherein n1 is 1, n2 is 1, $R^{46}$ is H, and $R^{44}$ is ($C_1$-$C_6$)alkyl optionally substituted with 1 to 3 J. In another embodiment is a compound of Formula (II), (IIa), (IIb), or (IIc) wherein n1 is 1, n2 is 1, $R^{46}$ is H, and $R^{44}$ is $CH_3$. In another embodiment is a compound of Formula (II), (IIa), (IIb), or (IIc) wherein n1 is 1, n2 is 1, $R^{46}$ is H, and $R^{44}$ is $CH_2CH_3$. In another embodiment is a compound of Formula (II), (IIa), (IIb), or (IIc) wherein n1 is 1, n2 is 1, $R^{46}$ is H, and $R^{44}$ is $CH_2CH(CH_3)_2$. In another embodiment is a compound of Formula (II), (IIa), (IIb), or (IIc) wherein n1 is 1, n2 is 1, $R^{46}$ is H, and $R^{44}$ is $CH_2OH$. In another embodiment is a compound of Formula (II), (IIa), (IIb), or (IIc) wherein n1 is 1, n2 is 1, $R^{46}$ is H, and $R^{44}$ is $CH(OH)CH_3$. In another embodiment is a compound of Formula (II), (IIa), (IIb), or (IIc) wherein n1 is 1, n2 is 1, $R^{46}$ is H, and $R^{44}$ is $CH_2C(O)NH_2$. In another embodiment is a compound of Formula (II), (IIa), (IIb), or (IIc) wherein n1 is 1, n2 is 1, $R^{46}$ is H, and $R^{44}$ is $CH_2CH_2CH_2CH_2NH_2$.

In another embodiment of the aforementioned embodiments is a compound of Formula (II), (IIa), (IIb), or (IIc) wherein $R^{47}$, $R^{47'}$, $R^{48}$, $R^{48'}$, $R^{49}$, $R^{49'}$, $R^{44'}$, $R^{410}$, and $R^{410'}$ are each independently H. In another embodiment of the aforementioned embodiments is a compound of Formula (II), (IIa), (IIb), or (IIc) wherein each m is 0. In another embodiment of the aforementioned embodiments is a compound of Formula (II), (IIa), (IIb), or (IIc) wherein $R^{41}$ $R^{41'}$, $R^{42}$, $R^{4'}$, and $R^{4''}$ are each independently H.

In another embodiment described herein are compounds of Formula (III):

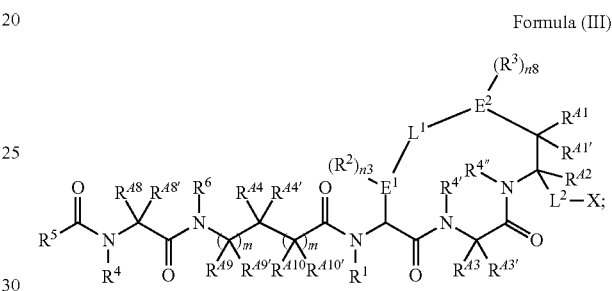

Formula (III)

wherein:
$E^1$ is ($C_1$-$C_6$)alkyl, ($C_2$-$C_7$)alkenyl, ($C_2$-$C_7$)alkynyl, ($C_3$-$C_7$)cycloalkyl, heterocyclyl, heteroaryl, or aryl;
$E^2$ is ($C_2$-$C_7$)alkenyl, ($C_2$-$C_7$)alkynyl, ($C_3$-$C_7$)cycloalkyl, heterocyclyl, heteroaryl, or aryl;
$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or ($C_1$-$C_4$) alkylene optionally substituted with OH, CN, $NO_2$, halogen, ($C_1$-$C_6$)alkyl;
$L^2$ is a bond, or optionally substituted ($C_1$-$C_6$)alkylene;
X is a group of formula

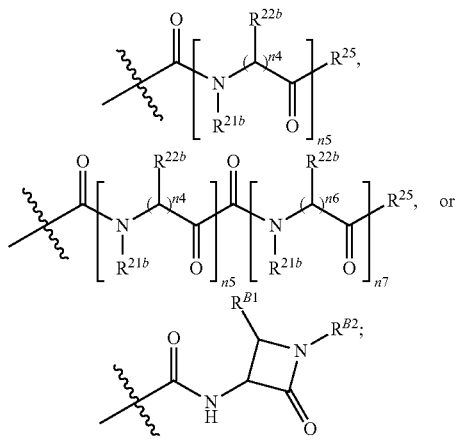

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

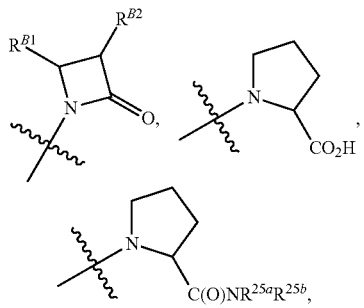

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$alkyl, $(C_3-C_6)$cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$alkyl, and a wavy line indicates a point of attachment of X to a carbon of formula (III) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

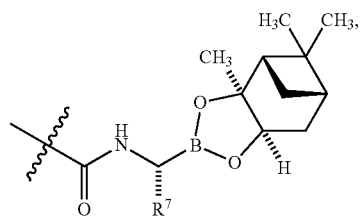

wherein $R^7$ is H, methyl, ethyl, or $—CH_2OH$; or $R^7$ and $R^{B3}$ together with the boron atom form a 5- or 6-membered boron containing ring; $R^{B3}$ and $R^{B4}$ are each independently H, $(C_1-C_6)$alkyl, $—CH_2CO_2H$, $—CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

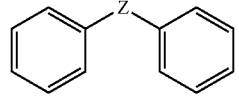

wherein Z is a bond, O, S, NH, $CH_2$ or $C≡C$;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (III) wherein $R^2$ or $R^3$ respectively is hydroxy, wherein any carbon atom is optionally substituted with J;

n3 and n8 are independently 0, 1, or 2;
each m is independently 0 or 1;
$R^1$ is hydrogen or $(C_1-C_6)$alkyl optionally substituted with 1 to 3 J; or $R^1$ together with $E^1$ form a ring;
$R^4$, $R^{4'}$, and $R^{4''}$ are each independently at each occurrence hydrogen, or $(C_1-C_6)$alkyl optionally substituted with 1 to 3 J;
$R^6$ is hydrogen, or $(C_1-C_6)$alkyl optionally substituted with 1 to 3 J; or $R^6$ together with $R^{44}$ form a ring;
$R^{41}$, $R^{41'}$, $R^{42}$, $R^{43}$, $R^{43'}$, $R^{44}$, $R^{4'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH—C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(=NH)N(R')_2$, wherein p is 4;

each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, $—CN$, $—NO_2$, $—OH$, $—CF_3$, $—OCF_3$, $—OCH_3$, $—NH_2$, $—N((C_1-C_4)alkyl)_2—$, $—NH(C_1-C_4)alkyl$, $C_1-C_6$alkyl, $C_3-C_8$cycloalkyl, or $C_1-C_6$heteroalkyl; or a pharmaceutically acceptable salt, solvate, or prodrug thereof.

In another embodiment described herein are compounds of Formula (III) having the structure of Formula (IIIa):

Formula (IIIa)

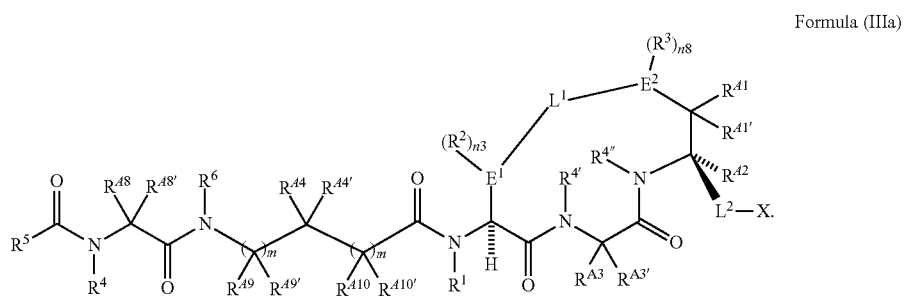

In another embodiment described herein are compounds of Formula (III) having the structure of Formula (IIIb):

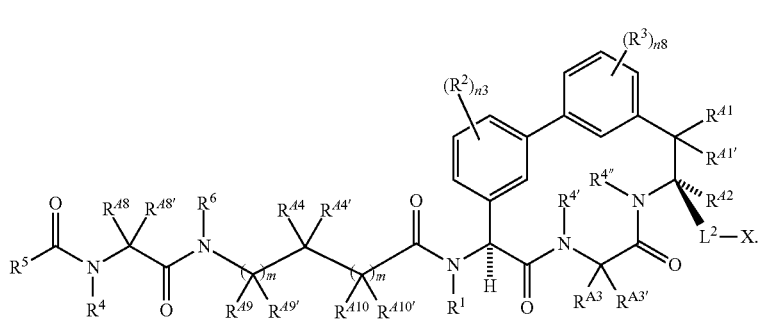

Formula (IIIb)

In another embodiment described herein are compounds of Formula (III) having the structure of Formula (IIIc):

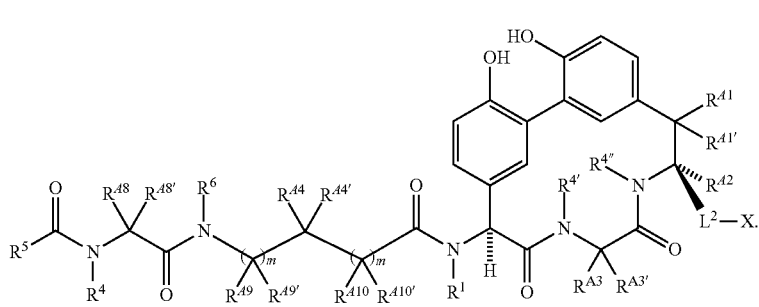

Formula (IIIc)

In another embodiment is a compound of Formula (III), (IIIa), (IIIb), or (IIIc) wherein $L^2$ is a bond. In another embodiment is a compound of Formula (III), (IIIa), (IIIb), or (IIIc) wherein $L^2$ is optionally substituted $(C_1\text{-}C_6)$alkylene. In a further embodiment, $L^2$ is methylene, ethylene, n-propylene, iso-propylene, n-butylene, iso-butylene, or tert-butylene.

In one embodiment is a compound of Formula (III), (IIIa), (IIIb), or (IIIc) wherein X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

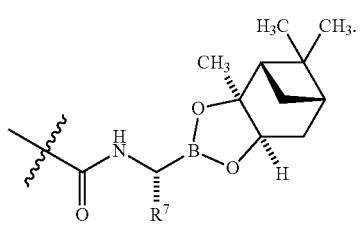

In some embodiments is a compound of Formula (III), (IIIa), (IIIb), or (IIIc) wherein X is $CO_2H$. In some embodiments is a compound of Formula (III), (IIIa), (IIIb), or (IIIc) wherein X is $CH_2CO_2H$. In some embodiments is a compound of Formula (III), (IIIa), (IIIb), or (IIIc) wherein X is $C(=O)NHCH_2C(=O)H$. In some embodiments is a compound of Formula (III), (IIIa), (IIIb), or (IIIc) wherein X is $CH_2C(=O)H$.

In some embodiments is a compound of Formula (III), (IIIa), (IIIb), or (IIIc) wherein X is $C(=O)N(H)CH(R^7)B(OR^{B3})(OR^{B4})$. In further embodiments is a compound of Formula (III), (IIIa), (IIIb), or (IIIc) wherein X is $C(=O)N(H)CH_2B(OH)_2$. In further embodiments is a compound of Formula (III), (IIIa), (IIIb), or (IIIc) wherein X is $C(=O)N(H)CH(CH_3)B(OH)_2$. In further embodiments is a compound of Formula (III), (IIIa), (IIIb), or (IIIc) wherein X is $C(=O)N(H)CH(CH_2CH_3)B(OH)_2$. In further embodiments is a compound of Formula (III), (IIIa), (IIIb), or (IIIc) wherein X is $C(=O)N(H)CH(CH_2OH)B(OH)_2$. In further embodiments is a compound of Formula (III), (IIIa), (IIIb), or (IIIc) wherein X is $C(=O)N(H)CH_2B(OCH_3)_2$. In further embodiments is a compound of Formula (III), (IIIa), (IIIb), or (IIIc) wherein X is $C(=O)N(H)CH(CH_3)B(OCH_3)_2$. In further embodiments is a compound of Formula (III), (IIIa), (IIIb), or (IIIc) wherein X is $C(=O)N(H)CH(CH_2CH_3)B(OCH_3)_2$. In further embodiments is a compound of Formula (III), (IIIa), (IIIb), or (IIIc) wherein X is $C(=O)N(H)CH(CH_2OH)B(OCH_3)_2$.

In some embodiments is a compound of Formula (III), (IIIa), (IIIb), or (IIIc) wherein X is $C(=O)N(H)CH(R^7)B(OR^{B3})(OR^{B4})$ and $R^{B3}$ and $R^7$ together with the boron atom form an optionally substituted 5- or 6-membered boron containing ring. In some embodiments is a compound of Formula (III), (IIIa), (IIIb), or (IIIc) wherein X is

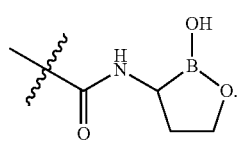 [SMILES: *C(=O)NC1CCOB1O]

In some embodiments is a compound of Formula (III), (IIIa), (IIIb), or (IIIc) wherein X is

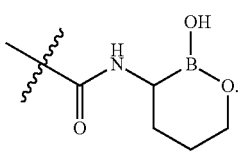 [SMILES: *C(=O)NC1CCCOB1O]

In some embodiments is a compound of Formula (III), (IIIa), (IIIb), or (IIIc) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring. In some embodiments is a compound of Formula (III), (IIIa), (IIIb), or (IIIc) wherein X is

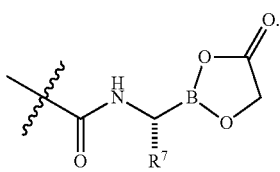

In some embodiments is a compound of Formula (III), (IIIa), (IIIb), or (IIIc) wherein X is

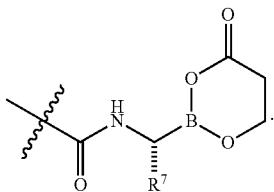

In some embodiments is a compound of Formula (III), (IIIa), (IIIb), or (IIIc) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring derived from a sugar. In some embodiments is a compound of Formula (III), (IIIa), (IIIb), or (IIIc) wherein X is

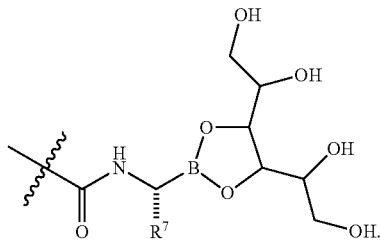

In some embodiments is a compound of Formula (III), (IIIa), (IIIb), or (IIIc) wherein X is

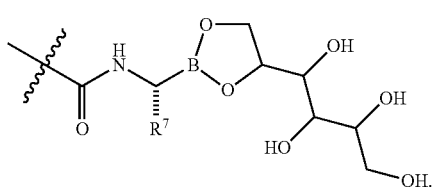

In some embodiments is a compound of Formula (III), (IIIa), (IIIb), or (IIIc) wherein X is

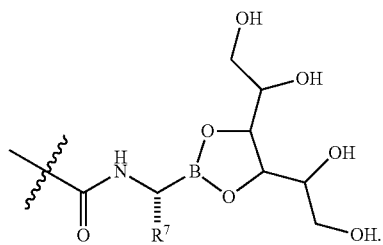

In some embodiments is a compound of Formula (III), (IIIa), (IIIb), or (IIIc) wherein X is

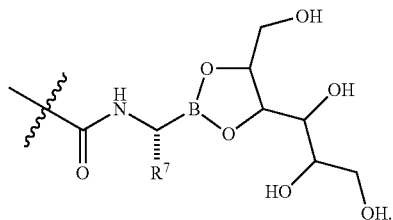

In some embodiments is a compound of Formula (III), (IIIa), (IIIb), or (IIIc) wherein X is

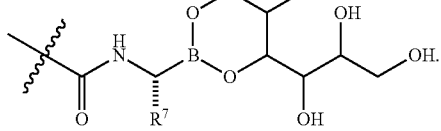

In some embodiments is a compound of Formula (III), (IIIa), (IIIb), or (IIIc) wherein X is

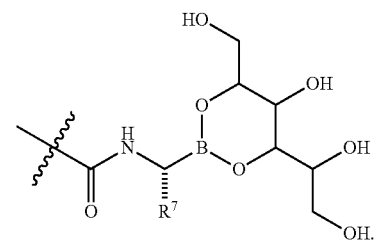

In some embodiments is a compound of Formula (III), (IIIa), (IIIb), or (IIIc) wherein X is

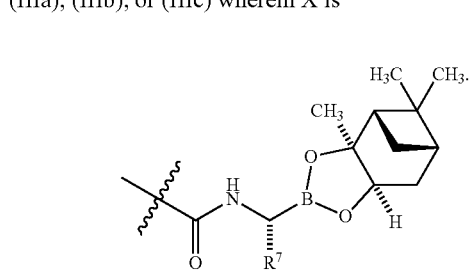

In further embodiments is a compound of Formula (III), (IIIa), (IIIb), or (IIIc) wherein X is

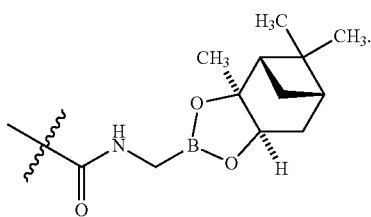 [SMILES: *C(=O)NCB1O[C@@H]2C[C@@H]3C[C@@H](C3(C)C)[C@]2(C)O1]

In further embodiments is a compound of Formula (III), (IIIa), (IIIb), or (IIIc) wherein X is

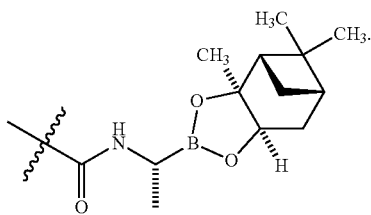 [SMILES: *C(=O)N[C@@H](C)B1O[C@@H]2C[C@@H]3C[C@@H](C3(C)C)[C@]2(C)O1]

In further embodiments is a compound of Formula (III), (IIIa), (IIIb), or (IIIc) wherein X is

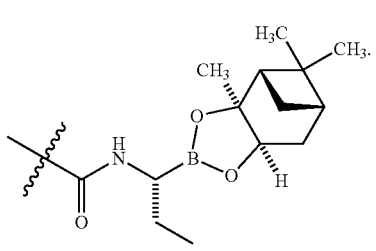 [SMILES: *C(=O)N[C@@H](CC)B1O[C@@H]2C[C@@H]3C[C@@H](C3(C)C)[C@]2(C)O1]

In further embodiments is a compound of Formula (III), (IIIa), (IIIb), or (IIIc) wherein X is

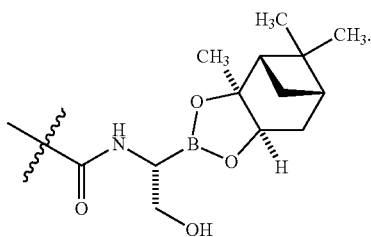 [SMILES: *C(=O)N[C@@H](CO)B1O[C@@H]2C[C@@H]3C[C@@H](C3(C)C)[C@]2(C)O1]

In some embodiments is a compound of Formula (III), (IIIa), (IIIb), or (IIIc) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

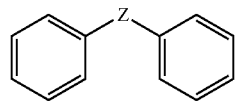

wherein Z is a bond, O, S, NH, $CH_2$ or C≡C. In some embodiments is a compound of Formula (III), (IIIa), (IIIb), or (IIIc) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

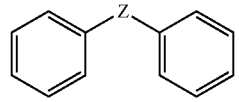

wherein Z is a bond, O, S, NH, $CH_2$ or C≡C. In some embodiments is a compound of Formula (III), (IIIa), (IIIb), or (IIIc) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

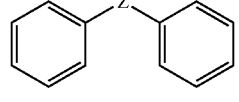

wherein Z is a bond. In some embodiments is a compound of Formula (III), (IIIa), (IIIb), or (IIIc) wherein $R^5$ is a linear alkyl chain of about 4-22 carbon atoms, wherein $R^5$ is bonded to the carbonyl carbon to which it is attached directly to provide an amide linkage, comprising at a chain terminus

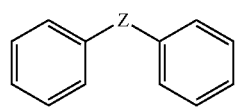

wherein Z is a bond. In some embodiments is a compound of Formula (III), (IIIa), (IIIb), or (IIIc) wherein $R^5$ is a linear alkyl chain of about 4-22 carbon atoms, wherein $R^5$ is bonded to the carbonyl carbon to which it is attached directly to provide an amide linkage, comprising within the chain

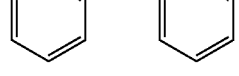

wherein Z is a bond. In some embodiments is a compound of Formula (III), (IIIa), (IIIb), or (IIIc) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (III), (IIIa), (IIIb), or (IIIc)

wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (III), (IIIa), (IIIb), or (IIIc) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (III), (IIIa), (IIIb), or (IIIc) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (III), (IIIa), (IIIb), or (IIIc) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (III), (IIIa), (IIIb), or (IIIc) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (III), (IIIa), (IIIb), or (IIIc) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (III), (IIIa), (IIIb), or (IIIc) wherein $R^{44}$ is H. In another embodiment is a compound of Formula (III), (IIIa), (IIIb), or (IIIc) wherein $R^{44}$ is $(C_1-C_6)$alkyl optionally substituted with 1 to 3 J. In another embodiment is a compound of Formula (III), (IIIa), (IIIb), or (IIIc) wherein $R^{44}$ is $CH_3$. In another embodiment is a compound of Formula (III), (IIIa), (IIIb), or (IIIc) wherein $R^{44}$ is $CH_2CH_3$. In another embodiment is a compound of Formula (III), (IIIa), (IIIb), or (IIIc) wherein $R^{44}$ is $CH_2CH(CH_3)_2$. In another embodiment is a compound of Formula (III), (IIIa), (IIIb), or (IIIc) wherein $R^{44}$ is $CH_2OH$. In another embodiment is a compound of Formula (III), (IIIa), (IIIb), or (IIIc) wherein $R^{44}$ is $CH(OH)CH_3$. In another embodiment is a compound of Formula (III), (IIIa), (IIIb), or (IIIc) wherein $R^{44}$ is $CH_2C(O)NH_2$. In another embodiment is a compound of Formula (III), (IIIa), (IIIb), or (IIIc) wherein $R^{44}$ is $CH_2CH_2CH_2CH_2NH_2$.

In another embodiment is a compound of Formula (III), (IIIa), (IIIb), or (IIIc) wherein $R^{48}$ is H, and $R^{44}$ is H. In another embodiment is a compound of Formula (III), (IIIa), (IIIb), or (IIIc) wherein $R^{48}$ is H, and $R^{44}$ is $(C_1-C_6)$alkyl optionally substituted with 1 to 3 J. In another embodiment is a compound of Formula (III), (IIIa), (IIIb), or (IIIc) wherein $R^{48}$ is H, and $R^{44}$ is $CH_3$. In another embodiment is a compound of Formula (III), (IIIa), (IIIb), or (IIIc) wherein $R^{48}$ is H, and $R^{44}$ is $CH_2CH_3$. In another embodiment is a compound of Formula (III), (IIIa), (IIIb), or (IIIc) wherein $R^{48}$ is H, and $R^{44}$ is $CH_2CH(CH_3)_2$. In another embodiment is a compound of Formula (III), (IIIa), (IIIb), or (IIIc) wherein $R^{48}$ is H, and $R^{44}$ is $CH_2OH$. In another embodiment is a compound of Formula (III), (IIIa), (IIIb), or (IIIc) wherein $R^{48}$ is H, and $R^{44}$ is $CH(OH)CH_3$. In another embodiment is a compound of Formula (III), (IIIa), (IIIb), or (IIIc) wherein $R^{48}$ is H, and $R^{44}$ is $CH_2C(O)NH_2$. In another embodiment is a compound of Formula (III), (IIIa), (IIIb), or (IIIc) wherein $R^{48}$ is H, and $R^{44}$ is $CH_2CH_2CH_2CH_2NH_2$.

In another embodiment of the aforementioned embodiments is a compound of Formula (III), (IIIa), (IIIb), or (IIIc) wherein $R^{44'}$, $R^{48'}$, $R^{49}$, $R^{49'}$, $R^{410}$, and $R^{410'}$ are each independently H. In another embodiment of the aforementioned embodiments is a compound of Formula (III), (IIIa), (IIIb), or (IIIc) wherein each m is 0. In another embodiment of the aforementioned embodiments is a compound of Formula (III), (IIIa), (IIIb), or (IIIc) wherein $R^{41}$, $R^{41'}$, $R^{42}$, $R^{4'}$, and $R^{4''}$ are each independently H.

Some embodiments of compounds of Formula (I), (Ia), (Ib), (Ic), (Id), (Ie), (II), (IIa), (IIb), (IIc), (III), (IIIa), (IIIb), or (IIIc) include, but are not limited to, compounds selected from the group consisting of:

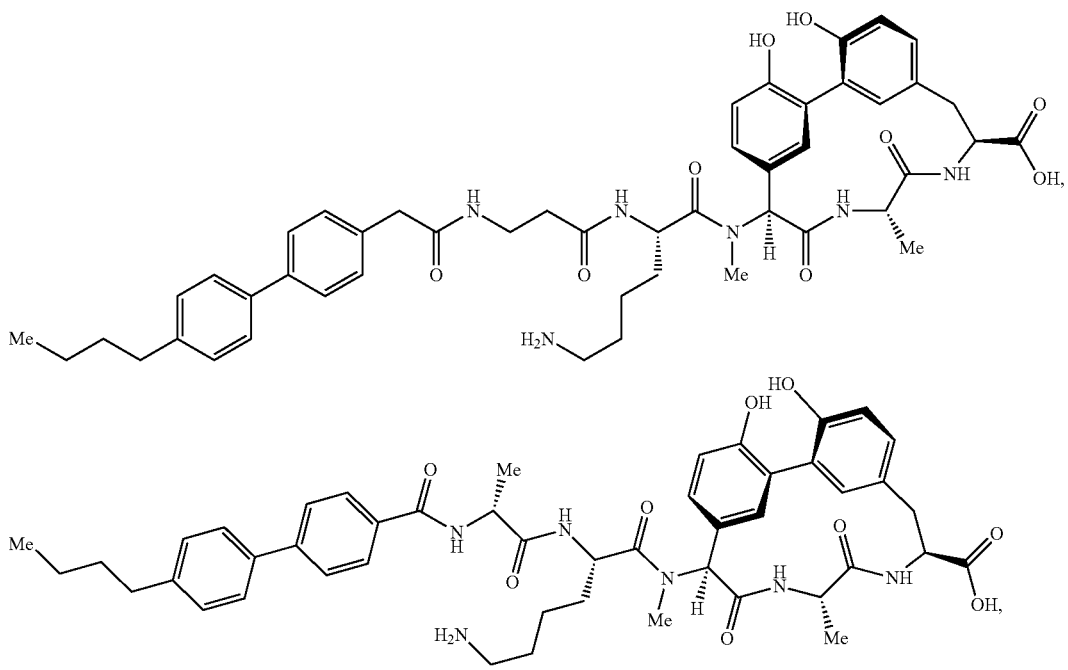

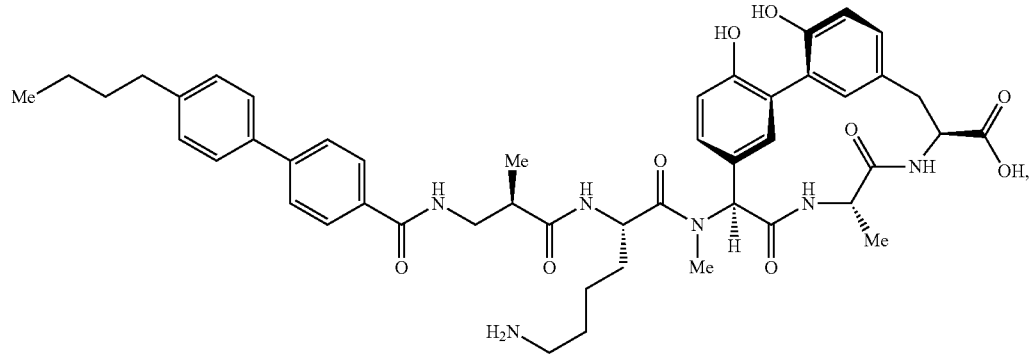
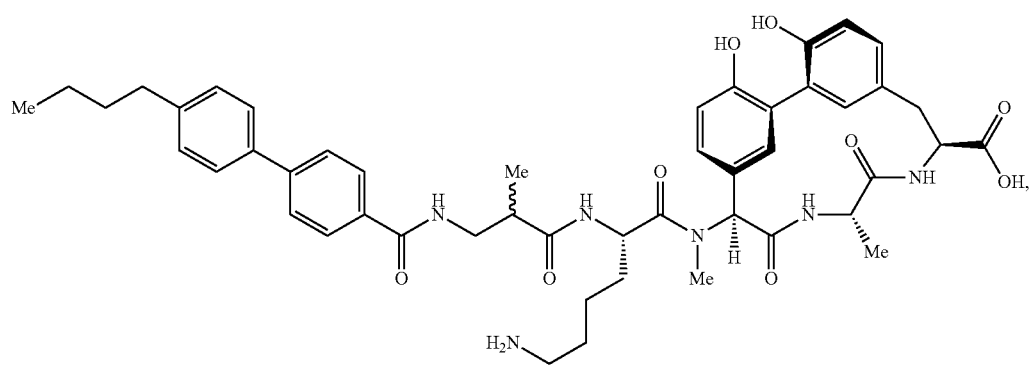
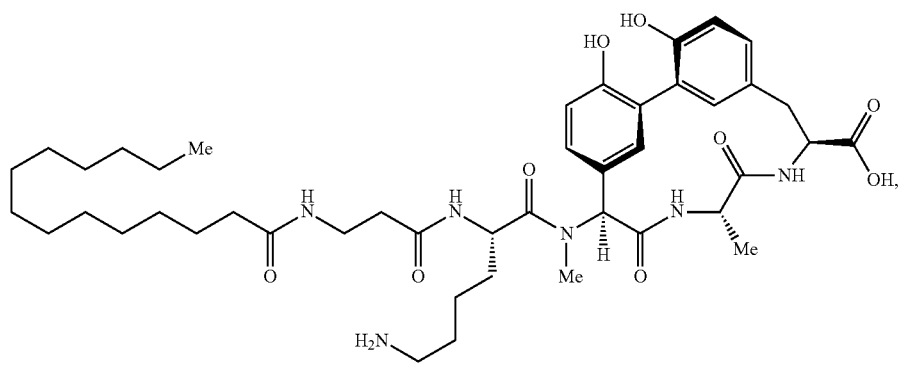
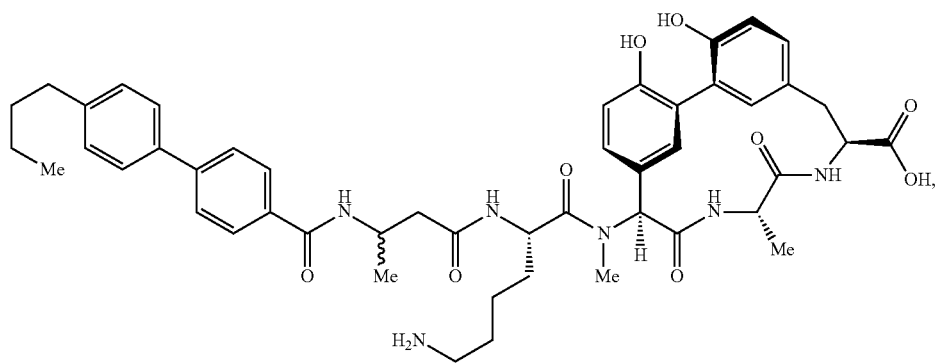

-continued
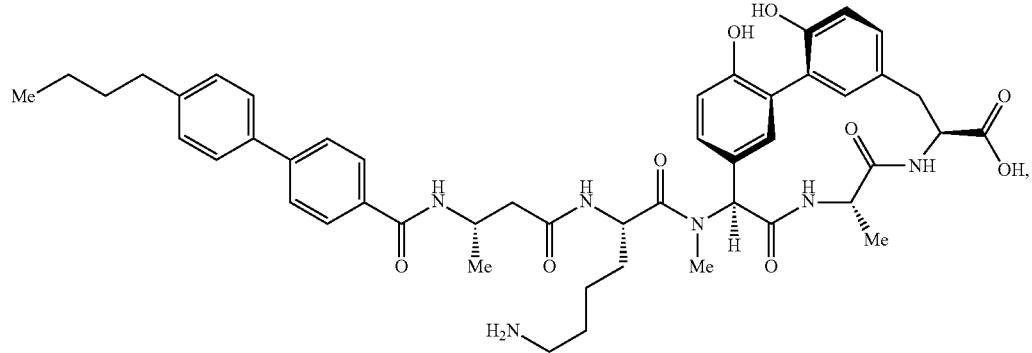
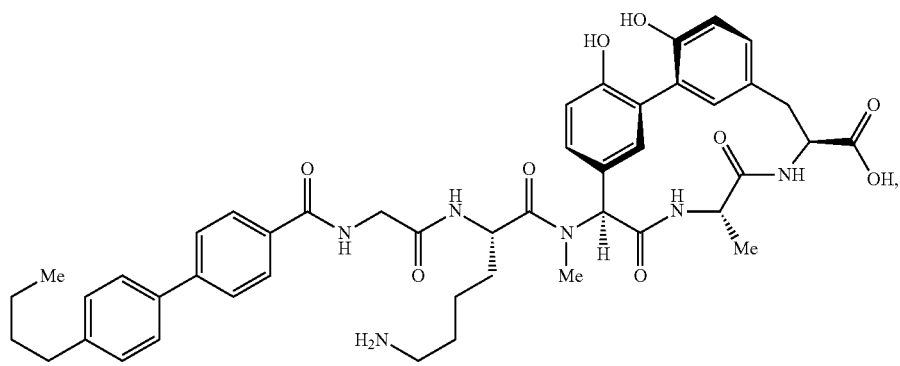
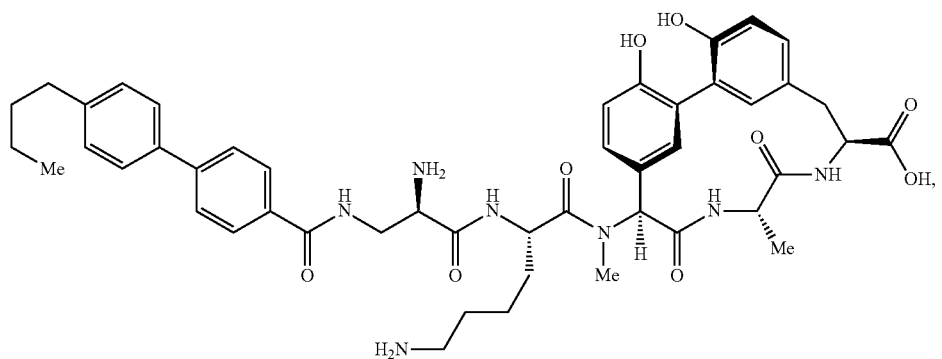
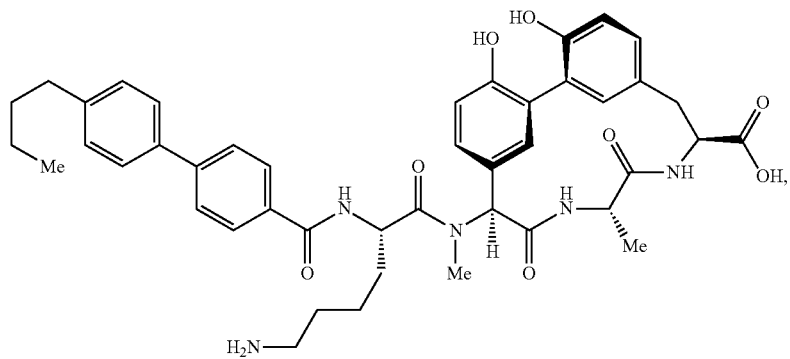

-continued
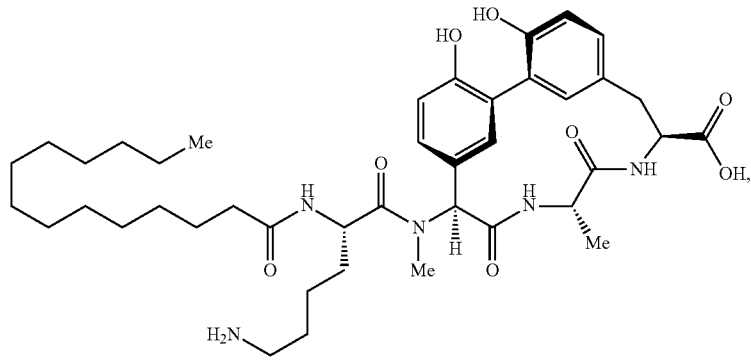
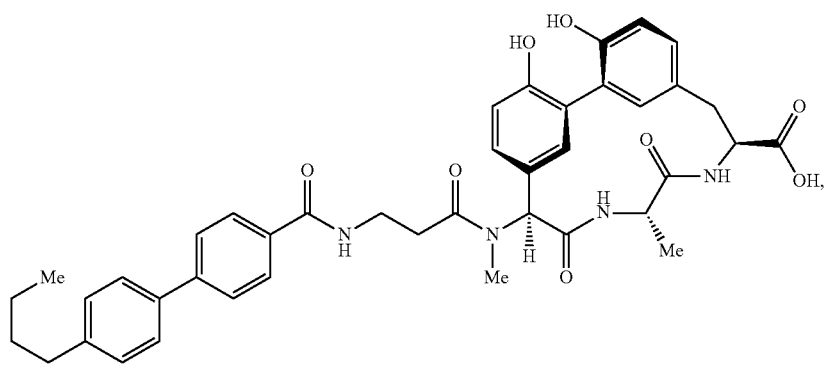
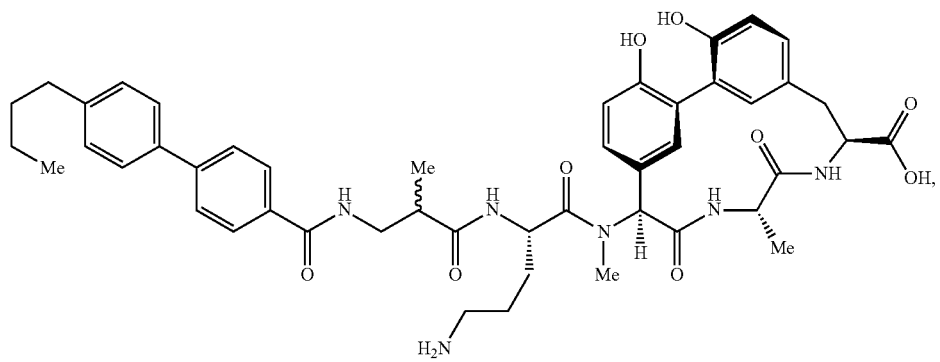
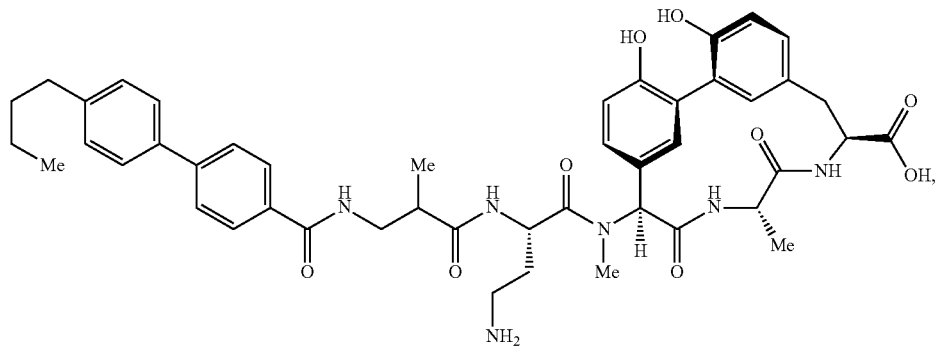

115
116
-continued
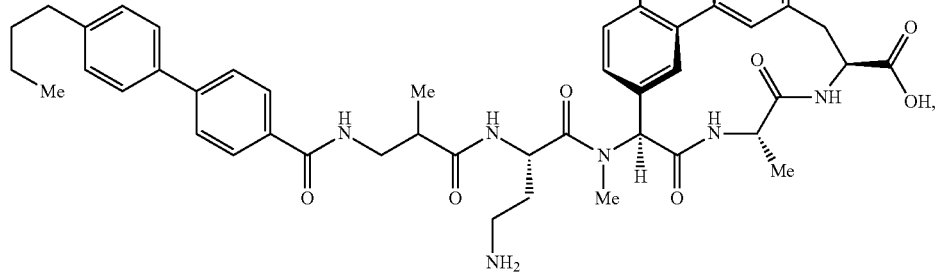
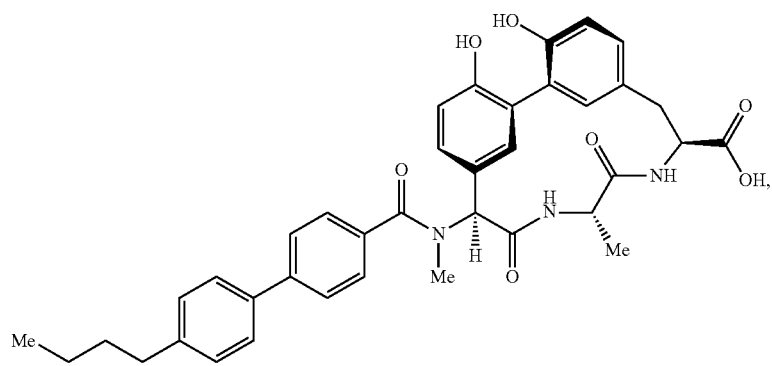
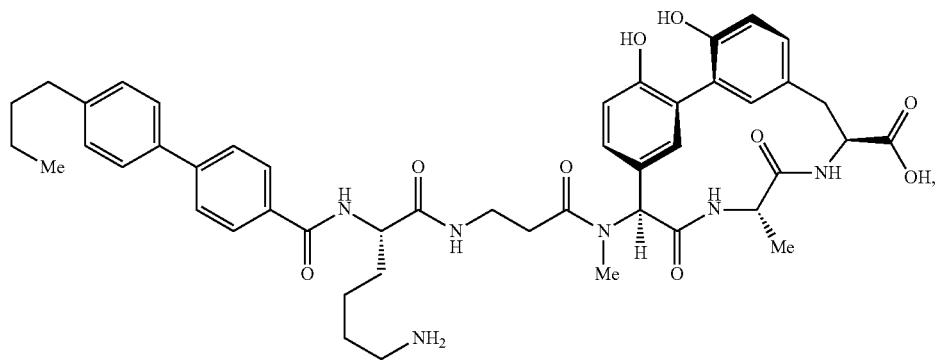
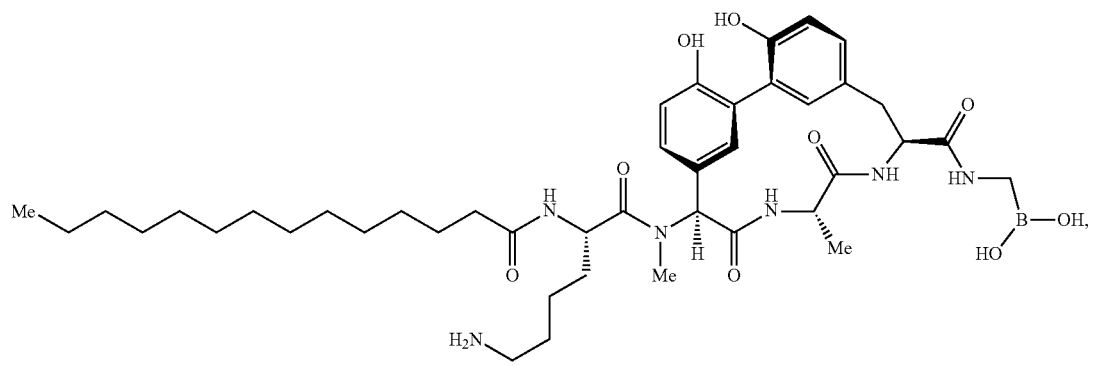

-continued
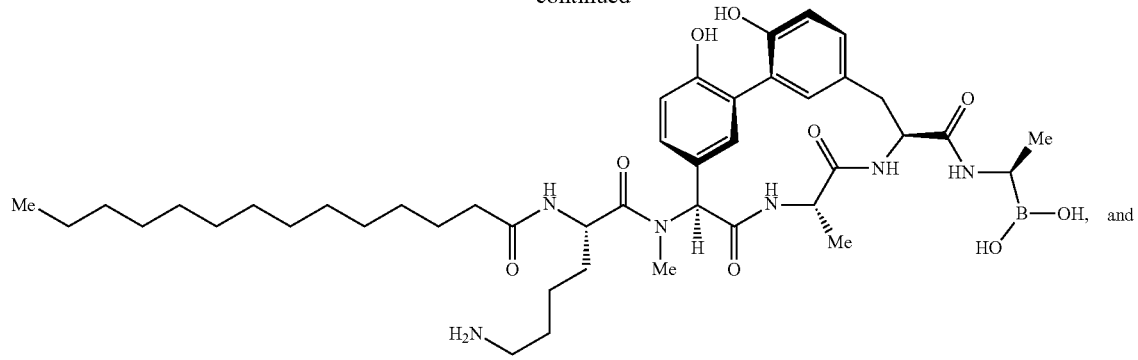
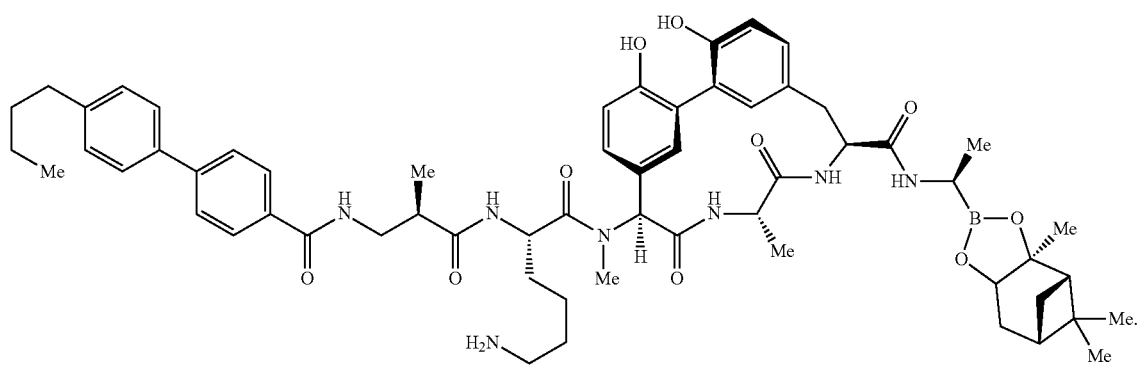
Some embodiments of compounds of Formula (I), (Ia), (Ib), (Ic), (Id), (Ie), (II), (IIa), (IIb), (IIc), (III), (IIIa), (IIIb), or (IIIc) include, but are not limited to, compounds selected from the group consisting of:
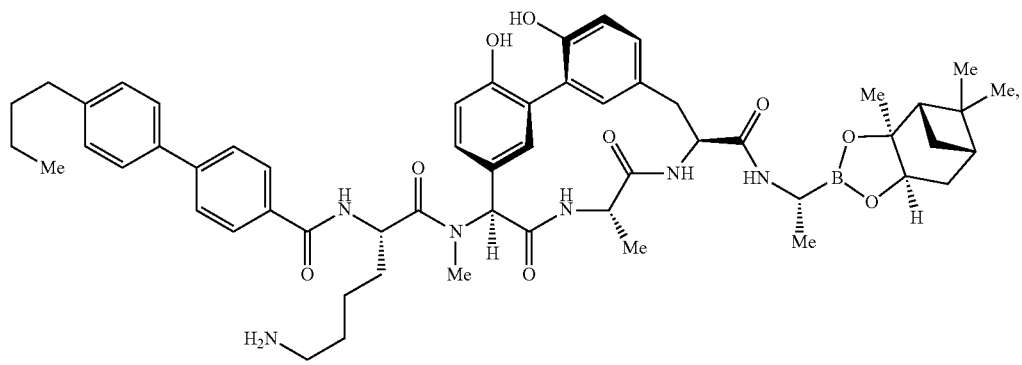
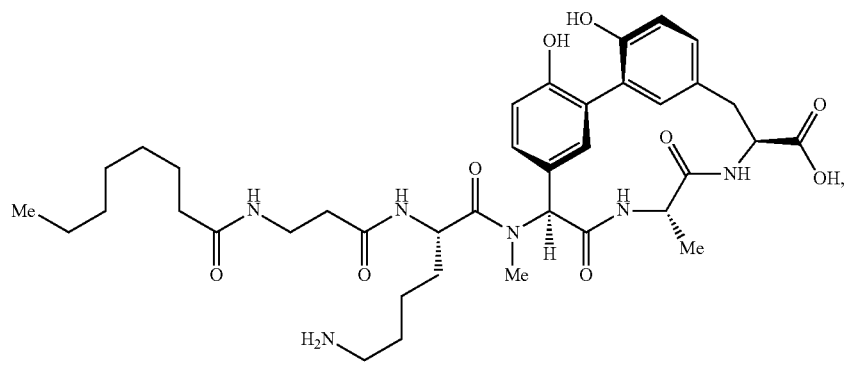

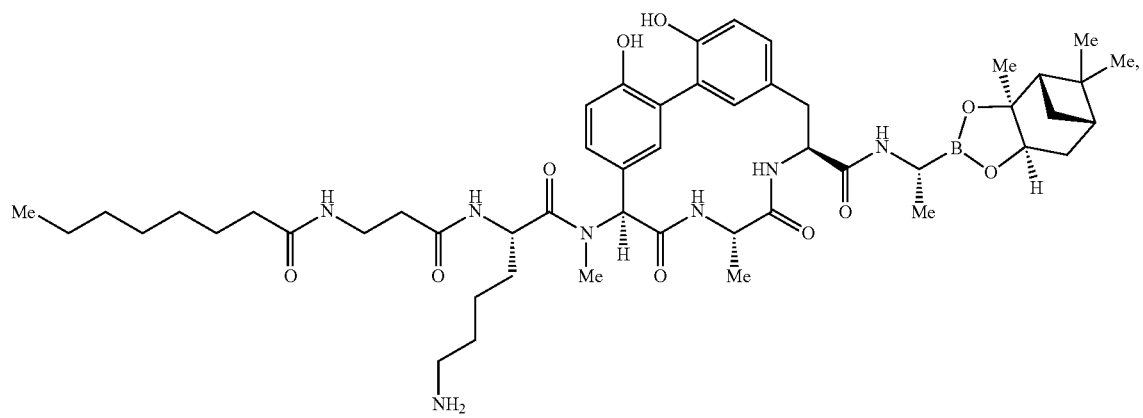
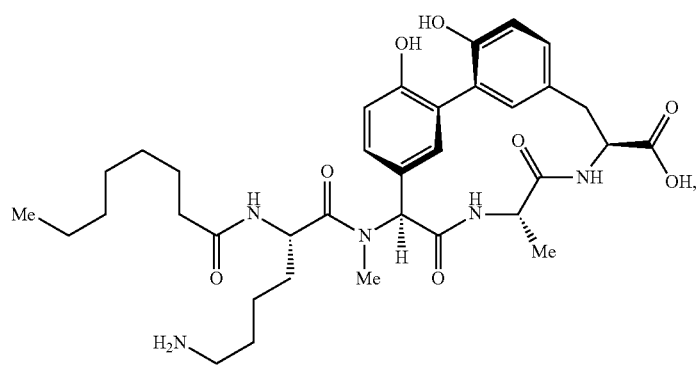
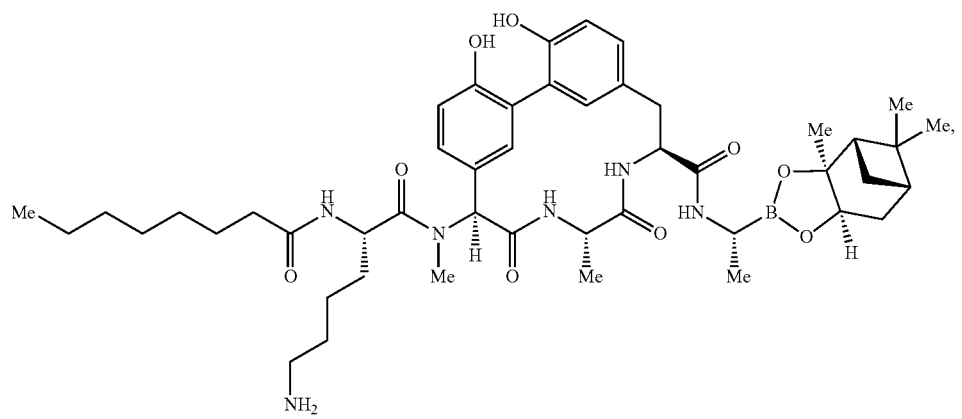
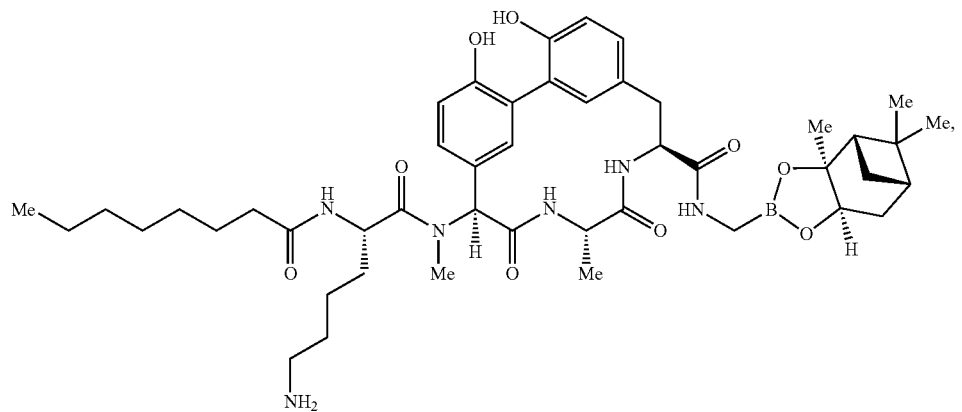

-continued
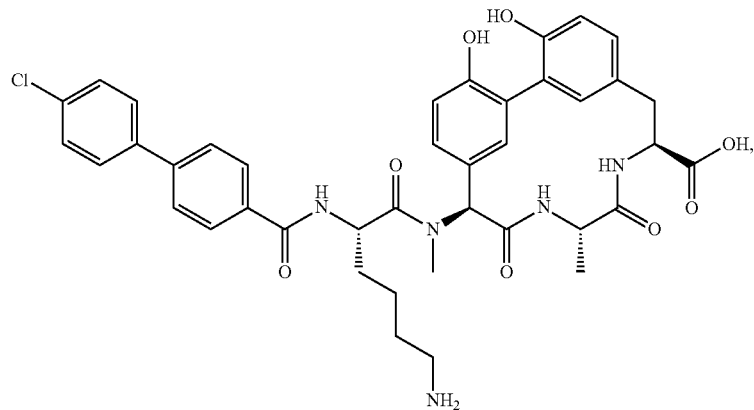
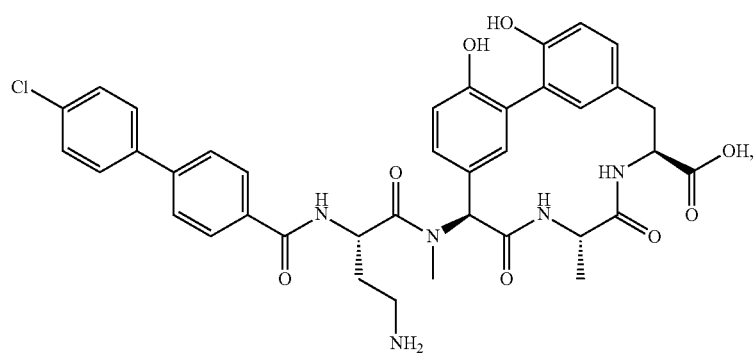
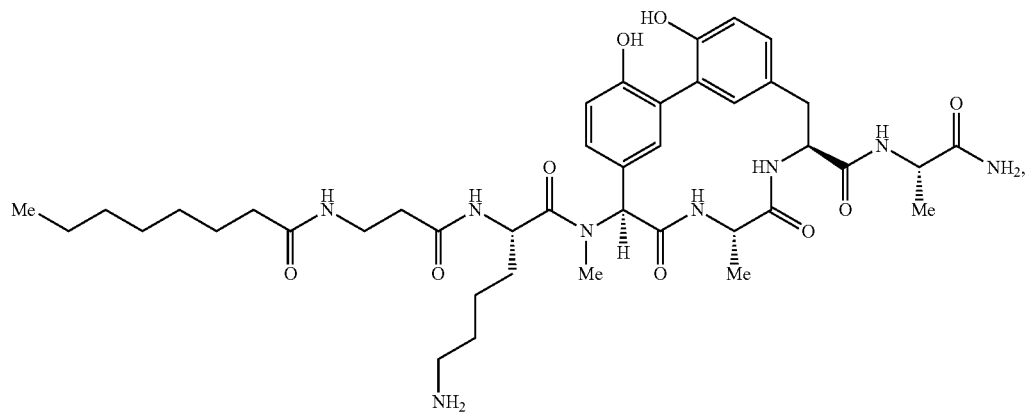
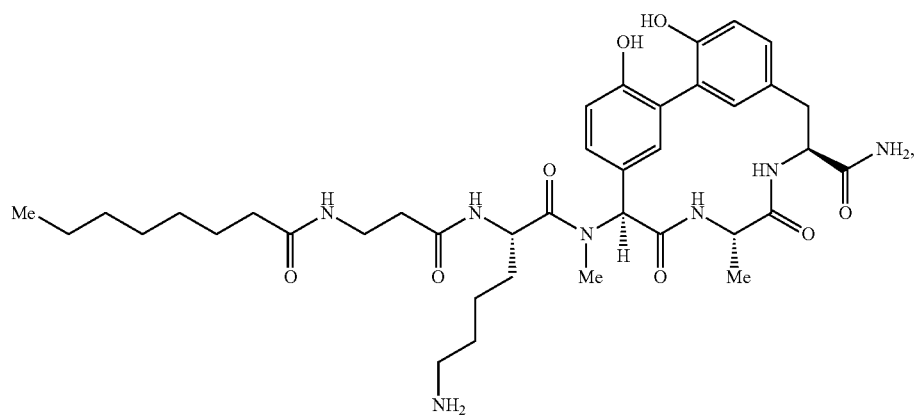

-continued
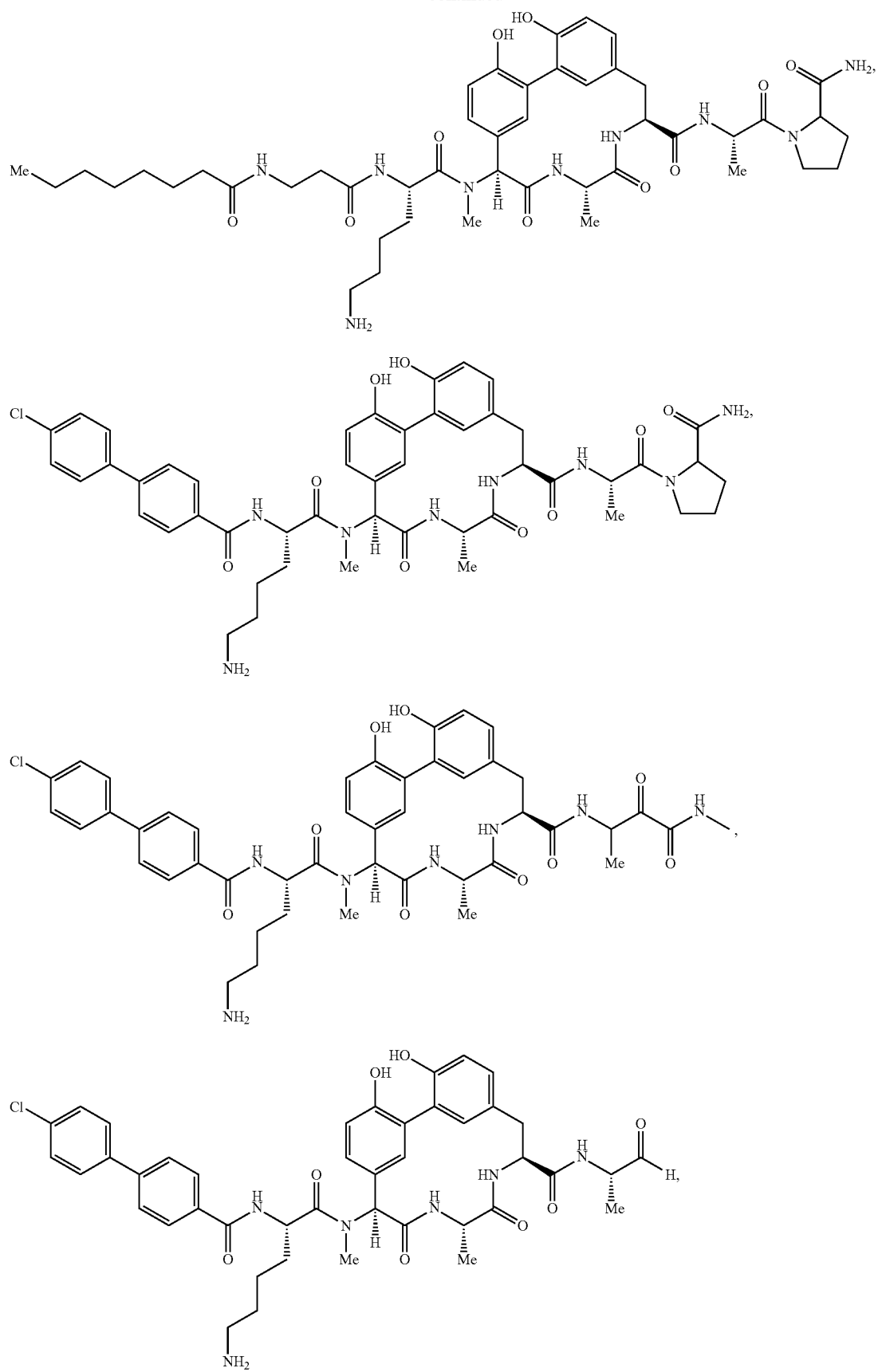

-continued
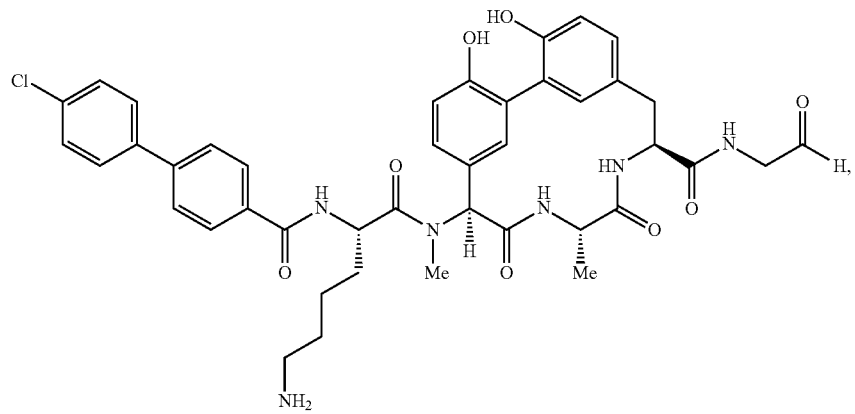
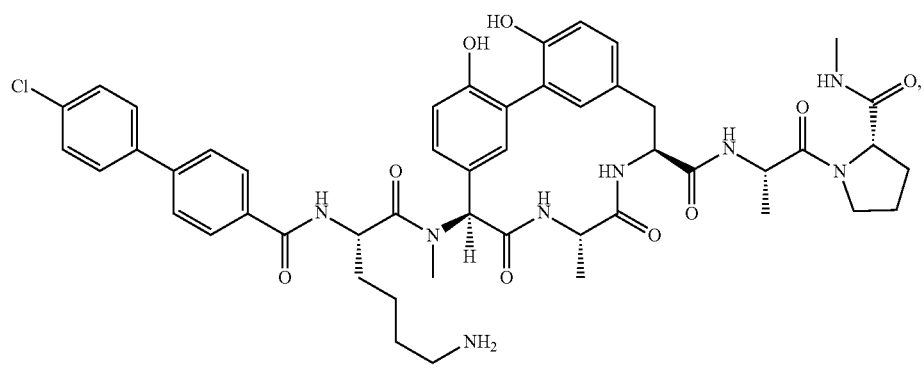
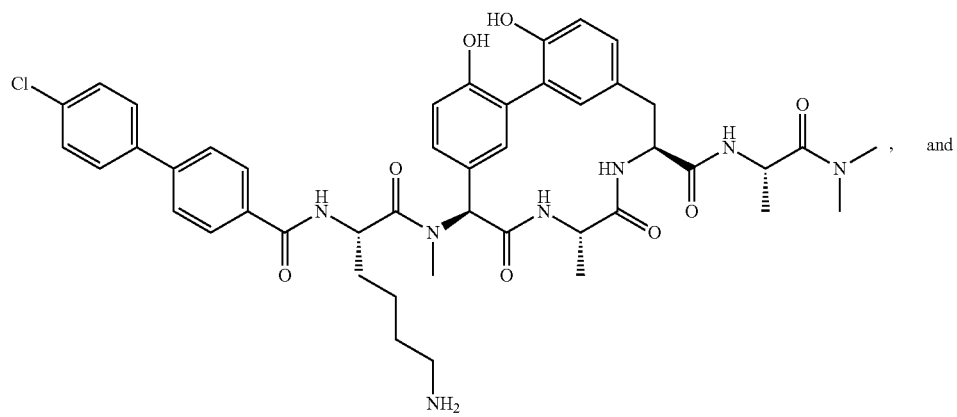
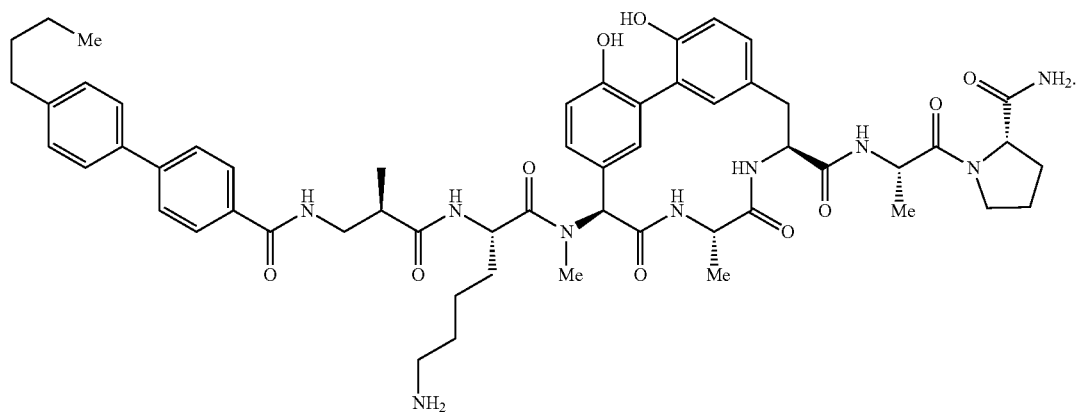

In another aspect described herein are compounds of Formula (IV):

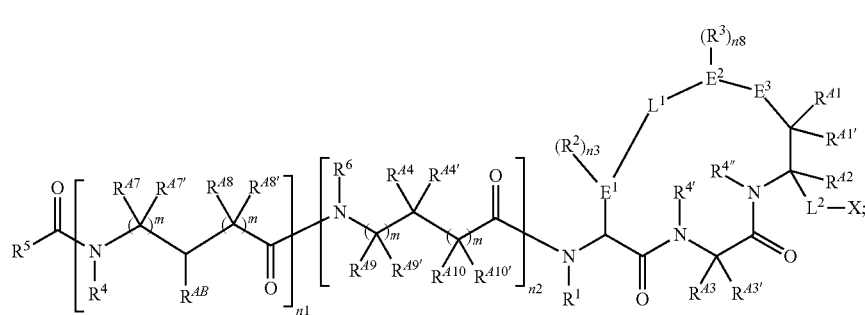

Formula (IV)

wherein:
$E^1$ is $(C_1\text{-}C_6)$alkyl, $(C_2\text{-}C_7)$alkenyl, $(C_2\text{-}C_7)$alkynyl, $(C_3\text{-}C_7)$cycloalkyl, heterocyclyl, heteroaryl, or aryl;

$E^2$ is independently $(C_1\text{-}C_6)$alkyl, $(C_2\text{-}C_7)$alkenyl, $(C_2\text{-}C_7)$alkynyl, $(C_3\text{-}C_7)$cycloalkyl, heterocyclyl, or heteroaryl;

$E^3$ is a bond or —O—;

$L^1$ is a bond, —O—, —S—, —NR$^4$—, —C(O)—, —CH$_2$O—, —OCH$_2$—, —OCH$_2$CH$_2$CH$_2$O—, —OCH$_2$CH$_2$CH$_2$CH$_2$O—, —CH$_2$S—, —SCH$_2$—, —CH$_2$NR$^4$—, —NR$^4$—CH$_2$—, —NR$^4$C(O)—, —C(O)NR$^4$—, —NR$^4$S(O)$_2$—, —S(O)$_2$NR$^4$—, —NR$^4$C(O)NR$^4$—, or $(C_1\text{-}C_4)$alkylene optionally substituted with OH, CN, NO$_2$, halogen, $(C_1\text{-}C_6)$alkyl;

$L^2$ is a bond, or optionally substituted $(C_1\text{-}C_6)$alkylene;

X is a group of formula

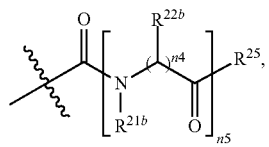

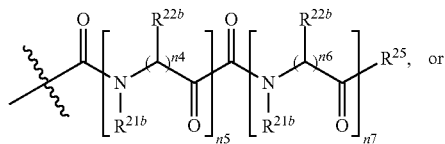

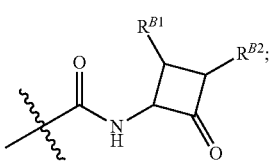

wherein n4, n5, and n6 are each independently 1, 2 or 3; n7 is 0, 1 or 2; $R^{21b}$ and $R^{22b}$ are independently at each occurrence hydrogen, hydroxy, $(C_1\text{-}C_6)$alkyl, $(C_3\text{-}C_7)$cycloalkyl, 5- to 7-membered heteroaryl, 5- to 7-membered heterocyclyl, or $(C_6\text{-}C_{10})$ aryl, wherein any alkyl, cycloalkyl, heterocyclyl, aryl or heteroaryl is optionally substituted with 1 to 3 J; $R^{25}$ is H, OH, OR$^C$,

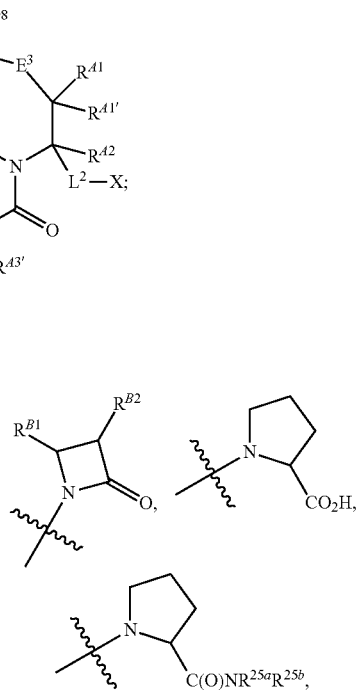

or NR$^{25a}$R$^{25b}$ where R$^{25a}$ and R$^{25b}$ are each independently H, SO$_2$(C$_1$-C$_6$)alkyl, or optionally substituted alkyl; RB1 and $R^{B2}$ are each independently H, (C$_1$-C$_6$)alkyl, (C$_3$-C$_6$)cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$)alkyl, and a wavy line indicates a point of attachment of X to a carbon of formula (IV) bearing X; or X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

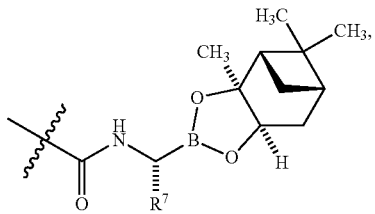

wherein R$^7$ is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, or —CH$_2$CH$_2$CO$_2$H; or R$^{B3}$ and R$^{B4}$ together with the boron atom form an optionally substituted 5- or 6-membered boron containing ring;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

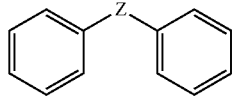

wherein Z is a bond, O, S, NH, $CH_2$ or C≡C;

$R^2$ and $R^3$ are each independently nitro, halo, cyano, hydroxy, glycosyloxy, amino, $(C_1$-$C_4)$alkoxy, $(C_1$-$C_4)$acyloxy, $(C_1$-$C_4)$alkyl, or a group cleavable under physiological conditions to provide a compound of formula (IV) wherein $R^2$ or $R^3$ respectively is hydroxy, wherein any carbon atom is optionally substituted with J;

n1 and n2 are independently 0 or 1;

n3 and n8 are independently 0, 1, or 2;

each m is independently 0 or 1;

$R^1$ is hydrogen or $(C_1$-$C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1$-$C_6)$alkyl optionally substituted with 1 to 3 J;

$R^6$ is hydrogen, or $(C_1$-$C_6)$alkyl optionally substituted with 1 to 3 J; or $R^6$ together with $R^{A4}$ form a ring;

$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1$-$C_6)$alkyl, $(C_3$-$C_7)$cycloalkyl, 5- to 7-membered heteroaryl, 5- to 7-membered heterocyclyl, or $(C_6$-$C_{10})$ aryl, wherein any alkyl, cycloalkyl, heterocyclyl, aryl or heteroaryl is optionally substituted with 1 to 3 J;

$R^{A6}$ is amino, $(C_1$-$C_6)$alkyl, $(C_3$-$C_7)$cycloalkyl, 5- to 7-membered heteroaryl, 5- to 7-membered heterocyclyl, or $(C_6$-$C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)OR'$, $(CH_2)_{0-p}C(O)N(R')_2$, $(CH_2)_{0-p}OC(O)N(R')_2$, $(CH_2)_{0-p}NH-C(O)R'$, $(CH_2)_{0-p}N(R')SO_2R'$, $(CH_2)_{0-p}N(R')C(O)OR'$, $(CH_2)_{0-p}N(R')C(O)R'$, $(CH_2)_{0-p}N(R')C(O)N(R')_2$, or $(CH_2)_{0-p}C(NH)N(R')_2$, wherein p is 4;

each R' is independently at each occurrence hydrogen, $(C_1$-$C_6)$-alkyl, $(C_2$-$C_7)$-alkenyl, $(C_2$-$C_7)$-alkynyl, $(C_3$-$C_{10})$-cycloalkyl, $(C_3$-$C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1$-$C_4)$alkyl$)_2$—, —NH$(C_1$-$C_4)$alkyl, $C_1$-$C_6$alkyl, $C_3$-$C_8$cycloalkyl, or $C_1$-$C_6$heteroalkyl; or a pharmaceutically acceptable salt, solvate, or prodrug thereof.

In one embodiment is a compound of Formula (IV) wherein $E^1$ and $E^2$ are each independently $(C_1$-$C_6)$alkyl, $E^3$ is —O—, and $L^1$ is —O—. In a further embodiment, $E^1$ is methyl, ethyl, or propyl. In yet a further embodiment, $E^2$ is methyl, ethyl, or propyl. In another embodiment is a compound of Formula (IV) wherein $E^1$ and $E^2$ are each independently $(C_1$-$C_6)$alkyl, $E^3$ is a bond, and $L^1$ is —O—. In a further embodiment, $E^1$ is methyl, ethyl, or propyl. In yet a further embodiment, $E^2$ is methyl, ethyl, propyl, or butyl. In another embodiment is a compound of Formula (IV) wherein $E^1$ and $E^2$ are each independently $(C_1$-$C_6)$alkyl, $E^3$ is a bond, and $L^1$ is —$OCH_2CH_2CH_2O$—. In a further embodiment, $E^1$ is methyl, ethyl, or propyl. In a further embodiment, $E^1$ is methyl. In yet a further embodiment, $E^2$ is methyl, ethyl, or propyl. In a further embodiment, $E^2$ is methyl. In another embodiment is a compound of Formula (IV) wherein $E^1$ and $E^2$ are each independently $(C_1$-$C_6)$alkyl, $E^3$ is a bond, and $L^1$ is —$OCH_2CH_2CH_2O$—. In a further embodiment, $E^1$ is methyl, ethyl, or propyl. In a further embodiment, $E^1$ is methyl. In yet a further embodiment, $E^2$ is methyl, ethyl, or propyl. In a further embodiment, $E^2$ is ethyl. In another embodiment is a compound of Formula (IV) wherein $E^1$ and $E^2$ are each independently $(C_1$-$C_6)$alkyl, $E^3$ is a bond, and $L^1$ is —C(O)NH—. In a further embodiment, $E^1$ is methyl, ethyl, or propyl. In a further embodiment, $E^1$ is ethyl or propyl. In a further embodiment, $E^2$ is methyl, ethyl, propyl, or butyl. In yet a further embodiment, $E^2$ is ethyl, or propyl. In another embodiment is a compound of Formula (IV) wherein $E^1$ aryl, $E^2$ is $(C_1$-$C_6)$alkyl, $E^3$ is a bond, and $L^1$ is a bond. In a further embodiment, $E^1$ is phenyl. In a further embodiment, $E^2$ is methyl, ethyl, propyl, or butyl. In yet a further embodiment, $E^2$ is ethyl, or propyl. In another embodiment is a compound of Formula (IV) wherein $E^1$ aryl, $E^2$ is $(C_1$-$C_6)$alkyl, $E^3$ is a —O—, and $L^1$ is a bond. In a further embodiment, $E^1$ is phenyl. In a further embodiment, $E^2$ is methyl, ethyl, propyl, or butyl. In yet a further embodiment, $E^2$ is ethyl, or propyl.

In another embodiment is a compound of Formula (IV) wherein $L^2$ is a bond. In another embodiment is a compound of Formula (IV) wherein $L^2$ is optionally substituted $(C_1$-$C_6)$ alkylene. In a further embodiment, $L^2$ is methylene, ethylene, n-propylene, iso-propylene, n-butylene, iso-butylene, or tert-butylene.

In one embodiment is a compound of Formula (IV) wherein X is $CO_2H$, $CH_2CO_2H$, C(=O)NHCH$_2$C(=O)H, $CH_2C$(=O)H, C(=O)N(H)CH($R^7$)B(O$R^{B3}$)(O$R^{B4}$), or

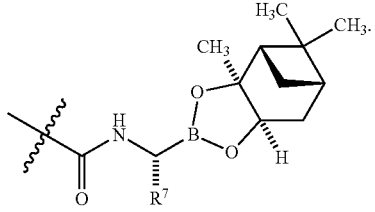

In some embodiments is a compound of Formula (IV) wherein X is $CO_2H$. In some embodiments is a compound of Formula (IV) wherein X is $CH_2CO_2H$. In some embodiments is a compound of Formula (IV) wherein X is C(=O)NHCH$_2$C(=O)H. In some embodiments is a compound of Formula (IV) wherein X is $CH_2$C(=O)H.

In some embodiments is a compound of Formula (IV) wherein X is C(=O)N(H)CH($R^7$)B(O$R^{B3}$)(O$R^{B4}$). In further embodiments is a compound of Formula (IV) wherein X is C(=O)N(H)CH$_2$B(OH)$_2$. In further embodiments is a compound of Formula (IV) wherein X is C(=O)N(H)CH(CH$_2$CH$_3$)B(OH)$_2$. In further embodiments is a compound of Formula (IV) wherein X is C(=O)N(H)CH(CH$_2$CH$_3$)B(OH)$_2$. In further embodiments is a compound of Formula (IV) wherein X is C(=O)N(H)CH(CH$_2$OH)B(OH)$_2$. In further embodiments is a compound of Formula (IV) wherein X is C(=O)N(H)CH$_2$B(OCH$_3$)$_2$. In further embodiments is a compound of Formula (IV) wherein X is C(=O)N(H)CH(CH$_3$)B(OCH$_3$)$_2$. In further embodiments is a compound of Formula (IV) wherein X is C(=O)N(H)CH(CH$_2$CH$_3$)B(OCH$_3$)$_2$. In further embodiments is a compound of Formula (IV) wherein X is C(=O)N(H)CH(CH$_2$OH)B(OCH$_3$)$_2$.

In some embodiments is a compound of Formula (IV) wherein X is C(=O)N(H)CH(R$^7$)B(OR$^{B3}$)(OR$^{B4}$) and R$^{B3}$ and R$^7$ together with the boron atom form an optionally substituted 5- or 6-membered boron containing ring. In some embodiments is a compound of Formula (IV) wherein X is

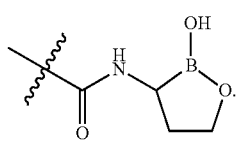 [SMILES: *C(=O)NC1CCOB1O]

In some embodiments is a compound of Formula (IV) wherein X is

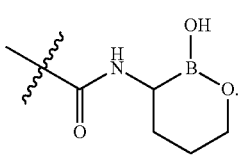 [SMILES: *C(=O)NC1CCCOB1O]

In some embodiments is a compound of Formula (IV) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring. In some embodiments is a compound of Formula (IV) wherein X is

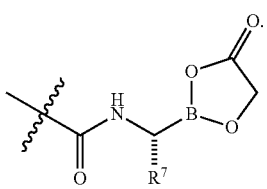

In some embodiments is a compound of Formula (IV) wherein X is

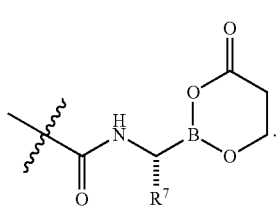

In some embodiments is a compound of Formula (IV) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring derived from a sugar. In some embodiments is a compound of Formula (IV) wherein X is

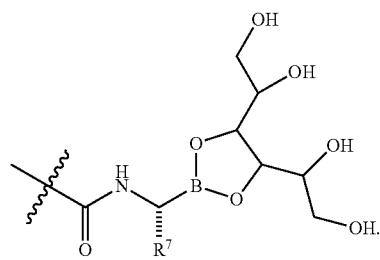

In some embodiments is a compound of Formula (IV) wherein X is

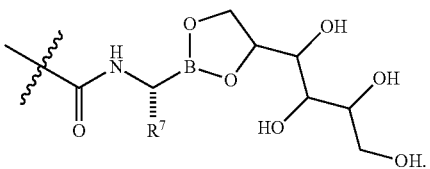

In some embodiments is a compound of Formula (IV) wherein X is

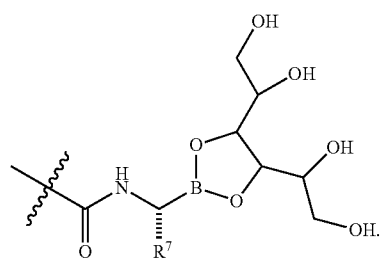

In some embodiments is a compound of Formula (IV) wherein X is

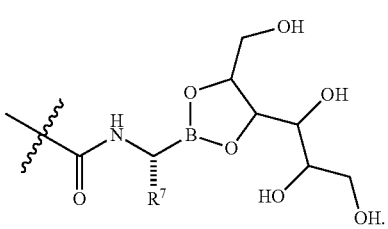

In some embodiments is a compound of Formula (IV) wherein X is

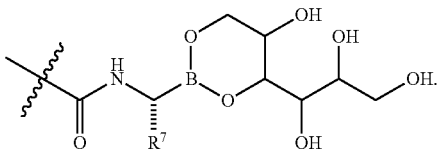

In some embodiments is a compound of Formula (IV) wherein X is

In some embodiments is a compound of Formula (IV) wherein X is

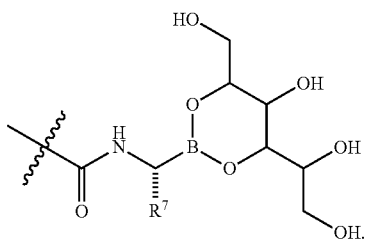

In further embodiments is a compound of Formula (IV) wherein X is

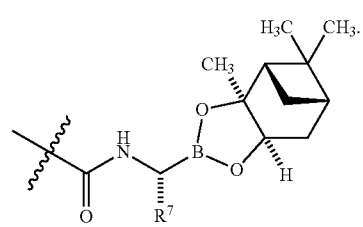

In further embodiments is a compound of Formula (IV) wherein X is

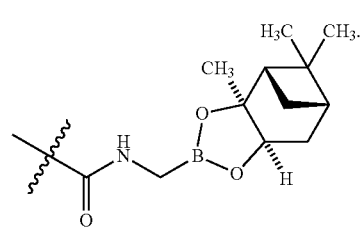 [SMILES: *C(=O)NCB1O[C@@H]2C[C@@H]3C[C@@H](C3(C)C)[C@]2(C)O1]

In further embodiments is a compound of Formula (IV) wherein X is

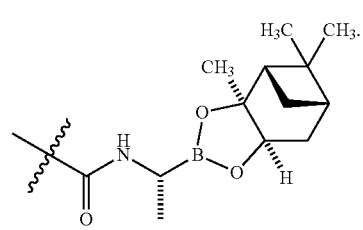

In further embodiments is a compound of Formula (IV) wherein X is

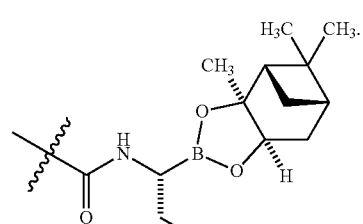 [SMILES: *C(=O)N[C@@H](C)B1O[C@@H]2C[C@@H]3C[C@@H](C3(C)C)[C@]2(C)O1]

In some embodiments is a compound of Formula (IV) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

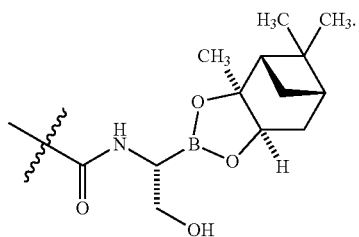

wherein Z is a bond, O, S, NH, $CH_2$ or C≡C. In some embodiments is a compound of Formula (IV) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

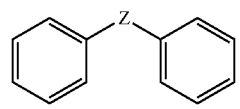

wherein Z is a bond, O, S, NH, $CH_2$ or C≡C. In some embodiments is a compound of Formula (IV) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

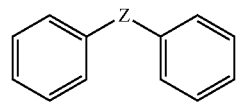

wherein Z is a bond. In some embodiments is a compound of Formula (IV) wherein $R^5$ is a linear alkyl chain of about 4-22 carbon atoms, wherein $R^5$ is bonded to the carbonyl carbon to which it is attached directly to provide an amide linkage, comprising at a chain terminus

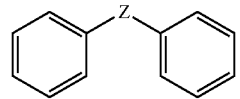

wherein Z is a bond. In some embodiments is a compound of Formula (IV) wherein $R^5$ is a linear alkyl chain of about 4-22 carbon atoms, wherein $R^5$ is bonded to the carbonyl carbon to which it is attached directly to provide an amide linkage, comprising within the chain

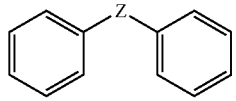

wherein Z is a bond. In some embodiments is a compound of Formula (IV) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (IV) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (IV) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (IV) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (IV) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (IV) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (IV) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (IV) wherein n1 is 0 and n2 is 1. In another embodiment is a compound of Formula (IV) wherein n1 is 0, n2 is 1, and $R^{44}$ is H. In another embodiment is a compound of Formula (IV) wherein n1 is 0, n2 is 1, and $R^{44}$ is $(C_1$-$C_6)$alkyl optionally substituted with 1 to 3 J. In another embodiment is a compound of Formula (IV) wherein n1 is 0, n2 is 1, and $R^{44}$ is $CH_3$. In another embodiment is a compound of Formula (IV) wherein n1 is 0, n2 is 1, and $R^{44}$ is $CH_2CH_3$. In another embodiment is a compound of Formula (IV) wherein n1 is 0, n2 is 1, and $R^{44}$ is $CH_2CH(CH_3)_2$. In another embodiment is a compound of Formula (IV) wherein n1 is 0, n2 is 1, and $R^{44}$ is $CH_2OH$. In another embodiment is a compound of Formula (IV) wherein n1 is 0, n2 is 1, and $R^{44}$ is $CH(OH)CH_3$. In another embodiment is a compound of Formula (IV) wherein n1 is 0, n2 is 1, and $R^{44}$ is $CH_2C(O)NH_2$. In another embodiment is a compound of Formula (IV) wherein n1 is 0, n2 is 1, and $R^{44}$ is $CH_2CH_2CH_2CH_2NH_2$.

In another embodiment is a compound of Formula (IV) wherein n1 is 1 and n2 is 1. In another embodiment is a compound of Formula (IV) wherein n1 is 1, n2 is 1, $R^{46}$ is $CH_3$, and $R^{44}$ is $(C_1$-$C_6)$alkyl optionally substituted with 1 to 3 J. In another embodiment is a compound of Formula (IV) wherein n1 is 1, n2 is 1, $R^{46}$ is $CH_3$, and $R^{44}$ is $CH_3$. In another embodiment is a compound of Formula (IV) wherein n1 is 1, n2 is 1, $R^{46}$ is $CH_3$, and $R^{44}$ is $CH_2CH_3$. In another embodiment is a compound of Formula (IV) wherein n1 is 1, n2 is 1, $R^{46}$ is $CH_3$, and $R^{44}$ is $CH_2CH(CH_3)_2$. In another embodiment is a compound of Formula (IV) wherein n1 is 1, n2 is 1, $R^{46}$ is $CH_3$, and $R^{44}$ is $CH_2OH$. In another embodiment is a compound of Formula (IV) wherein n1 is 1, n2 is 1, $R^{46}$ is $CH_3$, and $R^{44}$ is $CH(OH)CH_3$. In another embodiment is a compound of Formula (IV) wherein n1 is 1, n2 is 1, $R^{46}$ is $CH_3$, and $R^{44}$ is $CH_2C(O)NH_2$. In another embodiment is a compound of Formula (IV) wherein n1 is 1, n2 is 1, $R^{46}$ is $CH_3$, and $R^{44}$ is $CH_2CH_2CH_2CH_2NH_2$.

In another embodiment of the aforementioned embodiments is a compound of Formula (IV) wherein $R^{47}$, $R^{47'}$, $R^{48}$, $R^{48'}$, $R^{49}$, $R^{49'}$, $R^{44'}$, $R^{410}$, and $R^{410'}$ are each independently H. In another embodiment of the aforementioned embodiments is a compound of Formula (IV) wherein each m is 0. In another embodiment of the aforementioned embodiments is a compound of Formula (IV) wherein $R^{41}$, $R^{41'}$, $R^{42}$, $R^{4'}$, and $R^{4''}$ are each independently H. In another embodiment of the aforementioned embodiments is a compound of Formula (IV) wherein n3 is 0 and n8 is 0. In another embodiment of the aforementioned embodiments is a compound of Formula (IV) wherein n3 is 1 and n8 is 0.

In another embodiment is a compound of Formula (IV) having the structure of Formula (IVa):

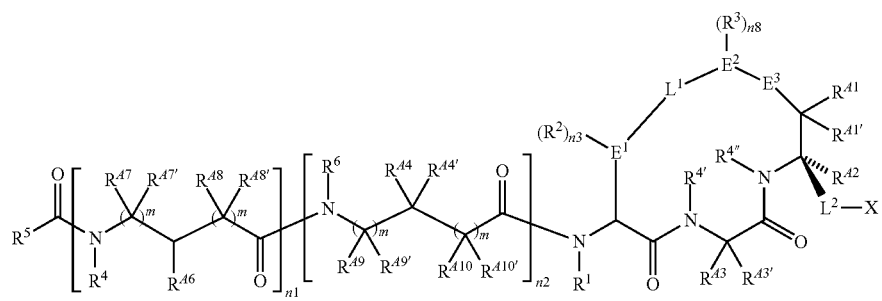

wherein $E^1$ is $(C_1$-$C_6)$alkyl, $(C_2$-$C_7)$alkenyl, $(C_2$-$C_7)$alkynyl, $(C_3$-$C_7)$cycloalkyl, heterocyclyl, heteroaryl, or aryl;

$E^2$ is independently $(C_1$-$C_6)$alkyl, $(C_2$-$C_7)$alkenyl, $(C_2$-$C_7)$alkynyl, $(C_3$-$C_7)$cycloalkyl, heterocyclyl, or heteroaryl;

$E^3$ is a bond or —O—;

L¹ is a bond, —O—, —S—, —NR⁴—, —C(O)—, —CH₂O—, —OCH₂—, —OCH₂CH₂CH₂O—, —OCH₂CH₂CH₂CH₂O—, —CH₂S—, —SCH₂—, —CH₂NR⁴—, —NR⁴—CH₂—, —NR⁴C(O)—, —C(O)NR⁴—, —NR⁴S(O)₂—, —S(O)₂NR⁴—, —NR⁴C(O)NR⁴—, or (C₁-C₄)alkylene optionally substituted with OH, CN, NO₂, halogen, (C₁-C₆)alkyl;

L² is a bond, or optionally substituted (C₁-C₆)alkylene;

X is a group of formula

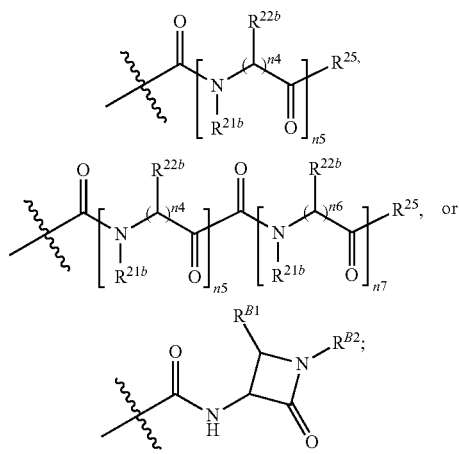

wherein n4, n5, and n6 are each independently 1, 2 or 3; n7 is 0, 1 or 2; $R^{21b}$ and $R^{22b}$ are independently at each occurrence hydrogen, hydroxy, (C₁-C₆)alkyl, (C₃-C₇)cycloalkyl, 5- to 7-membered heteroaryl, 5- to 7-membered heterocyclyl, or (C₆-C₁₀) aryl, wherein any alkyl, cycloalkyl, heterocyclyl, aryl or heteroaryl is optionally substituted with 1 to 3 J; $R^{25}$ is H, OH, OR$^C$,

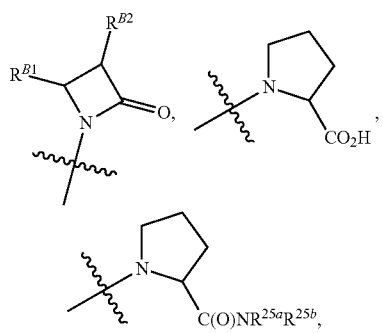

or NR$^{25a}$R$^{25b}$ where R$^{25a}$ and R$^{25b}$ are each independently H, SO₂(C₁-C₆)alkyl, or optionally substituted alkyl; R$^{B1}$ and R$^{B2}$ are each independently H, (C₁-C₆)alkyl, (C₃-C₆)cycloalkyl, OR$^C$, C(=O)N(R$^C$)₂, OC(=O)N(R$^C$)₂, C(=O)OR$^C$, OC(=O)OR$^C$, nitro, trifluoromethyl, trifluoromethoxy, (C₁-C₆)alkoxy, (C₁-C₆)thioalkoxy, N(R$^C$)₂, 5-7 membered heterocyclyl or 5-7 membered heteroaryl, or (C₆-C₁₀) aryl; R$^C$ is independently at each occurrence H or (C₁-C₆)alkyl, and a wavy line indicates a point of attachment of X to a carbon of formula (IVa) bearing X; or X is CO₂H, CH₂CO₂H, C(=O)NHCH₂C(=O)H, CH₂C(=O)H, C(=O)N(H)CH(R⁷)B(OR$^{B3}$)(OR$^{B4}$), or

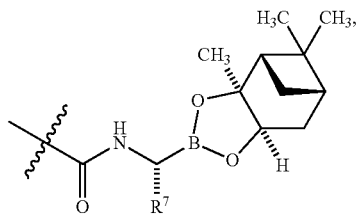

wherein R⁷ is H, methyl, ethyl, or —CH₂OH; or R⁷ and R$^{B3}$ together with the boron atom form a 5- or 6-membered boron containing ring; R$^{B3}$ and R$^{B4}$ are each independently H, (C₁-C₆)alkyl, —CH₂CO₂H, or —CH₂CH₂CO₂H; or R$^{B3}$ and R$^{B4}$ together with the boron atom form an optionally substituted 5- or 6-membered boron containing ring;

R⁵ is aryl, heteroaryl, or a linear or branched alkyl chain of about 1-22 carbon atoms, wherein R⁵ is bonded to the carbonyl carbon to which it is attached directly or by an O or NR⁴, to provide an amide, carbamate, or urea linkage, respectively; optionally comprising within the chain or at a chain terminus optionally substituted aryl, optionally substituted heteroaryl, or optionally substituted

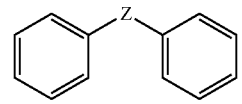

wherein Z is a bond, O, S, NH, CH₂ or C≡C;

R² and R³ are each independently nitro, halo, cyano, hydroxy, glycosyloxy, amino, (C₁-C₄)alkoxy, (C₁-C₄)acyloxy, (C₁-C₄)alkyl, or a group cleavable under physiological conditions to provide a compound of formula (IVa) wherein R² or R³ respectively is hydroxy, wherein any carbon atom is optionally substituted with J;

n1 and n2 are independently 0 or 1;
n3 and n8 are independently 0, 1, or 2;
each m is independently 0 or 1;
R¹ is hydrogen or (C₁-C₆)alkyl optionally substituted with 1 to 3 J; or R¹ together with E¹ form a ring;
R⁴, R⁴', and R⁴" are each independently at each occurrence hydrogen, or (C₁-C₆)alkyl optionally substituted with 1 to 3 J;
R⁶ is hydrogen, or (C₁-C₆)alkyl optionally substituted with 1 to 3 J; or R⁶ together with R$^{A4}$ form a ring;
$R^{41}$, $R^{41'}$, $R^{42}$, $R^{43}$, $R^{43'}$, $R^{44}$, $R^{44'}$, $R^{47}$, $R^{47'}$, $R^{48}$, $R^{48'}$, $R^{49}$, $R^{49'}$, $R^{410}$, and $R^{410'}$ are independently at each occurrence hydrogen, (C₁-C₆)alkyl, (C₃-C₇)cycloalkyl, 5- to 7-membered heteroaryl, 5- to 7-membered heterocyclyl, or (C₆-C₁₀) aryl, wherein any alkyl, cycloalkyl, heterocyclyl, aryl or heteroaryl is optionally substituted with 1 to 3 J;
$R^{46}$ is amino, (C₁-C₆)alkyl, (C₃-C₇)cycloalkyl, 5- to 7-membered heteroaryl, 5- to 7-membered heterocyclyl, or (C₆-C₁₀) aryl, wherein any alkyl, cycloalkyl, heterocyclyl, aryl or heteroaryl is optionally substituted with 1 to 3 J;
J is halogen, R', OR', CN, CF₃, OCF₃, (CH₂)₀₋ₚN(R')₂, (CH₂)₀₋ₚSR', (CH₂)₀₋ₚS(O)₂R', (CH₂)₀₋ₚS(O)₂N(R')₂, (CH₂)₀₋ₚSO₃R', (CH₂)₀₋ₚC(O)R', (CH₂)₀₋ₚC(O)OR', (CH₂)₀₋ₚC(O)N(R')₂, (CH₂)₀₋ₚOC(O)N(R')₂, (CH₂)₀₋ₚNH—C(O)R', (CH₂)₀₋ₚN(R')SO₂R', (CH₂)₀₋ₚN(R')C(O)OR', (CH₂)₀₋ₚN(R')C(O)R', (CH₂)₀₋ₚN(R')C(O)N(R')₂, or (CH₂)₀₋ₚC(=NH)N(R')₂, wherein p is 4;
each R' is independently at each occurrence hydrogen, (C₁-C₆)-alkyl, (C₂-C₇)-alkenyl, (C₂-C₇)-alkynyl, (C₃-C₁₀)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$—, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate or prodrug thereof.

In one embodiment is a compound of Formula (IVa) wherein E$^1$ and E$^2$ are each independently (C$_1$-C$_6$)alkyl, E$^3$ is —O—, and L$^1$ is —O—. In a further embodiment, E$^1$ is methyl, ethyl, or propyl. In yet a further embodiment, E$^2$ is methyl, ethyl, or propyl. In another embodiment is a compound of Formula (IVa) wherein E$^1$ and E$^2$ are each independently (C$_1$-C$_6$)alkyl, E$^3$ is a bond, and L$^1$ is —O—. In a further embodiment, E$^1$ is methyl, ethyl, or propyl. In yet a further embodiment, E$^2$ is methyl, ethyl, propyl, or butyl. In another embodiment is a compound of Formula (IVa) wherein E$^1$ and E$^2$ are each independently (C$_1$-C$_6$)alkyl, E$^3$ is a bond, and L$^1$ is —OCH$_2$CH$_2$CH$_2$CH$_2$O—. In a further embodiment, E$^1$ is methyl, ethyl, or propyl. In a further embodiment, E$^1$ is methyl. In yet a further embodiment, E$^2$ is methyl, ethyl, or propyl. In a further embodiment, E$^2$ is methyl. In another embodiment is a compound of Formula (IVa) wherein E$^1$ and E$^2$ are each independently (C$_1$-C$_6$)alkyl, E$^3$ is a bond, and L$^1$ is —OCH$_2$CH$_2$CH$_2$O—. In a further embodiment, E$^1$ is methyl, ethyl, or propyl. In a further embodiment, E$^1$ is methyl. In yet a further embodiment, E$^2$ is methyl, ethyl, or propyl. In a further embodiment, E$^2$ is ethyl. In another embodiment is a compound of Formula (IVa) wherein E$^1$ and E$^2$ are each independently (C$_1$-C$_6$)alkyl, E$^3$ is a bond, and L$^1$ is —C(O)NH—. In a further embodiment, E$^1$ is methyl, ethyl, or propyl. In a further embodiment, E$^1$ is ethyl or propyl. In a further embodiment, E$^2$ is methyl, ethyl, propyl, or butyl. In yet a further embodiment, E$^2$ is ethyl, or propyl. In another embodiment is a compound of Formula (IVa) wherein E$^1$ aryl, E$^2$ is (C$_1$-C$_6$)alkyl, E$^3$ is a bond, and L$^1$ is a bond. In a further embodiment, E$^1$ is phenyl. In a further embodiment, E$^2$ is methyl, ethyl, propyl, or butyl. In yet a further embodiment, E$^2$ is ethyl, or propyl. In another embodiment is a compound of Formula (IVa) wherein E$^1$ aryl, E$^2$ is (C$_1$-C$_6$)alkyl, E$^3$ is a —O—, and L$^1$ is a bond. In a further embodiment, E$^1$ is phenyl. In a further embodiment, E$^2$ is methyl, ethyl, propyl, or butyl. In yet a further embodiment, E$^2$ is ethyl, or propyl.

In another embodiment is a compound of Formula (IVa) wherein L$^2$ is a bond. In another embodiment is a compound of Formula (IVa) wherein L$^2$ is optionally substituted (C$_1$-C$_6$) alkylene. In a further embodiment, L$^2$ is methylene, ethylene, n-propylene, iso-propylene, n-butylene, iso-butylene, or tert-butylene.

In one embodiment is a compound of Formula (IVa) wherein X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

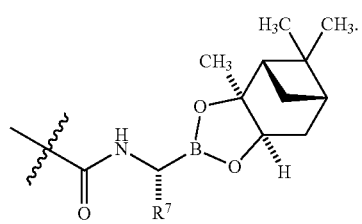

In some embodiments is a compound of Formula (IVa) wherein X is CO$_2$H. In some embodiments is a compound of Formula (IVa) wherein X is CH$_2$CO$_2$H. In some embodiments is a compound of Formula (IVa) wherein X is C(=O)NHCH$_2$C(=O)H. In some embodiments is a compound of Formula (IVa) wherein X is CH$_2$C(=O)H.

In some embodiments is a compound of Formula (IVa) wherein X is C(=O)N(H)CH(R$^7$)B(OR$^{B3}$)(OR$^{B4}$). In further embodiments is a compound of Formula (IVa) wherein X is C(=O)N(H)CH$_2$B(OH)$_2$. In further embodiments is a compound of Formula (IVa) wherein X is C(=O)N(H)CH(CH$_3$)B(OH)$_2$. In further embodiments is a compound of Formula (IVa) wherein X is C(=O)N(H)CH(CH$_2$CH$_3$)B(OH)$_2$. In further embodiments is a compound of Formula (IVa) wherein X is C(=O)N(H)CH(CH$_2$OH)B(OH)$_2$. In further embodiments is a compound of Formula (IVa) wherein X is C(=O)N(H)CH$_2$B(OCH$_3$)$_2$. In further embodiments is a compound of Formula (IVa) wherein X is C(=O)N(H)CH(CH$_3$)B(OCH$_3$)$_2$. In further embodiments is a compound of Formula (IVa) wherein X is C(O)N(H)CH(CH$_2$CH$_3$)B(OCH$_3$)$_2$. In further embodiments is a compound of Formula (IVa) wherein X is C(=O)N(H)CH(CH$_2$OH)B(OCH$_3$)$_2$.

In some embodiments is a compound of Formula (IVa) wherein X is C(=O)N(H)CH(R$^7$)B(OR$^{B3}$)(OR$^{B4}$) and R$^{B3}$ and R$^7$ together with the boron atom form an optionally substituted 5- or 6-membered boron containing ring. In some embodiments is a compound of Formula (IVa) wherein X is

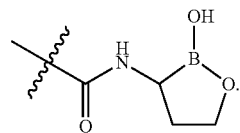 [SMILES: *C(=O)NC1CCOB1O]

In some embodiments is a compound of Formula (IVa) wherein X is

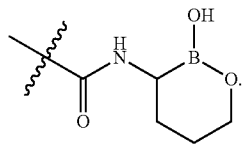 [SMILES: *C(=O)NC1CCCOB1O]

In some embodiments is a compound of Formula (IVa) wherein X is C(=O)N(H)CH(R$^7$)B(OR$^{B3}$)(OR$^{B4}$) and R$^{B3}$ and R$^{B4}$ together with the boron atom form an optionally substituted 5- or 6-membered boron containing ring. In some embodiments is a compound of Formula (IVa) wherein X is

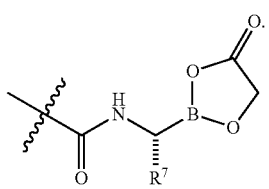

In some embodiments is a compound of Formula (IVa) wherein X is

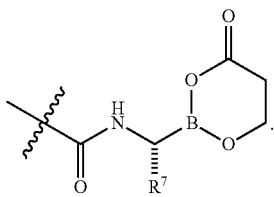

In some some embodiments is a compound of Formula (IVa) wherein X is C(=O)N(H)CH($R^7$)B($OR^{B3}$)($OR^{B4}$) and $R^{B3}$ and $R^{B4}$ together with the boron atom form an optionally substituted 5- or 6-membered boron containing ring derived from a sugar. In some embodiments is a compound of Formula (IVa) wherein X is

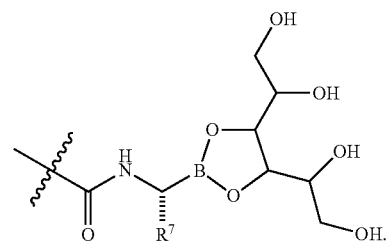

In some embodiments is a compound of Formula (IVa) wherein X is

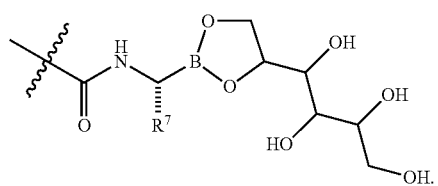

In some embodiments is a compound of Formula (IVa) wherein X is

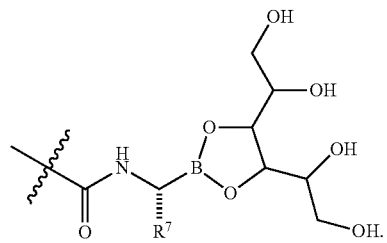

In some embodiments is a compound of Formula (IVa) wherein X is

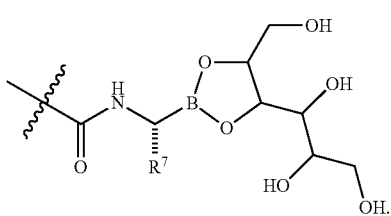

In some embodiments is a compound of Formula (IVa) wherein X is

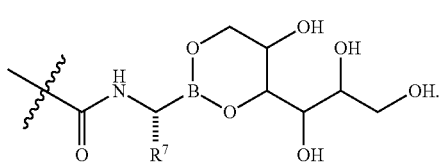

In some embodiments is a compound of Formula (IVa) wherein X is

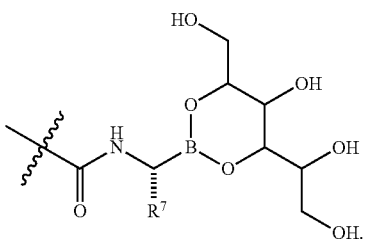

In some embodiments is a compound of Formula (IVa) wherein X is

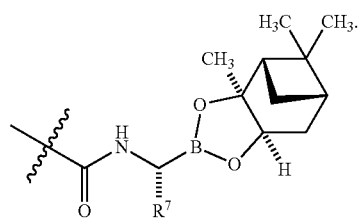

In further embodiments is a compound of Formula (IVa) wherein X is

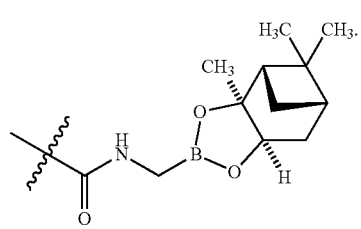 [SMILES: *C(=O)NCB1O[C@@H]2C[C@@H]3C[C@@H](C3(C)C)[C@]2(C)O1]

In further embodiments is a compound of Formula (IVa) wherein X is

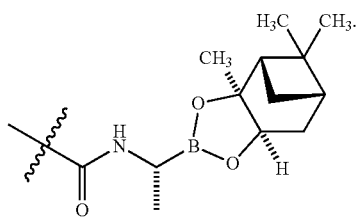 [SMILES: *C(=O)N[C@@H](C)B1O[C@@H]2C[C@@H]3C[C@@H](C3(C)C)[C@]2(C)O1]

In further embodiments is a compound of Formula (IVa) wherein X is

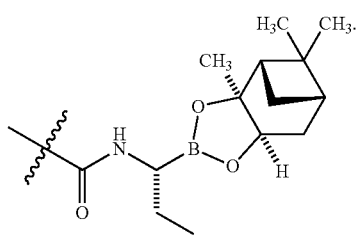 [SMILES: *C(=O)N[C@@H](CC)B1O[C@@H]2C[C@@H]3C[C@@H](C3(C)C)[C@]2(C)O1]

In further embodiments is a compound of Formula (IVa) wherein X is

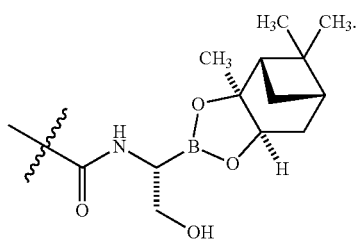 [SMILES: *C(=O)N[C@@H](CO)B1O[C@@H]2C[C@@H]3C[C@@H](C3(C)C)[C@]2(C)O1]

In some embodiments is a compound of Formula (IVa) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

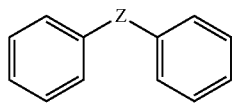

wherein Z is a bond, O, S, NH, $CH_2$ or C≡C. In some embodiments is a compound of Formula (IVa) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

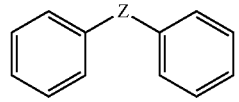

wherein Z is a bond, O, S, NH, $CH_2$ or C≡C. In some embodiments is a compound of Formula (IVa) wherein $R^5$ is a linear alkyl chain of about 1-22 carbon atoms, wherein $R^5$ is bonded to the carbonyl carbon to which it is attached directly to provide an amide linkage, comprising within the chain or at a chain terminus

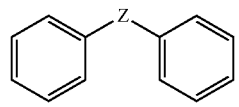

wherein Z is a bond. In some embodiments is a compound of Formula (IVa) wherein $R^5$ is a linear alkyl chain of about 4-22 carbon atoms, wherein $R^5$ is bonded to the carbonyl carbon to which it is attached directly to provide an amide linkage, comprising at a chain terminus

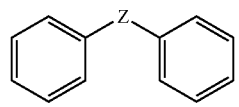

wherein Z is a bond. In some embodiments is a compound of Formula (IVa) wherein $R^5$ is a linear alkyl chain of about 4-22 carbon atoms, wherein $R^5$ is bonded to the carbonyl carbon to which it is attached directly to provide an amide linkage, comprising within the chain

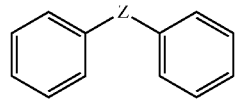

wherein Z is a bond. In some embodiments is a compound of Formula (IVa) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl. In some embodiments is a compound of Formula (IVa) wherein $R^5$ is a linear or branched alkyl chain of about 2-22 carbon atoms, wherein $R^5$ is bonded to the carbonyl carbon to which it is attached directly to provide an amide linkage, comprising within the chain or at a chain terminus optionally substituted aryl. In some embodiments is a compound of Formula (IVa) wherein $R^5$ is a linear or branched alkyl chain of about 2-22 carbon atoms, wherein $R^5$ is bonded to the carbonyl carbon to which it is attached directly to provide an amide linkage, comprising at a chain terminus optionally substituted aryl. In some embodiments is a compound of Formula (IVa) wherein $R^5$ is a linear or branched alkyl chain of about 2-22 carbon atoms, wherein $R^5$ is bonded to the carbonyl carbon to which it is attached directly to provide an amide linkage, comprising within the chain optionally substituted aryl. In some embodiments is a compound of Formula (IVa) wherein $R^5$ is a linear or branched alkyl chain of about 1-22 carbon atoms, wherein $R^5$ is bonded to the carbonyl carbon to which it is attached directly to provide an amide or urea linkage. In some embodiments is a compound of Formula (IVa) wherein $R^5$ is a linear or branched alkyl chain of about 4-18 carbon atoms, wherein $R^5$ is bonded to the carbonyl carbon to which it is attached directly to provide an amide or urea linkage. In some embodiments is a compound of Formula (IVa) wherein $R^5$ is a linear or branched alkyl chain of about 6-16 carbon atoms, wherein $R^5$ is bonded to the carbonyl carbon to which it is attached directly to provide an amide or urea linkage.

In another embodiment is a compound of Formula (IVa) wherein n1 is 0 and n2 is 1. In another embodiment is a compound of Formula (IVa) wherein n1 is 0, n2 is 1, and $R^{44}$ is H. In another embodiment is a compound of Formula (IVa) wherein n1 is 0, n2 is 1, and $R^{44}$ is $(C_1-C_6)$alkyl optionally substituted with 1 to 3 J. In another embodiment is a compound of Formula (IVa) wherein n1 is 0, n2 is 1, and $R^{44}$ is $CH_3$. In another embodiment is a compound of Formula (IVa) wherein n1 is 0, n2 is 1, and $R^{44}$ is $CH_2CH_3$. In another embodiment is a compound of Formula (IVa) wherein n1 is 0, n2 is 1, and $R^{44}$ is $CH_2CH(CH_3)_2$. In another embodiment is a compound of Formula (IVa) wherein n1 is 0, n2 is 1, and $R^{44}$ is $CH_2OH$. In another embodiment is a compound of Formula (IVa) wherein n1 is 0, n2 is 1, and $R^{44}$ is $CH(OH)CH_3$. In another embodiment is a compound of Formula (IVa) wherein n1 is 0, n2 is 1, and $R^{44}$ is $CH_2C(O)NH_2$. In another embodiment is a compound of Formula (IVa) wherein n1 is 0, n2 is 1, and $R^{44}$ is $CH_2CH_2CH_2CH_2NH_2$.

In another embodiment is a compound of Formula (IVa) wherein n1 is 1 and n2 is 1. In another embodiment is a compound of Formula (IVa) wherein n1 is 1, n2 is 1, $R^{46}$ is $CH_3$, and $R^{44}$ is $(C_1-C_6)$alkyl optionally substituted with 1 to 3 J. In another embodiment is a compound of Formula (IVa) wherein n1 is 1, n2 is 1, $R^{46}$ is $CH_3$, and $R^{44}$ is $CH_3$. In another embodiment is a compound of Formula (IVa) wherein n1 is 1, n2 is 1, $R^{46}$ is $CH_3$, and $R^{44}$ is $CH_2CH_3$. In another embodiment is a compound of Formula (IVa) wherein n1 is 1, n2 is 1, $R^{46}$ is $CH_3$, and $R^{44}$ is $CH_2CH(CH_3)_2$. In another embodiment is a compound of Formula (IVa) wherein n1 is 1, n2 is 1, $R^{46}$ is $CH_3$, and $R^{44}$ is $CH_2OH$. In another embodiment is a compound of Formula (IVa) wherein n1 is 1, n2 is 1, $R^{46}$ is $CH_3$, and $R^{44}$ is $CH(OH)CH_3$. In another embodiment is a compound of Formula (IVa) wherein n1 is 1, n2 is 1, $R^{46}$ is $CH_3$, and $R^{44}$ is $CH_2C(O)NH_2$. In another embodiment is a compound of Formula (IVa) wherein n1 is 1, n2 is 1, $R^{46}$ is $CH_3$, and $R^{44}$ is $CH_2CH_2CH_2CH_2NH_2$.

In another embodiment of the aforementioned embodiments is a compound of Formula (IVa) wherein $R^{47}$, $R^{47'}$, $R^{48}$, $R^{48'}$, $R^{49}$, $R^{49'}$, $R^{44}$, $R^{410}$, and $R^{410'}$ are each independently H. In another embodiment of the aforementioned embodiments is a compound of Formula (IVa) wherein each m is 0. In another embodiment of the aforementioned embodiments is a compound of Formula (IVa) wherein $R^{41}$, $R^{41'}$, $R^{42}$, $R^{4'}$, and $R^{4''}$ are each independently H. In another embodiment of the aforementioned embodiments is a compound of Formula (IVa) wherein n3 is 0 and n8 is 0. In another embodiment of the aforementioned embodiments is a compound of Formula (IVa) wherein n3 is 1 and n8 is 0.

In one embodiment is a compound of Formula (IV) having the structure of Formula (IVb):

Formula (IVb)

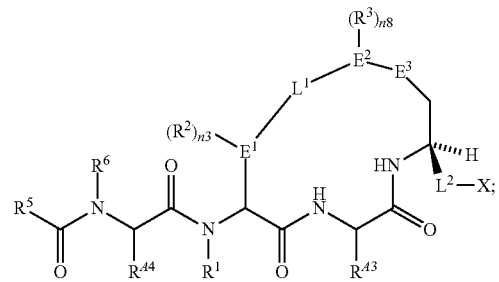

wherein
$E^1$ is $(C_1-C_6)$alkyl, $(C_2-C_7)$alkenyl, $(C_2-C_7)$alkynyl, $(C_3-C_7)$ cycloalkyl, heterocyclyl, heteroaryl, or aryl;
$E^2$ is independently $(C_1-C_6)$alkyl, $(C_2-C_7)$alkenyl, $(C_2-C_7)$ alkynyl, $(C_3-C_7)$cycloalkyl, heterocyclyl, or heteroaryl;
$E^3$ is a bond or —O—;
$L^1$ is a bond, —O—, —S—, —$NR^4$—, —C(O)—, —$CH_2O$—, —$OCH_2$—, —$OCH_2CH_2O$—, —$OCH_2CH_2CH_2CH_2O$—, —$CH_2S$—, —$SCH_2$—, —$CH_2NR^4$—, —$NR^4$—$CH_2$—, —$NR^4C(O)$—, —C(O)$NR^4$—, —$NR^4S(O)_2$—, —$S(O)_2NR^4$—, —$NR^4C(O)$ $NR^4$—, or $(C_1-C_4)$alkylene optionally substituted with OH, CN, $NO_2$, halogen, $(C_1-C_6)$alkyl;
$L^2$ is a bond, or optionally substituted $(C_1-C_6)$alkylene;
X is a group of formula

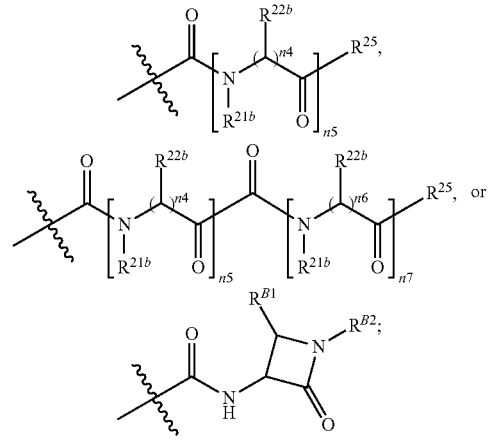

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

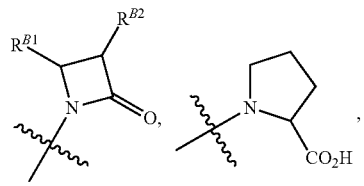

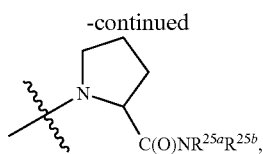

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and RB$^2$ are each independently H, (C$_1$-C$_6$)alkyl, (C$_3$-C$_6$)cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$)alkyl, and a wavy line indicates a point of attachment of X to a carbon of formula (IVb) bearing X; or X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

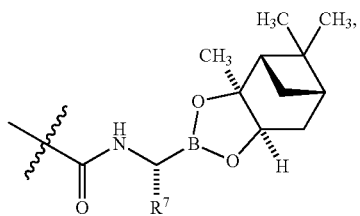

wherein R$^7$ is H, methyl, ethyl, or —CH$_2$OH; or R$^7$ and R$^{B3}$ together with the boron atom form a 5- or 6-membered boron containing ring; R$^{B3}$ and R$^{B4}$ are each independently H, (C$_1$-C$_6$)alkyl, —CH$_2$CO$_2$H, or —CH$_2$CH$_2$CO$_2$H; or R$^{B3}$ and R$^{B4}$ together with the boron atom form an optionally substituted 5- or 6-membered boron containing ring;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

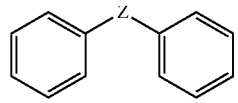

wherein Z is a bond, O, S, NH, CH$_2$ or C≡C;

R$^2$ and R$^3$ are each independently nitro, halo, cyano, hydroxy, glycosyloxy, amino, (C$_1$-C$_4$)alkoxy, (C$_1$-C$_4$)acyloxy, (C$_1$-C$_4$)alkyl, or a group cleavable under physiological conditions to provide a compound of formula (IVb) wherein R$^2$ or R$^3$ respectively is hydroxy, wherein any carbon atom is optionally substituted with J;

n3 and n8 are independently 0, 1, or 2;

R$^1$ is hydrogen or (C$_1$-C$_6$)alkyl optionally substituted with 1 to 3 J; or R$^1$ together with E$^1$ form a ring;

R$^4$ is hydrogen or (C$_1$-C$_6$)alkyl optionally substituted with 1 to 3 J;

R$^6$ is hydrogen, or (C$_1$-C$_6$)alkyl optionally substituted with 1 to 3 J; or R$^6$ together with R$^{44}$ form a ring;

R$^{43}$ is hydrogen, or (C$_1$-C$_6$)alkyl optionally substituted with 1 to 3 J; or R$^6$ together with R$^{44}$ form a ring;

R$^{44}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

J is halogen, R', OR', CN, CF$_3$, OCF$_3$, (CH$_2$)$_{0-p}$N(R')$_2$, (CH$_2$)$_{0-p}$SR', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$OC(O)N(R')$_2$, (CH$_2$)$_{0-p}$NH—C(O)R', (CH$_2$)$_{0-p}$N(R')SO$_2$R', (CH$_2$)$_{0-p}$N(R')C(O)OR', (CH$_2$)$_{0-p}$N(R')C(O)R', (CH$_2$)$_{0-p}$N(R')C(O)N(R')$_2$, or (CH$_2$)$_{0-p}$C(=NH)N(R')$_2$, wherein p is 4;

each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$—, —NH(C$_1$-C$_4$)alkyl, C$_1$-C$_6$alkyl, C$_3$-C$_8$cycloalkyl, or C$_1$-C$_6$heteroalkyl; or a pharmaceutically acceptable salt, solvate or prodrug thereof.

In one embodiment is a compound of Formula (IVb) wherein E$^1$ and E$^2$ are each independently (C$_1$-C$_6$)alkyl, E$^3$ is —O—, and L$^1$ is —O—. In a further embodiment, E$^1$ is methyl, ethyl, or propyl. In yet a further embodiment, E$^2$ is methyl, ethyl, or propyl. In another embodiment is a compound of Formula (IVb) wherein E$^1$ and E$^2$ are each independently (C$_1$-C$_6$)alkyl, E$^3$ is a bond, and L$^1$ is —O—. In a further embodiment, E$^1$ is methyl, ethyl, or propyl. In yet a further embodiment, E$^2$ is methyl, ethyl, propyl, or butyl. In another embodiment is a compound of Formula (IVb) wherein E$^1$ and E$^2$ are each independently (C$_1$-C$_6$)alkyl, E$^3$ is a bond, and L$^1$ is —OCH$_2$CH$_2$CH$_2$CH$_2$O—. In a further embodiment, E$^1$ is methyl, ethyl, or propyl. In a further embodiment, E$^1$ is methyl. In yet a further embodiment, E$^2$ is methyl, ethyl, or propyl. In a further embodiment, E$^2$ is methyl. In another embodiment is a compound of Formula (IVb) wherein E$^1$ and E$^2$ are each independently (C$_1$-C$_6$) alkyl, E$^3$ is a bond, and L is —OCH$_2$CH$_2$CH$_2$O—. In a further embodiment, E$^1$ is methyl, ethyl, or propyl. In a further embodiment, E$^1$ is methyl. In yet a further embodiment, E$^2$ is methyl, ethyl, or propyl. In a further embodiment, E$^2$ is ethyl. In another embodiment is a compound of Formula (IVb) wherein E$^1$ and E$^2$ are each independently (C$_1$-C$_6$)alkyl, E$^3$ is a bond, and L$^1$ is —C(O)NH—. In a further embodiment, E$^1$ is methyl, ethyl, or propyl. In a further embodiment, E$^1$ is ethyl or propyl. In a further embodiment, E$^2$ is methyl, ethyl, propyl, or butyl. In yet a further embodiment, E$^2$ is ethyl, or propyl. In another embodiment is a compound of Formula (IVb) wherein E$^1$ aryl, E$^2$ is (C$_1$-C$_6$)alkyl, E$^3$ is a bond, and L$^1$ is a bond. In a further embodiment, E$^1$ is phenyl. In a further embodiment, E$^2$ is methyl, ethyl, propyl, or butyl. In yet a further embodiment, E$^2$ is ethyl, or propyl. In another embodiment is a compound of Formula (IVb) wherein E$^1$ aryl, E$^2$ is (C$_1$-C$_6$)alkyl, E$^3$ is a —O—, and L$^1$ is a bond. In a further embodiment, E$^1$ is phenyl. In a further embodiment, E$^2$ is methyl, ethyl, propyl, or butyl. In yet a further embodiment, E$^2$ is ethyl, or propyl.

In another embodiment is a compound of Formula (IVb) wherein L$^2$ is a bond. In another embodiment is a compound of Formula (IVb) wherein L$^2$ is optionally substituted (C$_1$-C$_6$)alkylene. In a further embodiment, L$^2$ is methylene, ethylene, n-propylene, iso-propylene, n-butylene, iso-butylene, or tert-butylene.

In one embodiment is a compound of Formula (IVb) wherein X is CO$_2$H, CH$_2$CO$_2$H, C(=O)NHCH$_2$C(=O)H, CH$_2$C(=O)H, C(=O)N(H)CH(R$^7$)B(OR$^{B3}$)(OR$^{B4}$), or

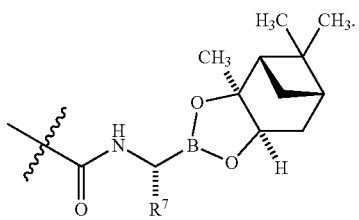

In some embodiments is a compound of Formula (IVb) wherein X is $CO^2H$. In some embodiments is a compound of Formula (IVb) wherein X is $CH_2CO_2H$. In some embodiments is a compound of Formula (IVb) wherein X is $C(=O)NHCH_2CO(=O)H$. In some embodiments is a compound of Formula (IVb) wherein X is $CH_2C(=O)H$.

In some embodiments is a compound of Formula (IVIVb) wherein X is $C(=O)N(H)CH(R^7)B(OR^{B3})(OR^{B4})$. In further embodiments is a compound of Formula (IVb) wherein X is $C(=O)N(H)CH_2B(OH)_2$. In further embodiments is a compound of Formula (IVb) wherein X is $C(=O)N(H)CH(CH_3)B(OH)_2$. In further embodiments is a compound of Formula (IVb) wherein X is $C(=O)N(H)CH(CH_2CH_3)B(OH)_2$. In further embodiments is a compound of Formula (IVb) wherein X is $C(=O)N(H)CH(CH_2OH)B(OH)_2$. In further embodiments is a compound of Formula (IVb) wherein X is $C(=O)N(H)CH_2B(OCH_3)_2$. In further embodiments is a compound of Formula (IVb) wherein X is $C(=O)N(H)CH(CH_3)B(OCH_3)_2$. In further embodiments is a compound of Formula (IVb) wherein X is $C(=O)N(H)CH(CH_2CH_3)B(OCH_3)_2$. In further embodiments is a compound of Formula (IVb) wherein X is $C(=O)N(H)CH(CH_2OH)B(OCH_3)_2$.

In some embodiments is a compound of Formula (IVb) wherein X is $C(=O)N(H)CH(R^7)B(OR^{B3})(OR^{B4})$ and $R^{B3}$ and $R^7$ together with the boron atom form an optionally substituted 5- or 6-membered boron containing ring. In some embodiments is a compound of Formula (IVb) wherein X is

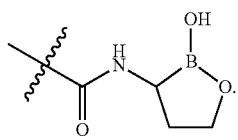 [SMILES: *C(=O)NC1CCOB1O]

In some embodiments is a compound of Formula (IVb) wherein X is

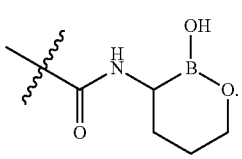 [SMILES: *C(=O)NC1CCCOB1O]

In some embodiments is a compound of Formula (IVb) wherein X is $C(=O)N(H)CH(R^7)B(OR^{B3})(OR^{B4})$ and $R^{B3}$ and $R^{B4}$ together with the boron atom form an optionally substituted 5- or 6-membered boron containing ring. In some embodiments is a compound of Formula (IVb) wherein X is

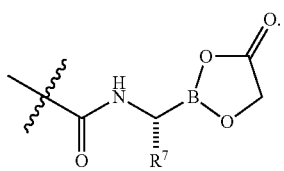

In some embodiments is a compound of Formula (IVb) wherein X is

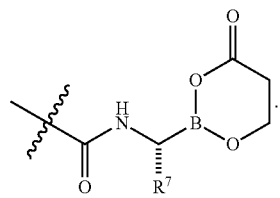

In some some embodiments is a compound of Formula (IVb) wherein X is $C(=O)N(H)CH(R^7)B(OR^{B3})(OR^{B4})$ and $R^{B3}$ and $R^{B4}$ together with the boron atom form an optionally substituted 5- or 6-membered boron containing ring derived from a sugar. In some embodiments is a compound of Formula (IVb) wherein X is

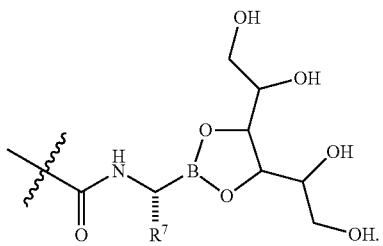

In some embodiments is a compound of Formula (IVb) wherein X is

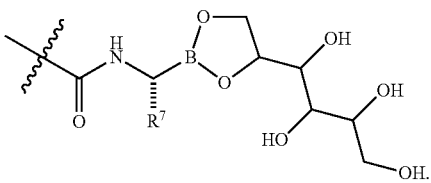

In some embodiments is a compound of Formula (IVb) wherein X is

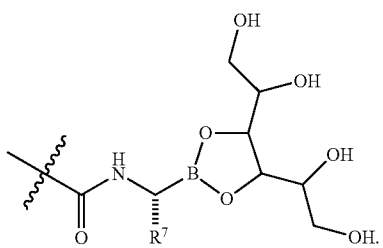

In some embodiments is a compound of Formula (IVb) wherein X is

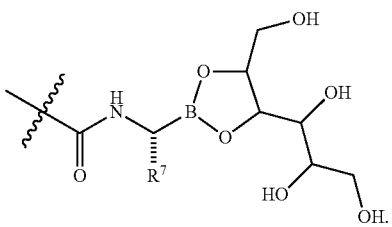

In some embodiments is a compound of Formula (IVb) wherein X is

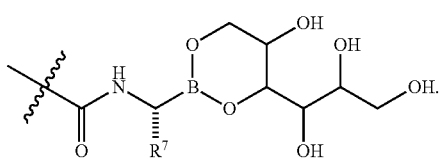

In some embodiments is a compound of Formula (IVb) wherein X is

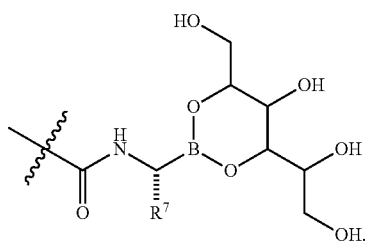

In some embodiments is a compound of Formula (IVb) wherein X is

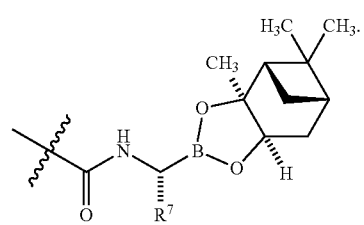

In further embodiments is a compound of Formula (IVb) wherein X is

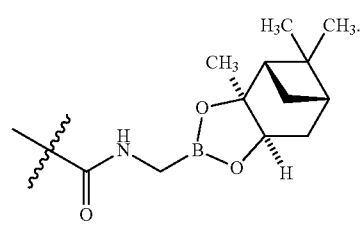

In further embodiments is a compound of Formula (IVb) wherein X is

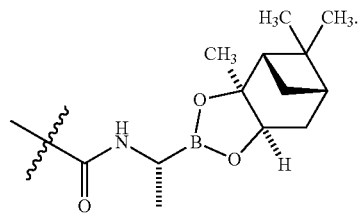 [SMILES: *C(=O)N[C@@H](C)B1O[C@@H]2C[C@@H]3C[C@@H](C3(C)C)[C@]2(C)O1]

In further embodiments is a compound of Formula (IVb) wherein X is

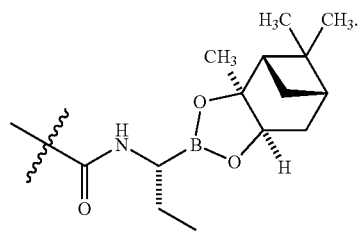 [SMILES: *C(=O)N[C@@H](CC)B1O[C@@H]2C[C@@H]3C[C@@H](C3(C)C)[C@]2(C)O1]

In further embodiments is a compound of Formula (IVb) wherein X is

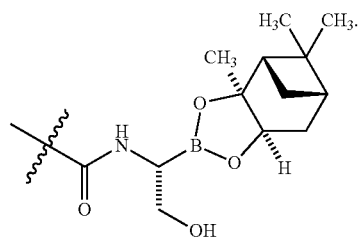 [SMILES: *C(=O)N[C@@H](CO)B1O[C@@H]2C[C@@H]3C[C@@H](C3(C)C)[C@]2(C)O1]

In some embodiments is a compound of Formula (IVb) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

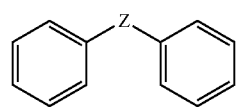

wherein Z is a bond, O, S, NH, $CH_2$ or C≡C. In some embodiments is a compound of Formula (IVb) wherein $R^5$ is a linear or branched alkyl chain of about 1-22 carbon atoms, wherein $R^5$ is bonded to the carbonyl carbon to which it is attached directly to provide an amide linkage, optionally comprising within the chain or at a chain terminus optionally substituted aryl, optionally substituted heteroaryl, or optionally substituted

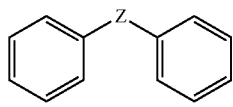

wherein Z is a bond, O, S, NH, CH$_2$ or C≡C. In some embodiments is a compound of Formula (IVb) wherein R$^5$ is a linear alkyl chain of about 1-22 carbon atoms, wherein R$^5$ is bonded to the carbonyl carbon to which it is attached directly to provide an amide linkage, comprising within the chain or at a chain terminus

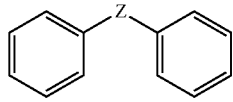

wherein Z is a bond. In some embodiments is a compound of Formula (IVb) wherein R$^5$ is a linear alkyl chain of about 4-22 carbon atoms, wherein R$^5$ is bonded to the carbonyl carbon to which it is attached directly to provide an amide linkage, comprising at a chain terminus

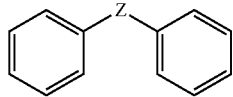

wherein Z is a bond. In some embodiments is a compound of Formula (IVb) wherein R$^5$ is a linear alkyl chain of about 4-22 carbon atoms, wherein R$^5$ is bonded to the carbonyl carbon to which it is attached directly to provide an amide linkage, comprising within the chain

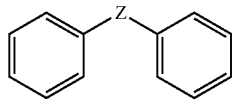

wherein Z is a bond. In some embodiments is a compound of Formula (IVb) wherein R$^5$ is a linear or branched alkyl chain of about 1-22 carbon atoms, wherein R$^5$ is bonded to the carbonyl carbon to which it is attached directly or by an NR$^4$, to provide an amide or urea linkage, respectively; optionally comprising within the chain or at a chain terminus optionally substituted aryl. In some embodiments is a compound of Formula (IVb) wherein R$^5$ is a linear or branched alkyl chain of about 2-22 carbon atoms, wherein R$^5$ is bonded to the carbonyl carbon to which it is attached directly to provide an amide linkage, comprising within the chain or at a chain terminus optionally substituted aryl. In some embodiments is a compound of Formula (IVb) wherein R$^5$ is a linear or branched alkyl chain of about 2-22 carbon atoms, wherein R$^5$ is bonded to the carbonyl carbon to which it is attached directly to provide an amide linkage, comprising at a chain terminus optionally substituted aryl. In some embodiments is a compound of Formula (IVb) wherein R$^5$ is a linear or branched alkyl chain of about 2-22 carbon atoms, wherein R$^5$ is bonded to the carbonyl carbon to which it is attached directly to provide an amide linkage, comprising within the chain optionally substituted aryl. In some embodiments is a compound of Formula (IVb) wherein R$^5$ is a linear or branched alkyl chain of about 1-22 carbon atoms, wherein R$^5$ is bonded to the carbonyl carbon to which it is attached directly to provide an amide or urea linkage. In some embodiments is a compound of Formula (IVb) wherein R$^5$ is a linear or branched alkyl chain of about 4-18 carbon atoms, wherein R$^5$ is bonded to the carbonyl carbon to which it is attached directly to provide an amide or urea linkage. In some embodiments is a compound of Formula (IVb) wherein R$^5$ is a linear or branched alkyl chain of about 6-16 carbon atoms, wherein R$^5$ is bonded to the carbonyl carbon to which it is attached directly to provide an amide or urea linkage.

In another embodiment is a compound of Formula (IVb) wherein R$^{44}$ is H. In another embodiment is a compound of Formula (IVb) wherein R$^{44}$ is (C$_1$-C$_6$)alkyl optionally substituted with 1 to 3 J. In another embodiment is a compound of Formula (IVb) wherein R$^{44}$ is CH$_3$. In another embodiment is a compound of Formula (IVb) wherein R$^{44}$ is CH$_2$CH$_3$. In another embodiment is a compound of Formula (IVb) wherein R$^{44}$ is CH$_2$CH(CH$_3$)$_2$. In another embodiment is a compound of Formula (IVb) wherein R$^{44}$ is CH$_2$OH. In another embodiment is a compound of Formula (IVb) wherein R$^{44}$ is CH(OH)CH$_3$. In another embodiment is a compound of Formula (IVb) wherein R$^{44}$ is CH$_2$C(O)NH$_2$. In another embodiment is a compound of Formula (IVb) wherein R$^{44}$ is CH$_2$CH$_2$CH$_2$CH$_2$NH$_2$.

In another embodiment of the aforementioned embodiments is a compound of Formula (IVb) wherein R$^1$ and R$^6$ are each independently H. In another embodiment of the aforementioned embodiments is a compound of Formula (IVb) wherein R$^{43}$ is CH$_3$. In another embodiment of the aforementioned embodiments is a compound of Formula (IVb) wherein n3 is 0 and n8 is 0. In another embodiment of the aforementioned embodiments is a compound of Formula (IVb) wherein n3 is 1 and n8 is 0.

Some embodiments of compounds of Formula (IV), (IVa), or (IVb) include, but are not limited to, compounds selected from the group consisting of:

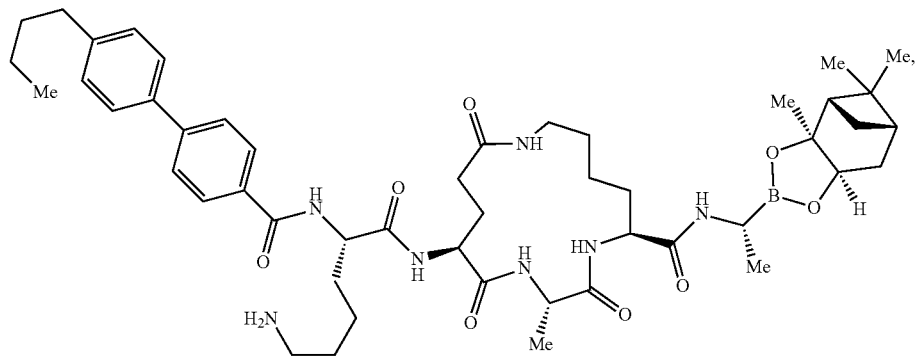

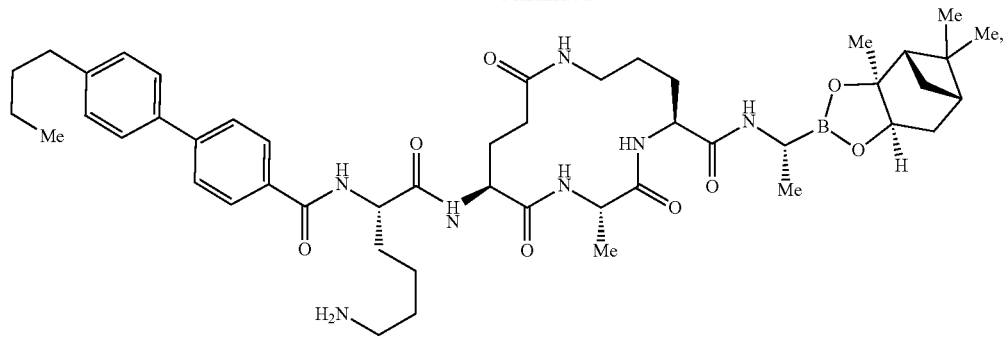
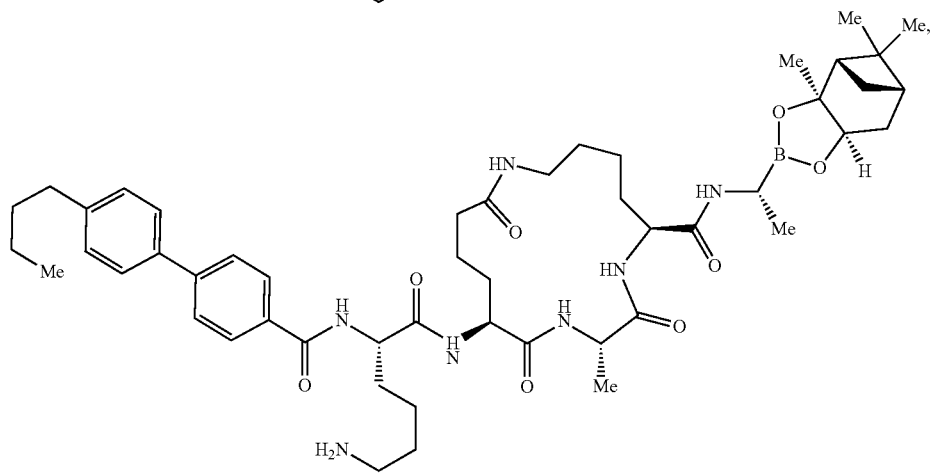
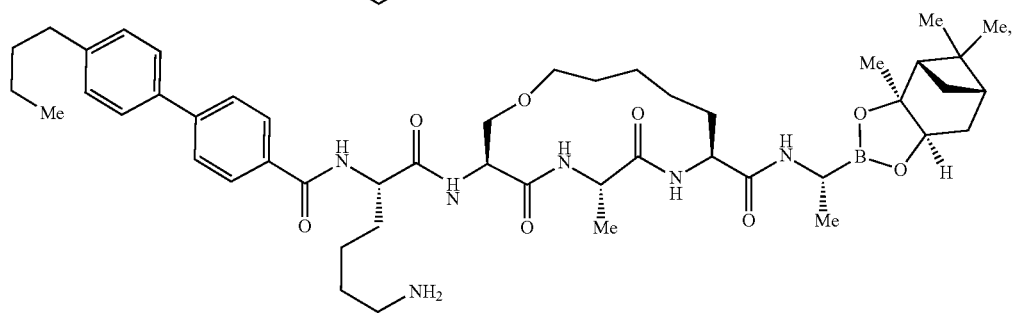
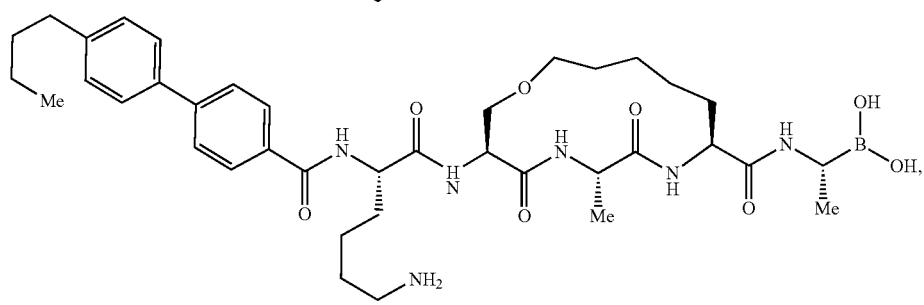
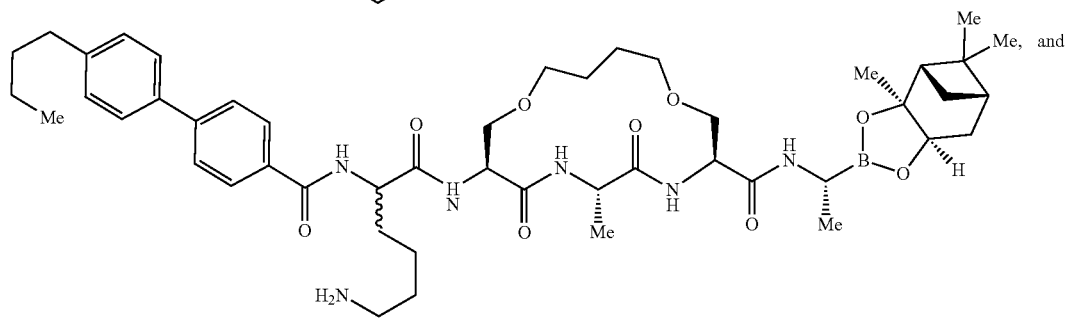

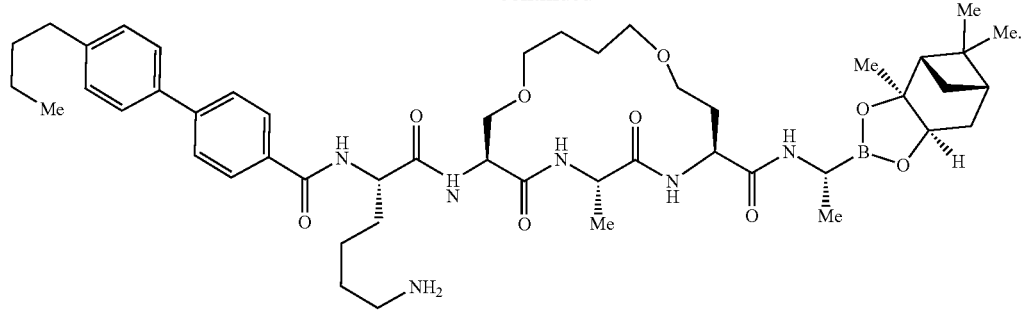
Further embodiments of compounds of Formula (IV), (IVa), or (IVb) include, but are not limited to, compounds selected from the group consisting of:
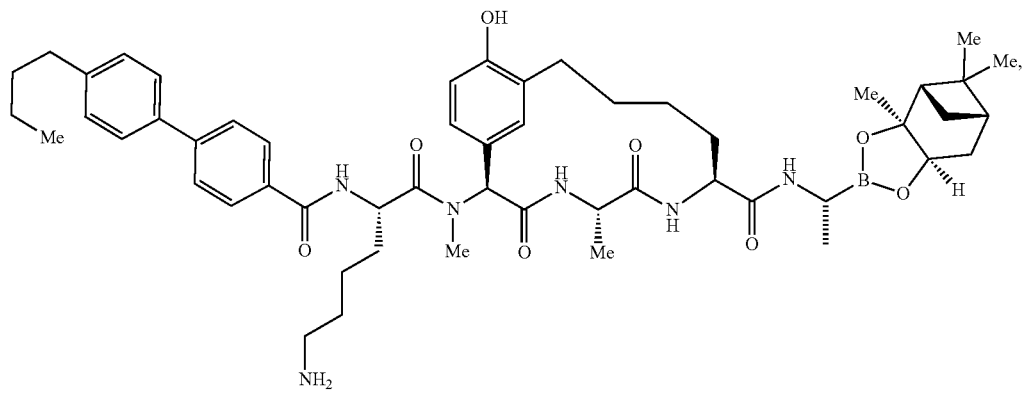
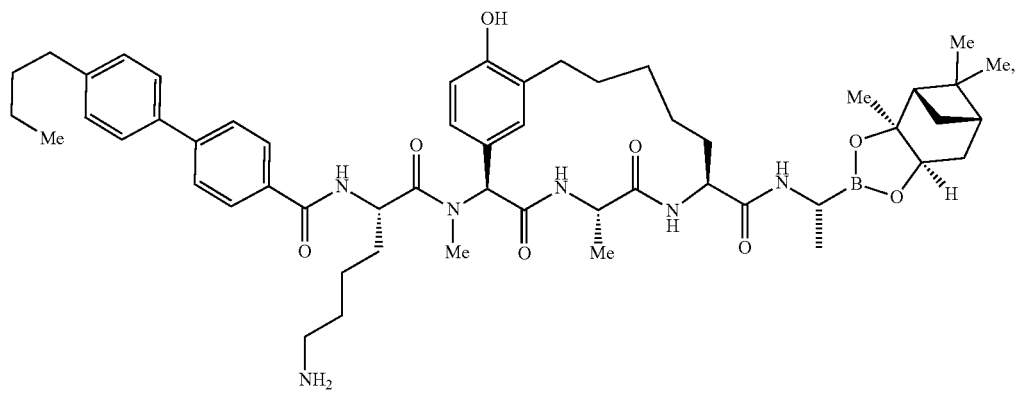
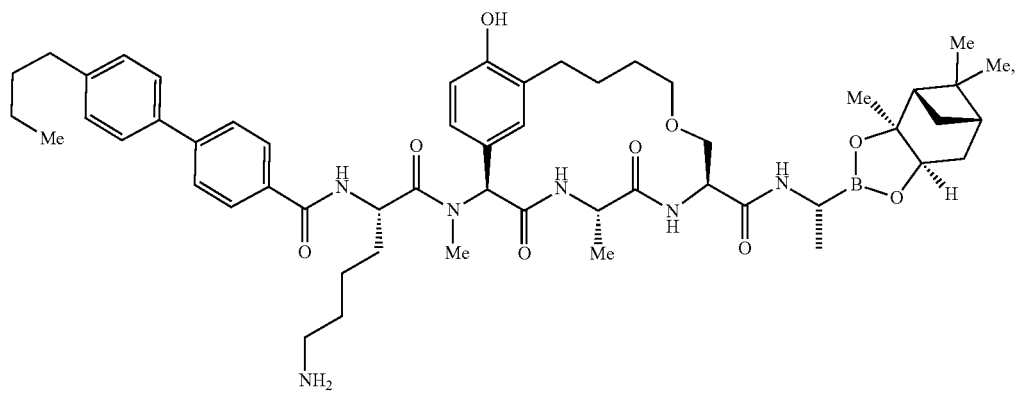

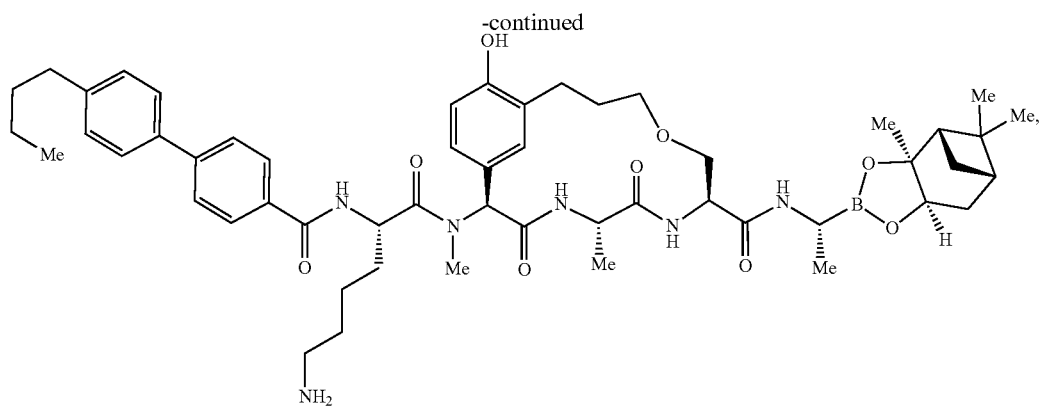
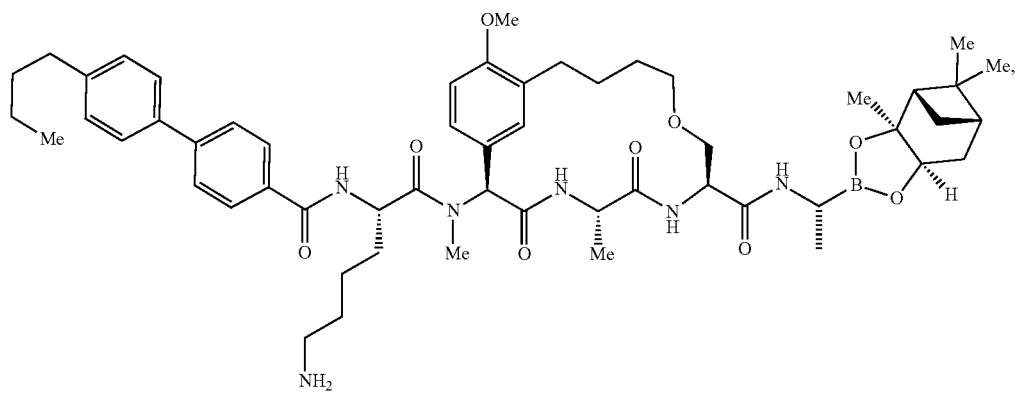
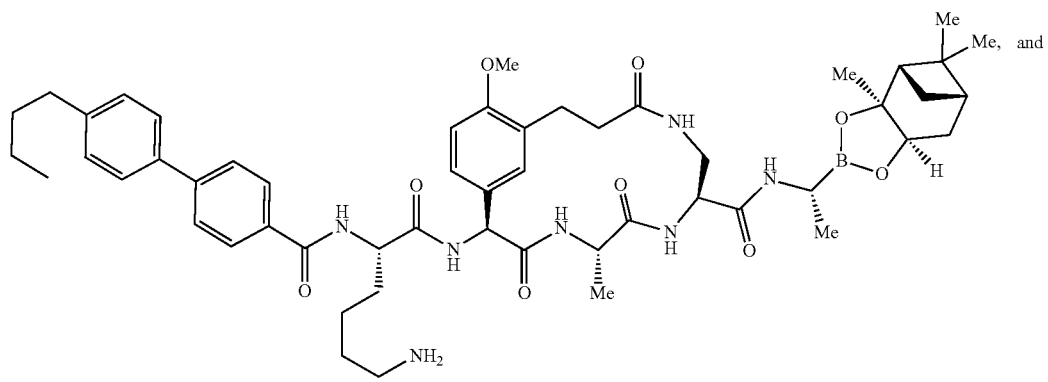
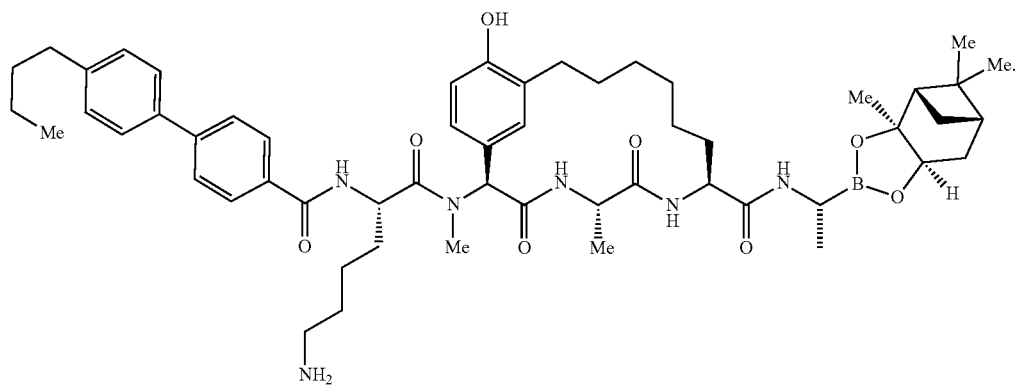

Further embodiments of compounds of Formula (IV), (IVa), or (IVb) include, but are not limited to, compounds selected from the group consisting of:

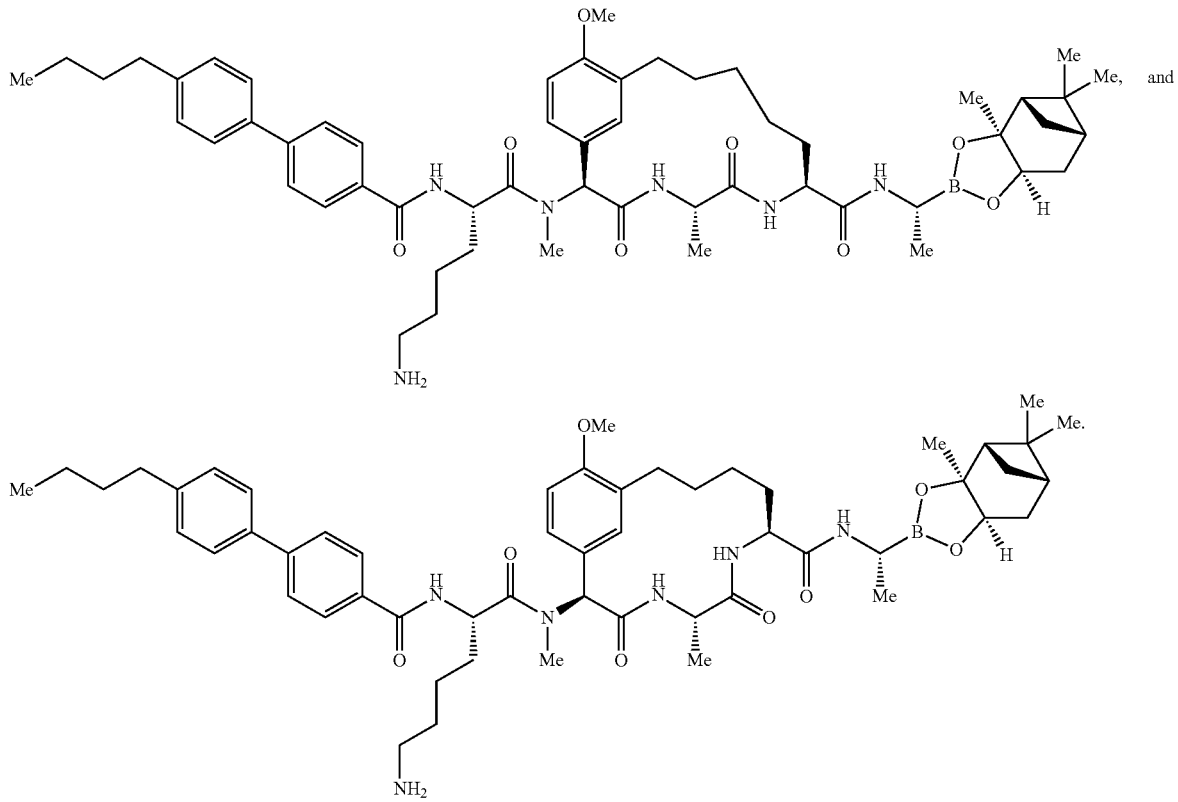

In another aspect are hydrates or metabolites comprising any of the aforementioned compounds.

In another aspect are pharmaceutical compositions comprising any of the aforementioned compounds together with a pharmaceutically acceptable excipient.

In another aspect described herein is the use of a compound described herein in the manufacture of a medicament for treatment of a bacterial infection in a patient.

In another aspect are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with arylomycin A2. In a further embodiment, the causative bacteria species of the bacteria infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainflu enzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus*. In another embodiment the bacterial infection is an infection involving a Gram-negative bacteria. In a further embodiment, the bacterial infection is an infection involving a Gram-positive bacteria.

In a further embodiment are methods of treating a mammal in need of such treatment comprising administering to the mammal a second therapeutic agent to any of the aforementioned methods of treatment. In another embodiment, the second therapeutic agent is a not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

In one embodiment, is a compound described herein which displays antibiotic activity useful in the treatment of bacterial infections, such as by way of example only, various strains of *S. aureus, S. pneumoniae, E. faecalis, E. faecium, B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

Methicillin-Resistant *Staphylococcus aureus*

*Staphylococcus aureus* (*S. aureus*), a spherical bacterium, is the most common cause of *staph* infections. *S. aureus* has been known to cause a range of illnesses from minor skin infections, such as pimples, impetigo, boils, cellulitis folliculitis, furuncles, carbuncles, scalded skin syndrome, abscesses, to life-threatening diseases such as pneumonia, meningitis, osteomyelitis endocarditis, toxic shock syndrome, and septicemia. Further, *S. aureus* is one of the most common causes of nosocomial infections, often causing post-surgical wound infections.

Methicillin was introduced in the late 1950s to treat infections caused by penicillin-resistant *S. aureus*. It has been reported previously that *S. aureus* isolates had acquired resistance to methicillin (methicillin-resistant *S. aureus*, MRSA). The methicillin resistance gene (mecA) encodes a methicillin-resistant penicillin-binding protein that is not present in susceptible strains. mecA is carried on a mobile genetic element, the staphylococcal cassette chromosome mec (SCCmec), of which four forms have been described that differ in size and genetic composition. The methicillin-resistant penicillin-binding protein allows for resistance to β-lactam antibiotics and obviates their clinical use during MRSA infections.

In one aspect is a method for treating a subject having a resistant bacterium comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof. In one embodiment, the bacterium is a Gram-positive bacteria. In another embodiment, the Gram-positive bacterium is *S. aureus*. In further embodiment, the *S. aureus* is resistant or refractory to a beta-lactam antibiotic. In yet a further embodiment, the beta-lactam antibiotic belongs to the class of penicillins. In a further embodiment, the beta-lactam antibiotic is methicillin. In yet another embodiment, the subject has a methicillin-resistant *S. aureus* bacteria. In one embodiment the beta-lactam antibiotic is flucloxacillin. In another embodiment is a method for treating a subject having a dicloxacillin-resistant bacteria comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject is refractory to dicloxacillin. Also disclosed herein is a method for treating a subject having a methicillin-resistant bacteria comprising administering a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject has been determined to have a methicillin-resistant bacteria. In one embodiment the subject is screened for methicillin-resistant bacteria. In another embodiment, the subject screening is performed through a nasal culture. In a further embodiment the methicillin-resistant bacteria is detected by swabbing the nostril(s) of the subject and isolating the bacteria. In another embodiment, Real-time PCR and/or Quantitative PCR is employed to determine whether the subject has a methicillin-resistant bacteria.

In one embodiment is a method for treating a subject having a first-generation cephalosporin-resistant bacteria comprising administering a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject is refractory to a first-generation cephalosporin. In one embodiment, the bacteria is resistant to a first-generation cephalosporin. In a further embodiment, the bacteria is resistant to cefacetrile. In another embodiment, the bacteria is resistant to cefadroxil. In yet another embodiment, the bacteria is resistant to cefalexin. In one embodiment, the bacteria is resistant to cefaloglycin. In another embodiment, the bacteria is resistant to cefalonium. In another embodiment, the bacteria is resistant to cefaloridine. In yet another embodiment, the bacteria is resistant to cefalotin. In a further embodiment, the bacteria is resistant to cefapirin. In yet a further embodiment, the bacteria is resistant to cefatrizine. In one embodiment, the bacteria is resistant to cefazaflur. In another embodiment, the bacteria is resistant to cefazedone. In yet another embodiment, the bacteria is resistant to cefazolin. In a further embodiment, the bacteria is resistant to cefradine. In yet a further embodiment, the bacteria is resistant to cefroxadine. In one embodiment, the bacteria is resistant to cefitezole.

In one embodiment is a method for treating a subject having a second-generation cephalosporin-resistant bacteria comprising administering a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject is refractory to a second-generation cephalosporin. In another embodiment, the bacteria is resistant to a second-generation cephalosporin. In a further embodiment, the bacteria is resistant to cefaclor. In another embodiment, the bacteria is resistant to cefonicid. In yet another embodiment, the bacteria is resistant to cefprozil. In one embodiment, the bacteria is resistant to cefuroxime. In another embodiment, the bacteria is resistant to cefuzonam. In another embodiment, the bacteria is resistant to cefmetazole. In yet another embodiment, the bacteria is resistant to cefotetan. In a further embodiment, the bacteria is resistant to cefoxitin.

In one embodiment is a method for treating a subject having a third-generation cephalosporin-resistant bacteria comprising administering a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject is refractory to a third-generation cephalosporin. In another embodiment, the bacteria is resistant to a third-generation cephalosporin. In a further embodiment, the bacteria is resistant to cefcapene. In another embodiment, the bacteria is resistant to cefdaloxime. In yet another embodiment, the bacteria is resistant to cefdinir. In one embodiment, the bacteria is resistant to cefditoren. In another embodiment, the bacteria is resistant to cefixime. In another embodiment, the bacteria is resistant to cefmenoxime. In yet another embodiment, the bacteria is resistant to cefodizime. In a further embodiment, the bacteria is resistant to cefotaxime. In yet a further embodiment, the bacteria is resistant to cefpimizole. In one embodiment, the bacteria is resistant to cefpodoxime. In another embodiment, the bacteria is resistant to cefteram. In yet another embodiment, the bacteria is resistant to ceftibuten. In a further embodiment, the bacteria is resistant to ceftiofur. In yet a further embodiment, the bacteria is resistant to ceftiolene. In one embodiment, the bacteria is resistant to ceftizoxime. In another embodiment, the bacteria is resistant to ceftriaxone. In yet another embodiment, the bacteria is resistant to cefoperazone. In yet a further embodiment, the bacteria is resistant to ceftazidime.

In one embodiment is a method for treating a subject having a fourth-generation cephalosporin-resistant bacteria comprising administering a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject is refractory to a fourth-generation cephalosporin. In another embodiment, the bacteria is resistant to a fourth-generation cephalosporin. In a further embodiment, the bacteria is resistant to cefclidine. In another embodiment, the bacteria is resistant to cefepime. In yet another embodiment, the bacteria is resistant to cefluprenam. In one embodiment, the bacteria is resistant to cefoselis. In another embodiment, the bacteria is resistant to cefozopran. In another embodiment, the bacteria is resistant to cefpirome. In yet another embodiment, the bacteria is refractory to cefquinome.

In one embodiment is a method for treating a subject having a carbapenem-resistant bacteria comprising administering a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the subject is refractory to a carbapenem. In another embodiment, the bacteria is resistant to a carbapenem. In a further embodiment, the bacteria is resistant to imipenem. In another embodiment, the bacteria is resistant to meropenem. In yet another embodiment, the bacteria is resistant to ertapenem. In one embodiment, the bacteria is resistant to faropenem. In another embodiment, the bacteria is resistant to doripenem. In another embodiment, the bacteria is resistant to panipenem. In yet another embodiment, the bacteria is resistant to biapenem, Vancomycin-Intermediate and Vancomycin-Resistant *Staphylococcus aureus*

Vancomycin-intermediate *Staphylococcus aureus* and vancomycin-resistant *staphylococcus aureus* are specific types of antimicrobial-resistant *Staph* bacteria that are refractory to vancomycin treatment. *S. aureus* isolates for which vancomycin MICs are 4-8 µg/mL are classified as vancomycin-intermediate and isolates for which vancomycin MICs are >16 µg/mL are classified as vancomycin-resistant (Clinical and Laboratory Standards Institute/NCCLS. Performance Standards for Antimicrobial Susceptibility Testing. Sixteenth informational supplement. M100-S16. Wayne, Pa.: CLSI, 2006).

As used herein, the term "minimum inhibitory concentration" (MIC) refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic is determined from the tube with the lowest concentration that shows no turbidity (no growth).

In one aspect is a method of treating a subject having a bacterial infection comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the bacterial infection comprises a vancomycin-intermediate *Staphylococcus aureus* bacterium. In one embodiment, the vancomycin-intermediate *Staphylococcus aureus* bacterium has a MIC of between about 4 to about 8 µg/mL. In another embodiment, the vancomycin-intermediate *Staphylococcus aureus* bacterium has a MIC of about 4 µg/mL. In yet another embodiment, the vancomycin-intermediate *Staphylococcus aureus* bacterium has a MIC of about 5 µg/mL. In a further embodiment, the vancomycin-intermediate *Staphylococcus aureus* bacterium has a MIC of about 6 µg/mL. In yet a further embodiment, the vancomycin-intermediate *Staphylococcus aureus* bacterium has a MIC of about 7 µg/mL. In one embodiment, the vancomycin-intermediate *Staphylococcus aureus* bacterium has a MIC of about 8 µg/mL.

In another aspect is a method of treating a subject having a bacterial infection comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the bacterial infection comprises a vancomycin-resistant *Staphylococcus aureus* bacterium. In one embodiment, the vancomycin-resistant *Staphylococcus aureus* bacterium has a MIC of between about 16 µg/mL. In another embodiment, the vancomycin-resistant *Staphylococcus aureus* bacterium has a MIC of about ≥16 µg/mL. In yet another embodiment, the vancomycin-resistant *Staphylococcus aureus* bacterium has a MIC of about 20 µg/mL. In a further embodiment, the vancomycin-resistant *Staphylococcus aureus* bacterium has a MIC of about 25 µg/mL.

In one embodiment, conditions treated by the compounds described herein include, but are not limited to, endocarditis, osteomyelitis, neningitis, skin and skin structure infections, genitourinary tract infections, abscesses, and necrotizing infections. In another embodiment, the compounds disclosed herein are used to treat conditions, such as, but not limited to, diabetic foot infections, decubitus ulcers, burn infections, animal or human bite wound infections, synergistic-necrotizing gangrene, necrotizing fasciitis, intra-abdominal infection associated with breeching of the intestinal barrier, pelvic infection associated with breeching of the intestinal barrier, aspiration pneumonia, and post-operative wound infections. In another embodiment, the conditions listed herein are caused by, contain, or result in the presence of VISA and/or VRSA.

Vancomycin-Resistant Enterococci

Enterococci are bacteria that are normally present in the human intestines and in the female genital tract and are often found in the environment. These bacteria sometimes cause infections. In some cases, enterococci have become resistant to vancomycin (also known as vancomycin-resistant enterococci or VRE.) Common forms of resistance to vancomycin occur in enterococcal strains that involve the acquisition of a set of genes endoding proteins that direct peptidoglycan precursors to incorporate D-Ala-D-Lac instead of D-Ala-D-Ala. The six different types of vancomycin resistance shown by *enterococcus* are: Van-A, Van-B, Van-C, Van-D, Van-E and Van-F. In some cases, Van-A VRE is resistant to both vancomycin and teicoplanin, while in other cases, Van-B VRE is resistant to vancomycin but sensitive to teicoplanin; in further cases Van-C is partly resistant to vancomycin, and sensitive to teicoplanin.

In one aspect, is a method of treating a subject having a vancomycin-resistant enterococci comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the enterococci has developed resistance to vancomycin. In one embodiment, the subject has been previously treated with vancomycin for a sustained period of time. In another embodiment, the subject has been hospitalized. In yet another embodiment, the subject has a weakened immune system such as patients in Intensive Care Units or in cancer or transplant wards. In a further embodiment, the subject has undergone surgical procedures such as, for example, abdominal or chest surgery. In yet a further embodiment, the subject has been colonized with VRE. In one embodiment, the subject has a medical device such that an infection has developed. In another embodiment, the medical device is a urinary catheter or central intravenous (IV) catheter.

In another embodiment, is a method of treating a subject having a vancomycin-resistant enterococci comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the *enterococcus* has Van-A resistance.

In another embodiment, is a method of treating a subject having a vancomycin-resistant enterococci comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the *enterococcus* has Van-B resistance.

In another embodiment, is a method of treating a subject having a vancomycin-resistant enterococci comprising administering to the subject a compound of Formula (I), (Ia), (Ib), (Ic), (Id), (Ie), (II), (IIa), (IIb), (IIc), (III), (IIIa), (IIIb), (IIIc), (IV), (IVa), or (IVb) or a pharmaceutically acceptable salt, ester, solvate, alkylated quaternary ammonium salt, stereoisomer, tautomer or prodrug thereof wherein the *enterococcus* has Van-C resistance.

Administration and Pharmaceutical Composition

Pharmaceutical compositions described herein comprise a therapeutically effective amount of a compound described herein (i.e., a compound of any of Formula (I), (Ia), (Ib), (Ic), (Id), (Ie), (II), (IIa), (IIb), (IIc), (III), (IIIa), (IIIb), (IIIc), (IV), (IVa), or (IVb)) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound of any of Formula (I), (Ia), (Ib), (Ic), (Id), (Ie), (II), (IIa), (IIb), (IIc), (III), (IIIa), (IIIb), (IIIc), (IV), (IVa), or (IVb)) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of a aerosol particles having with a mass medium average diameter predominantly between 1 to 5μ. Further, the formulation preferably has balanced osmolarity ionic strength and chloride concentration, and the smallest aerosolizable volume able to deliver effective dose of the compounds described herein compound described herein (i.e., a compound of any of Formula (I), (Ia), (Ib), (Ic), (Id), (Ie), (II), (IIa), (IIb), (IIc), (III), (IIIa), (IIIb), (IIIc), (IV), (IVa), or (IVb)) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, compounds described herein compound described herein (i.e., a compound of any of Formula (I), (Ia), (Ib), (Ic), (Id), (Ie), (II), (IIa), (IIb), (IIc), (III), (IIIa), (IIIb), (IIIc), (IV), (IVa), or (IVb)) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound of any of Formula (I), (Ia), (Ib), (Ic), (Id), (Ie), (II), (IIa), (IIb), (IIc), (III), (IIIa), (IIIb), (IIIc), (IV), (IVa), or (IVb)) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Some abbreviations used herein are as follows:

DIPEA: diisopropylethylamine

DMAP: 4-dimethylaminopyridine

DMF: dimethylformamide

DCM: dichloromethane

TFA: trifluoroacetic acid

EDC: 1-ethyl-3-(3-dimethylaminopropyl)carbodiimide

HATU: O-(7-azabenzotriazol-1-yl)-N,N,N',N'-tetramethyluronium hexafluorophosphate HCTU: O-(6-Chlorobenzotriazol-1-yl)-N,N,N',N'-tetramethyluronium hexafluorophosphate HOBt: hydroxybenzotriazole pyBOP: (Benzotriazol-1-yloxy)tripyrrolidinophosphonium hexafluorophosphate DMDO: 3,3-Dimethyldioxirane (R)-BoroAla-(+)-pinanediol HCl: (R)-1-((3aS,4S,6S,7aR)-3a,5,5-trimethylhexahydro-4,6-methanobenzo[d][1,3,2]dioxaborol-2-yl)ethanamine hydrochloride (1:1)

BoroGly-(+)-pinanediol HCl: ((3aS,4S,6S,7aR)-3a,5,5-trimethylhexahydro-4,6-methanobenzo[d][1,3,2]dioxaborol-2-yl)methanamine hydrochloride (1:1)

THF: tetrahydrofuran

MeOH: methanol

EtOAc: ethyl acetate

Trt resin: 2-Chlorotrityl chloride resin

Boc: t-butoxycarbonyl

TLC: thin-layer chromatography

General Method 1: Attachment of an Fmoc-protected amino acid onto a 2-chlorotrityl resin is depicted in Scheme I.

Scheme I

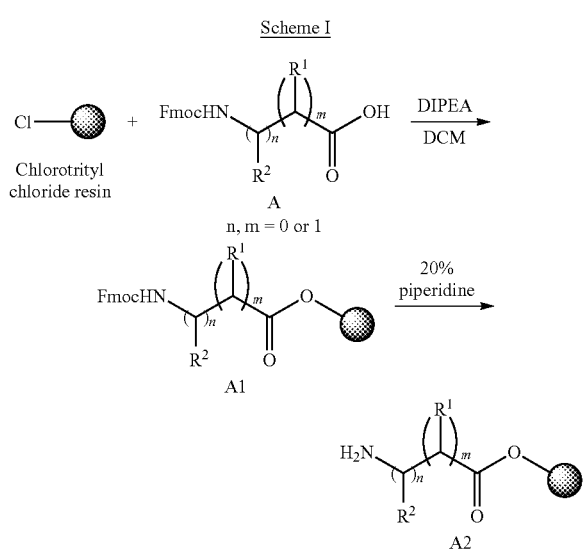

A mixture of 2-chlorotrityl resin (500 mg, 0.5 mmol), diisopropylethylamine (DIPEA) (0.26 g, 2 mmol) in dry DCM (10 mL) was added a solution of an Fmoc-protected amino acid (1.5 mmol) in dry DCM (10 ml) at 0° C. Then the mixture was shaken for 5 hr at room temperature. The mixture was filtered and the cake was washed with DCM (30 mL×3), DMF (30 mL×3) and MeOH (30 mL×3) to afford Compound A1. To the above resin was added approximately 20% piperidine/DMF (70 mL) to remove the Fmoc group. The mixture was shaken for 10 mins and the cycle was repeated three times. The mixture was washed with DCM (2×30 mL) and DMF (3×30 mL) to give Compound A2.

General Method 2: The solid phase peptide and/or amide coupling and cleavage from the resin is depicted in Scheme II.

Scheme II

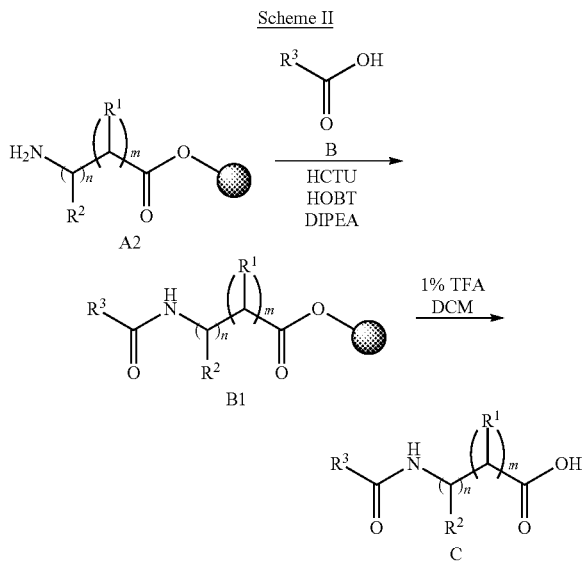

Step 1: A mixture of B (1.5 eq), HCTU (1.5 eq), HOBT (1.5 eq) and DIPEA (1.5 eq) in dry DMF (6-8 mL/eq) was stirred at 20° C. for 30 mins. Then the above mixture was added to Compound A2 (1 eq) and shaken at 20° C. for 1.5 hrs. After LCMS showed the reaction was completed, the mixture was filtered and the residue was washed with DMF (3×10 mL/mmol) and DCM (3×10 mL/mmol) to give Compound B1. An analytical portion of resin B1 was treated and mixed in 1% TFA/DCM to cleave the peptide from the resin, and the desired product was detected by MS with confirmation that no starting material remains. In cases where the peptide coupling is slow or does not go to completion, HCTU can be replaced with EDCI. In cases where a protected alpha-amino acid is used, the Fmoc-group is used as the protecting group.

Step 2: Cleavage of the Compound B1 is accomplished by repeated treatment of the resin with 1% TFA in $CH_2Cl_2$. A mixture of Compound B1 (3 mmol) was treated with 1% TFA/DCM (3-4 mL/mmol) for 5 mins and filtered. This operation was repeated three times. The filtrate was treated with saturated $NaHCO_3$ solution until pH=7~8. The aqueous layer was adjusted to pH=3~4 with citric acid. The mixture was extracted with DCM (6-8 mL/mmol) three times, then the combined organic layers were washed with brine, dried over $Na_2SO_4$ and concentrated to give Compound C. The reported yields are based on the theoretical loading of the chlorotrityl chloride resin.

General Method 3: Solid phase peptide coupling of varying lengths and cleavage from the resin. The alternative coupling of peptide and/or amide fragments of amino acids in length terminated by a lipophilic carboxylic acid tail is depicted in Scheme III.

Scheme III

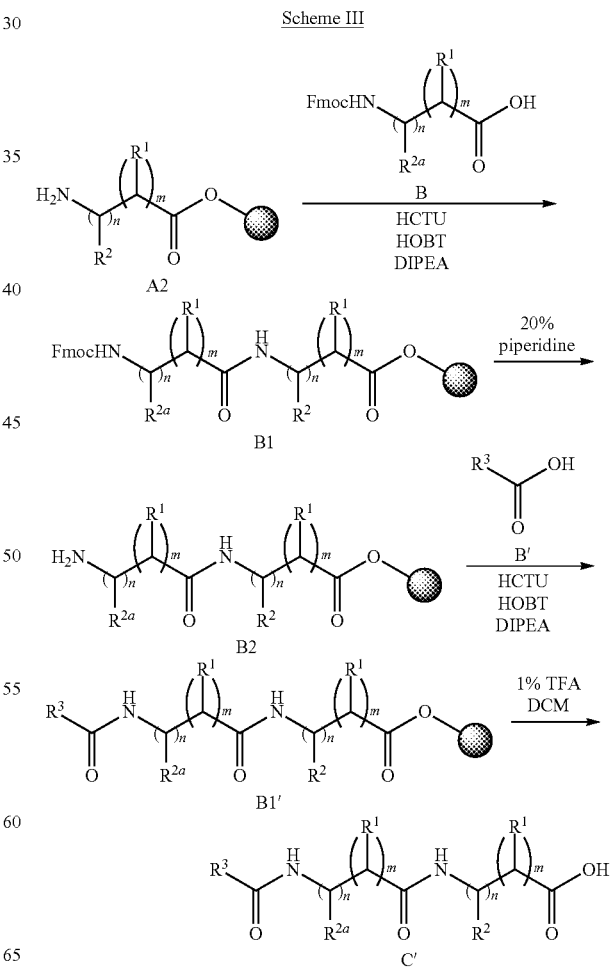

Step 1: A mixture of B (1.5 eq), HCTU (1.5 eq), HOBT (1.5 eq) and DIPEA (1.5 eq) in dry DMF (6-8 mL/eq) was stirred at 20° C. for 30 mins. Then the above mixture was added to Compound A2 (1 eq) and shaken at 20° C. for 1.5 hrs. After LCMS showed the reaction was completed, the mixture was filtered and the residue was washed with DMF (3×10 mL/mmol) and DCM (3×10 mL/mmol) to give Compound B1. An analytical portion of resin B1 was treated and mixed in 1% TFA/DCM to cleave the peptide from the resin, and the desired product was detected by MS with confirmation that no starting material remains. In cases where the peptide coupling is slow or does not go to completion, HCTU can be replaced with EDCI.

Step 2: To B1 was added 20% piperidine/DMF (70 mL) to remove the Fmoc group. The mixture was shaken for 10 min and the cycle was repeated three times. The mixture was washed with DCM (2×30 mL) and DMF (3×30 mL) to give Compound B2.

Step 3: The process of Step 1 can be repeated on B2 using B' to afford B1'.

Step 4: The Cleavage of the Compound B1' is accomplished by repeated treatment of the resin with 1% TFA in $CH_2Cl_2$ as shown in the following example. A mixture of Compound B1' (3 mmol) was treated with 1% TFA/DCM (3-4 mL/mmol mL) for 5 mins and filtered. This operation was repeated three times. The filtrate was treated with saturated $NaHCO_3$ solution until pH=7~8. The aqueous layer was adjusted to pH=3~4 with citric acid. The mixture was extracted with DCM (6-8 mL/mmol) three times, then the combined organic layers were washed with brine, dried over $Na_2SO_4$ and concentrated to give Compound C'. The reported yields are based on the theoretical loading of the chlorotrityl chloride resin.

General Method 4: The coupling of an N-methyl peptide to a carboxylic acid is depicted in Scheme IV.

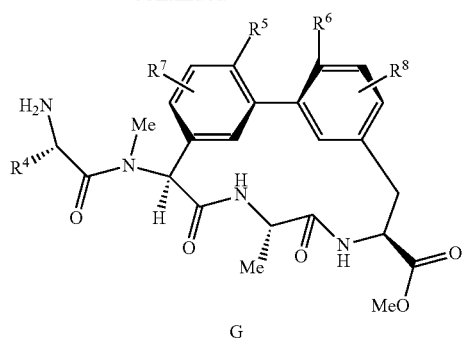

To a solution of N-methyl peptide Compound E (1 eq) in DMF (2 mL) were added HOBT (1.5-2.7 eq), DIPEA (1.5-2.7 eq), Compound I (1.1 eq) and EDCI (1.5-2.7 eq). The resulting solution was stirred at 20° C. overnight and diluted with water. The precipitate was filtered and the resulting filter cake was washed with water and dried by aspiration to give a crude product, which was recrystallized from PE to give Compound F, as a white solid.

General Method 5: Alternative coupling of an N-methyl peptide to a carboxylic acid using DEPBT.

A mixture of a carboxylic acid (1.2 eq), N-methyl peptide Compound E (1.0 eq) $NaHCO_3$ (5 eq), and DEPBT (3 eq) in dry THF (0.01 to 0.1 M) was heated to reflux overnight. After HPLC analysis showed the reaction to be complete, the mixture was concentrated under reduced pressure. The residue was treated with water and extracted with EtOAc (3×). The combined organic layers were washed with brine, dried over $Na_2SO_4$, filtered, and concentrated. Purification by preparative HPLC (AcCN/$H_2O$ with 0.05% TFA) followed by lyophilization afforded the desired compound.

General Method 6: An illustrative amide coupling is illustrated in Scheme V, an example of which is the coupling of Compound G to Compound C.

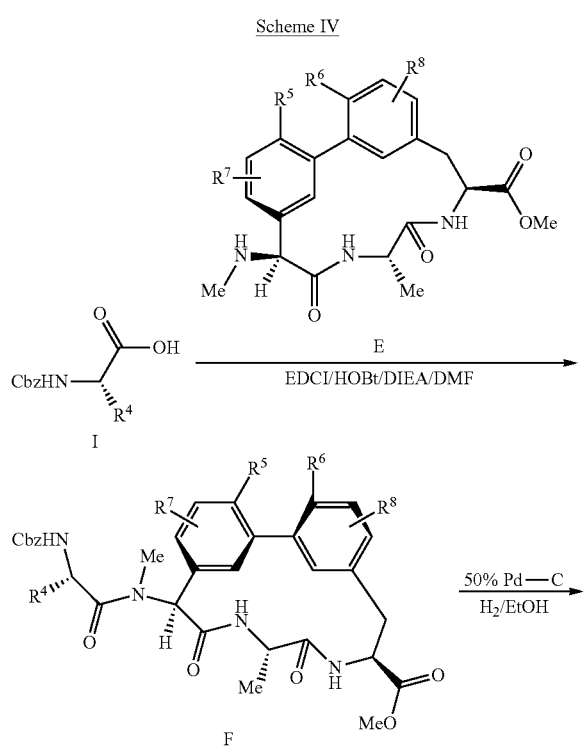

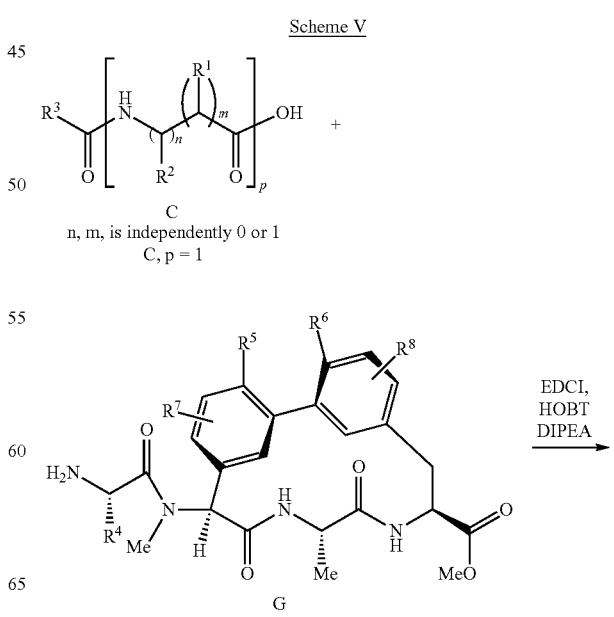

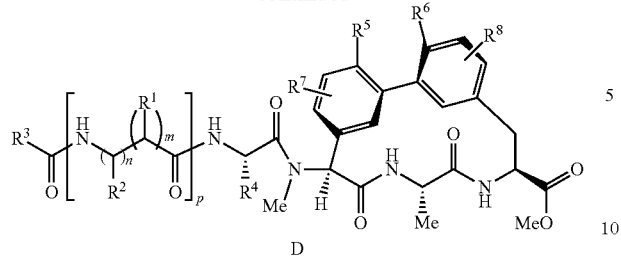

D

To a solution of Compound C (1.1 eq) in DMF (2 mL) were added EDCI (1.5-2.7 eq) HOBt (1.5-2.7 eq)) DIPEA (1.5-2.7 eq), the solution was stirred at room temperature for 30 min, whereupon Compound G (1 eq) was added. The resulting solution was stirred at room temperature overnight and diluted with water. The precipitate was filtered and the resulting cake was washed with water and dried under vacuum to give Compound D.

General Method 7: The deprotection of bis-arylmethyl ethers with $AlBr_3$ and EtSH is depicted in Scheme VI.

Scheme VI

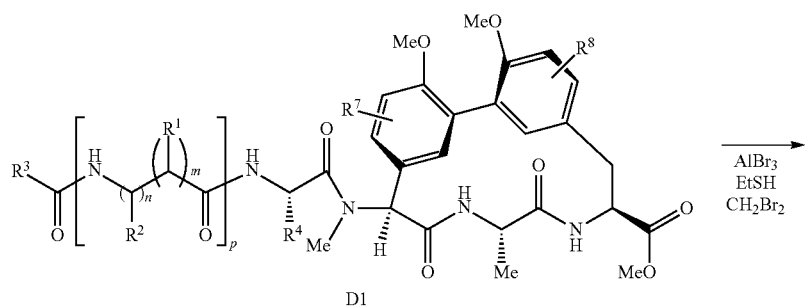

D1 m, n, p independently 0 or 1

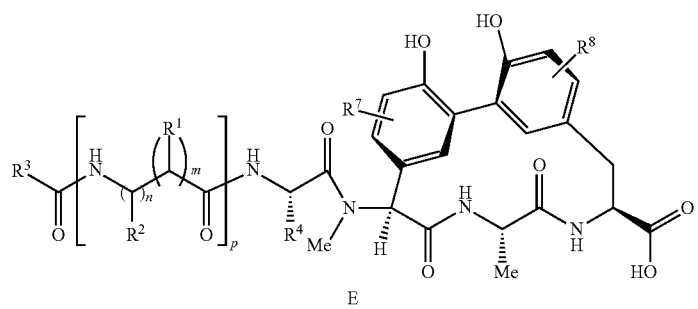

E

To a mixture of the bis-arylmethyl ether D1 (1 eq) in EtSH (50 mL/mmol) and $CH_2Br_2$ was added 1.0 M $ABr_3$ (25 eq) under Ar. The mixture was heated to 50° C. for 4 hr. After HPLC analysis showed the reaction was complete, the reaction was quenched with MeOH (16 mL/mmol), and then the solvent was evaporated to give a crude product, which was purified by preparative HPLC to afford the desired bis-phenol E.

Intermediate G1: The synthesis of Compound G1 is depicted in Scheme VII.

Scheme VII

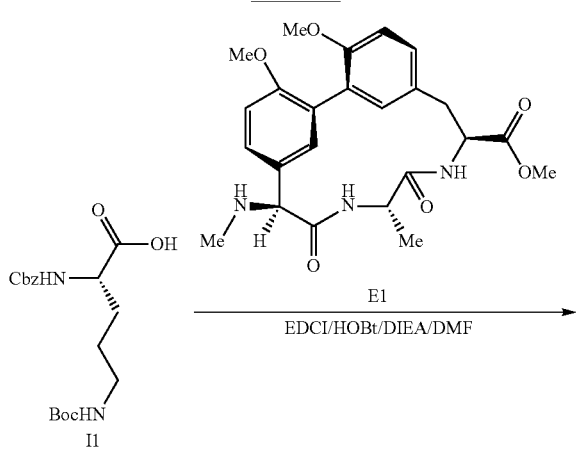

E1

$$\xrightarrow{\text{EDCI/HOBt/DIEA/DMF}}$$

-continued

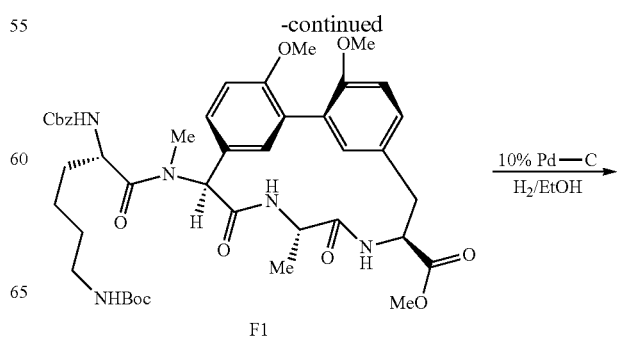

F1

$$\xrightarrow{\text{10% Pd—C}}_{\text{H}_2/\text{EtOH}}$$

-continued

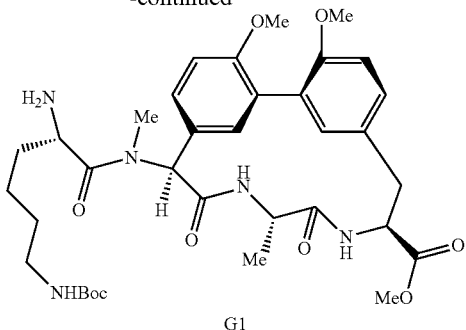

G1

Step 1: To a solution of Compound E[1] (275 mg, 0.73 mmol) in DMF (2 mL) were added HOBT (267 mg, 1.98 mmol), DIPEA (255 mg, 1.98 mmol), Compound II (300 mg, 0.66 mmol) and EDCI (378 mg, 1.98 mmol). The resulting solution was stirred at 20° C. overnight and diluted with water. The precipitate was filtered and the resulting filter cake was washed with water and dried by aspiration to give a crude product, which was recrystallized from PE to give Compound F1 (0.5 g, 84%), as a white solid.

Step 2: To a suspension of Compound F1 (500 mg, 0.61 mmol) and 10% Pd/C (0.7 g) in EtOH (15 mL) was stirred at 20° C. overnight under a hydrogen atmosphere until LC-MS showed the reaction was completed. Then the catalyst was filtered and the solvent was evaporated to afford Compound G1 (350 mg, 90%), which was used without further purification.

Intermediate H1: The synthesis of Compound H1 is depicted in Scheme VIII.

Scheme VIII

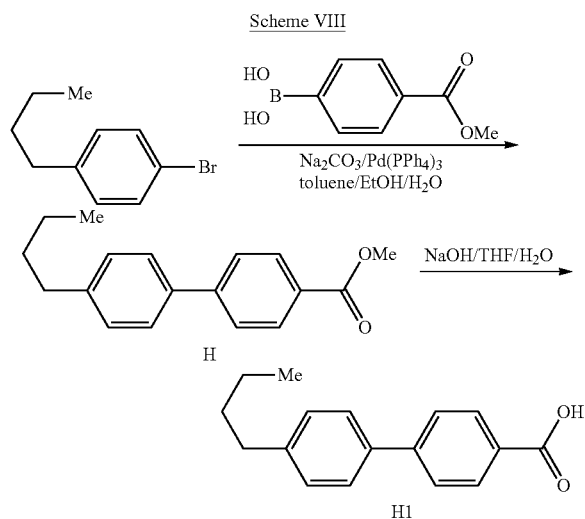

Step 1: A solution of 1-bromo-4-n-butylbenzene (100 g, 0.472 mol), 4-(methoxycarbonyl)benzeneboronic acid (82.0 g, 0.456 mol), 2 M $Na_2CO_3$ (150 g, 1.42 mol) in toluene/EtOH (900 mL/300 mL) was degassed with $N_2$ for three times, then $Pd(PPh_3)_4$ (27.2 g, 23.6 mmol) was added. The resulting mixture was degassed with $N_2$ for three times and then heated to reflux for 5 hrs. After TLC showed the reaction was complete, toluene and EtOH was removed under vacuum. The residue was extracted with EA (3×). The combined organic layers were washed with brine, dried with $Na_2SO_4$. The solvent was removed to give the crude product. The crude product was purified by column chromatography on silica gel eluted with PE, PE: EA (150:1). The solvent was removed to give Compound H (105 g, yield: 86.0%), as a white solid.

Step 2: A mixture of Compound H (89.0 g, 0.332 mol), NaOH (26.6 g, 0.664 mol) in THF/$H_2O$ (500 mL/100 mL) was heated to reflux overnight. After TLC showed the reaction was complete, THF was removed. The residue was adjusted pH=3-4 with 2 N HCl solution. The resulting mixture was filtered and the cake was washed with water, and dried to give Compound H1 (60.0 g, 71.1%), as a white solid.

Intermediate H2

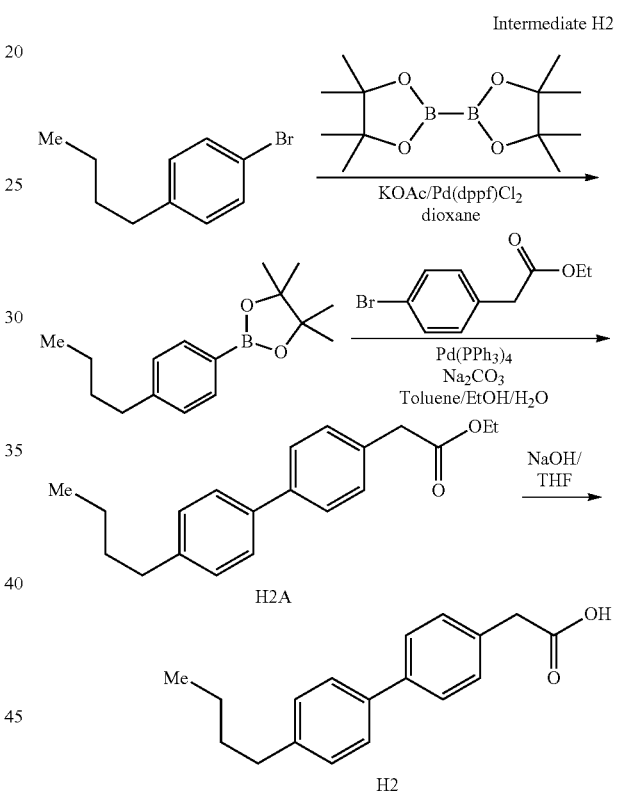

A mixture of 1-bromo-4-butylbenzene (5 g, 23.5 mmol), bis(pinacolato)diboron (6 g, 23.5 mmol), KOAc (6.9 g, 70.5 mmol), $Pd(dppf)Cl_2$ (860 mg, 1.2 mmol) in dioxane (50 mL) was degassed with $N_2$ for three times and heated to reflux for 5 hrs. After TLC showed the reaction was complete, the mixture was cooled, filtered, and the filtrate was concentrated. The crude product was purified by column chromatography on silica gel to give 2-(4-butylphenyl)-4,4,5,5-tetramethyl-1,3,2-dioxaborolane (3.8 g, yield: 76%).

A mixture of 2-(4-butylphenyl)-4,4,5,5-tetramethyl-1,3,2-dioxaborolane (2.1 g, 8.3 mmol), ethyl 2-(4-bromophenyl)acetate (1 g, 4.1 mmol), $Na_2CO_3$ (1.3 g, 12.3 mmol), $Pd(PPh_3)_4$ (237 mg, 0.21 mmol) in toluene/EtOH/$H_2O$ (20 mL/10 mL/2 mL) was degassed with $N_2$ for 3 times and then the mixture was heated to reflux for 8 hrs. After TLC showed the reaction was complete, the mixture was filtered, and the filtrate was concentrated. The crude product was purified by column chromatography on silica gel to give Compound H2A (0.7 g, yield: 58.3%).

A mixture of Compound H2A (0.8 g, 2.7 mmol), NaOH (213 mg, 5.3 mmol) in THF/H2O (10 mL/1 mL) was heated to reflux for 3 hrs. After TLC showed the reaction was complete, THF was removed. The mixture was adjusted pH=4~5 with 1N HCl. The resulting mixture was filtered and the cake was dried to give Compound H2 (0.5 g, yield: 69.4%).

Intermediate H3

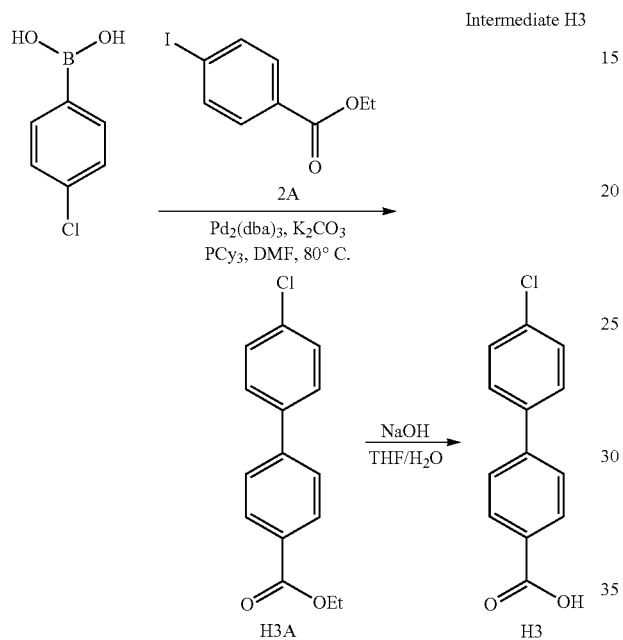

An oven-dried three neck flask (500 mL) was charged with (4-chlorophenyl)boronic acid (12 g, 74.7 mmol), ethyl 4-iodobenzoate (14.1 g 51.2 mmol), Pd$_2$(dba)$_3$ (4.68 g, 5.12 mmol), PCy$_3$(1.43 g, 5.12 mmol) and K$_2$CO$_3$ (21.21 g, 153.5 mmol). DMF (100 mL) was added and the reaction mixture was purged with N$_2$. The mixture was stirred at 80° C. for 12 h. The reaction mixture was cooled to room temperature and filtered to remove K$_2$CO$_3$. The solvent was removed and the brown residue was purified by column (1% to 5% EtOAc in petroleum ether) to give Compound H3A (9.52 g, 71.4%).

To a solution of ethyl 4'-chloro-[1,1'-biphenyl]-4-carboxylate (H3A) (9.52 g, 36.6 mmol) in a mixture of THF (150 mL) and H$_2$O (20 mL) was added NaOH (4N, 5.86 g, 146 mmol). After the mixture was stirred at 70° C. for 10 h, the organic solvent was removed under reduced pressure, and pH was adjusted to 3 with 4M HCl. The product was collected by filtration, wash with water and dried to give Compound H3 (8.5 g, 100%). $^1$H NMR (400 MHz, CDCl$_3$) δ 8.10 (d, J=8.4 Hz, 2 H), 7.70 (d, J=8 Hz, 2 H), 7.65 (d, J=8.8 Hz, 2 H), 7.47 (d, J=8.8 Hz, 2 H).

Intermediate E1: The preparation of E$^1$ is described in Roberts, et. al. *J. Am. Chem. Soc.* 2007, 129, 15830-15838, and Dufour, et. al. *Chem. Eur. J.* 2010, 16, 10523 10534 and is incorporated by reference. A modified synthesis of Compound E$^1$ is depicted in Scheme IX.

Scheme IX

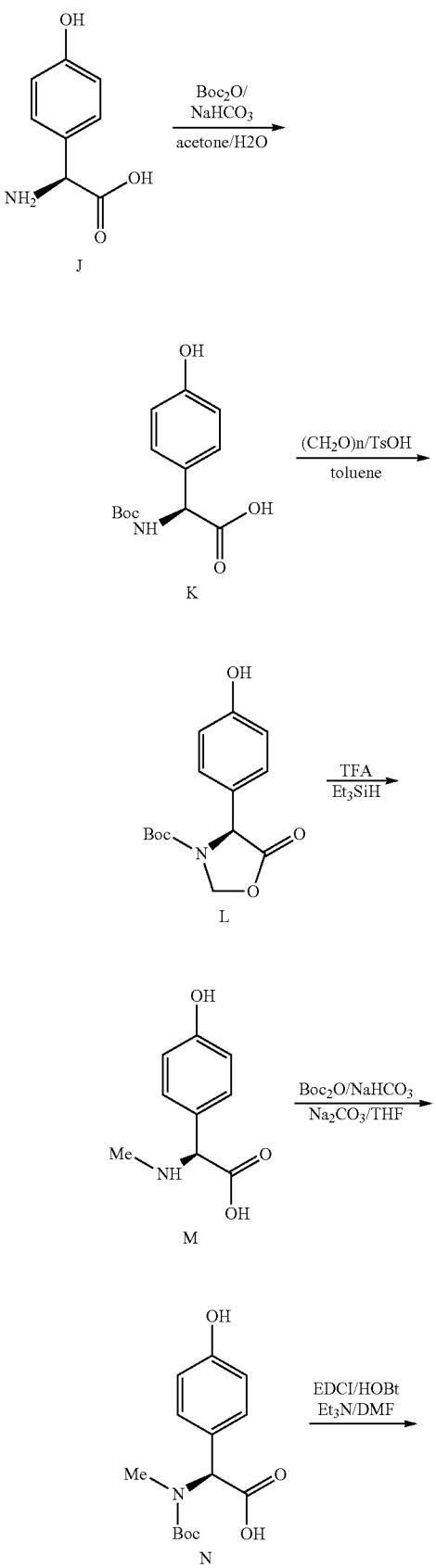

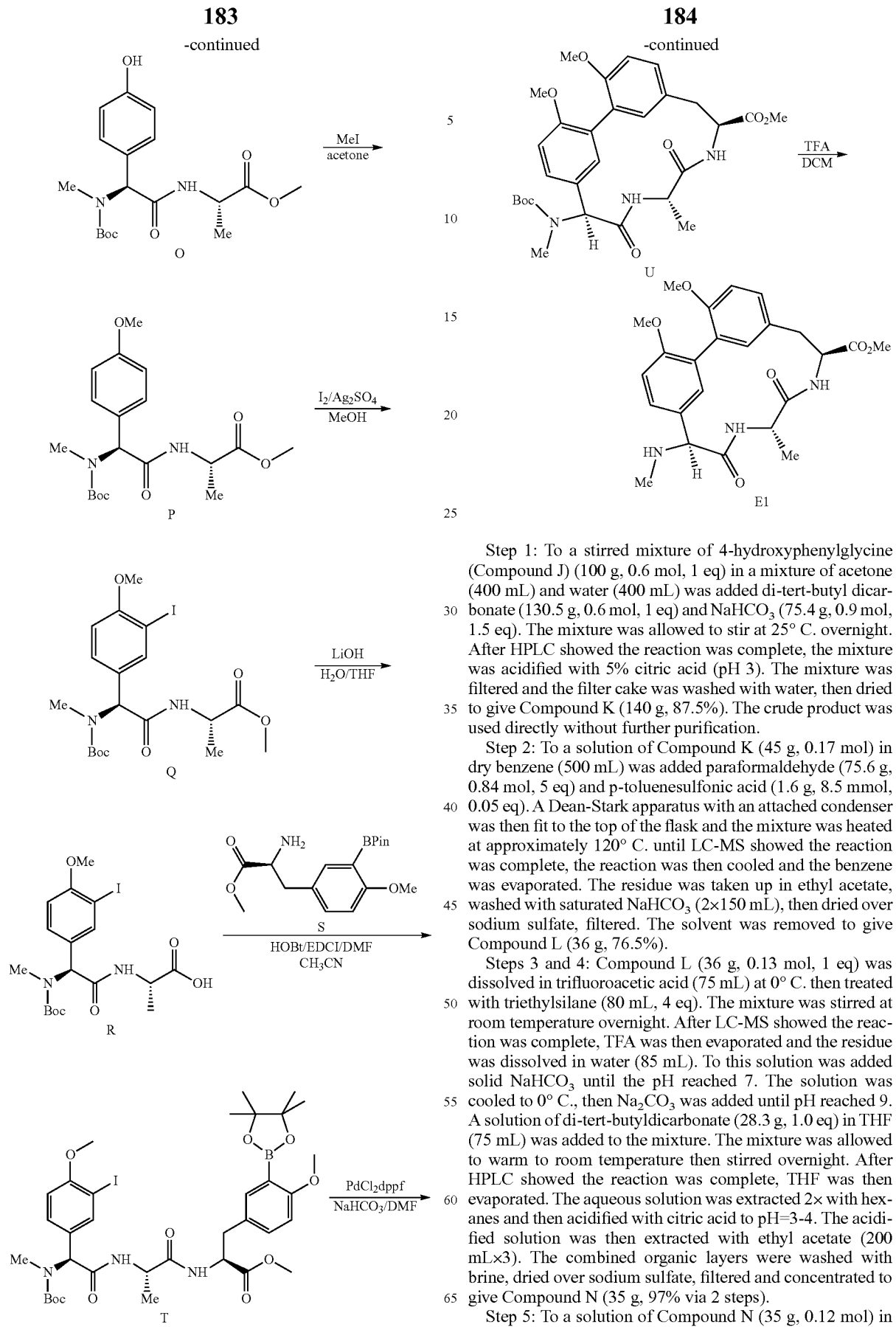

Step 1: To a stirred mixture of 4-hydroxyphenylglycine (Compound J) (100 g, 0.6 mol, 1 eq) in a mixture of acetone (400 mL) and water (400 mL) was added di-tert-butyl dicarbonate (130.5 g, 0.6 mol, 1 eq) and NaHCO$_3$ (75.4 g, 0.9 mol, 1.5 eq). The mixture was allowed to stir at 25° C. overnight. After HPLC showed the reaction was complete, the mixture was acidified with 5% citric acid (pH 3). The mixture was filtered and the filter cake was washed with water, then dried to give Compound K (140 g, 87.5%). The crude product was used directly without further purification.

Step 2: To a solution of Compound K (45 g, 0.17 mol) in dry benzene (500 mL) was added paraformaldehyde (75.6 g, 0.84 mol, 5 eq) and p-toluenesulfonic acid (1.6 g, 8.5 mmol, 0.05 eq). A Dean-Stark apparatus with an attached condenser was then fit to the top of the flask and the mixture was heated at approximately 120° C. until LC-MS showed the reaction was complete, the reaction was then cooled and the benzene was evaporated. The residue was taken up in ethyl acetate, washed with saturated NaHCO$_3$ (2×150 mL), then dried over sodium sulfate, filtered. The solvent was removed to give Compound L (36 g, 76.5%).

Steps 3 and 4: Compound L (36 g, 0.13 mol, 1 eq) was dissolved in trifluoroacetic acid (75 mL) at 0° C. then treated with triethylsilane (80 mL, 4 eq). The mixture was stirred at room temperature overnight. After LC-MS showed the reaction was complete, TFA was then evaporated and the residue was dissolved in water (85 mL). To this solution was added solid NaHCO$_3$ until the pH reached 7. The solution was cooled to 0° C., then Na$_2$CO$_3$ was added until pH reached 9. A solution of di-tert-butyldicarbonate (28.3 g, 1.0 eq) in THF (75 mL) was added to the mixture. The mixture was allowed to warm to room temperature then stirred overnight. After HPLC showed the reaction was complete, THF was then evaporated. The aqueous solution was extracted 2× with hexanes and then acidified with citric acid to pH=3-4. The acidified solution was then extracted with ethyl acetate (200 mL×3). The combined organic layers were washed with brine, dried over sodium sulfate, filtered and concentrated to give Compound N (35 g, 97% via 2 steps).

Step 5: To a solution of Compound N (35 g, 0.12 mol) in DMF (300 mL) was added triethylamine (18.4 mL, 0.14 mol, 1.1 eq), HOBt (16.2 g, 0.12 mol, 1 eq), Ala-OMe HCl (19.5 g, 0.14 mol, 1.1 eq) and EDC (26.7 g, 0.14 mol, 1.1 eq) and the reaction was stirred overnight. After LC-MS showed the reaction was complete, water and EtOAc were added. The aqueous layer was extracted with EtOAc (3×150 mL), and the combined organic layers were washed with 5% citric acid (pH −3), saturated NaHCO$_3$ (aq), water and brine. The combined organic layers were then dried over sodium sulfate, filtered and concentrated to give Compound O (30 g, 65.8%) as a white foam. The crude product was taken on to the next step directly without further purification.

Step 6: To a solution of the Compound O (30 g, 82 mmol) in acetone (400 mL) was added K$_2$CO$_3$ (56.6 g, 0.41 mol, 5 eq) and iodomethane (20.8 mL, 0.41 mol, 5 eq) and the reaction was stirred at reflux overnight. After LC-MS showed the reaction was complete, the reaction was then cooled to room temperature and the mixture was filtered. The filtrate was concentrated and the residue was taken up in water and ethyl acetate. The aqueous phase was extracted with EtOAc (3×150 mL). The combined organic layers were dried over sodium sulfate, filtered and concentrated to give Compound P (28 g, 90%), as a white foam.

Step 7: To a solution of Compound P (85 g, 0.22 mol, 1 eq) in methanol (1000 mL) was added sequentially Ag$_2$SO$_4$ (72.6 g, 0.23 mol, 1.05 eq) and I$_2$ (59.6 g, 1.05 eq). After LC-MS showed the reaction was complete, a solution of 10% (w/w) sodium thiosulfate was added till the reaction turned pale yellow. Most of the methanol was evaporated by rotary evaporation then water and ethyl acetate were added. The aqueous layer was extracted with ethyl acetate (3×300 mL). The combined organic layers were washed with brine, dried over sodium sulfate and concentrated to give Compound Q (100 g, 88.5%).

Step 8: To Compound Q (25 g, 49.4 mmol, 1 eq) in THF (300 mL) was added 0.2 M LiOH (500 mL, 98.8 mmol, 2 eq). The solution was stirred until TLC showed all starting material had been consumed. 5% citric acid (pH −3) was added to pH −3 then the THF was evaporated by rotary evaporation. The aqueous layer was extracted with EtOAc (3×100 mL). The combined organic layers were washed with brine, dried over sodium sulfate, filtered and concentrated to give Compound R (23 g, 94.6%), which was used directly without further purification.

Step 9: To a solution of Compound S (6.5 g, 19.4 mmol, 1 eq) and Compound R (10 g, 20.3 mmol, 1.05 eq) in acetonitrile: DMF (2.2:1, 168 mL) was added HOBt (6.5 g, 48.5 mmol, 2.5 eq) and EDC (8.1 g, 42.7 mmol, 2.2 eq). The reaction was stirred at room temperature overnight. After LC-MS showed the reaction was complete, diluted citric acid (pH −3) was added and the aqueous was extracted with EtOAc (3×150 mL). The combined organic layers were then washed with saturated NaHCO$_3$ solution, brine and dried over sodium sulfate. The mixture was filtered and the filtrate was concentrated to give the crude product Compound T, which was used directly without further purification.

Step 10: To crude product Compound T (16 g, 19.4 mmol, 1 eq) and NaHCO$_3$ (16.3 g, 0.19 mol) were sealed in a flask with a condenser and put under an atmosphere of argon. Then DMF (600 mL), in a round bottle flask was purged several times via cycling with vacuum and Ar and then PdCl$_2$(dppf) (3.3 g, 4.5 mmol) was added. The reaction was then degassed with Ar for 15 minutes. The solution of PdCl$_2$(dppf) dissolved in DMF was then transferred via syringe to the flask containing the substrate and NaHCO$_3$. The resulting mixture was submitted to several more cycles of vacuum and Ar then heated to 120° C. overnight. After LCMS showed the reaction was completed, DMF was evaporated under vacuum. The crude material was subjected to abbreviated column chromatography (40% EA in PE) to remove most of the Pd species then purified by prep HPLC to give Compound U (2.1 g, 19.5% over two steps).

Step 11: To a stirred solution of Compound U (2.1 g, 3.78 mmol) in DCM (25 mL) was added TFA (2 mL). The reaction was monitored via TLC and when starting material was consumed, the solvent was evaporated under vacuum. The residue was then dissolved in EtOAc and the organic layer was washed with saturated NaHCO$_3$ (10 mL), dried over sodium sulfate and concentrated to give Compound E1 (1.7 g, 98.8%). MS (ESI) m/z 456.2 (M+H)$^+$.

Intermediate S: The synthesis of Compound S is depicted in Scheme X.

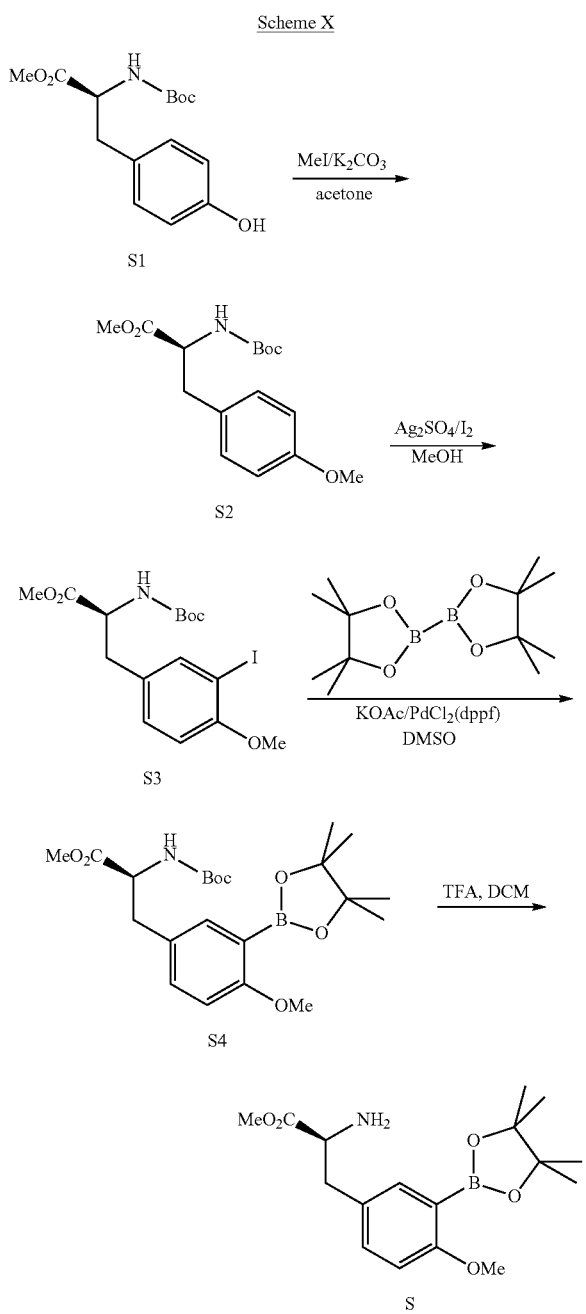

Step 1: To a solution of Compound S1 (100 g, 0.323 mol) in acetone (2.0 L) was added K₂CO₃ (37 g, 0.34 mol). After the addition, MeI (32 mL, 0.97 mol) was added dropwise, and the reaction mixture was stirred at room temperature for 72 h and monitored by TLC. The reaction had not yet gone to completion, so NaOH (0.1 eq) was added to the reaction mixture. And after 2 hrs, the reaction was completed. The solid was filtered and the solvent was removed. Then the residue was taken up in ethyl acetate and wash with H₂O, extracted with ethyl acetate (300 mL×3). The combined organic layers were washed with brine, dried over Na₂SO₄ and concentrated to give Compound S2 (100 g, 95.4%).

Step 2: To a solution of the Compound S2 (80 g, exactly 40 g each×2, run in two separate batches, 259 mmol overall) in methanol (1.5 L in each of the two flasks) was added sequentially Ag₂SO₄ (85 g, 272 mmol, ½-added to each flask) and I₂ (72 g, 283 mmol, ½-added to each flask). And the reaction mixture was stirred at room temperature for 2 hrs. The reaction was monitored by LCMS. When all the Compound S2 had been consumed, then a solution of 10% (w/w) sodium thiosulfate was added till the reaction turned pale yellow. Then the solid was filtered and most of the methanol was evaporated by rotary evaporation. Water and ethyl acetate were added to each batch. The aqueous layer was extracted with ethyl acetate (3×200 mL) then the combined organic layers were washed with brine, dried over sodium sulfate and concentrated. The crude material was combined for the two batches and they were purified together by flash column chromatography on silica gel (25% then 35% then 40% ethyl acetate in hexanes) to give Compound S3 (97 g, 89%).

Step 3: Compound S3 (92 g, exactly, 46 g each run in two separate batches, 211 mmol) was dissolved in anhydrous DMSO (1.5 L, ½-added for each batch) under argon and to the solution was added bis(pinacolato)diboron (80.5 g, 317 mmol, ½-added for each batch) and KOAc (103 g, 1.05 mol, ½-added for each batch). This mixture was degassed with argon for twenty minutes then Pd(dppf)Cl₂ (4.6 g, 6 mmol, ½-added for each batch) was added. The mixture was degassed with argon for 5 times, then it was kept under argon and heated to 80° C. for 3 hrs. TLC showed that the reaction was complete, and the reaction mixture was cooled to room temperature and filtered. Then the reaction mixture was dissolved in EA and washed by H₂O, the aqueous layer was extracted ethyl acetate (3×200 mL). The combined organic layers were dried over sodium sulfate, filtered and concentrated to give the crude product. The batches were then combined and purified together by flash column chromatography on silica gel (3% ethyl acetate in hexanes, then 20% to 25% ethyl acetate in hexanes to give Compound S4 (70 g, 76%).

Step 4: Compound S4 (22 g, 50.6 mmol) was dissolved in dichloromethane (150 mL) and treated with trifluoroacetic acid (50 mL). The reaction was stirred at room temperature and the reaction was monitored by HPLC. When all of the starting material had been consumed, the solvents were evaporated, DCM was added and Na₂CO₃ was added to neutralize the TFA. The mixture was filtered, and the solution was concentrated. DCM was added to the concentrated oil, and the mixture was cooled at 0° C. for 1 hr, whereupon the solid precipitates that formed were filtered. The filtrate was concentrated to give Compound S. The material was used without further purification.

Alternate methods to prepare macrocycles are depicted in Schemes XI and XII.

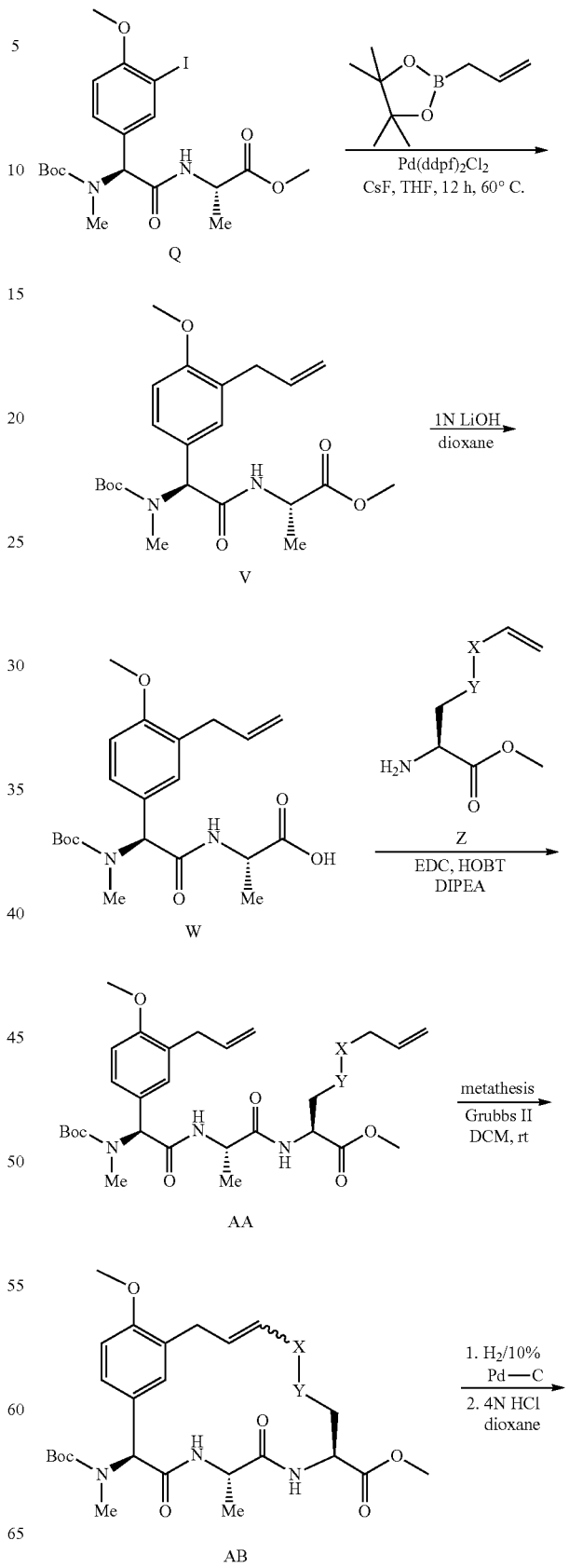

Scheme XI

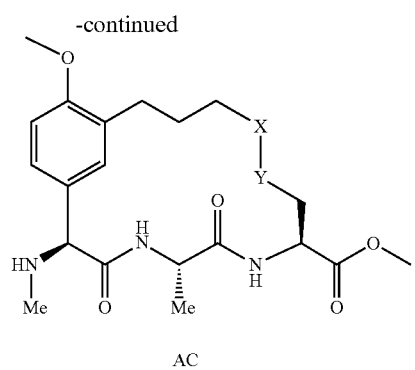

AC

The reaction of 2-allyl-4,4,5,5-tetramethyl-1,3,2-dioxaborolane under palladium catalysis, with Compound Q gives Compound V. Hydrolysis of the methyl ester with LiOH affords Compound W. Introduction of another fragment to facilitate macrocyclization is introduced at this stage. For example treatment of an olefinic amino acid such as Compound Z, for example where Y=O and X=CH$_2$) by treatment with EDC and HOBT with a base gives Compound AA. The use of cyclizing two olefins illustrate one example of a macrocyclization strategy. Treatment of Compound AA using the Grubbs Catalyst, $2^{nd}$ Generation affords the macrocycle Compound AB. Reduction of the double bond under metal catalysis, for example, 10% Pd—C under a hydrogen atmosphere, followed by Boc-protecting group removal under acidic conditions affords Compound AC. This scheme is employed to examine ring sizes of various sizes, for example when X=CH$_2$ and Y=bond to form a smaller ring, or conversely a longer olefin chain is used to form a larger macrocyclic ring.

Scheme XII

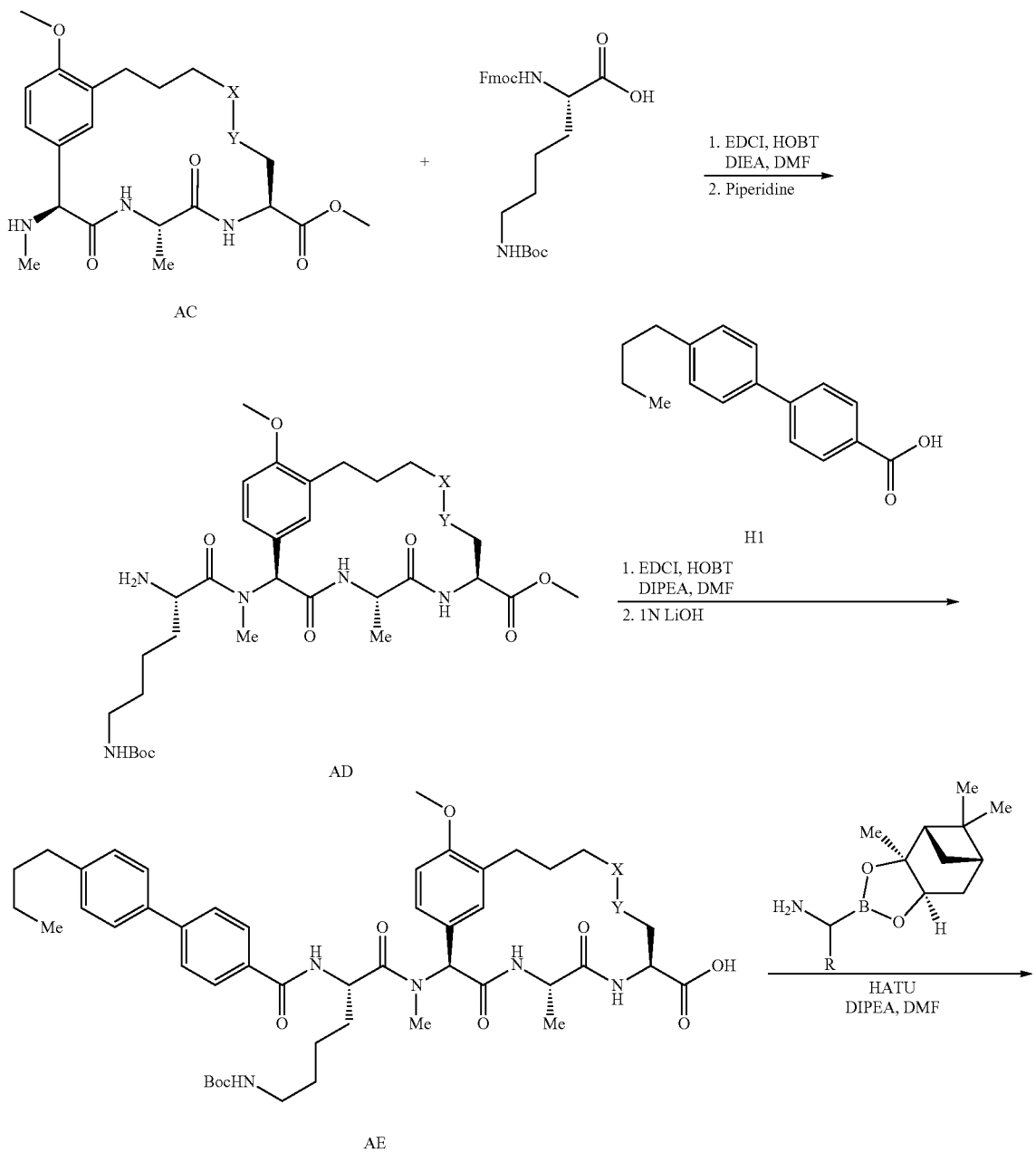

-continued

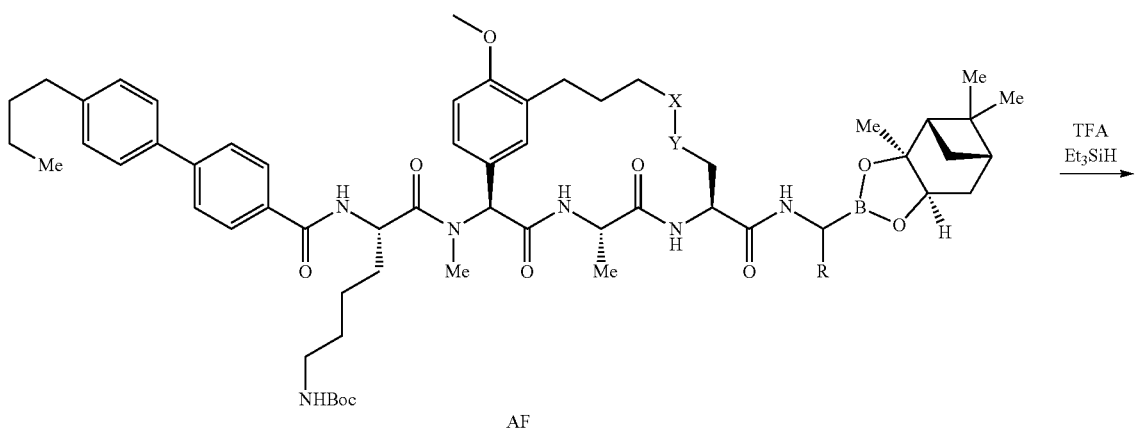

AF

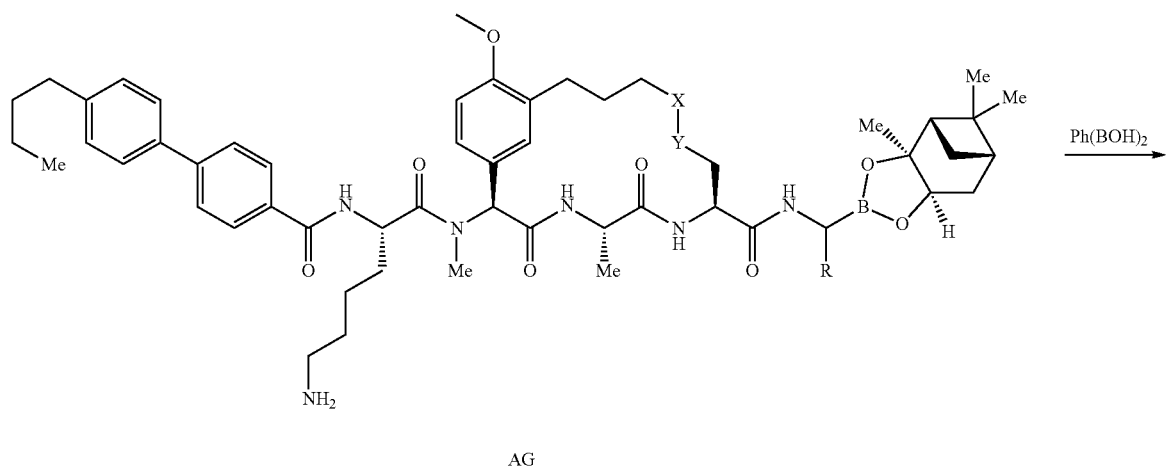

AG

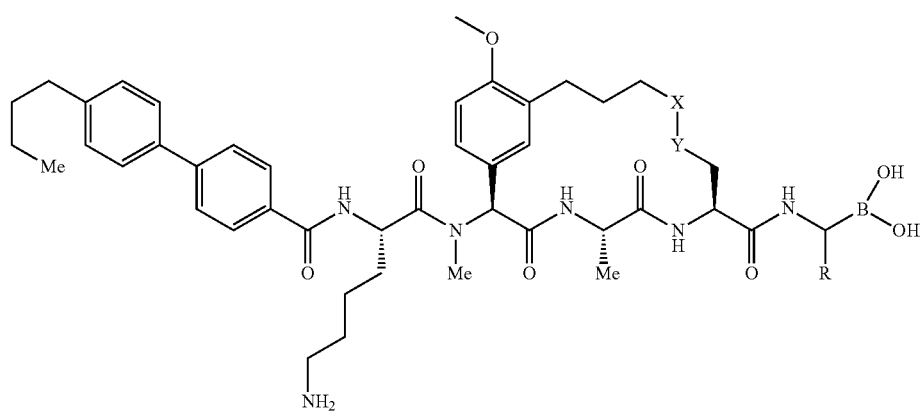

AH

Compound AC is treated with an protected amino acid, for example Fmoc-Lys(Boc)-OH, and EDCI and HOBT, followed by deprotection with piperidine to afford Compound AD. Compound AD is coupled with another fragment, for example Compound H1, with EDCI and HOBT to afford Compound AE. Introduction of a boronic acid fragment is achieved by reacting Compound AE with a protected boronic acid, for example Boro-Ala-pinanediol, and HATU and DIPEA, to afford Compound AF. Removal of the Boc protecting group with TFA and Et$_3$SiH leads to Compound AG. Removal of the boron protecting group with phenyl boronic acid affords Compound AH.

Example 1
Synthesis of Compound 101
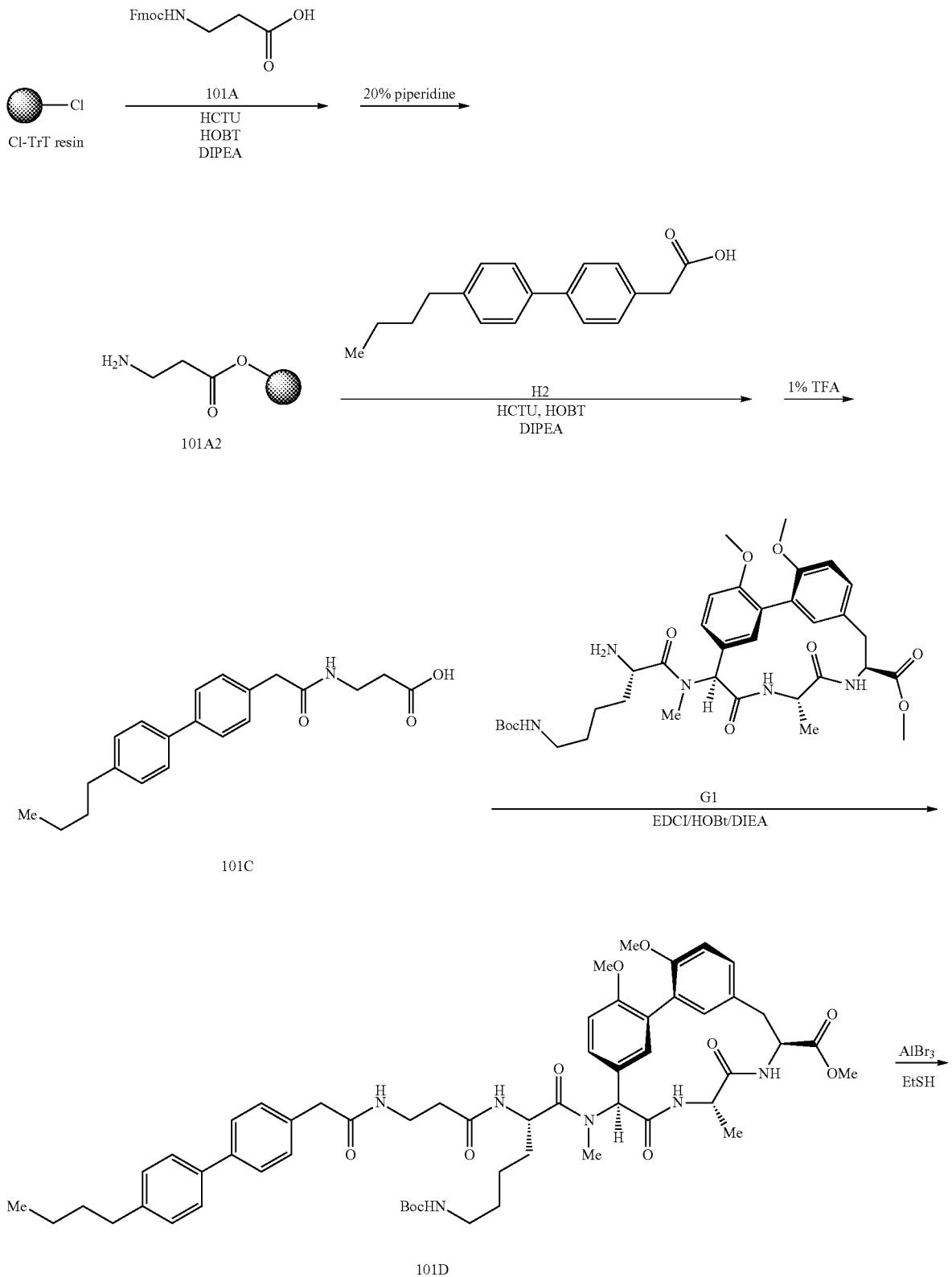

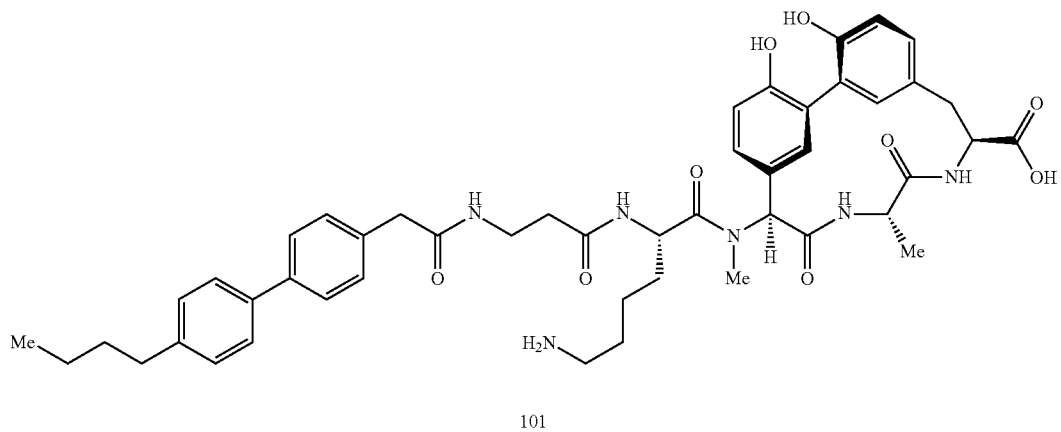

101

Synthesis of Compound 101A2: The compound was prepared according to General Methods 1 from chlorotritylchloride resin (500 mg, ca 0.5 mmol)), Fmoc-β-Ala-OH (Compound 101A, 0.46 g, 1.5 mmol), DIPEA (0.26 g, 2.0 mmol) to afford Compound 101A2.

Synthesis of Compound 101C: The compound was prepared according to General Method 2 from Compound H2 (0.40 g, 1.5 mmol) and Compound 101A2 (0.5 mmol) to afford of Compound 101C (110 mg, 65%).

Synthesis of Compound 101D: To a solution of Compound 101C (55 mg, 0.16 mmol) in DMF (3 mL) was added sequentially EDCI (86 mg, 1.5 mmol), HOBt (61 mg, 1.5 mmol) and DIPEA (58 mg, 1.5 mmol). The solution was stirred at room temperature for 30 mins, whereupon Compound G1 (100 mg, 0.15 mmol) was added. The resulting solution was stirred at room temperature for overnight and diluted with water. The precipitate was filtered and the resulting cake was washed with water and dried by aspiration to give Compound 101D (40 mg, 68%).

Synthesis of Compound 101: To a mixture of Compound 101D (80 mg, 0.081 mmol) in EtSH (4 mL) under Ar was added 1.0M AlBr$_3$ in CH$_2$Br$_2$ (2.5 mL). The reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 101 (40 mg, 47% yield). MS (ESI) m/z 863.5 (M+H)$^+$.

Example 2

Synthesis of Compound 102

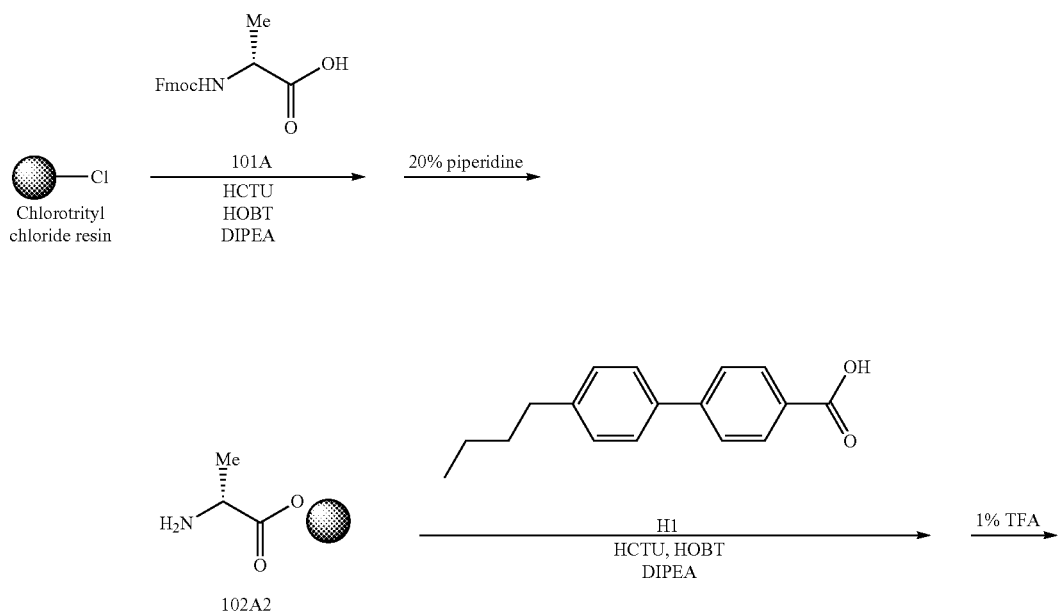

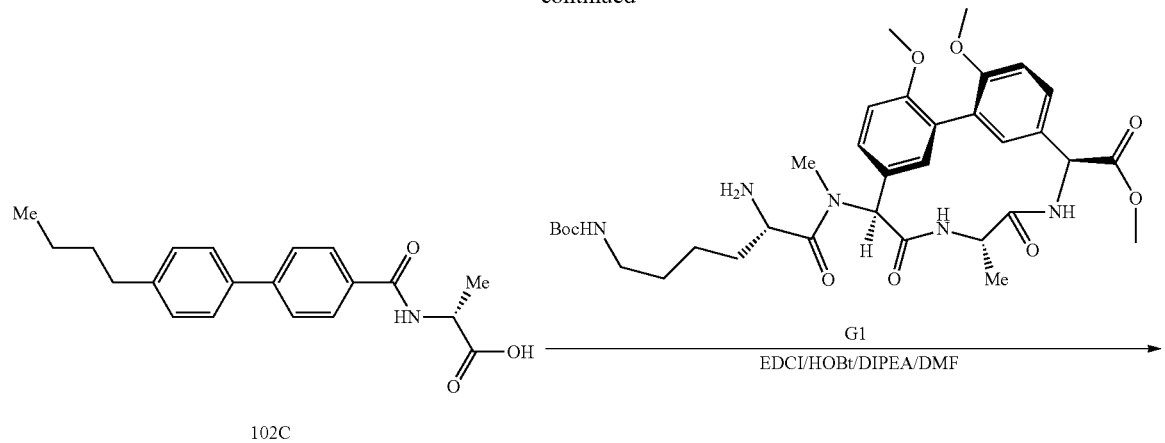

102C

G1
EDCI/HOBt/DIPEA/DMF

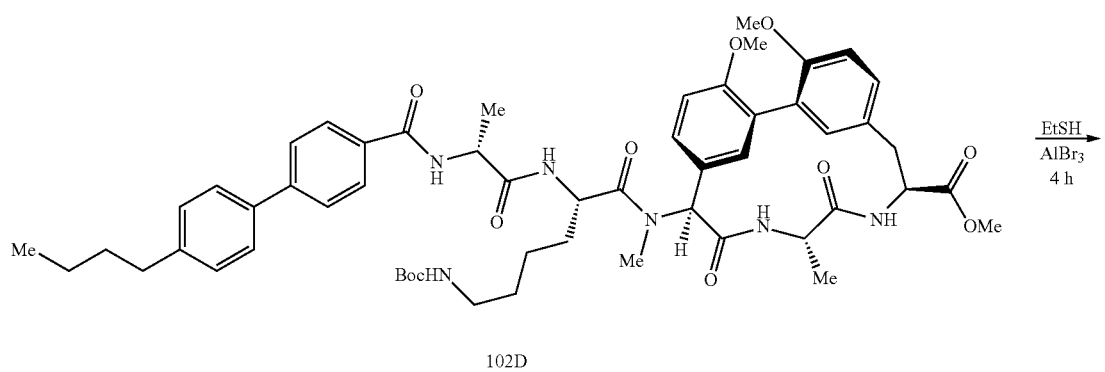

102D

EtSH
AlBr₃
4 h

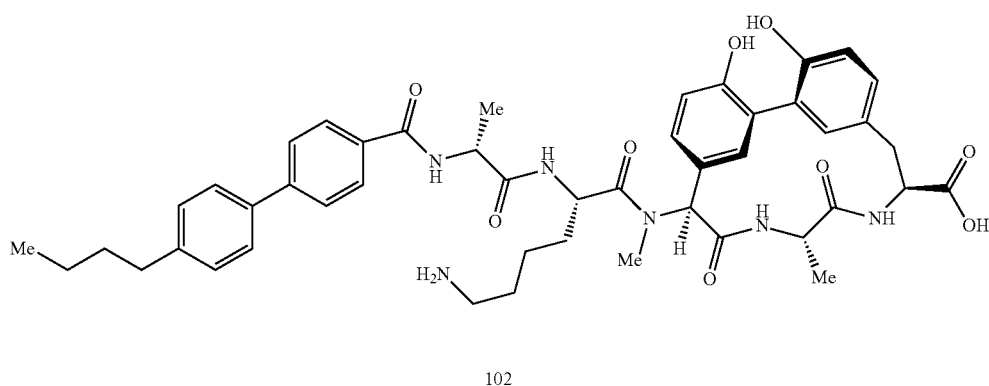

102

Synthesis of Compound 102A2: The compound was prepared according to General Method 1 from chlorotrityl chloride resin (0.5 g, ca. 0.5 mmol) and Fmoc-Ala-OH (Compound 102A, 0.47 g, 1.5 mmol) to afford compound 102A2.

Synthesis of Compound 102C: The compound was prepared according to General Method 2 from Compound H1 (0.25 g, 1.0 mmol) and Compound 102A2 (0.5 mmol) to afford Compound 102C (150 mg, 92%).

Synthesis of Compound 102D: To a solution of Compound 102C (60 mg, 0.18 mmol) in DMF (2 mL) were added EDCI (91.7 mg, 0.48 mmol) HOBt (64.8 mg, 0.48 mmol) and DIPEA (61.9 mg, 0.48 mmol). The solution was stirred at room temperature for 30 min, whereupon Compound G (112 mg, 0.16 mmol) was added. The resulting solution was stirred at room temperature overnight and diluted with water. The precipitate was filtered and the resulting cake was washed with water and dried under vacuum to give Compound 102D (110 mg, 60%).

Synthesis of Compound 102: To a mixture of Compound 102D (110 mg, 0.11 mmol) in EtSH (2 mL) under Ar was added 1.0M AlBr₃ in CH₂Br₂ (2.5 mL). The reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 102 (8 mg, 8.5%). MS (ESI) m/z 849.4 $(M+H)^+$.

Example 3
Synthesis of Compound 103
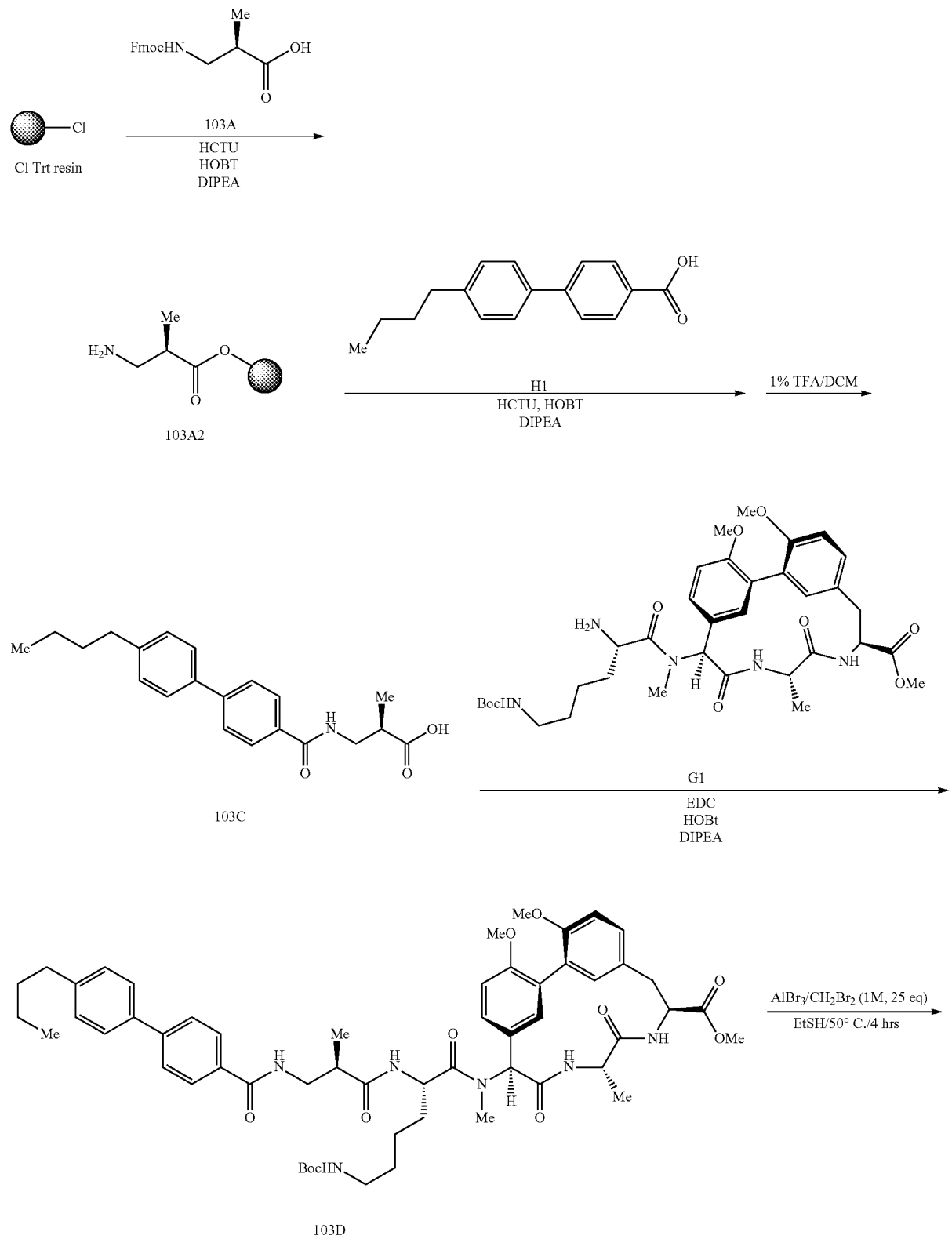

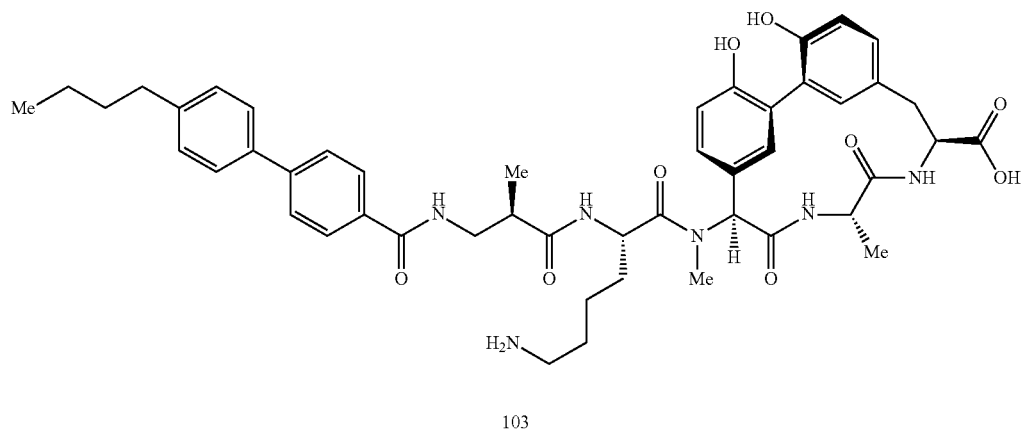

103

Synthesis of Compound 103A2: The compound was prepared according to General Methods 1 from chlorotritylchloride resin (1.5 g, ca 3 mmol), Compound 103A, (1.5 g, 4.5 mmol), and DIPEA (0.6 g, 2.0 mmol) to afford Compound 103A2.

Synthesis of Compound 103C: The compound was prepared according to General Method 2 from Compound H1 (1.14 g, 4.5 mmol) and Compound 103A2 (3 mmol) to afford Compound 103C (900 mg, 88%).

Synthesis of Compound 103D: A solution of Compound 103C (508.5 mg, 1.5 mmol) in anhydrous DMF (3 mL) was treated with EDCI (380 mg, 0.2 mmol) and HOBt (270 mg, 2 mmol) followed by DIPEA (260 mg, 2 mmol) and Compound G1 (683 mg, 1 mmol). The resulting solution was stirred at 20° C. overnight and diluted with water. The precipitate was filtered and the resulting cake was washed with water and dried to give Compound 103D (900 mg, 90%).

Synthesis of Compound 103: To a mixture of Compound 103D (900 mg, 0.896 mmol) in EtSH (30 mL) under Ar was added 1.0 M $AlBr_3$ in $CH_2Br_2$ (22.4 mL). The reaction vial was sealed and heated to 50° C. for 4 hrs. After LC-MS showed the reaction was completed, the mixture was cooled to room temperature, treated with MeOH (5 mL), and the solvent was removed. The crude product was purified by prep-HPLC to give Compound 103 (450 mg, 58%). MS (ESI) m/z 863.6 $(M+H)^+$.

Example 4

Synthesis of Compound 104

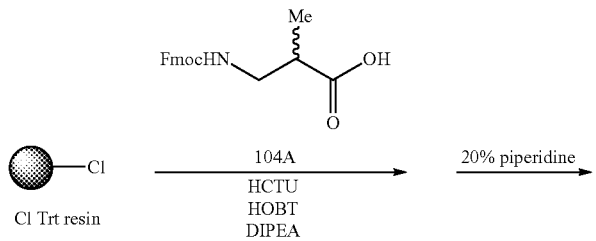

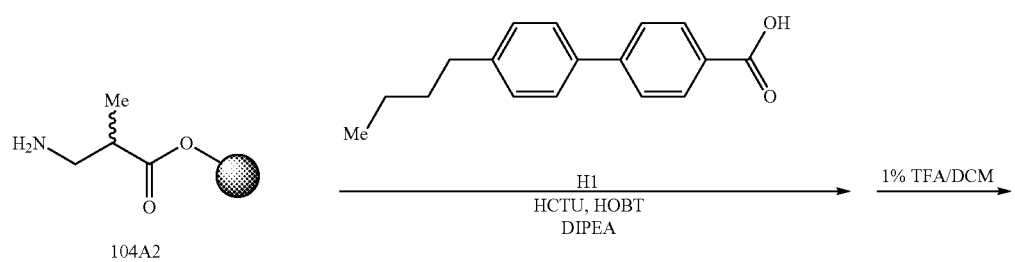

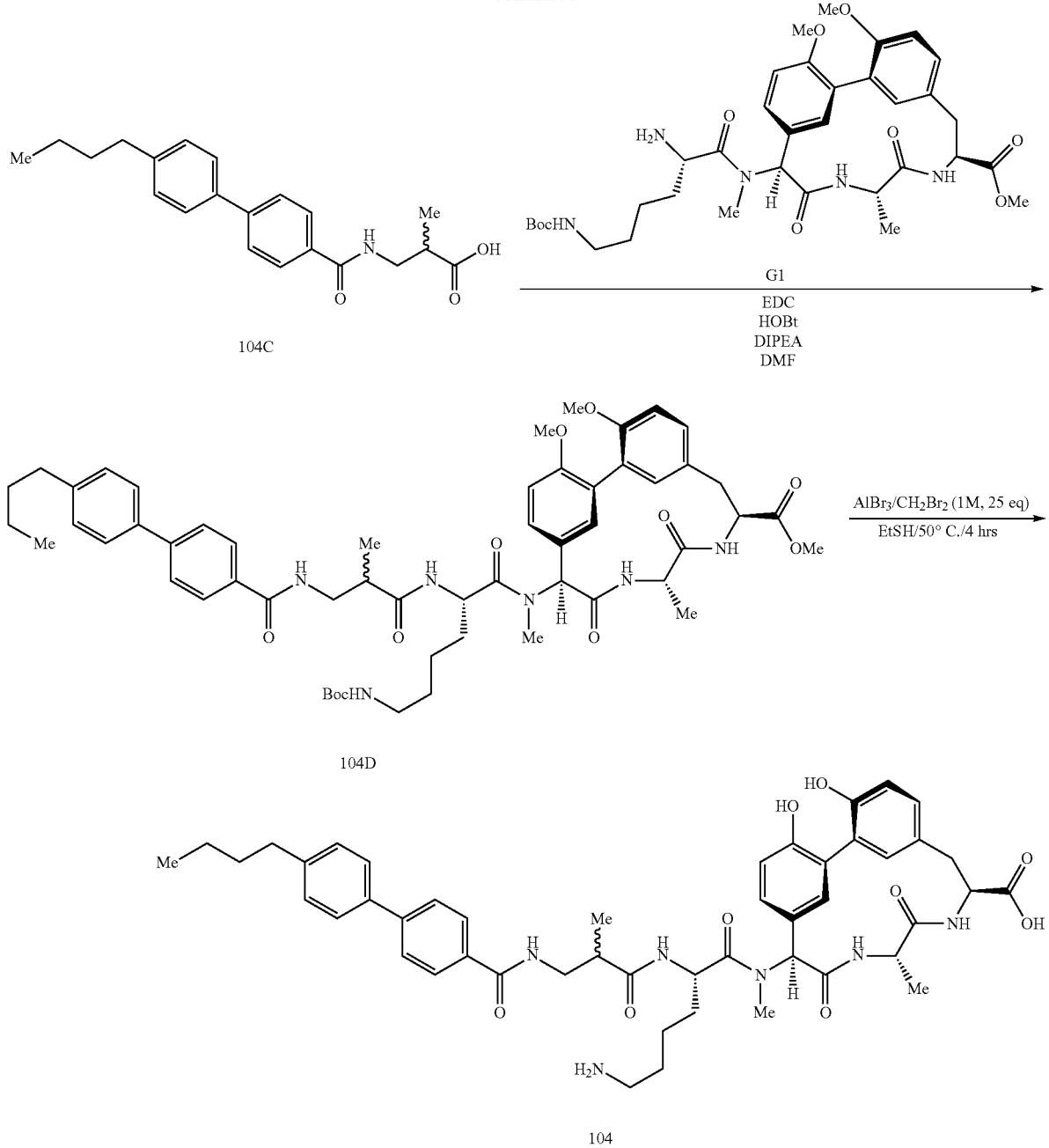

Synthesis of Compound 104A2: The compound was prepared according to General Method 1 from chlorotrityl chloride resin (0.5 g, ca 0.5 mmol), Compound 104A, 0.33 g, 1.0 mmol), and DIPEA (0.19 g, 1.5 mmol) to afford Compound 104A2.

Synthesis of Compound 104C: The compound was prepared according to General Method 2 from Compound H1 (0.25 g, 1.0 mmol) and Compound 104A2 (1 mmol) to afford Compound 104C (90 mg, 26%).

Synthesis of Compound 104D: A solution of Compound 104C (50 mg, 0.15 mmol) in anhydrous DMF (1 mL) was treated with EDCI (86 mg, 0.45 mmol) and HOBt (61 mg, 0.45 mmol) followed by DIEA (58 mg, 0.45 mmol) and Compound G1 (110 mg, 0.16 mmol). The resulting solution was stirred at room temperature overnight and diluted with water. The precipitate was filtered and the resulting cake was washed with water and dried by aspiration to give Compound 104D (100 mg, yield: 78%). MS (ESI) m/z 1005.5 (M+H)$^+$.

Synthesis of Compound 104: To a mixture of Compound 104D (100 mg, 0.15 mmol) in EtSH (4 mL) under Ar was added 1.0 M AlBr$_3$ in CH$_2$Br$_2$ (2.5 mL). The reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 104 (16.4 mg, 19%) as a mixture of diastereomers. MS (ESI) m/z 863.4 (M+H)$^+$.

Example 5
Synthesis of Compound 105
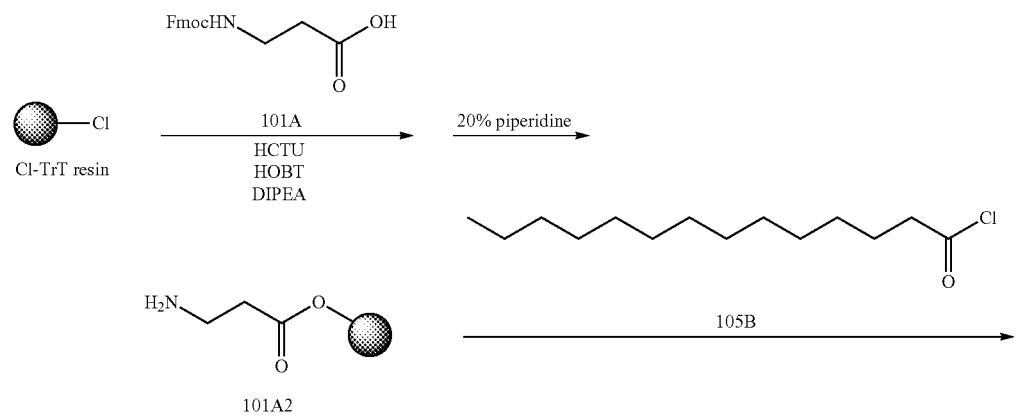
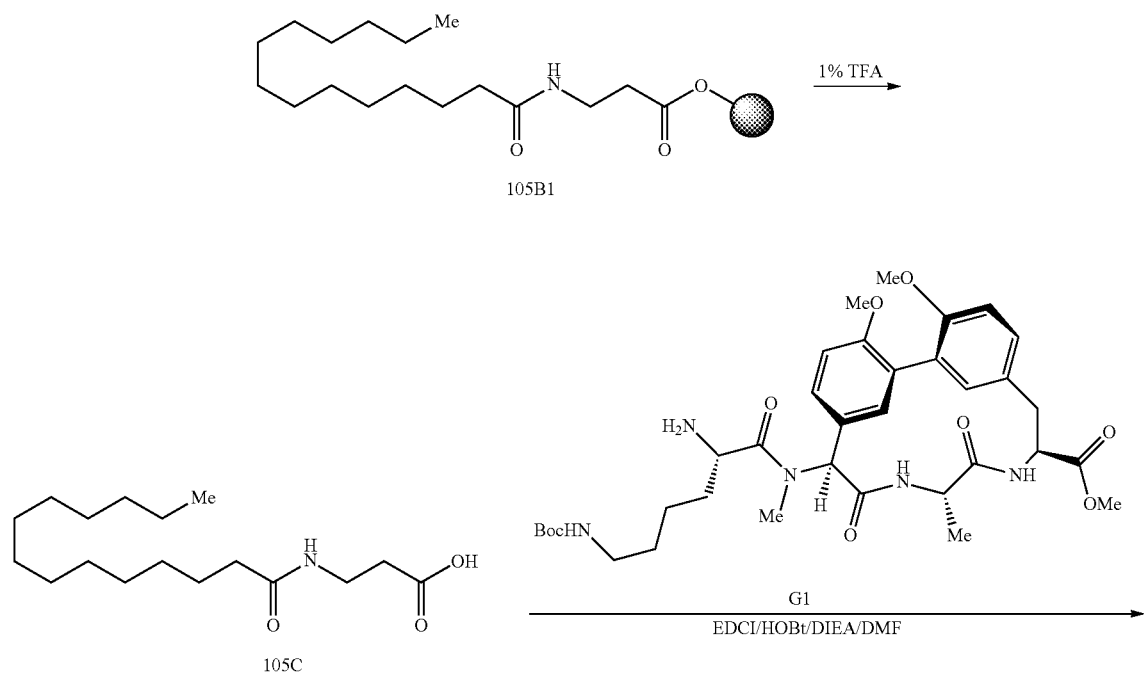
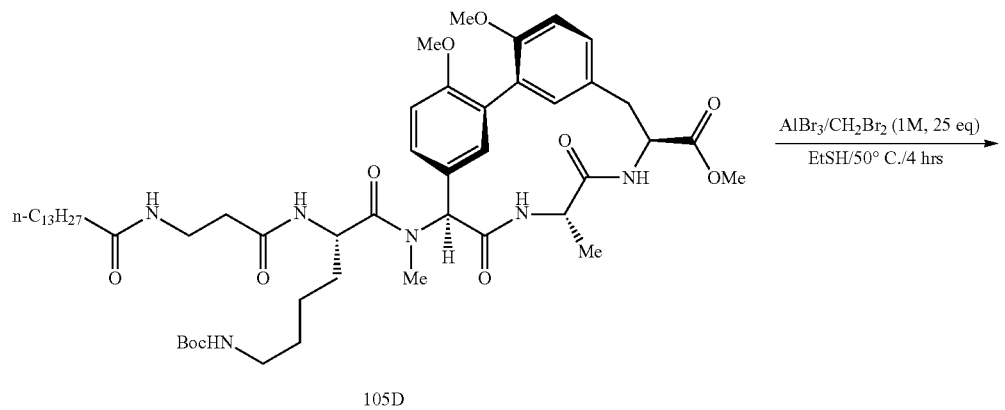

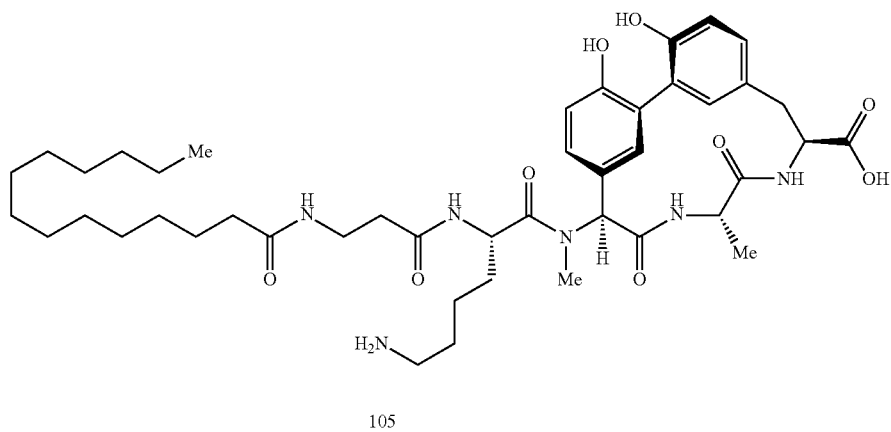

105

Synthesis of Compound 105B1: To a mixture of 101A2 (0.4 mmol) and DIPEA (0.52 g, 4 mmol) in dry DMF (20 mL) was added 105B (98 mg, 0.4 mmol) at 0° C. The mixture was stirred at 20° C. overnight. After LCMS showed the reaction was complete, the mixture was filtered and the cake was washed with DMF (3×30 mL) and DCM (3×30 mL) to give Compound 105B1.

Synthesis of Compound 105C: A mixture of Compound 105B1 (0.4 mmol) was treated with 1% TFA/DCM (5 mL) for 5 min and filtered. The operation was repeated three times to ensure complete removal of the compound from the resin. The filtrate was treated with saturated NaHCO$_3$ solution until pH=7~8. The aqueous layer was added citric acid until pH=3~4. The mixture was extracted with DCM (20 mL×3). The combined organic layers were washed with brine, dried over Na$_2$SO$_4$ and concentrated to give Compound 105C (110 mg, 92%). MS (ESI) m/z 300.2 (M+H)$^+$.

Synthesis of Compound 105D: A solution of Compound 105C (50 mg, 0.167 mmol) in anhydrous DMF (1 mL) was treated with EDCI (61.4 mg, 0.32 mmol) and HOBt (43.2 mg, 0.32 mmol) followed by DIPEA (41 mg, 0.32 mmol) and Compound G1 (114 mg, 0.167 mmol). The resulting solution was stirred at 20° C. overnight and diluted with water. The precipitate was filtered and the cake was washed with water and dried to give Compound 105D (80 mg, 50%).

Synthesis of Compound 105: To a mixture of Compound 105D (80 mg, 0.083 mmol) in EtSH (5 mL) was added 1.0M AlBr$_3$ in CH$_2$Br$_2$ (2 mL) under Ar. The mixture was heated to 50° C. for 4 hrs. After ELSD showed the reaction was complete, the mixture was cooled to room temperature, treated with MeOH (2 mL) and the solvent was removed. The crude product was purified by prep-HPLC to give Compound 105 (21 mg, 31%). MS (ESI) m/z 823.7 (M+H)$^+$.

Example 6

Synthesis of Compound 106

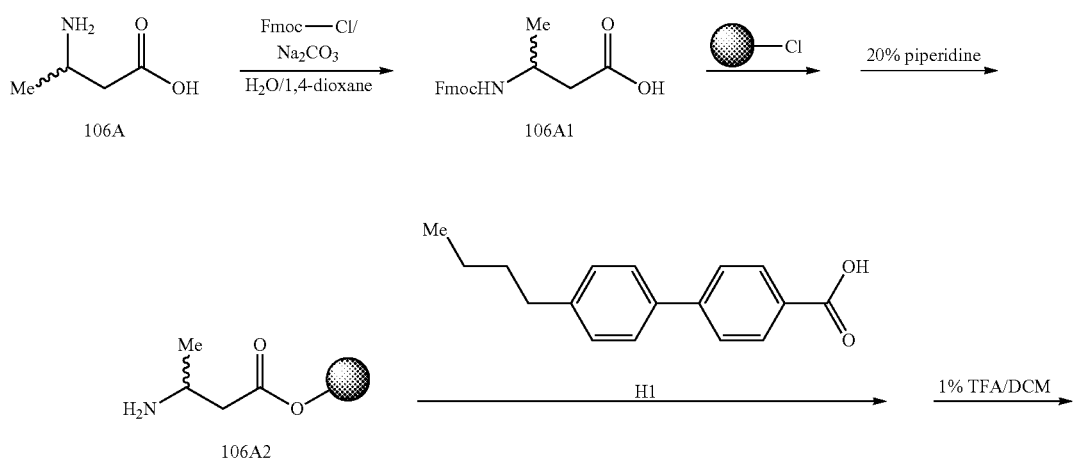

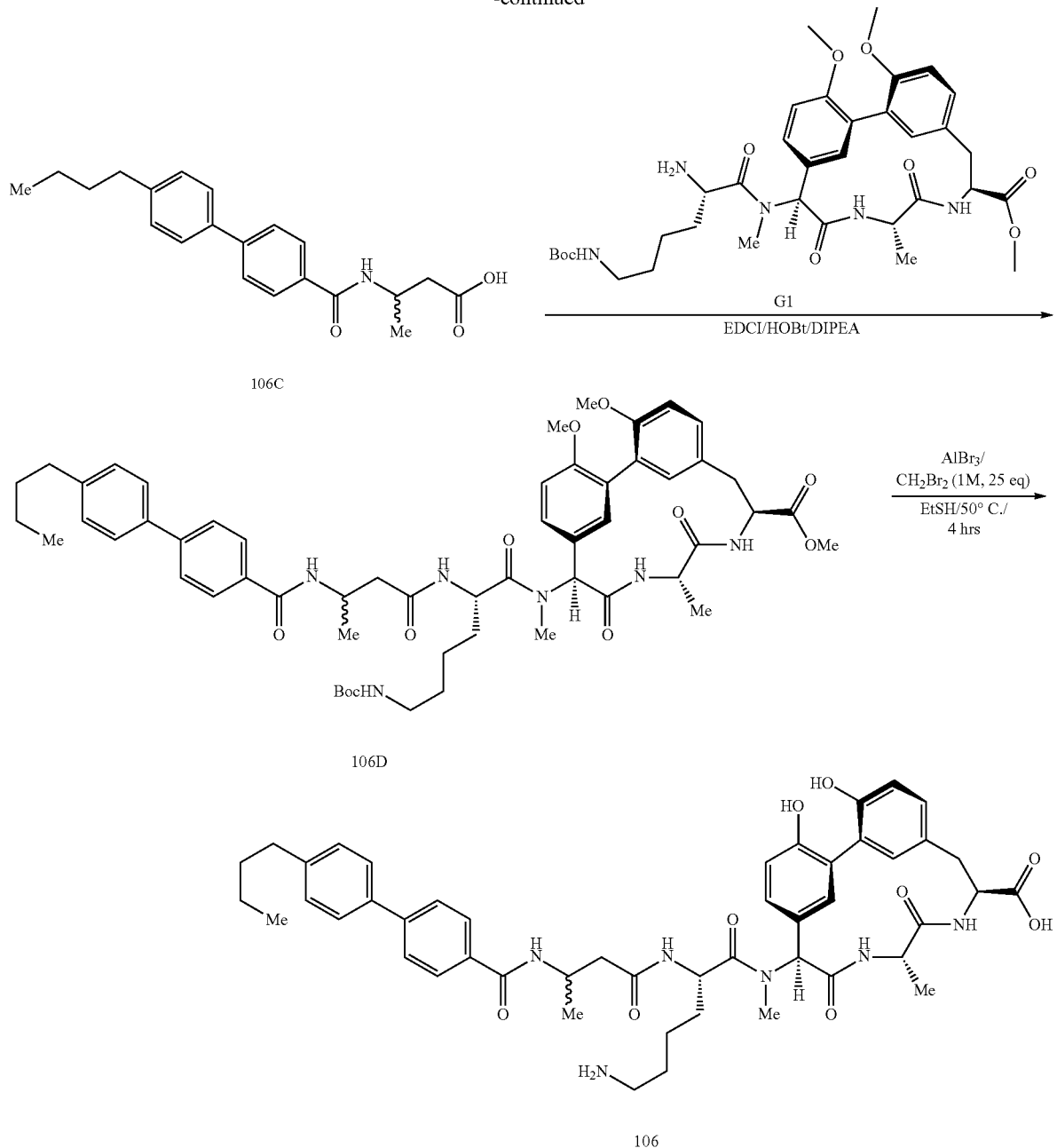

Synthesis of Compound 106A1: To a mixture of Compound 106A (0.5 g, 4.85 mmol) and NaHCO$_3$ (1 g, 9.7 mmol) in 5 mL of 1,4-dioxane and 0.5 mL of water was added a solution of Fmoc-Cl (2 g, 4.85 mmol) in 5 mL of 1,4-dioxane dropwise at 0° C. The mixture was allowed to warm to room temperature and stirred at room temperature overnight. The mixture was extracted with EA (5 mL×3). The combined organic layers were washed with brine, dried over Na$_2$SO$_4$. The solvent was removed to give Compound 106A1 (0.6 g, yield 38%).

Synthesis of Compound 106A2: The compound was prepared according to General Method 1 from chlorotrityl chloride resin (0.5 g, ca. 0.5 mmol) and Compound 106A1 (0.33 g, 1.0 mmol) to afford compound 106A2.

Synthesis of Compound 106C: The compound was prepared according to General Method 2 from Compound H1 (0.25 g, 1.0 mmol) and Compound 106A2 (1 mmol) to afford Compound 106C (50 mg, 29%).

Synthesis of Compound 106D: A solution of Compound 106C (50 mg, 0.15 mmol) in anhydrous DMF (1 mL) was treated with EDCI (86 mg, 0.45 mmol) and HOBt (61 mg, 0.45 mmol) followed by DIPEA (58 mg, 0.45 mmol) and Compound G1 (100 mg, 0.15 mmol). The resulting solution was stirred at room temperature overnight and diluted with water. The precipitate was filtered and the resulting cake was washed with water and dried by aspiration to give Compound 106D (110 mg, 74.3%).

Synthesis of Compound 106: To a mixture of Compound 106D (110 mg, 0.11 mmol) in EtSH (4 mL) under Ar was added 1.0 M AlBr$_3$ in CH$_2$Br$_2$ (2.5 mL). The reaction vial was sealed and heated to 50° C. for 4 hrs. After LC-MS showed the reaction was complete, the mixture was cooled to room temperature, treated with MeOH (0.5 mL) and the solvent was removed. The residue was purified by prep-HPLC to give Compound 106 as a diasteromeric mixture at the β-alanine methyl. MS (ESI) m/z 864.4 (M+H)$^+$.

Example 7

Synthesis of Compound 107

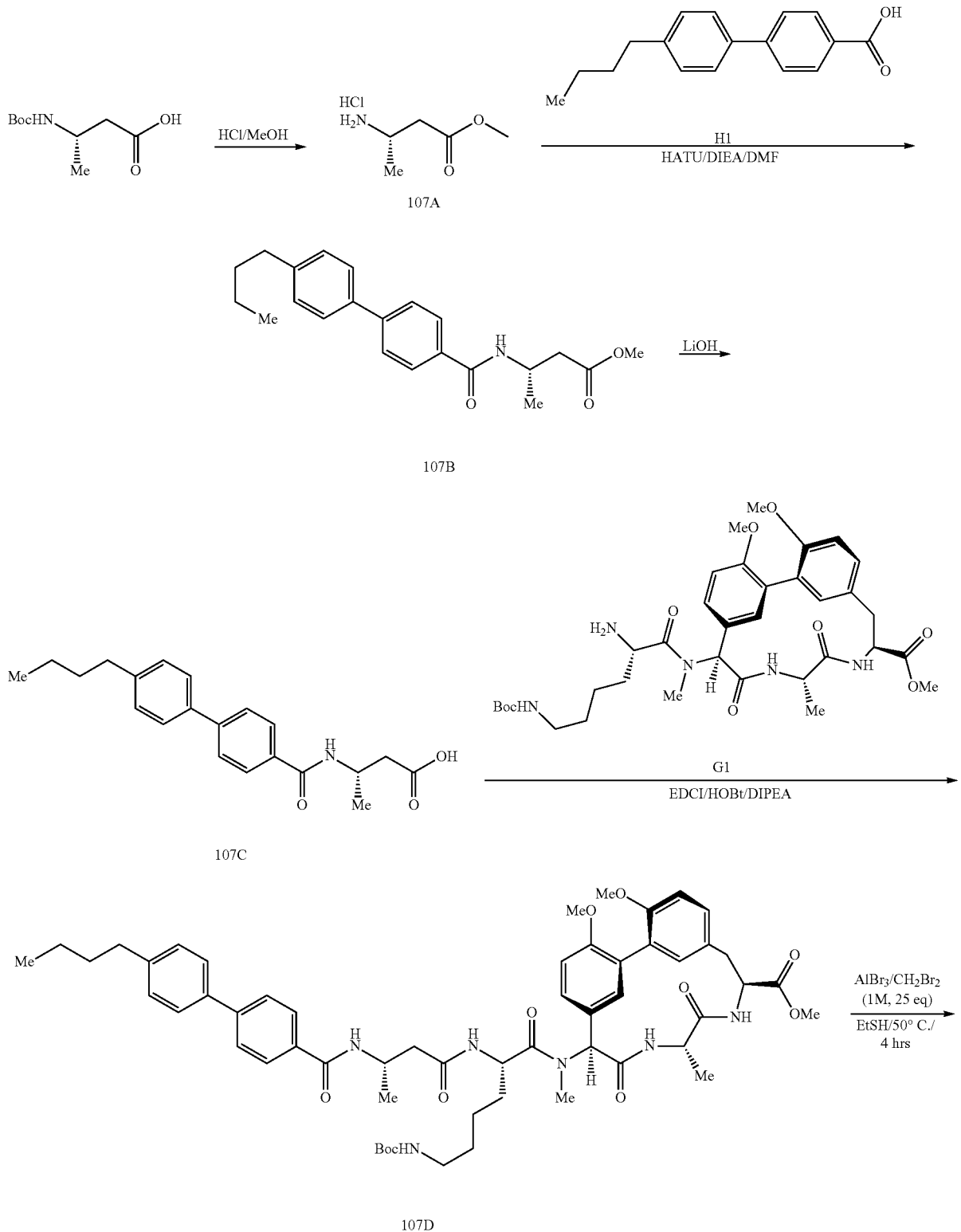

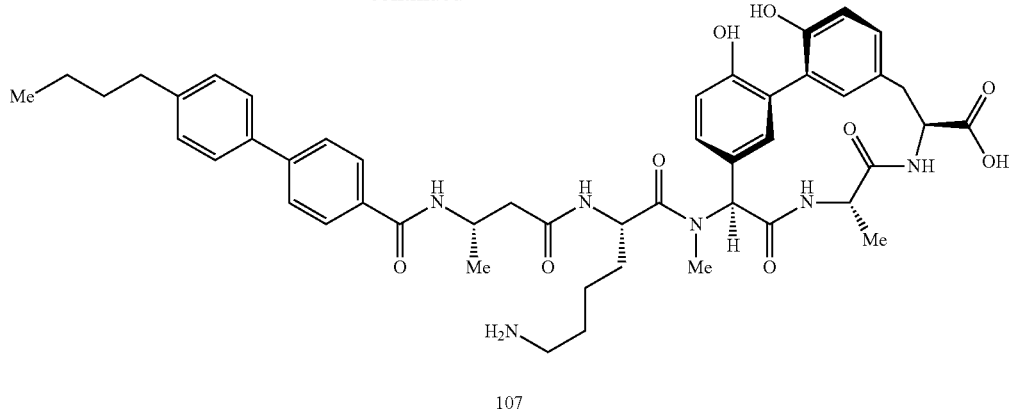

107

Synthesis of Compound 107A: A solution of (S)-3-[(tert-butoxycarbonyl)amino]butanoic acid (200 mg, 0.99 mmol) in HCl/MeOH (20 mL) was stirred at 50° C. for 2 hrs. After NMR showed the reaction was completed, the solvent was removed at reduced pressure to give Compound 107A (150 mg, yield: 99.5%).

Synthesis of Compound 107B: A solution of Compound H1 (201 mg, 0.79 mmol) in anhydrous DMF (3 mL) was treated with HATU (300 mg, 0.79 mmol), DIPEA (204 mg, 1.58 mmol) and Compound 107A (150 mg, 0.79 mmol). The resulting solution was stirred at 20° C. overnight until no starting material was detected by LC-MS. The mixture was diluted with water. The precipitate was filtered and the resulting cake was washed with water and dried to give Compound 107B (70 mg, 25%).

Synthesis of Compound 107C: To a solution of Compound 107B (70 mg, 0.198 mmol) in THF (2 mL) was added a solution of LiOH·H$_2$O (9.1 mg, 0.218 mmol) in water (2 mL). The reaction mixture was stirred at 50° C. for 2 hrs. After TLC showed the reaction was complete, the solvent was evaporated. The residue was adjusted to pH=3~4 with citric acid. The resulting mixture was extracted with EA (5 mL×3). The combined organic layers were washed with brine and dried over Na$_2$SO$_4$. The solvent was removed to give Compound 107C (67 mg, 99.7%). MS (ESI) m/z 340.1 (M+H)$^+$.

Synthesis of Compound 107D: A solution of Compound 107C (67 mg, 0.198 mmol) in anhydrous DMF (1 mL) was treated with EDCI (45.6 mg, 0.238 mmol) and HOBt (32.1 mg, 0.238 mmol) followed by DIPEA (30.7 mg, 0.238 mmol) and Compound G1 (135.2 mg, 0.198 mmol). The resulting solution was stirred at 20° C. overnight and diluted with water. The precipitate was filtered and the resulting cake was washed with water and dried to give Compound 107D (110 mg, 55.6%).

Synthesis of Compound 107: To a mixture of Compound 107D (110 mg, 0.11 mmol) in EtSH (4 mL) was added 1.0M AlBr$_3$ in CH$_2$Br$_2$ (2.7 mL) under Ar. The mixture was heated to 50° C. for 4 hrs. After ELSD showed the reaction was complete, the mixture was cooled to room temperature, treated with MeOH (2 mL) and the solvent was removed. The crude product was purified by prep-HPLC to give Compound 107 (34.5 mg, 36.5%). MS (ESI) m/z 863.7 (M+H)$^+$.

Example 8

Synthesis of Compound 108

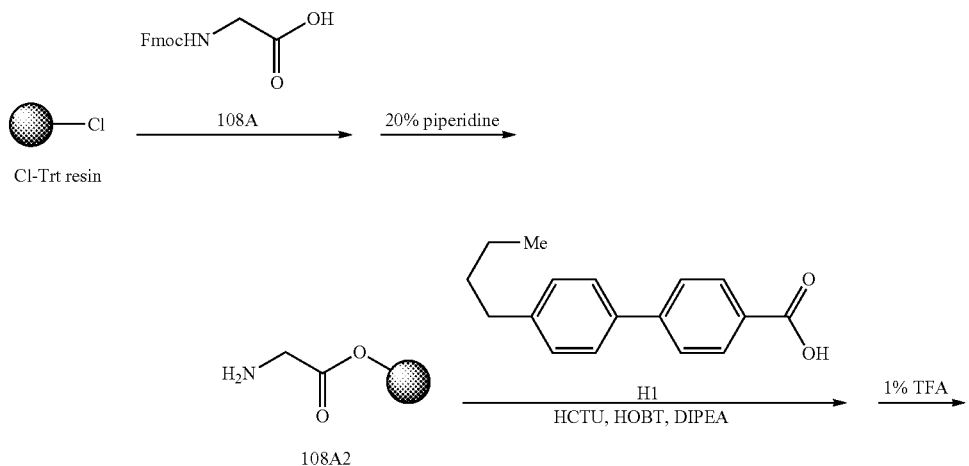

-continued

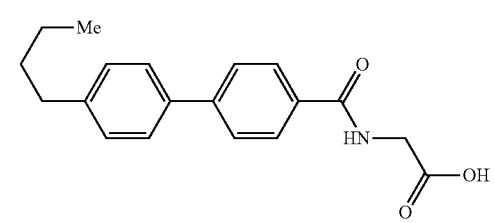

108C

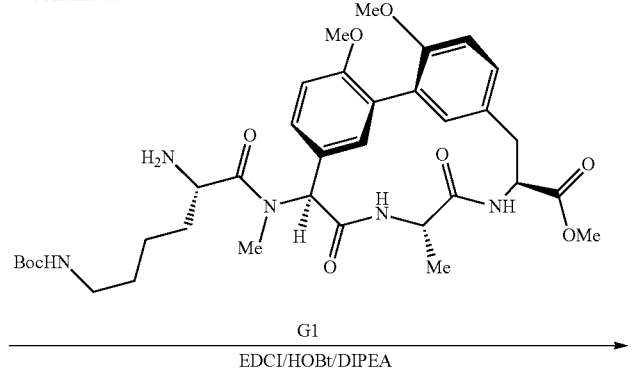

G1

EDCI/HOBt/DIPEA →

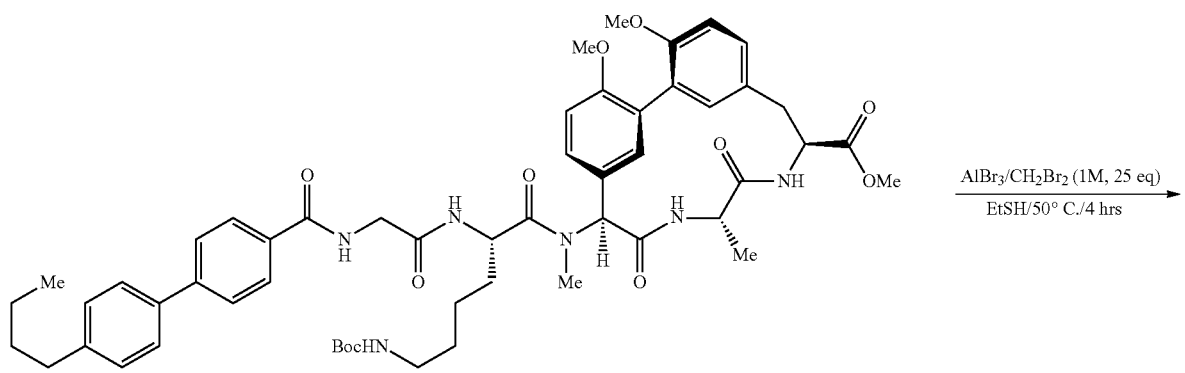

108D

AlBr₃/CH₂Br₂ (1M, 25 eq)
EtSH/50° C./4 hrs →

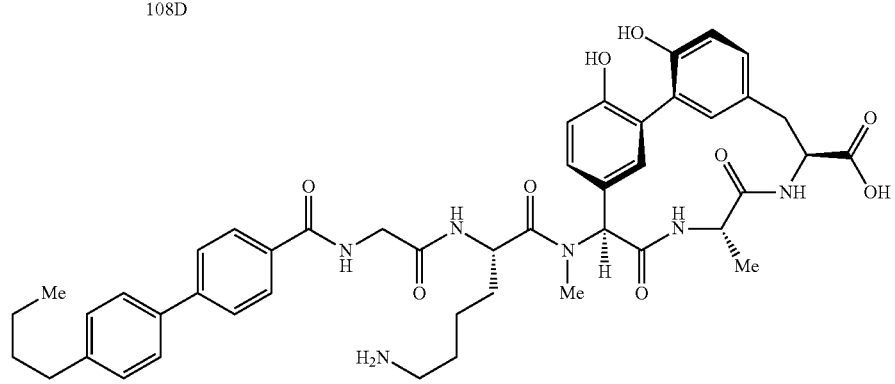

108

Synthesis of Compound 108A2: The compound was prepared according to General Methods 1 from chlorotritylchloride resin (0.5 g, ca 0.5 mmol)), Compound 108A, 0.3 g, 1.0 mmol), and DIPEA (0.13 g, 1.0 mmol) to afford Compound 108A2.

Synthesis of Compound 108C: The compound was prepared according to General Method 2 from Compound H1 (0.25 g, 1.0 mmol) and Compound 108A2 (0.5 mmol) to afford Compound 108C (0.12 g, 77%). MS (ESI) m/z 312.1 (M+H)⁺.

Synthesis of Compound 108D: A solution of Compound 108C (50 mg, 0.16 mmol) in anhydrous DMF (1 mL) was treated with EDCI (61.4 mg, 0.32 mmol) and HOBt (43 mg, 0.16 mmol) followed by DIPEA (41 mg, 0.32 mmol) and Compound G1 (110 mg, 0.16 mmol). The resulting solution was stirred at 20° C. overnight and diluted with water. The precipitate was filtered and the resulting cake was washed with water and dried to give Compound 181D (75 mg, 48%).

Synthesis of Compound 108: To a mixture of Compound 108D (75 mg, 0.0.077 mmol) in EtSH (4 mL) under Ar was added 1.0 M AlBr₃ in CH₂Br₂ (2 mL). The reaction vial was sealed and heated to 50° C. for 4 hrs. After LC-MS showed the reaction was completed, the mixture was cooled to room temperature, treated with MeOH (2 mL) and the solvent was removed. The crude product was purified by prep-HPLC to give Compound 108 (6.8 mg, 15%). MS (ESI) m/z 835.5 (M+H)⁺.

Example 9

Synthesis of Compound 109

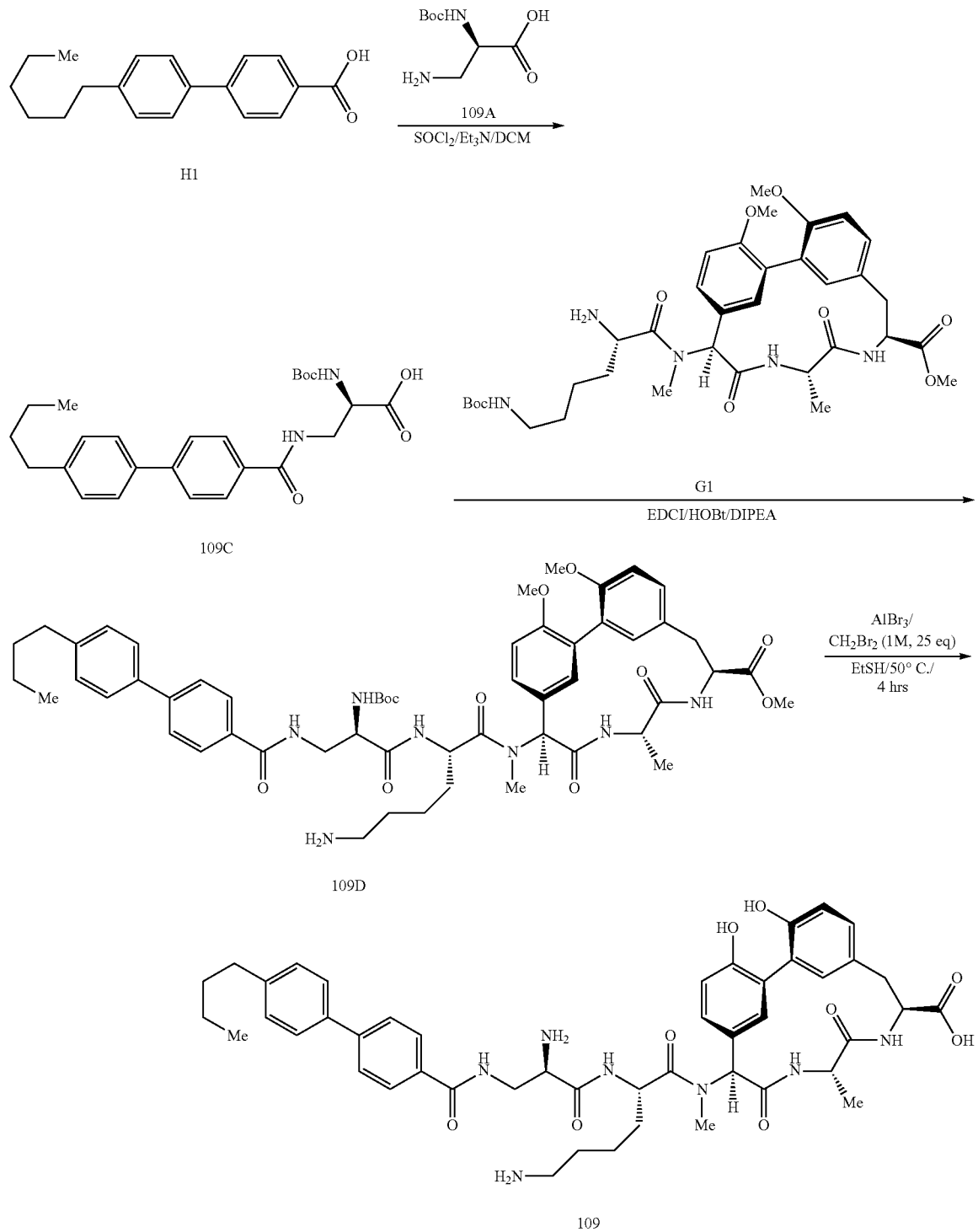

Synthesis of Compound 109C: A solution of Compound H1 (200 mg, 0.79 mmol) in $SOCl_2$ (5 mL) was heated at reflux until TLC showed the reaction was completed. After evaporation of the solvent, the residue was dissolved in 5 mL of anhydrous DCM and added dropwise to a mixture of Compound 109A (160 mg, 0.79 mmol) and $Et_3N$ (160 mg, 1.58 mmol) in 2 mL of anhydrous DCM. After LC-MS showed the reaction was complete, the solvent was removed. The residue was purified by prep-HPLC to give Compound 109C (24 mg, 6.9%). MS (ESI) m/z 385.1 (M t-Bu+H)$^+$.

Synthesis of Compound 109D: A solution of Compound 109C (24 mg, 0.055 mmol) in anhydrous DMF (1 mL) was treated with EDCI (21 mg, 0.11 mmol) and HOBt (15 mg, 0.11 mmol) followed by DIEA (14.2 mg, 0.11 mmol) and Compound G1 (37.5 mg, 0.055 mmol). The resulting solution was stirred at room temperature overnight and diluted with water. The precipitate was filtered and the resulting cake was washed with water and dried by aspiration to give Compound 109D (35 mg, 58%).

Synthesis of Compound 109: To a mixture of Compound 109D (30 mg, 0.03 mmol) in EtSH (4 mL) under Ar was added 1.0M AlBr$_3$ in CH$_2$Br$_2$ (0.75 mL). Then the reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 109 (8.5 mg, 31%). MS (ESI) m/z 864.4 (M+H)$^+$.

Example 10

Synthesis of Compound 110

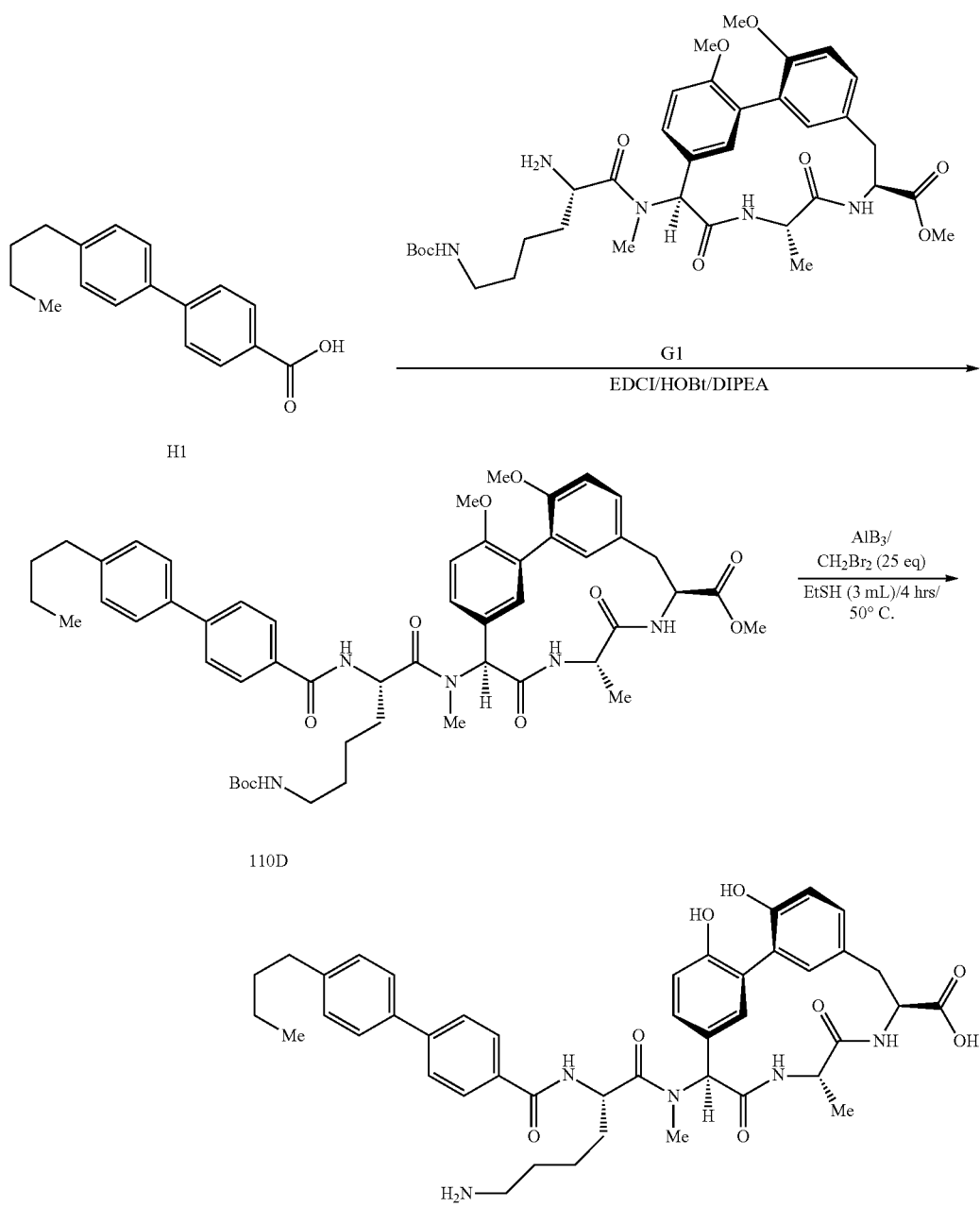

Synthesis of Compound 110D: To a solution of Compound H1 (30 mg, 0.11 mmol) in DMF (3 mL) were added EDCI (57.3 mg, 0.3 mmol) HOBt (40.5 mg, 0.3 mmol), and DIPEA (38.7 mg, 0.3 mmol). The solution was stirred at room temperature for 30 min, whereupon Compound G1 (70 mg, 0.11 mmol) was added. The resulting solution was stirred at room temperature for overnight and diluted with water. The precipitate was filtered and the resulting cake was washed with water and dried by vacuum to give Compound 110D (70 mg, 74%).

Synthesis of Compound 110: To a mixture of Compound 110D (70 mg, 0.076 mmol) in EtSH (3 mL) under Ar was added 1.0M AlBr$_3$ in CH$_2$Br$_2$ (2.1 mL). The reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 110 (35 mg, 59%).

Example 11

Synthesis of Compound III

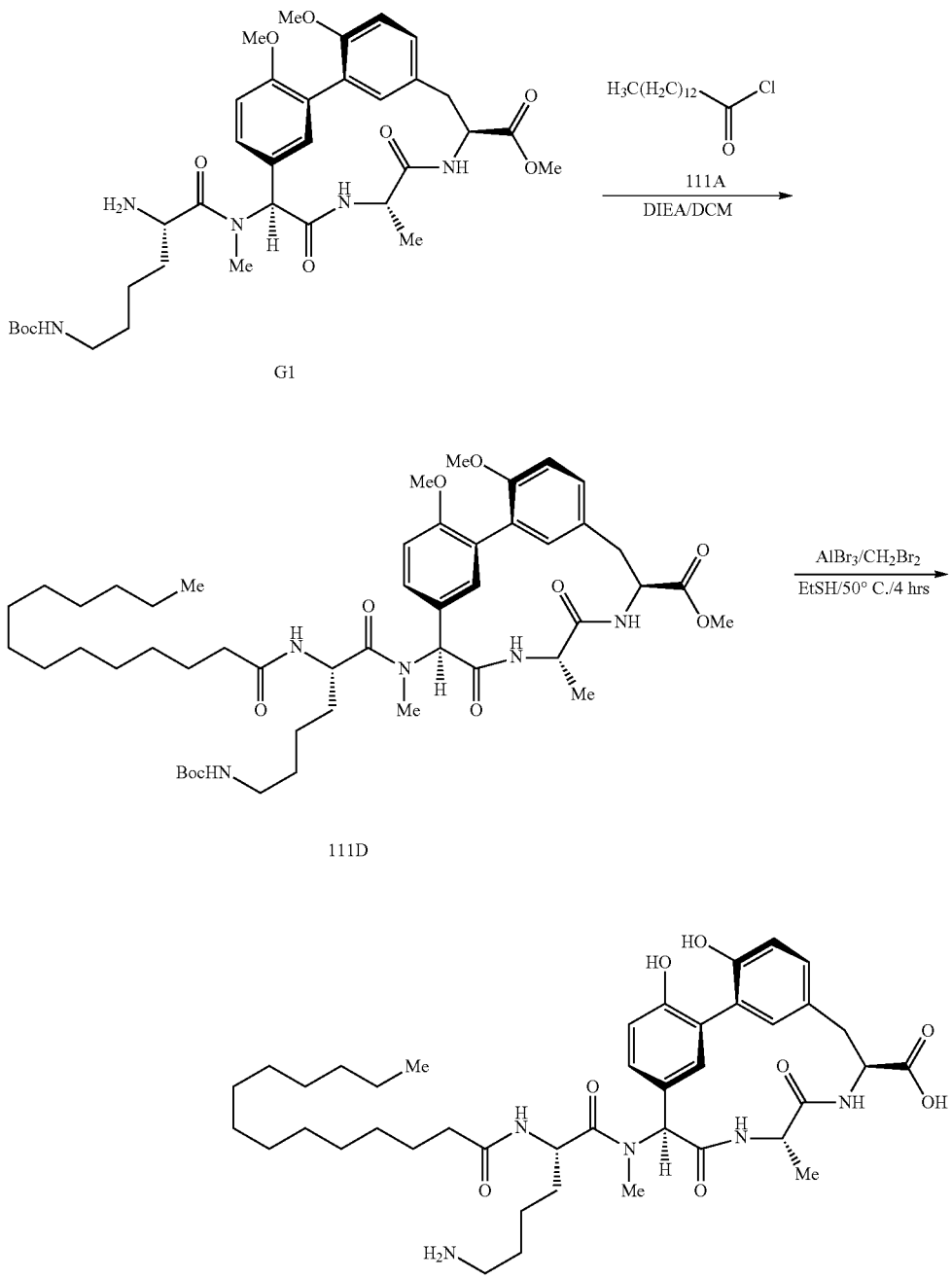

Synthesis of Compound 111D: To a mixture of Compound G1 (800 mg, 1.17 mmol) and DIPEA (302 mg, 2.34 mmol) in DCM was added a solution of Compound 111A (288 mg, 1.17 mmol) in DCM (5 mL) dropwise at 0° C. The mixture was stirred at room temperature overnight. After LC-MS showed the reaction was complete, the mixture was diluted with water. The precipitate was filtered and the cake was washed with CH₃CN and water. The solid was dried to give Compound 111D (700 mg, 67%). MS (ESI) m/z 894.5 (M+H)⁺.

Synthesis of Compound 111: To a mixture of Compound 111D (700 mg, 0.78 mmol) in EtSH (30 mL) was added 1.0 M AlBr₃ in CH₂Br₂ (20 mL) under Ar. The mixture was heated to 50° C. for 4 hrs. After ELSD showed the reaction was complete, the mixture was cooled to room temperature, treated with MeOH (20 mL) and the solvent was removed. The crude product was purified by prep-HPLC to give Compound III (400 mg, 68%). MS (ESI) m/z 752.4 (M+H)⁺.

Example 12

Synthesis of Compound 112

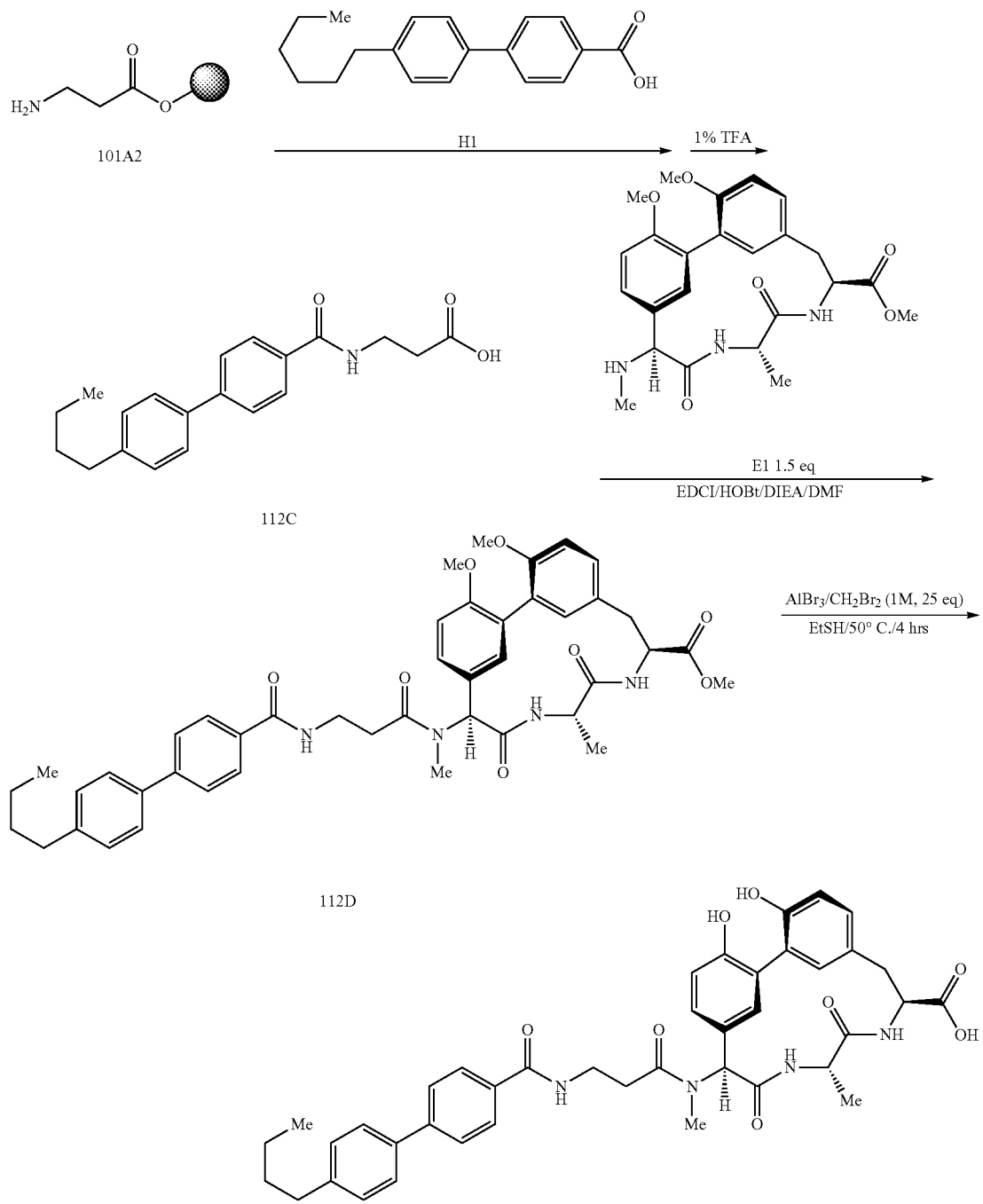

Synthesis of Compound 112C: The compound was prepared according to General Method 2 from Compound H1 (0.2 g, 0.8 mmol) and Compound 101A2 (0.4 mmol) to afford Compound 112C (80, 62% yield from chlorotrityl resin).

Synthesis of Compound 112D: A solution of Compound 112C (70 mg, 0.215 mmol) in anhydrous DMF (1 mL) was treated with EDCI (83 mg, 0.43 mmol) and HOBt (58 mg, 0.43 mmol) followed by DIEA (14.2 mg, 0.43 mmol) and Compound E1 (147 mg, 0.323 mmol). The resulting solution was stirred at 20° C. overnight and diluted with water. The precipitate was filtered and the cake was washed with water and dried to give Compound 112D (65 mg, 40%).

Synthesis of Compound 112: To a mixture of Compound 112D (65 mg, 0.085 mmol) in EtSH (4 mL) under Ar was added 1.0 M AlBr$_3$ in CH$_2$Br$_2$ (0.75 mL). The reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 112 (12.2 mg, 20%). MS (ESI) m/z 721.3 (M+H)$^+$.

Example 13

Synthesis of Compound 113

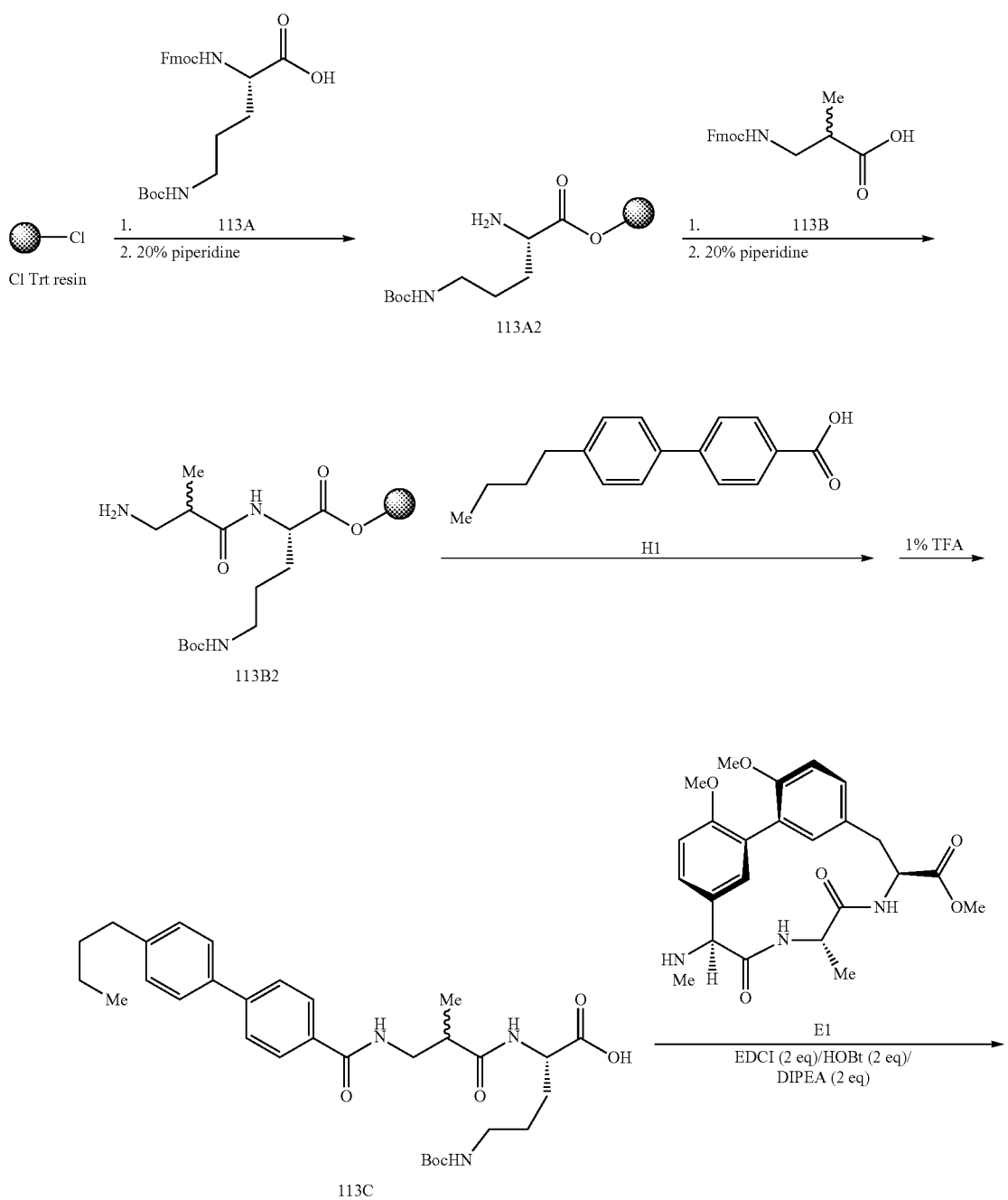

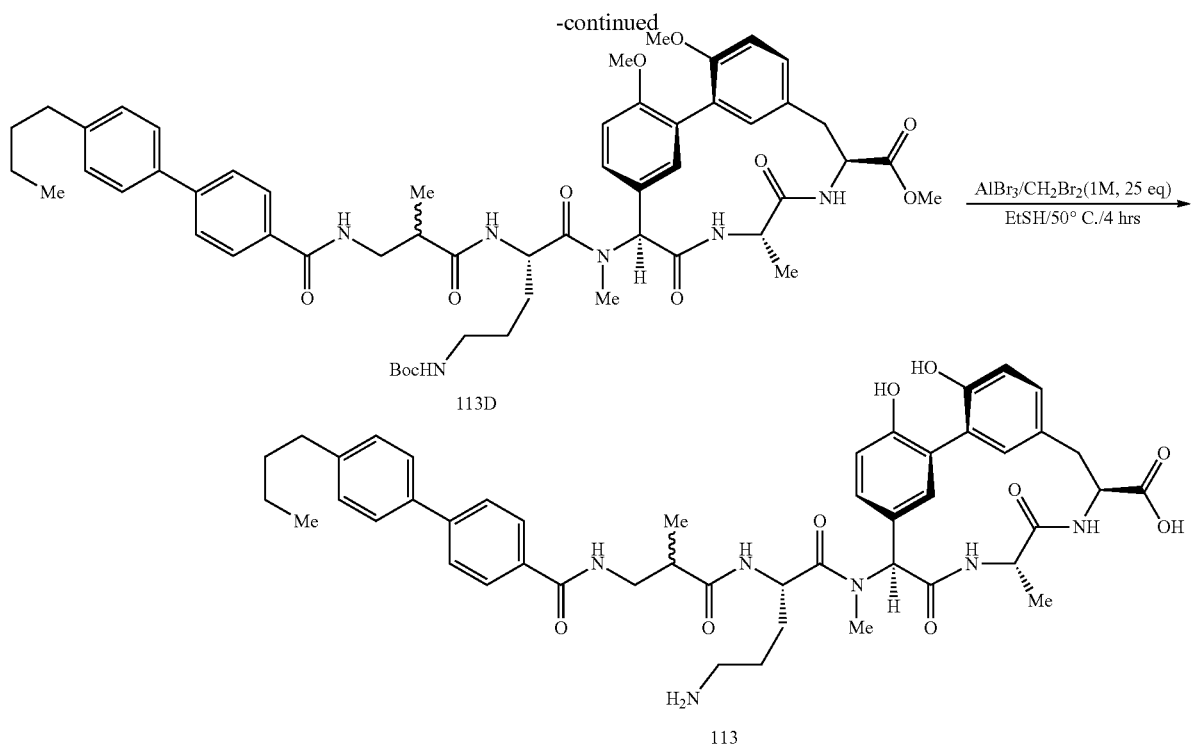

Synthesis of Compound 113A2: The compound was prepared according to General Method 1 from chlorotrityl chloride resin (0.5 g, ca. 0.5 mmol) and Fmoc-L-ORN-(BOC)-OH (Compound 113A, 0.62 g, 2.0 mmol) to afford compound 113A2.

Synthesis of Compound 113C: The compound was prepared according to General Method 3 from Fmoc-β-ALA-OH (Compound 113B, 0.23 g, 0.75 mmol), Compound 113A2 (0.5 mmol), and Compound H1 (0.75 mmol) to afford Compound 113C (120 mg, 43%). MS (ESI) m/z 554.3 (M+H)$^+$.

Synthesis of Compound 113D: To a solution of Compound 113C (70 mg, 0.13 mmol) in DMF (5 mL) was added EDCI (66 mg, 0.345 mmol), HOBt (46.6 mg, 0.345 mmol), DIPEA (44.5 mg, 0.345 mmol). The solution was stirred at room temperature for 30 mins, and Compound E1 (52.4 mg, 0.115 mmol) was added. The resulting solution was stirred at room temperature overnight and diluted with water. The precipitate was filtered and the resulting cake was washed with water and dried by lyophilization to give Compound 113D (50 mg, 44%). MS (ESI) m/z 991.7 (M+H)$^+$.

Synthesis of Compound 113: To a mixture of Compound 113D (40 mg, 0.04 mmol) in EtSH (3 mL) under Ar was added a solution of AlBr$_3$ in CH$_2$Br$_2$ (1.0M, 1 mL). The reaction vial was sealed and heated to 50° C. for 4 hrs. After LC-MS showed the reaction was complete, the mixture was cooled to room temperature, treated with MeOH (0.5 mL) and the solvent was evaporated. The crude product was purified by prep-HPLC to give Compound 113 (4 mg, 12%). MS (ESI) m/z 849.7 (M+H)$^+$.

Example 14

Synthesis of Compound 114 and Compound 115

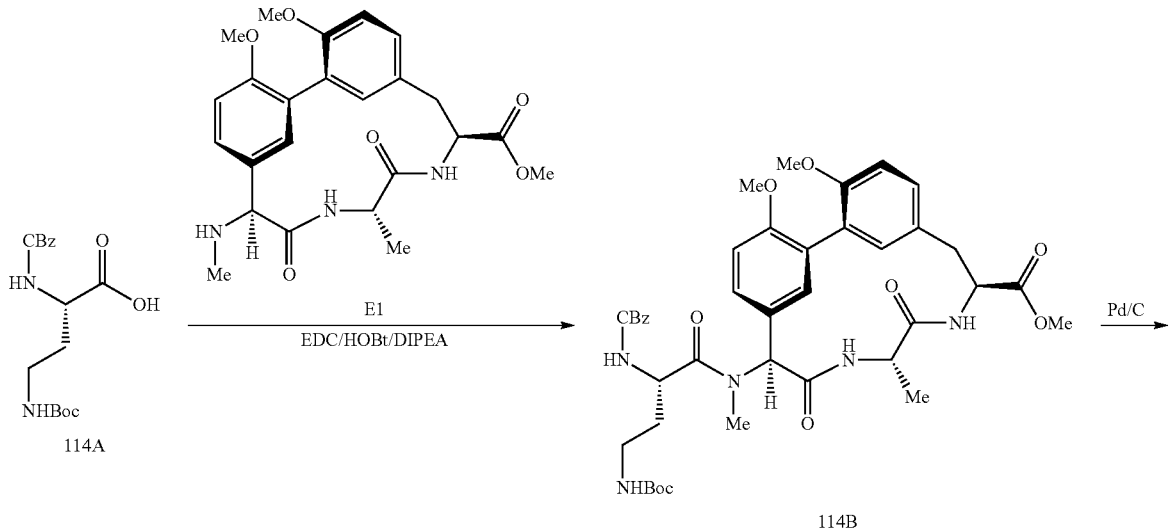

-continued
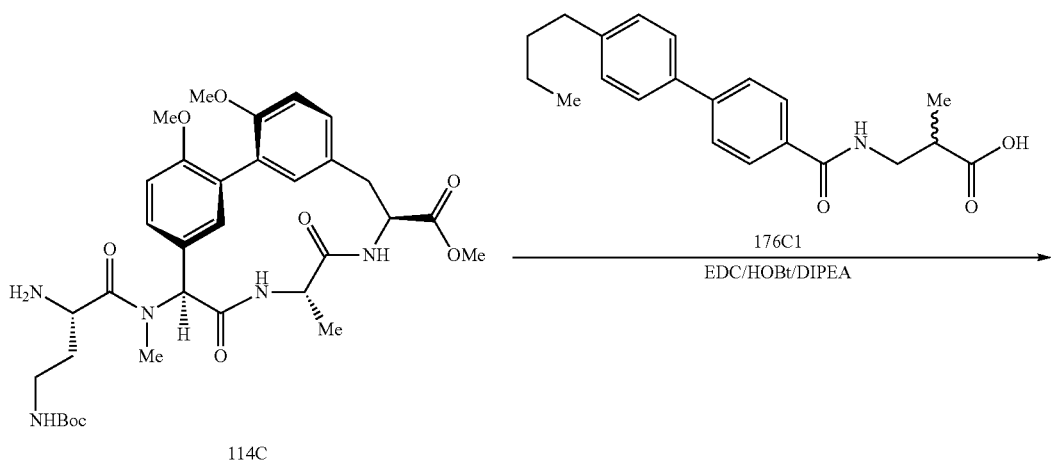
114C
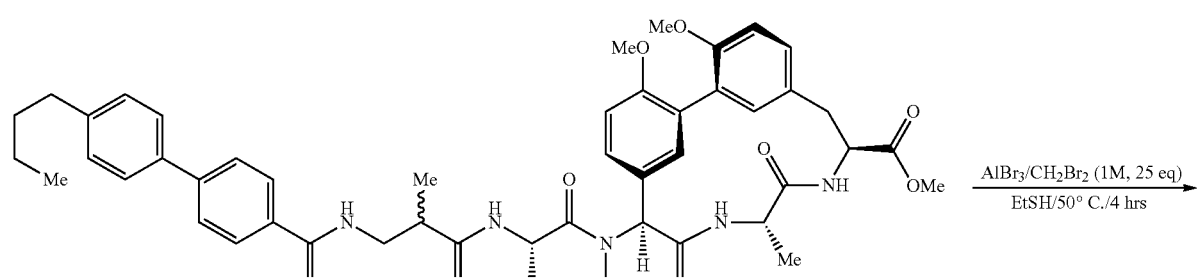
114D
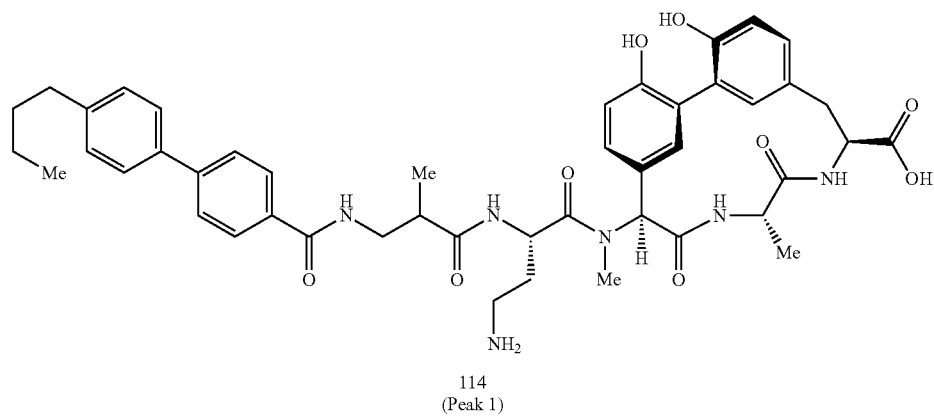
114
(Peak 1)
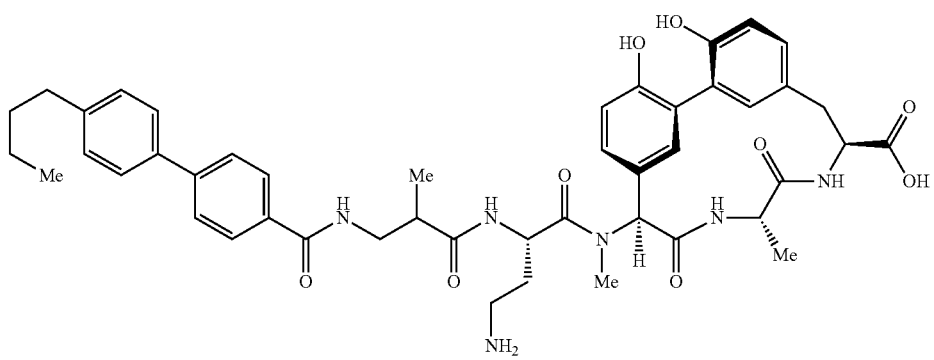
115
(Peak 2)

Synthesis of Compound 114B: A solution of Compound 114A (386 mg, 1.10 mmol) in anhydrous DMF (1 mL) was treated with EDCI (576 mg, 3.00 mmol) and HOBt (405 mg, 3.00 mmol) followed by DIPEA (387 mg, 3.00 mmol) and Compound E1 (455 mg, 1.00 mmol). The resulting solution was stirred at 20° C. overnight and diluted with water. The precipitate was filtered and the cake was washed with water and dried under vacuum to afford Compound 114B (400 mg, 51%).

Synthesis of Compound 114C: A suspension of Compound 114B (400 mg, 0.507 mmol) and 10% Pd/C (0.50 g) in EtOH (15 mL) (50 psi) was stirred at 25° C. under $H_2$ overnight. After LC-MS showed the reaction was completed, the mixture was filtered and the filtrate was evaporated to give a residue, which was purified by washing with water and PE to afford Compound 114C (220 mg, 66%).

Synthesis of Compound 114D: A solution of Compound 114C (40.0 mg, 0.119 mmol) in anhydrous DMF (1 mL) was treated with EDCI (45.3 mg, 0.236 mmol) and HOBt (31.9 mg, 0.236 mmol) followed by DIPEA (30.4 mg, 0.236 mmol) and Compound 176C1 (77.0 mg, 0.118 mmol). The resulting solution was stirred at 20° C. overnight and diluted with water. The precipitate was filtered and the resulting cake was washed with water and dried by vacuum to give of Compound 114D (80 mg, 69%).

Synthesis of Compounds 114 and 115: To a mixture of Compound 114D (80 mg, 0.0819 mmol) in EtSH (5 mL) was added 1.0M $ABr_3$ in $CH_2Br_2$ (2.00 mL) under Ar. The mixture was heated to 50° C. for 4 hrs. After ELSD showed the reaction was complete, the mixture was cooled to room temperature, treated with MeOH (2 mL) and the solvent was removed. The crude product was purified by prep-HPLC to afford Compound 114 (peak 1, 6.2 mg, 9%) and of Compound 115 (peak 2, 9.1 mg, 13%). The peaks corresponded to diastereomers at the b-Alanine methyl group. Compound 114: MS (ESI) m/z 835.3 (M+H)$^+$; $t_R$ 2.30 min (Venusil C18, 4.6×50 mm, 5 micron, 30%-90% AcCN/$H_2O$). Compound 115: MS (ESI) m/z 835.3 (M+H)$^+$; $t_R$ 2.36 min (Venusil C18, 4.6×50 mm, 5 micron, 30%-90% AcCN/$H_2O$).

Example 15

Synthesis of Compound 116

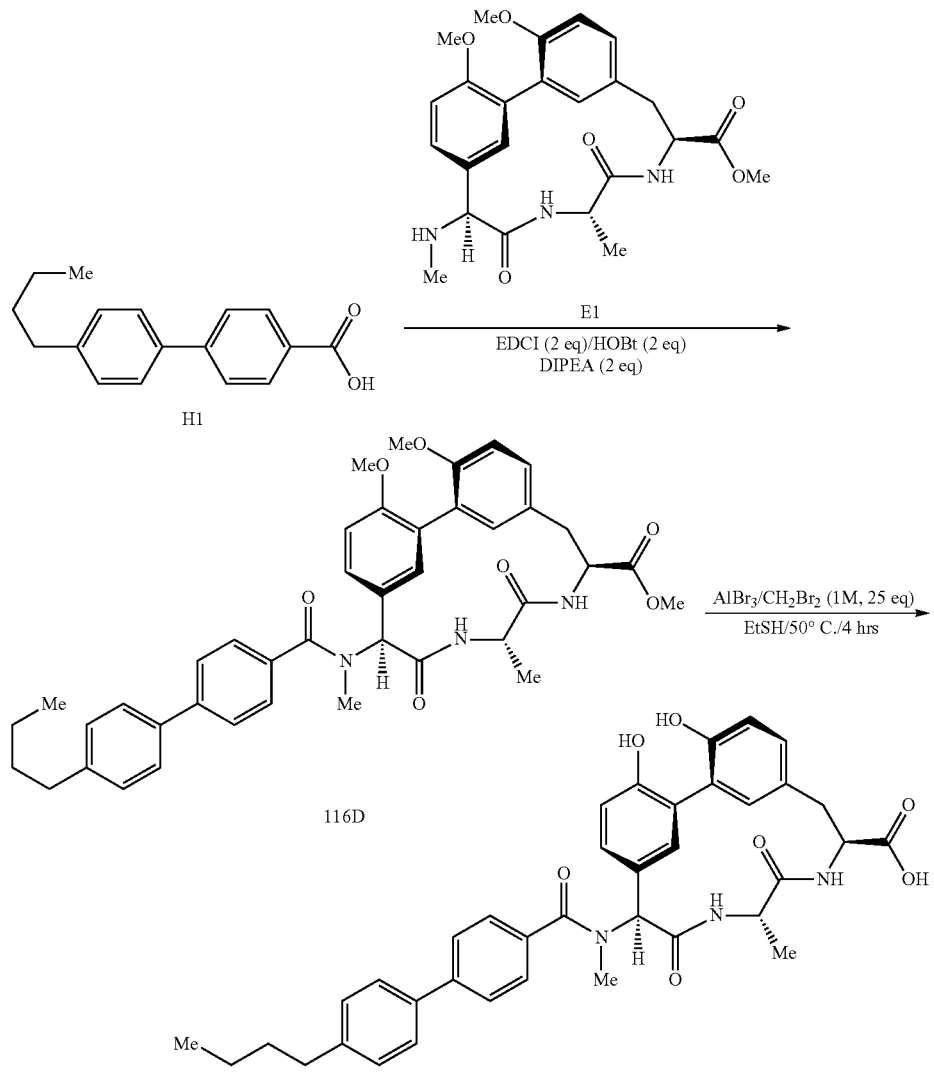

116

Synthesis of Compound 116D: To a solution of Compound H1 (31 mg, 0.12 mmol) in DMF (3 mL) was added EDCI (63 mg, 0.33 mmol), HOBt (44.6 mg, 0.33 mmol), DIPEA (42.6 mg, 0.33 mmol). The solution was stirred at room temperature for 30 mins, and then Compound E1 (50 mg, 0.11 mmol) was added. The resulting solution was stirred at room temperature overnight and diluted with water. The precipitate was filtered and the cake was washed with water and dried by vacuum to give Compound 116D (45 mg, 59%). MS (ESI) m/z 692.4 (M+H)⁺.

Synthesis of Compound 116: To a mixture of Compound 116D (45 mg, 0.076 mmol) in EtSH (3 mL) under Ar was added a solution of AlBr₃ in CH₂Br₂ (1.0M, 1.6 mL). The reaction vial was sealed and heated to 50° C. for 4 hrs. After LC-MS showed the reaction was complete, the mixture was cooled to room temperature, treated with MeOH (0.5 mL) and the solvent was removed. The crude product was purified by prep-HPLC to give Compound 116 (20 mg, 47%). MS (ESI) m/z 650.8 (M+H)⁺.

Example 16

Synthesis of Compound 117

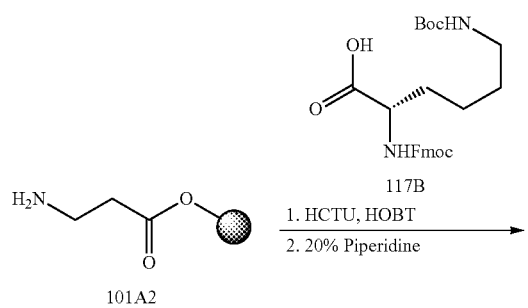

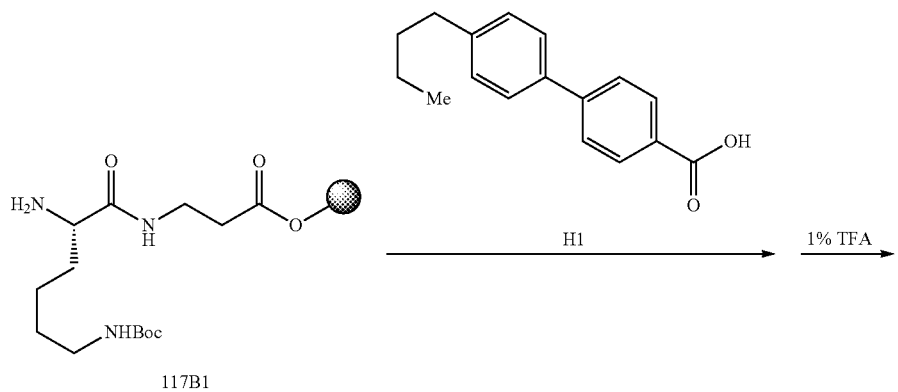

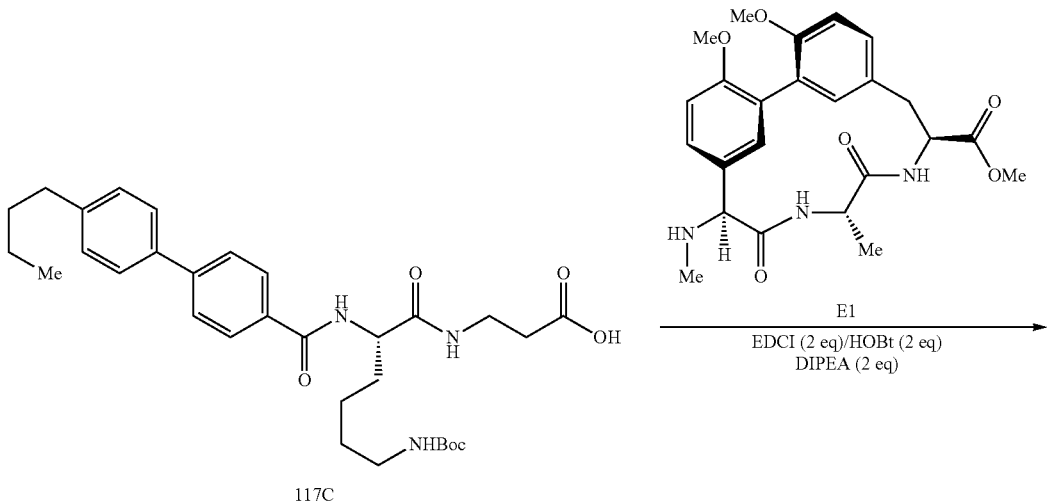

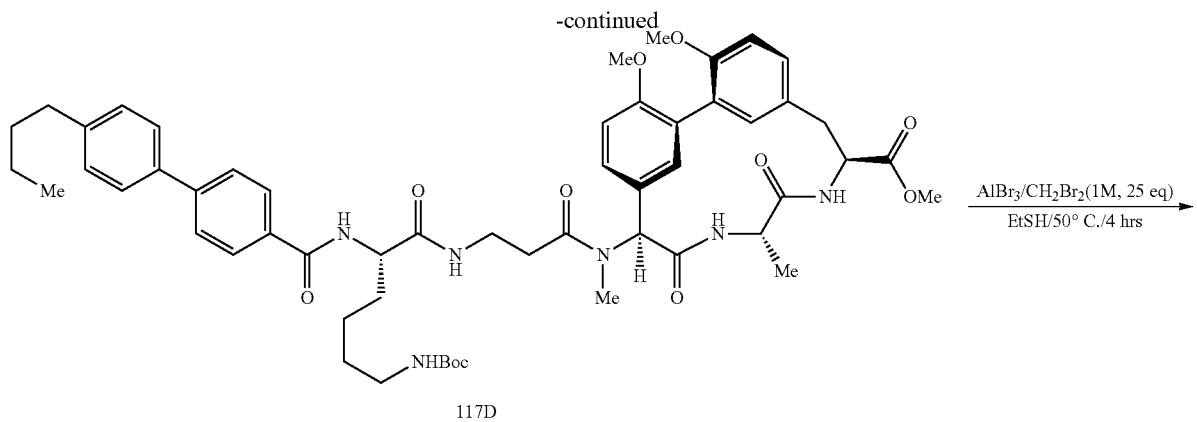

117D

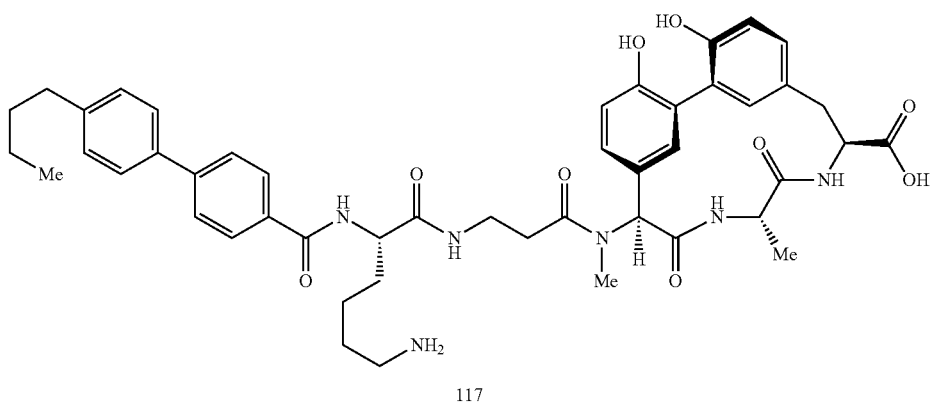

117

Synthesis of Compound 117C: The compound was prepared according to General Method 3 from Compound 101A2 (0.40 mmol), Fmoc-LYS-(BOC)—OH (Compound 117B, 0.37 g, 0.80 mmol), and Compound H1 (203 mg, 0.80 mmol).

Synthesis of Compound 117D: A solution of Compound 117C (70.0 mg, 0.127 mm(in anhydrous DMF (1 mL) was treated with EDCI (43.9 mg, 0.230 mmol) and HOBt (31.1 mg, 0.230 mmol) followed by DIEA (29.7 mg, 0.230 mmol) and Compound E1 (52.5 mg, 0.115 mmol). The resulting solution was stirred at 20° C. overnight and diluted with water. The precipitate was filtered and the resulting cake was washed with water and dried by aspiration to give Compound 117D (65.0 mg, yield: 56.9%).

Synthesis of Compound 117: The compound was prepared according to General Method 7 from Compound 117D (65 mg, 0.06 mmol) to afford Compound 117 (14 mg, 25%). MS (ESI) m/z 849.4 (M+H)$^+$.

Example 17

Synthesis of Compound 118

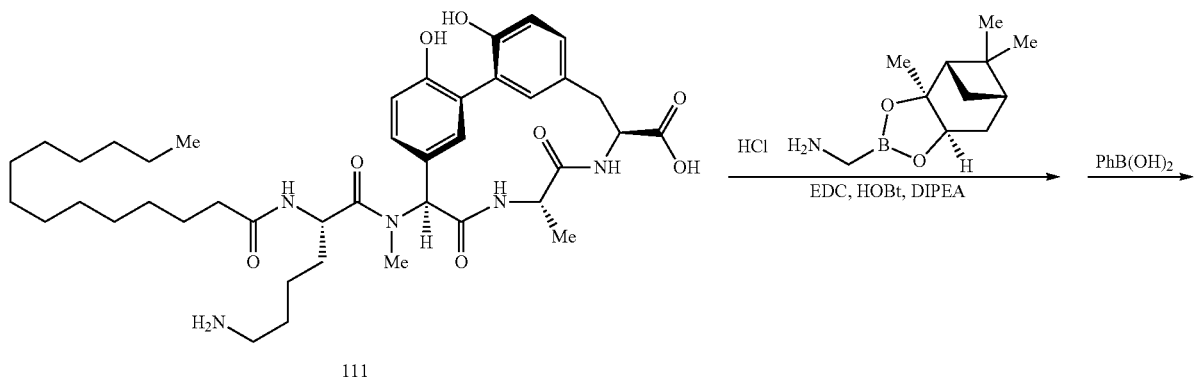

111

-continued

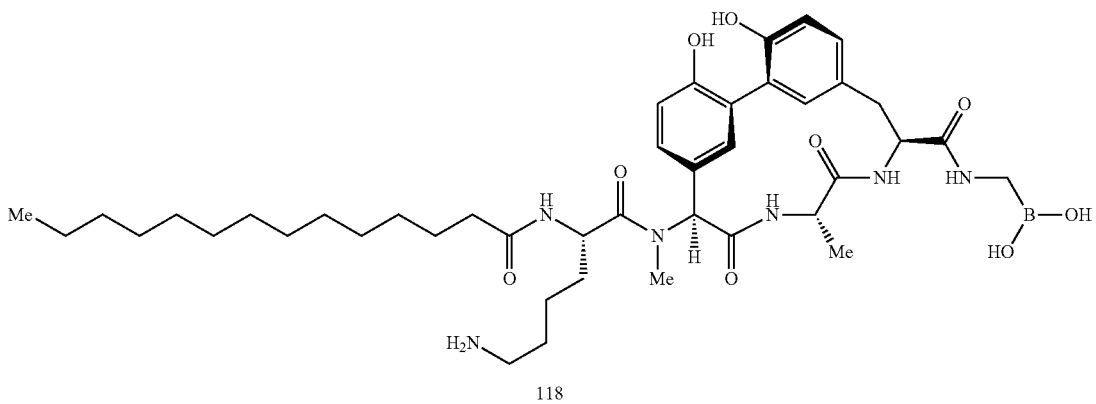
118

Synthesis of Compound 118: To a solution of Compound 111 (50 mg, 67 umol) in DCM (1.2 mL) and DMF (0.3 mL) was added BoroGly-(+)-pinanediol HCl (49 mg, 3 eq), HOBt (31 mg, 3 eq) and DIPEA (35 uL, 3 eq). The solution was then cooled to 0° C., then EDC HCl (38 mg, 3 eq) was added. After 10 min LCMS showed three products with the major product corresponding to the desired mass. To the reaction was then added 10% citric acid and DCM, the aqueous layer was extracted 3× with DCM. The combined organic layers were washed with brine dried over sodium sulfate and concentrated. The crude powder was then taken up in diethyl ether (2 mL) and water (2 mL), treated with phenylboronic acid (3.0 eq) and stirred vigorously for 4 hrs. The aqueous layer was then separated and purified by HPLC to give Compound 118 (4.7 mg, 9% yield). MS (ESI) for ($C_{42}H_{65}BN_6O_9$): m/z 809 (M+H)$^+$.

Example 18

Synthesis of Compound 119

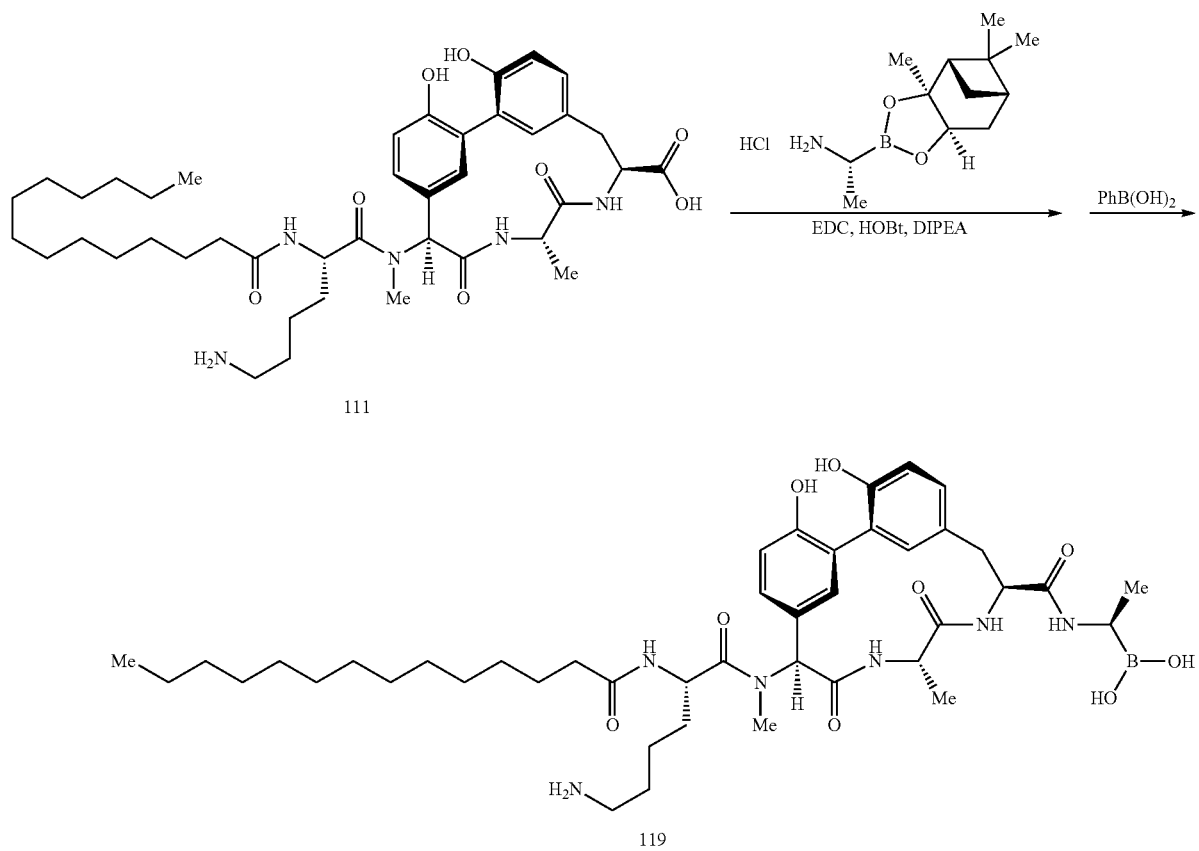

Synthesis of Compound 119: To a solution of Compound III (37 mg, 48 umol) in DCM (1.2 mL) and DMF (0.3 mL) was added (R)-BoroAla-(+)-pinanediol HCl (32 mg, 3 eq), HOBt (22 mg, 3 eq) and DIPEA (25 uL, 3 eq). The solution was then cooled to 0° C. and EDC HCl (28 mg, 3 eq) was added. After 10 min LCMS showed three products with the major product corresponding to the desired mass. To the reaction was then added 10% citric acid and DCM, the product was found in the aqueous layer so this layer was separated and lyophilized. The crude powder was then taken up in diethyl ether (3 mL) and water (3 mL), treated with phenylboronic acid (3.0 eq) and stirred vigorously for 2 hrs. The aqueous layer was then separated and purified by HPLC to give Compound 119 (3 mg, 8% yield). MS (ESI) for ($C_{42}H_{65}BN_6O_9$): m/z 823 (M+H)$^+$.

Example 19

Synthesis of Compound 120

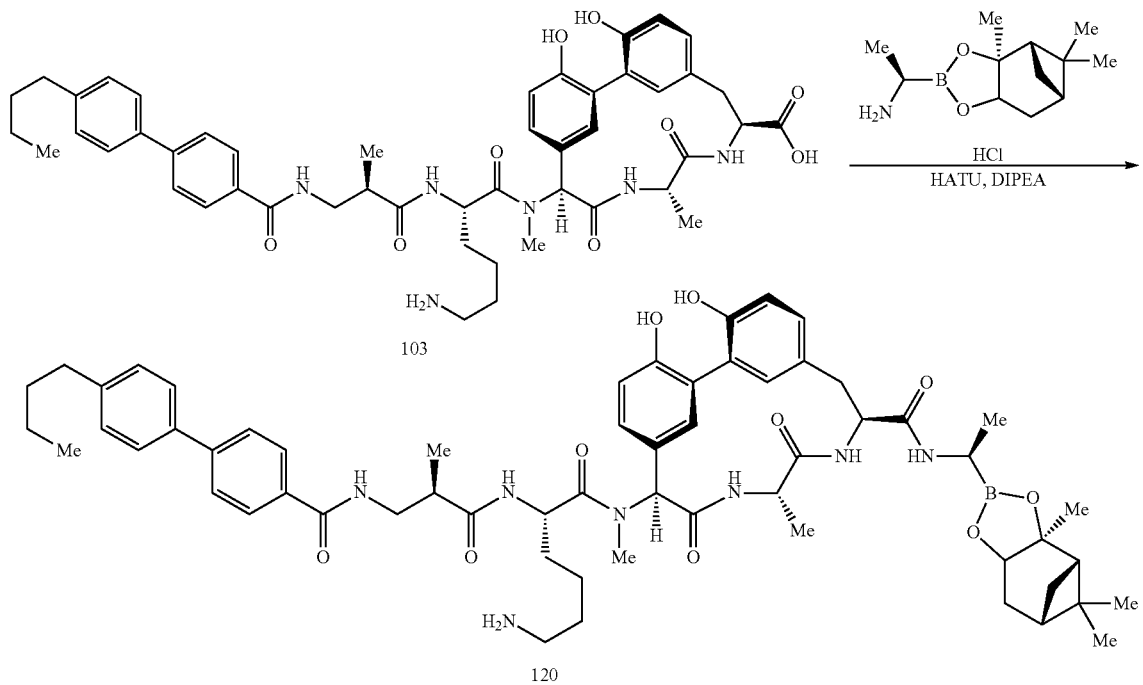

Synthesis of Compound 120: To a solution of Compound 103 (50 mg, 38 umol) in DCM (1.2 mL) and DMF (0.3 mL) was added (R)-BoroAla-(+)-pinanediol HCl (38 mg, 3 eq), HOBt (27 mg, 3 eq) and DIPEA (31 uL, 3 eq). The solution was then cooled to 0° C. and EDC HCl (33 mg, 3 eq) was added. After 10 min LCMS showed three products with the major product corresponding to the desired mass. To the reaction was then added 10% citric acid and DCM, the product was found in the aqueous layer so this layer was separated and lyophilized. The crude powder was purified by HPLC to give Compound 120 (2.5 mg, 4%). MS (ESI) m/z 1068.41 (M+H)$^+$.

Example 20

Preparation of Compound 121

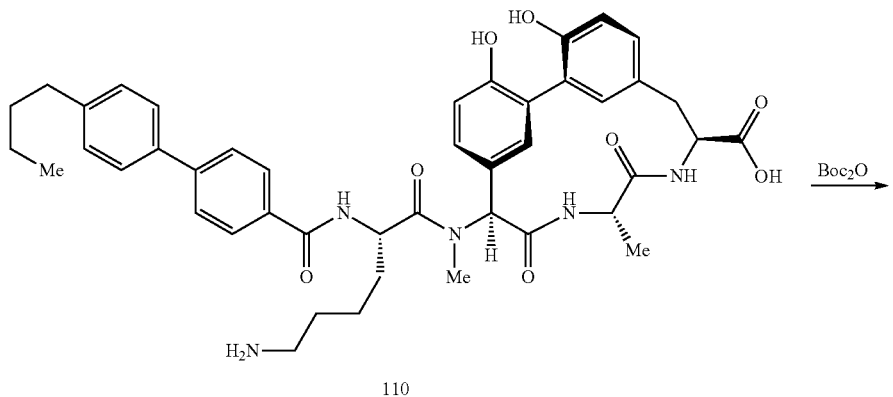

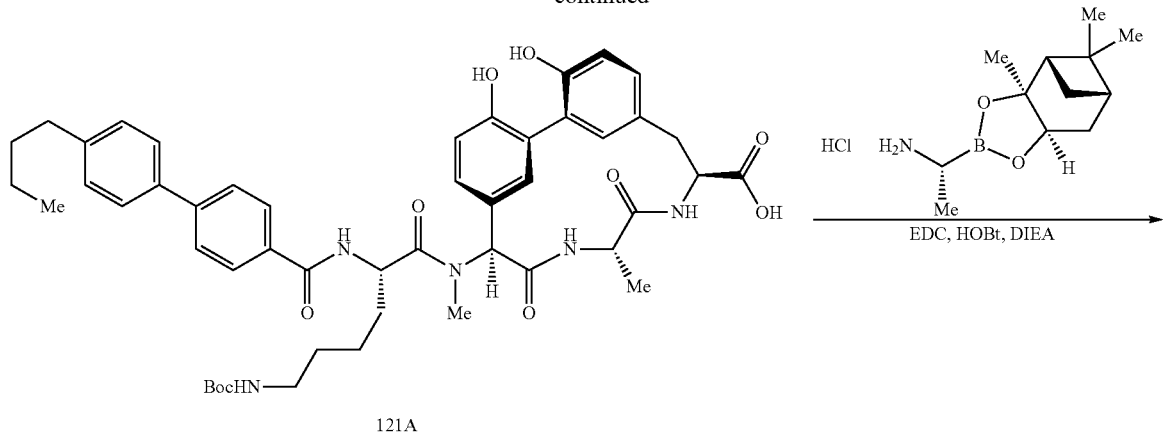

121A

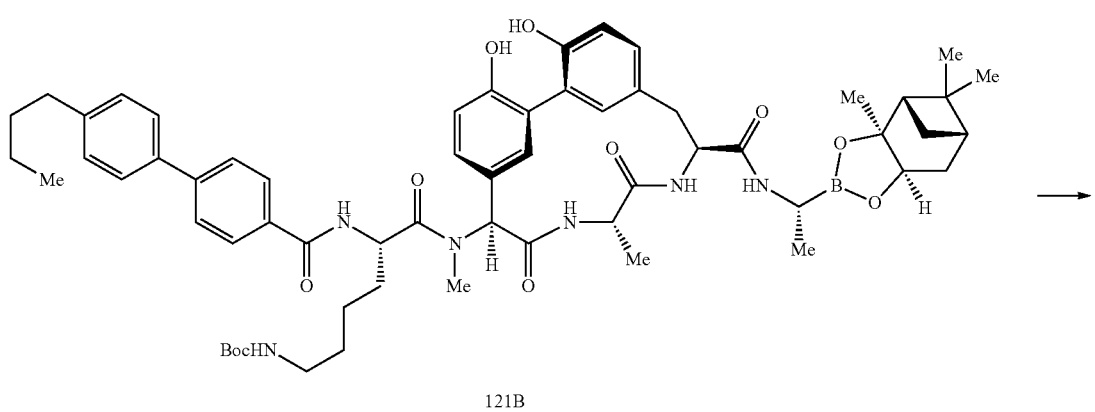

121B

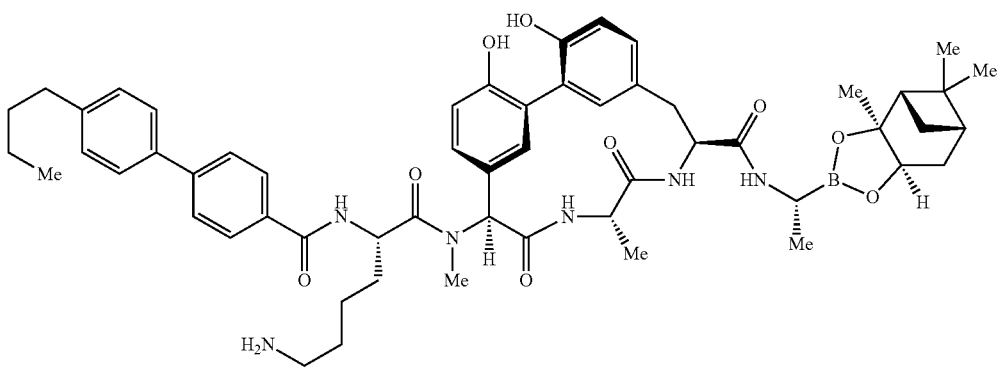

121

To a solution of Compound 110 (250 mg, 0.322 mmol) and Na₂SO₄ (68.3 mg, 0.644 mmol) in MeOH (3 ml) was added Boc₂O (84.2 mg, 0.386 mmol). The reaction was stirred at 15° C. for 24 h until TLC analysis showed the reaction was completed. The mixture was concentrated and partitioned between DCM and water. The aqueous layer was extracted twice with DCM (10 ml×2). The organic layers was dried, filtered and concentrated to give Compound 121A (200 mg, 70.9%) as an off-white solid.

To a mixture of Compound 121A (80 mg, 0.091 mmol), HATU (69.3 mg, 0.182 mmol) and (R)-BoroAla-(+)-pinanediol HCl (35.4 mg, 0.137 mmol) in DCM (2.4 mL) and DMF (0.8 mL) was added DIPEA (35 mg, 0.27 mmol) at −5° C. The reaction was stirred at −5° C. for 30 min. After LCMS showed the reaction was completed, the mixture was concentrated to a solid. Preparative HPLC purification afforded Compound 121B (20.0 mg, 20.3%).

A solution of Compound 121B (20.0 mg, 0.0185 mmol) in TFA: DCM:TES (50:45:5) (1.0 mL) was stirred at 16° C. for 1 h. The solvents were evaporated to afford a solid. Preparative HPLC purification afforded Compound 121 (5.5 mg, 30%). MS (ESI) m/z 982.8 (M)⁺.

Example 21

Preparation of Compound 122

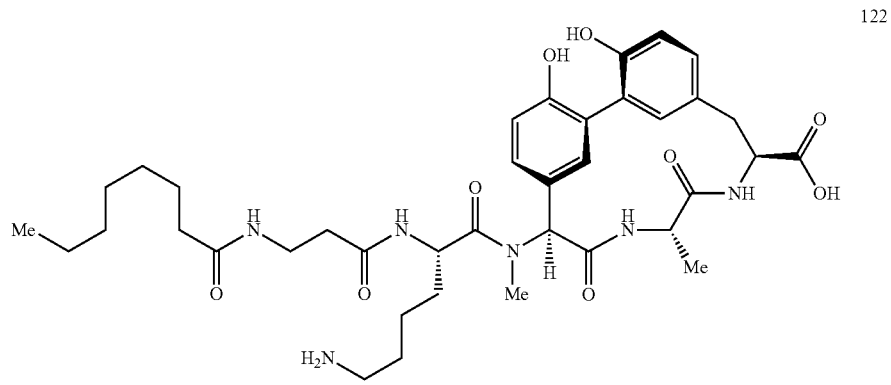

Compound 122 was prepared in a manner similar to Compound 112 from Compound G1 and octanoic acid. Data for Compound 122: MS (ESI) m/z 739.2 (M+H)$^+$. $^1$H NMR (400 MHz, CD$_3$OD), ppm δ:0.89 (t, J=6.8 Hz, 3H), 1.3 (s, 9H), 1.37 (d, J=6.4 Hz, 3H), 1.40-1.75 (m, 7H), 1.78-1.90 (m, 2H), 2.15 (t, J=8.0 Hz, 1H), 2.38-2.51 (m, 2H), 2.87 (s, 3H), 2.94 (t, J=7.6 Hz, 2H), 3.08-3.13 (m, 1H), 3.35-3.50 (m, 3H), 6.41 (s, 1H), 6.87 (d, J=8.4 Hz, 1H), 6.96 (d, J=8.4 Hz, 1H), 7.00-7.02 (m, 2H) 7.08-7.14 (m, 2H), 8.29 (d, J=7.2 Hz, 1H), 8.67 (d, J=8.8 Hz, 1H), 8.89 (d, J=7.6 Hz, 1H). MS (ESI) m/z 739.2 (M+H)$^+$. $t_R$ 2.24 min (10% AcCN/H$_2$O, 0.3 min; 10% 80% AcCN/H$_2$O, 5 min; 1 mL/min Luna C18, 2×50 mm).

Example 22

Preparation of Compound 123

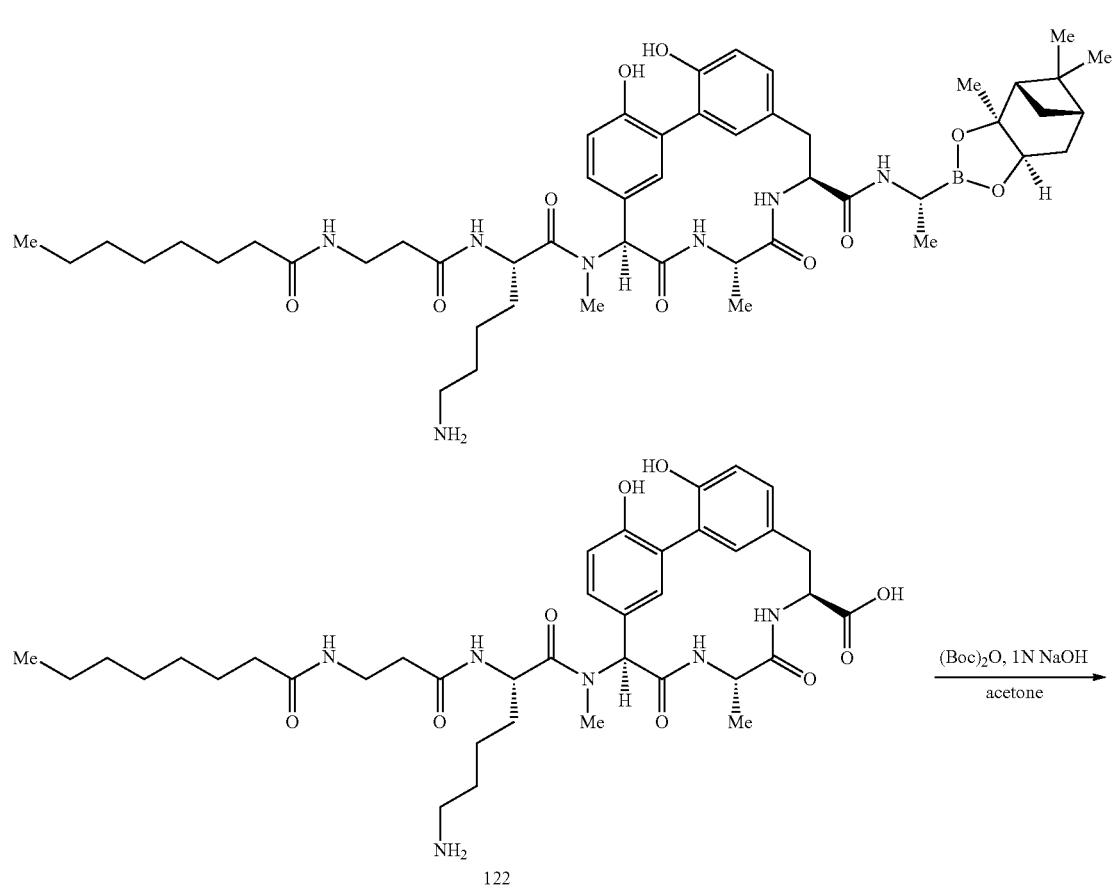

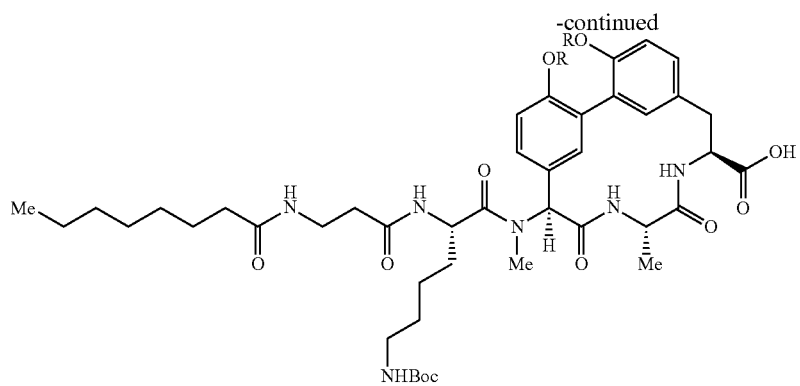

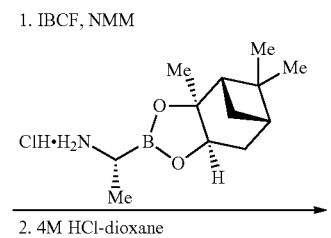

123A  R = Boc, H mixture of compounds

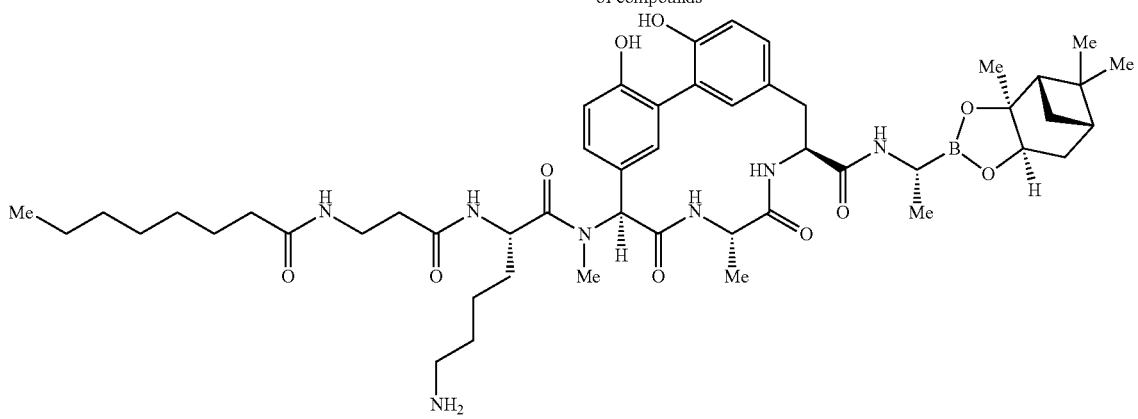

123

To a solution of Compound 122 (74 mg, 0.1 mmol) in acetone-$H_2O$ (1:1, 1 mL) was added 1M NaOH (0.5 mL, 0.5 mmol), $(Boc)_2O$ (0.115 mL, 0.5 mmol). The reaction mixture was stirred at room temperature for 2 days. The acetone was removed under vacuum and the reaction mixture was diluted with $H_2O$ (2 mL). The mixture was acidified with 1M HCl and the resultant white precipitate was filtered and dried to afford 92 mg (89%) in which either one of the bis-phenols are either Boc protected, or Boc-protected at both positions, to afford Compound 123A. MS (ESI) for ($C_{48}H_{70}N_6O_{13}$): m/z 939 (M+H)$^+$.

To a solution of Compound 123A (47 mg, 0.05 mmol) in anhydrous THF (1 mL) at 0 $^\circ$ C. in ice bath was added isobutyl chloroformate (19 µL, 0.15 mmol) followed by N-methyl morpholine (27 µL, 0.25 mmol) under $N_2$ atm. The reaction mixture was stirred for 30 min. After the starting material was consumed (monitored by TLC) (R)-BoroAla-(+)-pinanediol HCl (15.4 mg, 0.06 mmol) in THF (1.0 mL) was added and the reaction mixture was stirred for 1 h. After completion of the reaction (monitored by LCMS) the reaction mixture was quenched with saturated $NH_4Cl$ solution (1.0 mL). The reaction mixture was diluted with brine (2 mL) and extracted with EtOAc and the combined organic layers washed with brine. The organic layer dried over anhydrous $Na_2SO_4$, filtered and the solvent was removed under vacuum. MS (ESI) for ($C_{60}H_{90}BN_7O_{14}$): m/z 1166 (M+Na)$^+$.

The resultant solid was dissolved in dioxane (1.0 mL), and 4M HCl in dioxane (1.0 mL) was added at 0$^\circ$ C. The reaction mixture was stirred for about 1 h while monitoring the completion of the reaction by LCMS. After the completion of the reaction, solvent was removed under vacuum and the residue was purified by preparative HPLC using acetonitrile-water containing 0.05% TFA as mobile phase to afford Compound 123. MS (ESI) for ($C_{50}H_{74}BN_7O_{10}$): m/z 944 (M+H)$^+$.

Example 23

Preparation of Compound 124

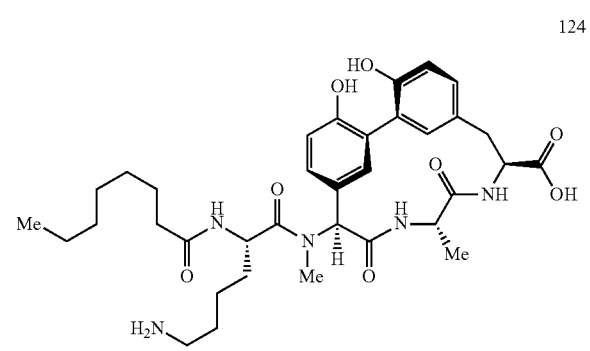

124

Compound 124 was prepared in a manner similar to Compound 101 from Compound G1 and octanoic acid. Data for Compound 124: MS (ESI) m/z 668.1 (M+H)$^+$; $^1$H NMR (400 MHz, $CD_3OD$) ppm δ:0.89 (t, J=6.8 Hz, 3H), 0.91-1.31 (m, 8H), 1.37 (d, J=6.8 Hz, 1H), 1.55-1.58 (m, 4H), 1.65-1.75 (m, 4H), 1.80-1.90 (m, 1H), 2.05-2.45 (m, 2H), 2.89 (s, 3H), 2.93 (t, J=7.6 Hz, 2H), 3.05-3.15 (m, 1H), 3.35-3.45 (m, 1H), 6.5

(s, 1H), 6.88 (d, J=8.0 Hz, 1H), 6.96 (d, J=8.4 Hz, 1H), 7.01-7.00 (m, 2H) 7.01-7.10 (m, 2H), 8.73 (d, J=9.2 Hz, 1H), 8.97 (d, J=8.0 Hz, 1H).
Example 24
Preparation of Compound 125
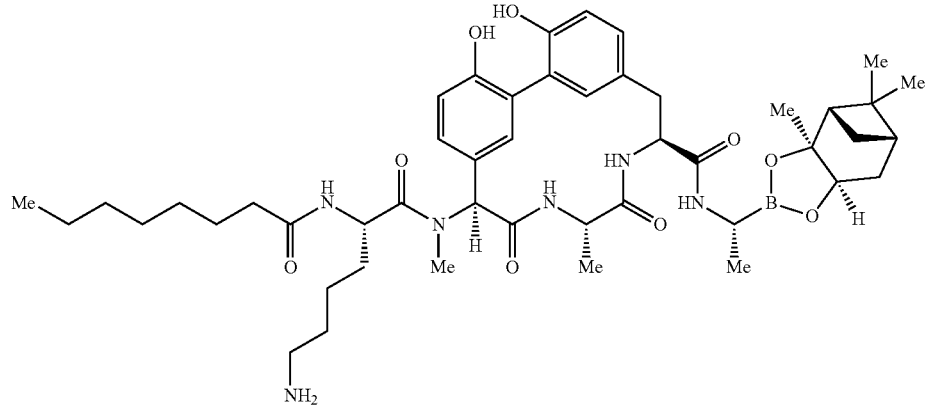
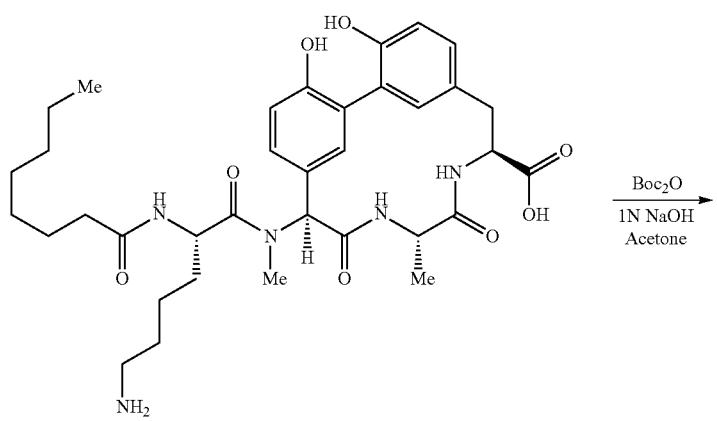
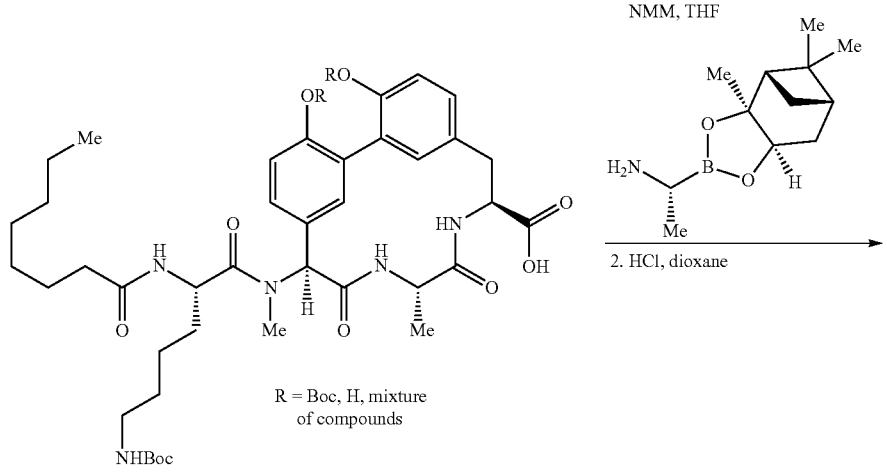

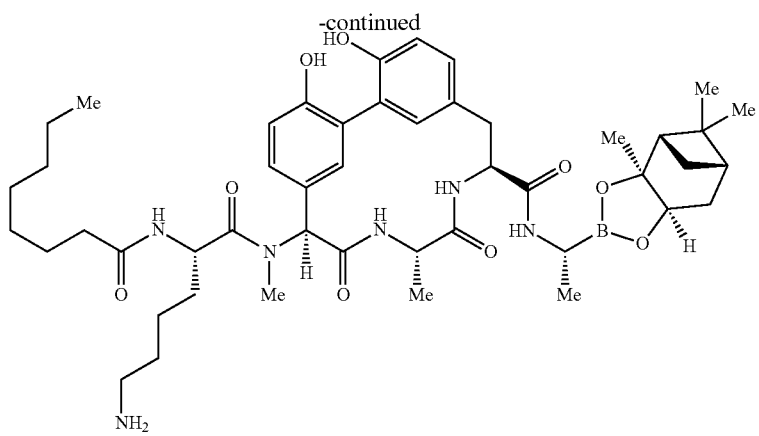

125

Compound 124 (67 mg, 0.1 mmol) was dissolved in acetone-H$_2$O (1:1, 1 mL) and 1M NaOH (0.5 mL, 0.5 mmol) and (Boc)$_2$O (0.115 mL, 0.5 mmol) was added and the reaction mixture was stirred at room temperature for 2 days. The acetone was removed under vacuum and the reaction mixture was diluted with H$_2$O (2 mL). The mixture was acidified with 1M HCl and the resultant white precipitate was filtered and dried to afford 60 mg (69%) as 30:70 mixture of tris and bis boc protected Compound 125A. MS (ESI) for tris-boc product (C$_{50}$H$_{73}$N$_5$O$_{14}$); m/z 968 (M+H)$^+$. and bis-boc product (C$_{45}$H$_{65}$N$_5$O$_{12}$): m/z 868 (M+H)$^+$.

Compound 125 was prepared in two steps from Compound 125A as described in Example 22. Step 1—Coupling using Compound 125A (44 mg, 0.05 mmol) in anhydrous THF (1 mL), isobutyl chloroformate (13 μL, 0.10 mmol), N-methyl morpholine (27 μL, 0.25 mmol) and (R)-BoroAla-(+)-pinanediol HCl (29.4 mg, 0.11 mmol). MS (ESI) for tris-boc product (C$_{62}$H$_{93}$BN$_6$O$_{15}$): m/z 1173 (M+H)$^+$ and bis-boc product (C$_{57}$H$_{85}$BN$_6$O$_{13}$) m/z 1073 (M+H)$^+$. Step 2—Deprotection using 4M HCl in dioxane to afford Compound 125. MS (ESI) for (C$_{47}$H$_{69}$BN$_6$O$_9$): m/z 873 (M+H)$^+$.

Example 25

Preparation of Compound 126

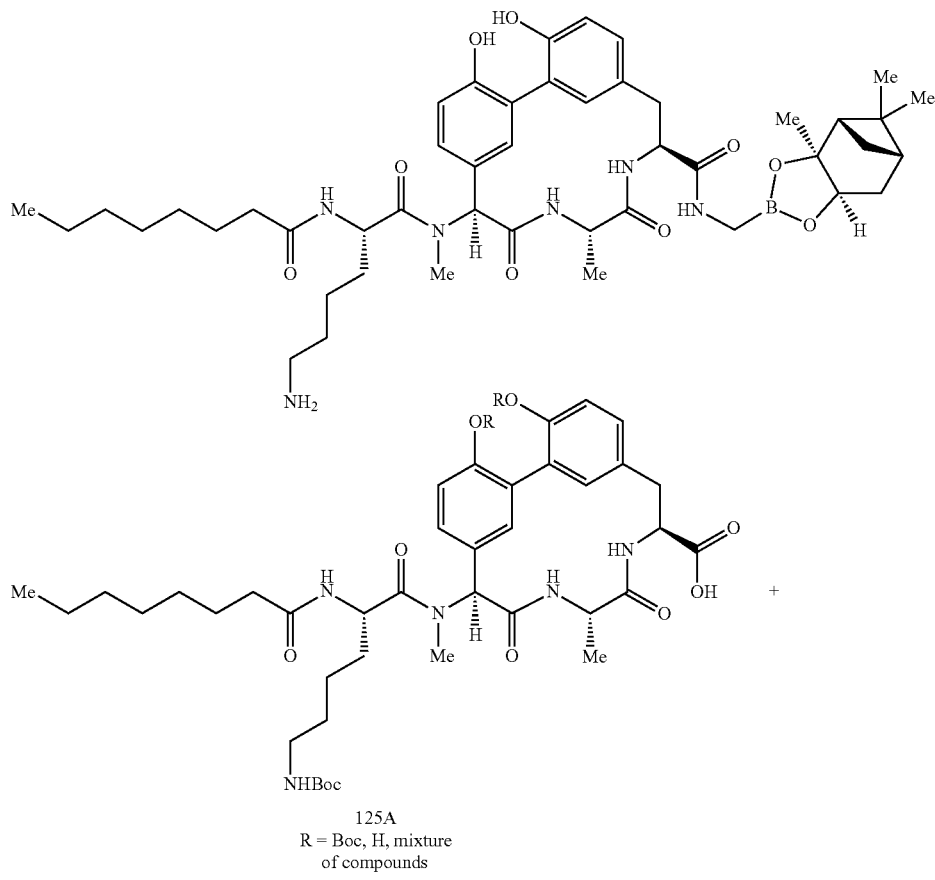

125A
R = Boc, H, mixture of compounds

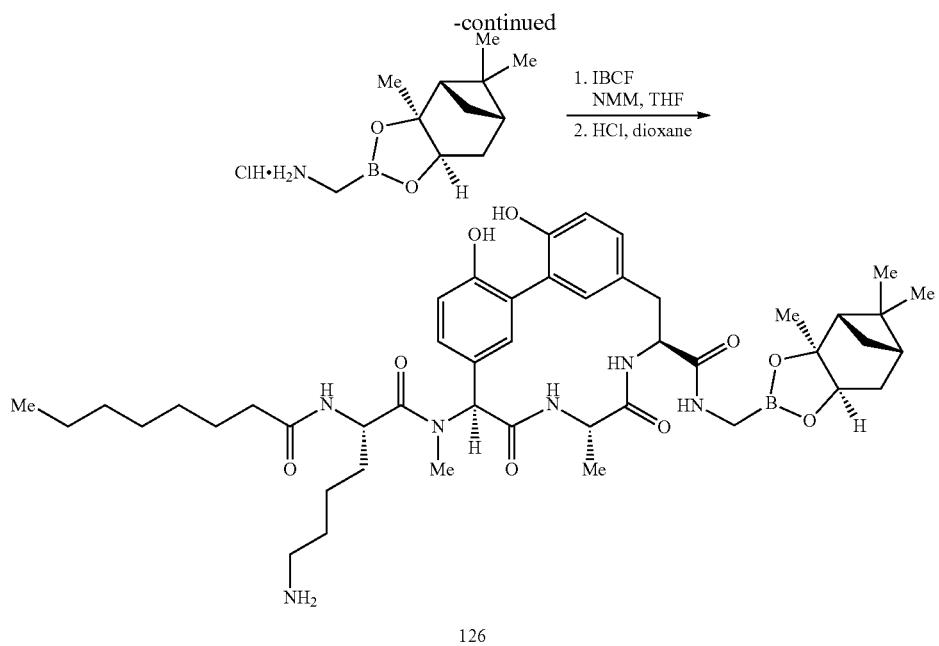

126

Compound 126 was prepared in two steps from Compound 125A as described in Example 22. Step 1—Coupling using Compound 125A (18 mg, 0.02 mmol) in anhydrous THF (1 mL), isobutyl chloroformate (5.2 µL, 0.04 mmol), N-methyl morpholine (11 µL, 0.1 mmol) and BoroGly-(+)-pinanediol HCl (11 mg, 0.044 mmol). MS (ESI) for tris boc product ($C_{61}H_{91}BN_6O_{15}$): m/z 1159 (M+H)$^+$ and bis boc product ($C_{56}H_{83}BN_6O_{13}$): m/z 1059 (M+H)$^+$. Step 2—Deprotection using 4M HCl in dioxane to afford Compound 126. MS (ESI) for ($C_{46}H_{67}BN_6O_9$): m/z 859 (M+H)$^+$.

Example 26

Preparation of Compound 127

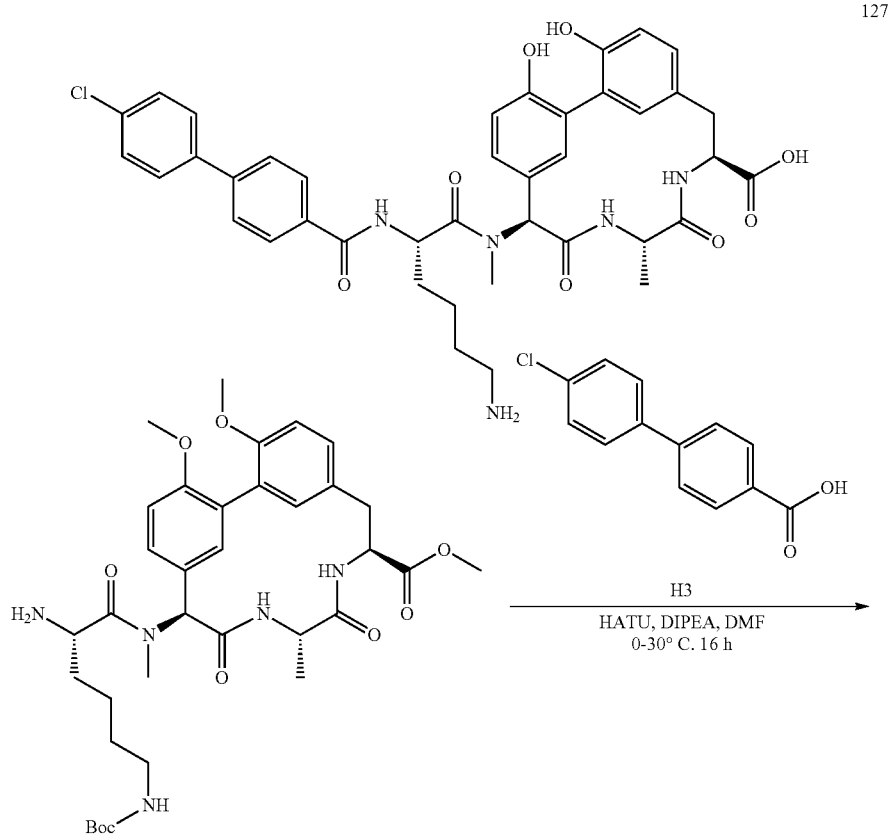

G1

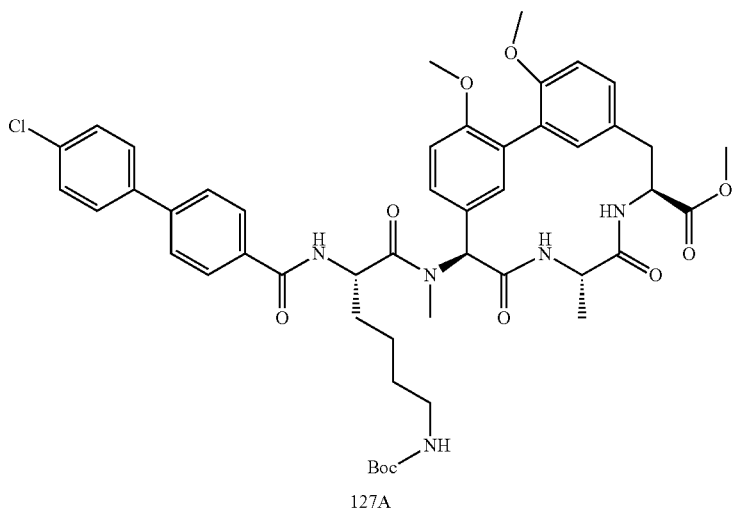

127A

DIPEA (226.8 mg, 1.75 mmol) and Compound H3 (204.1 mg, 0.87 mmol) was added to a solution of Compound G1 (400 mg, 0.58 mmol) in DMF (5 mL) at 0° C. After the mixture was kept at room temperature for 10 min, HATU (445 mg, 1.17 mmol) was added. After the mixture was stirred at room temperature for 16 h, it was poured into water (40 mL). The precipitate was collected by filtration, washed with water and dried in vacuo. The crude product was purified by silica chromatography (DCM/MeOH=60/1) to give Compound 127A as a white solid (500 mg, 96%).

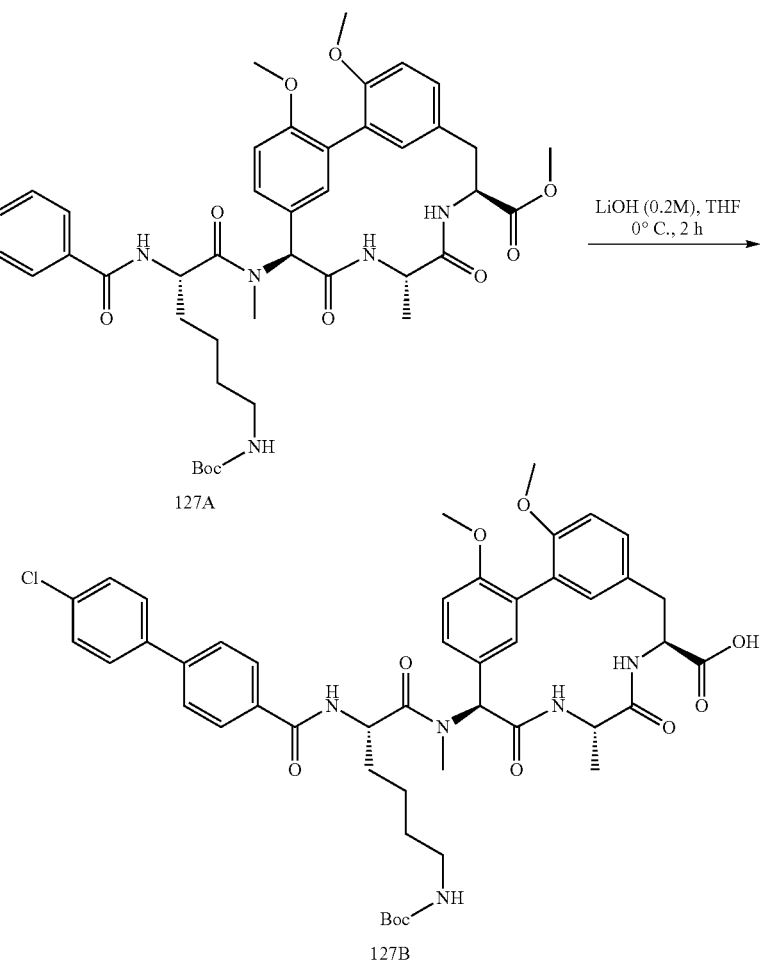

127A

LiOH (0.2M), THF
0° C., 2 h

127B

To a solution of Compound 127A (500 mg, 0.556 mmol) in THF (10 mL) was added aqueous LiOH solution (0.2M, 6 mL) at 0° C. After the reaction was stirred at 0° C. for 0.5 h, saturated NH$_4$Cl solution was added until pH reached below 7. The mixture was extracted with DCM (30 mL×3), washed with brine (30 mL×3), dried over Na$_2$SO$_4$, filtered and concentrated to give Compound 127B (480 mg, yield 96%). $^1$H NMR (400 MHz, DMSO-d$_6$) δ 0.79-0.85 (m, 2 H), 1.15 (d, J=6.4 Hz, 2 H), 1.21 (s, 1 H), 1.29-1.35 (m, 9 H), 1.39 (d, J=6.4 Hz, 2 H), 1.73 (m, 3 H), 2.76 (s, 2 H), 2.87-3.01 (m, 3 H), 3.30 (d, J=10 Hz, 2 H), 3.57 (t, J=6.4 Hz, 1 H), 3.65-3.79 (m, 6 H), 4.41 (brs, 1 H), 4.59-4.67 (m, 1 H), 4.60-4.70 (m, 1H), 4.78 (d, J=6.80 Hz, 1 H), 6.28 (s, 1 H), 6.63-6.79 (m, 3 H), 6.90 (d, J=8.60 Hz, 1 H), 7.00-7.13 (m, 3 H), 7.53 (d, J=8.4, 2 H), 7.74-7.79 (m, 4 H), 8.01 (d, J=8.0 Hz, 2 H), 8.38 (m, 1 H), 8.69 (d, J=7.60 Hz, 1 H).

To a solution of Compound 127B (500 mg, 565 umol) in EtSH (5 mL) at 0° C. was added a solution of AlBr$_3$ in dibromomethane (1M, 5.65 mL, 5.65 mmol). After the reaction mixture was stirred at room temperature for 16 h, the solvent was removed under vacuum. The residue was dissolved in DCM (2 mL), quenched with MeOH (0.5 mL) at 0° C., and the mixture was concentrated under reduced pressure. The residue was purified by prep-HPLC (Luna C18, AcCN/Water plus HCOOH) to give (250 mg, 58.5%) of Compound 127. $^1$H NMR (400 MHz, DMSO-d$_6$) δ 1.09-1.15 (m, 3 H), 1.55-1.57 (m, 1 H), 2.64-2.76 (m, 5 H), 3.23-3.36 (m, 2 H), 4.74-4.83 (m, 1 H), 6.24 (s, 1 H), 6.53-6.57 (m, 1 H), 6.58-6.78 (m, 1 H), 6.83-6.92 (m, 3 H), 7.53 (d, J=8.4 Hz, 2H), 7.75-7.78 (m, 4 H), 8.00 (d, J=8.4 Hz, 2H 2 H), 8.55 (d, J=8.0 Hz, 1H), 8.70 (d, J=7.2 Hz, 1 H). MS (ESI): 756.1 (M+H)$^+$.

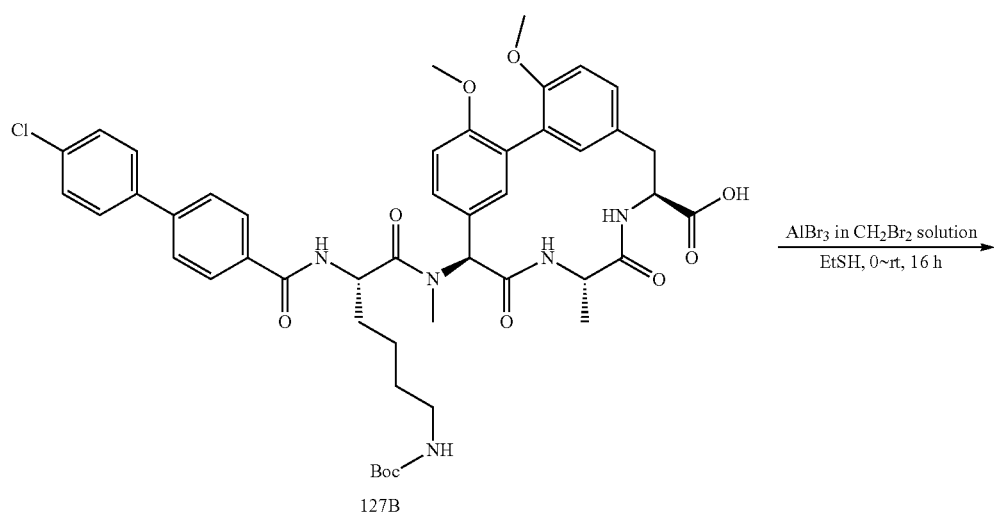

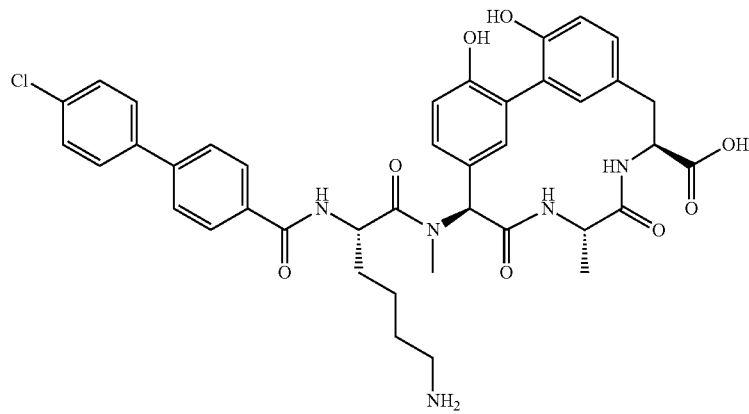

Example 27
Preparation of Compound 128
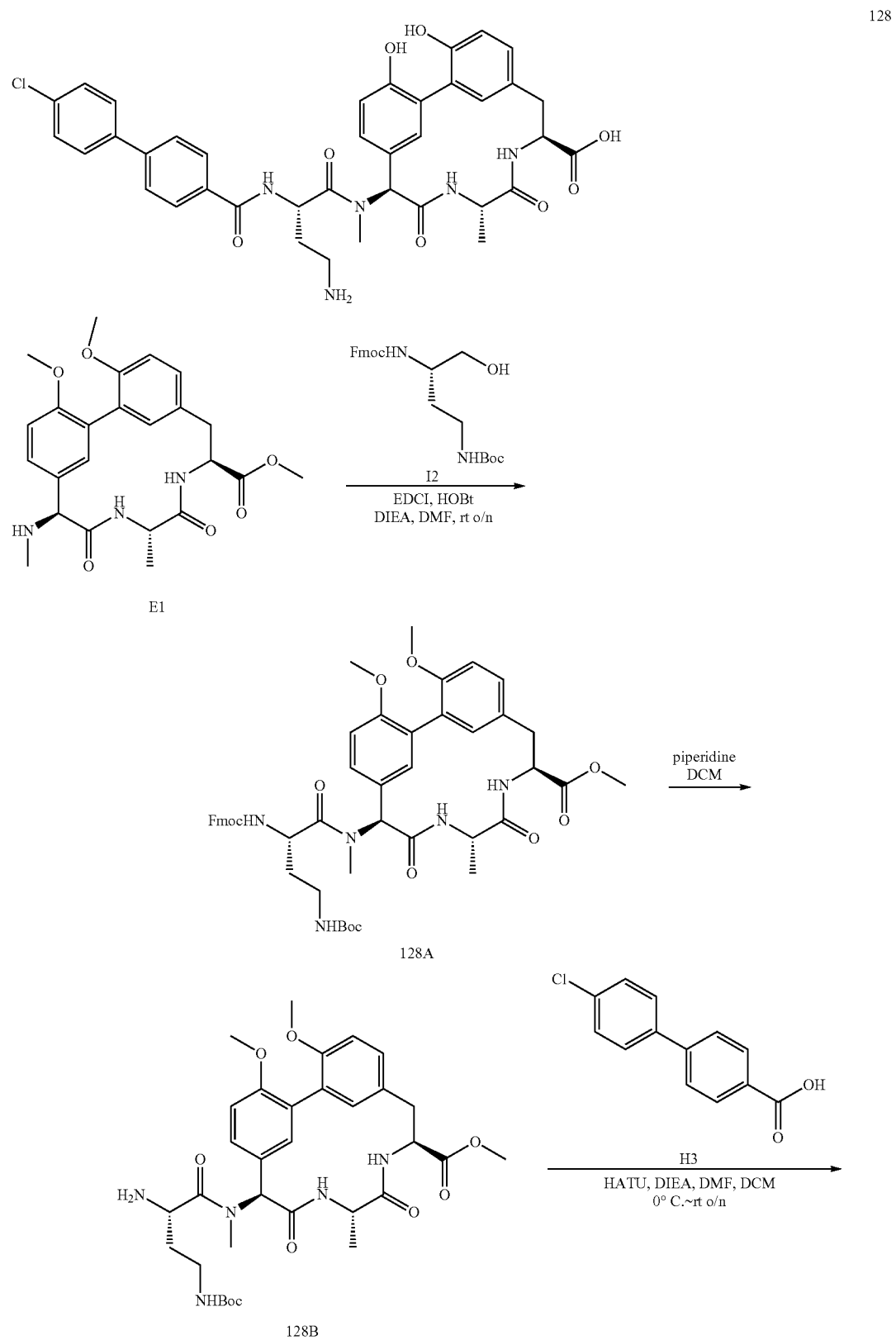

-continued
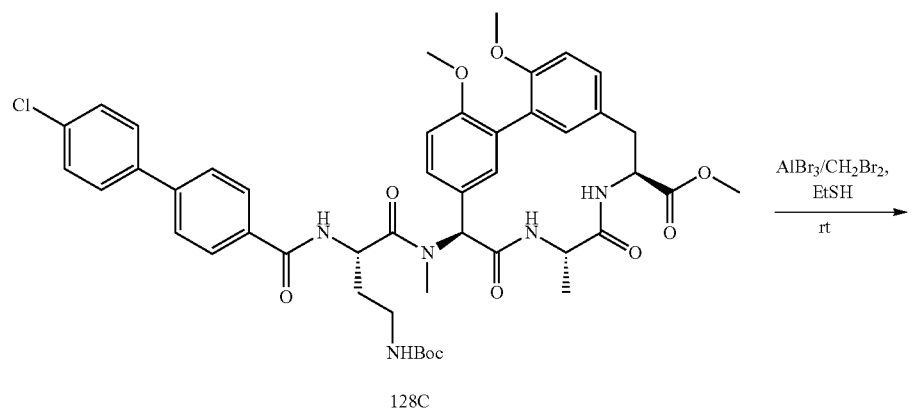
128C
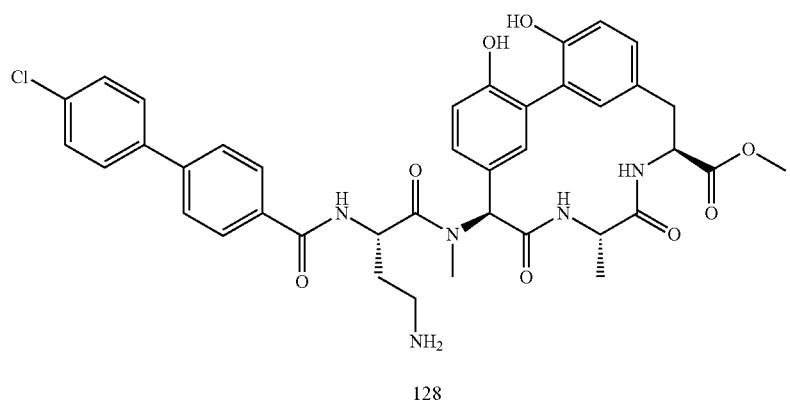
128
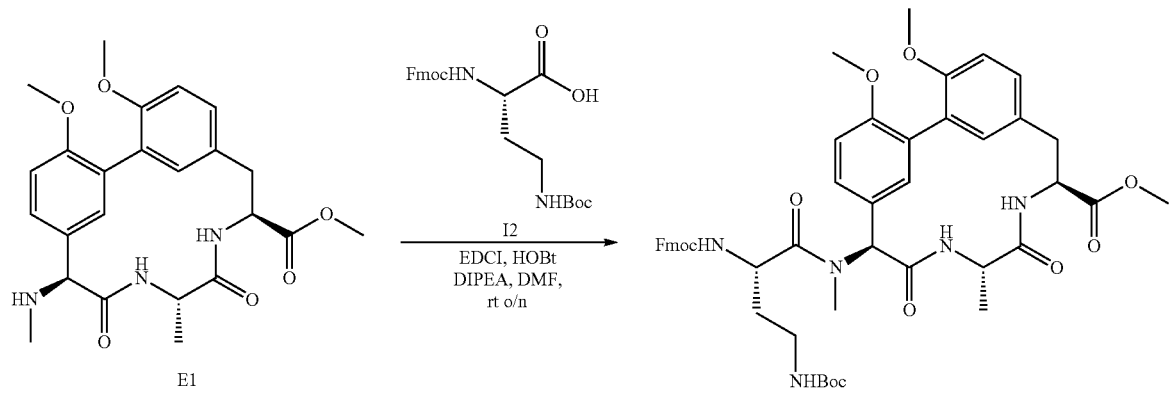

A mixture of DIPEA (284 mg, 2.2 mmol) and Compound E1 (500 mg, 1.1 mmol) was added to a solution of N$^{\alpha}$-Fmoc-N$^{\gamma}$-Boc-L-2,4-diaminobutyric acid (580 mg, 1.1 mmol) in DMF (10 mL) at 0° C. After the mixture was stirred at room temperature for 10 min, EDCI (420 mg, 2.2 mmol) and HOBt (297 mg, 2.2 mmol) was added. After the mixture was stirred at room temperature overnight, it was diluted with water. The precipitate was collected by filtration, washed with water, and dried by lyophilization. The crude product was purified by silica column to give Compound 128A as a yellow solid (870 mg, 90.2%).

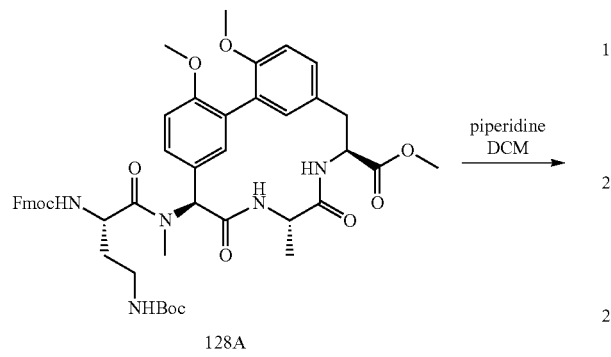

128A

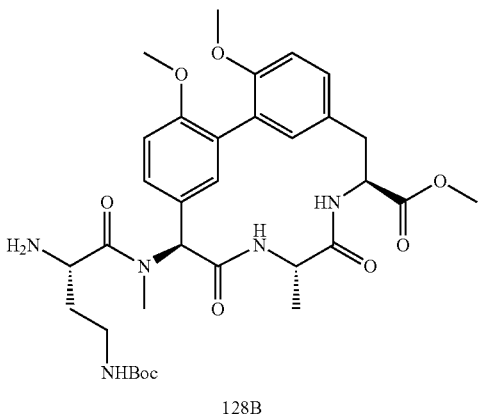

128B

A mixture of Compound 128A (870 mg, 1.0 mmol) in DCM (15 mL) and piperidine (425 mg) was stirred at room temperature for 2 h. The reaction mixture was washed with H$_2$O (50 mL×2), dried over Na$_2$SO$_4$, concentrated, and purified by silica column to give Compound 128B (600 mg, 91.6%).

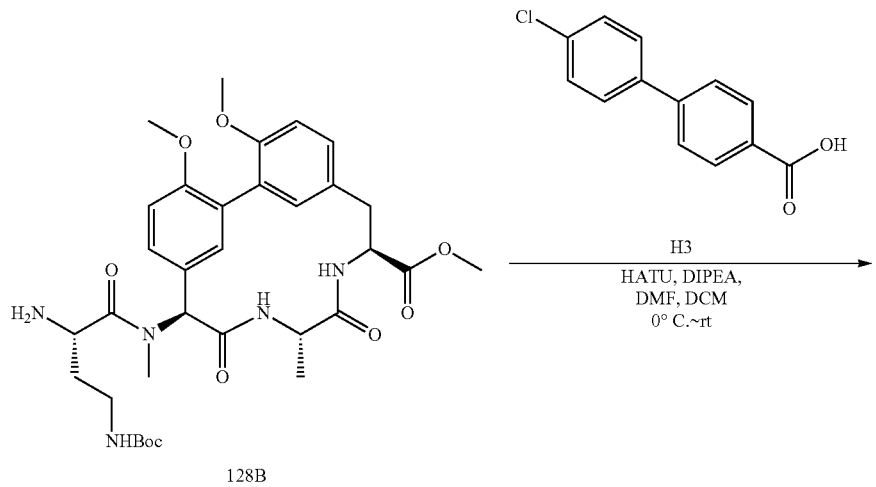

128B

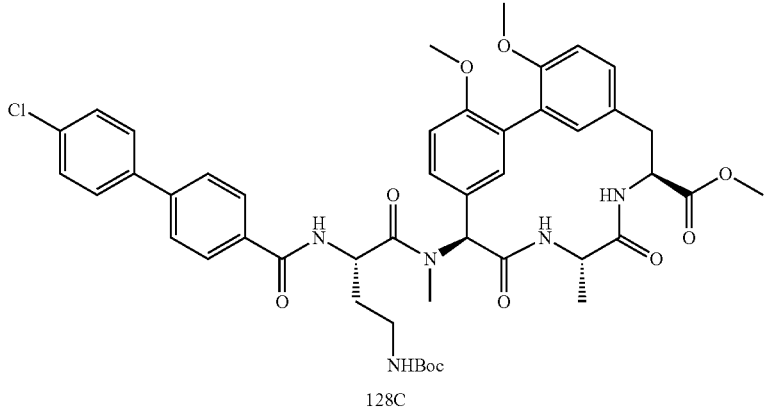

128C

DIPEA (158 mg, 1.22 mmol) and Compound 128B (400 mg, 0.61 mmol) were added to a solution of Compound H3 (213 mg, 0.92 mmol) in DMF (20 mL) at 0° C. at room temperature. After 10 min, HATU (350 mg, 0.92 mmol) was added. The mixture was stirred at room temperature overnight, and then diluted with water. The solid was collected by filtration, washed with water and dried in vacuo. The crude product was purified by silica column to give Compound 128C as a white solid (400 mg, 75.4%).

taken up in DCM (10 mL) and quenched with few drops of isopropanol at 0° C. The inorganic salt was removed by silica column and the crude product was purified by prep-HPLC (AcCN/H$_2$O with 0.1% HCOOH) to give Compound 128 (12.1 mg, 9.0%). $^1$H NMR (400 MHz, DMSO-d$_6$) δ 8.96-8.83 (d, J=7.09 Hz, 1 H), 8.63-8.52 (d, J=8.80 Hz, 1 H), 8.45 (s, 1 H), 8.27 (s, 1 H), 8.05-7.94 (d, J=7.83 Hz, 2 H), 7.83-7.70 (m, 5H), 7.56-7.47 (d, J=8.07 Hz, 2 H), 6.93-6.84 (m, 4 H), 6.75-6.67 (d, J=7.83 Hz, 1 H), 6.64-6.56 (d, J=7.83 Hz, 1 H),

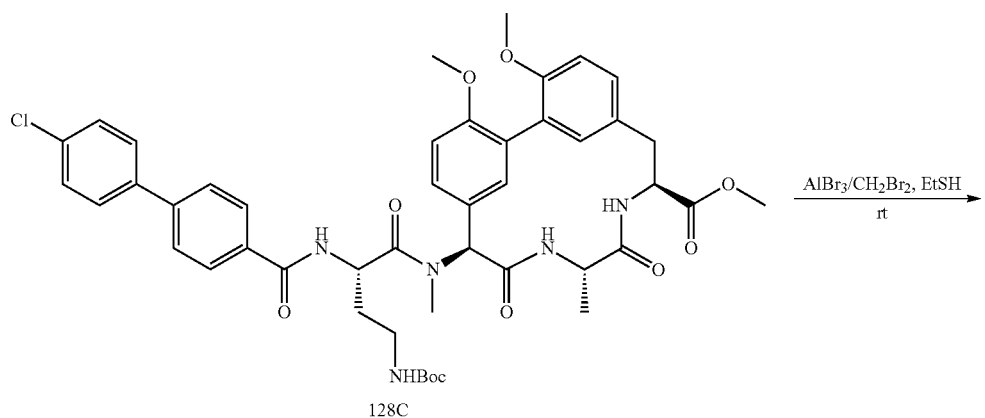

128C

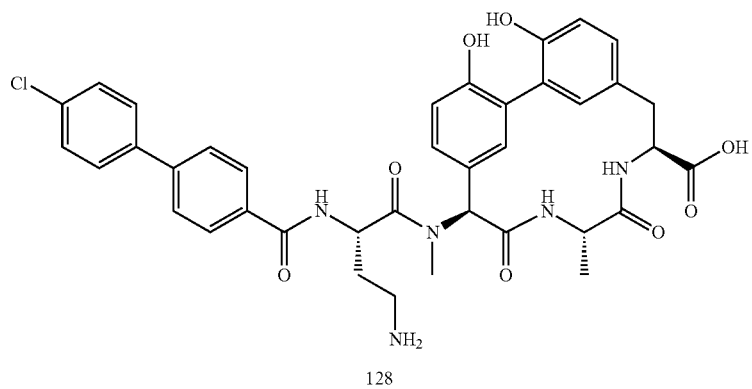

128

To a mixture of Compound 128C (200 mg, 0.23 mmol) in EtSH (1 mL) was added AlBr$_3$ in CH$_2$Br$_2$ (1.0M, 4 mL, 20 eq) under N$_2$ at 0° C. The mixture was warmed to room temperature overnight. Solvent was removed and the residue was 6.21 (s, 1H), 4.94 (s, 1 H), 4.81-4.70 (m, 1 H), 4.35 (s, 1 H), 3.22-3.12 (d, J=15.41 Hz, 3 H), 2.92-2.83 (d, J=6.85 Hz, 2 H), 2.71 (s, 3 H), 1.20 (s, 1 H), 1.17-1.09 (d, J=6.11 Hz, 3 H); MS (ESI): 728.2 (M+H)$^+$.

Example 28
Preparation of Compound 129
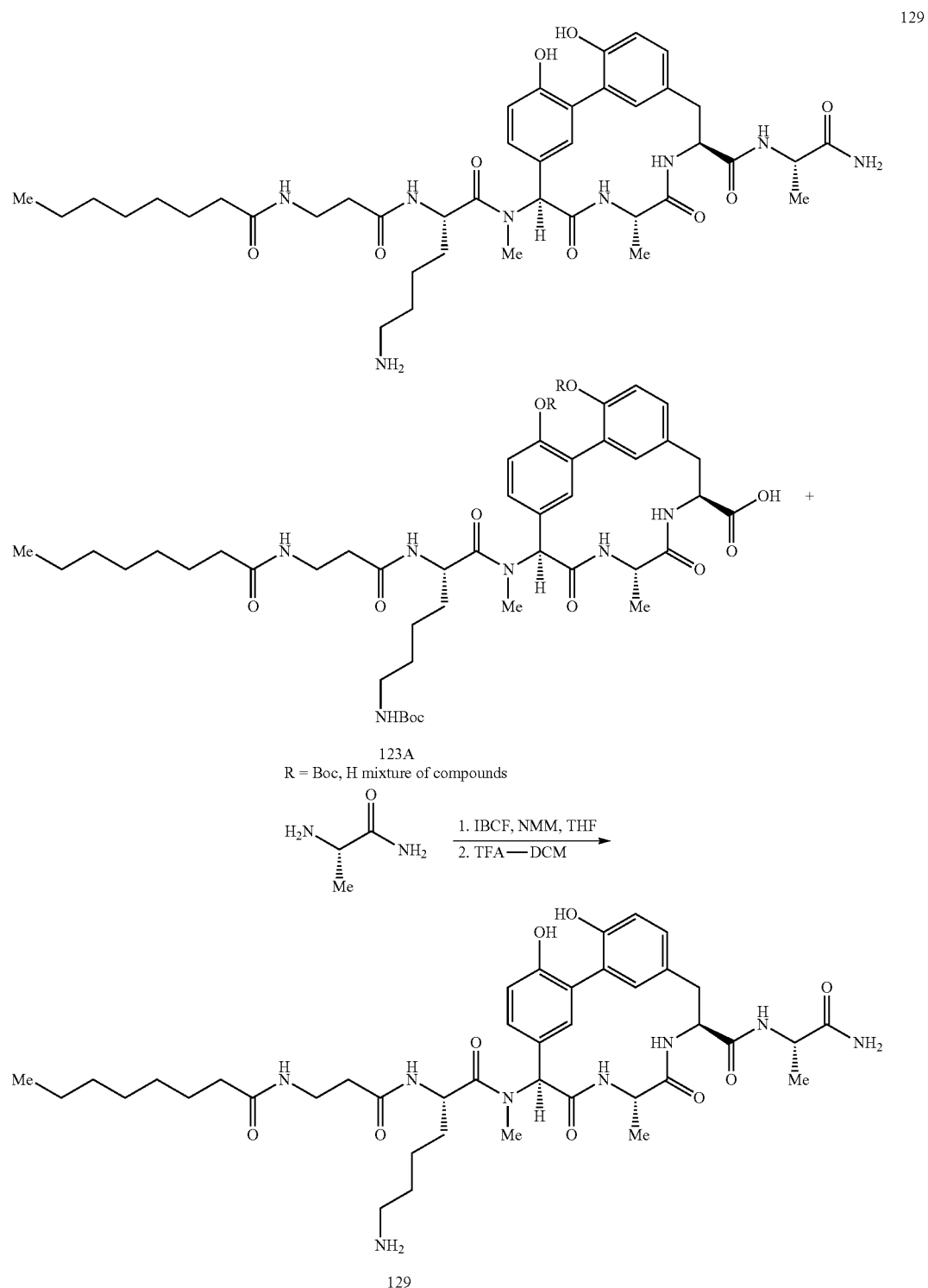
The coupling of Compound 123A with (S)-2-aminopropanamide was carried out as described in Example 22 using a solution of Compound 123A (19 mg, 0.02 mmol) in anhydrous THF (1 mL), isobutyl chloroformate (7.0 μL, 0.05 mmol), N-methyl morpholine (10 μL, 0.1 mmol), and (S)-2-aminopropanamide (8 mg, 0.06 mmol) to give a solid as mixture of bis-boc and tris-boc products. MS (ESI) for tris-boc product ($C_{56}H_{84}N_8O_{15}$): m/z 1109 (M+H)$^+$ and bis-boc product ($C_{51}H_{76}N_8O_{13}$): m/z 1009 (M+H)$^+$.

The resultant solid was dissolved in a 1:4 mixture of TFA and DCM (2 mL) and the mixture was stirred for 2 h at room temperature. After the reaction was completed (monitored by LCMS), the solvent was removed under reduced pressure and the residue was purified by preparative HPLC using $H_2O$ and acetonitrile with 0.05% TFA as mobile phase to afford Compound 129. Data for Compound 129: MS (ESI) for ($C_{41}H_{60}N_8O_9$): m/z 809 (M+H)$^+$.

Example 29

Preparation of Compound 130

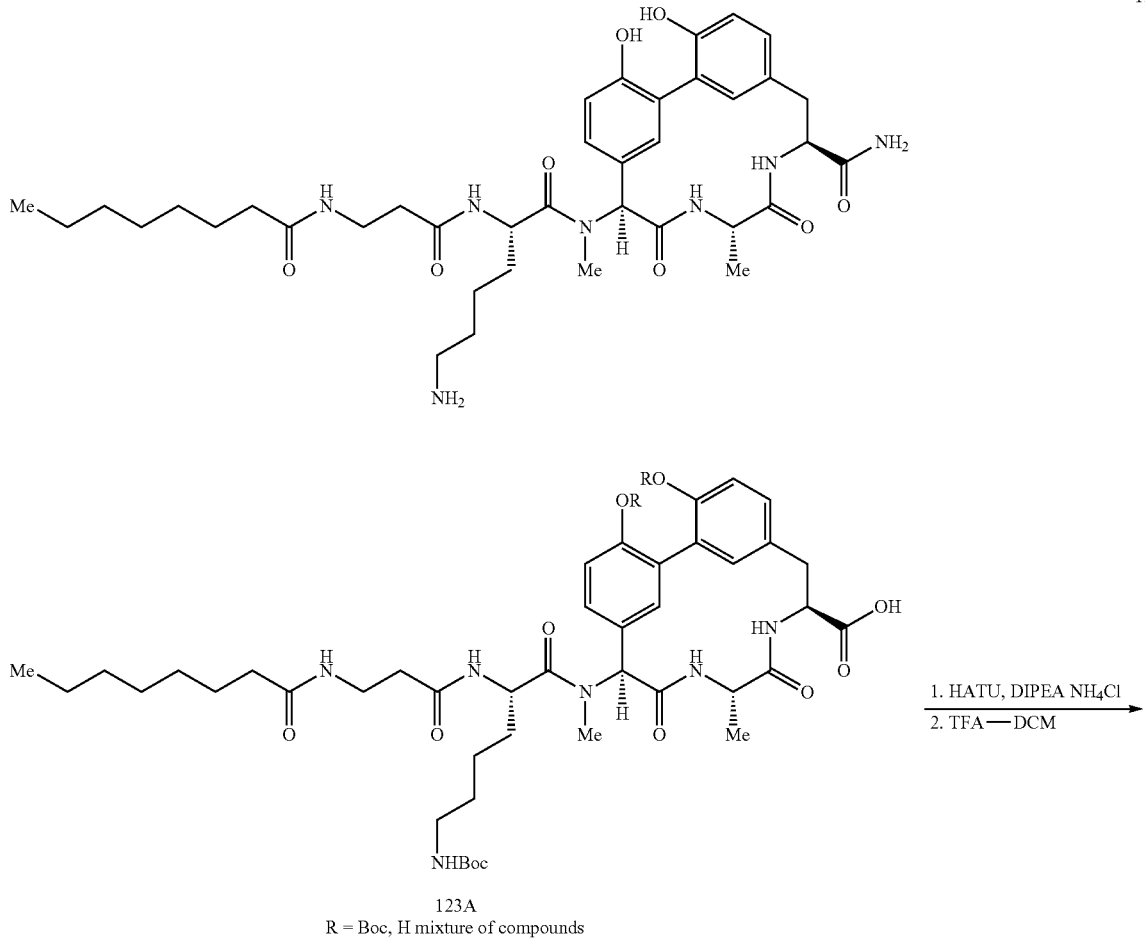

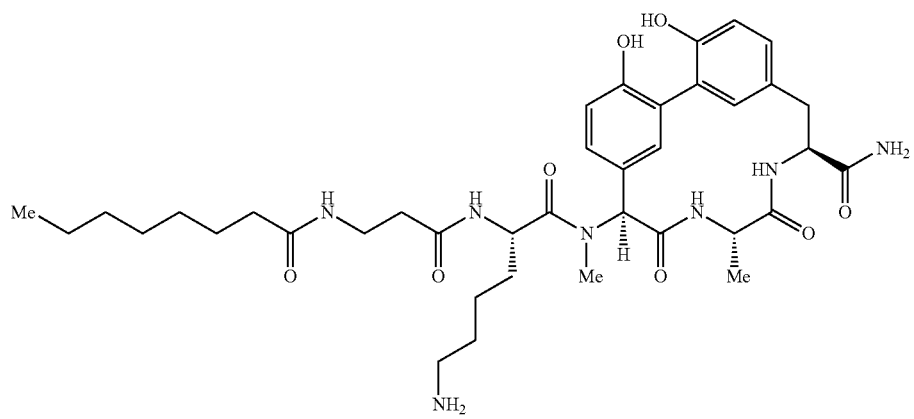

To a solution of Compound 123A (19 mg, 0.02 mmol) in anhydrous DMF (1 mL) was added HATU (12.0 mg, 0.03 mmol) and DIPEA (10 µL, 0.06 mmol), followed by solid NH$_4$Cl (10 mg, 0.2 mmol). The reaction mixture was stirred at room temperature overnight. To the reaction mixture was added crushed ice, and the resultant white solid was collected by filtration and dried. The solid was dissolved in 1:4 TFA-DCM (2.0 mL) and the mixture was stirred at 0° C. to room temperature for 2 h and the solvent was removed. The residue was purified by prep HPLC using acetonitrile-water containing 0.05% TFA as mobile phase to afford Compound 130. MS (ESI) for ($C_{38}H_{55}N_7O_8$): m/z 738 (M+H)$^+$.

Example 30

Preparation of Compound 131

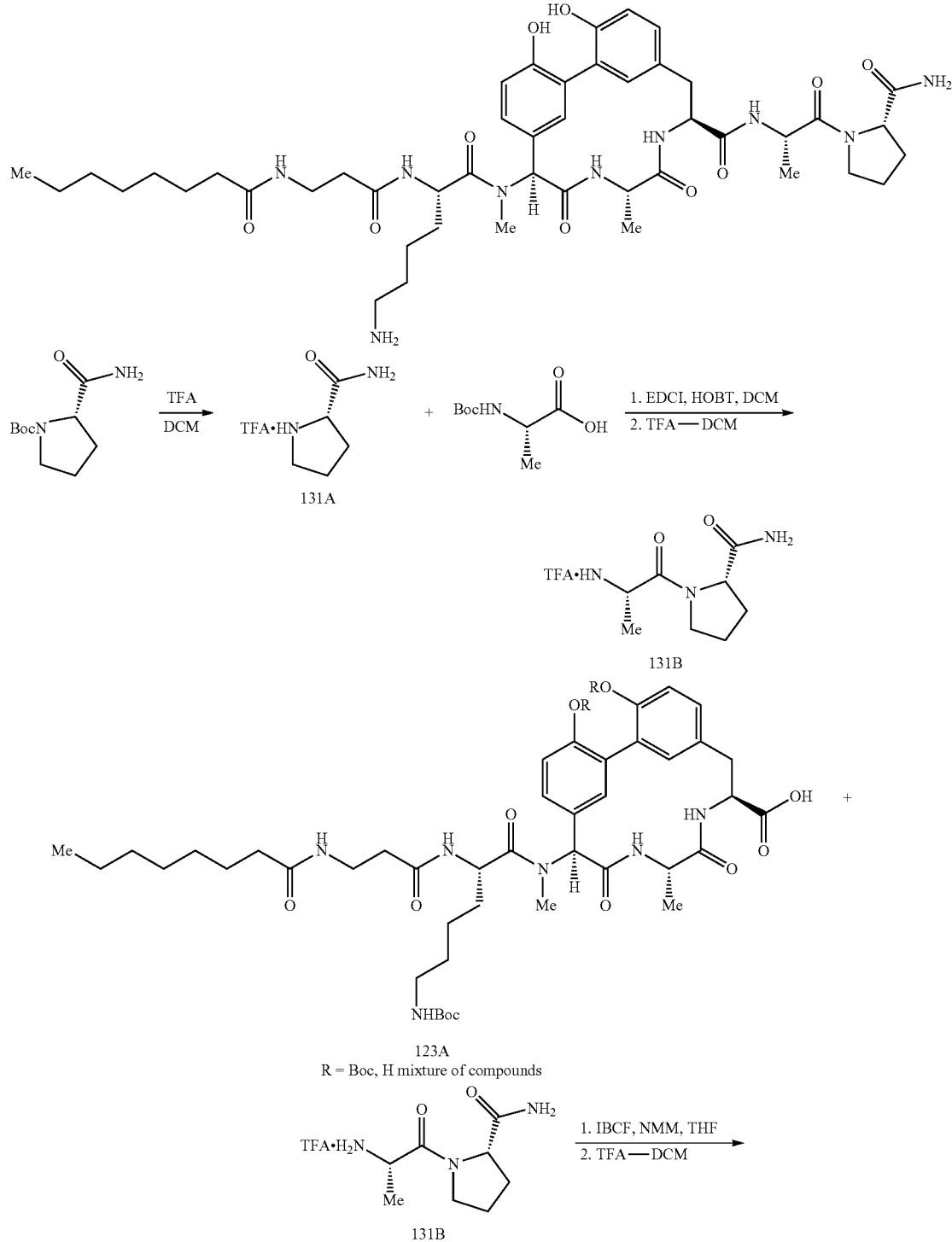

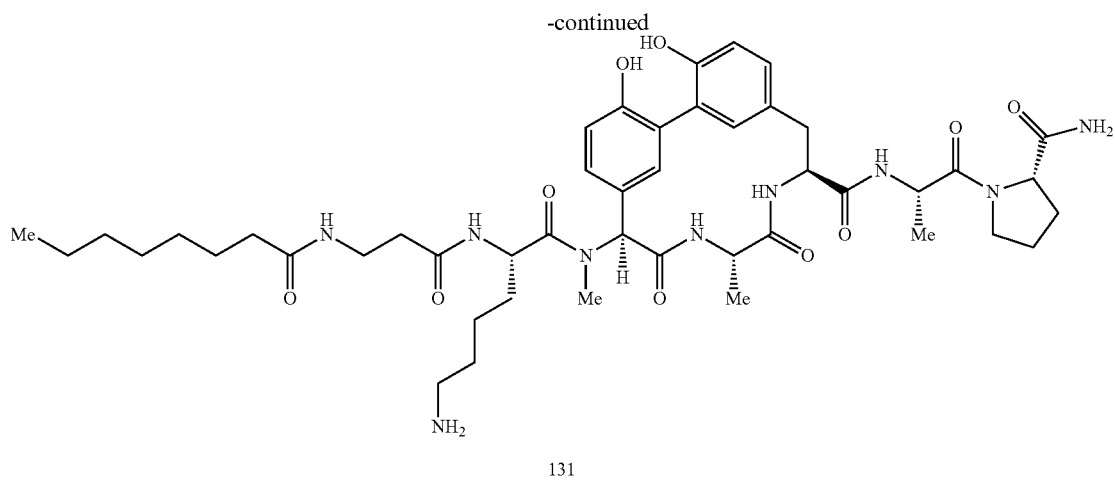

131

A mixture of t-butyl (S)-2-carbamoylpyrrolidine-1-carboxylate (214 mg, 1.0 mmol) in TFA-DCM (1:4, 2.0 mL) was stirred at room temperature for 3 h. After completion of the reaction (monitored by TLC), the solvent was removed under high vacuum to afford Compound 131A. The residue was dissolved in DCM (2 mL) and DIPEA (0.42 mL, 2.5 mmol), EDCI (230 mg, 1.2 mmol) followed by (tert-butoxycarbonyl)-L-alanine (208 mg, 1.1 mmol) was added. The reaction mixture was stirred at room temperature overnight. After completion of the reaction (monitored by TLC), water was added and the mixture was extracted with ethyl acetate. The combined organic layer washed with brine, dried over anhydrous $Na_2SO_4$, filtered and concentrated. The residue was purified by flash chromatography using ethyl acetate/hexanes to afford 170 mg (60%) of oily material. MS (ESI) for ($C_{13}H_{23}N_3O_4$): m/z 186 (M−Boc+H)$^+$. The resultant oily material was dissolved in TFA-DCM (1:4, 2.0 mL) and the mixture was stirred at room temperature for 3 h. After completion of the reaction (monitored by TLC), the solvent was removed under high vacuum to afford Compound 131B.

A solution of Compound 123A (19 mg, 0.02 mmol) in anhydrous THF (1 mL) was treated with isobutyl chloroformate (4.0 μL, 0.03 mmol), N-methyl morpholine (10 μL, 0.1 mmol) and Compound 131B (15 mg, 0.05 mmol) by following the procedure described in Example 22 to give a solid as mixture of bis-boc and tris-boc products. MS (ESI) for tris boc product ($C_{61}H_{91}N_9O_{16}$): m/z 1206 (M+H)$^+$ and bis boc product ($C_{56}H_{83}N_9O_{14}$): m/z 1106 (M+H)$^+$.

Boc protecting groups of the resultant solid were removed using TFA in DCM by following the procedure described in Example 28 to afford Compound 131. MS (ESI) for ($C_{46}H_{67}N_9O_{10}$): m/z 906 (M+H)$^+$.

Example 31

Preparation of Compound 132

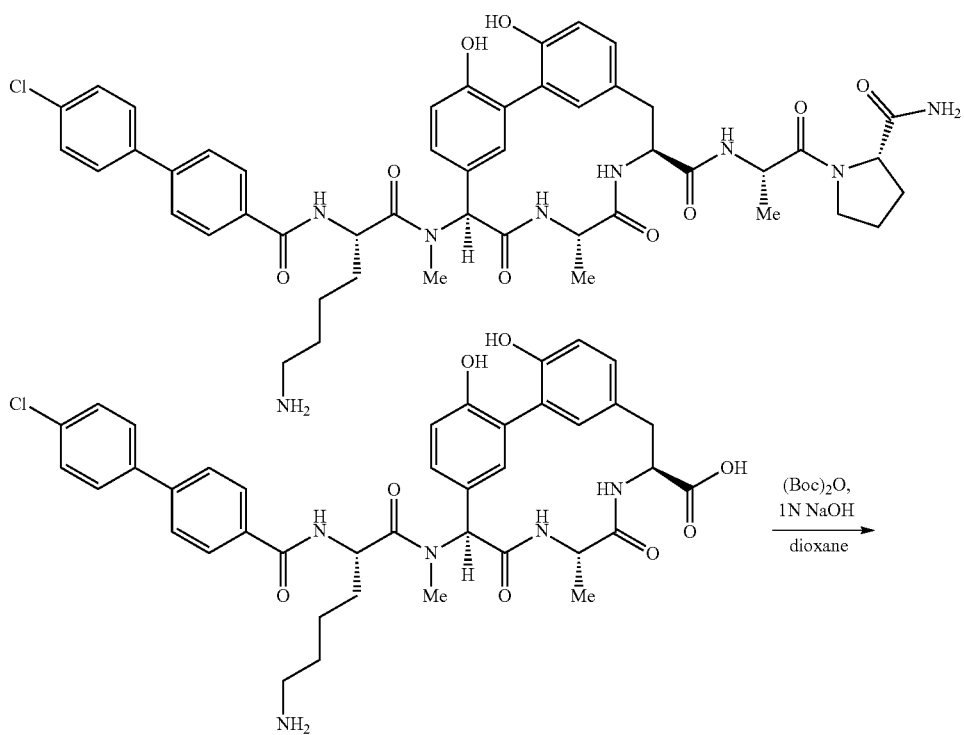

132

127

273

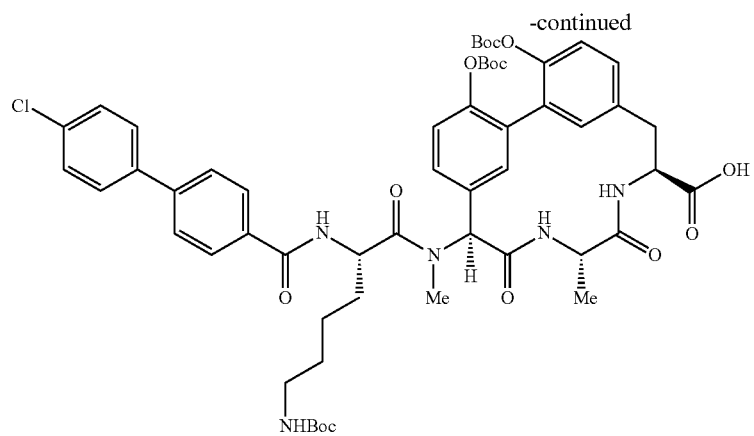

132C

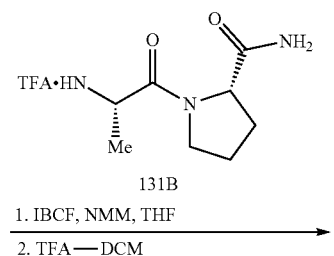

131B

1. IBCF, NMM, THF
2. TFA—DCM

274

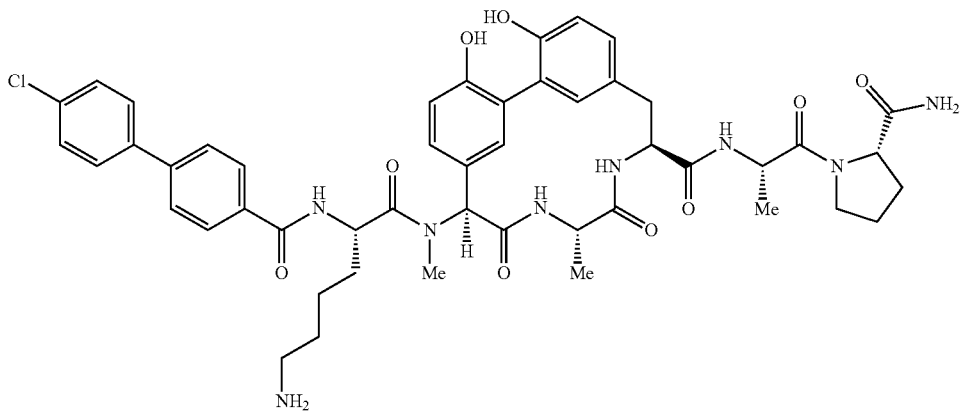

132

To a solution of Compound 127 (500 mg, 0.5 mmol) in dioxane (20 mL) was added 1M NaOH (10 mL, 10 mmol) and (Boc)$_2$O (1.2 mL, 5 mmol). The reaction mixture was stirred at room temperature overnight. The dioxane was removed under reduced pressure and the mixture was acidified with 1M HCl. The resultant white pasty material was dried to afford Compound 132C (507 mg, 96%). MS (ESI) for (C$_{55}$H$_{66}$ClN$_5$O$_{14}$): m/z 1056 (M+H)$^+$.

Compound 132 was prepared in two steps from Compound 132C as described in Example 28. Step 1—Coupling using Compound 132C (22 mg, 0.02 mmol) in anhydrous THF (1 mL), isobutyl chloroformate (4.0 µL, 0.03 mmol), N-methyl morpholine (11 µL, 0.1 mmol) and Compound 131B (15 mg, 0.05 mmol) to give a solid. MS (ESI) for (C$_{63}$H$_{79}$ClN$_8$O$_{15}$): m/z 1223 (M+H)$^+$. Step 2—Deprotection using TFA in DCM to give Compound 132. Data for Compound 132: MS (ESI) for (C$_{48}$H$_{55}$ClN$_8$O$_9$): m/z 923 (M+H)$^+$.

Example 32

Preparation of Compound 133

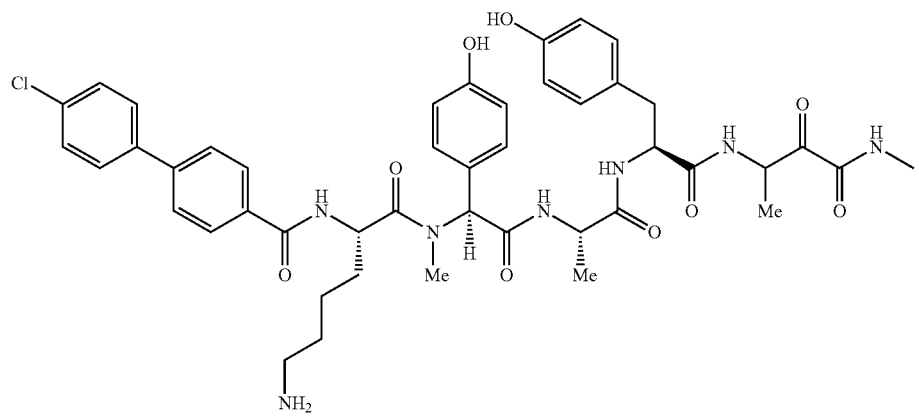

133

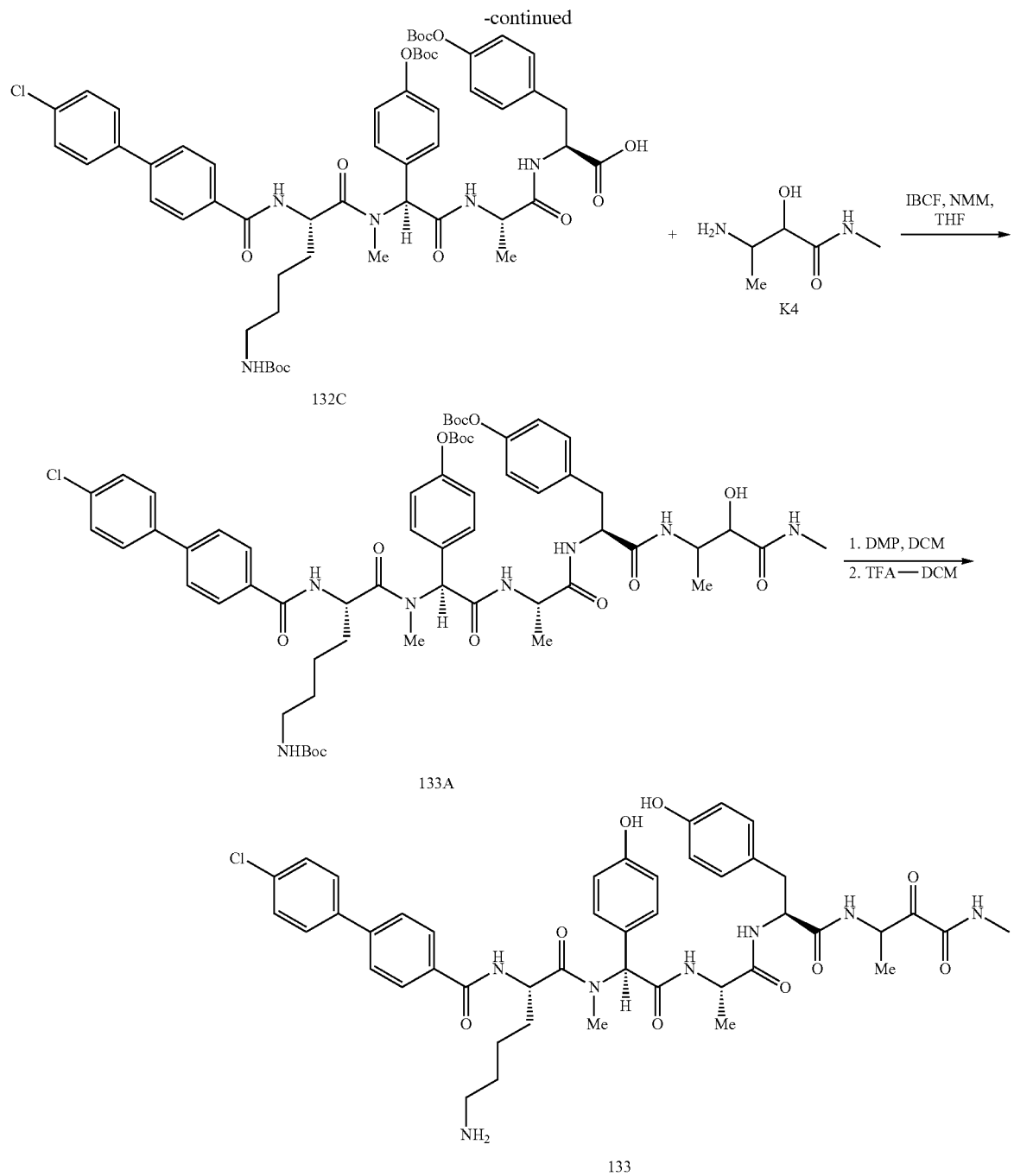

To a solution of Compound 132C (64 mg, 0.06 mmol) in anhydrous THF (2 mL) was added isobutyl chloroformate (12 μL, 0.09 mmol), N-methylmorpholine (33 μL, 0.3 mmol) 3-amino-2-hydroxy-N-methylbutanamide ($K_4$) (28 mg, 0.12 mmol) by following the procedure described in Example 22 to give Compound 133A. MS (ESI) for ($C_{60}H_{76}ClN_7O_{15}$): m/z 1170 (M+H, broad HPLC peak)$^+$.

To a solution of Compound 133A (70 mg, 0.06 mmol) in DCM (2 mL) was added Dess-Martin-Periodinane (127 mg, 0.3 mmol). The resultant heterogeneous reaction mixture was stirred at room temperature for 2 h. After completion of the reaction, (monitored by LCMS), the reaction mixture was filtered through a pad of celite and the celite bed was washed with DCM. The filtrate was washed with saturated $NaHCO_3$ solution and brine. The organic layer dried over anhydrous $Na_2SO_4$ and the solvent was removed under vacuum. The residue was purified by flash chromatography using 100% DCM to 20% MeOH/DCM to afford 40 mg (57%) of the desired product as white solid. MS (ESI) for ($C_{60}H_{74}ClN_7O_{15}$): m/z 1168 (M+H)$^+$, two peaks, 1:1 mixture at alpha-Me of ketoamide.

Compound 133 was prepared by removing the Boc protecting groups using TFA in DCM by following the procedure described in Example 28. MS (ESI) for ($C_{45}H_{50}ClN_7O_9$): m/z 886 (M+$H_2O$+H)$^+$, two peaks, 1:1 mixture at alpha Me of ketamide.

Example 33
Preparation of Compound 134
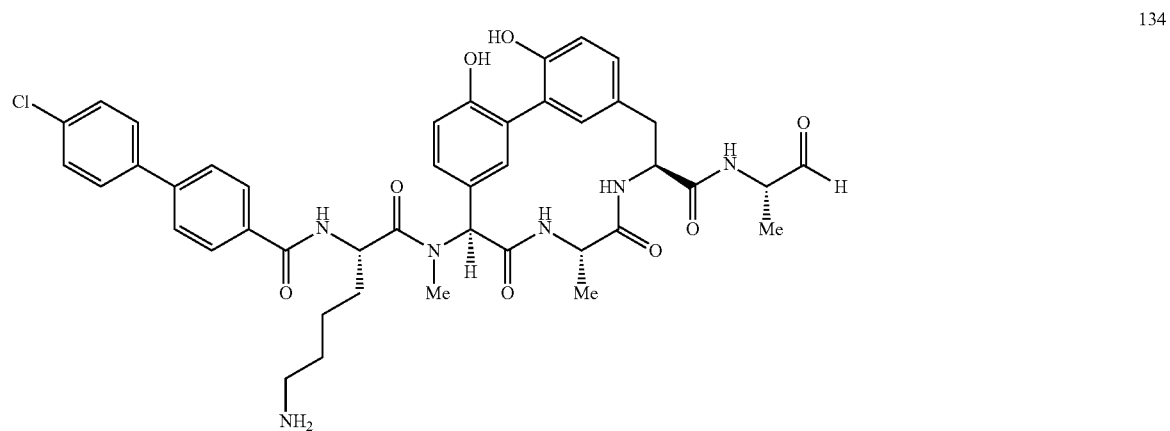
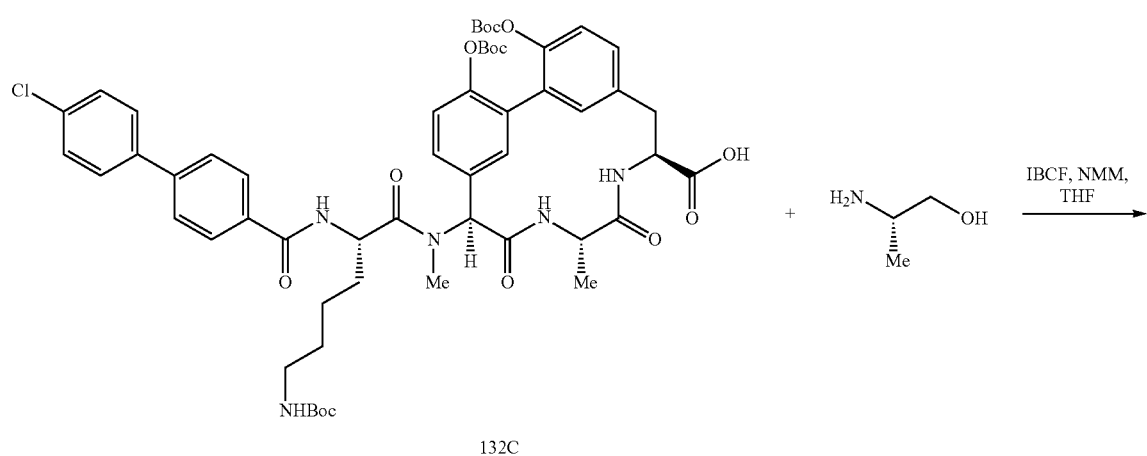
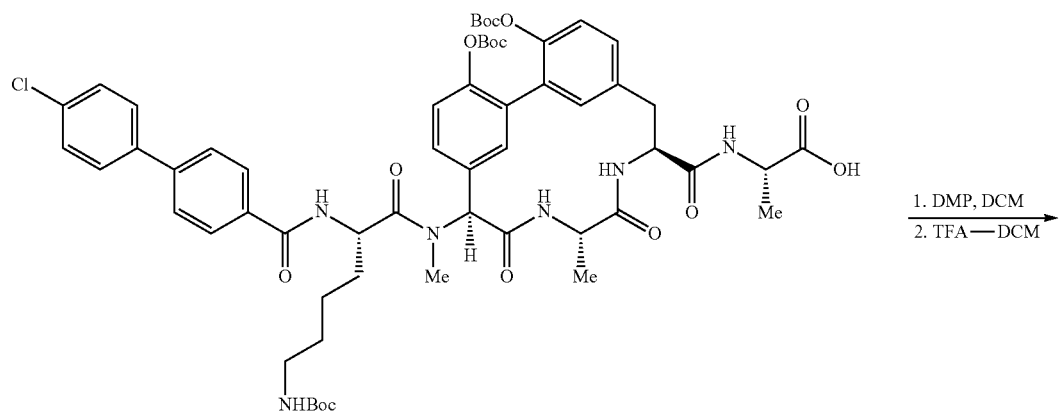

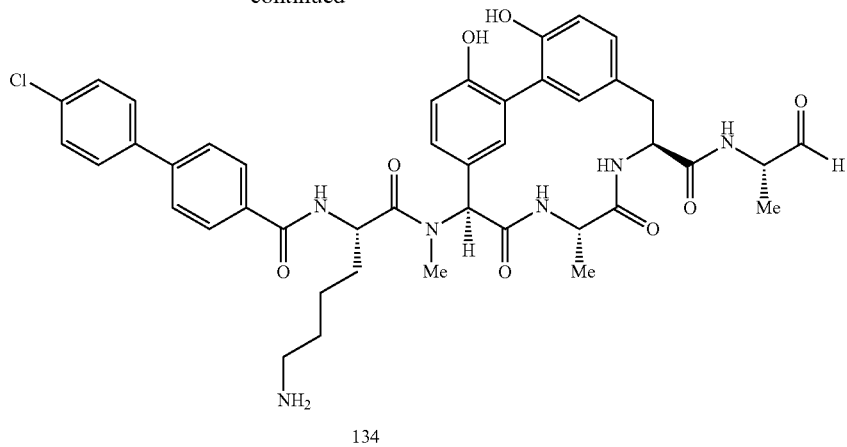

134

To a solution of Compound 132C (53 mg, 0.05 mmol) in anhydrous THF (2 mL) was added isobutyl chloroformate (10 µL, 0.075 mmol), N-methylmorpholine (30 µL, 0.25 mmol) and L-alaminol (8 mg, 0.1 mmol) by following the procedure described in Example 28 to afford Compound 134A. MS (ESI) for ($C_{58}H_{73}ClN_6O_{14}$): m/z 1113 (M+H)$^+$.

Compound 134A (55 mg, 0.05 mmol) was dissolved in DCM (5 mL) and Dess-Martin-Periodinane (106 mg, 0.25 mmol) was added. The resultant heterogeneous reaction mixture was stirred at room temperature for 2 h. After completion of the reaction (monitored by LCMS), the reaction mixture was filtered through a pad of celite and the celite bed was washed with DCM. The filtrate was washed with saturated NaHCO$_3$ solution and brine. The organic layer was dried over anhydrous Na$_2$SO$_4$ and solvent was removed under vacuum. The residue was purified by flash chromatography using 100% DCM to 20% MeOH/DCM to afford 40 mg (57%) of the desired product as white solid. MS (ESI) for ($C_{58}H_{72}ClN_6O_{14}$): m/z 1111 (M+H)$^+$.

Compound 134 was prepared by removing the Boc protecting groups using TFA in DCM by following the procedure described in Example 28. Data for Compound 134: MS (ESI) for ($C_{43}H_{47}ClN_6O_8$): m/z 829 (M+H$_2$O+H)$^+$.

Example 34

Preparation of Compound 135

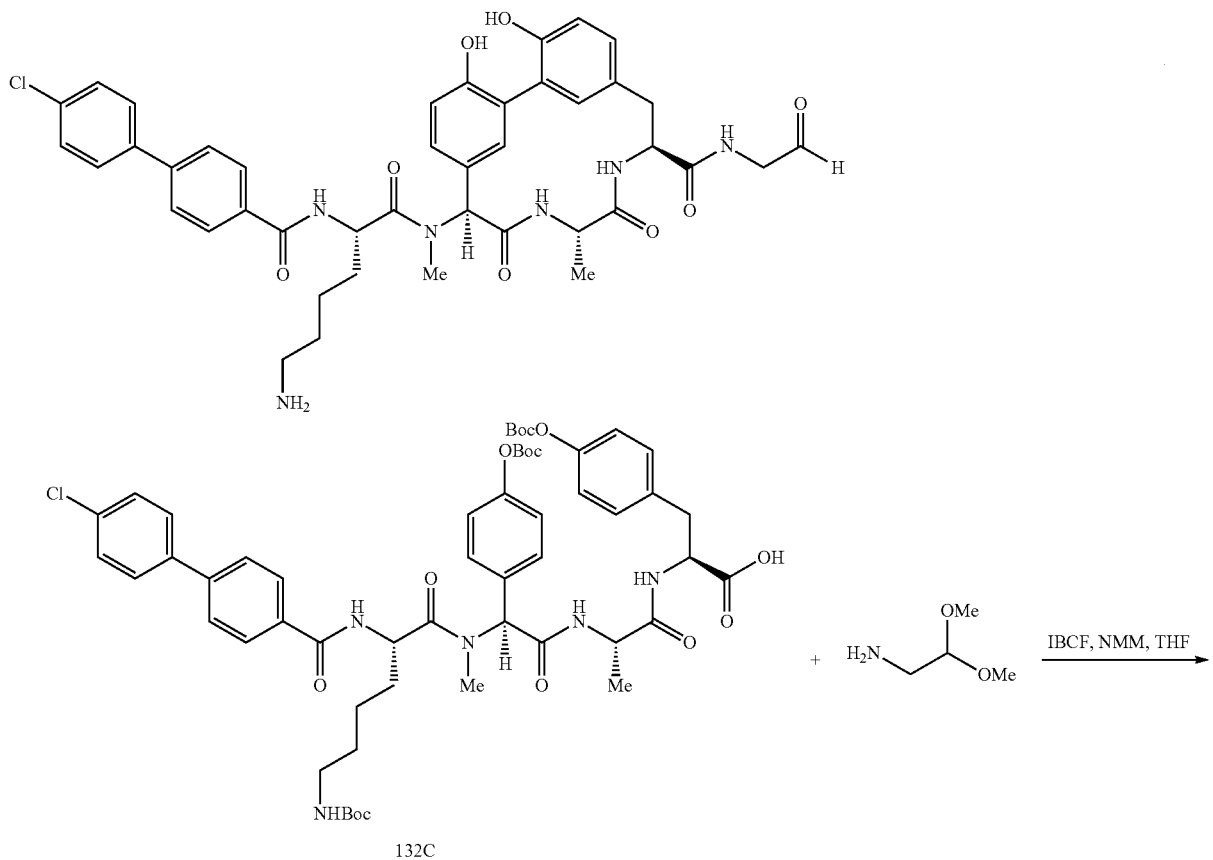

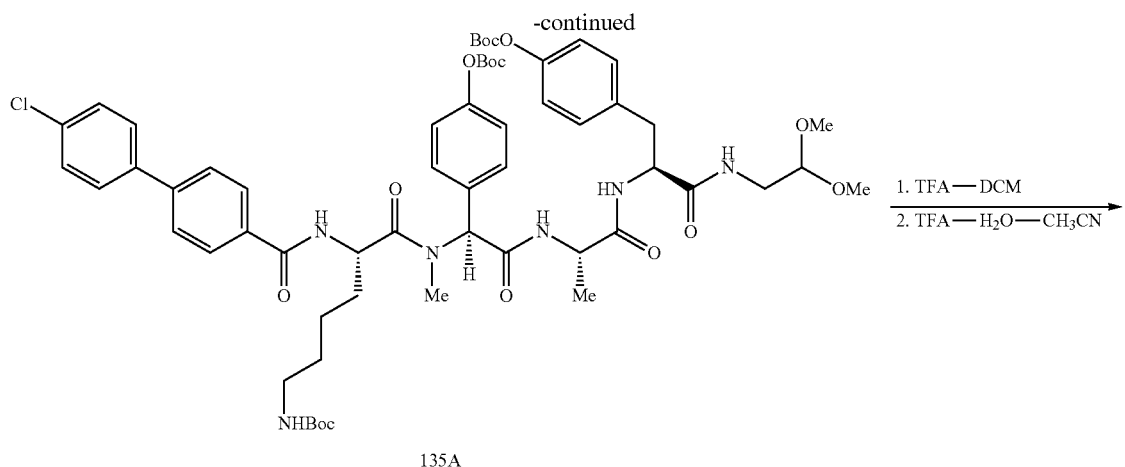

135A

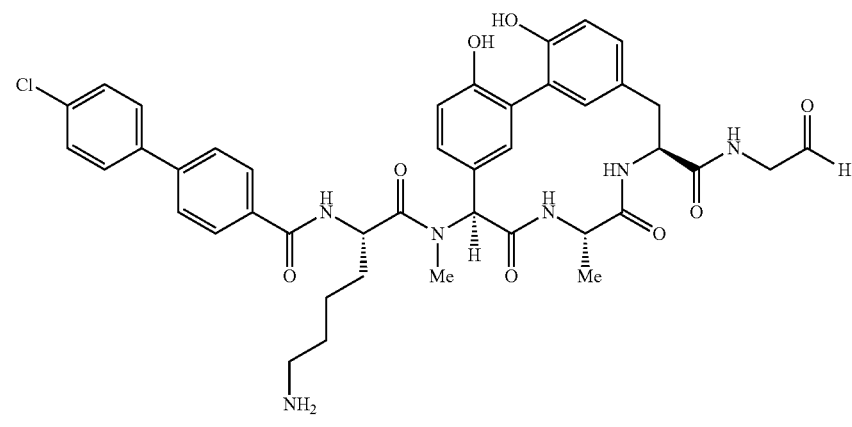

135

Compound 135A was prepared as described in Example 22 from a solution of Compound 132C (53 mg, 0.05 mmol) in anhydrous THF (2 mL), isobutyl chloroformate (10 μL, 0.075 mmol), N-methylmorpholine (30 μL, 0.25 mmol) and aminoacetaldehyde dimethylacetal (11 mg, 0.1 mmol). MS (ESI) for ($C_{59}H_{75}ClN_6O_{15}$): m/z 1142 (M+H)$^+$.

Compound 135 was prepared from Compound 135A by removing the Boc protecting groups using TFA in DCM and the solvent was removed under vacuum as described in Example 28. The residue was dissolved in 1:1:1 mixture of TFA-$H_2O$—$CH_3CN$ (2 mL) and stirred for 1 h to remove the acetal protecting groups. The material was purified by preparative HPLC using acetonitrile-water containing 0.05% TFA as mobile phase to afford Compound 135. MS (ESI) for ($C_{41}H_{43}ClN_6O_8$): m/z 815 (M+$H_2O$+H)$^+$.

Example 35

Preparation of Compound 136

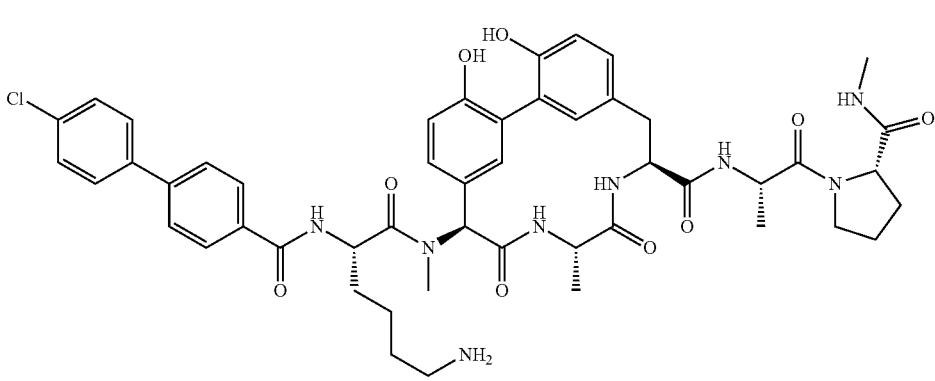

136

-continued
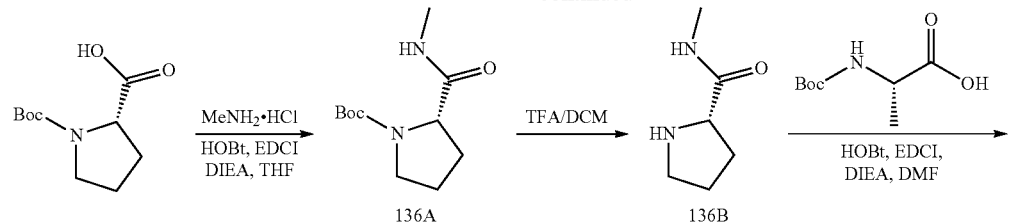
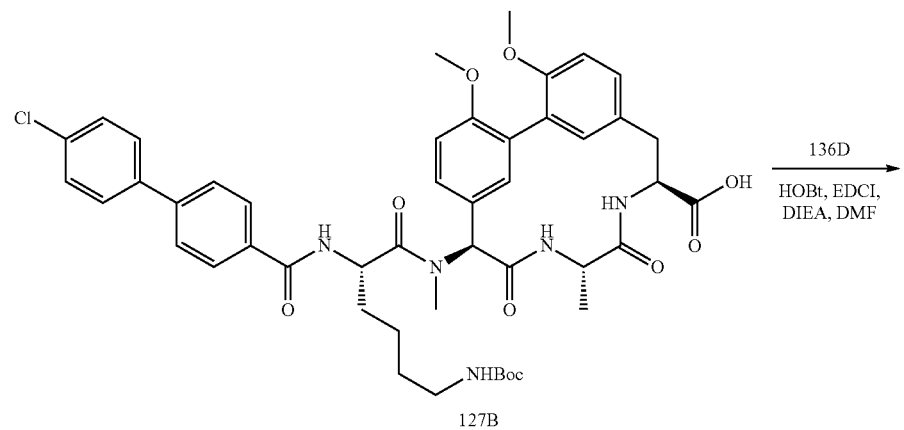
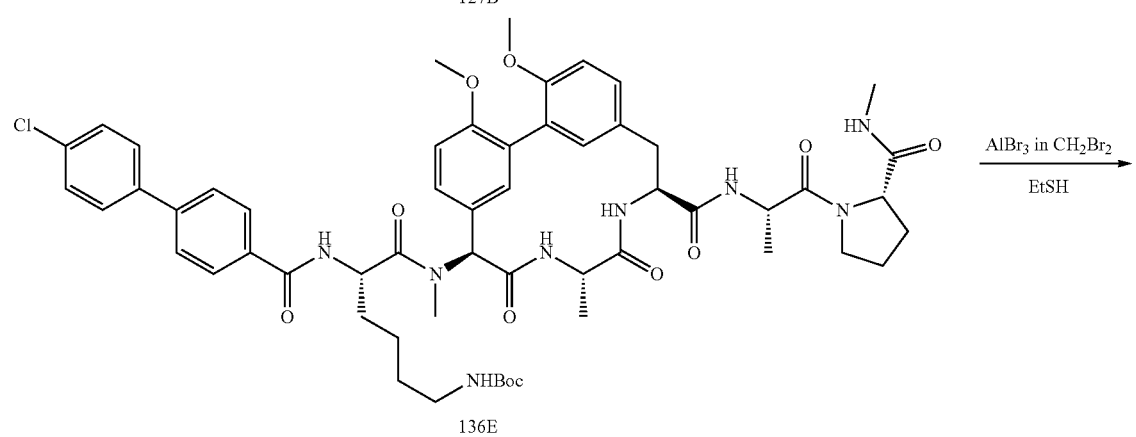
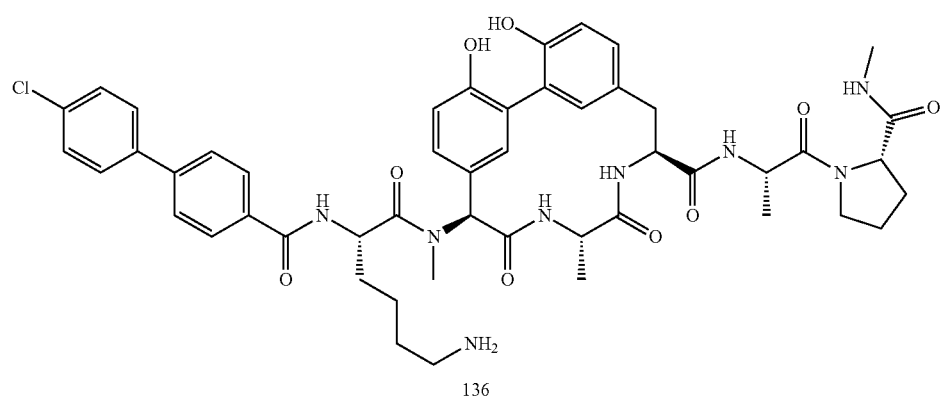

-continued

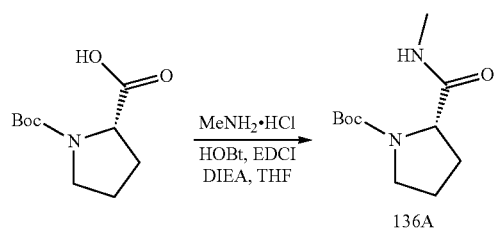

136A

To a solution of Boc-L-proline (4.0 g, 18.58 mmol) and methanamine hydrochloride (1.88 g, 27.88 mmol) in THF (30 mL) was added DIPEA (7.21 g, 55.75 mmol), HOBt (5.02 g, 37.17 mmol) and EDCI (7.12 g, 37.17 mmol) at 0° C. The reaction mixture was stirred at room temperature for 16 h, and then concentrated. The residue was purified by column silica gel (25-50% EtOAc in petroleum ether) to give Compound 136A (3.0 g, 71.4%) as a white solid. $^1$H NMR (400 MHz, CDCl$_3$) δ 4.23 (m, 1 H), 3.40 (m, 2 H), 2.78 (d, J=4.0 Hz, 3 H), 2.33 (m, 1 H), 1.85 (m, 3 H), 1.43 (s, 9 H).

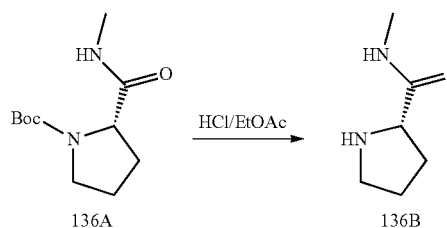

A solution of Compound 136A (3.0 g, 13.14 mmol) in HCl/EtOAc (20 mL) was stirred at 0° C. for 3 h. Solvent was removed and Compound 136B was used directly without further purification (2.16 g, 100%).

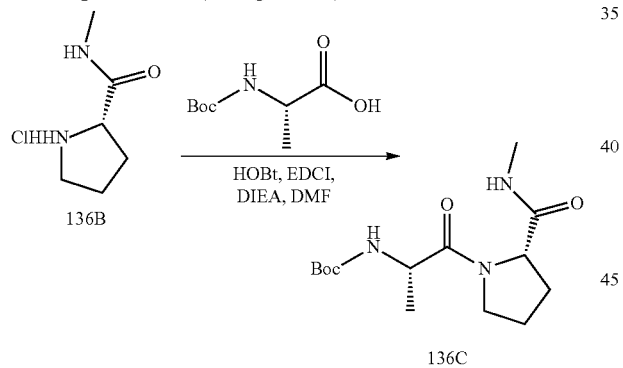

To a solution of (S)-2-((tert-butoxycarbonyl)amino)propanoic acid (2.5 g, 13.21 mmol) and Compound 136B (2.18 g, 13.21 mmol) in DMF (10 mL) was added DIPEA (2.56 g, 19.82 mmol), then HOBt (2.68 g, 19.82 mmol) and EDCI (3.80 g, 19.82 mmol) at 0° C. The reaction mixture was stirred at room temperature for 16 h, and then was poured into water (50 mL) and extracted with DCM (100 mL×3). The combined DCM layer was washed with brine (50 mL×3), dried over Na$_2$SO$_4$, and concentrated. The residue was purified by column silica gel (3-5% MeOH in DCM) to give Compound 136C (2.8 g, 70.8%) as a white solid. MS (ESI): m/z 321.9 (M+Na)$^+$.

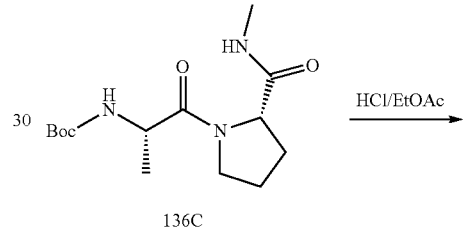

136C

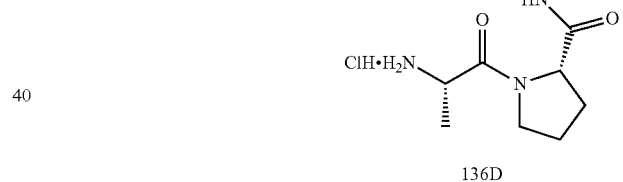

136D

A solution of Compound 136C (500 mg, 1.67 mmol) in HCl/EtOAc (20 mL) was stirred at 0° C. for 3 h. The solvent was removed and the residue, Compound 136D (394 mg, 100%), was used directly without further purification.

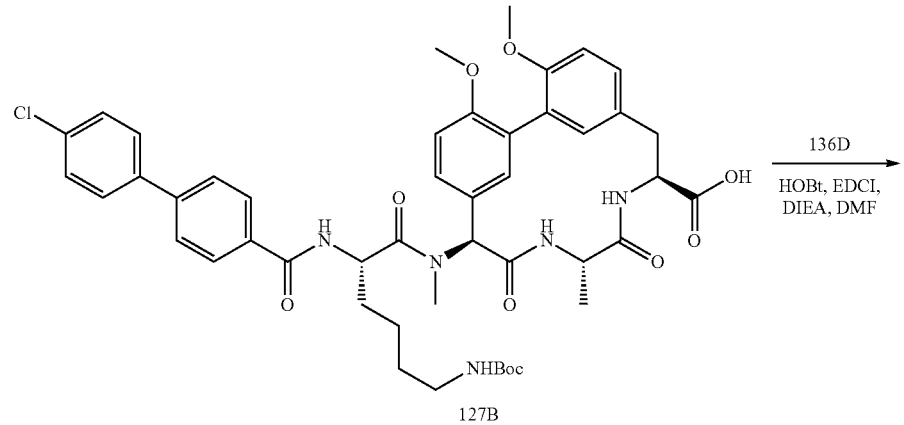

127B

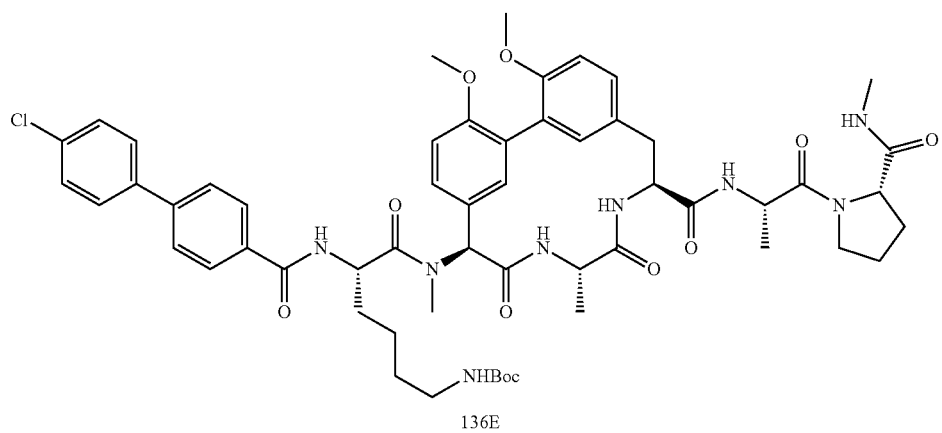

136E

To a solution of Compound 127B (0.25 g, 0.283 mmol) and Compound 136D (0.2 g, 0.848 mmol) in DMF (5 mL) was added DIPEA (0.11 g, 0.848 mmol), then HOBt (76.4 mg, 0.565 mmol) and EDCI (108.3 mg, 0.565 mmol) at 0° C. The reaction mixture was stirred at room temperature for 14 h, and then poured into water (40 mL). The solid was collected by filtration and washed with water (10 mL×3). The solid was dissolved with DCM (50 mL), dried over Na$_2$SO$_4$, concentrated and purified by silica gel column (3-5% MeOH in DCM) to give Compound 136E (0.22 g, 73.0%) as a white solid. MS (ESI): m/z 1087.7 (M+Na)$^+$.

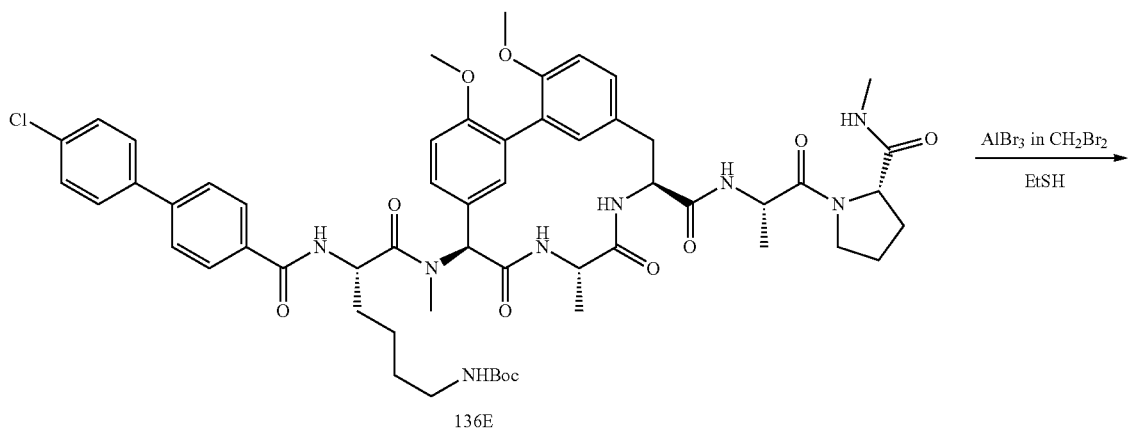

136E

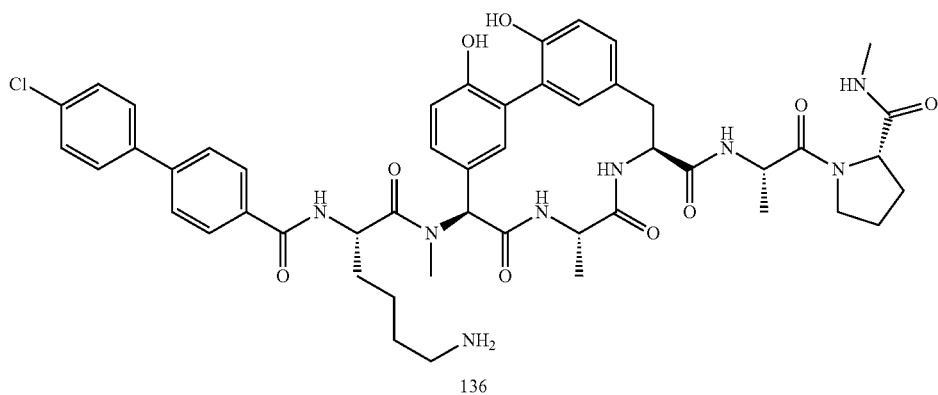

136

To a solution of Compound 136E (0.21 g, 0.197 mol) in EtSH (3 mL) at 0° C. was added a solution of AlBr$_3$ in dibromomethane (1M, 1.97 mL, 1.97 mmol). The reaction mixture was stirred at room temperature for 10 h and the solvent was removed. The residue was dissolved in DCM (2 mL), and quenched with MeOH (0.5 mL) at 0° C. Solvents were removed in vacuo and the residue was purified by prep-HPLC (with formic acid as an additive) to give Compound 136 (84 mg, 45.4%) as a white solid. $^1$H NMR (400 MHz, CD$_3$OD) δ 8.50 (s, 1H), 7.78 (d, J=8.0 Hz, 2H), 7.61 (d, J=8.0 Hz, 2H), 7.40-7.49 (m, 4H), 6.96 (d, J=6.0 Hz, 1H), 6.73-6.93 (m, 6H), 4.98-5.01 (m, 3H), 4.80 (m, 4H), 4.63-4.65 (m, 1H), 4.35-4.38 (m, 1H), 3.74-3.77 (m, 1H), 3.63-3.66 (m, 1H), 2.94-3.12 (m, 7H), 2.71 (s, 3H), 1.189-1.98 (m, 6H), 1.71-1.72 (m, 1H), 1.34 (d, J=6.8 Hz, 3H). MS (ESI): m/z 937.3 (M+H)$^+$.

Example 36

Preparation of Compound 137

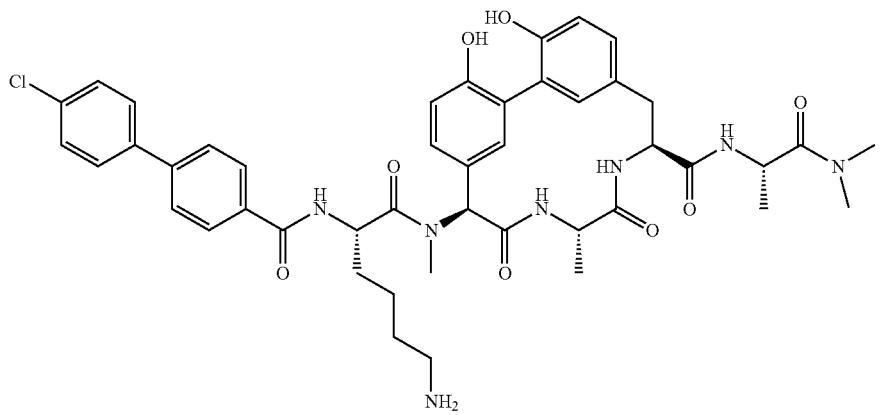

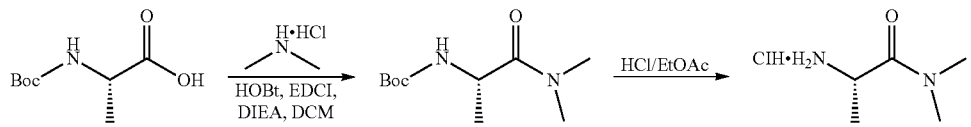

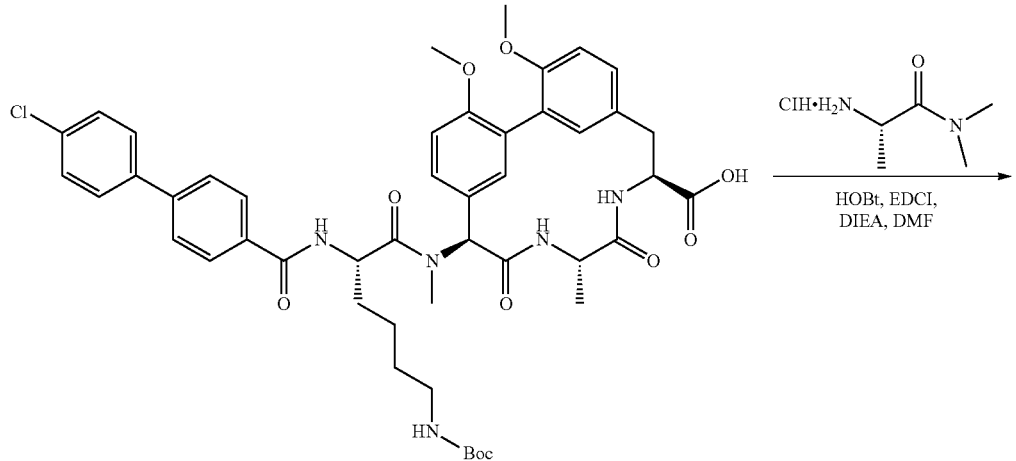

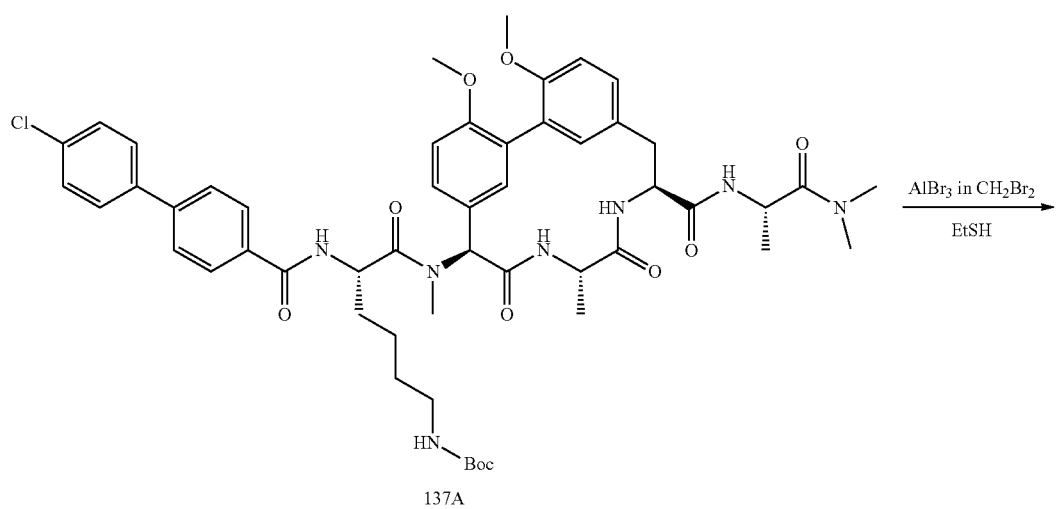

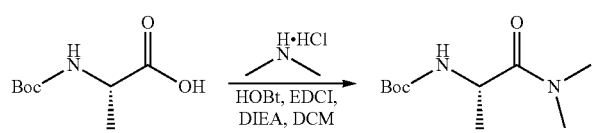

To a solution of Boc-L-alanine (2.32 g, 12.26 mmol) in DCM (20 mL) was added dimethylamine hydrochloride (2 g, 24.5 mmol) and DIPEA (3.1 g, 24.53 mmol). The solution was kept at 0° C. for 10 min, then HOBt (3.31 g, 24.5 mmol) and EDCI (4.6 g, 24.5 mmol) were added. The mixture was stirred at room temperature for 10 h, and then poured into water (40 mL) and extracted with DCM (100 mL×3). The extracts was washed with brine (50 mL), dried over anhydrous $Na_2SO_4$, and filtered. The filtrate was concentrated under reduced pressure. The residue was purified by silica gel column (10-20% EtOAc in petroleum ether) to give Boc-L-alanine N,N-dimethyl amide as a colorless oil (1.1 g, 42%). $^1$H NMR (400 MHz, $CDCl_3$) δ 8.48 (s, 1 H), 5.51 (brs, 1H), 4.56-4.63 (m, 1H), 3.03 (s, 3H), 2.93 (s, 3 H), 1.39 (s, 9H), 1.26 (d, J=6.8, 3 H).

To a solution of Boc-L-alanine N,N-dimethyl amide (250 mg, 1.1 mmol) in EtOAc (1 mL) was added HCl/EtOAc (4M, 3 mL) at 0° C. The solution was kept at room temperature for 30 min, and then concentrated under reduced pressure to give L-alanine N,N-dimethyl amide hydrochloride as a white solid (176 mg, 100%).

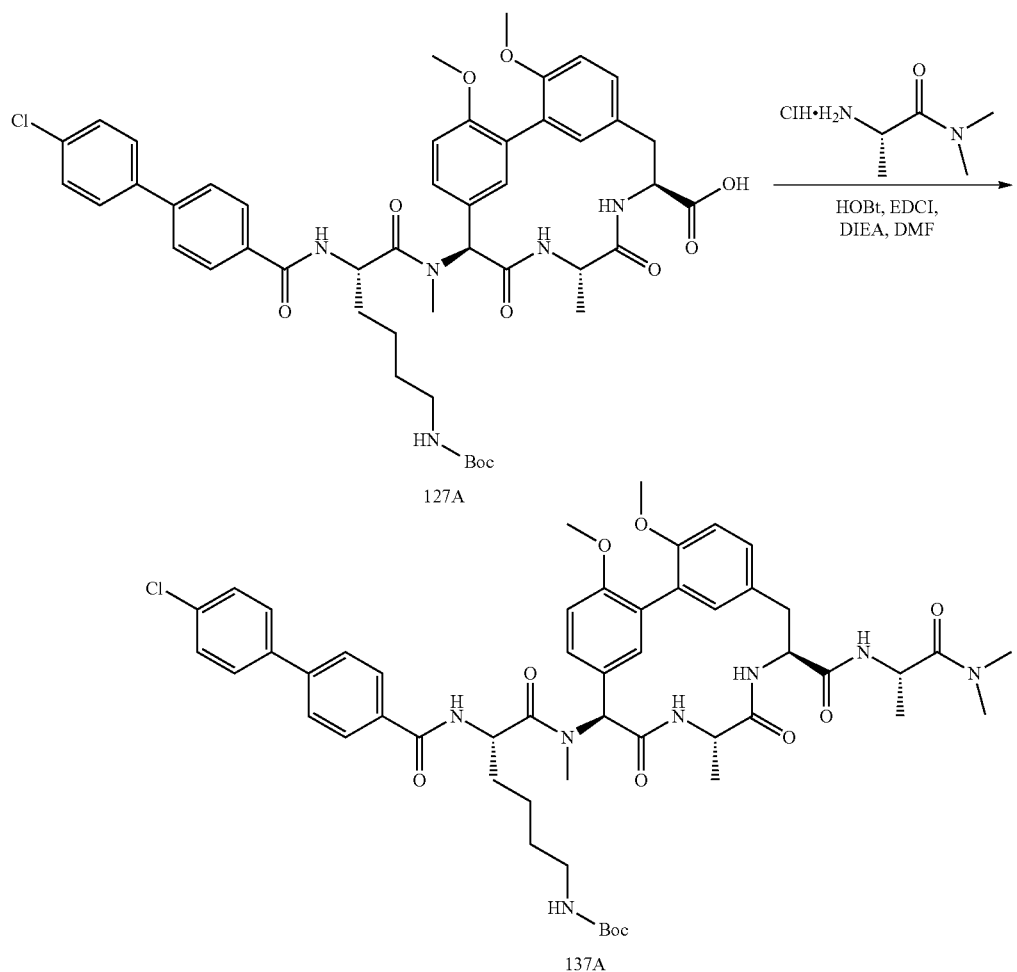

DIPEA (84 mg, 0.672 mmol) and L-alanine N,N-dimethyl amide hydrochloride (130 mg, 1.15 mmol) was added to a stirred suspension of Compound 127B (200 mg, 0.188 mmol) in DMF (2 mL). The mixture was kept at 0° C. for 10 min and HOBt (88 mg, 0.672 mmol) and EDCI (128 mg, 0.672 mmol) were added. After the mixture was stirred at room temperature for 6 h, it was poured into water (10 mL). The solid was collected by filtration and washed with water (3 mL×2). The solid was dissolved in DCM (30 mL), dried over $Na_2SO_4$, concentrated, and purified by prep-TLC (DCM/MeOH=20/1) to give Compound 137A (200 mg, 90%). MS (ESI): m/z 981.6 $(M+H)^+$.

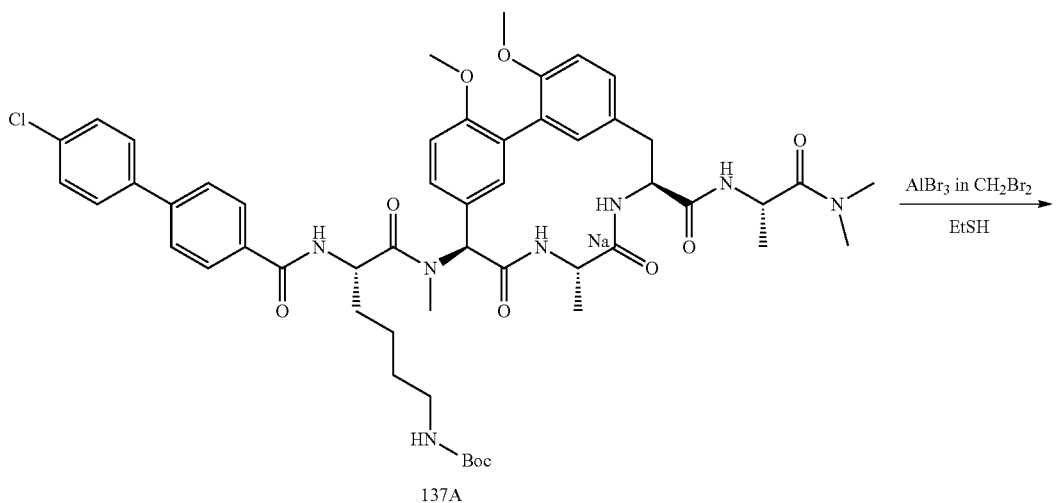

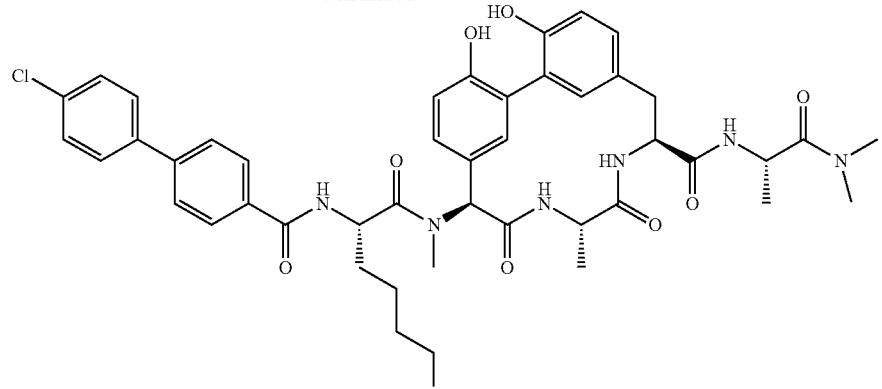

137

To a solution of Compound 137A (200 mg, 0.203 mmol) in EtSH (3 mL) was added AlBr₃ (1M, 3.05 mL, 3.05 mmol). The solution was kept at 0° C. for 10 min, and then at room temperature for 16 h. The reaction mixture was concentrated and the residue was purified by prep-HPLC (with formic acid as an additive) to give Compound 137 as a white solid (70 mg, 40%). ¹H NMR (400 MHz, Methanol-d₄) δ 8.48 (s, 1 H), 7.73 (d, J=7.2 Hz, 2H), 7.57 (d, J=8 Hz, 2H), 7.44-7.38 (m, 4H), 6.97 (d, J=8 Hz, 1 H), 6.89-6.67 (m, 6 H), 4.99-4.96 (m, 2 H), 4.84-4.75 (m, 4 H), 3.19-3.11 (m, 1 H), 3.06 (s, 3 H), 3.03-2.91 (m, 10 H), 2.00-1.98 (m, 2 H), 1.72 (br, 2 H), 1.37 (d, J=6.8 Hz, 3 H), 1.29 (d, J=6.8 Hz, 3 H). MS (ESI): m/z 854.5 (M+H)⁺.

Example 37

Preparation of Compound 138

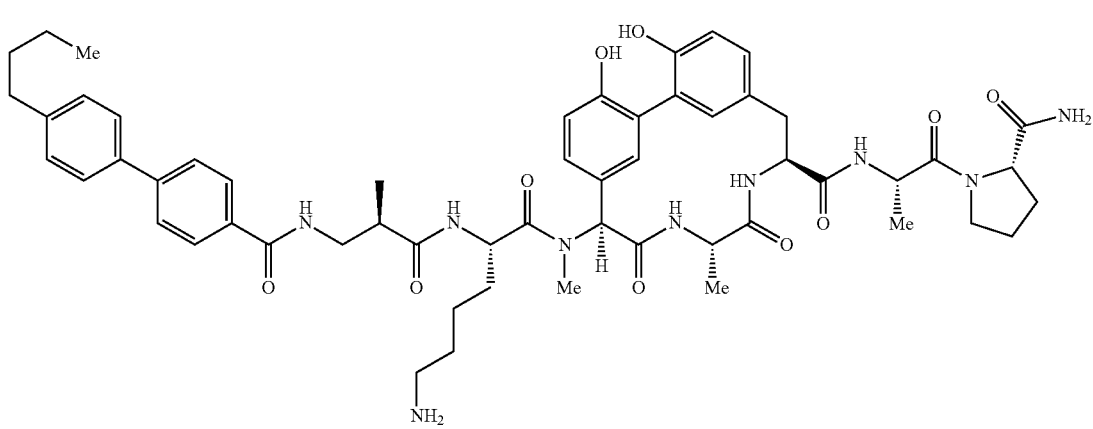

138

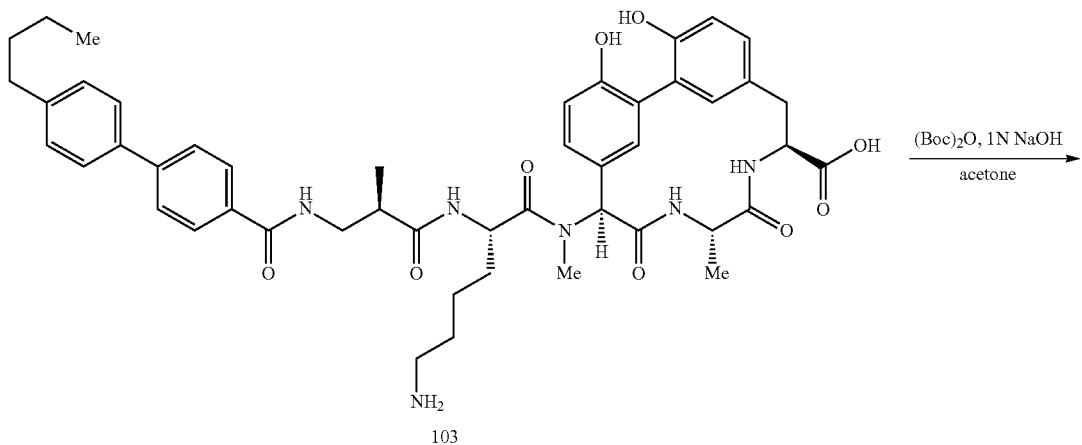

103

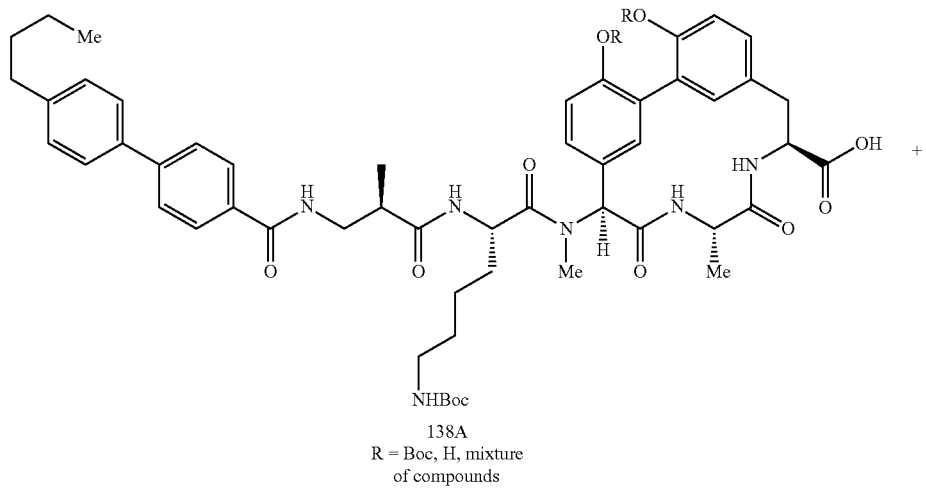

138A
R = Boc, H, mixture
of compounds

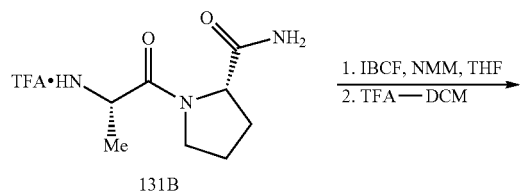

131B

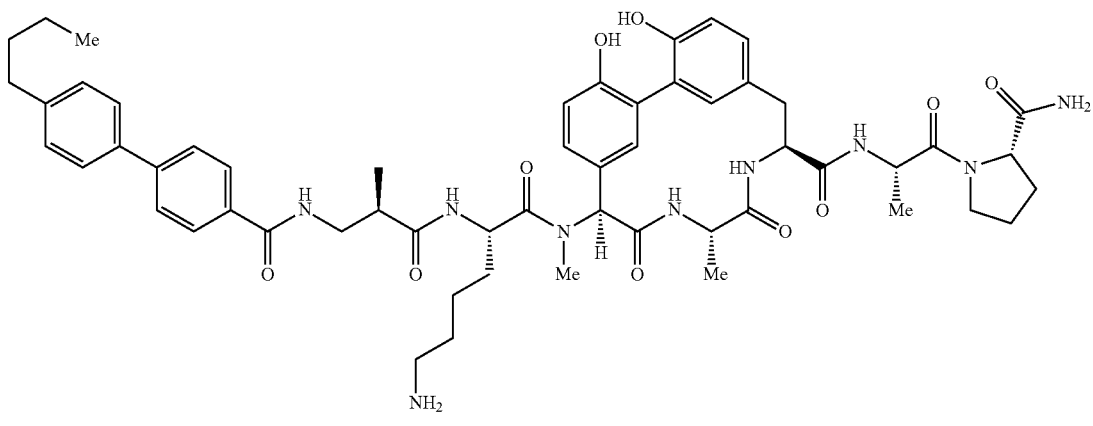

138

To a solution of Compound 103 (65 mg, 0.075 mmol) in acetone-H$_2$O (1:1, 1 mL) was added 1M NaOH (0.36 mL, 0.36 mmol) and (Boc)$_2$O (86 μL, 0.36 mmol). The reaction mixture was stirred at room temperature overnight. The acetone was removed and the mixture acidified with 1M HCl. The resultant white solid was filtered and dried to afford Compound 138A (74 mg, 92%) as a mixture of bis-Boc protected (mixture with either one of the phenols protected) along with a small amount of mono-Boc protected. MS (ESI) for bis-Boc (C$_{58}$H$_{74}$N$_6$O$_{13}$): m/z 1063 (M+H)$^+$; mono-Boc for (C$_{53}$H$_{66}$N$_6$O$_{11}$);): m/z 963 (M+H)$^+$.

Compound 138 was prepared from Compound 138A (21 mg, 0.02 mmol) in anhydrous THF (1 mL), isobutyl chloroformate (4.0 μL, 0.03 mmol), N-methyl morpholine (11 μL, 0.1 mmol) and Compound 131B (12 mg, 0.04 mmol) following the procedure described for Example 30 and subsequent hydrolysis of the Boc-protecting groups as described in Example 28. MS (ESI) for (C$_{56}$H$_{71}$N$_9$O$_{10}$): m/z 1030 (M+H)$^+$.

Example 38
Synthesis of Compound 201
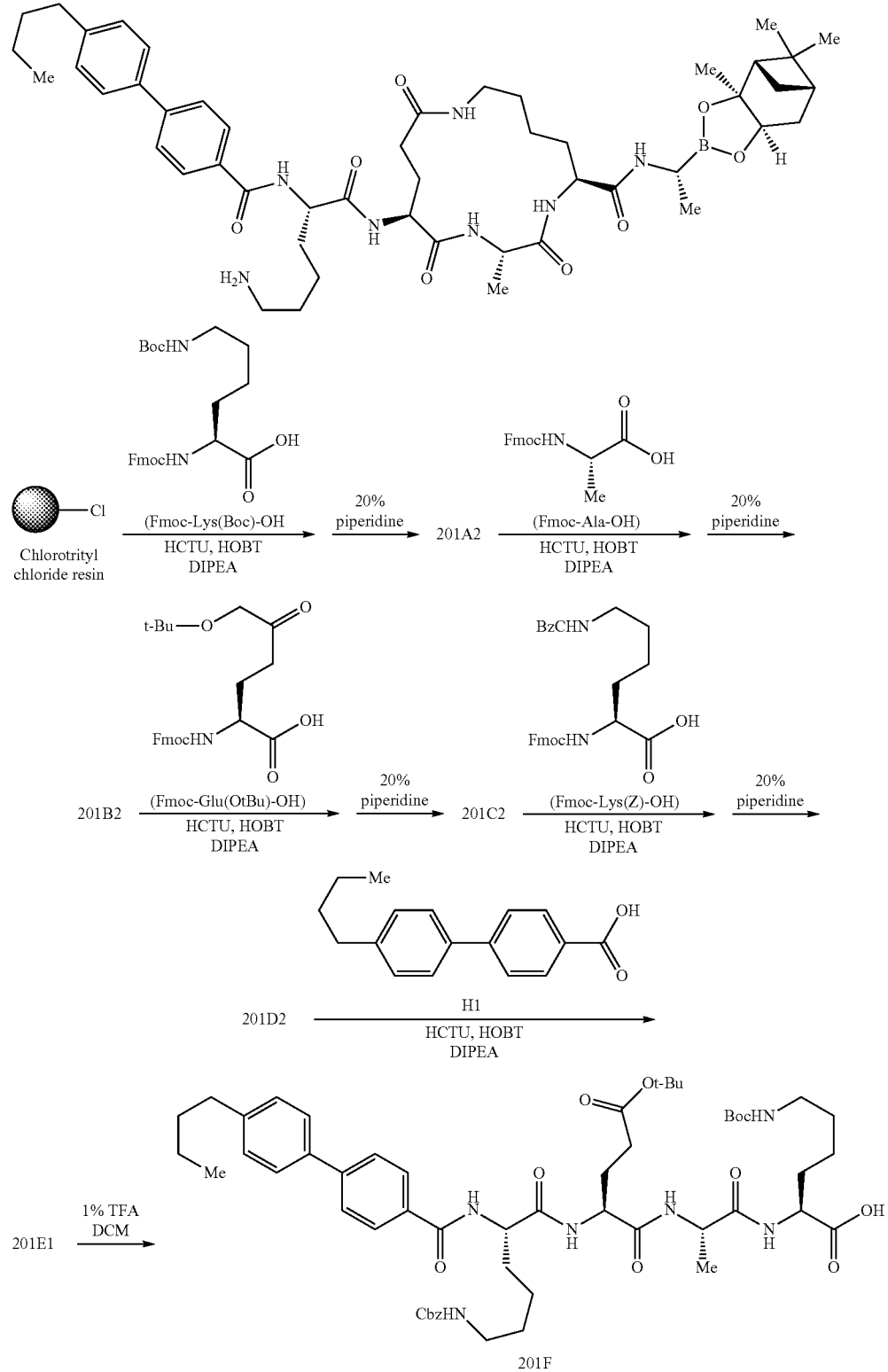

Synthesis of Compound 201A2: The compound was prepared according to General Method 1 from chlorotrityl chloride resin (1 g, 1 mmol) and Fmoc-Lys(Boc)-OH (0.97 g, 2 mmol) and DIPEA (258 mg, 2 mmol) to afford Compound 201A2.

Synthesis of Compound 201F: The compound was prepared according to General Methods 2-3 from Compound 201A2 to afford Compound 201F (800 mg, 80%). MS (ESI) m/z 1001.4 (M+H)+.

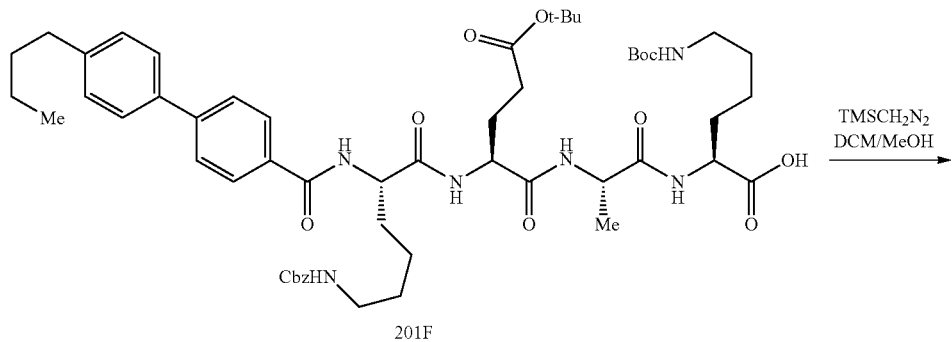

Synthesis of 201G: To a solution of Compound 201F (800 mg, 0.8 mmol) in DCM (8 mL) and MeOH (2 mL) was added TMSCH$_2$N$_2$ (0.88 mmol, 2 M in ether) dropwise over 15 mins at 0° C. The reaction mixture was stirred at 0° C. for 30 mins. The operation was repeated until no starting material was detected by TLC, whereupon 0.5 mL of water was added and the solvent was removed by vacumm to give a residue. The residue was purified by column chromatography to give Compound 201G (475 mg, 59%). MS (ESI) m/z 1015.4 (M+H)+.

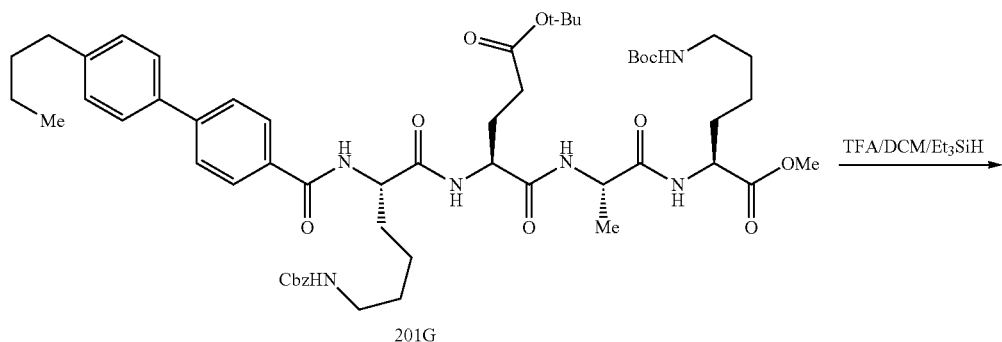

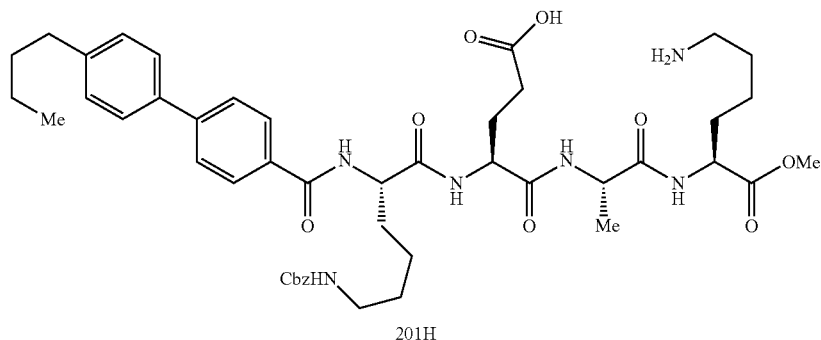

201H

Synthesis of Compound 201H: A solution of Compound 201G (950 mg, 0.937 mmol) in TFA (3 mL), DCM (2.7 mL) and Et₃SiH (0.3 mL) was stirred at 20° C. for 1 hr. The reaction solution was concentrated to give Compound 201H (750 mg, 93%). MS (ESI) m/z 1015.4 (M+H)⁺.

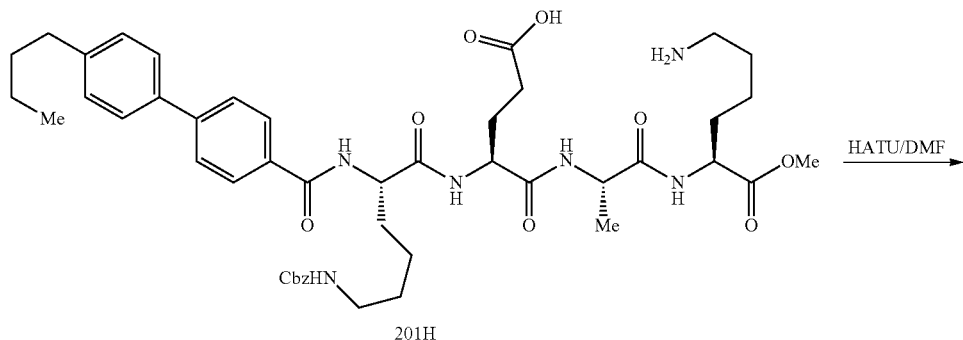

201H

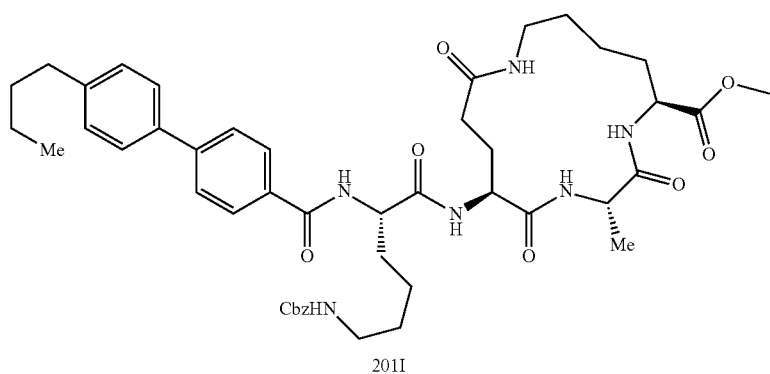

201I

Synthesis of Compound 201I: To a solution of Compound 201H (100 mg, 0.11 mmol) in DMF (20 mL) was added HATU (83 mg, 0.2 mmol) and DIPEA (52 mg, 0.4 mmol). The mixture was stirred at 20° C. for 1 h at which time no starting material was detected by LCMS. The mixture was diluted with water (80 mL) until a solid precipitated. After filtration, the filter cake was collected and dried to give Compound 201I, used without further purification (100 mg crude). MS (ESI) m/z 841.3 (M+H)⁺.

305
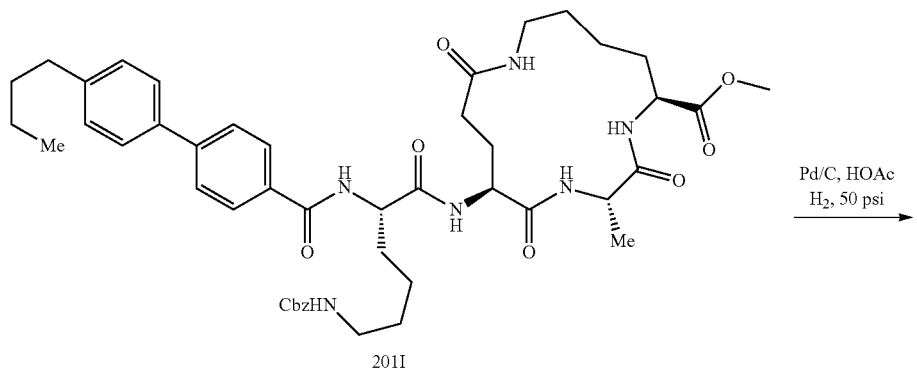
201I
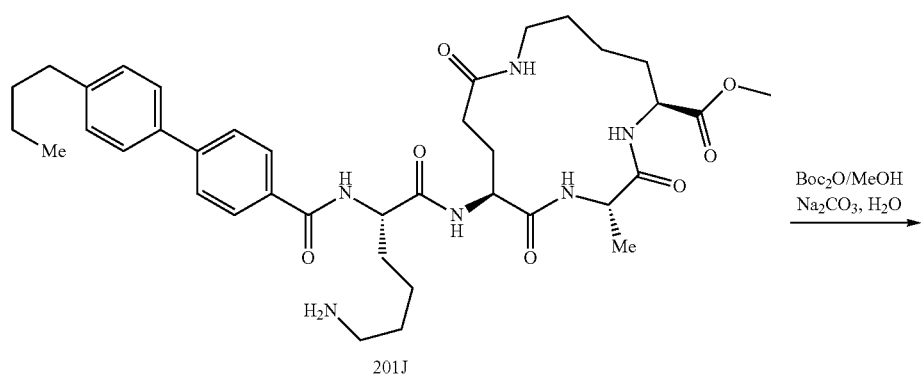
201J
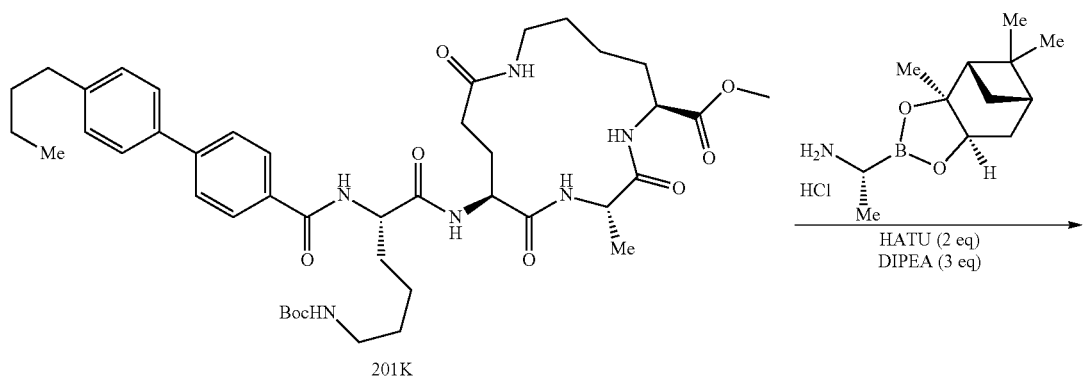
201K
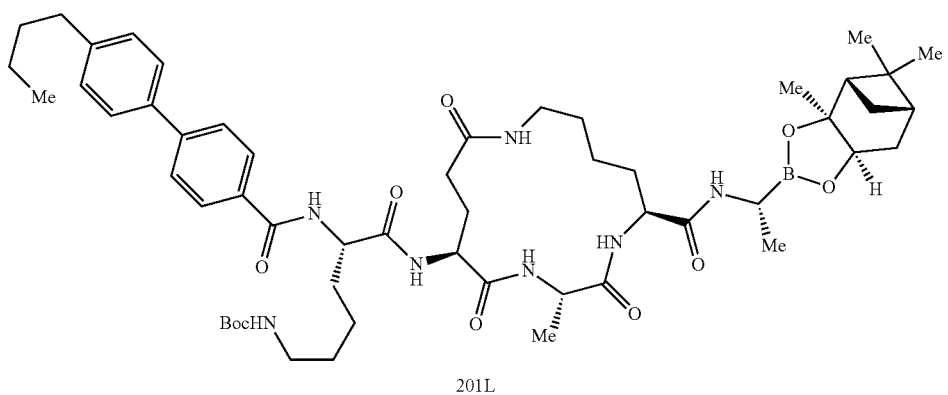
201L

Synthesis of Compound 201L: To a solution of Compound 201I (110 mg, 0.131 mmol) in AcOH (10 mL) was added Pd/C (20 mg). The reaction mixture was stirred under $H_2$ (50 psi). After LCMS showed the reaction was completed, the reaction mixture was filtered and concentrated to give Compound 201J. The product was used in the next step without any further purification. MS (ESI) m/z 707.4 (M+H)$^+$.

To a solution of Compound 201J (110 mg, crude) in MeOH (10 mL) was added saturated $Na_2CO_3$ (2 mL) and $Boc_2O$ (3 drops). The reaction mixture was stirred at reflux overnight. After LCMS showed the reaction was complete, 0.5M HCl was added until pH=7. The solvent was evaporated under $N_2$ and the residue was washed with PE to give Compound 201K which was used in the next step without any further purification. MS (ESI) m/z 793.5 (M+H)$^+$.

To Compound 201K (used crude from the previous reaction), HATU (33.4 mg, 0.088 mmol), and (R)-BoroAla-(+)-Pinanediol (17 mg, 0.066 mmol) in a flask in an ice bath was added DCM (2 mL), DMF (4 mL) and DMSO (4 mL). To the mixture was added DIPEA (17 mg, 0.132 mmol). After ELSD showed the reaction was complete, water (30 mL) was added. The resulting mixture was extracted with DCM (30 mL×2). The combined organic layers were concentrated. The crude product was dissolved in DMSO (2.5 mL) and purified by prep-HPLC to give Compound 201L (15 mg, 32% over 3 steps from Compound 201I).

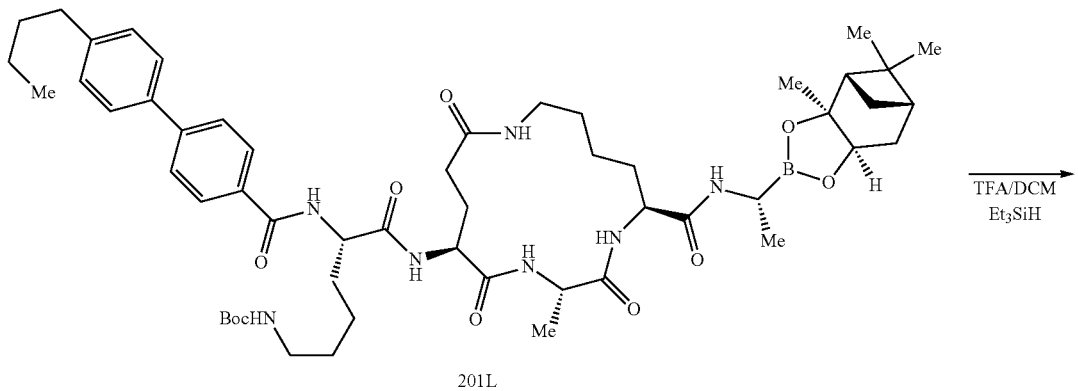

201L

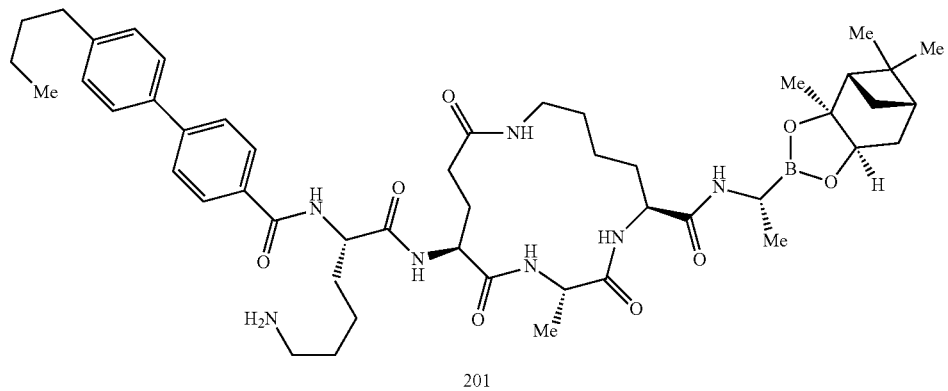

201

Synthesis of Compound 201: A solution of Compound 201L (50 mg, 0.05 mmol) in TFA:DCM:triethylsilane (50:45:5) (2 mL) was stirred at room temperature for 1 hr. The reaction solution was concentrated. The crude residue was taken up in DMSO and purified to give Compound 201 (36 mg, 80%). MS (ESI) m/z 898.8 (M+H)+.
Example 39
Synthesis of Compound 202
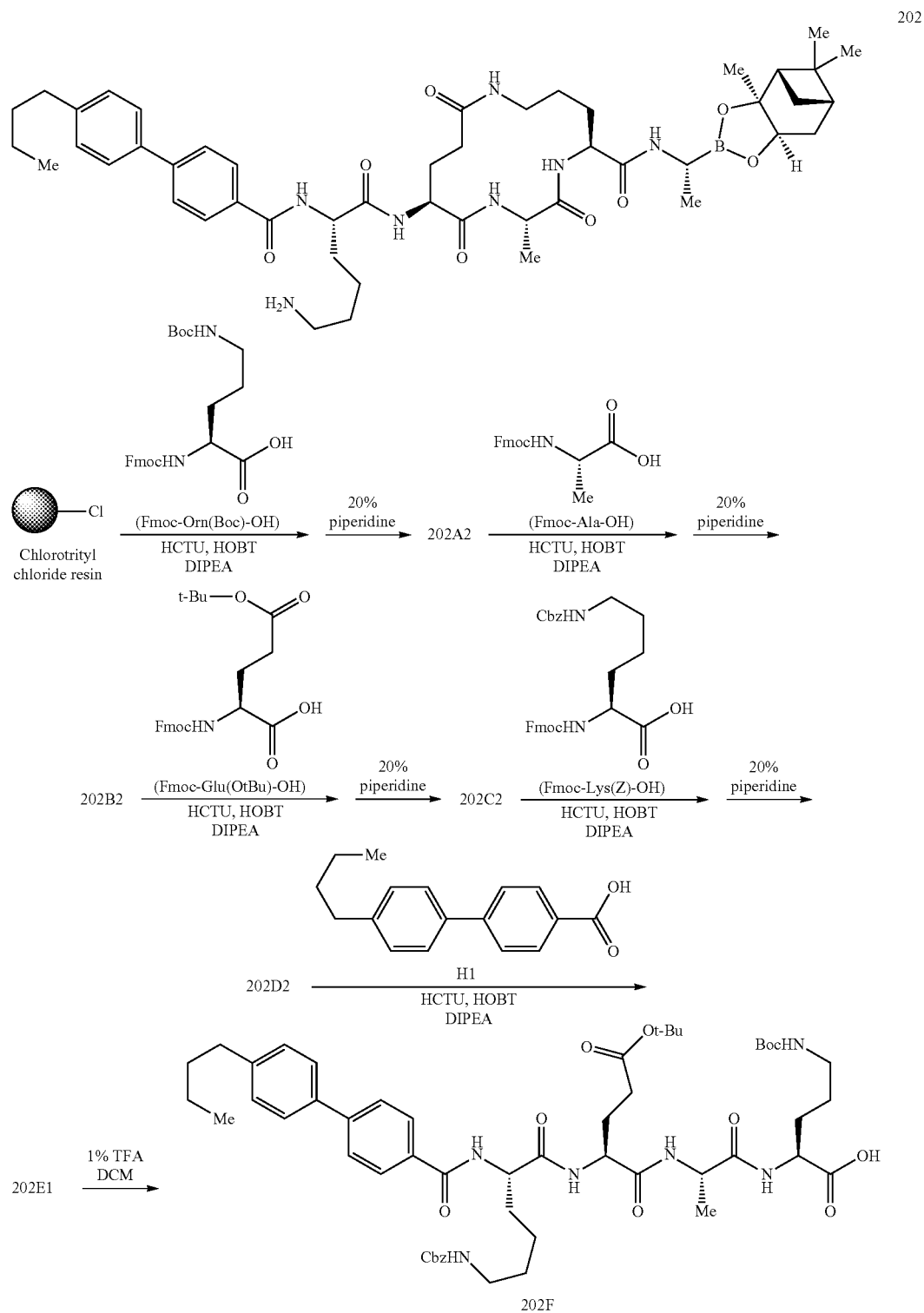

Synthesis of Compound 202A2: The compound was prepared according to General Method 1 from chlorotrityl chloride resin (5 g, 5 mmol) and Fmoc-Orn(Boc)-OH (6.8 g, 15 mmol) and DIPEA (1.94 g, 15 mmol) to afford Compound 202A2.

Synthesis of Compound 202F: This compound was prepared according to General Methods 2-3 from Compound 202A2 to afford Compound 202F (3.8 g, 96%).

mL) was added TMSCH$_2$N$_2$ (0.22 mmol, 1 M in ether) dropwise over 15 mins at 0° C. The reaction mixture was stirred at 0° C. for 30 mins. The operation was repeated until no starting material was detected by TLC, whereupon 0.5 mL of water was added and the solvent was removed by vacumm to give a residue. The residue was purified by column chromatography to give Compound 202G (89 mg, 59%). MS (ESI) m/z 1001.4 (M+H)$^+$.

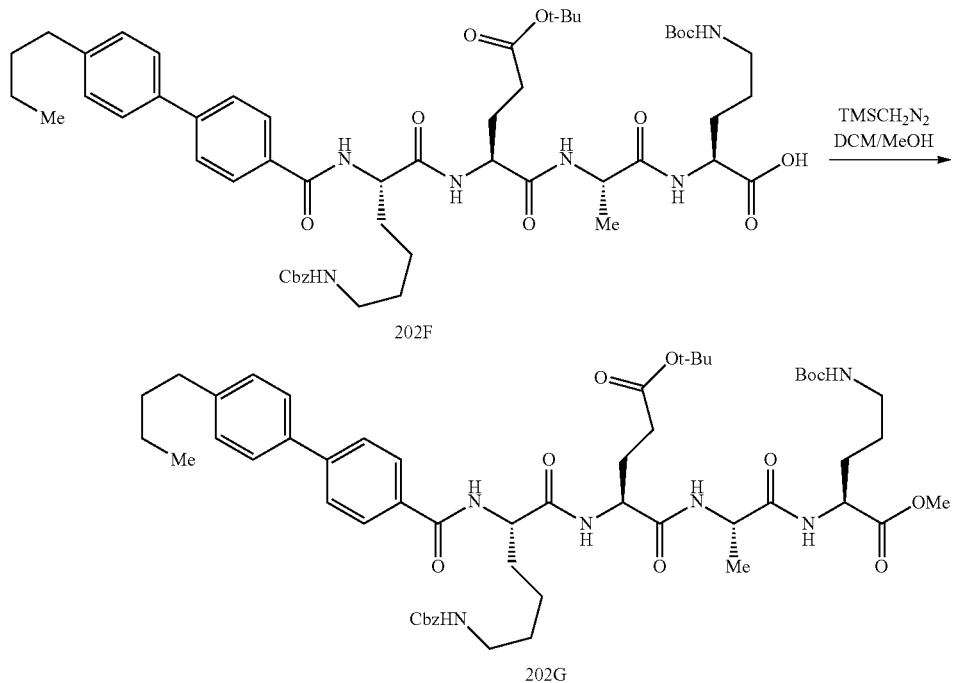

Synthesis of Compound 202G: To a solution of Compound 202F (200 mg, 0.20 mmol) in DCM (4 mL) and MeOH (1

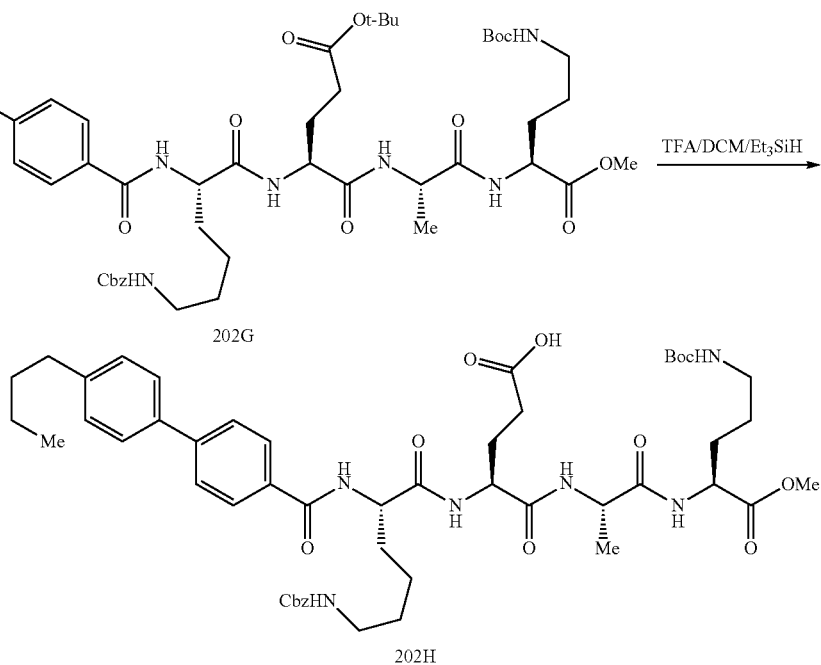

Synthesis of Compound 202H: A solution of Compound 202G (1.0 g, 1.0 mmol) in TFA (10 mL), DCM (9 mL) and Et₃SiH (1 mL) was stirred at 20° C. for 1 hr. The reaction solution was then concentrated to give Compound 202H (761 mg, 90%).

The mixture was stirred at 20° C. for 1 h at which time no starting material was detected by LCMS. The mixture was diluted with water (80 mL) until a solid precipitated. The solid was removed by filtration. The filter cake was collected and

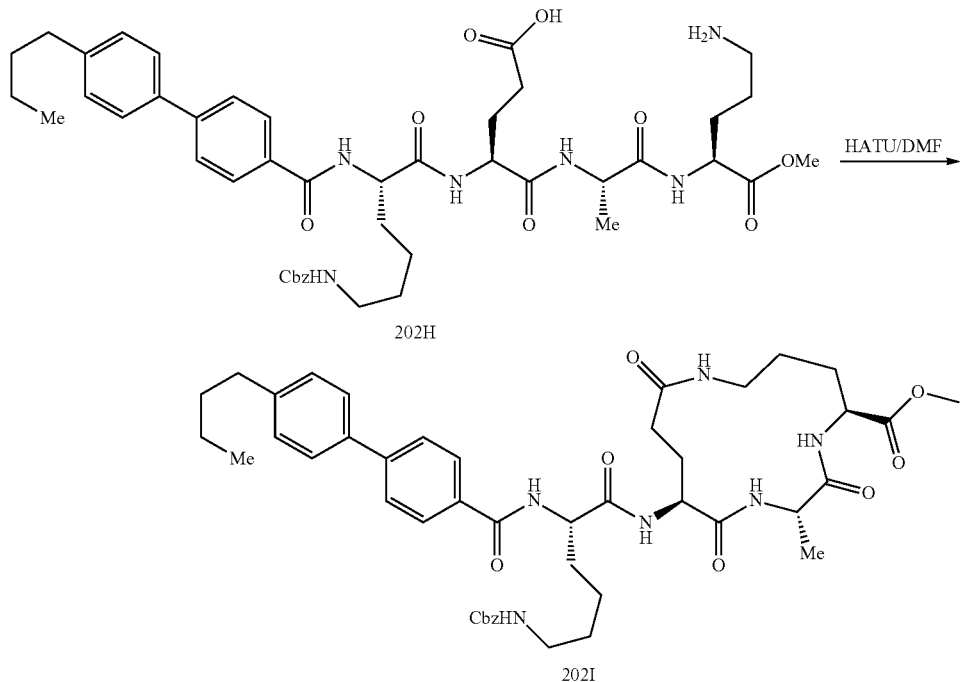

Synthesis of Compound 202I: To a solution of Compound 202H (100 mg, 0.12 mmol) in DMF (20 mL) was added HATU (83 mg, 0.2 mmol) and DIPEA (52 mg, 0.4 mmol).

dried to give Compound 202I, which was used in the next step without further purification (100 mg crude). MS (ESI) m/z 827.4 (M+H)⁺.

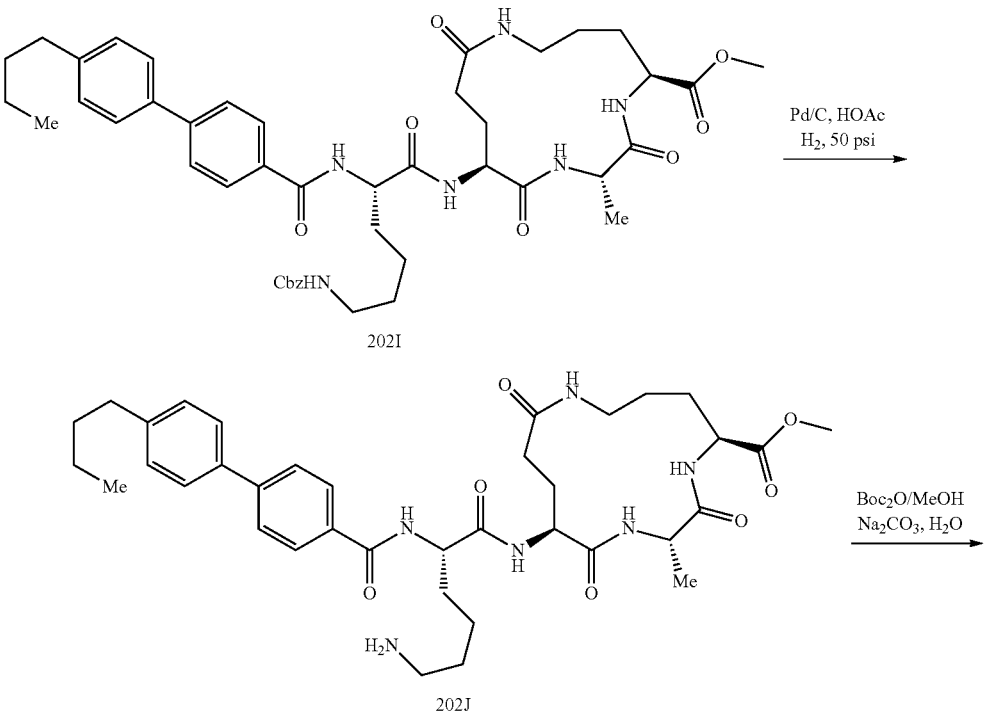

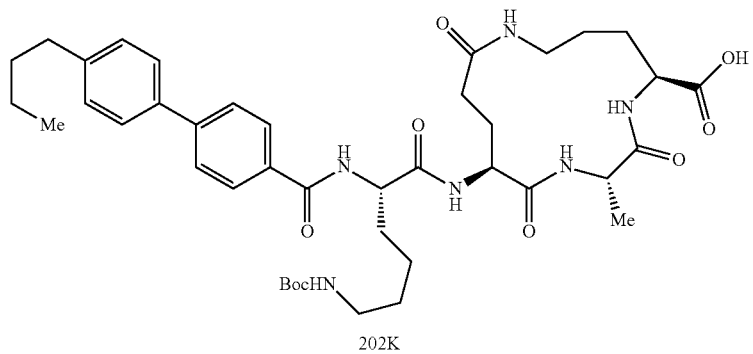
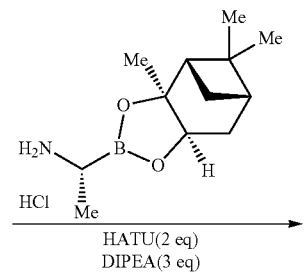

202K

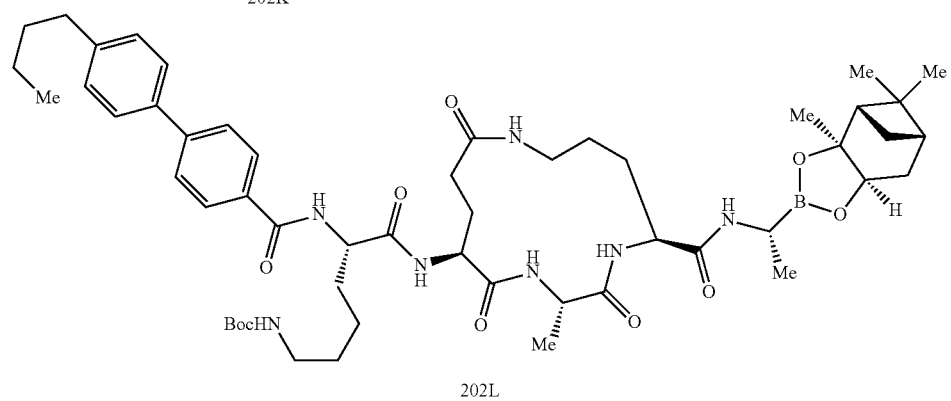

202L

Synthesis of Compound 202L: A solution of Compound 202I (100 mg, 0.121 mmol) in AcOH (10 mL) was added Pd/C (20 mg) and the reaction mixture was stirred under $H_2$ (50 psi). After LCMS showed the reaction was completed, the reaction mixture was filtered and concentrated to give Compound 202J. The product was used in the next step without any further purification. MS (ESI) m/z 693.2 $(M+H)^+$.

A solution of Compound 202J (100 mg, crude) in MeOH (10 mL) was added saturated $Na_2CO_3$ (2 mL) and $Boc_2O$ (3 drops). Then the reaction mixture was stirred at reflux overnight. After LCMS showed the reaction was complete, 0.5M HCl was added until pH=7. The solvent was evaporated under $N_2$ and the residue was washed by PE, to afford Compound 202K, which was used in the next step without any further purification. MS (ESI) m/z 779.3 $(M+H)^+$.

Compound 202K (used crude from the previous reaction), HATU (33.4 mg, 0.088 mmol), then (R)-BoroAla-(+)-Pinanediol (17 mg, 0.066 mmol), place the flask in an ice bath. DCM (2 mL), DMF (4 mL) and DMSO (4 mL) was added. To the mixture was added DIPEA (17 mg, 0.132 mmol). After ELSD showed the reaction was complete, water (30 mL) was added. The resulting mixture was extracted with DCM (30 mL×2). The combined organic layers were concentrated. The crude product was dissolved in DMSO (2.5 mL) and purified by prep-HPLC to give Compound 202L (9 mg, 22% over 3 steps from Compound 202I). MS (ESI) m/z 984.5 $(M+H)^+$.

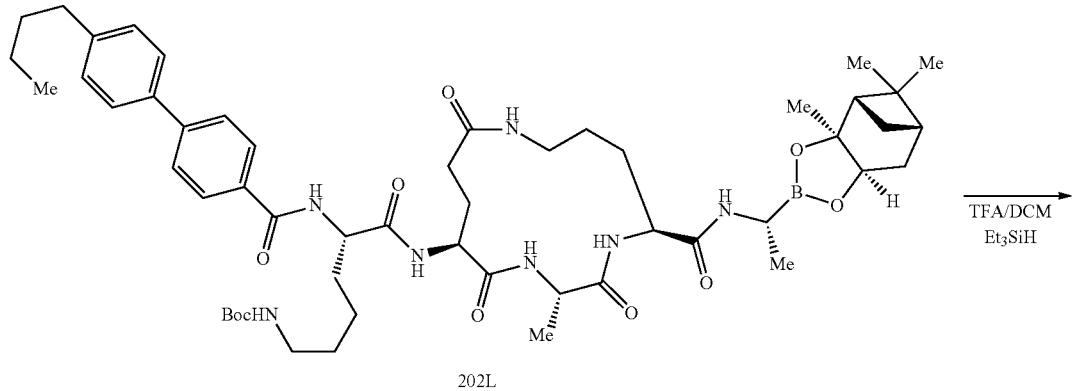

202L

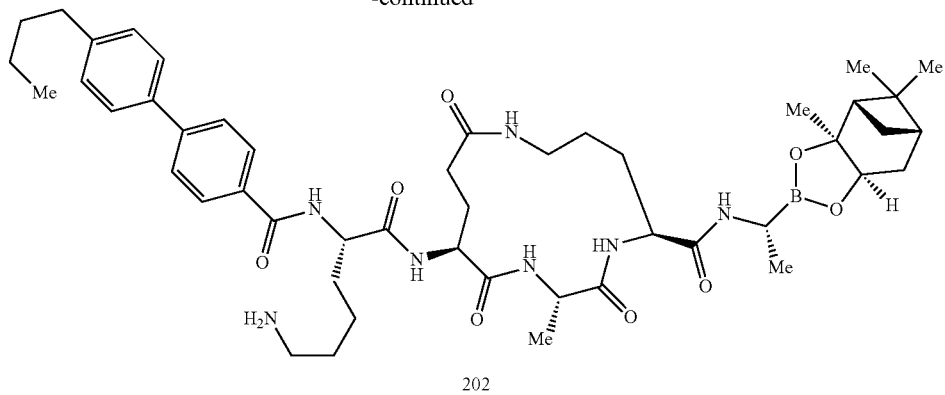
Synthesis of Compound 202: A solution of Compound 202L (23 mg, 0.023 mmol in TFA:DCM:triethylsilane (50:45:5) (2 mL) was stirred at room temperature for 1 hr, and then TFA was evaporated. The crude residue was taken up in DMSO and purified to give Compound 202 (16 mg, 78%). MS (ESI) m/z 884.3 (M+H)$^+$.
Example 40
Synthesis of Compound 203
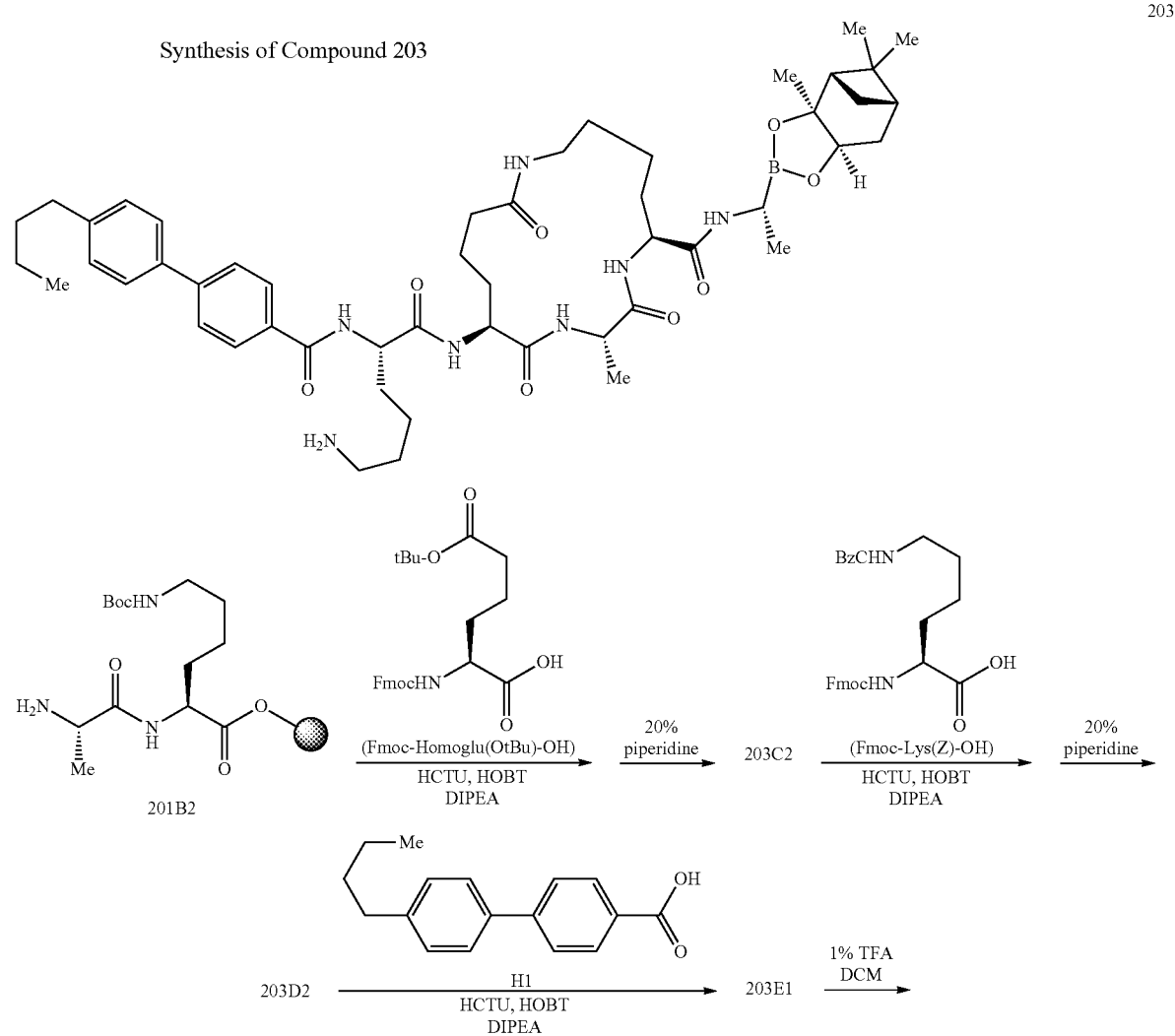

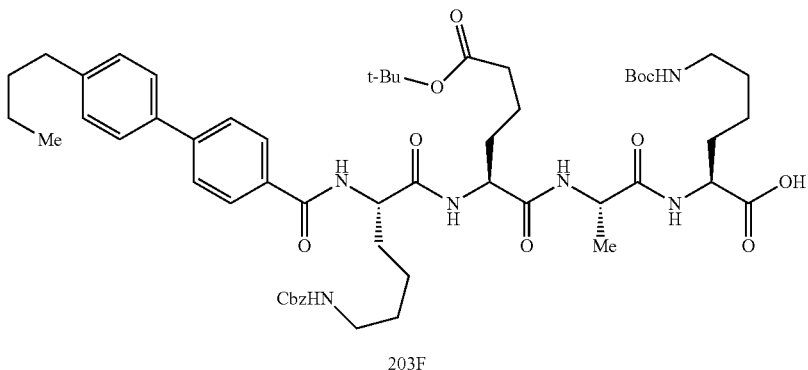

203F

Synthesis of Compound 203F: This compound was prepared according to General Methods 2-3 from Compound 201B2 to afford Compound 203F. MS (ESI) m/z 1015.4 (M+H)$^+$.

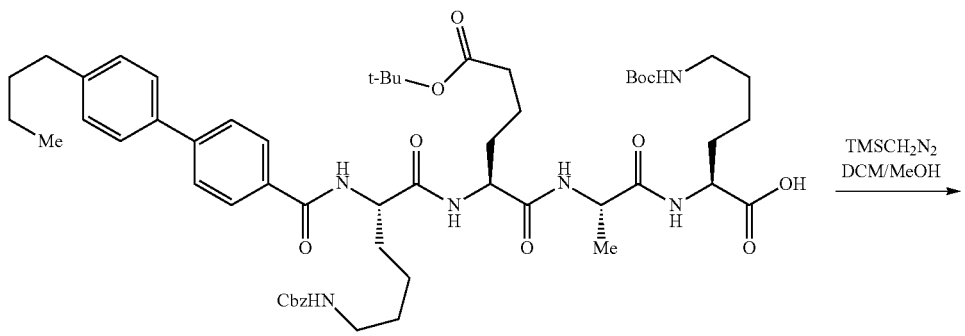

203F wise over 15 min at 0° C. The reaction mixture was stirred at 0° C. for 30 min. The operation was repeated until no starting material was detected by TLC, whereupon 0.5 mL of water was added, and the solvent was removed under vacuum to

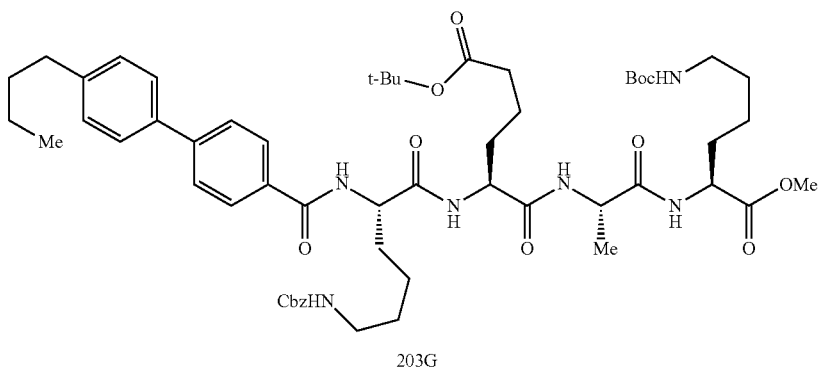

203G

Synthesis of Compound 203G: To a solution of Compound 203F (200 mg, 0.197 mmol) in DCM (4 mL) and MeOH (1 mL) was added TMSCH$_2$N$_2$ (0.22 mmol, 1 M in ether) dropgive a solid which was purified by column chromatography to afford Compound 203G (83.5 mg, 41%). MS (ESI) m/z 1029.7 (M+H)$^+$.

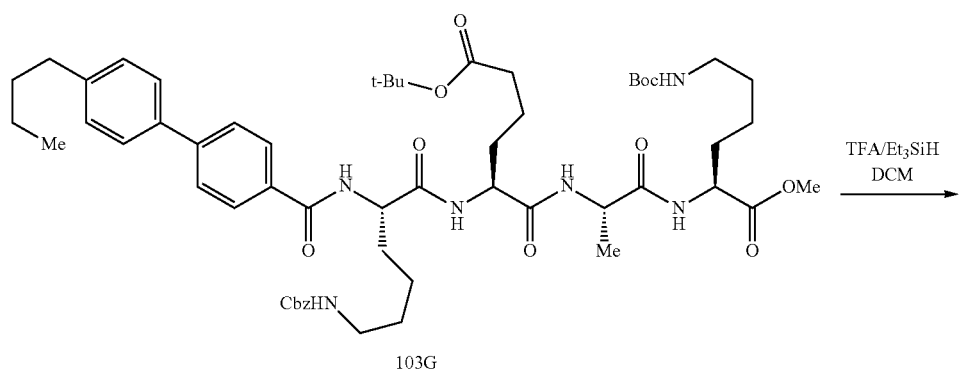
103G
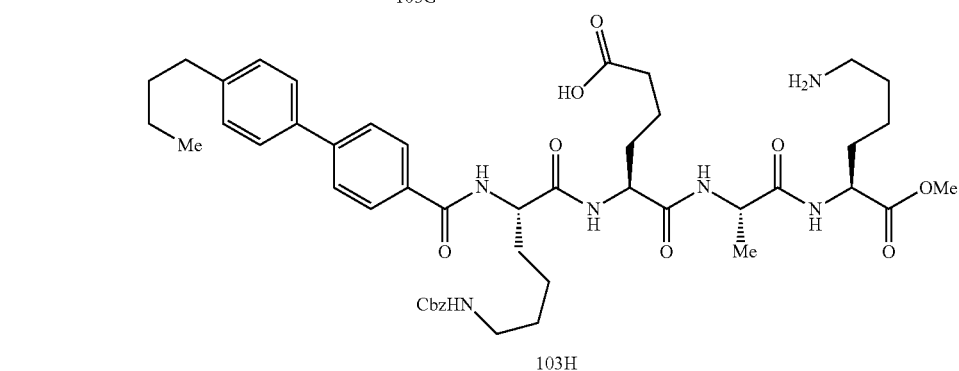
103H
Synthesis of Compound 203H: A solution of Compound 203G (500 mg, 0.486 mmol) in TFA (5 mL), DCM (4.5 mL) and Et$_3$SiH (0.5 mL) was stirred at 20° C. for 1 hr. The reaction solution was concentrated to give Compound 203H (382 mg, 90%). MS (ESI) m/z 873.4 (M+H)$^+$.
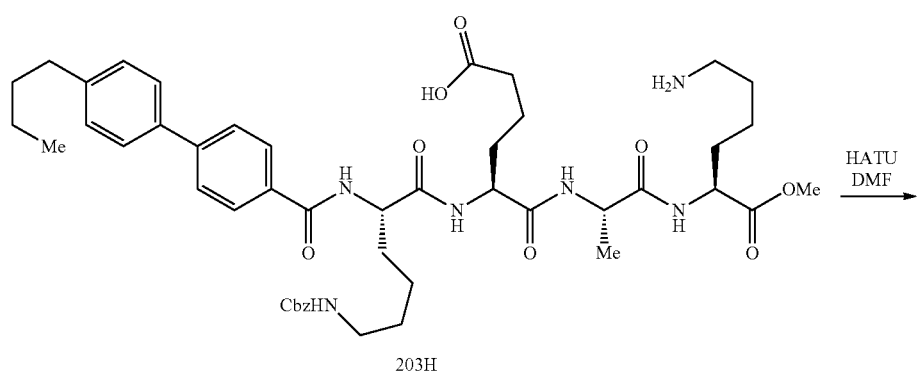
203H
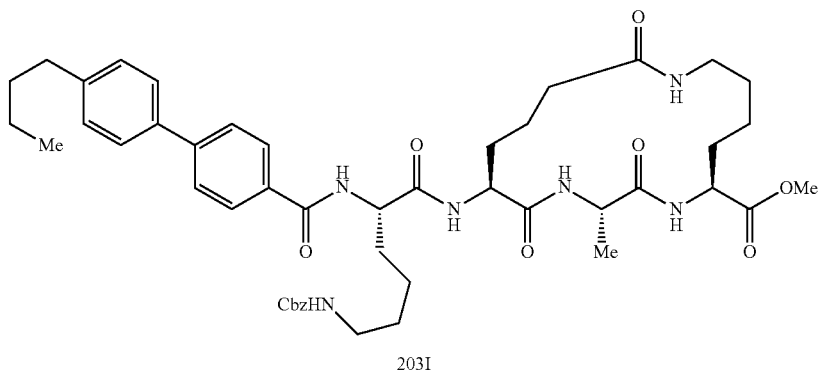
203I Synthesis of Compound 203I: To a solution of Compound 203H (100 mg, 0.12 mmol) in DMF (20 mL) was added HATU (83 mg, 0.2 mmol) and DIPEA (52 mg, 0.4 mmol). The mixture was stirred at 20° C. for 1 h after which time no starting material was detected by LCMS. The mixture was diluted with water (80 mL) until a solid precipitate formed. The mixture was filtered, and the filter cake was collected and dried to afford Compound 203I which was used without further purification. MS (ESI) m/z 855.3 (M+H)$^+$.

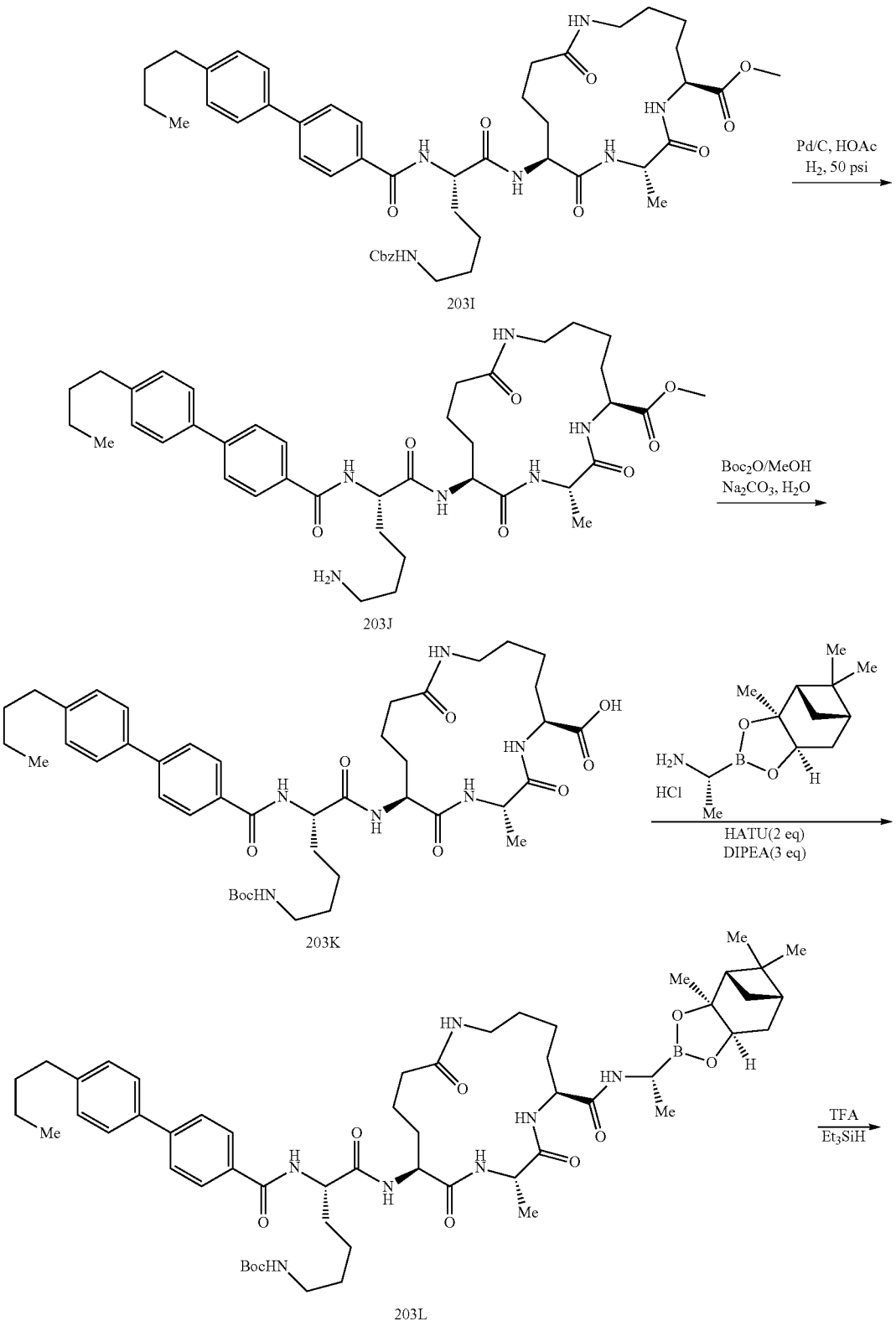

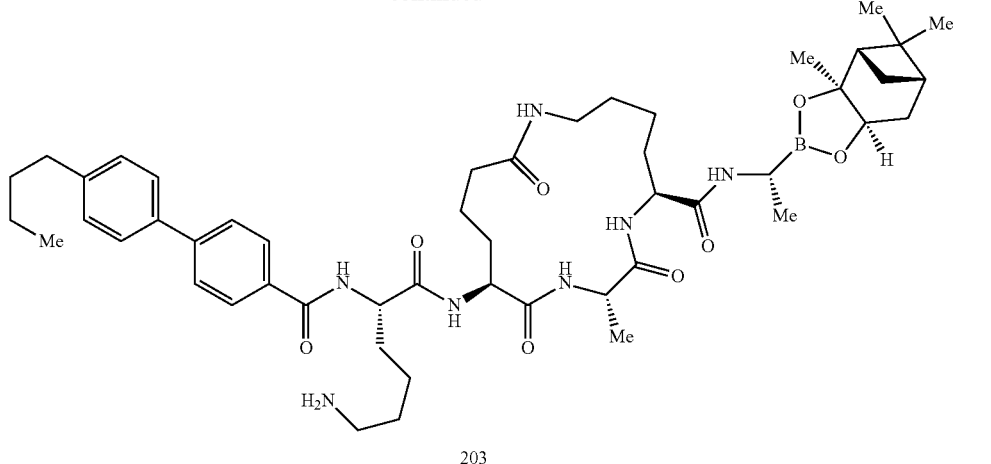

203

Synthesis of Compound 203. To a solution of Compound 203I (0.12 mmol) in AcOH (10 mL) was added 10% Pd/C (20 mg). The reaction mixture was stirred under H$_2$ (50 psi). After LCMS showed the reaction was complete, the reaction mixture was filtered and concentrated to give Compound 203J (90 mg, crude). The product was used in the next step without any further purification. MS (ESI) m/z 721.3 (M+H)$^+$.

To a solution of Compound 203J (90 mg crude) in MeOH (10 mL) was added saturated Na$_2$CO$_3$ (2 mL) and Boc$_2$O (3 drops). The reaction mixture was stirred at reflux overnight. After LCMS showed the reaction was complete, 0.5M HCl was added until pH=7. The solvent was evaporated under N$_2$ and the residue was washed with PE to afford Compound 203K (76 mg, crude), which was used in the next step without purification. MS (ESI) m/z 807.5 (M+H)$^+$.

Compound 203K, HATU (33.4 mg, 0.088 mmol), and (R)-BoroAla-(+)-pinanediol (17 mg, 0.066 mmol) were combined in a flask and the flask was placed in an ice bath. DCM (2 mL), DMF (4 mL) and DMSO (4 mL) were added. To the mixture was added DIPEA (17 mg, 0.13 mmol). After ELSD showed the reaction was complete, water (30 mL) was added. The resulting mixture was extracted with DCM (30 mL×2). The combined organic layers were concentrated to give Compound 203L (20 mg, crude). The crude product was used in the next step without any further purification.

A solution of Compound 203L (20 mg, crude) in TFA: DCM:triethylsilane (50:45:5) (3 mL) was stirred at room temperature for 1 hr, and then the TFA was evaporated. The crude residue was taken up in DMSO and purified by prep HPLC to afford Compound 203 (6 mg, 8%). MS (ESI) m/z 912.3 (M+H)$^+$.

Example 41

Synthesis of Compound 204 and Compound 205

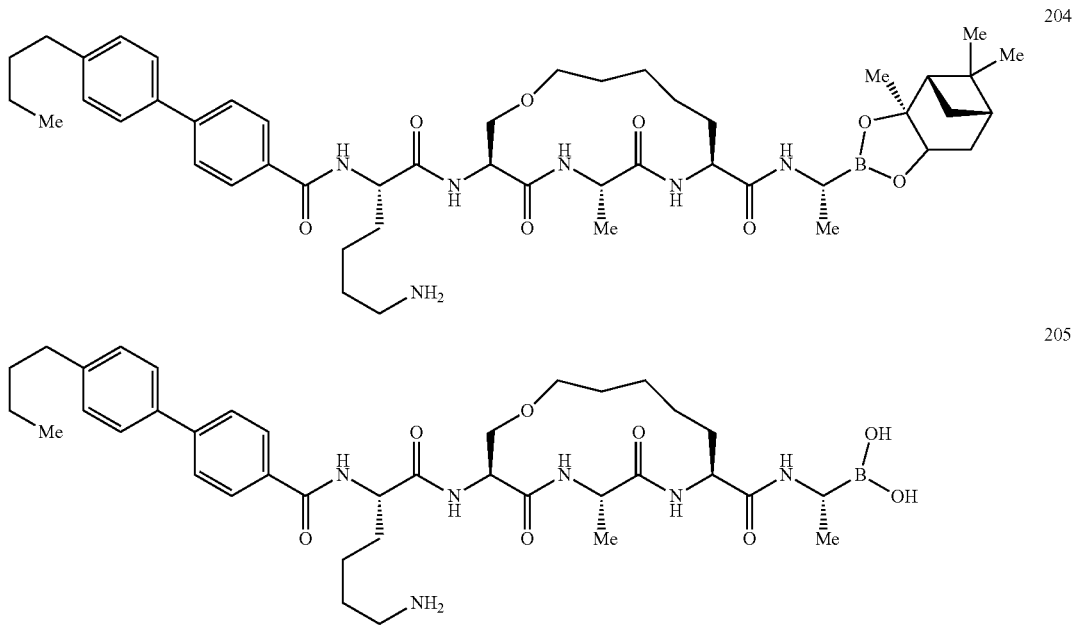

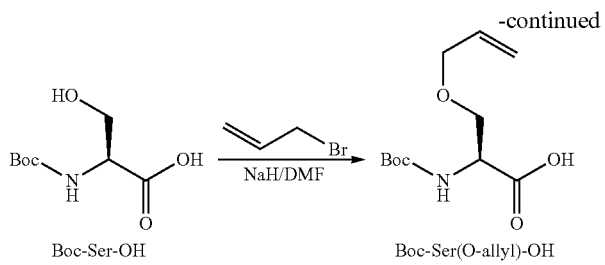

Synthesis of Boc-Ser(O-allyl)-OH HCl: To a mixture of Boc-Ser-OH (21.5 g, 0.105 mol) in DMF at 0° C. was added sodium hydride (8.4 g, 0.21 mol). The reaction mixture was stirred at 0° C. for 15 mins, and then allyl bromide (13.3 g, 0.105 mol) was added. The mixture was stirred at 40° C. overnight. After TLC showed the reaction was completed, the mixture was quenched with aqueous NH₄Cl solution and concentrated in vacuum. The residue was diluted with water, and sequentially washed with hexane and ether. The organic layers were discarded, and the aqueous layer was carefully adjusted to pH=3 with 1 N HCl. The acidic aqueous solution was extracted with ethyl acetate. The organic phase was washed with brine, dried over MgSO₄, and concentrated in vacuum to give Boc-Ser(O-allyl)-OH (14.0 g, 54.4%).

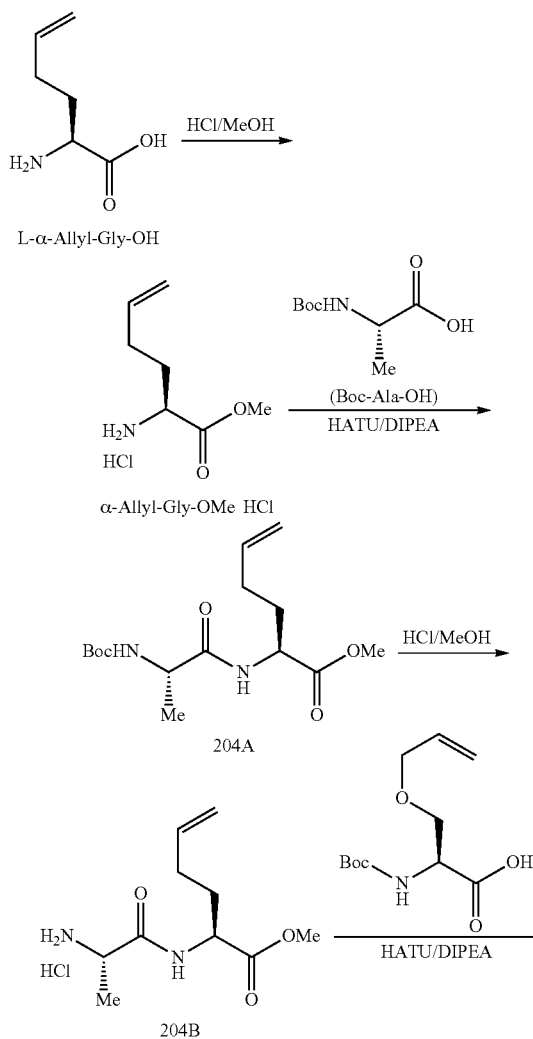

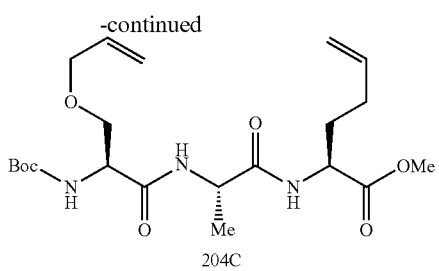

Synthesis of Compound 204C: A solution of α-Allyl-Gly-OH (1.00 g, 7.75 mmol) in MeOH/HCl (20 mL) was heated at reflux for 3 hrs. After TLC showed the reaction was complete, the mixture was evaporated to give α-Allyl-Gly-OMe HCl (1.10 g, 79.2%).

To a mixture of α-Allyl-Gly-OMe HCl (1.10 g, 6.14 mmol) and Boc-Ala-OH (1.28 g, 6.76 mmol) in dry DMF (10 mL) was added HATU (3.50 g, 9.22 mmol) and DIPEA (3.17 g, 24.6 mmol) at 0° C. The mixture was stirred overnight at 23° C. After ELSD showed the reaction was complete, the mixture was extracted with EA and H₂O. The organic layers were combined, dried with Na₂SO₄, filtered and concentrated. The crude product was purified by column chromatography on silica gel eluted to give Compound 204A (1.39 g, 72.0%). MS (ESI) m/z 315.1 (M+H)⁺.

A solution of Compound 204A (1.39 g, 4.42 mmol) in MeOH/HCl (20 mL) was stirred for 3 hrs at 24° C. After TLC showed the reaction was complete, the mixture was evaporated and purified by prep-HPLC to give Compound 204B (0.950 g, 86.0%). MS (ESI) m/z 215.1 (M+H)⁺.

To a mixture of Compound 204B (0.95 g, 3.80 mmol) and Boc-Ser(O-allyl)-OH (1.02 g, 4.18 mmol) in dry DMF (10 mL) was added HATU (2.17 g, 5.70 mmol) and DIEA (1.96 g, 15.2 mmol) at 0° C. The mixture was stirred overnight at 23° C. After ELSD showed the reaction was complete, the mixture was extracted with EA and H₂O. The organic layers were combined, dried with Na₂SO₄, filtered and concentrated. The crude product was purified by column chromatography on silica gel eluted to give Compound 204C (1.50 g, yield: 89.5%). MS (ESI) m/z 442.2 (M+H)⁺.

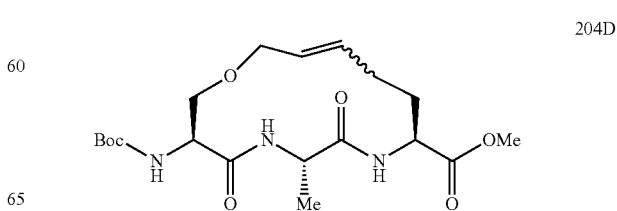

Synthesis of Compound 204D: A solution of Compound 204C (250 mg, 0.57 mmol) in dichloromethane (250 mL) was sparged with argon, treated with $2^{nd}$ Generation Grubbs catalyst (48 mg, 0.1 eq) and allowed to stir overnight under argon. TLC showed complete consumption of the starting material and the solvent was evaporated by rotary evaporation. The crude product was purified via silica gel chromatography (3% MeOH in DCM) to give Compound 204D, two isomers (3:1) as a white powder (158 mg, 67% yield). MS (ESI) for ($C_{19}H_{31}N_3O_7$): m/z 436.0 (M+Na).

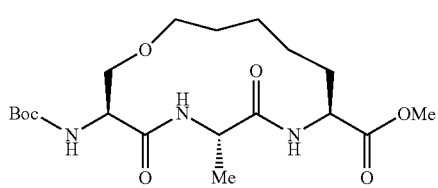

Synthesis of Compound 204E: To a solution of Compound 204D (151 mg, 0.37 mmol) in THF (12 mL) was added 10% palladium on carbon (50 mg, 30% w/w) and the reaction was put under an atmosphere of $H_2$. LCMS indicated complete consumption of the starting material after 2.5 hrs. The reaction mixture was filtered through celite and concentrated. Compound 204E, a crude white powder (150 mg), was used without further purification. MS (ESI) for ($C_{19}H_{33}N_3O_7$): m/z 438.1 (M+Na)$^+$.

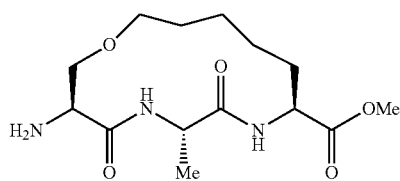

Synthesis of Compound 204F: A 3:1 mixture of DCM and TFA (4 mL) was added to Compound 204E (150 mg, 0.36 mmol) and the reaction was allowed to stir at room temperature. LCMS analysis indicated complete consumption of the starting material after 3.5 hr and the solvents were evaporated. The crude product was taken up multiple times in DCM and evaporated to dryness to remove any residual TFA to afford Compound 204F and used without further purification. MS (ESI) for ($C_{14}H_{25}N_3O_5$): m/z 316.0 (M+H). The following reactions use crude material.

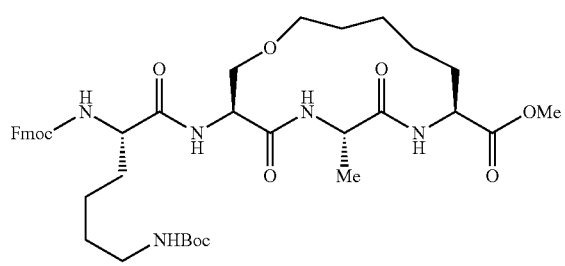

Synthesis of Compound 204G: To a solution of Compound 204F (0.12 mmol) in DMF (0.5 mL) and DCM (2 mL) was added Fmoc-Lys(Boc)-OH (240 mg, 1.1 eq), HATU (73 mg, 0.8 eq), DEPBT (56 mg, 0.4 eq and DIEA (652 uL, 8 eq). The reaction mixture was allowed to stir overnight and then ethyl acetate was added to precipitate the product. The mixture was sonicated and filtered. The precipitate was dried under vacuum to afford Compound 204G which was used without further purification (241 mg). MS (ESI) for ($C_{41}H_{57}N_5O_{11}$): m/z 788.2 (M+Na).

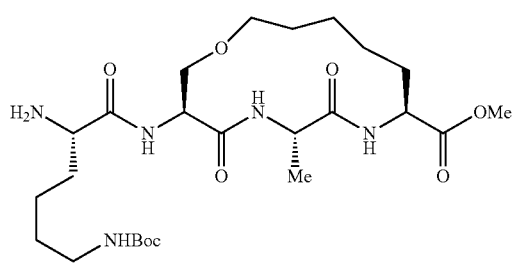

Synthesis of Compound 204H: To a solution of Compound 204G (0.32 mmol (assumed)) in DMF (20 mL) was added diethylamine (650 uL, 20 eq). After 2 hrs, the starting material had been consumed as judged by TLC. The solvent and diethylamine were evaporated and the product was dried under vacuum to give crude Compound 204H (198 mg). MS (ESI) for ($C_{25}H_{45}N_5O_8$): m/z 566.2 (M+H).

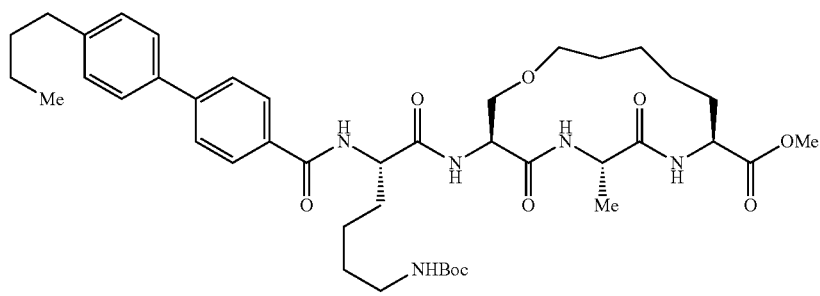

Synthesis of Compound 204I: To a solution of crude Compound 204H (0.32 mmol (assumed) in DMF (5 mL) and DCM (5 mL) was added Compound H1 (120 mg, 1.5 eq), HATU (180 mg, 1.5 eq) and DIPEA (208 uL, 4 eq). The reaction mixture was allowed to stir overnight and then ethyl acetate was added. The mixture was sonicated and heated, and then put in an ice bath to precipitate the product. The mixture was filtered and the collected solid was washed with cold ethyl acetate and dried to give Compound 204I(134 mg). MS (ESI) for ($C_{42}H_{61}N_5O_9$): m/z 802.2 (M+Na).

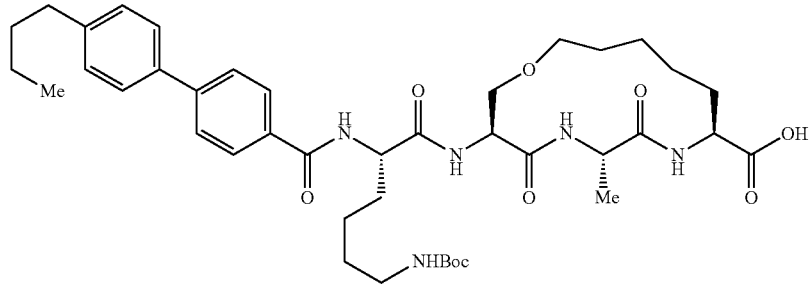

204J

Synthesis of Compound 204J: To a slightly cloudy solution of Compound 204I (80 mg, 0.1 mmol) in AcCN (10 mL) was added 0.2 N LiOH (2.0 mL, 4 eq). The mixture was heated to 45° C. for 9 hrs, cooled to room temperature, and stirred overnight. LCMS indicated the presence of a small amount of starting material remaining that was present throughout the reaction, therefore the reaction was stopped by evaporation of the AcCN. The residue was then taken up in ethyl acetate, 0.25 N HCl was added, and the aqueous layer was extracted 2× with ethyl acetate each time giving a precipitate confined to the organic layer. The combined organic layers with precipitate were washed with brine then concentrated to give Compound 204J. Compound 204J (90% pure by LCMS) was taken forward without further purification (137 mg). MS (ESI) for ($C_{41}H_{59}N_5O_9$): m/z 788.2 (M+Na).

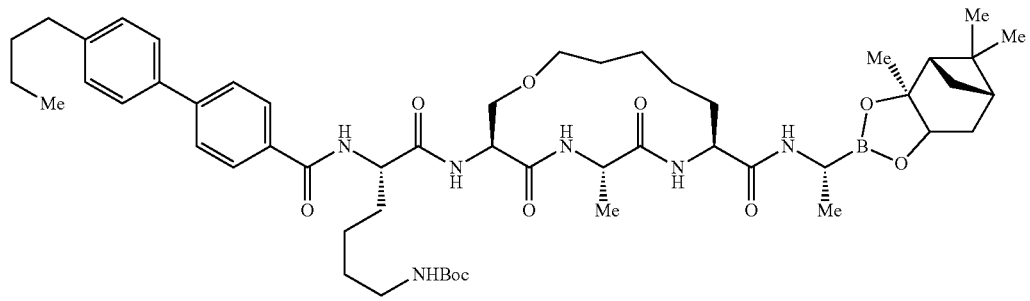

204K

Synthesis of Compound 204K: To a cloudy solution of Compound 204J (28 mg, 37 umol) in a 2:2:1 mixture of DCM, DMSO, and DMF (6.2 mL) was added (R)-Boro-Ala-(+)-pinanediol HCl (15 mg, 1.5 eq), HATU (28 mg, 2 eq), and DIPEA (28 uL, 4.5 eq) at 0° C. The mixture was allowed to warm to room temperature and the reaction was stirred overnight. Water and ethyl acetate were added and the aqueous layer was extracted 2× with EtOAc giving a white precipitate confined to the organic layer. The combined organic layers were washed with brine then concentrated to give Compound 204K (45 mg). MS (ESI) for ($C_{53}H_{79}BN_6O_{10}$): m/z 993.4 (M+H).

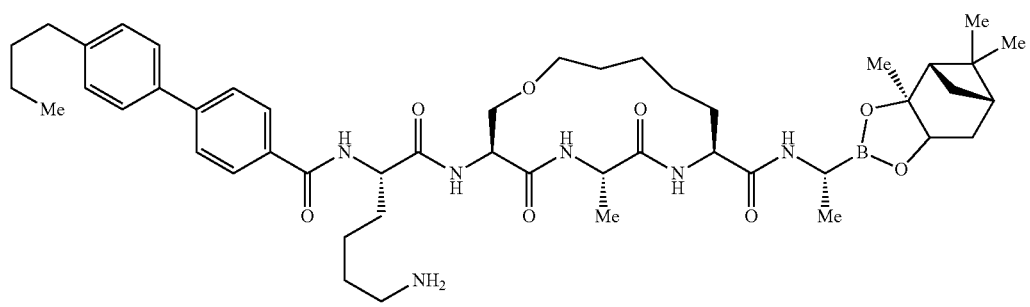

204

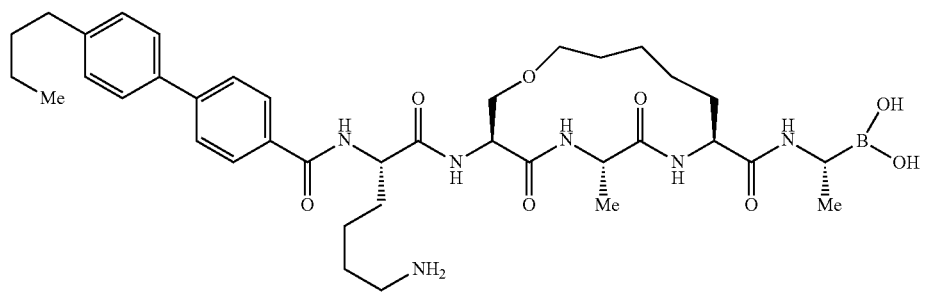

Synthesis of Compound 204 and Compound 205: A 4:1 mixture of TFA and DCM (3 mL) was added to crude Compound 204K (45 mg, 37 umol). The solution was allowed to stir for 40 min before LCMS indicated complete consumption of the starting material. The solvents were evaporated and the crude was taken up multiple times in DCM and then evaporated to dryness to remove any residual TFA. The crude product was then taken up in MeOH, the precipitate was centrifuged and the supernatant was decanted and purified by HPLC. Two peaks were collected, Compound 205 (4.5 mg) and Compound 204 (7.5 mg). Compound 205: MS (ESI) for ($C_{38}H_{57}BN_6O_8$): m/z 759.4 (M+Na). Compound 204: MS (ESI) for ($C_{48}H_{71}BN_6O_8$): m/z 871.4 (M+H)$^+$.

Example 42

Synthesis of Compound 206

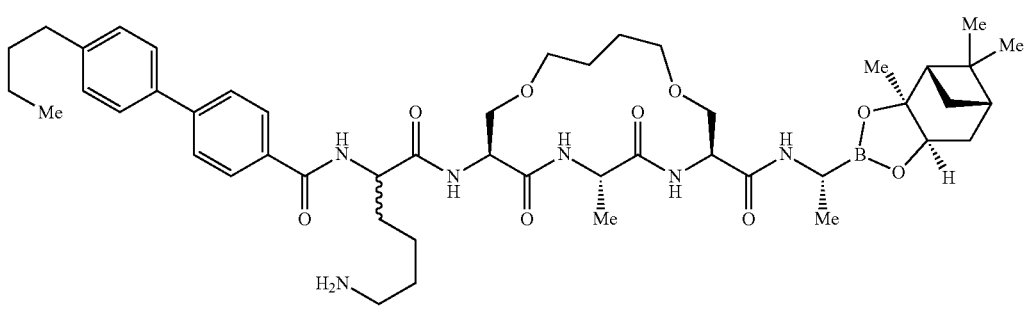

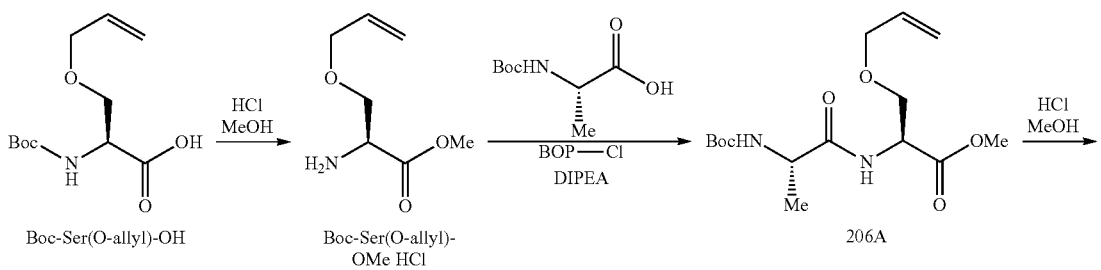

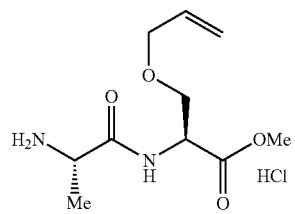

Synthesis of Compound 206B: A solution of Boc-Ser(O-allyl)-OH (25.0 g, 102 mmol) in HC/MeOH (300 mL) was stirred at 26° C. overnight. The solvent was removed at reduced pressure to give Boc-Ser(O-allyl)-OMe HCl (7.50 g, 38%).

A mixture of Boc-Ala-OH (8.90 g, 47.2 mmol), BoPCl (24.0 g, 94.4 mmol) and DIPEA (8.90 g, 68.8 mmol) in DMF (50 mL) was stirred at 0° C. for 10 mins and then Boc-Ser(O-allyl)-OMe HCl (7.50 g, 38.4 mmol) was added. The mixture was warmed up to 20° C. and stirred for 1 hr. After ELSD showed the reaction was complete, the mixture was treated with H$_2$O (30 mL), and extracted with EA (20 mL×3). The combined organic layers were washed with brine, and dried over Na$_2$SO$_4$. The solvent was removed to give Compound 206A (3.00 g, 23.6%). MS (ESI) m/z 331.1 (M+H)$^+$.

A solution of Compound 206A (3.00 g, 9.08 mmol) in HCl/MeOH (50 mL) was stirred at 20° C. for 10 hrs. The solvent was removed at reduced pressure to give Compound 206B (2.40 g, 99.3%).

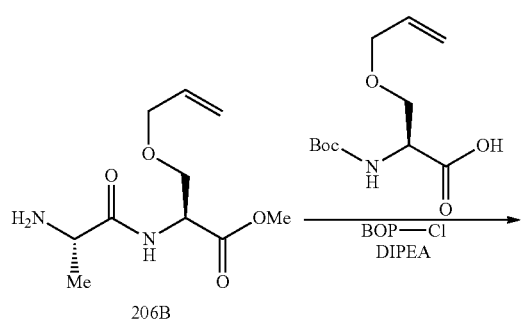

206B

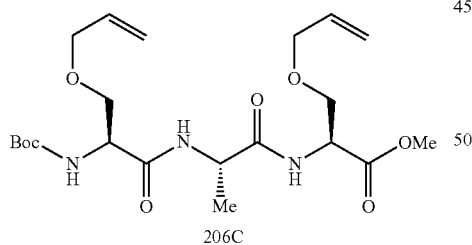

206C

Synthesis of Compound 206C: To a mixture of Compound 206B (1.10 g, 4.78 mmol) and Boc-Ser(O-allyl)-OH (1.17 g, 4.78 mmol) in dry DMF (30 mL) was added BOP—Cl (1.34 g, 5.26 mmol) and DIEA (1.23 g, 9.56 mmol) at 0° C. The reaction mixture was stirred overnight at 23° C. After ELSD showed the reaction was completed, H$_2$O (100 mL) was added to the solution. The mixture was filtered. The filter cake was washed with water and dried to give Compound 206C (2.00 g, yield: 91.7%). MS (ESI) m/z 458.1 (M+H)$^+$.

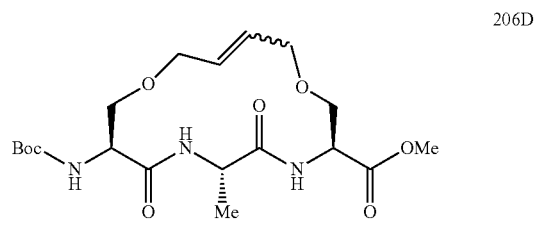 [SMILES: COC(=O)[C@@H]1COCC=CCOC[C@H](NC(=O)OC(C)(C)C)C(=O)N[C@@H](C)C(=O)N1]

206D

Synthesis of Compound 206D: A solution of Compound 206C (228 mg, 0.5 mmol) in dichloromethane (250 mL, 2 mM) was sparged with argon, treated with 2$^{nd}$ Generation Grubbs catalyst (21 mg, 0.05 eq) and allowed to stir overnight under argon. TLC analysis after 16 hrs showed incomplete consumption of the starting material so a second batch of catalyst (4 mg, 0.01 eq) was added. After an additional 8 hrs TLC showed complete consumption of the starting material and the solvent was evaporated by rotary evaporation. The crude was purified via silica gel chromatography (2.75% MeOH in DCM) to give Compound 206D as two isomers in a 3.3:1 ratio as a white powder (143 mg, 66% yield). MS (ESI) for (C$_{19}$H$_{31}$N$_3$O$_8$): m/z 452.1 (M+Na).

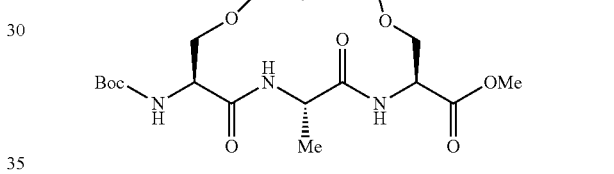

206E

Synthesis of Compound 206E: To a solution of Compound 206D (137 mg, 0.32 mmol) in THF (12 mL) was added 10% palladium on carbon (14 mg, 10% w/w) followed by ammonium formate (202 mg, 10 eq). The reaction was then stirred and heated at 65° C. until analysis by LC-MS indicated complete consumption of the starting material. The reaction mixture was then filtered through celite and concentrated to afford Compound 206E. The crude material (137 mg) was used without further purification. MS (ESI) for (C$_{19}$H$_{33}$N$_3$O$_8$): m/z 454.0 (M+Na).

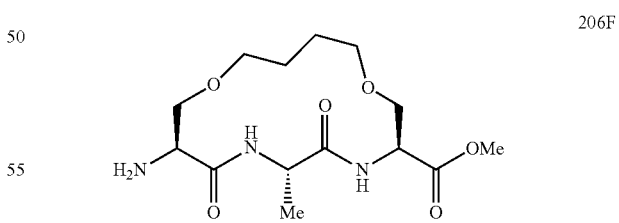

206F

Synthesis of Compound 206F: A 3:1 mixture of DCM and TFA (4 mL) was added to Compound 206E (134 mg, 0.31 mmol) and the reaction was allowed to stir at room temperature. LCMS analysis indicated complete consumption of the starting material after 2 hrs and the solvents were evaporated. The crude was taken up multiple times in DCM and the evaporated to dryness to remove any residual TFA to afford Compound 206F and was used without further purification. MS (ESI) for (C$_{14}$H$_{25}$N$_3$O$_6$): m/z 332.0 (M+H).

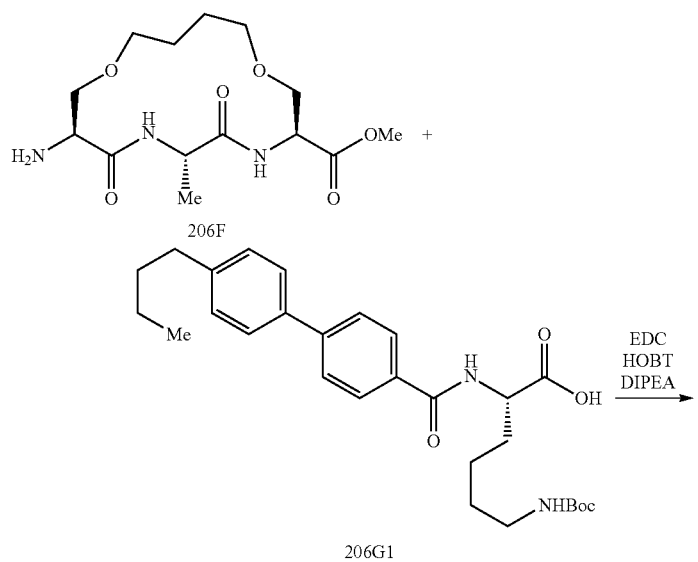

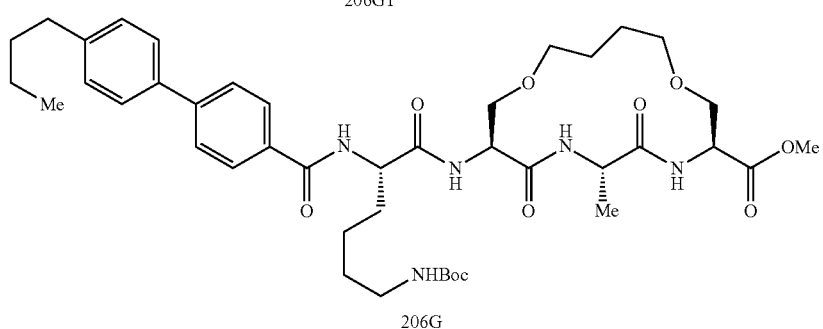

Synthesis of Compound 206G: To a solution of Compound 206F (35 mg, 0.11 mmol) in DMF (4.5 mL) and DCM (1.5 mL) was added Compound 206G1 (prepared from Compound H1 and Fmoc-Lys(Boc)-OMe followed by LiOH hydrolysis) (103 mg, 2 eq), N,N-diisopropylethylamine (20 uL, 1 eq), HOBt (37 mg, 2.5 eq) and EDC (53 mg, 2.5 eq). The reaction was allowed to stir for 18 h and then 5% citric acid and DCM were added to the reaction mixture. The aqueous layer was extracted 3× with DCM. The combined organic layers were washed with saturated NaHCO$_3$, water and brine, dried over sodium sulfate and concentrated. The crude residue was purified by silica gel chromatography using a gradient of MeOH in DCM (2% to 4.5%) to afford Compound 206G (29.7 mg, 37%). MS (ESI) for (C$_{42}$H$_{61}$N$_5$O$_{10}$): m/z 818.2 (M+Na).

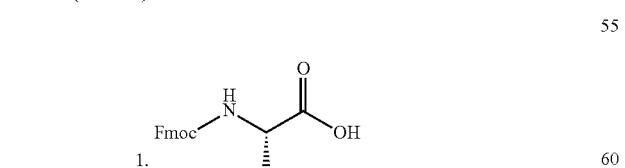

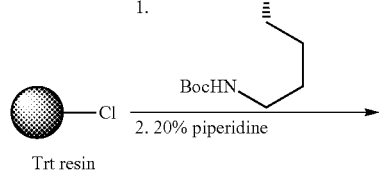

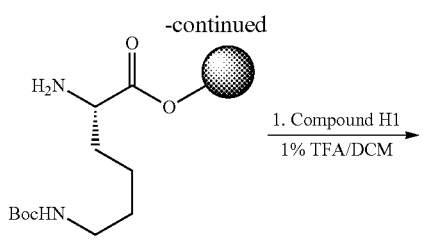

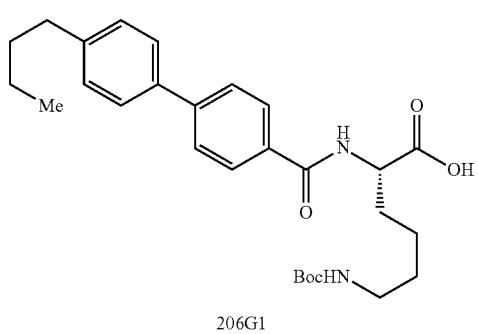

Synthesis of Compound 206G1: The compound was prepared as previously described in General Methods 1 and 2 from chlorotrityl resin, Fmoc-Lys(Boc)-OH and Compound H1 to afford Compound 206G1. MS (ESI) m/z 483.2 (M+H)$^+$.

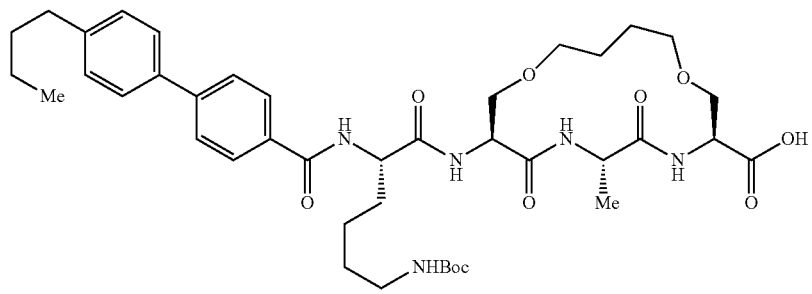

206H

Synthesis of Compound 206H: To a slightly cloudy solution of Compound 206G (23 mg, 29 umol) in THF (7 mL) was added 0.2 N LiOH (0.29 mL). The solution turned slightly yellow upon addition of LiOH and became clear. The reaction solution was heated to 40° C. and stirred. After 3 hrs TLC indicated the presence of starting material so an additional 0.2 N LiOH (0.29 mL) was added. After another 40 min, TLC indicated the complete consumption of starting material and a small amount of 10% citric acid was added to quench the reaction. Most of the THF was then evaporated by rotary evaporation, and then 10% citric acid, water and ethyl acetate were added to the mixture. The aqueous layer was extracted 3× with ethyl acetate. The combined organic layers were dried over sodium sulfate and concentrated to afford Compound 206H. The crude material (19.6 mg) was taken forward without further purification. MS (ESI) for ($C_{41}H_{59}N_5O_{10}$): m/z 804.2 (M+Na).

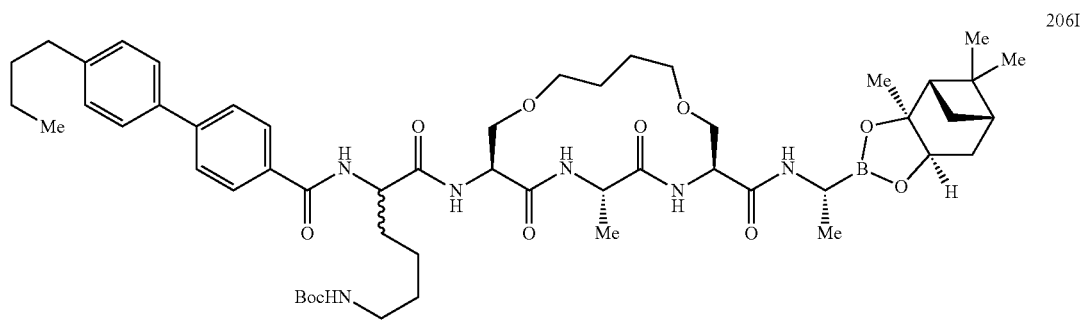 [SMILES: CCCCc1ccc(-c2ccc(C(=O)NC(CCCCNC(=O)OC(C)(C)C)C(=O)N[C@H]3COCCCCOC[C@@H](C(=O)N[C@@H](C)B4O[C@@H]5C[C@@H]6C[C@@H](C6(C)C)[C@]5(C)O4)NC(=O)[C@H](C)NC3=O)cc2)cc1]

206I

Synthesis of Compound 206I: To a solution of Compound 206H (19.6 mg, 25 umol) in DMF (1 mL) was added DCM (2 mL) and the solution was cooled to 0° C. HATU (19 mg, 2 eq), (R)-Boro-Ala-(+)-pinanediol HCl (10 mg, 1.5 eq) and DIPEA (13 uL, 3 eq) were then added to the reaction. The reaction solution was allowed to warm to room temperature and stirred for 2 hrs. DCM and water were added to the reaction and the aqueous layer was extracted 3× with DCM. The combined organic layers were washed with 10% citric acid, saturated $NaHCO_3$ and then concentrated. The product was dissolved in ethyl acetate, washed with water and brine, dried over sodium sulfate and concentrated to give Compound 206I (37.7 mg). MS (ESI) for ($C_{53}H_{79}BN_6O_{11}$): m/z 987.3 (M+H).

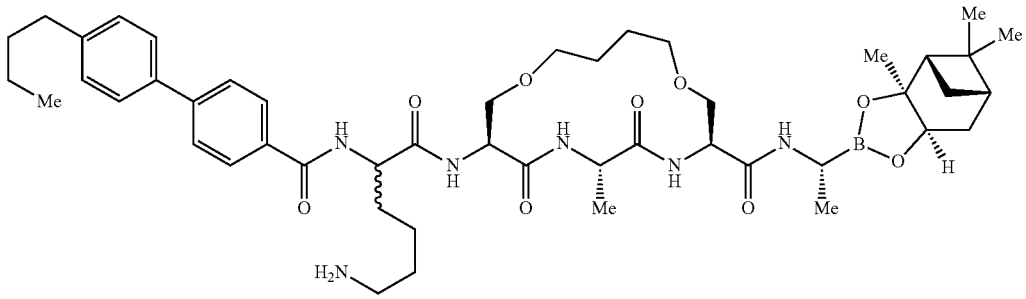

206

Synthesis of Compound 206: A 4:1 mixture of TFA and DCM (2.5 mL) was added to crude Compound 206I (37 mg, 37 umol). The reaction solution was stirred for 4 hr and then the solvents were evaporated. DMSO was added to the crude solid and the mixture was heated slightly and sonicated. The mixture was filtered and the DMSO solution was purified by reverse phase HPLC. Two peaks of similar intensity were collected corresponding to the pinane deprotected compound, which results from epimerization of the lysine stereocenter after the fragment coupling. All peaks were combined to give the racemized product, Compound 206 (5.4 mg, 16%). MS (ESI) for ($C_{48}H_{71}BN_6O_9$): m/z 887.4 (M+H).

Example 43

Synthesis of Compound 207

A solution of Boc-L-HomoSer(O-allyl)-OH (4.50 g, 17.4 mmol) in HCl/MeOH (50 mL) was stirred at 20° C. for 6 hrs. The solvent was removed at reduced pressure to give Boc-L-HomoSer(allyl)-OMe HCl (3.60 g, 98.9%).

A mixture of Boc-Ala-OH (3.30 g, 17.2 mmol), BoPCl (6.56 g, 25.8 mmol) and DIPEA (8.90 g, 68.8 mmol) in DMF (30 mL) was stirred at 0° C. for 10 mins and then Boc-L-HomoSer(allyl)-OMe HCl (3.60 g, 17.2 mmol) was added. The reaction mixture was warmed to 20° C. and stirred for 1 hr. After ELSD showed the reaction was complete, the mixture was treated with $H_2O$ (30 mL) and extracted with EA (20 mL×3). The combined organic layers were washed with brine, and dried over $Na_2SO_4$. The solvent was removed to give Compound 207A (5.40 g, 91.3%).

A solution of Compound 207A (5.40 g, 15.7 mmol) in HCl/MeOH (50 mL) was stirred at 20° C. for 6 hrs. The

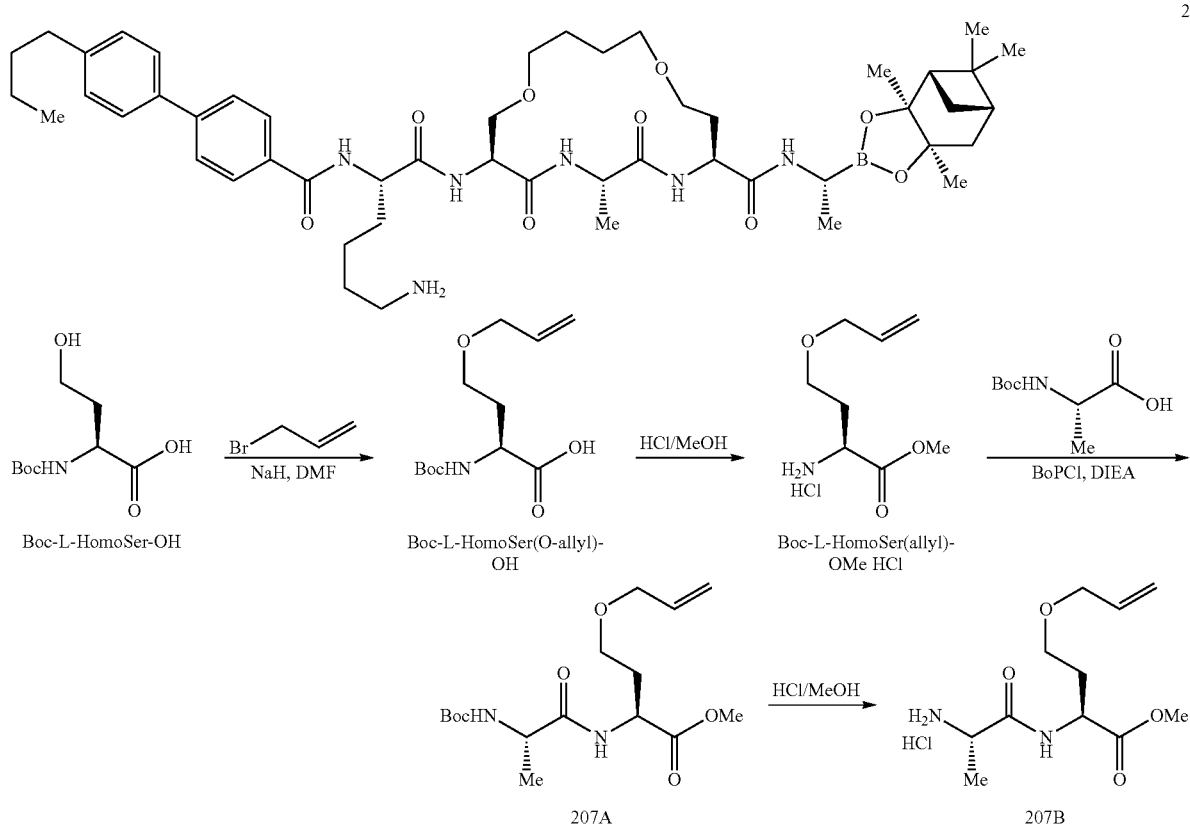

Synthesis of Compound 207B: To a solution of Boc-L-HomoSer-OH (10.0 g, 45.6 mmol) in DMF was added sodium hydride (2.74 g, 114 mmol) at 0° C. The reaction mixture was stirred at 0° C. for 15 mins, and then allyl bromide (6.90 g, 57.0 mmol) was added. The mixture was warmed to 20° C. and stirred for 2 hrs. The mixture was quenched with saturated $NH_4Cl$ solution and then concentrated in vacuum. The residue was diluted with water, and sequentially washed with hexane and ether. The organic layers were discarded, and the aqueous layer was carefully adjusted to pH=3 with 1 N HCl. The acidic aqueous solution was extracted with ethyl acetate. The organic phase was dried over $MgSO_4$ and concentrated in vacuum to give Boc-L-HomoSer(O-allyl)-OH (8.00 g, 67.8%).

solvent was removed at reduced pressure to give Compound 207B (3.80 g, 86.6%).

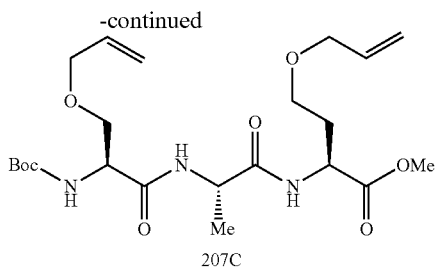

207C

Synthesis of Compound 207C: A solution of Boc-Ser(O-allyl)-OH (3.20 g, 13.1 mmol), HATU (7.50 g, 19.8 mmol) and DIPEA (6.80 g, 52.8 mmol) in DMF (30 mL) was stirred at 0° C. for 10 mins and then Compound 207B (3.70 g, 13.2 mmol) was added. The mixture was warmed to 20° C. and stirred for 1 h. After ELSD showed the reaction was complete, the mixture was treated with $H_2O$ (30 mL) and then extracted with EA (20 mL×3). The combined organic layers were washed with brine, and dried over $Na_2SO_4$. The solvent was removed to give Compound 207C (5.00 g, 80.9%).

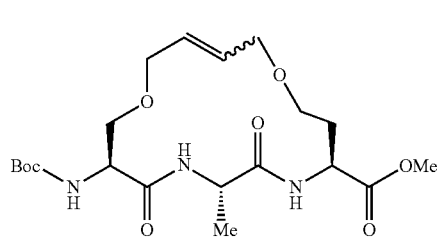

207D

Synthesis of Compound 207D: A solution of Compound 207C (300 mg, 0.66 mmol) in dichloromethane (340 mL) was sparged with argon, treated with $2^{nd}$ Generation Grubbs catalyst (58 mg, 0.1 eq) and allowed to stir overnight under argon. TLC showed complete consumption of the starting material and the solvent was evaporated by rotary evaporation. The crude product was then taken up in DCM, sonicated, slightly heated and then chilled on ice. The mixture was filtered to give Compound 207D, a white precipitate comprising two isomers (146 mg, 52% yield). MS (ESI) for ($C_{20}H_{33}N_3O_8$): m/z 466.0 (M+Na).

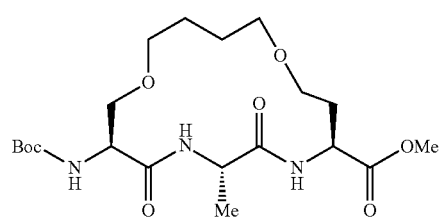

207E

Synthesis of Compound 207E: To a solution of Compound 207D (142 mg, 0.32 mmol) in THF (25 mL) was added 10% palladium on carbon (47 mg, 30% w/w) and the reaction was put under an atmosphere of $H_2$. LCMS indicated complete consumption of the starting material after 3 hrs. The reaction mixture was filtered through celite and concentrated to afford Compound 207E. The crude white powder (157 mg) was used without further purification. MS (ESI) for ($C_{20}H_{35}N_3O_8$): m/z 468.1 (M+Na).

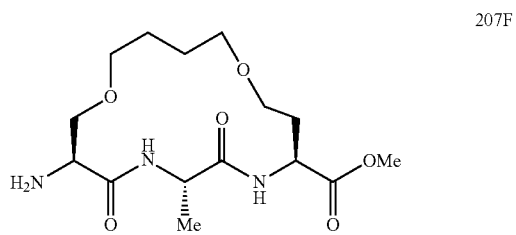 [SMILES: COC(=O)[C@@H]1CCOCCCCOC[C@H](N)C(=O)N[C@@H](C)C(=O)N1]

207F

Synthesis of Compound 207F: A 3:1 mixture of DCM and TFA (4 mL) was added to Compound 207E (157 mg, 0.35 mmol) and the reaction mixture was allowed to stir at room temperature. LCMS analysis indicated complete consumption of the starting material after 3.5 hr and the solvents were evaporated. The crude product was taken up multiple times in DCM and the evaporated to dryness to remove any residual TFA to afford Compound 207F which was used without further purification (219 mg). MS (ESI) for ($C_{15}H_{27}N_3O_6$): m/z 346.0 (M+H).

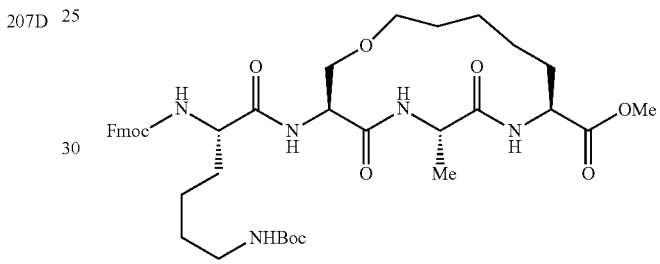

207G

Synthesis of Compound 207G: To a solution of Compound 207F (0.43 mmol) in DMF (2.5 mL) and DCM (5 mL) was added DIPEA (170 uL, 8 eq), Fmoc-Lys(Boc)-OH (83 mg, 1.5 eq) and HATU (73 mg, 1.5 eq). The reaction mixture was allowed to stir until LCMS analysis indicated complete consumption of starting material (4 hrs), and then DCM and water were added. The aqueous layer was extracted 2× with DCM and the combined organic layers containing a white precipitate were washed with 5% citric acid and saturated $NaHCO_3$. The organic solution were dried over sodium sulfate and filtered. The crude product was then taken up in ethyl acetate, sonicated, slightly heated, cooled on an ice bath and filtered to afford Compound 207G (31 mg, 32% yield). MS (ESI) for ($C_{41}H_{57}N_5O_{11}$): m/z 818.2 (M+Na).

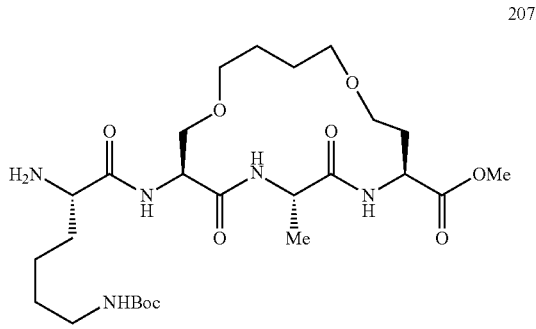

207H

Synthesis of Compound 207H: To a solution of Compound 207G (73 mg, 0.92 mmol (assumed)) in DMF (3 mL) was added diethylamine (190 uL, 20 eq). After 40 mins the starting material had been consumed as judged by LCMS. The solvent and diethylamine were evaporated and the crude product was dried under vacuum to give Compound 207H (198 mg). MS (ESI) for ($C_{25}H_{45}N_5O_8$): m/z 596.2 (M+Na).

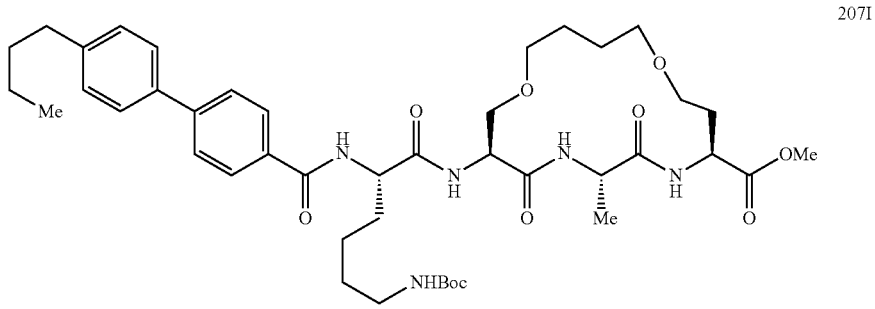 [SMILES: CCCCc1ccc(-c2ccc(C(=O)N[C@@H](CCCCNC(=O)OC(C)(C)C)C(=O)N[C@H]3COCCCCOCC[C@@H](C(=O)OC)NC(=O)[C@H](C)NC3=O)cc2)cc1]

Synthesis of Compound 207I: To a solution of Compound 207H (53 mg, 92 umol (assumed)) in DMF (4 mL) and DCM (4 mL) was added Compound H1 (Example 1) (35 mg, 1.5 eq), HATU (52 mg, 1.5 eq) and DIPEA (65 uL, 4 eq). The reaction mixture was allowed to stir for 1.5 hrs and then the solvents were evaporated. The residue was dried overnight under vacuum. Ethyl acetate was added to the residue. The mixture was sonicated and heated, and then put in an ice bath to precipitate the product. The mixture was filtered and the collected solid was washed with cold ethyl acetate and dried to give Compound 207I (73 mg). MS (ESI) for ($C_{42}H_{61}N_5O_9$): m/z 832.3 (M+Na).

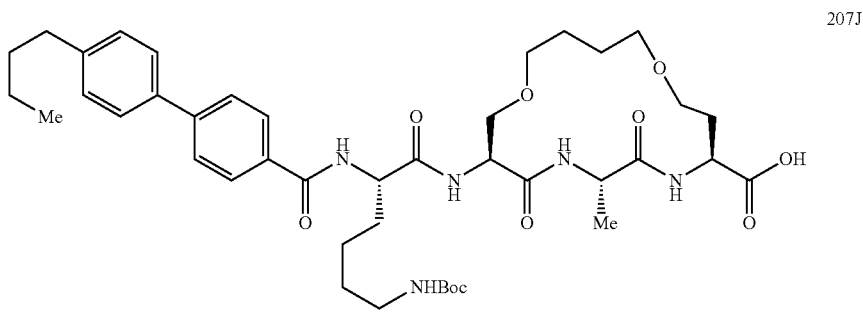 [SMILES: CCCCc1ccc(-c2ccc(C(=O)N[C@@H](CCCCNC(=O)OC(C)(C)C)C(=O)N[C@H]3COCCCCOCC[C@@H](C(=O)O)NC(=O)[C@H](C)NC3=O)cc2)cc1]

Synthesis of Compound 207J: To a slightly cloudy solution of Compound 207I (71 mg, 88 umol) in AcCN (18 mL) was added 0.2 N LiOH (2.2 mL, 5 eq). The reaction solution was heated to 70° C. for 2.5 hrs and then cooled to room temperature. The acetonitrile was evaporated, 2% citric acid and ethyl acetate were added and the organic layer (with a white precipitate) was separated. The organic layer was then evaporated to dryness and the residue was taken up in DCM and filtered to give Compound 207J, a crude waxy solid (33 mg). MS (ESI) for ($C_{41}H_{59}N_5O_9$): m/z 818.2 (M+Na).

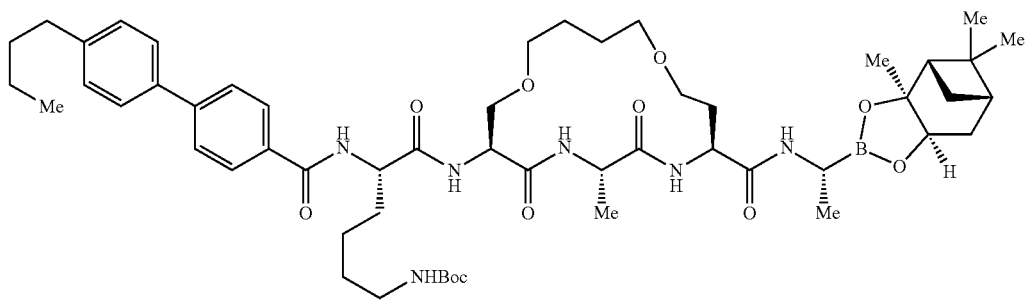

Synthesis of Compound 207K: To a cloudy solution of Compound 207J (31 umol) in a 2:2:1 mixture of DCM, DMSO and DMF (6.25 mL) was added (R)-Boro-Ala-(+)-pinanediol HCl (10 mg, 1.5 eq), HATU (24 mg, 2 eq), and DIPEA (23 uL, 4.5 eq). After 20 min, LCMS indicated a significant amount of starting material remaining so (R)-Boro-Ala-(+)-pinanediol HCl (10 mg, 1.5 eq) HATU (24 mg, 2 eq), and DIPEA (23 uL, 4.5 eq) was added. After 1 hr, the reaction was 95% complete and the reaction was allowed to stir overnight. After 30 hrs, water was added and the aqueous was extracted 2× with ethyl acetate. The combined organic layers were washed with saturated NaHCO$_3$, dried over sodium sulfate and concentrated to give Compound 207K (22 mg). MS (ESI) for ($C_{54}H_{81}BN_6O_{11}$): m/z 1023.4 (M+Na).

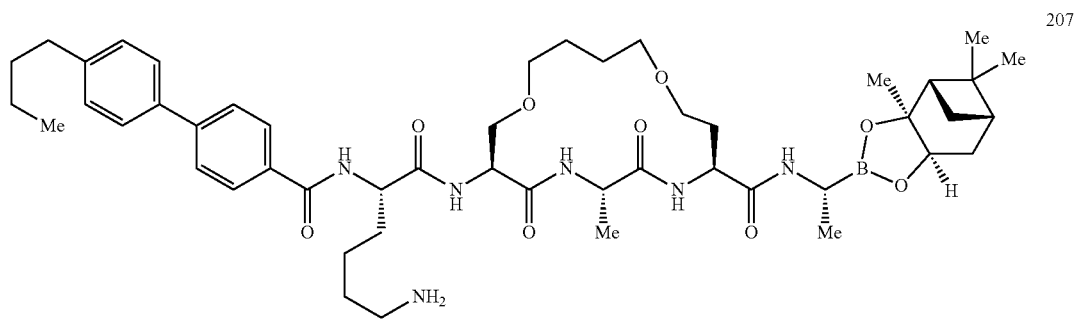 [SMILES: CCCCc1ccc(-c2ccc(C(=O)N[C@@H](CCCCN)C(=O)N[C@H]3COCCCCOCC[C@@H](C(=O)N[C@@H](C)B4O[C@@H]5C[C@@H]6C[C@@H](C6(C)C)[C@]5(C)O4)NC(=O)[C@H](C)NC3=O)cc2)cc1]

Synthesis of Compound 207: A 4:1 mixture of TFA and DCM (3 mL) was added to Compound 207K (22 mg, 22 umol). The cloudy solution was allowed to stir for 1 hr before LCMS indicated complete consumption of the starting material. The solvents were evaporated and the crude product was taken up multiple times in DCM and the evaporated to dryness to remove any residual TFA. The crude product was then taken up in MeOH. The precipitate was centrifuged and the supernatant was decanted and purified by HPLC. Two peaks were collected corresponding to the pinane deprotected and pinane protected compound and pooled to give Compound 207 (1.7 mg). MS (ESI) for ($C_{49}H_{73}BN_6O_9$) (Compound 207): m/z 923.5 (M+Na)$^+$.

Example 44

Synthesis of Compound 208

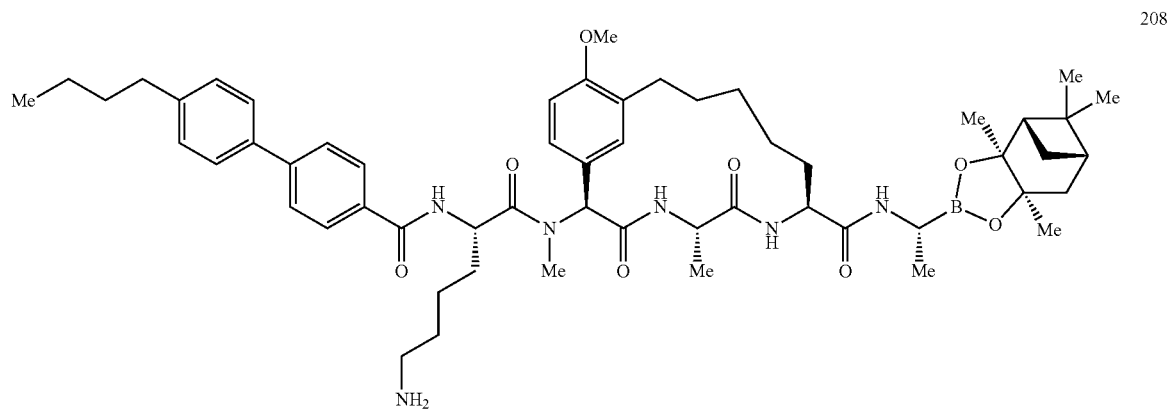

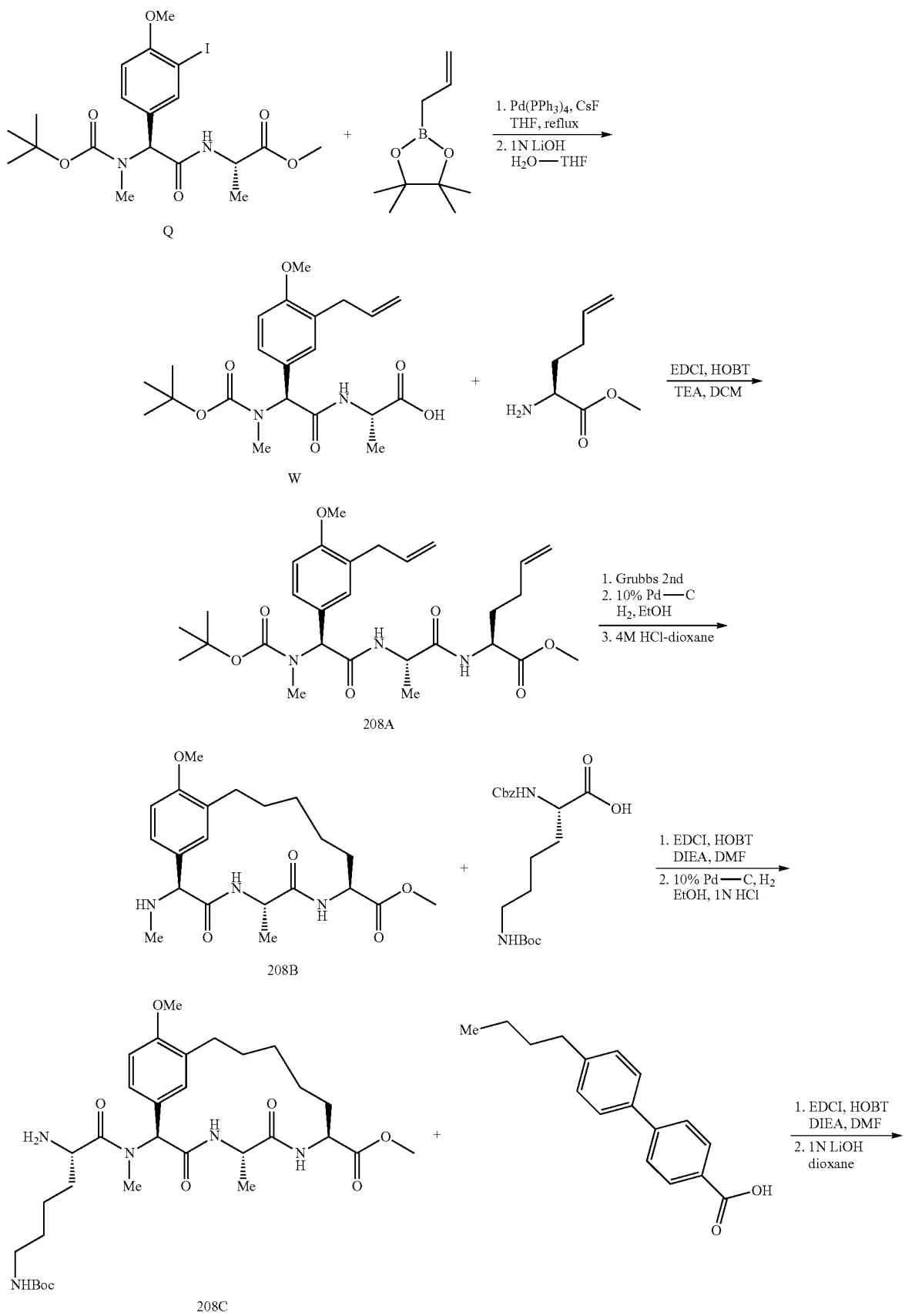

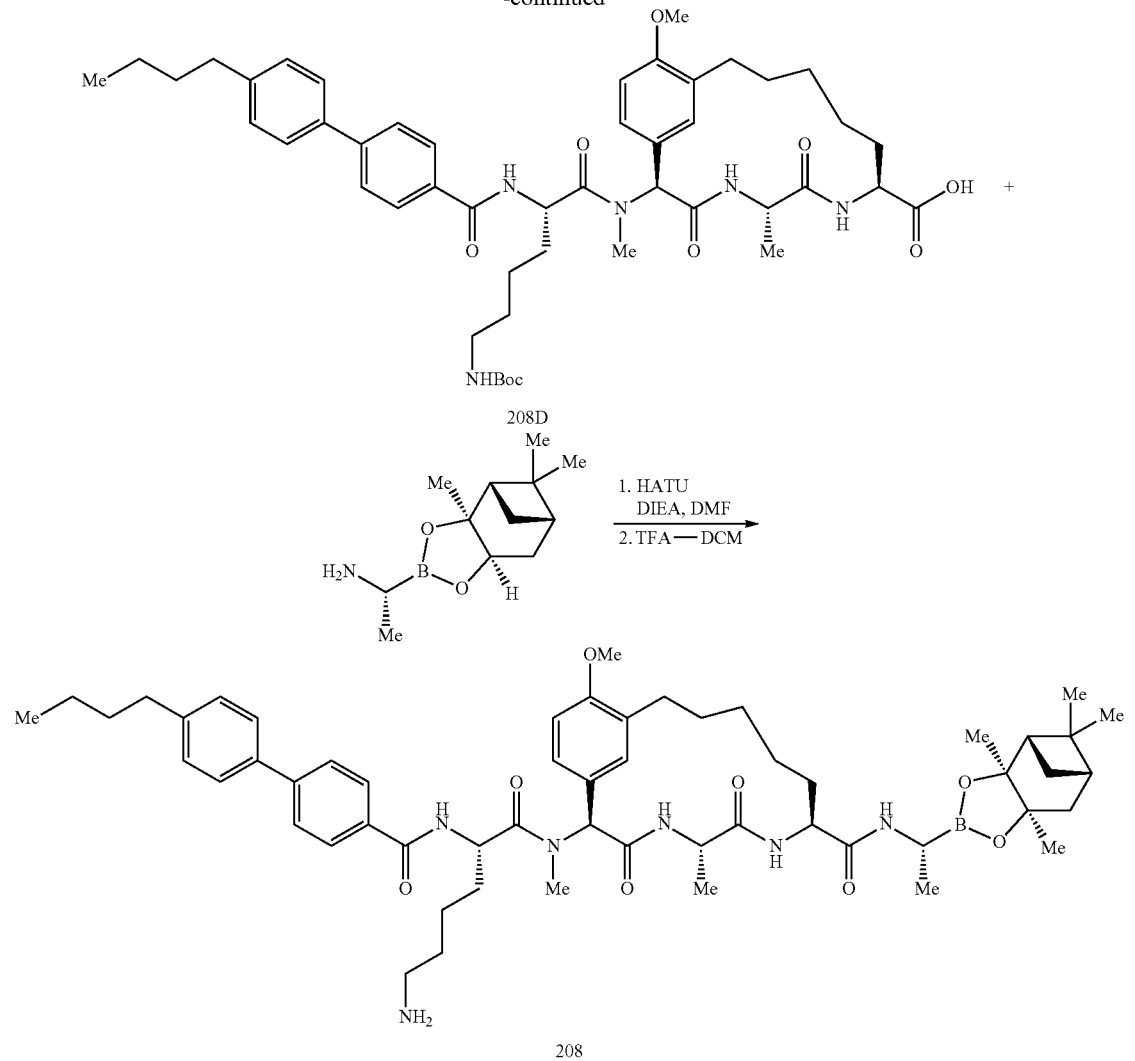

Preparation of Intermediate W:

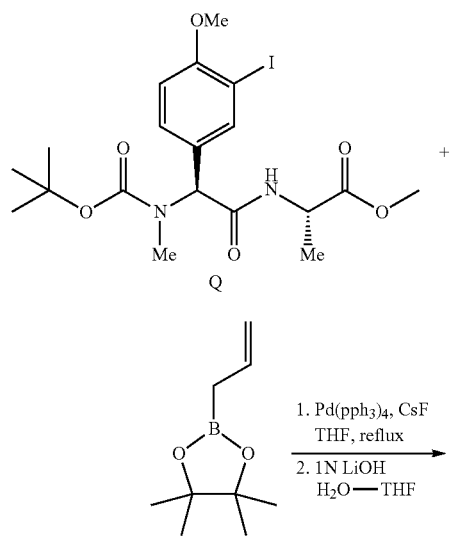

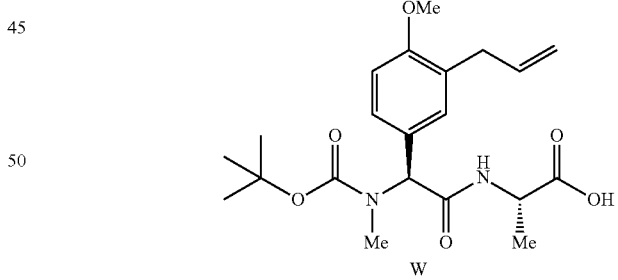

To a solution of Compound Q (506 mg, 1.0 mmol) in anhydrous THF (5 mL) was added allylboronic acid pinacol ester (252 mg, 1.5 mmol), CsF (456 mg, 3.0 mmol) and Pd(PPh$_3$)$_4$ (18.3 mg, 0.02 mmol) and the mixture was bubbled with N$_2$ for 2 min and heated at 65° C. overnight. The mixture was cooled to room temperature, filtered through celite and washed with ethyl acetate. The filtrate was washed with water, brine, dried (Na$_2$SO$_4$) and concentrated. The resulting dark brown residue was purified by flash chromatography using EtOAc-hexanes to afford Compound V (321 mg, 76%) as a light brown oil. MS (ESI) for (C$_{22}$H$_{32}$N$_2$O$_6$): m/z 443 (M+Na)$^+$.

Compound V (315 mg, 0.75 mmol) was dissolved in dioxane (5 mL) and 1N LiOH (3 mL) was added at 0° C. The reaction mixture was stirred for 3 h. The reaction mixture was extracted with ether and the aqueous layer acidified with 1N HCl and extracted with ethyl acetate. The combined organic layers were washed with brine, dried ($Na_2SO_4$) and concentrated. The residue was purified by flash chromatography using EtOAc-hexanes to afford Compound W (253 mg, 82%) as a colorless foamy solid. MS (ESI) for ($C_{21}H_{30}N_2O_6$): m/z 306 (M−Boc H)+.

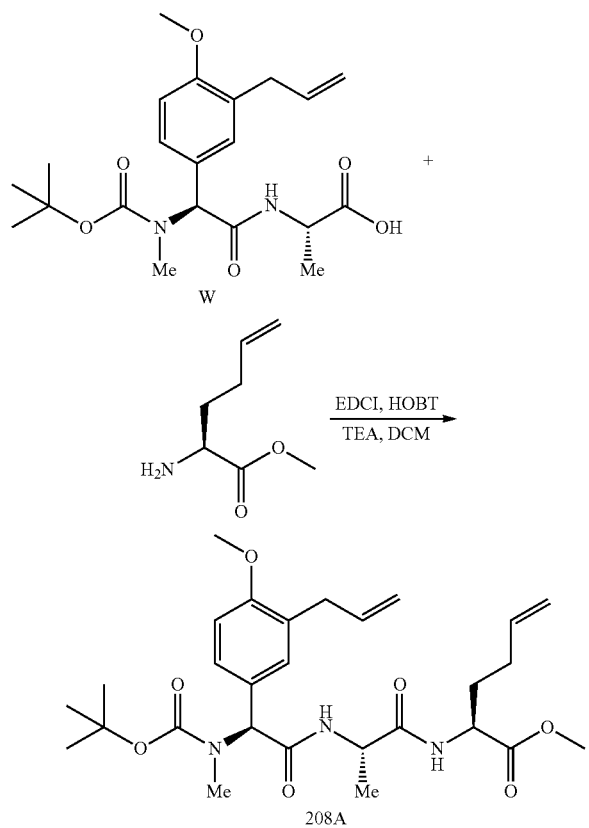

To a solution of Compound W (812 mg, 2.0 mmol) in anhydrous DCM (5 mL) was added methyl (S)-2-aminohex-5-enoate (343 mg, 2.4 mmol), HOBT (337 mg, 2.2 mmol), triethylamine (0.84 mL, 6.0 mmol) and EDCI (573 mg, 3.0 mmol). The reaction mixture was stirred at room temperature overnight. LCMS shows completion of the reaction and water was added. The mixture was extracted with EtOAc (3 times) and the combined organic layers were washed with brine, dried ($Na_2SO_4$) and concentrated. The residue was purified by flash chromatography using EtOAc-hexanes to afford Compound 208A (701 mg, 66%) as a colorless oil. MS (ESI) for ($C_{28}H_{41}N_3O_7$): m/z 554 (M+Na)+.

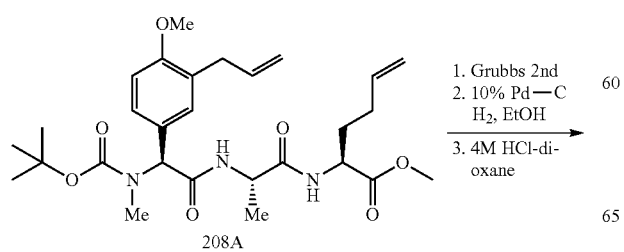

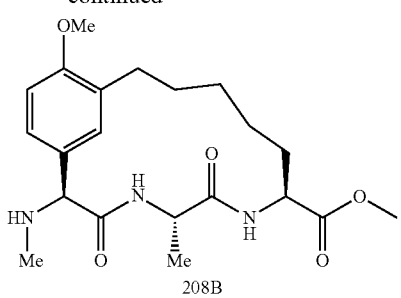

To a solution of Compound 208A (638 mg, 1.2 mmol) in DCM (bubbled $N_2$ for 2 min) was added Grubb's catalyst, second generation (102 mg, 0.12 mmol) at room temperature under $N_2$ atmosphere. The reaction mixture was stirred at room temperature overnight. After the completion of reaction by LCMS, the solvent was removed. The residue was purified by flash chromatography using EtOAc-hexanes to afford a brown oil (228 mg, 51%). MS (ESI) for ($C_{26}H_{37}N_3O_7$): m/z 526 (M+Na)+.

To a solution of the brown oil (201 mg, 0.4 mmol) in EtOH (5 mL) was added 10% Pd—C (20 mg). The reaction mixture was evacuated and flushed with $H_2$ three times and stirred under $H_2$ (balloon) for 4 h. LCMS shows completion of the reaction. The mixture was filtered through a pad of celite and the filtrate concentrated to give a white solid. MS (ESI) for ($C_{26}H_{39}N_3O_6$): m/z 528 (M+Na)+.

To a solution of the white solid in dioxane (1 mL) was added 4N HCl in dioxane (1.0 mL, 4 mmol) at 0° C. The reaction mixture was stirred at room temperature for 3 h. After completion of the reaction, the mixture was concentrated to afford Compound 208B, a white solid, which was used as is for the next reaction without further purification. MS (ESI) for ($C_{21}H_{31}N_3O_5$): m/z 406 (M+H)+.

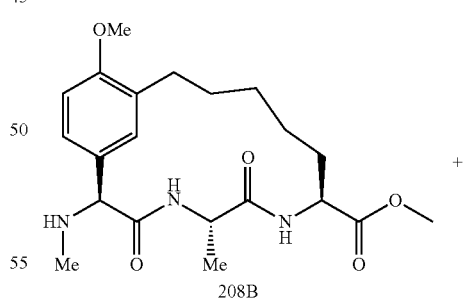

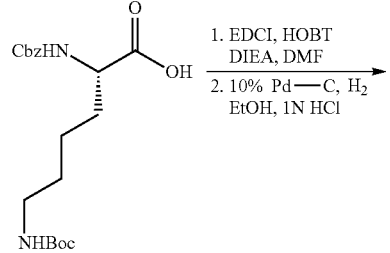

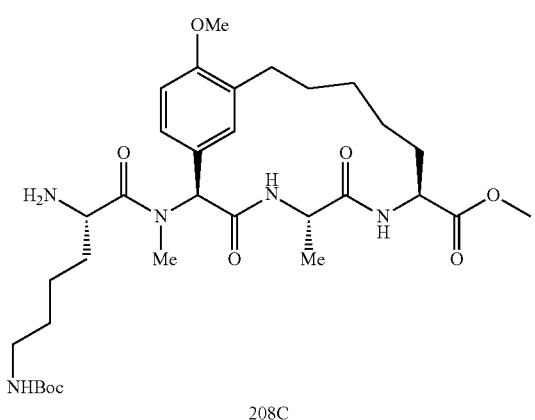

208C

To a solution of Compound 208B (202 mg, 0.5 mmol) in DMF (1 mL) was added Boc-Lys (Z)—OH (280 mg, 0.6 mmol), HOBT (85 mg, 0.55 mmol), DIEA (260 μL, 1.5 mmol) and EDCI (150 mg, 0.75 mmol). The reaction mixture was stirred at room temperature overnight. After completion of the reaction, crushed ice was added. The resultant white solid was filtered and dried to afford 253 mg (66%) of a white solid. MS (ESI) for ($C_{40}H_{57}N_5O_{10}$): m/z 790 (M+Na)$^+$.

To a solution of the white solid (246 mg, 0.32 mmol) in EtOH—$H_2O$ (9:1, 10 mL) was added 10% Pd—C (25 mg) and 1N HCl (0.64 mL, 0.64 mmol). The reaction mixture was evacuated and flushed with $H_2$ three times and stirred under $H_2$ (balloon) for overnight. LCMS shows completion of the reaction. The mixture was filtered through a pad of celite and to the filtrate was added DIPEA (0.17 mL, 0.96 mmol). The mixture was concentrated to afford Compound 208C, a white solid, which was used without further purification. MS (ESI) for ($C_{32}H_{51}N_5O_8$ m/z 634 (M+H)$^+$.

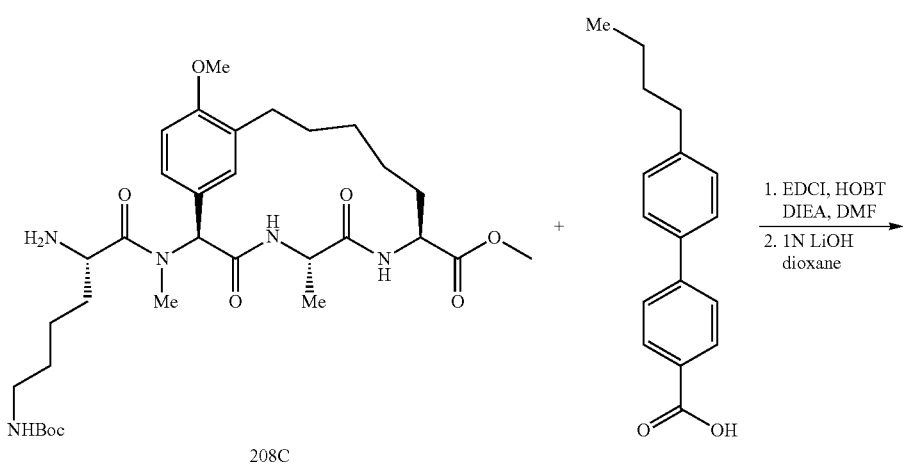

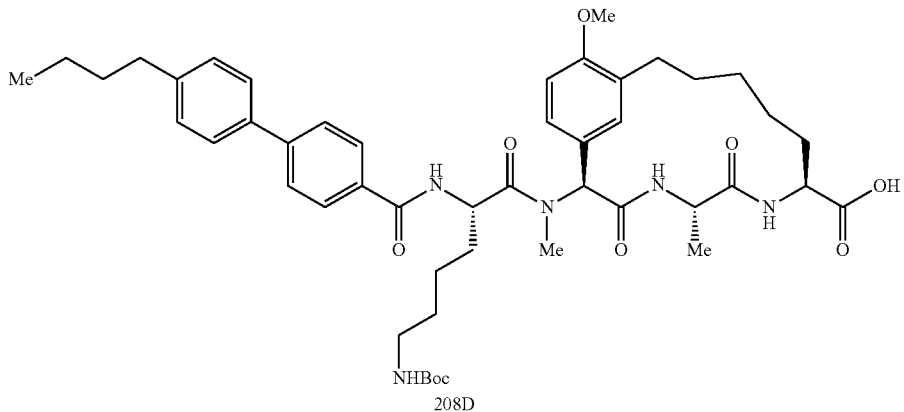

208D

To a solution of Compound 208C (225 mg, 0.36 mmol) in DMF (2 mL) was added 4'-butyl-[1,1'-biphenyl]-4-carboxylic acid (109 mg, 0.043 mmol), HOBT (60 mg, 0.4 mmol), DIPEA (0.2 mL, 1.08 mmol) and EDCI (103 mg, 0.54 mmol). The reaction mixture was stirred at room temperature for 4 h. LCMS shows completion of the reaction. To the reaction mixture was added ice, and the resultant off-white solid was filtered and dried. MS (ESI) for ($C_{49}H_{67}N_5O_9$): m/z 892 (M+Na)$^+$.

To a solution of the off-white solid in dioxane was added 1 N LiOH solution (1.08 mL, 1.08 mmol) at 0° C. The reaction mixture was stirred for 2 h. LCMS shows completion of the reaction. The reaction mixture was acidified with 1N HCl and the resultant white solid was filtered and dried to give Compound 208D which was purified by preparative HPLC using acetonitrile-water containing 0.05% TFA as mobile phase. MS (ESI) for ($C_{48}H_{65}N_5O_9$): m/z 878 (M+Na)$^+$.

To a solution of Compound 208D (17 mg, 0.02 mmol) in DMF (1 mL) was added (R)-BoroAla-(+)-pinanediol HCl (6.3 mg, 0.024 mmol) and HATU (15.2 mg, 0.04 mmol) and the reaction mixture was cooled to 0° C. DIPEA (10.5 μL, 0.06 mmol) was then added and the reaction mixture was stirred for 60 minutes. LCMS shows completion of the reaction. To the reaction mixture was added ice and the resultant solid was filtered and dried. MS (ESI) for ($C_{60}H_{85}BN_6O_{10}$): m/z 1061 (M+H)$^+$.

To the resultant solid was added TFA-DCM (1:4, 1 mL) at 0° C. and the reaction mixture was stirred for about 1 h while monitoring the completion of the reaction by LCMS. After the completion of the reaction, the solvent was removed and the residue was purified by preparative HPLC using acetonitrile-water containing 0.05% TFA as mobile phase to afford Compound 208. MS (ESI) for ($C_{55}H_{77}BN_6O_8$): m/z 961 (M+H)$^+$.

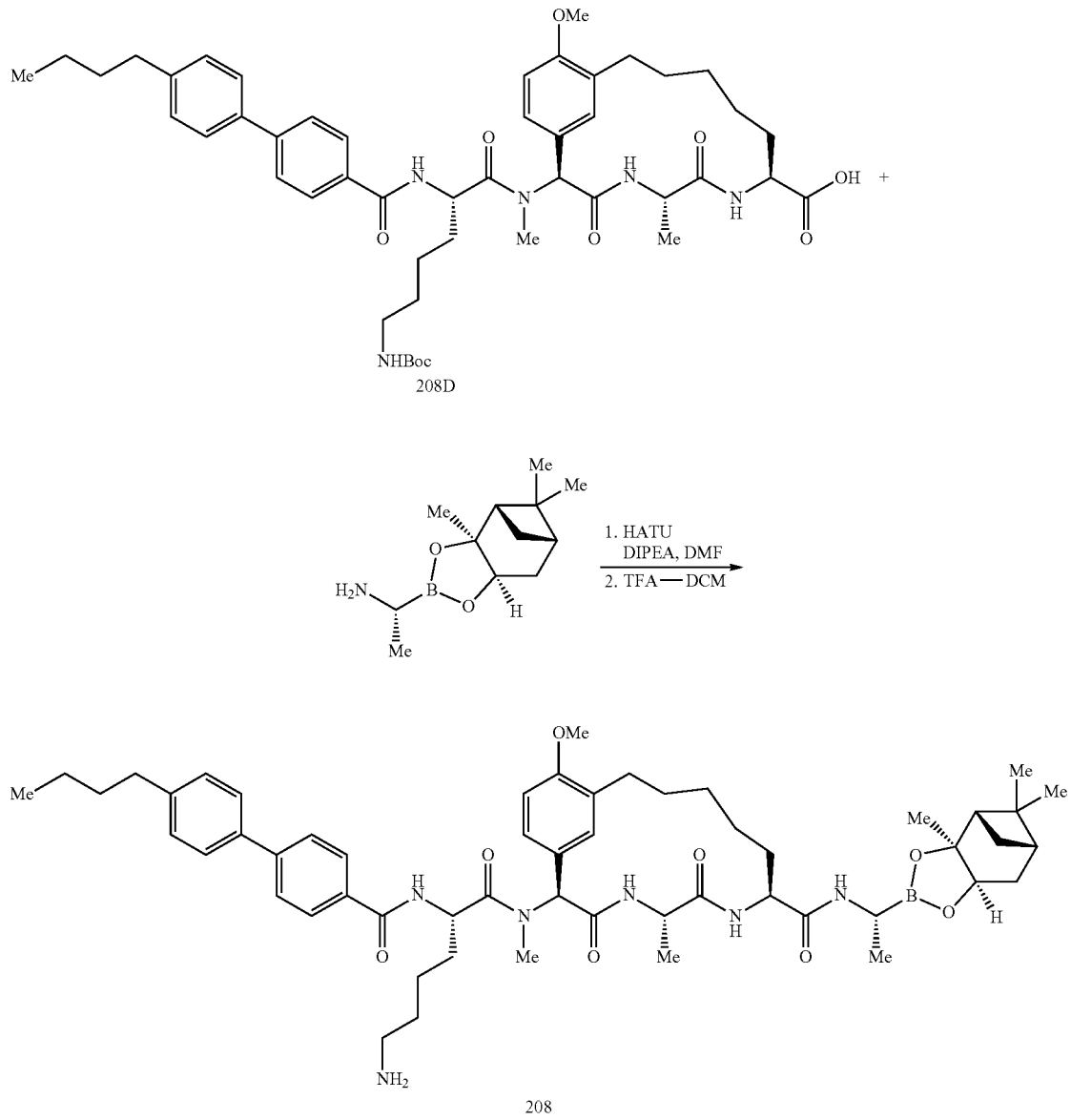

Example 45
Synthesis of Compound 209
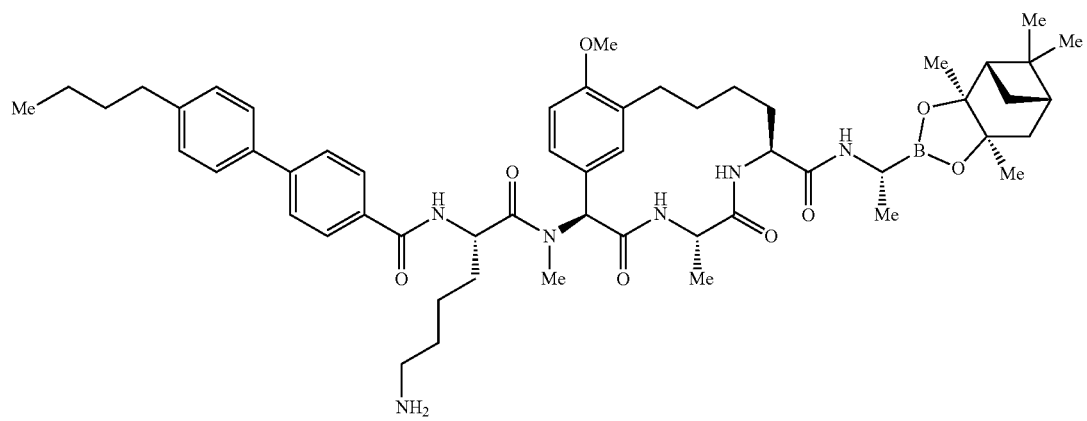
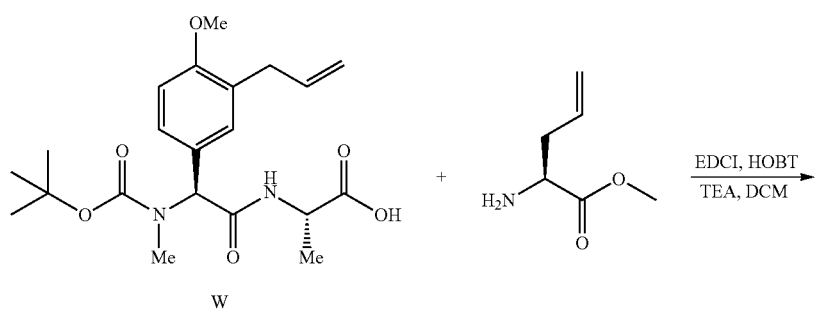
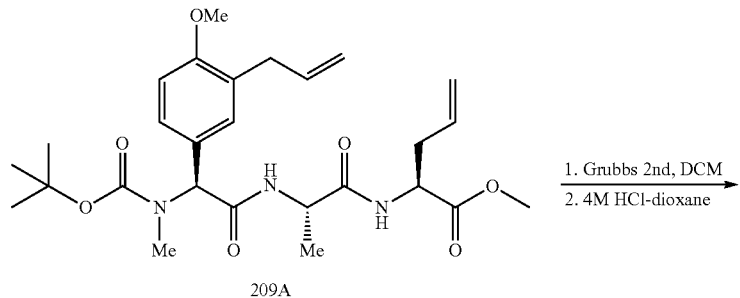
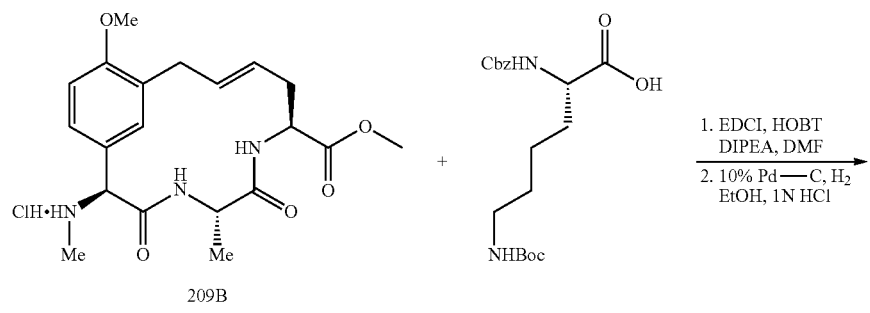

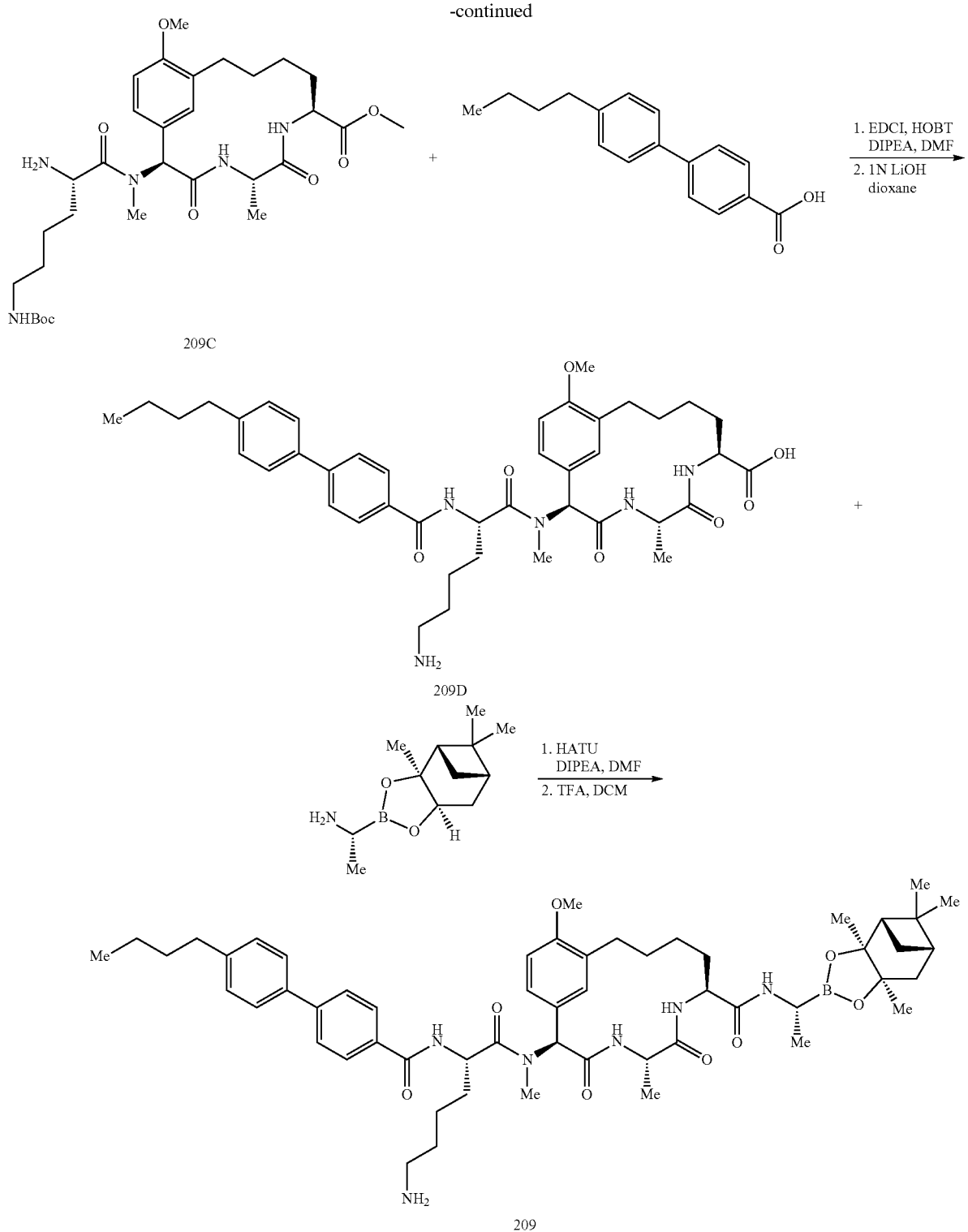

Synthesis of Compound 209A: Compound 209A was prepared using the procedures described in Example 44 from Compound W (203 mg, 0.5 mmol), anhydrous DCM (2 mL), methyl (S)-2-aminopent-4-enoate (99 mg, 0.6 mmol), HOBT (84 mg, 0.55 mmol), DIPEA (0.26 mL, 1.5 mmol) and EDCI (143 mg, 0.75 mmol). Data for Compound 209A: MS (ESI) for ($C_{27}H_{39}N_3O_7$): m/z 540 (M+Na)$^+$.

Compound 209B was prepared from Compound 209A using the procedures described in Example 44. Macrocyclization was performed using Compound 209A (1.04 g, 2.0 mmol), DCM (200 mL, bubbled $N_2$ for 2 min) and Grubb's catalyst, second generation (170 mg, 0.2 mmol). MS (ESI) for ($C_{25}H_{35}N_3O_7$): m/z 512 (M+Na)$^+$. Deprotection with 4N HCl in dioxane gave Compound 209B. Data for Compound 209B: MS (ESI) for ($C_{20}H_{27}N_3O_5$): m/z 390 (M+H).

Compound 209C was prepared from Compound 209B using the procedures described in Example 44. Compound 209B (389 mg, 1.0 mmol) with Boc-Lys (Z)—OH (456 mg, 1.2 mmol), DMF (2 mL), HOBT (168 mg, 1.1 mmol), DIPEA (530 µL, 3.0 mmol) and EDCI (287 mg, 1.5 mmol) was used. MS (ESI) for ($C_{39}H_{53}N_5O_{10}$): m/z 774 (M+Na)$^+$. The Cbz deprotection and hydrogenation of the ring olefin was performed on the resultant solid (376 mg, 0.5 mmol) using EtOH—H$_2$O (9:1, 10 mL), 10% Pd—C (40 mg), 1N HCl (0.75 mL, 0.75 mmol) to give Compound 209C. Data for Compound 209C: MS (ESI) for ($C_{31}H_{49}N_5O_8$): m/z 620 (M+H)$^+$.

Compound 209D was prepared from Compound 209C using the procedures described in Example 44. Coupling of Compound 209C (309 mg, 0.5 mmol) with 4'-butyl-[1,1'-biphenyl]-4-carboxylic acid (160 mg, 0.6 mmol), was performed using DMF (2 mL) HOBT (100 mg, 0.55 mmol), DIPEA (0.26 mL, 1.5 mmol) and EDCI (150 mg, 0.75 mmol). MS (ESI) for ($C_{48}H_{65}N_5O_9$): m/z 878 (M+Na)$^+$. The resultant solid was hydrolyzed using dioxane (2 mL) and 1N LiOH solution (1.5 mL, 1.5 mmol) to give Compound 209D. Data for Compound 209D: MS (ESI) for ($C_{47}H_{63}N_5O_9$):

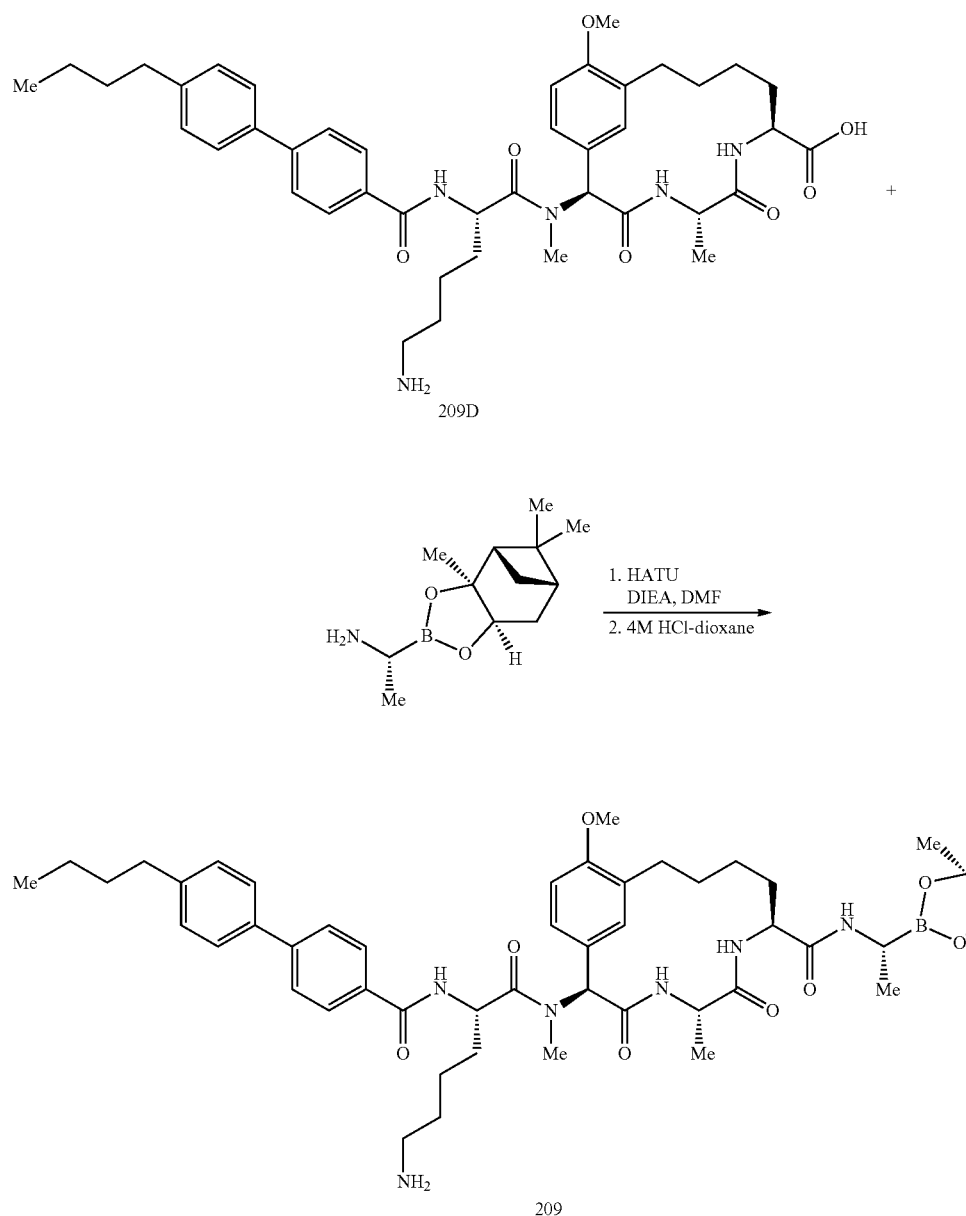

m/z 864 (M + Na)$^+$.

Compound 209 was prepared from Compound 209D using the procedures described in Example 44. Coupling of Compound 209D (21 mg, 0.025 mmol) with (R)-BoroAla-(+)-pinanediol HCl (8.0 mg, 0.03 mmol) was performed using DMF (1 mL), HATU (20 mg, 0.05 mmol), and DIPEA (13 μL, 0.075 mmol). MS (ESI) for ($C_{59}H_{83}BN_6O_{10}$): m/z 1047 (M+H)$^+$. The Boc group was removed from the resultant solid using TFA-DCM (1:4, 1 mL) and purified by preparative HPLC using acetonitrile-water containing 0.05% TFA as mobile phase to give Compound 209. Data for Compound 209: MS (ESI) for ($C_{54}H_{75}BN_6O_8$): m/z 947 (M+H)$^+$.

Example 46

Synthesis of Compound 210

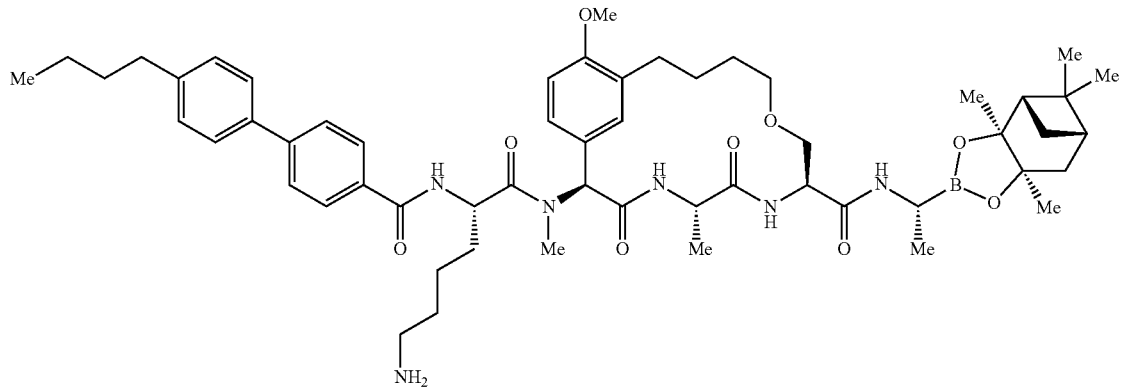

210

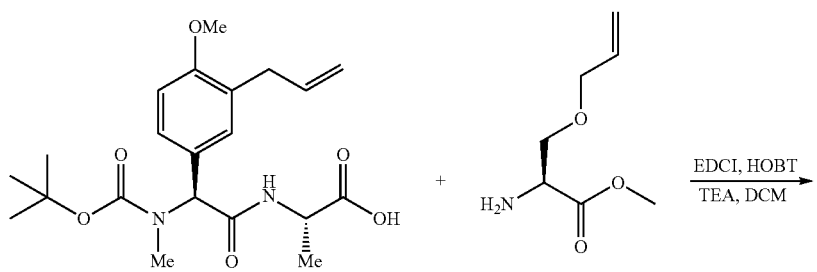

W

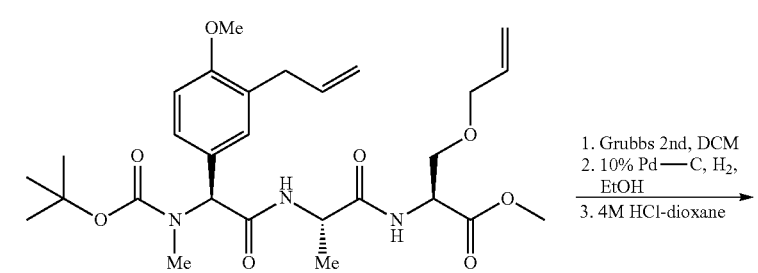

210A

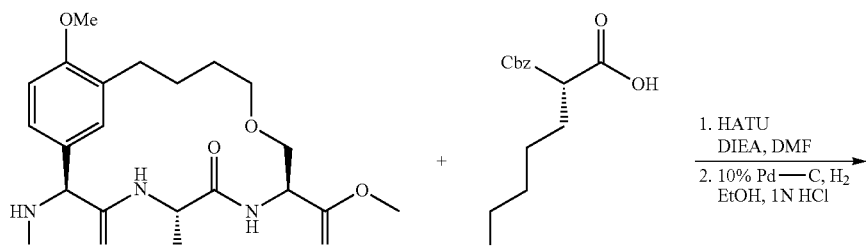

210B

367
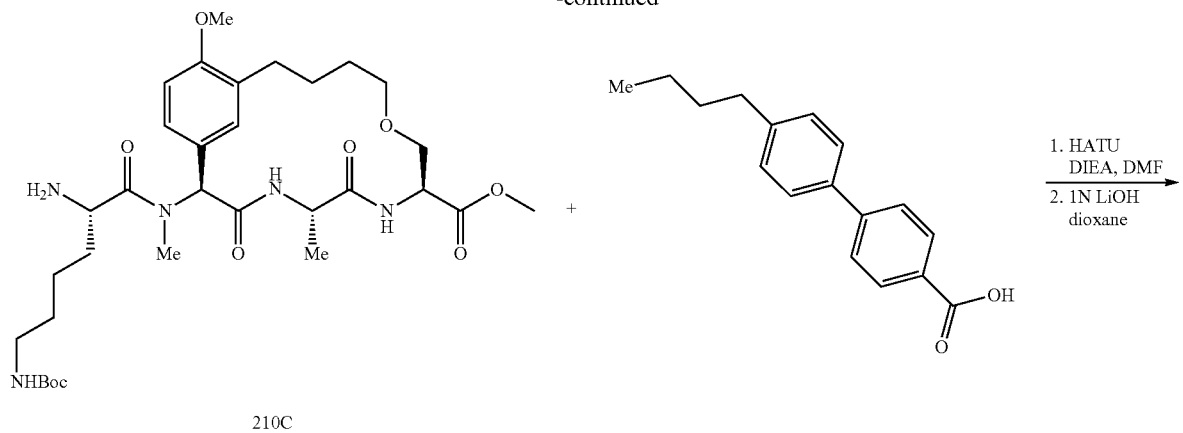
210C
368
1. HATU
   DIEA, DMF
2. 1N LiOH
   dioxane
-continued
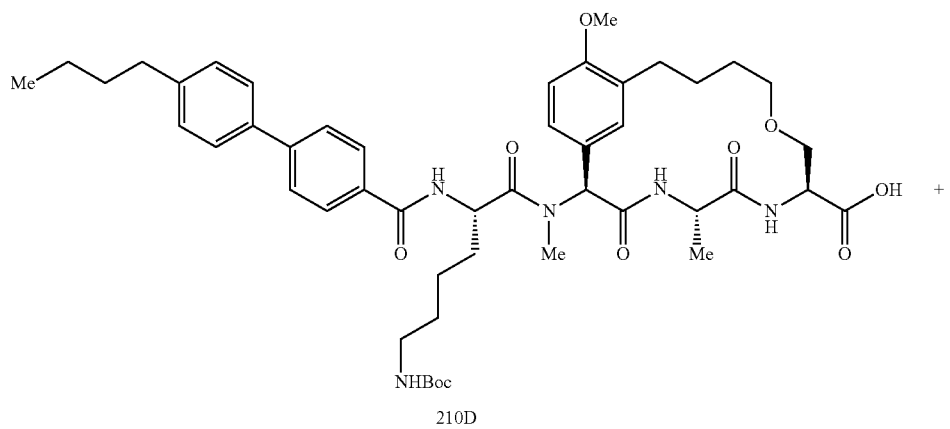
210D
1. HATU
   DIEA, DMF
2. TFA, DCM, TES
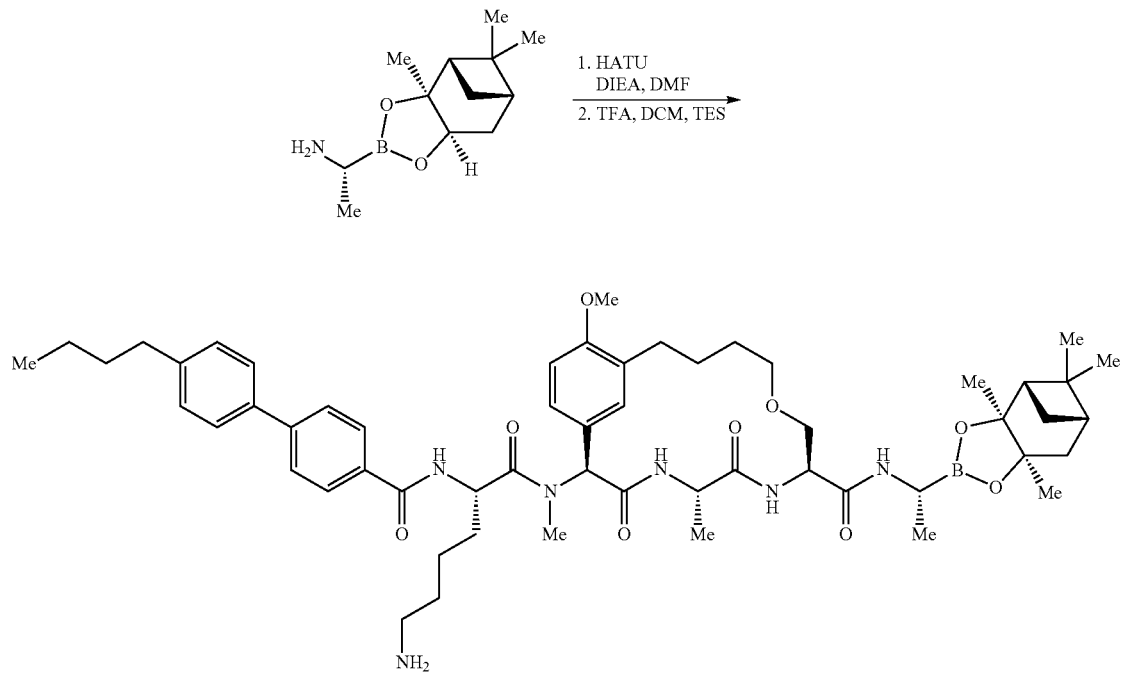
210

Synthesis of Preparation of Compound 210A: Compound 210A was prepared using the procedures described in Example 44 from Compound W (2.64 g, 6.50 mmol)), anhydrous DCM (40 mL), methyl O-allyl-L-serinate (1.39 g, 7.15 mmol), HOBT (1.76 g, 13.0 mmol)), Et$_3$N (2.63 mg, 26.0 mmol) and EDCI (2.48 g, 13.0 mmol). Data for Compound 210A: MS (ESI) for (C$_{28}$H$_{41}$N$_3$O$_8$): m/z 570 (M+Na)$^+$.

Compound 210B was prepared from Compound 210A using the procedures described in Example 44. Macrocyclization was performed using Compound 210A (1.70 g, 3.11 mmol), DCM (30 mL, bubbled N$_2$ for 2 min), and Grubb's catalyst, second generation [CAS#246047-72-3](74.6 mg, 0.0933 mmol). MS (ESI) for (C$_{25}$H$_{35}$N$_3$O$_7$): m/z 512 (M+Na)$^+$. This material (1.00 g, 1.93 mmol) was subjected for hydrogenation of the ring olefin using EtOH (10 mL) and 10% Pd—C (300 mg). MS (ESI) for (C$_{26}$H$_{39}$N$_3$O$_8$): m/z 544 (M+Na)$^+$. The Boc protecting group was removed with 4N HCl in dioxane to afford Compound 210B. Data for Compound 210B: MS (ESI) for (C$_{21}$H$_{31}$N$_3$O$_5$): m/z 422 (M+H)$^+$.

Compound 210C was prepared from Compound 210B using the procedures described in Example 44. Compound 210B (450 mg, 1.07 mmol) with Boc-Lys (Z)—OH (813 mg, 2.14 mmol), using DMF (5 mL), HATU 813 mg, 2.14 mmol) and DIPEA (271 mg, 2.14 mmol). MS (ESI) for (C$_{39}$H$_{53}$N$_5$O$_{10}$): m/z 774 (M+Na)$^+$. The Cbz deprotection and hydrogenation of the ring olefin was performed on the resultant compound (330 mg, 42.1 mmol), EtOH—H$_2$O (9:1, 5 mL), 10% Pd—C (50 mg), 1N HCl (0.200 mmol, 0.2 mL) to give Compound 210C. Data for Compound 210C: MS (ESI) for (C$_{32}$H$_{51}$N$_5$O$_9$): m/z 672 (M+Na)$^+$.

Compound 210D was prepared from Compound 210C using the procedures described in Example 44. Coupling of Compound 210C (230 mg, 0.354 mmol) with 4'-butyl-[1,1'-biphenyl]-4-carboxylic acid (98.9 mg, 0.389 mmol) was performed using DMF (3 mL) HATU (269 mg, 0708 mmol) and DIPEA (137 mg, 1.06 mmol). MS (ESI) for (C$_{49}$H$_{67}$N$_5$O$_{10}$): m/z 908 (M+Na)$^+$. The resultant solid (200 mg, 0.226 mmol) was hydrolyzed using dioxane (5 mL) and 1N LiOH solution (28.5 mg, 0.678 mmol) to give Compound 210D. Data for Compound 210D: MS (ESI) for (C$_{48}$H$_{65}$N$_5$O$_{10}$): m/z 873 (M+Na)$^+$.

Compound 210 was prepared from Compound 210D using the procedures described in Example 44. Coupling of Compound 210D (95.0 mg, 0.109 mmol) with (R)-BoroAla-(+)-pinanediol HCl (42.3 mg, 0.164 mmol) was performed using DMF-DCM (1:3, 3 mL), HATU (82.8 mg, 0.218 mmol) and DIPEA (42.2 mg, 0.327 mmol). MS (ESI) for (C$_{60}$H$_{85}$BN$_6$O$_{11}$): m/z 1077 (M+H)$^+$. The Boc group was removed from the resultant solid (25.0 mg, 0.0287 mmol) by treatment with TFA-triethylsilane and DCM to give Compound 210. Data for Compound 210: MS (ESI) for (C$_{55}$H$_{77}$BN$_6$O$_9$): m/z 977 (M+H)$^+$.

Biological Assays

Example 47

Determination of Minimum Inhibitory Concentration

In vitro antimicrobial activity of each compound was determined by measuring minimal inhibitor concentrations (MICs) using the broth micro-dilution technique as approved by the Clinical and Laboratory Standards Institute (CLSI) (Methods for Dilution Antimicrobial Susceptibility Tests for Bacteria that Grow Aerobically; Approved Standard—Eighth Edition. CLSI document M07-A8. Wayne, Pa.: Clinical and Laboratroy Standards; 2009). Antibacterial activity was measure against two strains of bacteria: a Methicillin Resistant *Staphylococcus aureus* strain USA 300 (NRS384) and a strain of *Escherichia coli* MC4100 harboring the IMP4213, which results in increased outer-membrane permeability (B Martin and Silhavy T. Imp/OstA is required for cell envelope biogenesis in *Escherichia coli*. (2002) Molecular Microbiology, 45(5), 1289-1302). Cells were inoculated onto plates of Trypyticase Soy Agar or Luria Agar respectively and grown at 35° C. for 20 hours. Inocula suspensions were prepared by scraping cells into 1 ml of testing media (cation adjusted Mueller Hinton Broth supplemented with 0.002% v/v Tween-80) and diluting to a final OD$_{600\,nm}$ of 0.01.

Test compounds were prepared in DMSO at a concentration of 10 mg/ml. These compound stocks were diluted into testing media at a concentration of 64 µg/ml and serial 2-fold dilutions were made in the same media, in 96-well U bottom microtiter dishes, for a total of 10 compound concentrations. Inocula suspensions were added to the 2-fold serial dilutions of test compounds to a final density of OD OD$_{600\,nm}$ of 0.0005 and incubated at 35° C. for 22 hours. After incubation the plates were examined visually and the lowest concentration of test compound that completely prevented bacterial growth were recorded as the MICs. The results are listed in Table 1.

TABLE 1

| Compound | MIC (µg/mL) E. coli | MIC (µg/mL) S. aureus |
|---|---|---|
| 101 | >64 | 6.3 |
| 102 | >64 | 10 |
| 103 | 2.6 | 2.1 |
| 104 | nt | 4 |
| 105 | >64 | 0.63 |
| 106 | >64 | 2 |
| 107 | >64 | 11 |
| 108 | 2 | 8 |
| 109 | 32 | >64 |
| 110 | 0.28 | 2.2 |
| 111 | 0.3 | 1.3 |
| 112 | >64 | >64 |
| 113 | 4 | 4 |
| 114 | >64 | 64 |
| 115 | >64 | 64 |
| 116 | >64 | >64 |
| 117 | 64 | >64 |
| 118 | 0.18 | 0.5 |
| 119 | 1 | 0.35 |
| 120 | 5.7 | 1.4 |
| 121 | 0.5 | 0.71 |
| 122 | >64 | >64 |
| 123 | 45 | 64 |
| 124 | >64 | >64 |
| 125 | 16 | 23 |
| 126 | 32 | 32 |
| 127 | 23 | 40 |
| 128 | >64 | >64 |
| 129 | nt | >64 |
| 130 | nt | >64 |
| 131 | nt | >64 |
| 132 | 64 | 6.1 |
| 133 | 16 | 19 |
| 134 | 9.5 | 10 |
| 135 | nt | 4 |
| 136 | 64 | 23 |
| 137 | 64 | >64 |
| 201 | 0.4 | 0.84 |
| 202 | 1.6 | 1.6 |
| 203 | 0.4 | 2 |
| 204 | 0.35 | 1.4 |
| 205 | 0.79 | 2.8 |
| 206 | 2.6 | 4 |
| 207 | 0.63 | 1.3 |
| 208 | 1 | 4.8 |
| 209 | 1 | 4 |
| 210 | 1.4 | 4 | nt = not tested

Example 48

Enzyme Inhibition Assay

Full length His-tagged E. coli and S. aureus SPase proteins were expressed in E. coli BL21 (DE$^3$) containing the plasmid pET23-lepB and pCDF1-SaSpsB respectively, as described previously (P A Smith, T C Roberts, F E Romesberg, Broad-spectrum antibiotic activity of the arylomycin natural products is masked by natural target mutations, Chem Biol, 2010, 17:1223-1231. PMCID: 3003444). Briefly, for expression of E. coli SPase, saturated overnight cultures grown in 20 ml of Luria-Bertani medium supplemented with ampicillin were subcultures into 1.5 L of Luria-Bertani, and shaken at 37° C. until an optical density at 600 nm of 0.4-0.5 was achieved. Protein expression was induced with Isopropyl β-D-1-thiogalactopyranoside (ITPG) at a final concentration of 0.5 µM, and purified using nickel affinity chromatography as described previously (3). S. aureus SPase was expressed and purified similarly, with the following exceptions. SPase protein was solubilized using 300 mM NaCl, 20 mM Tris pH 8.06, 5 mM Imidazole, 10% glycerol, 1% Triton X-100, prior to purification on Ni-NTA Superflow resin. Resin bound protein was washed in a similar buffer containing 1% Elugent in place of Triton X-100 prior to protein elution in wash buffer supplemented with 300 mM imidazole. Protein purify was judged to exceed 95% by visual inspection of SDS-PAGE followed by Comassie staining. All protein concentrations were determined by BCA assay.

Enzymatic activity of the above proteins was measured using two fluorogenic peptide substrates (decanoyl-LSSPAY$^{NO2}$A⇓ADK$^{abz}$PD (SEQ ID NO: 1) and decanoyl-LTPTAY$^{NO2}$A⇓ASKK$^{abz}$DD (SEQ ID NO: 2)), where abz is the fluorescence donor 2-aminobenzamide, Y$_{NO2}$ is the fluorescence acceptor 3-nitrotyrosine, and the cleavage site is indicated with an arrow. Enzyme master solution was prepared by diluting Escherichia coli or Staphylococcus aureus SPase protein into reaction buffer to a final concentration of 3 nM or 10 nM respectively. Reaction buffer consisted of 20 mM NaKHPO$_4$ pH 7.4, 100 mM NaCl, and 1% v/v Elugent™ detergent. Reactions were initiated by the addition of substrate to a final concentration of 20 µM. Reaction progress was monitored by measuring the increase in fluorescence signal (excitation at 314 nm, emission at 416 nm) using a SpectraMax M2 fluorescence microplate reader. To determine IC50 values of test compounds, compound stock solutions were prepared in DMSO at a concentration of 1 mM. Three-folder serial dilutions of test compounds, starting at 10 µM, were prepared in enzyme mix solution and incubated at room temperature for 10 minutes. Following this incubation, fluorogenic substrate was added to a final concentration of 20 µM and the increase in fluorescence, corresponding to substrate cleavage, was monitored continuously at room temperature for 1 hour. Initial reaction rates were calculated based on the rate of increase in fluorescence during the reaction. Reaction rates were plotted as a function of compound concentration, and IC$_{50}$ values were determined nonlinear regression analysis (SoftMaxPro 5.4, Molecular Devices™) of the sigmoidal dose-response curve. The results are listed in Table 2.

TABLE 2

| Cpd | IC 50 (nM) E. coli | IC 50 (nM) S. aureus |
|---|---|---|
| 101 | 5.4 | 30 |
| 102 | 11 | 280 |
| 103 | 1.3 | 8 |
| 104 | 3.7 | 12 |
| 105 | 1.3 | 16 |
| 106 | 2.9 | 8.8 |
| 107 | 0.6 | 2.6 |
| 108 | 2.4 | 110 |
| 109 | 11 | 15 |
| 110 | 1.4 | 350 |
| 111 | 2.2 | 160 |
| 112 | 850 | 7200 |
| 113 | 3.6 | 69 |
| 114 | 730 | 2200 |
| 115 | 630 | 1900 |
| 116 | >10,000 | >10,000 |
| 117 | 760 | 3900 |
| 118 | 7.6 | 31 |
| 119 | 8.6 | 33 |
| 120 | 18 | 220 |
| 121 | 29 | 110 |
| 122 | 27 | 130 |
| 123 | 20 | 18 |
| 124 | 23 | 1000 |
| 125 | 26 | 64 |
| 126 | 13 | 130 |
| 127 | 1.4 | 440 |
| 128 | 1.5 | 3500 |
| 129 | 370 | 140 |
| 130 | 160 | 580 |
| 131 | 180 | 3.3 |
| 132 | 26 | 5.9 |
| 133 | 1.8 | 33 |
| 134 | 0.8 | 8.2 |
| 135 | nt | nt |
| 136 | 44 | 47 |
| 137 | 350 | 3100 |
| 138 | 30 | 78 |
| 201 | 15 | 150 |
| 202 | 28 | 200 |
| 203 | 8.9 | 81 |
| 204 | 25 | 250 |
| 205 | 30 | 280 |
| 206 | 81 | 600 |
| 207 | 21 | 210 |
| 208 | 680 | >10,000 |
| 209 | 84 | 3700 |
| 210 | 96 | 210 | nt = not tested

Example 49

Clinical Trial of the Safety and Efficacy of Compounds of Formula (I), (Ia), (Ib), (Ic), (Id), (Ie), (II), (IIa), (IIb), (IIc), (III), (IIIa), (IIb), (IIIc), (IV), (IVa), or (IVb) in Patients with C. Difficile-Associated Diarrhea Purpose: This study aims to determine the safety and efficacy of compounds presented herein for the treatment of symptoms of C. difficile-associated diarrhea and lowering the risk of repeat episodes of diarrhea. The compounds are evaluated in comparison to current standard antibiotic treatment, so all patients will receive active medication. All study-related care is provided including doctor visits, physical exams, laboratory tests and study medication. Total length of participation is approximately 10 weeks.

Patients: Eligible subjects will be men and women 18 years and older.

Criteria:

Inclusion Criteria:

Be at least 18 years old;

Have active mild to moderate *C. difficile*-Associated Diarrhea (CDAD);

Be able to tolerate oral medication;

Not be pregnant or breast-feeding; and

Sign and date an informed consent form.

Study Design: This is a randomized, double-blind, active control study of the efficacy, safety, and tolerability of a compound of Formula (I), (Ia), (Ib), (Ic), (Id), (Ie), (II), (IIa), (IIb), (IIc), (III), (IIIa), (IIIb), (IIIc), (IV), (IVa), or (IVb) in patients with *C. difficile*-associated diarrhea.

Example 50:

Clinical Trial Comparing a Compound of Formula (I), (Ia), (Ib), (Ic), (Id), (Ie), (II), (IIa), (IIb), IIc), (III), (IIIa), (IIIb), (II), (IV), (IVa), or (IVb) with Vancomycin for the Treatment of MRSA Osteomyelitis Purpose: This study aims to determine the efficacy of compounds presented herein as compared to vancomycin for the treatment of methicillin-resistant *Staphylococcus aureus* (MRSA) osteomyelitis.

Patients: Eligible subjects will be men and women 18 years and older.

Criteria:

Inclusion Criteria:

Culture-proven MRSA, obtained in operating room or sterile biopsy procedure from bone site. The infection and sampling site is either within the bone or a deep soft-tissue site that is contiguous with bone; OR radiographic abnormality consistent with osteomyelitis in conjunction with a positive blood culture for MRSA;

Surgical debridement of infection site, as needed;

Subject is capable of providing written informed consent; and

Subject capable of receiving outpatient parenteral therapy for 12 weeks.

Exclusion Criteria:

Hypersensitivity to a compound of Formula (I), (Ia), (Ib), (Ic), (Id), (Ie), (II), (IIa), (IIb), (IIc), (III), (IIIa), (IIIb), (IIIc), (IV), (IVa), or (IVb) or vancomycin;

*S. aureus* resistant to a compound of Formula (I), (Ia), (Ib), (Ic), (Id), (Ie), (II), (IIa), (IIb), (IIc), (III), (IIIa), (IIIb), (IIIc), (IV), (IVa), or (IVb) or vancomycin;

Osteomyelitis that develops directly from a chronic, open wound;

Polymicrobial culture (the only exception is if coagulase-negative *staphylococcus* is present in the culture and the clinical assessment is that it is a contaminant);

Subject has a positive pregnancy test at study enrollment;

Baseline renal or hepatic insufficiency that would preclude administration of study drugs;

Active injection drug use without safe conditions to administer intravenous antibiotics for 3 months; and Anticipated use of antibiotics for greater than 14 days for an infection other than osteomyelitis.

Study Design: This is a randomized, open-label, active control, efficacy trial comparing vancomycin with a compound of Formula (I), (Ia), (Ib), (Ic), (Id), (Ie), (II), (IIa), (IIb), (IIc), (III), (IIIa), (IIIb), (IIIc), (IV), (IVa), or (IVb) for the treatment of MRSA Osteomyelitis.

Example 51

Clinical Trial Evaluating a Compound of Formula (I), (Ia), (Ib), (Ic), (Id), (Ie), (II), (Ia), (IIb), (IIc), (III), (IIIa), (IIb), (IIIc), (IV), (IVa), or (IVb) in Selected Serious Infections Caused by Vancomycin-Resistant *Enterococcus* (VRE)

Purpose: This study aims to determine the safety and efficacy of a compound of Formula (I), (Ia), (b), (Ic), (Id), (Ie), (II), (IIa), (IIb), (IIc), (III), (IIIa), (IIb), (IIIc), (IV), (IVa), or (IVb) in the treatment of selected serious infections caused by VRE.

Patients: Eligible subjects will be men and women 18 years and older.

Criteria:

Inclusion Criteria:

Isolation of one of the following multi-antibiotic resistant bacteria: vancomycin-resistant *Enterococcus faecium*, vancomycin-resistant *Enterococcus faecalis* alone or as part of a polymicrobial infection; and Have a confirmed diagnosis of a serious infection (eg, bacteremia [unless due to an excluded infection], complicated intra-abdominal infection, complicated skin and skin structure infection, or pneumonia) requiring administration of intravenous (IV) antibiotic therapy.

Exclusion Criteria:

Subjects with any concomitant condition or taking any concomitant medication that, in the opinion of the investigator, could preclude an evaluation of a response or make it unlikely that the contemplated course of therapy or follow-up assessment will be completed or that will substantially increase the risk associated with the subject's participation in this study. Anticipated length of antibiotic therapy less than 7 days Study Design: This is a randomized, double-blind, safety and efficacy study of a compound of Formula (I), (Ia), (Ib), (Ic), (Id), (Ie), (II), (IIa), (IIb), (IIc), (III), (IIIa), (IIIb), (IIIc), (IV), (IVa), or (IVb) in the treatment of selected serious infections caused by VRE.

Pharmaceutical Compositions

I. Parenteral Composition

To prepare a parenteral pharmaceutical composition suitable for administration by injection, 100 mg of a compound of Formula (I), (Ia), (Ib), (Ic), (Id), (Ie), (II), (IIa), (IIb), (IIc), (III), (IIIa), (IIIb), (IIIc), (IV), (IVa), or (IVb) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I), (Ia), (Ib), (Ic), (Id), (Ie), (II), (IIa), (IIb), (IIc), (III), (IIIa), (IIIb), (IIIc), (IV), (IVa), or (IVb) | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formula (I), (Ia), (Ib), (Ic), (Id), (Ie), (II), (IIa), (IIb), (IIc), (III), (IIIa), (IIIb), (IIIc), (IV), (IVa), or (IVb) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I), (Ia), (Ib), (Ic), (Id), (Ie), (II), (IIa), (IIb), (IIc), (III), (IIIa), (IIIb), (IIIc), (IV), (IVa), or (IVb) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I), (Ia), (Ib), (Ic), (Id), (Ie), (II), (IIa), (IIb), (IIc), (III), (IIIa), (IIIb), (IIIc), (IV), (IVa), or (IVb) | 200 |
| lactose, spray-dried | 148 |
| magnesium stearate | 2 |

In yet another embodiment, the following ingredients are mixed to form a solution/suspension for oral administration:

| Ingredient | Amount |
| --- | --- |
| Compound of Formula (I), (Ia), (Ib), (Ic), (Id), (Ie), (II), (IIa), (IIb), (IIc), (III), (IIIa), (IIIb), (IIIc), (IV), (IVa), or (IVb) | 1 g |
| Anhydrous Sodium Carbonate | 0.1 g |
| Ethanol (200 proof), USP | 10 mL |
| Purified Water, USP | 90 mL |
| Aspartame | 0.003 g |

Topical Gel Composition

To prepare a pharmaceutical topical gel composition, 100 mg of a compound of Formula (I), (Ia), (Ib), (Ic), (Id), (Ie), (II), (IIa), (IIb), (IIc), (III), (IIIa), (IIIb), (IIIc), (IV), (IVa), or (IVb) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A compound of Formula (I):

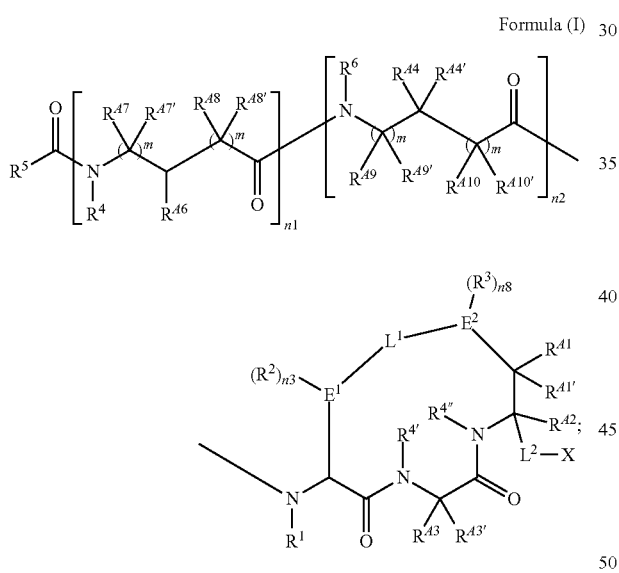

Formula (I)

wherein:

$E^1$ is $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$E^2$ is $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$ alkylene optionally substituted with OH, CN, $NO_2$, halogen, or $(C_1-C_6)$alkyl;

$L^2$ is a bond;

X is a group of formula

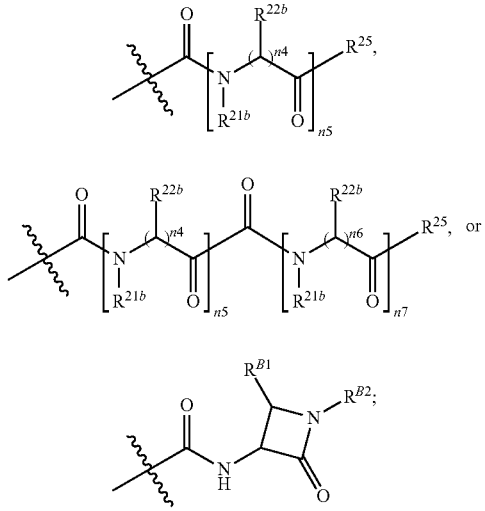

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$ cycloalkyl, 5- to 7-membered heteroaryl, 5- to 7- membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

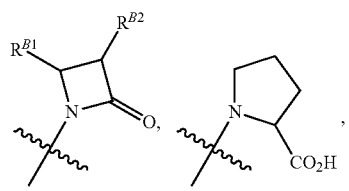

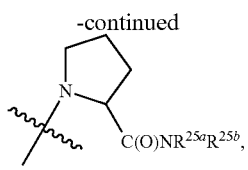

or $NR^{25a}R^{25b}$ where $R^{25a}$ and $R^{25b}$ are each independently H, $SO_2(C_1\text{-}C_6)$alkyl, or alkyl; $R^{B1}$ and $R^{B2}$ are each independently H, $(C_1\text{-}C_6)$ alkyl, $(C_3\text{-}C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1\text{-}C_6)$alkoxy, $(C_1\text{-}C_6)$thioalkoxy, $N(R^C)_2$, 5-7 membered heterocyclyl or 5-7 membered heteroaryl, or $(C_6\text{-}C_{10})$ aryl;

$R^C$ is independently at each occurrence H or $(C_1\text{-}C_6)$ alkyl, and a wavy line indicates a point of attachment of X to a carbon of formula (I) bearing X; or X is $CO_2H$, $CH_2CO_2H$, $C(=O)NHCH_2C(=O)H$, $CH_2C(=O)H$, $C(=O)N(H)CH(R^7)B(OR^{B3})(OR^{B4})$, or

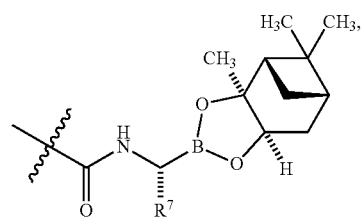

wherein $R^7$ is H, methyl, ethyl, or $-CH_2OH$; or $R^7$ and $R^{B3}$ together with the boron atom form a 5- or 6-membered boron containing ring; $R^{B3}$ and $R^{B4}$ are each independently H, $(C_1\text{-}C_6)$alkyl, $-CH_2CO_2H$, or $-CH_2CH_2CO_2H$; or $R^{B3}$ and $R^{B4}$ together with the boron atom form an optionally substituted 5- or 6-membered boron containing ring;

$R^5$ is aryl, heteroaryl, or a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus

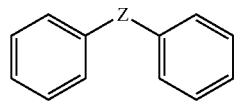

wherein Z is a bond, O, S, NH, $CH_2$ or $C\equiv C$;

$R^2$ and $R^3$ are each independently nitro, halo, cyano, hydroxy, glycosyloxy, amino, $(C_1\text{-}C_4)$alkoxy, $(C_1\text{-}C_4)$acyloxy, $(C_1\text{-}C_4)$alkyl, or a group cleavable under physiological conditions to provide a compound of formula (I) wherein $R^2$ or $R^3$ respectively is hydroxy, wherein any carbon atom is optionally substituted with J;

n1 is 1;

n2 is 0;

n3 and n8 are independently 0, 1, or 2;

each m is independently 0 or 1;

$R^1$ is hydrogen or $(C_1\text{-}C_6)$alkyl optionally substituted with 1 to 3 J; or $R^1$ together with $E^1$ form a ring;

$R^4$, $R^{4'}$, and $R^{4''}$ are each independently at each occurrence hydrogen, or $(C_1\text{-}C_6)$alkyl optionally substituted with 1 to 3 J;

$R^6$ is hydrogen, or $(C_1\text{-}C_6)$alkyl optionally substituted with 1 to 3 J; or $R^6$ together with $R^{44}$ form a ring;

$R^{A1}$, $R^{A1'}$, $R^{A2}$, $R^{A3}$, $R^{A3'}$, $R^{A4}$, $R^{A4'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1\text{-}C_6)$alkyl, $(C_3\text{-}C_7)$cycloalkyl, 5- to 7- membered heteroaryl, 5- to 7- membered heterocyclyl, or $(C_6\text{-}C_{10})$ aryl, wherein any alkyl, cycloalkyl, heterocyclyl, aryl or heteroaryl is optionally substituted with 1 to 3 J;

$R^{A6}$ is amino, $(C_1\text{-}C_6)$alkyl, $(C_3\text{-}C_7)$cycloalkyl, 5- to 7- membered heteroaryl, 5- to 7- membered heterocyclyl, or $(C_6\text{-}C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0\text{-}p}N(R')_2$, $(CH_2)_{0\text{-}p}SR'$, $(CH_2)_{0\text{-}p}S(O)_2R'$, $(CH_2)_{0\text{-}p}S(O)_2N(R')_2$, $(CH_2)_{0\text{-}p}SO_3R'$, $(CH_2)_{0\text{-}p}C(O)R'(CH_2)_{0\text{-}p}C(O)OR'$ $(CH_2)_{0\text{-}p}C(O)N(R')_2$, $(CH_2)_{0\text{-}p}OC(O)N(R')_2$, $(CH_2)_{0\text{-}p}NH-C(O)R'(CH_2)_{0\text{-}p}N(R')SO_2R'(CH_2)_{0\text{-}p}N(R')C(O)OR'(CH_2)_{0\text{-}p}N(R')C(O)R'$, $(CH_2)_{0\text{-}p}N(R')C(O)N(R')_2$, or $(CH_2)_{0\text{-}p}C(=NH)N(R')_2$, wherein p is 4;

each R' is independently at each occurrence hydrogen, $(C_1\text{-}C_6)$-alkyl, $(C_2\text{-}C_7)$-alkenyl, $(C_2\text{-}C_7)$-alkynyl, $(C_3\text{-}C_{10})$-cycloalkyl, $(C_3\text{-}C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, $-CN$, $-NO_2$, $-OH$, $-CF_3$, $-OCF_3$, $-OCH_3$, $-NH_2$, $-N((C_1\text{-}C_4)$alkyl$)_2$, $-NH(C_1\text{-}C_4)$alkyl, $C_1\text{-}C_6$alkyl, $C_3\text{-}C_8$cycloalkyl, or $C_1\text{-}C_6$heteroalkyl; or a pharmaceutically acceptable salt, solvate, or prodrug thereof.

2. The compound of claim 1 having the structure of Formula (Ia):

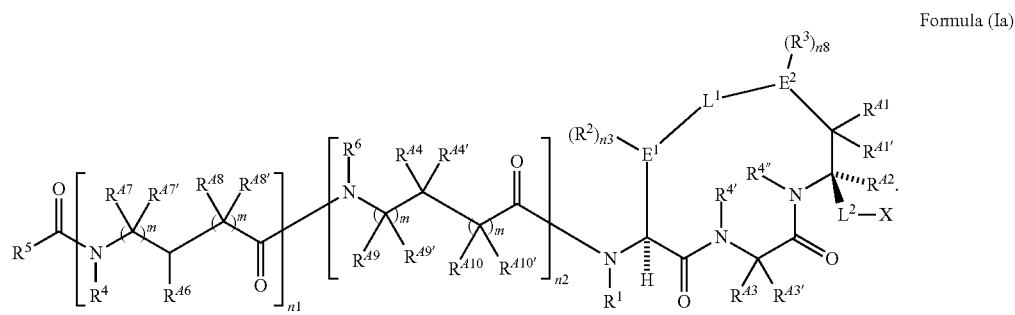

Formula (Ia)

3. The compound of claim 2 having the structure of Formula (Ib):

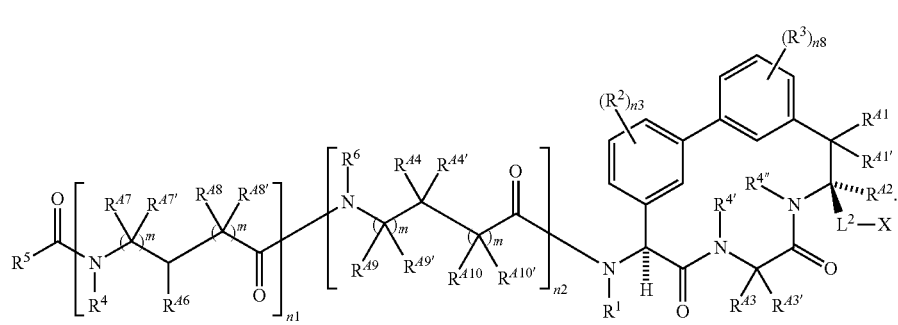

Formula (Ib)

4. The compound of claim 3 having the structure of Formula (Ic):

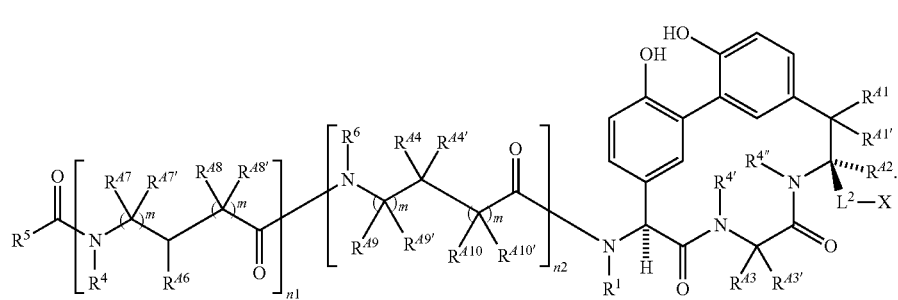

Formula (Ic)

5. The compound of claim 4 wherein $R^{A1}$, $R^{A1'}$, $R^{4'}$, $R^{4''}$ are H.
6. The compound of claim 5 wherein $L^2$ is a bond.
7. The compound of claim 5 wherein $R^1$ is $CH_3$.
8. The compound of claim 7 wherein $R^{A2}$, $R^{A3}$, and $R^{A3'}$ are each independently hydrogen, or $(C_1-C_6)$alkyl optionally substituted with 1 to 3 J.
9. The compound of claim 4 wherein X is $CO_2H$.
10. The compound of claim 4 wherein X is $C(=O)NHCH_2B(OH)_2$.
11. The compound of claim 4 wherein X is $C(=O)NHCH(CH_3)B(OH)_2$.
12. The compound of claim 4 wherein X is

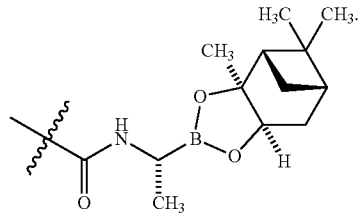 [SMILES: *C(=O)N[C@@H](C)B1O[C@@H]2C[C@@H]3C[C@@H](C3(C)C)[C@]2(C)O1]

13. A pharmaceutical composition comprising the compound of claim 1 and a pharmaceutically acceptable excipient.
14. A method of treatment of a bacterial infection in a mammal, comprising administering to the mammal an effective amount of a compound of claim 1 to the animal at a frequency and for a duration sufficient to provide a beneficial effect to the mammal.
15. The method of claim 14, wherein the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis,*

*Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

16. The method of claim 14, wherein the bacterial infection is an infection involving a Gram-negative bacteria.

\* \* \* \* \*